(12) United States Patent
Bajwa et al.

(10) Patent No.: US 12,234,473 B2
(45) Date of Patent: Feb. 25, 2025

(54) CD8 POLYPEPTIDES, COMPOSITIONS, AND METHODS OF USING THEREOF

(71) Applicant: Immatics US, Inc., Houston, TX (US)

(72) Inventors: Gagan Bajwa, Houston, TX (US); Mamta Kalra, Houston, TX (US); Melinda Mata, Missouri City, TX (US)

(73) Assignee: Immatics US, INC., Stafford, TX (US)

( * ) Notice: Subject to any disclaimer, the term of this patent is extended or adjusted under 35 U.S.C. 154(b) by 0 days.

(21) Appl. No.: 17/563,599

(22) Filed: Dec. 28, 2021

(65) Prior Publication Data

US 2022/0202862 A1 Jun. 30, 2022

Related U.S. Application Data

(60) Provisional application No. 63/247,775, filed on Sep. 23, 2021, provisional application No. 63/132,824, filed on Dec. 31, 2020.

(30) Foreign Application Priority Data

Jan. 4, 2021 (DE) .......................... 102021100038.6

(51) Int. Cl.
| | | |
|---|---|---|
| *A61K 35/17* | (2015.01) | |
| *A61K 39/00* | (2006.01) | |
| *C07K 14/705* | (2006.01) | |
| *C07K 14/725* | (2006.01) | |
| *C12N 5/0783* | (2010.01) | |
| *C12N 15/86* | (2006.01) | |

(52) U.S. Cl.
CPC .......... *C12N 15/86* (2013.01); *A61K 39/4611* (2023.05); *A61K 39/4632* (2023.05); *A61K 39/464411* (2023.05); *A61K 39/464489* (2023.05); *C07K 14/7051* (2013.01); *C07K 14/70517* (2013.01); *C12N 5/0636* (2013.01); *C12N 2810/55* (2013.01)

(58) Field of Classification Search
CPC ................ A61K 35/17; C07K 14/7051; C07K 14/70517; C12N 5/0636; C12N 15/86; C12N 2810/55; C12N 2510/00; C12N 2740/16043
See application file for complete search history.

(56) References Cited

U.S. PATENT DOCUMENTS

| | | | |
|---|---|---|---|
| 5,348,878 A | 9/1994 | Rock | |
| 5,540,926 A | 7/1996 | Aruffo et al. | |
| 7,425,339 B2 | 9/2008 | Jakobsen et al. | |
| 7,700,739 B2 * | 4/2010 | Lacy ........................ | A61P 37/08 424/130.1 |
| 8,088,379 B2 | 1/2012 | Robbins et al. | |
| 8,124,084 B2 | 2/2012 | Lefrancois et al. | |
| 8,206,702 B2 | 6/2012 | Winqvist et al. | |
| 8,361,794 B2 | 1/2013 | Jakobsen | |
| 8,883,495 B2 | 11/2014 | Nakamura et al. | |
| 8,940,288 B2 | 1/2015 | Lefrancois et al. | |
| 9,090,875 B2 | 7/2015 | Turtle et al. | |
| 9,115,372 B2 | 8/2015 | Jakobsen | |
| 9,128,080 B2 | 9/2015 | Robbins et al. | |
| 9,255,135 B2 | 2/2016 | Jakobsen et al. | |
| 9,371,368 B2 | 6/2016 | Lefrancois et al. | |
| 9,540,657 B2 | 1/2017 | Yu et al. | |
| 9,623,049 B2 | 4/2017 | Eshhar et al. | |
| 9,629,877 B2 | 4/2017 | Cooper et al. | |
| 9,848,587 B2 | 12/2017 | Macdonald et al. | |
| 9,931,377 B2 | 4/2018 | Pavlakis et al. | |
| 9,931,384 B2 | 4/2018 | Turtle et al. | |
| 9,975,937 B2 | 5/2018 | Pavlakis et al. | |
| 9,987,308 B2 | 6/2018 | Riddell et al. | |
| 10,117,897 B2 | 11/2018 | Sadelain et al. | |
| 10,202,433 B2 | 2/2019 | Jacques et al. | |
| 10,265,382 B2 | 4/2019 | Felber et al. | |
| 10,358,477 B2 | 7/2019 | Jacques et al. | |
| 10,400,215 B2 | 9/2019 | Riddell et al. | |
| 10,464,993 B2 | 11/2019 | Lefrancois et al. | |
| 10,894,816 B2 | 1/2021 | Pavlakis et al. | |
| 10,905,743 B2 | 2/2021 | Qu et al. | |
| 11,008,374 B2 | 5/2021 | Jacques et al. | |
| 11,008,378 B2 | 5/2021 | Lefrancois et al. | |
| 11,110,150 B2 | 9/2021 | Felber et al. | |
| 2002/0111474 A1 | 8/2002 | Capon et al. | |
| 2002/0155604 A1 | 10/2002 | Ledbetter et al. | |

(Continued)

FOREIGN PATENT DOCUMENTS

| | | | | |
|---|---|---|---|---|
| CA | 3110922 A1 * | 3/2020 | ............ | A61K 35/17 |
| JP | 2018517674 A | 7/2018 | | |

(Continued)

OTHER PUBLICATIONS

Xue et al., "Human MHC Class I-restricted high avidity CD4+ T cells generated by co-transfer of TCR and CD8 mediate efficient tumor rejection in vivo," OncoImmunology, (2013), vol. 2, No. 1, e22590.

Arber et al., "Mouse Models in Bone Marrow Transplantation and Adoptive Cellular Therapy," Semin Hematol., (2013), vol. 50, No. 2: 131-144.

Arber et al., "Survivin-specific T cell receptor targets tumor but not T cells," The Journal of Clinical Investigation, (2015), vol. 125, No. 1: 157-168.

Bohner et al., "Double Positive CD4+CD8+ T Cells Are Enriched in Urological Cancers and Favor T Helper-2 Polarization," Frontiers in Immunology, (2019), vol. 10: Article 622.

Gao et al., "Post-transcriptional regulation associated with control of human CD8A expression of CD4+ T cells," Immunogenetics, (1996), vol. 45, No. 2: 130-5. Abstract Only.

(Continued)

Primary Examiner — Jeremy C Flinders
Assistant Examiner — Masudur Rahman
(74) Attorney, Agent, or Firm — McBee, Moore & Vanik IP, LLC

(57) ABSTRACT

The present disclosure relates to T cells capable of co-expressing T cell receptors ("TCR") together with CD8 polypeptides and the use thereof in adoptive cellular therapy. The present disclosure further provides for modified CD8 sequences, vectors, and associated methods thereof.

12 Claims, 98 Drawing Sheets

Specification includes a Sequence Listing.

(56) References Cited

U.S. PATENT DOCUMENTS

| | | |
|---|---|---|
| 2003/0109042 A1 | 6/2003 | Wu et al. |
| 2003/0118592 A1 | 6/2003 | Ledbetter et al. |
| 2003/0138409 A1 | 7/2003 | Pancre et al. |
| 2003/0219463 A1 | 11/2003 | Falkenburg et al. |
| 2004/0253250 A1 | 12/2004 | Ledbetter et al. |
| 2005/0118676 A1 | 6/2005 | Qi et al. |
| 2005/0221435 A1 | 10/2005 | Acres et al. |
| 2007/0054262 A1* | 3/2007 | Baker ............... C07K 7/06 435/5 |
| 2007/0209083 A1 | 9/2007 | Thiam et al. |
| 2009/0053249 A1 | 2/2009 | Qi et al. |
| 2010/0166722 A1 | 7/2010 | Bennett et al. |
| 2017/0037369 A1 | 2/2017 | Ramsborg et al. |
| 2017/0291934 A1 | 10/2017 | Reed et al. |
| 2019/0038671 A1 | 2/2019 | Fan et al. |
| 2019/0062394 A1 | 2/2019 | Yarlagadda et al. |
| 2019/0127696 A1 | 5/2019 | Li |
| 2019/0151363 A1 | 5/2019 | Brentjens et al. |
| 2019/0194283 A1 | 6/2019 | Hauskins et al. |
| 2019/0209652 A1 | 7/2019 | Pierce et al. |
| 2019/0263928 A1 | 8/2019 | Watanabe et al. |
| 2020/0017568 A1 | 1/2020 | Chapuis et al. |
| 2020/0231649 A1 | 7/2020 | Bleakley et al. |
| 2021/0361705 A1* | 11/2021 | Arber Barth ...... C07K 14/7051 |
| 2023/0348548 A1 | 11/2023 | Justin et al. |
| 2023/0348561 A1 | 11/2023 | Farrar et al. |
| 2023/0355678 A1 | 11/2023 | Mehta et al. |

FOREIGN PATENT DOCUMENTS

| | | |
|---|---|---|
| JP | 7470640 B2 | 4/2024 |
| WO | 2002102852 A2 | 12/2002 |
| WO | 2017146767 A1 | 8/2017 |
| WO | 2018058002 A1 | 3/2018 |
| WO | 2018170338 A2 | 9/2018 |
| WO | 2019034703 A2 | 2/2019 |
| WO | 2019204662 A1 | 10/2019 |
| WO | 2020049496 A1 | 3/2020 |
| WO | 2020109616 A1 | 6/2020 |
| WO | 2023212655 A1 | 11/2023 |
| WO | 2023212691 A1 | 11/2023 |
| WO | 2023212697 A1 | 11/2023 |
| WO | 2023215825 A1 | 11/2023 |

OTHER PUBLICATIONS

Wong et al., "Stalk Region of Beta-Chain Enhances the Coreceptor Function of CD8," J Immunol, (2003), vol. 171: 867-874.

Anderson et al., "Enhanced Activity of Second-Generation MAGE-A4 SPEAR T-Cells Through Co-Expression of a CD8α Homodimer," American Association for Cancer Research Annual Meeting, Mar. 29-Apr. 3, 2019, Atlanta, Georgia, USA.

Kessels et al., "Generation of T Cell Help through a MHC Class I-Restricted TCR," J Immunol, (2006), vol. 177: 976-982.

Morris et al., "A critical role of T cell antigen receptor-transduced MHC class I-restricted helper T cells in tumor protection," PNAS, (2005), vol. 102, No. 22: 7934-7939.

Willemsen, et al., "Redirecting human CD4+ T lymphocytes to the MHC class I-restricted melanoma antigen MAGE-A1 by TCR (alpha beta) gene transfer requires CD8(alpha)," Gene Therapy, (2005), vol. 12: 140-146.

Petersen, CT, et al., "Improving T-cell expansion and function for adoptive T-cell therapy using ex vivo treatment With PI3Kd inhibitors and VIP antagonists", Blood Advances, vol. 2, No. 3, pp. 210-223, Feb. 13, 2018. doi: https://doi.org/10.1182/bloodadvances.2017011254.

GenBank: Synthetic construct FHVH33-CD8BBZ gene, complete cds; GenBank: MN366107.1; retrieved from https://www.ncbi.nlm.nih.gov/nucleotide/MN366107.1?report=genbank&log$=nuclalign&blast_rank=5&RID=WMXBDYEK016 Dec. 4, 2020.

GenBank: Synthetic construct Hu19-CD828Z gene, complete cds; GenBank: MN698642.1; retrieved from https://www.ncbi.nlm.nih.gov/nucleotide/MN698642.1?report=genbank&log$=nuclalign&blast_rank=1&RID=WMXBDYEK016 Dec. 4, 2020.

GenBank: Synthetic construct FMC63-CD828Z gene, complete cds; GenBank: MN702884.1; retrieved from https://www.ncbi.nlm.nih.gov/nucleotide/MN702884.1?report=genbank&log$=nuclalign&blast_rank=2&RID=WMXBDYEK016 Dec. 4, 2020.

GenBank: Synthetic construct IC9-Luc90-CD828Z gene, complete cds; GenBank: MW218436.1; retrieved from https://www.ncbi.nlm.nih.gov/nucleotide/MW218436.1?report=genbank&log$=nuclalign&blast_rank=7&RID=WMXBDYEK016 Dec. 4, 2020.

GenBank: Synthetic construct 11D5-3-CD8BBZ gene, complete cds; GenBank: MN366105.1; retrieved from https://www.ncbi.nlm.nih.gov/nucleotide/MN366105.1?report=genbank&log$=nuclalign&blast_rank=3&RID=WMXBDYEK016 Dec. 4, 2020.

GenBank: Synthetic construct FHVH33-CD828Z gene, complete cds; GenBank: MN366106.1; retrieved from https://www.ncbi.nlm.nih.gov/nucleotide/MN366106.1?report=genbank&log$=nuclalign&blast_rank=6&RID=WMXBDYEK016 Dec. 4, 2020.

GenPept T-cell surface glycoprotein CD8 alpha chain isoform 1 precursor [*Homo sapiens*]; NCBI Reference Sequence: NP_001139345.1; retrieved from https://www.ncbi.nlm.nih.gov/protein/NP_001139345.1?report=genbank&log$=protalign&blast_rank=1&RID=WN0MCYXS013 Dec. 4, 2020.

* cited by examiner

```
CD8α1   1    MALPVTALLLPLALLLHAARPSQFRVSPLDRTWNLGETVELKCQVLLSNPTSGCSWLFQP   60
             MALPVTALLLPLALLLHAARPSQFRVSPLDRTWNLGETVELKCQVLLSNPTSGCSWLFQP
mlCD8α  1    MALPVTALLLPLALLLHAARPSQFRVSPLDRTWNLGETVELKCQVLLSNPTSGCSWLFQP   60

CD8α1   61   RGAAASPTFLLYLSQNKPKAAEGLDTQRFSGKRLGDTFVLTLSDFRRENEGYYFCSALSN  120
             RGAAASPTFLLYLSQNKPKAAEGLDTQRFSGKRLGDTFVLTLSDFRRENEGYYFCSALSN
mlCD8α  61   RGAAASPTFLLYLSQNKPKAAEGLDTQRFSGKRLGDTFVLTLSDFRRENEGYYFCSALSN  120

CD8α1   121  SIMYFSHFVPVFLPAKPTT-TPAPRPPTPAPTIASQPLSL-RPEACRPAAGGAVHTRGLD  178
             SIMYFSHFVPVFLPA   P   PT   T+  +   L RPE            T+
mlCD8α  121  SIMYFSHFVPVFLPASVVDFLPTTAQPTKKSTLKKRVCRLPRPE------------TQKGP  169

CD8α1   179  FACDIYIWAPLAGTCGVLLLSLVITLYCNHRNRRRVCKCPRPVVKSGDKPSLSARYV     235
                  YIWAPLAGTCGVLLLSLVITLYCNHRNRRRVCKCPRPVVKSGDKPSLSARYV
mlCD8α  170  LCSPIYIWAPLAGTCGVLLLSLVITLYCNHRNRRRVCKCPRPVVKSGDKPSLSARYV     226
```

FIG. 2

```
CD8α2    1  MALPVTALLLPLALLLHAARPSQFRVSPLDRTWNLGETVELKCQVLLSNPTSGCSWLFQP   60
            MALPVTALLLPLALLLHAARPSQFRVSPLDRTWNLGETVELKCQVLLSNPTSGCSWLFQP
m2CD8α   1  MALPVTALLLPLALLLHAARPSQFRVSPLDRTWNLGETVELKCQVLLSNPTSGCSWLFQP   60
                                                                       ↓
CD8α2   61  RGAAASPTFLLYLSQNKPKAAEGLDTQRFSGKRLGDTFVLTLSDFRRENEGCYFCSALSN  120
            RGAAASPTFLLYLSQNKPKAAEGLDTQRFSGKRLGDTFVLTLSDFRRENEGCYFCSALSN
m2CD8α  61  RGAAASPTFLLYLSQNKPKAAEGLDTQRFSGKRLGDTFVLTLSDFRRENEGCYFCSALSN  120

CD8α2  121  SIMYFSHFVPVFLPA KPTT-TPAPRPPTPAPTIASQFLSL-RPEACRPAAGGAVHTRGLD  178
            SIMYFSHFVPVFLPA   P    PT    T+  +    L  RPE           T+
m2CD8α 121  SIMYFSHFVPVFLPA SVVDFLPTTAQPTKKSTLKKRVCRLPRPE-----------TQKGP  169

CD8α2  179  FACD YIWAPLAGTCGVLLLSLVITLYCNHRNRRRVCKCPRPVVKSGDKPSLSARYV     235
                 YIWAPLAGTCGVLLLSLVITLYCNHRNRRRVCKCPRPVVKSGDKPSLSARYV
m2CD8α 170  LCSP YIWAPLAGTCGVLLLSLVITLYCNHRNRRRVCKCPRPVVKSGDKPSLSARYV     226
```

FIG. 3

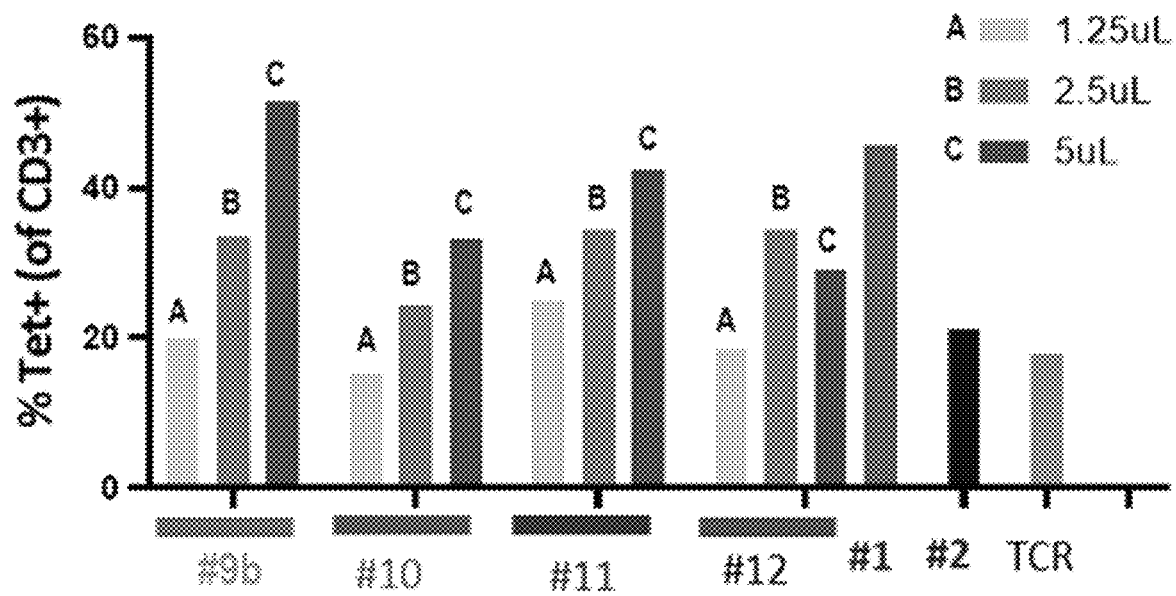
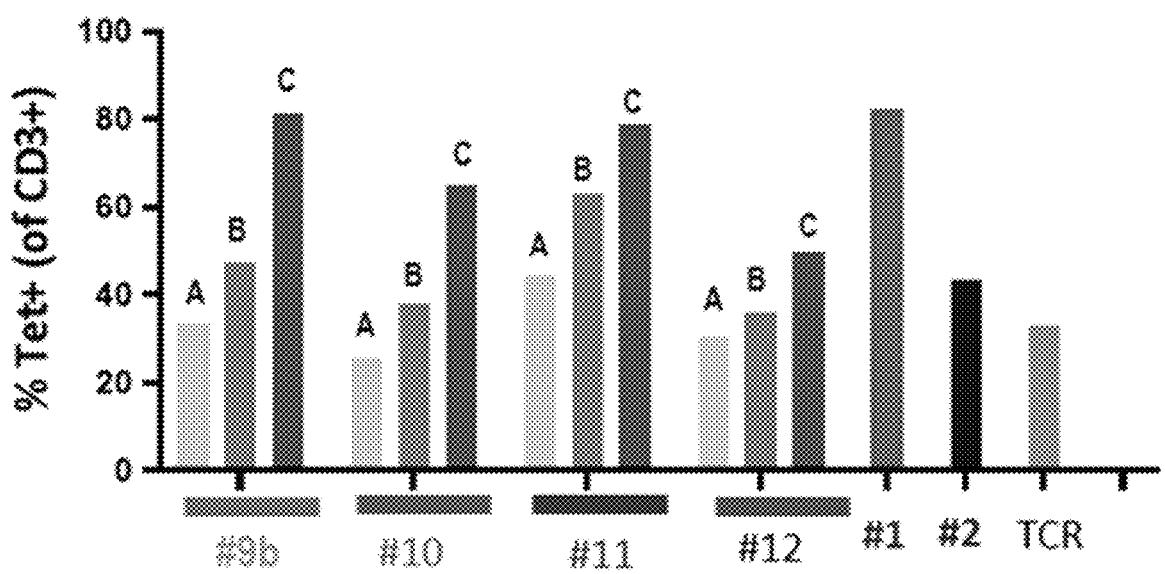
FIG. 18

Gated on CD4+CD8+

Gated on CD4-CD8+

Gated on CD3+TCR+

| CD4+ selected | CD8ba.TCR | CD8a+.TCR | TCR |
|---|---|---|---|
| Donor #1 | 0.51 | 10.6 | - |
| Donor #2 | 0.43 | 4.0 | - |
| Donor #3 | 1.21 | 60.0 | - |

FIG. 63D

CD8 POLYPEPTIDES, COMPOSITIONS, AND METHODS OF USING THEREOF

CROSS-REFERENCE TO RELATED APPLICATION

This application claims priority to U.S. Provisional Patent Application No. 63/132,824, filed Dec. 31, 2020, U.S. Provisional Patent Application No. 63/247,775, filed Sep. 23, 2021 and German Patent Application No. 10 2021 100 038.6, filed Jan. 4, 2021, the contents of which are incorporated herein by reference in their entirety.

REFERENCE TO SEQUENCE LISTING SUBMITTED ELECTRONICALLY

The official copy of the sequence listing is submitted concurrently via EFS-Web as an ASCII-formatted sequence listing with a file named "Sequence_Listing_3000011-022002_ST25" created on Dec. 28, 2021, and having a size of 514,618 bytes, and is filed concurrently with the specification. The sequence listing contained in this ASCII-formatted document is part of the specification and is herein incorporated by reference in its entirety.

BACKGROUND

Field

The present disclosure relates to T cells capable of co-expressing T cell receptors ("TCR") together with CD8 polypeptides and the use thereof in adoptive cellular therapy. The present disclosure further provides for modified CD8 sequences, vectors, compositions, transformed T cells, and associated methods thereof.

Background

CD8 and CD4 are transmembrane glycoproteins characteristic of distinct populations of T lymphocytes whose antigen responses are restricted by class I and class II MHC molecules, respectively. They play major roles both in the differentiation and selection of T cells during thymic development and in the activation of mature T lymphocytes in response to antigen presenting cells. Both CD8 and CD4 are immunoglobulin superfamily proteins. They determine antigen restriction by binding to MHC molecules at an interface distinct from the region presenting the antigenic peptide, but the structural basis for their similar functions appears to be very different. Their sequence similarity is low and, whereas CD4 is expressed on the cell surface as a monomer, CD8 is expressed as an αα homodimer (e.g., FIG. 55C) or an αβ heterodimer (e.g., FIG. 55A). In humans, this CD8αα homodimer may functionally substitute for the CD8αβ heterodimer. CD8 contacts an acidic loop in the αβ domain of Class I MHC, thereby increasing the avidity of the T cell for its target. CD8 is also involved in the phosphorylation events leading to CTL activation through the association of its α chain cytoplasmic tail with the tyrosine kinase p56$^{lck}$.

It is desirable to develop methods of manufacturing T cells with enhanced, specific cytotoxic activity for immunotherapy.

BRIEF SUMMARY

In an embodiment, CD8 polypeptides described herein may comprise a CD8α immunoglobulin (Ig)-like domain, a CD8β region, a CD8α transmembrane domain, and a CD8α cytoplasmic domain. In another embodiment, the CD8β region is a CD8β stalk region or domain.

In an embodiment, CD8 polypeptides described herein may comprise (a) an immunoglobulin (Ig)-like domain comprising at least about 80%, 85%, 90%, 91%, 92%, 93%, 94%, 95%, 96%, 97%, 98%, 99%, or 100% sequence identity to the amino acid sequence of SEQ ID NO: 1, (b) a CD8β region comprising at least about 80%, 85%, 90%, 91%, 92%, 93%, 94%, 95%, 96%, 97%, 98%, 99%, or 100% identity sequence identity to the amino acid sequence of SEQ ID NO: 2, (c) a transmembrane domain comprising at least about 80%, 85%, 90%, 91%, 92%, 93%, 94%, 95%, 96%, 97%, 98%, 99%, or 100% sequence identity to the amino acid sequence of SEQ ID NO: 3, and (d) a cytoplasmic domain comprising at least about 80%, 85%, 90%, 91%, 92%, 93%, 94%, 95%, 96%, 97%, 98%, 99%, or 100% sequence identity to the amino acid sequence of SEQ ID NO: 4.

In an embodiment, CD8 polypeptides described herein have at least about 80%, 85%, 90%, 91%, 92%, 93%, 94%, 95%, 96%, 97%, 98%, 99%, or 100% sequence identity to the amino acid sequence of SEQ ID NO: 5.

In an embodiment, CD8 polypeptides described herein have at least about 80%, 85%, 90%, 91%, 92%, 93%, 94%, 95%, 96%, 97%, 98%, 99%, or 100% sequence identity to the amino acid sequence of SEQ ID NO: 7.

In an embodiment, the CD8 polypeptides described herein may comprise a signal peptide with at least about 80%, 85%, 90%, 91%, 92%, 93%, 94%, 95%, 96%, 97%, 98%, 99%, or 100% sequence identity to the amino acid sequence of any one of SEQ ID NO: 6, SEQ ID NO: 293, or SEQ ID NO: 294 fused to the N-terminus or to the C-terminus of CD8 polypeptides described herein.

In an embodiment, CD8 polypeptides described herein may comprise (a) SEQ ID NO: 1 comprising one, two, three, four, or five amino acid substitutions; (b) SEQ ID NO: 2 comprising one, two, three, four, or five amino acid substitutions; (c) SEQ ID NO: 3 comprising one, two, three, four, or five amino acid substitutions, and (d) SEQ ID NO: 4 comprising one, two, three, four, or five amino acid substitutions.

In an embodiment, CD8 polypeptides described herein may be CD8α or modified CD8α polypeptides.

In an embodiment, the disclosure provides for nucleic acids encode polypeptides described herein.

In an embodiment, a vector may comprise a nucleic acid encoding CD8 polypeptides described herein.

In an embodiment, the vector may comprise a nucleic acid encoding T cell receptor (TCR) comprising an α chain and a β chain. In another embodiment, the vector may comprise a nucleic acid encoding a CAR-T.

In an embodiment, TCR α chain and TCR β chain may be selected from SEQ ID NO: 15 and 16; 17 and 18; 19 and 20; 21 and 22; 23 and 24; 25 and 26; 27 and 28; 29 and 30; 31 and 32; 33 and 34; 35 and 36; 37 and 38; 39 and 40; 41 and 42; 43 and 44; 45 and 46; 47 and 48; 49 and 50; 51 and 52; 53 and 54; 55 and 56; 57 and 58; 59 and 60; 61 and 62; 63 and 64; 65 and 66; 67 and 68; 69 and 70; 71 and 303; 304 and 74; 75 and 76; 77 and 78; 79 and 80; 81 and 82; 83 and 84; 85 and 86; 87 and 88; 89 and 90; and 91 and 92.

In an embodiment, the vector may comprise a nucleic acid encoding a CD8β polypeptide.

In an embodiment, CD8β polypeptide may comprise the amino acid sequence of any one of SEQ ID NO: 8, 9, 10, 11, 12, 13, or 14.

In an embodiment, the vector may comprise nucleic acid encoding a 2A peptide or an internal ribosome entry site (IRES) positioned between the nucleic acid encoding the modified CD8α polypeptide and the nucleic acid encoding a CD8β polypeptide.

In an embodiment, the vector may comprise nucleic acid encoding a 2A peptide positioned between the nucleic acid encoding a TCR α chain and the nucleic acid encoding a TCR β chain.

In an embodiment, the 2A peptide may be selected from P2A (SEQ ID NO: 93), T2A (SEQ ID NO: 94), E2A (SEQ ID NO: 95), or F2A (SEQ ID NO: 96).

In an embodiment, the IRES may be selected from the group consisting of IRES from picornavirus, IRES from flavivirus, IRES from pestivirus, IRES from retrovirus, IRES from lentivirus, IRES from insect RNA virus, and IRES from cellular mRNA.

In an embodiment, the vector may further comprise a post-transcriptional regulatory element (PRE) sequence selected from a Woodchuck PRE (WPRE) and variants thereof, a hepatitis B virus (HBV) PRE (HPRE), or a combination thereof.

In an embodiment, the vector may further comprise a promoter selected from cytomegalovirus (CMV) promoter, phosphoglycerate kinase (PGK) promoter, myelin basic protein (MBP) promoter, glial fibrillary acidic protein (GFAP) promoter, modified MoMuLV LTR comprising myeloproliferative sarcoma virus enhancer (MNDU3), Ubiqitin C promoter, EF-1 alpha promoter, Murine Stem Cell Virus (MSCV) promoter, or a combination thereof.

In an embodiment, the vector may be a viral vector or a non-viral vector.

In an embodiment, the vector may be selected from adenoviruses, poxviruses, alphaviruses, arenaviruses, flaviruses, rhabdoviruses, retroviruses, lentiviruses, herpesviruses, paramyxoviruses, picornaviruses, or a combination thereof.

In an embodiment, the vector may be pseudotyped with an envelope protein of a virus selected from the native feline endogenous virus (RD114), a chimeric version of RD114 (RD114TR), gibbon ape leukemia virus (GALV), a chimeric version of GALV (GALV-TR), amphotropic murine leukemia virus (MLV 4070A), baculovirus (GP64), vesicular stomatitis virus (VSV-G), fowl plague virus (FPV), Ebola virus (EboV), or baboon retroviral envelope glycoprotein (BaEV), lymphocytic choriomeningitis virus (LCMV), or a combination thereof.

In an embodiment, the vector may further comprise a nucleic acid encoding a T cell receptor (TCR).

In another embodiment, the vector may further comprise a nucleic acid encoding a chimeric antigen receptor (CAR).

In an embodiment, an isolated nucleic acid may comprise a nucleic acid sequence encoding a T-cell receptor comprising an α chain and a β chain and a CD8 polypeptide comprising an α chain and a β chain. The isolated nucleic acid may comprise a nucleic acid at least 80% identical to the nucleic acid sequence of SEQ ID NO: 267, 269, 271, 273, 275, 277, 279, 281, 283, 285, 287, 289, 291, 295, 297, 299, or 301. The isolated nucleic acid may be at least 90%, 91%, 92%, 93%, 94%, 95%, 96%, 97%, 98%, 99%, or 100% identical to the nucleic acid sequence of SEQ ID NO: 267, 269, 271, 273, 275, 277, 279, 281, 283, 285, 287, 289, 291, 295, 297, 299, or 301. In an aspect, sequences described herein may be isolated or recombinant sequences.

In an embodiment, the isolated nucleic acid comprises the nucleic acid sequence of SEQ ID NO: 267.

In an embodiment, the isolated nucleic acid comprises the nucleic acid sequence of SEQ ID NO: 279.

In an embodiment, the isolated polypeptide(s) may be encoded by the nucleic acids described herein.

In an embodiment, the isolated polypeptide may comprise the amino acid sequence at least about 80% identical to the amino acid sequence of SEQ ID NO: 268, 270, 272, 274, 276, 278, 280, 282, 284, 286, 288, 290, 292, 296, 298, 300, or 302. The amino acid sequence may be at least 90%, 91%, 92%, 93%, 94%, 95%, 96%, 97%, 98%, 99%, or 100% identical to the amino acid sequence of SEQ ID NO: 268, 270, 272, 274, 276, 278, 280, 282, 284, 286, 288, 290, 292, 296, 298, 300, or 302. In another aspect, SEQ ID NO: 268, 270, 272, 274, 276, 278, 280, 282, 284, 286, 288, 290, 292, 296, 298, 300, or 302 comprise 1, 2, 3, 4, 5, 10, 15, or 20 or more amino acid substitutions or deletions. In yet another aspect, SEQ ID NO: 268, 270, 272, 274, 276, 278, 280, 282, 284, 286, 288, 290, 292, 296, 298, 300, or 302 comprise at most 1, 2, 3, 4, 5, 10, 15, or 20 amino acid substitutions or deletions.

In an embodiment, the isolated polypeptide may comprise the amino acid sequence of SEQ ID NO: 268.

In an embodiment, the isolated polypeptide may comprise the amino acid sequence of SEQ ID NO: 280. In an embodiment, a cell may be transduced with the vector.

In an embodiment, the cell may comprise αβ T cell, γδ T cell, natural killer cell, CD4+/CD8+ cell, or combinations thereof.

In an embodiment, αβ T cell may comprise CD4+ T cell and CD8+ T cell.

In an embodiment, a method of preparing T cells for immunotherapy may comprise isolating T cells from a blood sample of a human subject, activating the isolated T cells, transducing the activated T cells with the vector, and expanding the transduced T cells.

In an embodiment, the T cell may be CD4+ T cell.

In an embodiment, the T cell may be CD8+ T cell.

In an embodiment, the T cell may be γδ T cell.

In an embodiment, the T cells may be a αβ T cell and express a CD8 polypeptide described herein.

In an embodiment, the T cells may be a γδ T cell and express a modified CD8 polypeptide described herein, for example, a modified CD8α polypeptide or a modified CD8α polypeptide with a CD8β stalk region, e.g., m1CD8α in Constructs #11 and #12 (FIG. 4) and CD8α* (FIG. 55B).

In an embodiment, a method of treating a patient who has cancer may comprise administering to the patient a composition comprising the population of expanded T cells, wherein the T cells kill cancer cells that present a peptide in a complex with an MHC molecule on the surface, wherein the peptide is selected from SEQ ID NO: 98-255, wherein the cancer is selected from the group consisting of non-small cell lung cancer, small cell lung cancer, melanoma, liver cancer, breast cancer, uterine cancer, Merkel cell carcinoma, pancreatic cancer, gallbladder cancer, bile duct cancer, colorectal cancer, urinary bladder cancer, kidney cancer, leukemia, ovarian cancer, esophageal cancer, brain cancer, gastric cancer, prostate cancer, or a combination thereof.

In an embodiment, the composition may further comprise an adjuvant.

In an embodiment, the adjuvant may be selected from anti-CD40 antibody, imiquimod, resiquimod, GM-CSF, cyclophosphamide, sunitinib, bevacizumab, atezolizumab, interferon-alpha, interferon-beta, CpG oligonucleotides and derivatives, poly(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, IL-23, or combinations thereof.

In an embodiment, a method of eliciting an immune response in a patient who has cancer may comprise administering to the patient a composition comprising the population of expanded T cells, wherein the T cells kill cancer cells that present a peptide in a complex with an MHC molecule on the surface, wherein the peptide is selected from SEQ ID NO: 98-255, wherein the cancer is selected from the group consisting of non-small cell lung cancer, small cell lung cancer, melanoma, liver cancer, breast cancer, uterine cancer, Merkel cell carcinoma, pancreatic cancer, gallbladder cancer, bile duct cancer, colorectal cancer, urinary bladder cancer, kidney cancer, leukemia, ovarian cancer, esophageal cancer, brain cancer, gastric cancer, prostate cancer, or a combination thereof.

The disclosure further provides for a population of modified T cells that present an exogenous CD8 co-receptor comprising a polypeptide described herein, for example, amino acid sequences at least 80%, at least 85%, at least 90%, or at least 95%, at least 99%, or 100% to SEQ ID NO: 5, 7, 258, 259, 8, 9, 10, 11, 12, 13, or 14 and a T cell receptor.

BRIEF DESCRIPTION OF THE DRAWINGS

FIG. 2 shows a sequence alignment between CD8α1 (SEQ ID NO: 258) and m1CD8α (SEQ ID NO: 7).

FIG. 3 shows a sequence alignment between CD8α2 (SEQ ID NO: 259) and m2CD8α (SEQ ID NO: 262), in which the cysteine substitution at position 112 is indicated by an arrow.

FIG. 18 shows % Tet+(of CD3+) of cells transduced with various constructs. The constructs are as follows: Construct #9b; Construct #10; Construct #11; Construct #12; Construct #1; Construct #2; TCR=R11KEA.WPRE$^{wt}$ (TCR with wild type WPRE); NT=Non-transduced T cells (as a negative control).

FIG. 63D shows EC50 values (ng/ml) in FIG. 63A-63C.

DETAILED DESCRIPTION

Modified CD8 Polypeptides

Figure 1:
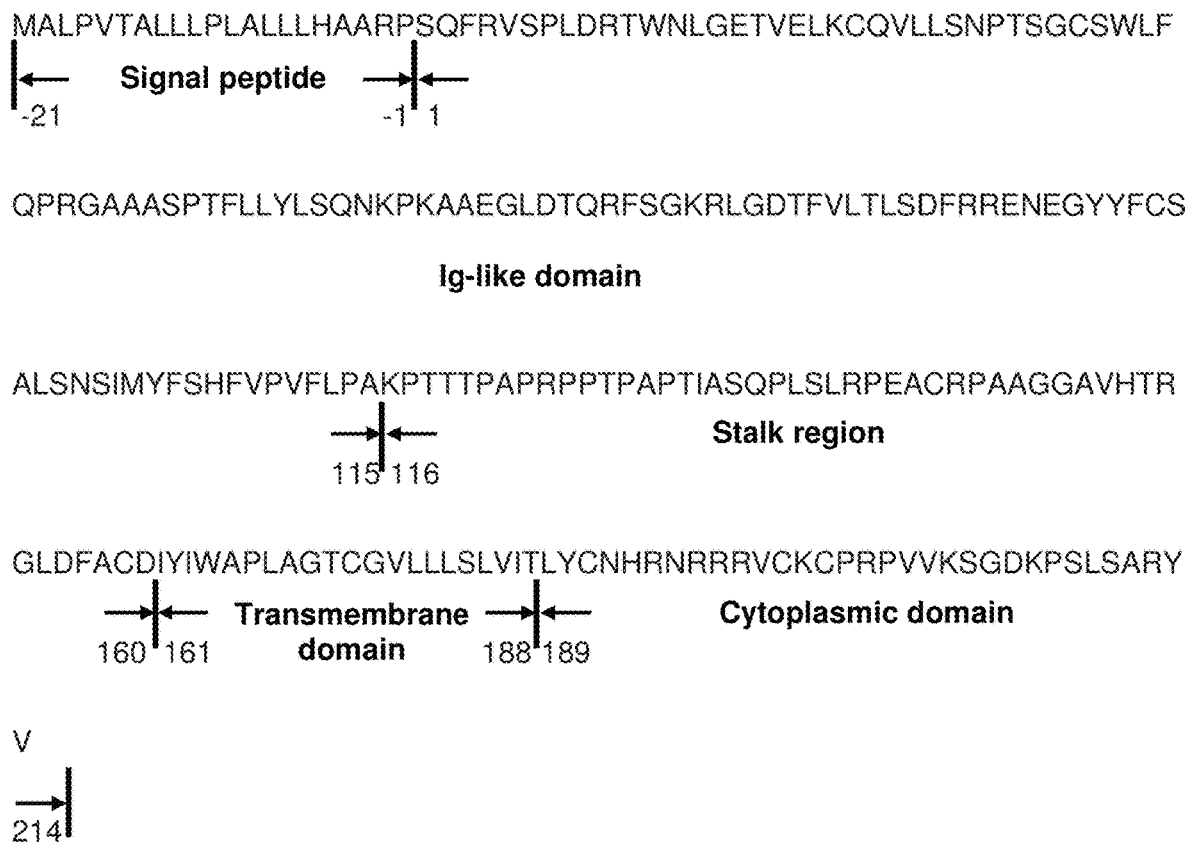
FIG. 1 shows a representative CD8α subunit, e.g., SEQ ID NO: 258 (CD8α1). In this embodiment, CD8α1 includes five domains: (1) signal peptide, (2) Ig-like domain-1, (3) a stalk region, (4) transmembrane (TM) domain, and (5) a cytoplasmic tail (Cyto) comprising a lck-binding motif.

CD8 polypeptides described herein may comprise the general structure of a N-terminal signal peptide (optional), CD8α immunoglobulin (Ig)-like domain, CD8☐ region (domain), CD8α transmembrane domain, and a CD8α cytoplasmic domain. The modified CD8 polypeptides described herein shown an unexpected improvement in functionality of T cells co-transduced with a vector expressing a TCR and CD8 polypeptide.

CD8 polypeptides described herein may comprise the general structure of a N-terminal signal peptide (optional), CD8α immunoglobulin (Ig)-like domain, a stalk domain or region, CD8α transmembrane domain, and a CD8α cytoplasmic domain.

In an embodiment, CD8 polypeptides described herein may comprise (a) an immunoglobulin (Ig)-like domain comprising at least about 80%, at least 85%, at least 90%, at least 95%, at least 98%, at least 99%, or 100% sequence identity to the amino acid sequence of SEQ ID NO: 1; (b) a region comprising at least about 80%, at least 85%, at least 90%, at least 95%, at least 98%, at least 99%, or 100% sequence identity to the amino acid sequence of SEQ ID NO: 2; (c) a transmembrane domain comprising at least about 80%, at least 85%, at least 90%, at least 95%, at least 98%, at least 99%, or 100% sequence identity to the amino acid sequence of SEQ ID NO: 3, and (d) a cytoplasmic domain comprising at least about 80%, at least 85%, at least 90%, at least 95%, at least 98%, at least 99%, or 100% sequence identity to the amino acid sequence of SEQ ID NO: 4. The CD8 polypeptides described herein may be co-expressed with a T-cell receptor or CAR-T in a T-cell and used in methods of adoptive cell therapy (ACT). The T-cell may be an αβ T-cell or a γδ T-cell.

In another embodiment, CD8 polypeptides described herein may comprise (a) at least about 80%, at least 85%, at least 90%, at least 95%, at least 98%, at least 99%, or 100% sequence identity to the amino acid sequence of SEQ ID NO: 1; (b) at least about 80%, at least 85%, at least 90%, at least 95%, at least 98%, at least 99%, or 100% sequence identity to the amino acid sequence of SEQ ID NO: 2; (c) at least about 80%, at least 85%, at least 90%, at least 95%, at least 98%, at least 99%, or 100% sequence identity to the amino acid sequence of SEQ ID NO: 3, and (d) a at least about 80%, at least 85%, at least 90%, at least 95%, at least 98%, at least 99%, or 100% sequence identity to the amino acid sequence of SEQ ID NO: 4. The CD8 polypeptides described herein may be co-expressed with a T-cell receptor or CAR-T in a T-cell and used in methods of adoptive cell therapy (ACT). The T-cell may be an αβ T-cell or a γδ T-cell.

In another embodiment, CD8 polypeptides described herein may comprise (a) SEQ ID NO: 1 comprising one, two, three, four, or five amino acid substitutions; (b) SEQ ID NO: 2 comprising one, two, three, four, or five amino acid substitutions; (c) SEQ ID NO: 3 comprising one, two, three, four, or five amino acid substitutions, and (d) SEQ ID NO: 4 comprising one, two, three, four, or five amino acid substitutions. In an embodiment, the substitutions are conservative amino acid substitutions. The CD8 polypeptides described herein may be co-expressed with a T-cell receptor or CAR-T in a T-cell and used in methods of adoptive cell therapy (ACT). The T-cell may be an γδ T-cell or a γδ T-cell.

CD8 is a membrane-anchored glycoprotein that functions as a coreceptor for antigen recognition of the peptide/MHC class I complexes by T cell receptors (TCR) and plays an important role in T cell development in the thymus and T cell activation in the periphery. Functional CD8 is a dimeric protein made of either two α chains (CD8αα) or an α chain and a β chain (CD8αβ), and the surface expression of the β chain may require its association with the coexpressed α chain to form the CD8αβ heterodimer. CD8αα and CD8αβ may be differentially expressed on a variety of lymphocytes. CD8αβ is expressed predominantly on the surface of αβTCR+ T cells and thymocytes, and CD8αα on a subset of αβTCR+, γδTCR+ intestinal intraepithelial lymphocytes, NK cells, dendritic cells, and a small fraction of CD4+ T cells.

For example, human CD8 gene may express a protein of 235 amino acids. FIG. 1 shows a CD8α protein (CD8α1—SEQ ID NO: 258), which in an aspect is divided into the following domains (starting at the amino terminal and ending at the carboxy terminal of the polypeptide): (1) signal peptide (amino acids -21 to -1), which may be cleaved off in human cells during the transport of the receptor to the cell surface and thus may not constitute part of the mature, active receptor; (2) immunoglobulin (Ig)-like domain (in this embodiment, amino acids 1-115), which may assume a structure, referred to as the immunoglobulin fold, which is similar to those of many other molecules involved in regulating the immune system, the immunoglobulin family of proteins. The crystal structure of the CD8αα receptor in complex with the human MHC molecule HLA-A2 has demonstrated how the Ig domain of CD8αα receptor binds the ligand; (3) membrane proximal region (in this embodiment, amino acids 116-160), which may be an extended linker region allowing the CD8αα receptor to "reach" from the surface of the T-cell over the top of the MHC to the a3 domain of the MHC where it binds. The stalk region may be glycosylated and may be inflexible; (4) transmembrane domain (in this embodiment, amino acids 161-188), which may anchor the CD8αα receptor in the cell membrane and is therefore not part of the soluble recombinant protein; and (5) cytoplasmic domain (in this embodiment, amino acids 189-214), which can mediate a signaling function in T-cells through its association with p56$^{lck}$ which may be involved in the T cell activation cascade of phosphorylation events.

CD8α sequences may generally have a sufficient portion of the immunoglobulin domain to be able to bind to MHC. Generally, CD8α molecules may contain all or a substantial part of immunoglobulin domain of CD8α, e.g., SEQ ID NO: 258, but in an aspect may contain at least 10, 15, 20, 25, 30, 35, 40, 45, 50, 55, 60, 65, 70, 75, 80, 85, 90, 95, 100, 105, 110 or 115 amino acids of the immunoglobulin domain. The CD8α molecules of the present disclosure may be preferably dimers (e.g., CD8αα or CD8αβ), although CD8α monomer may be included within the scope of the present disclosure. In an aspect, CD8α of the present disclosure may comprise CD8α1 (SEQ ID NO: 258) and CD8α2 (SEQ ID NO: 259).

CD8α and β subunits may have similar structural motifs, including an Ig-like domain, a stalk region of 30-40 amino acids, a transmembrane region, and a short cytoplasmic domain of about 20 amino acids. CD8α and β chains have two and one N-linked glycosylation sites, respectively, in the Ig-like domains where they share <20% identity in their amino acid sequences. The CD8β stalk region is 10-13 amino acids shorter than the CD8α stalk and is highly glycosylated with O-linked carbohydrates. These carbohydrates on the β, but not the α, stalk region appear to be quite heterogeneous due to complex sialylations, which may be differentially regulated during the developmental stages of thymocytes and upon activation of T cells. Glycan adducts have been shown to play regulatory roles in the functions of glycoproteins and in immune responses. Glycans proximal to transmembrane domains can affect the orientation of adjacent motifs. The unique biochemical properties of the CD8β chain stalk region may present a plausible candidate for modulating the coreceptor function.

The CD8 polypeptide may be modified, in which CD8α region, for example a stalk region, may be replaced by CD8β region. In another aspect, to create a CD8☐-CD8☐ polypeptide. In an embodiment, the modified CD8 polypeptides described herein may have a region comprising at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 2. The modified CD8α polypeptides described herein may have an immunoglobulin (Ig)-like domain having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 1. Modified CD8 polypeptides may have a transmembrane domain comprising at least at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 3. Modified CD8 polypeptides described herein may have a cytoplasmic tail comprising at least at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 4. The CD8 polypeptides described herein may have at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 5. The CD8 polypeptides described herein may comprise a signal peptide comprising at least 80%, at least 85%, at least 90%, at least 95%, at least 99%, or 100% sequence identity to the amino acid sequence of SEQ ID NO: 6 or SEQ ID NO: 294 fused to the N-terminus or fused to the C-terminus of mCD8α polypeptide. The CD8 polypeptides described herein may have at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 7.

T-Cells

T-cells may express the modified CD8 polypeptides described herein. For example, a T-cell may co-express a T-cell Receptor (TCR) and modified CD8 polypeptides described herein. T-cells may also express a chimeric antigen receptor (CAR), CAR-analogues, or CAR derivatives.

The T-cell may be a αβ T cell, γδ T cell, natural killer T cell, or a combination thereof if in a population. The T cell may be a CD4+ T cell, CD8+ T cell, or a CD4+/CD8+ T cell.

T-cell Receptors

A T-cell may co-express a T-cell receptor (TCR), antigen binding protein, or both, with modified CD8 polypeptides described herein, including, but are not limited to, those listed in Table 3 (SEQ ID NOs: 15-92). Further, a T-cell may express a TCRs and antigen binding proteins described in U.S. Patent Application Publication No. 2017/0267738; U.S. Patent Application Publication No. 2017/0312350; U.S. Patent Application Publication No. 2018/0051080; U.S. Patent Application Publication No. 2018/0164315; U.S. Patent Application Publication No. 2018/0161396; U.S. Patent Application Publication No. 2018/0162922; U.S. Patent Application Publication No. 2018/0273602; U.S.

Patent Application Publication No. 2019/0016801; U.S. Patent Application Publication No. 2019/0002556; U.S. Patent Application Publication No. 2019/0135914; U.S. Pat. Nos. 10,538,573; 10,626,160; U.S. Patent Application Publication No. 2019/0321478; U.S. Patent Application Publication No. 2019/0256572; U.S. Pat. Nos. 10,550,182; 10,526,407; U.S. Patent Application Publication No. 2019/0284276; U.S. Patent Application Publication No. 2019/0016802; U.S. Patent Application Publication No. 2019/0016803; U.S. Patent Application Publication No. 2019/0016804; U.S. Pat. No. 10,583,573; U.S. Patent Application Publication No. 2020/0339652; U.S. Pat. Nos. 10,537,624; 10,596,242; U.S. Patent Application Publication No. 2020/0188497; U.S. Pat. No. 10,800,845; U.S. Patent Application Publication No. 2020/0385468; U.S. Pat. Nos. 10,527,623; 10,725,044; U.S. Patent Application Publication No. 2020/0249233; U.S. Pat. No. 10,702,609; U.S. Patent Application Publication No. 2020/0254106; U.S. Pat. No. 10,800,832; U.S. Patent Application Publication No. 2020/0123221; U.S. Pat. Nos. 10,590,194; 10,723,796; U.S. Patent Application Publication No. 2020/0140540; U.S. Pat. No. 10,618,956; U.S. Patent Application Publication No. 2020/0207849; U.S. Patent Application Publication No. 2020/0088726; and U.S. Patent Application Publication No. 2020/0384028; the contents of each of these publications and sequence listings described therein are herein incorporated by reference in their entireties. The T-cell may be a αβ T cell, γδ T cell, natural killer T cell. Natural killer cell. In an embodiment, TCRs described herein are single-chain TCRs or soluble TCRs.

Further, the TCRs that may be co-expressed with the modified CD8 polypeptides described herein in a T-cell may be TCRs comprised of an alpha chain (TCR☐) and a beta chain (TCR☐). The TCRα chains and TCRβ chains that may be used in TCRs may be selected from R11KEA (SEQ ID NO: 15 and 16), R20P1H7 (SEQ ID NO: 17 and 18), R7P1D5 (SEQ ID NO: 19 and 20), R10P2G12 (SEQ ID NO: 21 and 22), R10P1A7 (SEQ ID NO: 23 and 24), R4P1D10 (SEQ ID NO: 25 and 26), R4P3F9 (SEQ ID NO: 27 and 28), R4P3H3 (SEQ ID NO: 29 and 30), R36P3F9 (SEQ ID NO: 31 and 32), R52P2G11 (SEQ ID NO: 33 and 34), R53P2A9 (SEQ ID NO: 35 and 36), R26P1A9 (SEQ ID NO: 37 and 38), R26P2A6 (SEQ ID NO: 39 and 40), R26P3H1 (SEQ ID NO: 41 and 42), R35P3A4 (SEQ ID NO: 43 and 44), R37P1C9 (SEQ ID NO: 45 and 46), R37P1H1 (SEQ ID NO: 47 and 48), R42P3A9 (SEQ ID NO: 49 and 50), R43P3F2 (SEQ ID NO: 51 and 52), R43P3G5 (SEQ ID NO: 53 and 54), R59P2E7 (SEQ ID NO: 55 and 56), R11P3D3 (SEQ ID NO: 57 and 58), R16P1C10 (SEQ ID NO: 59 and 60), R16P1E8 (SEQ ID NO: 61 and 62), R17P1A9 (SEQ ID NO: 63 and 64), R17P1D7 (SEQ ID NO: 65 and 66), R17P1G3 (SEQ ID NO: 67 and 68), R17P2B6 (SEQ ID NO: 69 and 70), R11P3D3KE (SEQ ID NO: 71 and 303), R39P1C12 (SEQ ID NO: 304 and 74), R39P1F5 (SEQ ID NO: 75 and 76), R40P1C2 (SEQ ID NO: 77 and 78), R41P3E6 (SEQ ID NO: 79 and 80), R43P3G4 (SEQ ID NO: 81 and 82), R44P3B3 (SEQ ID NO: 83 and 84), R44P3E7 (SEQ ID NO: 85 and 86), R49P2B7 (SEQ ID NO: 87 and 88), R55P1G7 (SEQ ID NO: 89 and 90), or R59P2A7 (SEQ ID NO: 91 and 92). The T-cell may be a αβ T cell, γδ T cell, or a natural killer T cell.

Table 1 shows examples of the peptides to which TCRs bind when the peptide is in a complex with an MHC molecule. (MHC molecules in humans may be referred to as HLA, human leukocyte-antigens).

TABLE 1

T-Cell Receptor and Peptides

| TCR name | Peptide (SEQ ID NO:) |
|---|---|
| R20P1H7, R7P1D5, R10P2G12 | KVLEHVVRV (SEQ ID NO: 215) |
| R10P1A7 | KIQEILTQV (SEQ ID NO: 123) |
| R4P1D10, R4P3F9, R4P3H3 | FLLDGSANV (SEQ ID NO: 238) |
| R36P3F9, R52P2G11, R53P2A9 | ILQDGQFLV (SEQ ID NO: 193) |
| R26P1A9, R26P2A6, R26P3H1, R35P3A4, R37P1C9, R37P1H1, R42P3A9, R43P3F2, R43P3G5, R59P2E7 | KVLEYVIKV (SEQ ID NO: 202) |
| R11KEA, R11P3D3, R16P1C10, R16P1E8, R17P1A9, R17P1D7, R17P1G3, R17P2B6, R11P3D3KE | SLLQHLIGL (SEQ ID NO: 147) |
| R39P1C12, R39P1F5, R40P1C2, R41P3E6, R43P3G4, R44P3B3, R44P3E7, R49P2B7, R55P1G7, R59P2A7 | ALSVLRLAL (SEQ ID NO: 248) |

Tumor Associated Antigens (TAA)

Tumor associated antigen (TAA) peptides may be used with the CD8 polypeptides constructs, methods and embodiments described herein. For example, the T-cell receptors (TCRs) described herein may specifically bind to the TAA peptide when bound to a human leukocyte antigen (HLA). This is also known as a major histocompatibility complex (MHC) molecule. The MHC-molecules of the human are also designated as human leukocyte-antigens (HLA).

Tumor associated antigen (TAA) peptides that may be used with the CD8 polypeptides described herein include, but are not limited to, those listed in Table 3 and those TAA peptides described in U.S. Patent Application Publication No. 2016/0187351; U.S. Patent Application Publication No. 2017/0165335; U.S. Patent Application Publication No. 2017/0035807; U.S. Patent Application Publication No. 2016/0280759; U.S. Patent Application Publication No. 2016/0287687; U.S. Patent Application Publication No. 2016/0346371; U.S. Patent Application Publication No. 2016/0368965; U.S. Patent Application Publication No. 2017/0022251; U.S. Patent Application Publication No.

2017/0002055; U.S. Patent Application Publication No. 2017/0029486; U.S. Patent Application Publication No. 2017/0037089; U.S. Patent Application Publication No. 2017/0136108; U.S. Patent Application Publication No. 2017/0101473; U.S. Patent Application Publication No. 2017/0096461; U.S. Patent Application Publication No. 2017/0165337; U.S. Patent Application Publication No. 2017/0189505; U.S. Patent Application Publication No. 2017/0173132; U.S. Patent Application Publication No. 2017/0296640; U.S. Patent Application Publication No. 2017/0253633; U.S. Patent Application Publication No. 2017/0260249; U.S. Patent Application Publication No. 2018/0051080; U.S. Patent Application Publication No. 2018/0164315; U.S. Patent Application Publication No. 2018/0291082; U.S. Patent Application Publication No. 2018/0291083; U.S. Patent Application Publication No. 2019/0255110; U.S. Pat. Nos. 9,717,774; 9,895,415; U.S. Patent Application Publication No. 2019/0247433; U.S. Patent Application Publication No. 2019/0292520; U.S. Patent Application Publication No. 2020/0085930; U.S. Pat. Nos. 10,336,809; 10,131,703; 10,081,664; 10,081,664; 10,093,715; 10,583,573; and U.S. Patent Application Publication No. 2020/00085930; the contents of each of these publications, sequences, and sequence listings described therein are herein incorporated by reference in their entireties. The Tumor associated antigen (TAA) peptides described herein may be bound to an HLA (MHC molecule). The Tumor associated antigen (TAA) peptides bound to an HLA may be recognized by a TCR described herein, optionally co-expressed with CD8 polypeptides described herein.

T cells may be engineered to express a chimeric antigen receptor (CAR) comprising a ligand binding domain derived from NKG2D, NKG2A, NKG2C, NKG2F, LLT1, AICL, CD26, NKRP1, NKp30, NKp44, NKp46, CD244 (2B4), DNAM-1, and NKp80, or an anti-tumor antibody such as anti-Her2neu or anti-EGFR and a signaling domain obtained from CD3-ζ, Dap 10, CD28, 4-1BB, and CD40L. In some examples, the chimeric receptor binds MICA, MICB, Her2neu, EGFR, mesothelin, CD38, CD20, CD 19, PSA, RON, CD30, CD22, CD37, CD38, CD56, CD33, CD30, CD138, CD123, CD79b, CD70, CD75, CA6, GD2, alpha-fetoprotein (AFP), carcinoembryonic antigen (CEA), CEACAM5, CA-125, MUC-16, 5T4, NaPi2b, ROR1, ROR2, 5T4, PLIF, Her2/Neu, EGFRvIII, GPMNB, LIV-1, glycolipidF77, fibroblast activating protein, PSMA, STEAP-1, STEAP-2, c-met, CSPG4, Nectin-4, VEGFR2, PSCA, folate binding protein/receptor, SLC44A4, Cripto, CTAG1B, AXL, IL-13R, IL-3R, SLTRK6, gp100, MART1, Tyrosinase, SSX2, SSX4, NYESO-1, epithelial tumor antigen (ETA), MAGEA family genes (such as MAGE3A, MAGE4A), KKLC1, mutated ras, Praf, p53, MHC class I chain-related molecule A (MICA), or MHC class I chain-related molecule B (MICB), HPV, or CMV. The T-cell may be a αβ T cell, γδ T cell, or a natural killer T cell.

Culturing T-Cells

Methods for the activation, transduction, and/or expansion of T cells, e.g., tumor-infiltrating lymphocytes, CD8+ T cells, CD4+ T cells, and T cells, that may be used for transgene expression are described herein. T cells may be activated, transduced, and expanded, while depleting α- and/or β-TCR positive cells. The T-cell may be a αβ T cell, γδ T cell, or a natural killer T cell.

Methods for the ex vivo expansion of a population of engineered γδ T-cells for adoptive transfer therapy are described herein. Engineered γδ T cells of the disclosure may be expanded ex vivo. Engineered T cells described herein can be expanded in vitro without activation by APCs, or without co-culture with APCs, and aminophosphates. Methods for transducing T cells are described in U.S. Patent Application No. Patent Application No. 2019/0175650, published on Jun. 13, 2019, the contents of which are incorporated by reference in their entirety. Other methods for transduction and culturing of T-cells may be used.

T cells, including γδ T cells, may be isolated from a complex sample that is cultured in vitro. In an embodiment, whole PBMC population, without prior depletion of specific cell populations, such as monocytes, αβ T-cells, B-cells, and NK cells, can be activated and expanded. In an embodiment, enriched T cell populations can be generated prior to their specific activation and expansion. In an embodiment, activation and expansion of γδ T cells may be performed with or without the presence of native or engineered antigen presenting cells (APCs). In an embodiments, isolation and expansion of T cells from tumor specimens can be performed using immobilized T cell mitogens, including antibodies specific to γδ TCR, and other γδ TCR activating agents, including lectins. In an embodiment, isolation and expansion of γδ T cells from tumor specimens can be performed in the absence of γδ T cell mitogens, including antibodies specific to γδ TCR, and other γδ TCR activating agents, including lectins.

T cells, including γδ T cells, may be isolated from leukapheresis of a subject, for example, a human subject. In an embodiment, γδ T cells are not isolated from peripheral blood mononuclear cells (PBMC). The T cells may be isolated using anti-CD3 and anti-CD28 antibodies, optionally with recombinant human Interleukin-2 (rhIL-2), e.g., between about 50 and 150 U/mL rhIL-2.

The isolated T cells can rapidly expand in response to contact with one or more antigens. Some γδ T cells, such as Vγ9Vδ2+ T cells, can rapidly expand in vitro in response to contact with some antigens, like prenyl-pyrophosphates, alkyl amines, and metabolites or microbial extracts during tissue culture. Stimulated T-cells can exhibit numerous antigen-presentation, co-stimulation, and adhesion molecules that can facilitate the isolation of T-cells from a complex sample. T cells within a complex sample can be stimulated in vitro with at least one antigen for 1 day, 2 days, 3 days, 4 days, 5 days, 6 days, 7 days, or another suitable period of time. Stimulation of T cells with a suitable antigen can expand T cell population in vitro.

Activation and expansion of γδ T cells can be performed using activation and co-stimulatory agents described herein to trigger specific γδ T cell proliferation and persistence populations. In an embodiment, activation and expansion of γδ T-cells from different cultures can achieve distinct clonal or mixed polyclonal population subsets. In an embodiment, different agonist agents can be used to identify agents that provide specific γδ activating signals. In an embodiment, agents that provide specific γδ activating signals can be different monoclonal antibodies (MAbs) directed against the γδ TCRs. In an embodiment, companion co-stimulatory agents to assist in triggering specific γδ T cell proliferation without induction of cell energy and apoptosis can be used. These co-stimulatory agents can include ligands binding to receptors expressed on γδ cells, such as NKG2D, CD161, CD70, JAML, DNAX accessory molecule-1 (DNAM-1), ICOS, CD27, CD137, CD30, HVEM, SLAM, CD122, DAP, and CD28. In an embodiment, co-stimulatory agents can be antibodies specific to unique epitopes on CD2 and CD3 molecules. CD2 and CD3 can have different conformation structures when expressed on αβ or γδ T-cells. In an embodiment, specific antibodies to CD3 and CD2 can lead to distinct activation of γδ T cells.

Non-limiting examples of antigens that may be used to stimulate the expansion of T cells, including γδ T cells, from a complex sample in vitro may comprise, prenyl-pyrophosphates, such as isopentenyl pyrophosphate (IPP), alkylamines, metabolites of human microbial pathogens, metabolites of commensal bacteria, methyl-3-butenyl-1-pyrophosphate (2M3B1PP), (E)-4-hydroxy-3-methyl-but-2-enyl pyrophosphate (HMB-PP), ethyl pyrophosphate (EPP), farnesyl pyrophosphate (FPP), dimethylallyl phosphate (DMAP), dimethylallyl pyrophosphate (DMAPP), ethyl-adenosine triphosphate (EPPPA), geranyl pyrophosphate (GPP), geranylgeranyl pyrophosphate (GGPP), isopentenyl-adenosine triphosphate (IPPPA), monoethyl phosphate (MEP), monoethyl pyrophosphate (MEPP), 3-formyl-1-butyl-pyrophosphate (TUBAg 1), X-pyrophosphate (TUBAg 2), 3-formyl-1-butyl-uridine triphosphate (TUBAg 3), 3-formyl-1-butyl-deoxythymidine triphosphate (TUBAg 4), monoethyl alkylamines, allyl pyrophosphate, crotoyl pyrophosphate, dimethylallyl-7-uridine triphosphate, crotoyl-7-uridine triphosphate, allyl-7-uridine triphosphate, ethylamine, isobutylamine, sec-butylamine, iso-amylamine and nitrogen containing bisphosphonates.

A population of T-cells, including γδ T cells, may be expanded ex vivo prior to engineering of the T-cells. Non-limiting example of reagents that can be used to facilitate the expansion of a T-cell population in vitro may comprise anti-CD3 or anti-CD2, anti-CD27, anti-CD30, anti-CD70, anti-OX40 antibodies, IL-2, IL-15, IL-12, IL-9, IL-33, IL-18, or IL-21, CD70 (CD27 ligand), phytohaemagglutinin (PHA), concavalin A (ConA), pokeweed (PWM), protein peanut agglutinin (PNA), soybean agglutinin (SBA), Les Culinaris Agglutinin (LCA), Pisum aativum Agglutinin (PSA), Helix pomatia agglutinin (HPA), Vicia graminea Lectin (VGA), or another suitable mitogen capable of stimulating T-cell proliferation. Further, the T-cells may be expanded using MCSF, IL-6, eotaxin, IFN-alpha, IL-7, gamma-induced protein 10, IFN-gamma, IL-1RA, IL-12, MIP-1alpha, IL-2, IL-13, MIP-1beta, IL-2R, IL-15, and combinations thereof.

The ability of γδ T cells to recognize a broad spectrum of antigens can be enhanced by genetic engineering of the γδ T cells. The γδ T cells can be engineered to provide a universal allogeneic therapy that recognizes an antigen of choice in vivo. Genetic engineering of the γδ T-cells may comprise stably integrating a construct expressing a tumor recognition moiety, such as αβ TCR, γδ TCR, chimeric antigen receptor (CAR), which combines both antigen-binding and T-cell activating functions into a single receptor, an antigen binding fragment thereof, or a lymphocyte activation domain into the genome of the isolated γδ T-cell(s), a cytokine (for example, IL-15, IL-12, IL-2. IL-7. IL-21, IL-18, IL-19, IL-33, IL-4, IL-9, IL-23, or IL1β) to enhance T-cell proliferation, survival, and function ex vivo and in vivo. Genetic engineering of the isolated γδ T-cell may also include deleting or disrupting gene expression from one or more endogenous genes in the genome of the isolated γδ T-cells, such as the MHC locus (loci).

Engineered (or transduced) T cells, including γδ T cells, can be expanded ex vivo without stimulation by an antigen presenting cell or aminobisphosphonate. Antigen reactive engineered T cells of the present disclosure may be expanded ex vivo and in vivo. In an embodiment, an active population of engineered T cells may be expanded ex vivo without antigen stimulation by an antigen presenting cell, an antigenic peptide, a non-peptide molecule, or a small molecule compound, such as an aminobisphosphonate but using certain antibodies, cytokines, mitogens, or fusion proteins, such as IL-17 Fc fusion, MICA Fc fusion, and CD70 Fc fusion. Examples of antibodies that can be used in the expansion of a γδ T-cell population include anti-CD3, anti-CD27, anti-CD30, anti-CD70, anti-OX40, anti-NKG2D, or anti-CD2 antibodies, examples of cytokines may comprise IL-2, IL-15, IL-12, IL-21, IL-18, IL-9, IL-7, and/or IL-33, and examples of mitogens may comprise CD70 the ligand for human CD27, phytohaemagglutinin (PHA), concavalin A (ConA), pokeweed mitogen (PWM), protein peanut agglutinin (PNA), soybean agglutinin (SBA), les culinaris agglutinin (LCA), Pisum sativum agglutinin (PSA), Helix pomatia agglutinin (HPA), Vicia graminea Lectin (VGA) or another suitable mitogen capable of stimulating T-cell proliferation.

A population of engineered T cells, including γδ T cells, can be expanded in less than 60 days, less than 48 days, less than 36 days, less than 24 days, less than 12 days, or less than 6 days. In an embodiment, a population of engineered T cells can be expanded from about 7 days to about 49 days, about 7 days to about 42 days, from about 7 days to about 35 days, from about 7 days to about 28 days, from about 7 days to about 21 days, or from about 7 days to about 14 days. The T-cells may be expanded for between about 1 and 21 days. For example, the T-cells may be expanded for about at least 1, 2, 3, 4, 5, 6, 7, 8, 9, 10, 11, 12, 13, 14, 15, 16, 17, 18, 19, or 20 days.

In an embodiment, the same methodology may be used to isolate, activate, and expand αβ T cells.

In an embodiment, the same methodology may be used to isolate, activate, and expand γδ T cells.

Vectors

Engineered T-cells may be generated using various methods, including those recognized in the literature. For example, a polynucleotide encoding an expression cassette that comprises a tumor recognition, or another type of recognition moiety, can be stably introduced into the T-cell by a transposon/transposase system or a viral-based gene transfer system, such as a lentiviral or a retroviral system, or another suitable method, such as transfection, electroporation, transduction, lipofection, calcium phosphate ($CaPO_4$), nanoengineered substances, such as Ormosil, viral delivery methods, including adenoviruses, retroviruses, lentiviruses, adeno-associated viruses, or another suitable method. A number of viral methods have been used for human gene therapy, such as the methods described in WO 1993/020221, the content of which is incorporated herein in its entirety. Non-limiting examples of viral methods that can be used to engineer T cells may comprise γ-retroviral, adenoviral, lentiviral, herpes simplex virus, vaccinia virus, pox virus, or adeno-virus associated viral methods. The T cells may be αβ T cells or γδ T cells.

Viruses used for transfection of T-cells include naturally occurring viruses as well as artificial viruses. Viruses may be either an enveloped or non-enveloped virus. Parvoviruses (such as AAVs) are examples of non-enveloped viruses. The viruses may be enveloped viruses. The viruses used for transfection of T-cells may be retroviruses and in particular lentiviruses. Viral envelope proteins that can promote viral infection of eukaryotic cells may comprise HIV-1 derived lentiviral vectors (LVs) pseudotyped with envelope glycoproteins (GPs) from the vesicular stomatitis virus (VSV-G), the modified feline endogenous retrovirus (RD114TR) (SEQ ID NO: 97), and the modified gibbon ape leukemia virus (GALVTR). These envelope proteins can efficiently promote entry of other viruses, such as parvoviruses, including adeno-associated viruses (AAV), thereby demonstrating their broad efficiency. For example, other viral envelop proteins may be used including Moloney murine leukemia virus (MLV) 4070 env (such as described in Merten et al., *J. Virol.* 79:834-840, 2005; the content of which is incorporated herein by reference), RD114 env, chimeric envelope protein RD114pro or RDpro (which is an RD114-HIV chimera that was constructed by replacing the R peptide cleavage sequence of RD114 with the HIV-1 matrix/capsid (MA/CA) cleavage sequence, such as described in Bell et al. *Experimental Biology and Medicine* 2010; 235: 1269-1276; the content of which is incorporated herein by reference), baculovirus GP64 env (such as described in Wang et al. *J. Virol.* 81:10869-10878, 2007; the content of which is incorporated herein by reference), or GALV env (such as described in Merten et al., *J. Virol.* 79:834-840, 2005; the content of which is incorporated herein by reference), or derivatives thereof.

A single lentiviral cassette can be used to create a single lentiviral vector, expressing at least four individual monomer proteins of two distinct dimers from a single multi-cistronic mRNA so as to co-express the dimers on the cell surface. For example, the integration of a single copy of the lentiviral vector was sufficient to transform T cells to co-express TCRαβ and CD8αβ, optionally αβ T cells or γδ T cells.

Vectors may comprise a multi-cistronic cassette within a single vector capable of expressing more than one, more than two, more than three, more than four genes, more than five genes, or more than six genes, in which the polypeptides encoded by these genes may interact with one another or may form dimers. The dimers may be homodimers, e.g., two identical proteins forming a dimer, or heterodimers, e.g., two structurally different proteins forming a dimer.

Additionally, multiple vectors may be used to transfect cells with the constructs and sequences described herein. For example, the TCR transgene may be on one vector and the CD8 transgene encoding a polypeptide described herein may be on a second that are transfected either simultaneously or sequentially using recognized methods. A T-cell line may be stably transfected with a CD8 transgene encoding a CD8 polypeptide described herein and then sequentially transfected with a TCR transgene or visa verse.

In some embodiments, the transgene may further include one or more multicistronic element(s) and the multicistronic element(s) may be positioned, for example, between the nucleic acid sequence encoding the TCRα or a portion thereof and the nucleic acid sequence encoding the TCRβ or a portion thereof; between the nucleic acid sequence encoding the CD8α or a portion thereof and the nucleic acid sequence encoding the CD8β or a portion thereof, or between any two nucleic acid sequences encoding of TCRα, TCRβ, CD8α, and CD8β. In some embodiments, the multicistronic element(s) may include a sequence encoding a ribosome skip element selected from among a T2A, a P2A, a E2A or a F2A or an internal ribosome entry site (IRES).

As used herein, the term "self-cleaving 2A peptide" refers to relatively short peptides (of the order of 20 amino acids long, depending on the virus of origin) acting co-translationally, by preventing the formation of a normal peptide bond between the glycine and last proline, resulting in the ribosome skipping to the next codon, and the nascent peptide cleaving between the Gly and Pro. After cleavage, the short 2A peptide remains fused to the C-terminus of the 'upstream' protein, while the proline is added to the N-terminus of the 'downstream' protein. Self-cleaving 2A peptide may be selected from porcine teschovirus-1 (P2A), equine rhinitis A virus (E2A), Thosea asigna virus (T2A), foot-and-mouth disease virus (F2A), or any combination thereof (see, e.g., Kim et al., PLOS One 6:e18556, 2011, the content of which including 2A nucleic acid and amino acid sequences are incorporated herein by reference in their entireties). By adding the linker sequences (GSG or SGSG (SEQ ID NO: 266)) before the self-cleaving 2A sequence, this may enable efficient synthesis of biologically active proteins, e.g., TCRs.

As used herein, the term "internal ribosome entry site (IRES)" refers to a nucleotide sequence located in a messenger RNA (mRNA) sequence, which can initiate translation without relying on the 5' cap structure. IRES is usually located in the 5' untranslated region (5'UTR) but may also be located in other positions of the mRNA. In one embodiment IRES may be selected from IRES from viruses, IRES from cellular mRNAs, in particular IRES from picornavirus, such as polio, EMCV and FMDV, flavivirus, such as hepatitis C virus (HCV), pestivirus, such as classical swine fever virus (CSFV), retrovirus, such as murine leukaemia virus (MLV), lentivirus, such as simian immunodeficiency virus (SIV), and insect RNA virus, such as cricket paralysis virus (CRPV), and IRES from cellular mRNAs, e.g. translation initiation factors, such as eIF4G, and DAP5, transcription factors, such as c-Myc, and NF-κB-repressing factor (NRF), growth factors, such as vascular endothelial growth factor (VEGF), fibroblast growth factor 2 (FGF-2), platelet-derived growth factor B (PDGF-B), homeotic genes, such as antennapedia, survival proteins, such as X-linked inhibitor of apoptosis (XIAP), and Apaf-1, and other cellular mRNA, such as BiP.

Constructs and vectors described herein are used with the methodology described in U.S. Patent Application Publication No. 2019/0175650, published on Jun. 13, 2019, the contents of which are incorporated by reference in their entirety.

Non-viral vectors may also be used with the sequences, constructs, and cells described herein.

The cells may be transfected by other means known in the art including lipofection (liposome-based transfection), electroporation, calcium phosphate transfection, biolistic particle delivery (e.g., gene guns), microinjection, or combinations thereof. Various methods of transfecting cells are known in the art. See, e.g., Sambrook & Russell (Eds.) *Molecular Cloning: A Laboratory Manual* (3$^{rd}$ Ed.) Volumes 1-3 (2001) Cold Spring Harbor Laboratory Press; Ramamoorth & Narvekar "Non Viral Vectors in Gene Therapy—An Overview." *J Clin Diagn Res.* (2015) 9(1): GE01-GE06.

Compositions

Compositions may comprise the modified CD8 polypeptides described herein. Further, compositions described herein may comprise a T-cell expressing CD8 polypeptides described herein. The compositions described herein may comprise a T-cell expressing CD8 polypeptides described herein and a T-cell receptor (TCR), optionally a TCR that specifically binds one of the TAA described herein complexed with an antigen presenting protein, e.g., MHC, referred to as HLA in humans, for human leukocyte antigen.

To facilitate administration, the T cells described herein can be made into a pharmaceutical composition or made into an implant appropriate for administration in vivo, with pharmaceutically acceptable carriers or diluents. The means of making such a composition or an implant are described in the art. See, e.g., Remington's Pharmaceutical Sciences, 16th Ed., Mack, ed. (1980).

The T cells described herein can be formulated into a preparation in semisolid or liquid form, such as a capsule, solution, infusion, or injection. Means known in the art can be utilized to prevent or minimize release and absorption of the composition until it reaches the target tissue or organ, or to ensure timed-release of the composition. Desirably, however, a pharmaceutically acceptable form is employed that does not hinder the cells from expressing the CARs or TCRs. Thus, desirably the T cells described herein can be made into a pharmaceutical composition comprising a carrier. The T cells described herein can be formulated with a physiologically acceptable carrier or excipient to prepare a pharmaceutical composition. The carrier and composition can be sterile. Preferred carriers include, for example, a balanced salt solution, preferably Hanks' balanced salt solution, or normal saline. The formulation should suit the mode of administration. Suitable pharmaceutically acceptable carriers include but are not limited to water, salt solutions (e.g., NaCl), saline, buffered saline, as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, that do not deleteriously react with the T-cells. The T-cells may be $\alpha\beta$ T cells or $\gamma\delta$ T cells that express CD8 polypeptides described herein, optionally a TCR described herein.

A composition of the present invention can be provided in unit dosage form wherein each dosage unit, e.g., an injection, contains a predetermined amount of the composition, alone or in appropriate combination with other active agents.

The compositions described herein may be a pharmaceutical composition. Pharmaceutical composition described herein may further comprise an adjuvant selected from the group consisting of colony-stimulating factors, including but not limited to Granulocyte Macrophage Colony Stimulating Factor (GM-CSF, sargramostim), cyclophosphamide, imiquimod, resiquimod, interferon-alpha, or a combination thereof.

Pharmaceutical composition described herein may comprise an adjuvant selected from the group consisting of colony-stimulating factors, e.g., Granulocyte Macrophage Colony Stimulating Factor (GM-CSF, sargramostim), cyclophosphamide, imiquimod and resiquimod.

Preferred adjuvants include but are not limited to cyclophosphamide, imiquimod or resiquimod. Even more preferred adjuvants are Montanide IMS 1312, Montanide ISA 206, Montanide ISA 50V, Montanide ISA-51, poly-ICLC (Hiltonol®) and anti-CD40 mAB, or combinations thereof.

Other examples for useful adjuvants include, but are not limited to chemically modified CpGs (e.g. CpR, Idera), dsRNA analogues such as Poly(I:C) and derivates thereof (e.g. AmpliGen®, Hiltonol®, poly-(ICLC), poly(IC-R), poly(I:C12U), non-CpG bacterial DNA or RNA as well as immunoactive small molecules and antibodies such as cyclophosphamide, sunitinib, immune checkpoint inhibitors including ipilimumab, nivolumab, pembrolizumab, atezolizumab, avelumab, durvalumab, and cemiplimab, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Other adjuvants include but are not limited to anti-CD40, imiquimod, resiquimod, GM-CSF, cyclophosphamide, sunitinib, bevacizumab, atezolizumab, interferon-alpha, interferon-beta, CpG oligonucleotides and derivatives, poly-(I:C) and derivatives, RNA, sildenafil, and particulate formulations with poly(lactide co-glycolide) (PLG), Polyinosinic-polycytidylic acid-poly-l-lysine carboxymethylcellulose (poly-ICLC), virosomes, and/or interleukin-1 (IL-1), IL-2, IL-4, IL-7, IL-12, IL-13, IL-15, IL-18, IL-21, and IL-23. See, e.g., Narayanan et al. *J. Med. Chem.* (2003) 46(23): 5031-5044; Pohar et al. *Scientific Reports* 7 14598 (2017); Grajkowski et al. *Nucleic Acids Research* (2005) 33(11): 3550-3560; Martins et al. *Expert Rev Vaccines* (2015) 14(3): 447-59.

The composition described herein may also include one or more adjuvants. Adjuvants are substances that non-specifically enhance or potentiate the immune response (e.g., immune responses mediated by CD8-positive T cells and helper-T (TH) cells to an antigen and would thus be considered useful in the medicament of the present invention. Suitable adjuvants include, but are not limited to, 1018 ISS, aluminium salts, AMPLIVAX®, AS15, BCG, CP-870,893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactide co-glycolide) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously. Also, cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, incorporated herein by reference in its entirety) and acting as immunoadjuvants (e.g., IL-12, IL-15, IL-23, IL-7, IFN-alpha. IFN-beta).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Methods of Treatment and Preparing

Engineered T cells may express modified CD8 polypeptides described herein. Further, the Engineered T cells may express a TCR described herein. The TCR expressed by the engineered T cells may recognize a TAA bound to an HLA as described herein. Engineered T cells of the present disclosure can be used to treat a subject in need of treatment for a condition, for example, a cancer described herein. The T cells may be αβ T cells or γδ T cells that express a modified CD8 polypeptide, optionally a TCR described herein.

A method of treating a condition (e.g., ailment) in a subject with T cells described herein may comprise administering to the subject a therapeutically effective amount of engineered T cells described herein, optionally γδ T cells. T cells described herein may be administered at various regimens (e.g., timing, concentration, dosage, spacing between treatment, and/or formulation). A subject can also be preconditioned with, for example, chemotherapy, radiation, or a combination of both, prior to receiving engineered T cells of the present disclosure. A population of engineered T cells may also be frozen or cryopreserved prior to being administered to a subject. A population of engineered T cells can include two or more cells that express identical, different, or a combination of identical and different tumor recognition moieties. For instance, a population of engineered T-cells can include several distinct engineered T cells that are designed to recognize different antigens, or different epitopes of the same antigen. The T cells may be αβ T cells or γδ T cells that express a CD8 polypeptide described herein, optionally a TCR described herein.

T cells described herein, including αβ T-cells and γδ T cells, may be used to treat various conditions. The T cells may be αβ T cells or γδ T cells that express a CD8 polypeptide, optionally a TCR described herein. T cells described herein may be used to treat a cancer, including solid tumors and hematologic malignancies. Non-limiting examples of cancers include: acute lymphoblastic leukemia, acute myeloid leukemia, adrenocortical carcinoma, AIDS-related cancers, AIDS-related lymphoma, anal cancer, appendix cancer, astrocytomas, neuroblastoma, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenstrom macroglobulinemia, and Wilms tumor.

The T cells described herein may be used to treat an infectious disease. The T cells described herein may be used to treat an infectious disease, an infectious disease may be caused a virus. The T cells described herein may be used to treat an immune disease, such as an autoimmune disease. The T cells may be αβ T cells or γδ T cells that express a CD8 polypeptide, optionally a TCR described herein.

Treatment with T cells described herein, optionally γδ T cells, may be provided to the subject before, during, and after the clinical onset of the condition. Treatment may be provided to the subject after 1 day, 1 week, 6 months, 12 months, or 2 years after clinical onset of the disease. Treatment may be provided to the subject for more than 1 day, 1 week, 1 month, 6 months, 12 months, 2 years, 3 years, 4 years, 5 years, 6 years, 7 years, 8 years, 9 years, 10 years or more after clinical onset of disease. Treatment may be provided to the subject for less than 1 day, 1 week, 1 month, 6 months, 12 months, or 2 years after clinical onset of the disease. Treatment may also include treating a human in a clinical trial. A treatment can include administering to a subject a pharmaceutical composition comprising engineered T cells described herein. The T cells may be αβ T cells or γδ T cells that express a CD8 polypeptide, optionally a TCR described herein.

In an embodiment, administration of engineered T cells of the present disclosure to a subject may modulate the activity of endogenous lymphocytes in a subject's body. In an embodiment, administration of engineered T cells to a subject may provide an antigen to an endogenous T-cell and may boost an immune response. In an embodiment, the memory T cell may be a CD4+ T-cell. In an embodiment, the memory T cell may be a CD8+ T-cell. In an embodiment, administration of engineered T cells of the present disclosure to a subject may activate the cytotoxicity of another immune cell. In an embodiment, the other immune cell may be a CD8+ T-cell. In an embodiment, the other immune cell may be a Natural Killer T-cell. In an embodiment, administration of engineered γδ T-cells of the present disclosure to a subject may suppress a regulatory T-cell. In an embodiment, the regulatory T-cell may be a FOX3+ Treg cell. In an embodiment, the regulatory T-cell may be a FOX3− Treg cell. Non-limiting examples of cells whose activity can be modulated by engineered T cells of the disclosure may comprise: hematopoietic stem cells; B cells; CD4; CD8; red blood cells; white blood cells; dendritic cells, including dendritic antigen presenting cells; leukocytes; macrophages; memory B cells; memory T-cells; monocytes; natural killer cells; neutrophil granulocytes; T-helper cells; and T-killer cells. The T cells may be αβ T cells or γδ T cells that express a CD8 polypeptide, optionally a TCR described herein.

During most bone marrow transplants, a combination of cyclophosphamide with total body irradiation may be conventionally employed to prevent rejection of the hematopoietic stem cells (HSC) in the transplant by the subject's immune system. In an embodiment, incubation of donor bone marrow with interleukin-2 (IL-2) ex vivo may be performed to enhance the generation of killer lymphocytes in the donor marrow. Interleukin-2 (IL-2) is a cytokine that may be necessary for the growth, proliferation, and differentiation of wild-type lymphocytes. Current studies of the adoptive transfer of γδ T-cells into humans may require the co-administration of γδ T-cells and interleukin-2. However, both low- and high-dosages of IL-2 can have highly toxic side effects. IL-2 toxicity can manifest in multiple organs/systems, most significantly the heart, lungs, kidneys, and central nervous system. In an embodiment, the disclosure provides a method for administrating engineered T cells to a subject without the co-administration of a native cytokine or modified versions thereof, such as IL-2, IL-15, IL-12, IL-21. In an embodiment, engineered T cells can be administered to a subject without co-administration with IL-2. In an embodiment, engineered T cells may be administered to a subject during a procedure, such as a bone marrow transplant without the co-administration of IL-2.

In an embodiment, the methods may further comprise administering a chemotherapy agent. The dosage of the chemotherapy agent may be sufficient to deplete the patient's T-cell population. The chemotherapy may be administered about 5-7 days prior to T-cell administration. The chemotherapy agent may be cyclophosphamide, fludarabine, or a combination thereof. The chemotherapy agent may comprise dosing at about 400-600 mg/m²/day of cyclophosphamide. The chemotherapy agent may comprise dosing at about 10-30 mg/m²/day of fludarabine.

In an embodiment, the methods may further comprise pre-treatment of the patient with low-dose radiation prior to administration of the composition comprising T-cells. The low dose radiation may comprise about 1.4 Gy for 1-6 days, preferably about 5 days, prior to administration of the composition comprising T-cells.

In an embodiment, the patient may be HLA-A*02.

In an embodiment, the patient may be HLA-A*06.

In an embodiment, the methods may further comprise administering an anti-PD1 antibody. The anti-PD1 antibody may be a humanized antibody. The anti-PD1 antibody may be pembrolizumab. The dosage of the anti-PD1 antibody may be about 200 mg. The anti-PD1 antibody may be administered every 3 weeks following T-cell administration.

In an embodiment, the dosage of T-cells may be between about 0.8-1.2×10⁹ T cells. The dosage of the T cells may be about 0.5×10⁸ to about 10×10⁹ T cells. The dosage of T-cells may be about 1.2-3×10⁹ T cells, about 3-6×10⁹ T cells, about 10×10⁹ T cells, about 5×10⁹ T cells, about 0.1×10⁹ T cells, about 1×10⁸ T cells, about 5×10⁸ T cells, about 1.2-6×10⁹ T cells, about 1-6×10⁹ T cells, or about 1-8×10⁹ T cells.

In an embodiment, the T cells may be administered in 3 doses. The T-cell doses may escalate with each dose. The T-cells may be administered by intravenous infusion.

In an embodiment, the CD8 sequences described herein and associated products and compositions may be used autologous or allogenic methods of adoptive cellular therapy. In another embodiment, CD8 sequences, T cells thereof, and compositions may be used in, for example, methods described in U.S. Patent Application Publication 2019/0175650; U.S. Patent Application Publication 2019/0216852; U.S. Patent Application Publication 2019/024743; and U.S. Provisional Patent Application 62/980,844, each of which are incorporated by reference in their entireties.

The disclosure also provides for a population of modified T cells that present an exogenous CD8 polypeptide described herein and a T cell receptor wherein the population of modified T cells is activated and expanded with a combination of IL-2 and IL-15. In another embodiment, the population of modified T cells are expanded and/or activated with a combination of IL-2, IL-15, and zoledronate. In yet another embodiment, the population of modified T cells are activated with a combination of IL-2, IL-15, and zoledronate while expanded with a combination of IL-2, IL-15, and without zoledronate. The disclosure further provides for use of other interleukins during activation and/or expansion, such as IL-12, IL-18, IL-21, and combinations thereof.

In an aspect, IL-21, a histone deacetylase inhibitor (HDACi), or combinations thereof may be utilized in the field of cancer treatment, with methods described herein, and/or with ACT processes described herein. In an embodiment, the present disclosure provides methods for re-programming effector T cells to a central memory phenotype comprising culturing the effector T cells with at least one HDACi together with IL-21. Representative HDACi include, for example, trichostatin A, trapoxin B, phenylbutyrate, valproic acid, vorinostat (suberanilohydroxamic acid), belinostat, panobinostat, dacinostat, entinostat, tacedinaline, and mocetinostat.

Compositions comprising engineered T cells described herein may be administered for prophylactic and/or therapeutic treatments. In therapeutic applications, pharmaceutical compositions can be administered to a subject already suffering from a disease or condition in an amount sufficient to cure or at least partially arrest the symptoms of the disease or condition. An engineered T-cell can also be administered to lessen a likelihood of developing, contracting, or worsening a condition. Effective amounts of a population of engineered T-cells for therapeutic use can vary based on the severity and course of the disease or condition, previous therapy, the subject's health status, weight, and/or response to the drugs, and/or the judgment of the treating physician. The T cells may be αβ T cells or γδ T cells engineered to express modified CD8 polypeptides described herein and optionally a TCR described herein. T-cell therapy has been successful in treating various cancers. Li et al. *Signal Transduction and Targeted Therapy* 4(35): (2019), the content of which is incorporated by reference in its entirety.

Methods of Administration

One or multiple engineered T cell populations described herein may be administered to a subject in any order or simultaneously. If simultaneously, the multiple engineered T cell can be provided in a single, unified form, such as an intravenous injection, or in multiple forms, for example, as multiple intravenous infusions, subcutaneous injections or pills. Engineered T-cells can be packed together or separately, in a single package or in a plurality of packages. One or all of the engineered T cells can be given in multiple doses. If not simultaneous, the timing between the multiple doses may vary to as much as about a week, a month, two months, three months, four months, five months, six months, or about a year. In an embodiment, engineered T cells can expand within a subject's body, in vivo, after administration to a subject. Engineered T cells can be frozen to provide cells for multiple treatments with the same cell preparation. Engineered T cells of the present disclosure, and pharmaceutical compositions comprising the same, can be packaged as a kit. A kit may comprise instructions (e.g., written instructions) on the use of engineered T cells and compositions comprising the same.

A method of treating a cancer may comprise administering to a subject a therapeutically-effective amount of engineered T cells, in which the administration treats the cancer. In an embodiments, the therapeutically-effective amount of engineered γδ T cells may be administered for at least about 10 seconds, 30 seconds, 1 minute, 10 minutes, 30 minutes, 1 hour, 2 hours, 3 hours, 4 hours, 5 hours, 6 hours, 12 hours, 24 hours, 2 days, 3 days, 4 days, 5 days, 6 days, 1 week, 2 weeks, 3 weeks, 1 month, 2 months, 3 months, 4 months, 5 months, 6 months, or 1 year. In an embodiment, the therapeutically-effective amount of the engineered T cells may be administered for at least one week. In an embodiment, the therapeutically-effective amount of engineered T cells may be administered for at least two weeks.

Engineered T-cells described herein, optionally γδ T cells, can be administered before, during, or after the occurrence of a disease or condition, and the timing of administering a pharmaceutical composition comprising an engineered T-cell can vary. For example, engineered T cells can be used as a prophylactic and can be administered continuously to subjects with a propensity to conditions or diseases in order to lessen the likelihood of occurrence of the disease or condition. Engineered T-cells can be administered to a subject during or as soon as possible after the onset of the symptoms. The administration of engineered T cells can be initiated immediately within the onset of symptoms, within the first 3 hours of the onset of the symptoms, within the first 6 hours of the onset of the symptoms, within the first 24 hours of the onset of the symptoms, within 48 hours of the onset of the symptoms, or within any period of time from the onset of symptoms. The initial administration can be via any route practical, such as by any route described herein using any formulation described herein. In an embodiment, the administration of engineered T cells of the present disclosure may be an intravenous administration. One or multiple dosages of engineered T cells can be administered as soon as is practicable after the onset of a cancer, an infectious disease, an immune disease, sepsis, or with a bone marrow transplant, and for a length of time necessary for the treatment of the immune disease, such as, for example, from about 24 hours to about 48 hours, from about 48 hours to about 1 week, from about 1 week to about 2 weeks, from about 2 weeks to about 1 month, from about 1 month to about 3 months. For the treatment of cancer, one or multiple dosages of engineered T cells can be administered years after onset of the cancer and before or after other treatments. In an embodiment, engineered γδ T cells can be administered for at least about 10 minutes, 30 minutes, 1 hour, 2 hours, 3 hours, 4 hours, 5 hours, 6 hours, 12 hours, 24 hours, at least 48 hours, at least 72 hours, at least 96 hours, at least 1 week, at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 1 year, at least 2 years at least 3 years, at least 4 years, or at least 5 years. The length of treatment can vary for each subject. The T cells may be αβ T cells or γδ T cells that express a CD8 polypeptide described herein, optionally a TCR described herein.

Engineered T-cell expressing a CD8 polypeptides described herein, optionally αβ T cells or γδ T cells, may be present in a composition in an amount of at least $1\times10^3$ cells/ml, at least $2\times10^3$ cells/ml, at least $3\times10^3$ cells/ml, at least $4\times10^3$ cells/ml, at least $5\times10^3$ cells/ml, at least $6\times10^3$ cells/ml, at least $7\times10^3$ cells/ml, at least $8\times10^3$ cells/ml, at least $9\times10^3$ cells/ml, at least $1\times10^4$ cells/ml, at least $2\times10^4$ cells/ml, at least $3\times10^4$ cells/ml, at least $4\times10^4$ cells/ml, at least $5\times10^4$ cells/ml, at least $6\times10^4$ cells/ml, at least $7\times10^4$ cells/ml, at least $8\times10^4$ cells/ml, at least $9\times10^4$ cells/ml, at least $1\times10^5$ cells/ml, at least $2\times10^5$ cells/ml, at least $3\times10^5$ cells/ml, at least $4\times10^5$ cells/ml, at least $5\times10^5$ cells/ml, at least $6\times10^5$ cells/ml, at least $7\times10^5$ cells/ml, at least $8\times10^5$ cells/ml, at least $9\times10^5$ cells/ml, at least $1\times10^6$ cells/ml, at least $2\times10^6$ cells/ml, at least $3\times10^6$ cells/ml, at least $4\times10^6$ cells/ml, at least $5\times10^6$ cells/ml, at least $6\times10^6$ cells/ml, at least $7\times10^6$ cells/ml, at least $8\times10^6$ cells/ml, at least $9\times10^6$ cells/ml, at least $1\times10^7$ cells/ml, at least $2\times10^7$ cells/ml, at least $3\times10^7$ cells/ml, at least $4\times10^7$ cells/ml, at least $5\times10^7$ cells/ml, at least $6\times10^7$ cells/ml, at least $7\times10^7$ cells/ml, at least $8\times10^7$ cells/ml, at least $9\times10^7$ cells/ml, at least $1\times10^8$ cells/ml, at least $2\times10^8$ cells/ml, at least $3\times10^8$ cells/ml, at least $4\times10^8$ cells/ml, at least $5\times10^8$ cells/ml, at least $6\times10^8$ cells/ml, at least $7\times10^8$ cells/ml, at least $8\times10^8$ cells/ml, at least $9\times10^8$ cells/ml, at least $1\times10^9$ cells/ml, or more, from about $1\times10^3$ cells/ml to about at least $1\times10^8$ cells/ml, from about $1\times10^5$ cells/ml to about at least $1\times10^8$ cells/ml, or from about $1\times10^6$ cells/ml to about at least $1\times10^8$ cells/ml.

Sequences

The sequences described herein may comprise about 80%, about 85%, about 90%, about 85%, about 96%, about 97%, about 98%, or about 99% or 100% identity to the sequence of any of SEQ ID NO: 1-97, 256-266, 293 and 294. The sequences described herein may comprise at least 80%, at least 85%, at least 90%, at least 85%, at least 96%, at least 97%, at least 98%, at least 99% or 100% identity to the sequence of any of SEQ ID NO: 1-97 and 256-266. A sequence "at least 85% identical to a reference sequence" is a sequence having, on its entire length, 85%, or more, in particular 90%, 91%, 92%, 93%, 94%, 95%, 96%, 97%, 98%, 99%, or 100% sequence identity with the entire length of the reference sequence.

In another embodiment, the disclosure provides for sequences at least 80%, at least 85%, at least 90%, at least 85%, at least 96%, at least 97%, at least 98%, at least 99% or 100% identity to WPREmut1 (SEQ ID NO: 256), or WPRE version 2, e.g., WPREmut2 (SEQ ID NO: 257). In another aspect, the disclosure provides for sequences at least 1, 2, 3, 4, 5, 10, 15, or 20 amino acid substitutions in WPREmut1 (SEQ ID NO: 256), or WPRE version 2, e.g., WPREmut2 (SEQ ID NO: 257). In yet another aspect, the disclosure provides for sequences at most 1, 2, 3, 4, 5, 10, 15, or 20 amino acid substitutions in WPREmut1 (SEQ ID NO: 256), or WPRE version 2, e.g., WPREmut2 (SEQ ID NO: 257). In another aspect, the sequence substitutions are conservative substitutions.

Percentage of identity may be calculated using a global pairwise alignment (e.g., the two sequences are compared over their entire length). Methods for comparing the identity of two or more sequences are well known in the art. The «needle» program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk World Wide Web site and is further described in the following publication (*EMBOSS: The European Molecular Biology Open Software Suite* (2000) Rice, P. Longden, I. and Bleasby, A. Trends in Genetics 16, (6) pp. 276-277). The percentage of identity between two polypeptides, in accordance with the invention, is calculated using the EMBOSS: needle (global) program with a "Gap Open" parameter equal to 10.0, a "Gap Extend" parameter equal to 0.5, and a Blosum62 matrix.

Proteins consisting of an amino acid sequence "at least 80%, 85%, 90%, 95%, 96%, 97%, 98% or 99% identical" to a reference sequence may comprise mutations such as deletions, insertions and/or substitutions compared to the reference sequence. In case of substitutions, the protein consisting of an amino acid sequence at least 80%, 85%, 90%, 95%, 96%, 97%, 98% or 99% identical to a reference sequence may correspond to a homologous sequence derived from another species than the reference sequence.

Amino acid substitutions may be conservative or non-conservative. Preferably, substitutions are conservative substitutions, in which one amino acid is substituted for another amino acid with similar structural and/or chemical properties.

Conservative substitutions may comprise those, which are described by Dayhoff in "The Atlas of Protein Sequence and Structure. Vol. 5", Natl. Biomedical Research, the contents of which are incorporated by reference in their entirety. For example, in an embodiment, amino acids, which belong to one of the following groups, can be exchanged for one another, thus, constituting a conservative exchange: Group 1: alanine (A), proline (P), glycine (G), asparagine (N), serine (S), threonine (T); Group 2: cysteine (C), serine (S), tyrosine (Y), threonine (T); Group 3: valine (V), isoleucine (I), leucine (L), methionine (M), alanine (A), phenylalanine (F); Group 4: lysine (K), arginine (R), histidine (H); Group 5: phenylalanine (F), tyrosine (Y), tryptophan (W), histidine (H); and Group 6: aspartic acid (D), glutamic acid (E). In an embodiment, a conservative amino acid substitution may be selected from the following of T→A, G→A, A→I, T→V, A→M, T→I, A→V, T→G, and/or T→S.

A conservative amino acid substitution may comprise the substitution of an amino acid by another amino acid of the same class, for example, (1) nonpolar: Ala, Val, Leu, Ile, Pro, Met, Phe, Trp; (2) uncharged polar: Gly, Ser, Thr, Cys, Tyr, Asn, Gln; (3) acidic: Asp, Glu; and (4) basic: Lys, Arg, His. Other conservative amino acid substitutions may also be made as follows: (1) aromatic: Phe, Tyr, His; (2) proton donor: Asn, Gln, Lys, Arg, His, Trp; and (3) proton acceptor: Glu, Asp, Thr, Ser, Tyr, Asn, Gln (see, for example, U.S. Pat. No. 10,106,805, the contents of which are incorporated by reference in their entirety).

Conservative substitutions may be made in accordance with Table A. Methods for predicting tolerance to protein modification may be found in, for example, Guo et al., Proc. Natl. Acad. Sci., USA, 101(25):9205-9210 (2004), the contents of which are incorporated by reference in their entirety.

TABLE A

Conservative Amino Acid substitution
Conservative Amino Acid Substitutions

| Amino Acid | Substitutions (others are known in the art) |
|---|---|
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Tip, Phe, His |
| Val | Ile, Leu, Met, Ala, Thr |

The sequences described herein may comprise 1, 2, 3, 4, 5, 10, 15, 20, 25, or 30 amino acid or nucleotide mutations, substitutions, deletions. Any one of SEQ ID NO: 1-97, 256-266, 293, and 294 may comprise 1, 2, 3, 4, 5, 10, 15, 20, 25, or 30 mutations, substitutions, or deletions. In another aspect, any one of SEQ ID NO: 1-97, 256-266, 293, and 294 may comprise at most 1, 2, 3, 4, 5, 10, 15, 20, or 30 mutations, substitutions, or deletions. In an aspect, the mutations or substitutions may be conservative amino acid substitutions.

Conservative substitutions in the polypeptides described herein may be those shown in Table B under the heading of "conservative substitutions." If such substitutions result in a change in biological activity, then more substantial changes, denominated "exemplary substitutions" in Table B, may be introduced and the products screened if needed.

TABLE B

Amino Acid substitution
Amino Acid Substitutions

| Original Residue (naturally occurring amino acid) | Conservative Substitutions | Exemplary Substitutions |
|---|---|---|
| Ala (A) | Val | Val.; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |

TABLE B-continued

Amino Acid substitution
Amino Acid Substitutions

| Original Residue (naturally occurring amino acid) | Conservative Substitutions | Exemplary Substitutions |
|---|---|---|
| Tyr (Y) | Phe | Trp; Phe; Thr; Ser |
| Val (V) | Leu | Ile; Leu; Met; Phe; Ala; Norleucine |

Unless otherwise indicated, all terms used herein have the same meaning as they would to one skilled in the art.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

Activation" as used herein refers broadly to the state of a T cell that has been sufficiently stimulated to induce detectable cellular proliferation. Activation can also be associated with induced cytokine production, and detectable effector functions. The term "activated T cells" refers to, among other things, T cells that are proliferating.

"Antibodies" as used herein refer broadly to antibodies or immunoglobulins of any isotype, fragments of antibodies, which retain specific binding to antigen, including, but not limited to, Fab, Fab', Fab'-SH, (Fab')$_2$ Fv, scFv, divalent scFv, and Fd fragments, chimeric antibodies, humanized antibodies, single-chain antibodies, and fusion proteins including an antigen-specific targeting region of an antibody and a non-antibody protein. Antibodies are organized into five classes-IgG, IgE, IgA, IgD, and IgM.

"Antigen" or "Antigenic," as used herein, refers broadly to a peptide or a portion of a peptide capable of being bound by an antibody which is additionally capable of inducing an animal to produce an antibody capable of binding to an epitope of that antigen. An antigen may have one epitope or have more than one epitope. The specific reaction referred to herein indicates that the antigen will react, in a highly selective manner, with its corresponding antibody and not with the multitude of other antibodies which may be evoked by other antigens.

"Chimeric antigen receptor" or "CAR" or "CARs" as used herein refers broadly to genetically modified receptors, which graft an antigen specificity onto cells, for example T cells, NK cells, macrophages, and stem cells. CARs can include at least one antigen-specific targeting region (ASTR), a hinge or stalk domain, a transmembrane domain (TM), one or more co-stimulatory domains (CSDs), and an intracellular activating domain (IAD). In certain embodiments, the CSD is optional. In another embodiment, the CAR is a bispecific CAR, which is specific to two different antigens or epitopes. After the ASTR binds specifically to a target antigen, the IAD activates intracellular signaling. For example, the IAD can redirect T cell specificity and reactivity toward a selected target in a non-MHC-restricted manner, exploiting the antigen-binding properties of antibodies. The non-MHC-restricted antigen recognition gives T cells expressing the CAR the ability to recognize an antigen independent of antigen processing, thus bypassing a major mechanism of tumor escape. Moreover, when expressed in T cells, CARs advantageously do not dimerize with endogenous T cell receptor (TCR) alpha and beta chains.

"Cytotoxic T lymphocyte" (CTL) as used herein refers broadly to a T lymphocyte that expresses CD8 on the surface thereof (e.g., a CD8+ T cell). Such cells may be preferably "memory" T cells ($T_M$ cells) that are antigen-experienced.

"Effective amount", "therapeutically effective amount", or "efficacious amount" as used herein refers broadly to the amount of an agent, or combined amounts of two agents, that, when administered to a mammal or other subject for treating a disease, is sufficient to affect such treatment for the disease. The "therapeutically effective amount" will vary depending on the agent(s), the disease and its severity and the age, weight, etc., of the subject to be treated.

"Genetically modified" as used herein refers broadly to methods to introduce exogenous nucleic acids into a cell, whether or not the exogenous nucleic acids are integrated into the genome of the cell. "Genetically modified cell" as used herein refers broadly to cells that contain exogenous nucleic acids whether or not the exogenous nucleic acids are integrated into the genome of the cell.

"Immune cells" as used herein refers broadly to white blood cells (leukocytes) derived from hematopoietic stem cells (HSC) produced in the bone marrow "Immune cells" include, without limitation, lymphocytes (T cells, B cells, natural killer (NK) (CD3−CD56+) cells) and myeloid-derived cells (neutrophil, eosinophil, basophil, monocyte, macrophage, dendritic cells). "T cells" include all types of immune cells expressing CD3 including T-helper cells (CD4+ cells), cytotoxic T-cells (CD8+ cells), T-regulatory cells (Treg) and gamma-delta T cells, and NK T cells (CD3+ and CD56+). A skilled artisan will understand T cells and/or NK cells, as used throughout the disclosure, can include only T cells, only NK cells, or both T cells and NK cells. In certain illustrative embodiments and aspects provided herein, T cells are activated and transduced. Furthermore, T cells are provided in certain illustrative composition embodiments and aspects provided herein. A "cytotoxic cell" includes CD8+ T cells, natural-killer (NK) cells, NK-T cells, γδ T cells, and neutrophils, which are cells capable of mediating cytotoxicity responses.

"Individual," "subject," "host," and "patient," as used interchangeably herein, refer broadly to a mammal, including, but not limited to, humans, murines (e.g., rats, mice), lagomorphs (e.g., rabbits), non-human primates, canines, felines, and ungulates (e.g., equines, bovines, ovines, porcines, caprines).

"Peripheral blood mononuclear cells" or "PBMCs" as used herein refers broadly to any peripheral blood cell having a round nucleus. PBMCs include lymphocytes, such as T cells, B cells, and NK cells, and monocytes.

"Polynucleotide" and "nucleic acid", as used interchangeably herein, refer broadly to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer including purine and pyrimidine bases or other natural, chemically or biochemically modified, non-natural, or derivatized nucleotide bases.

"T cell" or "T lymphocyte," as used herein, refer broadly to thymocytes, naïve T lymphocytes, immature T lymphocytes, mature T lymphocytes, resting T lymphocytes, or activated T lymphocytes. Illustrative populations of T cells suitable for use in particular embodiments include, but are not limited to, helper T cells (HTL; CD4+ T cell), a cytotoxic T cell (CTL; CD8+ T cell), CD4+CD8+ T cell, CD4−CD8− T cell, natural killer T cell, T cells expressing αβ TCR (αβ T cells), T cells expressing γδ TCR (γδ T cells), or any other subset of T cells. Other illustrative populations of T cells suitable for use in particular embodiments include, but are not limited to, T cells expressing one or more of the following markers: CD3, CD4, CD8, CD27, CD28, CD45RA, CD45RO, CD62L, CD127, CD197, and HLA-DR and if desired, can be further isolated by positive or negative selection techniques.

In the present invention, the term "homologous" refers to the degree of identity (see percent identity above) between sequences of two amino acid sequences, e.g., peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

The terms "sequence homology" or "sequence identity" are used interchangeably herein. For the purpose of this invention, it is defined here that in order to determine the percentage of sequence homology or sequence identity of two amino acid sequences or of two nucleotide sequences, the sequences are aligned for optimal comparison purposes. In order to optimize the alignment between the two sequences, gaps may be introduced in any of the two sequences that are compared. Such alignment can be carried out over the full-length of the sequences being compared. Alternatively, the alignment may be carried out over a shorter length, for example over about 5, about 10, about 20, about 50, about 100 or more nucleotides or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison. In D. Sankoff and J. B. Kruskal, (ed.), Time warps, string edits and macromolecules: the theory and practice of sequence comparison, Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mal. Biol. 48, 443-453). Both amino acid sequences and nucleotide sequences can be aligned by the algorithm. The Needleman-Wunsch algorithm has been implemented in the computer program NEEDLE. For the purpose of this invention, the NEEDLE program from the EMBOSS package was used (version 2.8.0 or higher, EMBOSS: The European Molecular Biology Open Software Suite (2000) Rice, Longden, and Bleasby, Trends in Genetics 16, (6) 276-277, emboss.bioinformatics.nl/). For amino acid sequences, EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labelled in the output of the program as "longest-identity". The nucleotide and amino acid sequences of the present invention can further be used as a "query sequence" to perform a search against sequence databases to, for example, identify other family members or related sequences. Such searches can be performed using the NBLAST and XBLAST programs (version 2.0) of Altschul et al. (1990) J. Mal. Biol. 215:403-10. BLAST nucleotide searches can be performed with the NBLAST program, score=100, word length=12 to obtain nucleotide sequences homologous to polynucleotides of the invention. BLAST protein searches can be performed with the XBLAST program, score=50, word length=3 to obtain amino acid sequences homologous to polypeptides of the invention. To obtain gapped alignments for comparison purposes, Gapped BLAST can be utilized as described in Altschul et al. (1997) *Nucleic Acids Res.* 25(17): 3389-3402. When utilizing BLAST and Gapped BLAST programs, the default parameters of the respective programs (e.g., XBLAST and NBLAST) can be used.

"T-cell receptor (TCR)" as used herein refers broadly to a protein receptor on T cells that is composed of a heterodimer of an alpha (α) and beta (β) chain, although in some cells the TCR consists of gamma and delta (γ/δ) chains. The TCR may be modified on any cell comprising a TCR, including a helper T cell, a cytotoxic T cell, a memory T cell, regulatory T cell, natural killer T cell, or a gamma delta T cell.

The TCR is generally found on the surface of T lymphocytes (or T cells) that is generally responsible for recognizing antigens bound to major histocompatibility complex (MHC) molecules. It is a heterodimer consisting of an alpha and beta chain in 95% of T cells, while 5% of T cells have TCRs consisting of gamma and delta chains. Engagement of the TCR with antigen and MHC results in activation of its T lymphocyte through a series of biochemical events mediated by associated enzymes, co-receptors, and specialized accessory molecules. In immunology, the CD3 antigen (CD stands for cluster of differentiation) is a protein complex composed of four distinct chains (CD3-γ, CD3δ, and two times CD3ε) in mammals, that associate with molecules known as the T-cell receptor (TCR) and the ζ-chain to generate an activation signal in T lymphocytes. The TCR, ζ-chain, and CD3 molecules together comprise the TCR complex. The CD3-γ, CD3δ, and CD3ε chains are highly related cell surface proteins of the immunoglobulin superfamily containing a single extracellular immunoglobulin domain. The transmembrane region of the CD3 chains is negatively charged, a characteristic that allows these chains to associate with the positively charged TCR chains (TCRα and TCRβ). The intracellular tails of the CD3 molecules contain a single conserved motif known as an immunoreceptor tyrosine-based activation motif or ITAM for short, which is essential for the signaling capacity of the TCR.

"Treatment," "treating," and the like, as used herein refer broadly to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, e.g., arresting its development; and (c) relieving the disease, e.g., causing regression of the disease.

The ability of dendritic cells (DC) to activate and expand antigen-specific CD8+ T cells may depend on the DC maturation stage and that DCs may need to receive a "licensing" signal, associated with IL-12 production, in order to elicit cytolytic immune response. In particular, the provision of signals through CD40 Ligand (CD40L)-CD40 interactions on CD4+ T cells and DCs, respectively, may be considered important for the DC licensing and induction of cytotoxic CD8+ T cells. DC licensing may result in the upregulation of co-stimulatory molecules, increased survival and better cross-presenting capabilities of DCs. This process may be mediated via CD40/CD40L interaction [S. R. Bennet et al., "Help for cytotoxic T-cell responses is mediated by CD40 signalling," Nature 393(6684):478-480 (1998); S. P. Schoenberger et al., "T-cell help for cytotoxic T-cell help is mediated by CD40-CD40L interactions," Nature 393(6684):480-483 (1998)], but CD40/CD40L-independent mechanisms also exist (CD70, LTβR). In addition, a direct interaction between CD40L expressed on DCs and CD40 on expressed on CD8+ T-cells has also been suggested, providing a possible explanation for the generation of helper-independent CTL responses [S. Johnson et al., "Selected Toll-like receptor ligands and viruses promote helper-independent cytotoxic T-cell priming by upregulating CD40L on dendritic cells," Immunity 30(2):218-227 (2009)].

Example 1

Exemplary Nucleic Acid and Amino Acid Sequences

TABLE 2

| CD8-TCR Constructs | | |
|---|---|---|
| Construct # | Nucleic Acid (SEQ ID NO) | Amino Acid (SEQ ID NO) |
| 1 | 295 | 296 |
| 2 | 297 | 298 |

TABLE 2-continued

| CD8-TCR Constructs | | |
|---|---|---|
| Construct # | Nucleic Acid (SEQ ID NO) | Amino Acid (SEQ ID NO) |
| 8 | 299 | 300 |
| 9 | 287 | 288 |
| 9b | 287 | 288 |
| 10 | 291 | 292 |
| 10n | 291 | 292 |
| 11 | 285 | 286 |
| 11n | 285 | 286 |
| 12 | 301 | 302 |
| 13 | 267 | 268 |
| 14 | 269 | 270 |
| 15 | 271 | 272 |
| 16 | 273 | 274 |
| 17 | 275 | 276 |
| 18 | 277 | 278 |
| 19 | 279 | 280 |
| 21 | 281 | 282 |
| 22 | 283 | 284 |
| 25 | 289 | 290 |

Figure 9A:
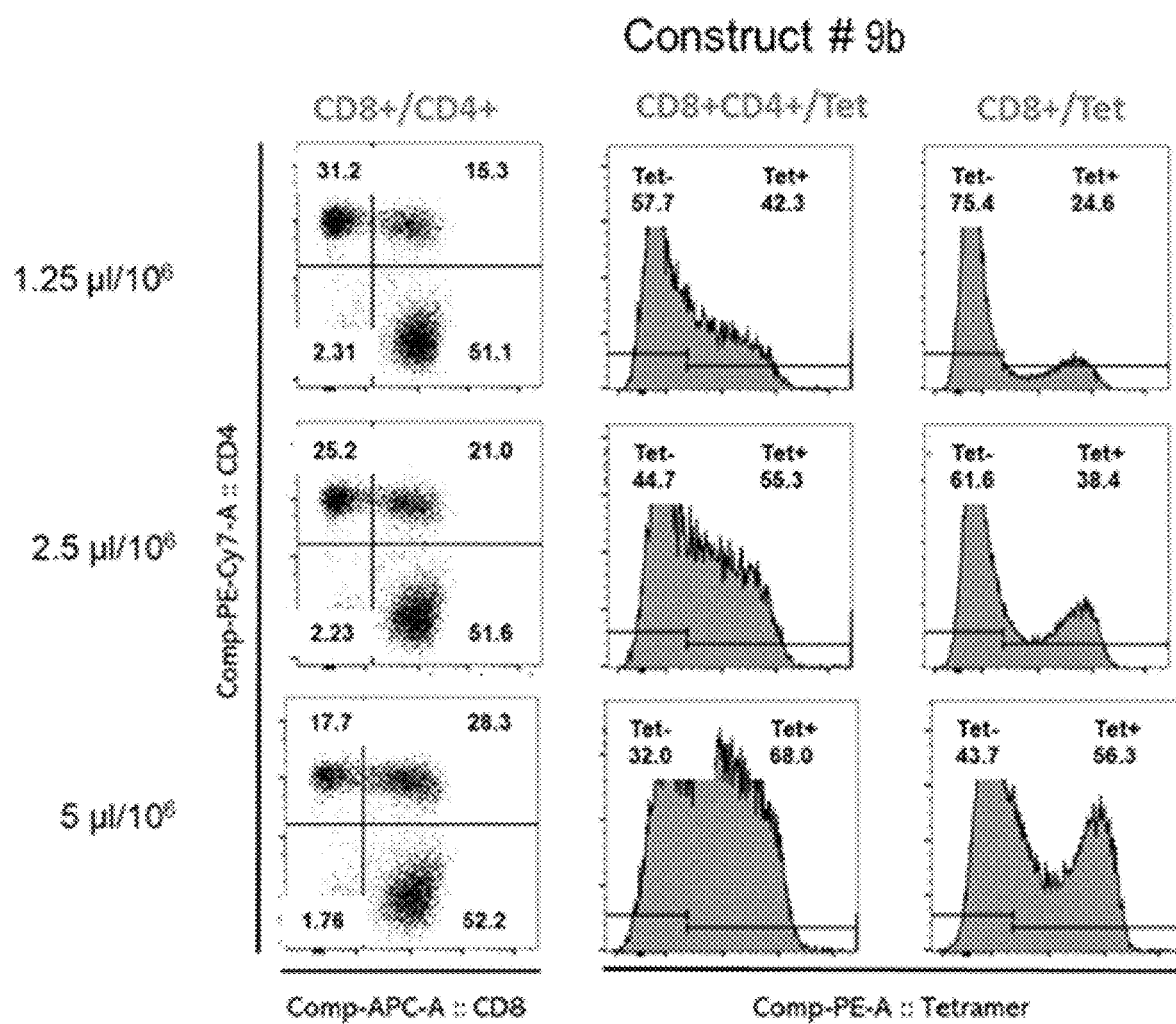
FIG. 9A shows flow plots of cells transduced with Construct #9.
Figure 9B:
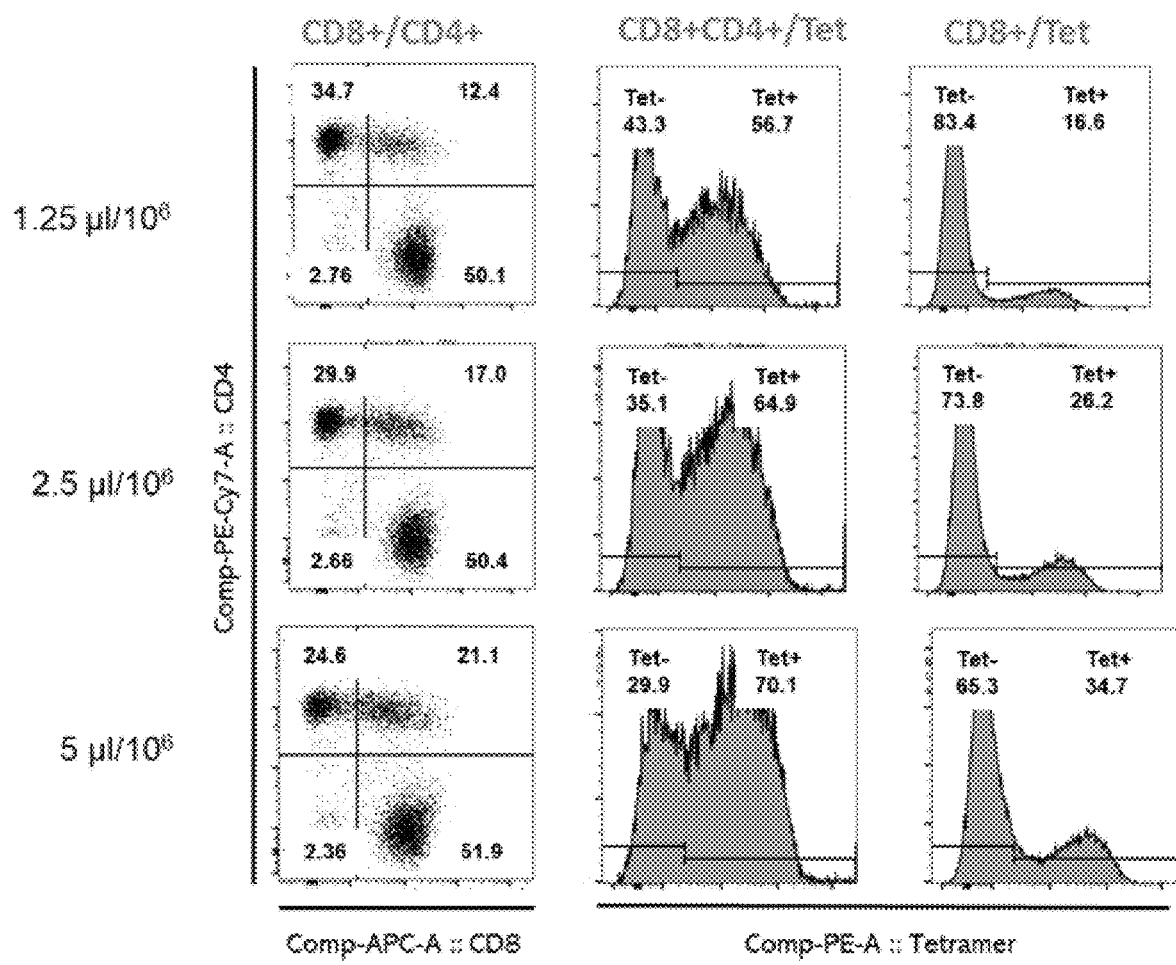
FIG. 9B shows flow plots of cells transduced with Construct #10 in accordance with one embodiment of the present disclosure.
Figure 9C:
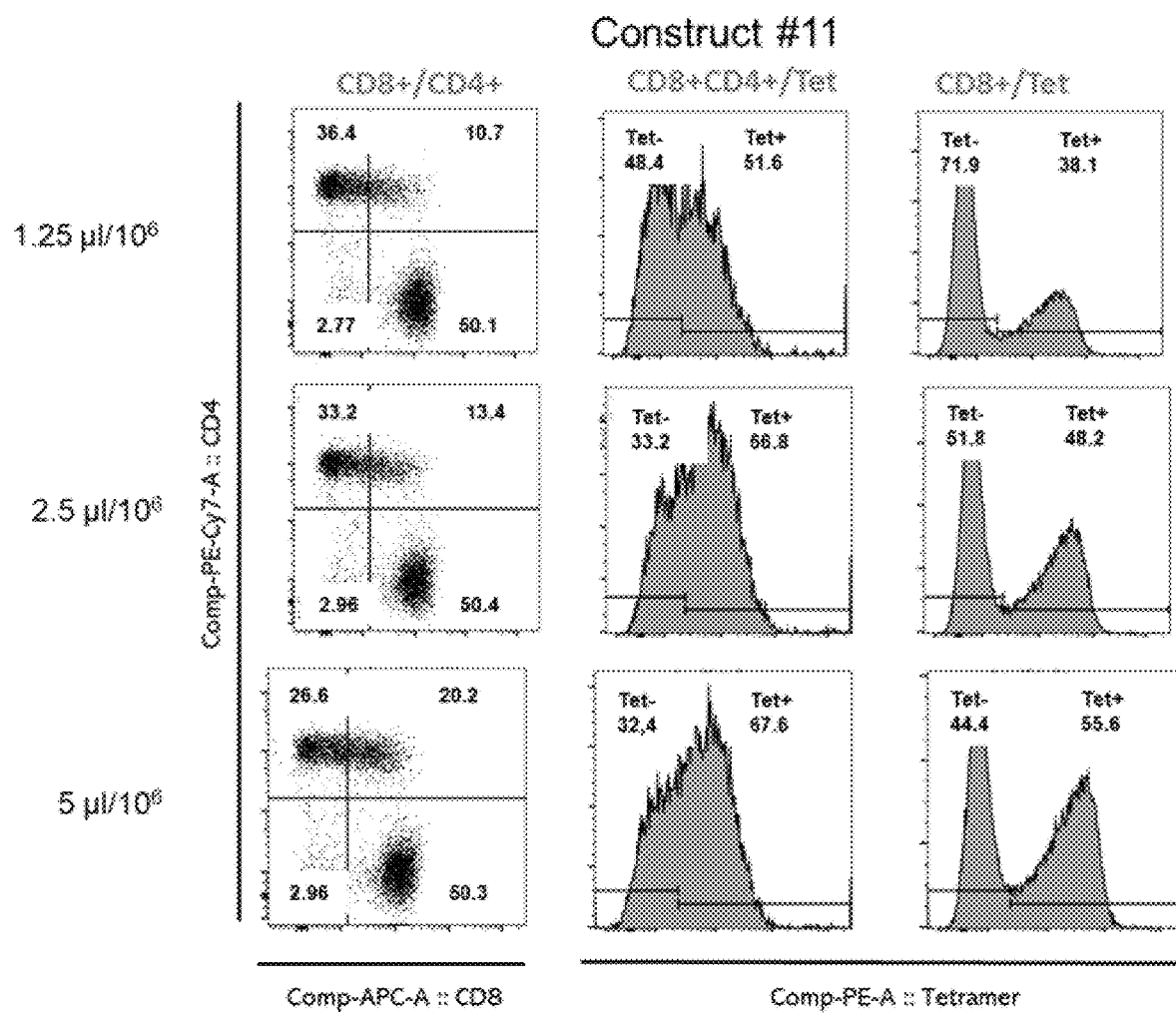
FIG. 9C shows flow plots of cells transduced with Construct #11.
Figure 9D:
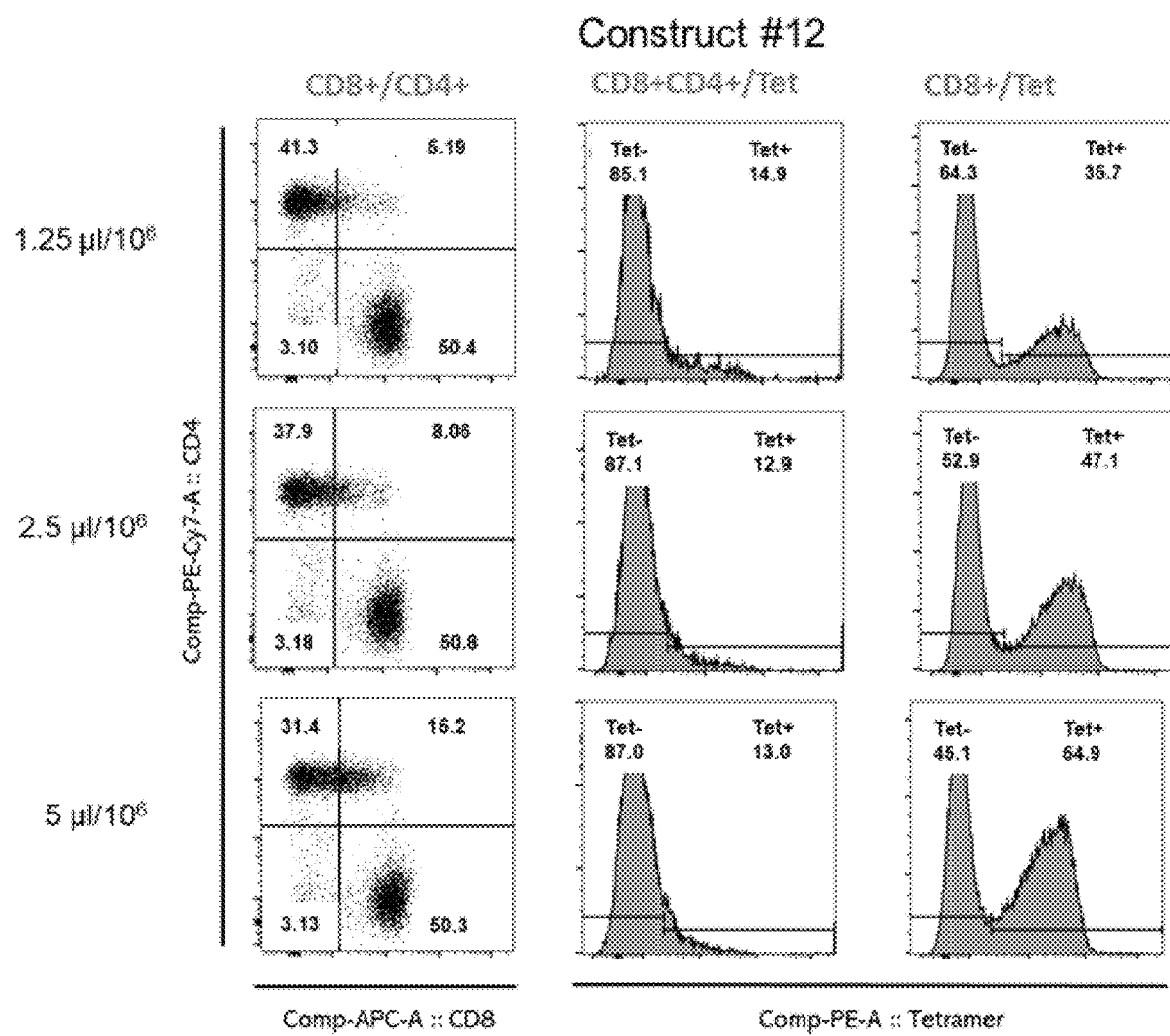
FIG. 9D shows flow plots of cells transduced with Construct #12.

The inventors found that the various CD8 elements in the vector lead to a surprising increase in expression and activity. For example, despite the observation that Construct #10 has lower viral titers than Constructs #9b, #11, and #12 (FIG. 5A), T cells transduced with Construct #10 expressing CD8αβ heterodimer and TCR at the lowest viral volumetric concentration, e.g., 1.25 μl/$10^6$ cells, generated higher CD8+ CD4+TCR+ cells (56.7%, FIG. 9B) than that of transduced with Construct #9b expressing CD8α and TCR (42.3%, FIG. 9A), Construct #11 expressing CD8αCD8βstalk with CD8α transmembrane and intracellular domain and TCR (51.6%, FIG. 9C), and Construct #12 expressing CD8αCD8βstalk with Neural Cell Adhesion Molecule 1 (NCAM1) transmembrane and intracellular domain and TCR (14.9%, FIG. 9D).

A vector may comprise any one of nucleic acid sequences of SEQ ID NO: 267, 269, 271, 273, 275, 277, 279, 281, 283, 285, 287, 289, 291, 295, 297, 299, or 301.

A T-cell may be transduced to express the nucleic acid of SEQ ID NO: 267, 269, 271, 273, 275, 277, 279, 281, 283, 285, 287, 289, 291, 295, 297, 299, or 301.

Several of the elements of the constructs in Table 2 are described in Table 3.

TABLE 3

Representative Protein and DNA sequences

| SEQ ID NO: | Description | Sequence |
|---|---|---|
| 1 | CD8α Ig-like domain-1 | SQFRVSPLDRTWNLGETVELKCQVLLSNPTSGCSWLFQ PRGAAASPTFLLYLSQNKPKAAEGLDTQRFSGKRLGDT FVLTLSDFRRENEGYYFCSALSNSIMYFSHFVPVFLPA |
| 2 | CD8β region | SVVDFLPTTAQPTKKSTLKKRVCRLPRPETQKGPLCSP |
| 3 | CD8α transmembrane domain | IYIWAPLAGTCGVLLLSLVIT |
| 4 | CD8α cytoplasmic tail | LYCNHRNRRRVCKCPRPVVKSGDKPSLSARYV |
| 5 | m1CD8α (signal-less) | SQFRVSPLDRTWNLGETVELKCQVLLSNPTSGCSWLFQ PRGAAASPTFLLYLSQNKPKAAEGLDTQRFSGKRLGDT FVLTLSDFRRENEGYYFCSALSNSIMYFSHFVPVFLPAS |

TABLE 3-continued

Representative Protein and DNA sequences

| SEQ ID NO: | Description | Sequence |
|---|---|---|
|  |  | VVDFLPTTAQPTKKSTLKKRVCRLPRPETQKGPLCSPIYI<br>WAPLAGTCGVLLLSLVITLYCNHRNRRRVCKCPRPVVK<br>SGDKPSLSARYV |
| 6 | CD8α Signal peptide | MALPVTALLLPLALLLHAARP |
| 7 | m1CD8α | MALPVTALLLPLALLLHAARPSQFRVSPLDRTWNLGET<br>VELKCQVLLSNPTSGCSWLFQPRGAAASPTFLLYLSQN<br>KPKAAEGLDTQRFSGKRLGDTFVLTLSDFRRENEGYYF<br>CSALSNSIMYFSHFVPVFLPASVVDFLPTTAQPTKKSTL<br>KKRVCRLPRPETQKGPLCSPIYIWAPLAGTCGVLLLSLVI<br>TLYCNHRNRRRVCKCPRPVVKSGDKPSLSARYV |
| 8 | CD8β1 | MRPRLWLLLAAQLTVLHGNSVLQQTPAYIKVQTNKMV<br>MLSCEAKISLSNMRIYWLRQRQAPSSDSHHEFLALWDS<br>AKGTIHGEEVEQEKIAVFRDASRFILNLTSVKPEDSGIYF<br>CMIVGSPELTFGKGTQLSVVDFLPTTAQPTKKSTLKKRV<br>CRLPRPETQKGPLCSPITLGLLVAGVLVLLVSLGVAIHL<br>CCRRRRARLRFMKQPQGEGISGTFVPQCLHGYYSNTTT<br>SQKLLNPWILKT |
| 9 | CD8β2 | MRPRLWLLLAAQLTVLHGNSVLQQTPAYIKVQTNKMV<br>MLSCEAKISLSNMRIYWLRQRQAPSSDSHHEFLALWDS<br>AKGTIHGEEVEQEKIAVFRDASRFILNLTSVKPEDSGIYF<br>CMIVGSPELTFGKGTQLSVVDFLPTTAQPTKKSTLKKRV<br>CRLPRPETQKGLKGKVYQEPLSPNACMDTTAILQPHRS<br>CLTHGS |
| 10 | CD8β3 | LQQTPAYIKVQTNKMVMLSCEAKISLSNMRIYWLRQRQ<br>APSSDSHHEFLALWDSAKGTIHGEEVEQEKIAVFRDASR<br>FILNLTSVKPEDSGIYFCMIVGSPELTFGKGTQLSVVDFL<br>PTTAQPTKKSTLKKRVCRLPRPETQKGPLCSPITLGLLV<br>AGVLVLLVSLGVAIHLCCRRRRARLRFMKQFYK |
| 11 | CD8β4 | LQQTPAYIKVQTNKMVMLSCEAKISLSNMRIYWLRQRQ<br>APSSDSHHEFLALWDSAKGTIHGEEVEQEKIAVFRDASR<br>FILNLTSVKPEDSGIYFCMIVGSPELTFGKGTQLSVVDFL<br>PTTAQPTKKSTLKKRVCRLPRPETQKGPLCSPITLGLLV<br>AGVLVLLVSLGVAIHLCCRRRRARLRFMKQLRLHPLEK<br>CSRMDY |
| 12 | CD8β5 | LQQTPAYIKVQTNKMVMLSCEAKISLSNMRIYWLRQRQ<br>APSSDSHHEFLALWDSAKGTIHGEEVEQEKIAVFRDASR<br>FILNLTSVKPEDSGIYFCMIVGSPELTFGKGTQLSVVDFL<br>PTTAQPTKKSTLKKRVCRLPRPETQKGPLCSPITLGLLV<br>AGVLVLLVSLGVAIHLCCRRRRARLRFMKQFNIVCLK<br>ISGFTTCCCFQILQISREYGFGVLLQKDIGQ |
| 13 | CD8β6 | LQQTPAYIKVQTNKMVMLSCEAKISLSNMRIYWLRQRQ<br>APSSDSHHEFLALWDSAKGTIHGEEVEQEKIAVFRDASR<br>FILNLTSVKPEDSGIYFCMIVGSPELTFGKGTQLSVVDFL<br>PTTAQPTKKSTLKKRVCRLPRPETQKGPLCSPITLGLLV<br>AGVLVLLVSLGVAIHLCCRRRRARLRFMKQKFNIVCLK<br>ISGFTTCCCFQILQISREYGFGVLLQKDIGQ |
| 14 | CD8β7 | LQQTPAYIKVQTNKMVMLSCEAKISLSNMRIYWLRQRQ<br>APSSDSHHEFLALWDSAKGTIHGEEVEQEKIAVFRDASR<br>FILNLTSVKPEDSGIYFCMIVGSPELTFGKGTQLSVVDFL<br>PTTAQPTKKSTLKKRVCRLPRPETQKGPLCSPITLGLLV<br>AGVLVLLVSLGVAIHLCCRRRRARLRFMKQPQGEGISG<br>TFVPQCLHGYYSNTTTSQKLLNPWILKT |
| 15 | R11KEA alpha chain | MEKNPLAAPLLILWFHLDCVSSILNVEQSPQSLHVQEGD<br>STNFTCSFPSSNFYALHWYRKETAKSPEALFVMTLNGD<br>EKKKGRISATLNTKEGYSYLYIKGSQPEDSATYLCALYN<br>NNDMRFGAGTRLTVKPNIQNPDPAVYQLRDSKSSDKSV<br>CLFTDFDSQTNVSQSKDSDVYITDKTVLDMRSMDFKSN<br>SAVAWSNKSDFACANAFNNSIIPEDTFFPSPESSCDVKL<br>VEKSFETDTNLNFQNLSVIGFRILLLKVAGFNLLMTLRL<br>WSS |
| 16 | R11KE beta chain | MDSWTFCCVSLCILVAKHTDAGVIQSPRHEVTEMGQEV<br>TLRCKPISGHNLFWYRETMMRGLELLIYFNNNVPIDDS<br>GMPEDRFSAKMPNASFSTLKIQPSEPRDSAVYFCASSPG |

TABLE 3-continued

Representative Protein and DNA sequences

| SEQ ID NO: | Description | Sequence |
|---|---|---|
| | | STDTQYFGPGTRLTVLEDLKNVFPPEVAVFEPSEAEISHT QKATLVCLATGFYPDHVELSWWVNGKEVHSGVSTDPQ PLKEQPALNDSRYCLSSRLRVSATFWQNPRNHFRCQVQ FYGLSENDEWTQDRAKPVTQIVSAEAWGRADCGFTSES YQQGVLSATILYEILLGKATLYAVLVSALVLMAMVKR KDSRG |
| 17 | R20P1H7 alpha chain | MEKMLECAFIVLWLQLGWLSGEDQVTQSPEALRLQEG ESSSLNCSYTVSGLRGLFWYRQDPGKGPEFLFTLYSAGE EKEKERLKATLTKKESFLHITAPKPEDSATYLCAVQGEN SGYSTLTFGKGTMLLVSPDIQNPDPAVYQLRDSKSSDKS VCLFTDFDSQTNVSQSKDSDVYITDKTVLDMRSMDFKS NSAVAWSNKSDFACANAFNNSIIPEDTFFPSPESSCDVK LVEKSFETDTNLNFQNLSVIGFRILLLKVAGFNLLMTLR LWSS |
| 18 | R20P1H7 beta chain | MGPQLLGYVVLCLLGAGPLEAQVTQNPRYLITVTGKKL TVTCSQNMNHEYMSWYRQDPGLGLRQIYYSMNVEVT DKGDVPEGYKVSRKEKRNFPLILESPSPNQTSLYFCASS LGPGLAAYNEQFFGPGTRLTVLEDLKNVFPPEVAVFEPS EAEISHTQKATLVCLATGFYPDHVELSWWVNGKEVHS GVSTDPQPLKEQPALNDSRYCLSSRLRVSATFWQNPRN HFRCQVQFYGLSENDEWTQDRAKPVTQIVSAEAWGRA DCGFTSESYQQGVLSATILYEILLGKATLYAVLVSALVL MAMVKRKDSRG |
| 19 | R7P1D5 alpha chain | MKTFAGFSFLFLWLQLDCMSRGEDVEQSLFLSVREGDS SVINCTYTDSSSTYLYWYKQEPGAGLQLLTYIFSNMDM KQDQRLTVLLNKKDKHLSLRIADTQTGDSAIYFCAEYS SASKIIFGSGTRLSIRPNIQNPDPAVYQLRDSKSSDKSVC LFTDFDSQTNVSQSKDSDVYITDKTVLDMRSMDFKSNS AVAWSNKSDFACANAFNNSIIPEDTFFPSPESSCDVKLV EKSFETDTNLNFQNLSVIGFRILLLKVAGFNLLMTLRLW SS |
| 20 | R7P1D5 beta chain | MGSWTLCCVSLCILVAKHTDAGVIQSPRHEVTEMGQEV TLRCKPISGHDYLFWYRQTMMRGLELLIYFNNNVPIDD SGMPEDRFSAKMPNASFSTLKIQPSEPRDSAVYFCASRA NTGELFFGEGSRLTVLEDLKNVFPPEVAVFEPSEAEISHT QKATLVCLATGFYPDHVELSWWVNGKEVHSGVSTDPQ PLKEQPALNDSRYCLSSRLRVSATFWQNPRNHFRCQVQ FYGLSENDEWTQDRAKPVTQIVSAEAWGRADCGFTSES YQQGVLSATILYEILLGKATLYAVLVSALVLMAMVKR KDSRG |
| 21 | R10P2G12 alpha chain | MLTASLLRAVIASICVVSSMAQKVTQAQTEISVVEKED VTLDCVYETRDTTYYLFWYKQPPSGELVFLIRRNSFDE QNEISGRYSWNFQKSTSSFNFTITASQVVDSAVYFCALS EGNSGNTPLVFGKGTRLSVIANIQNPDPAVYQLRDSKSS DKSVCLFTDFDSQTNVSQSKDSDVYITDKTVLDMRSMD FKSNSAVAWSNKSDFACANAFNNSIIPEDTFFPSPESSCD VKLVEKSFETDTNLNFQNLSVIGFRILLLKVAGFNLLMT LRLWSS |
| 22 | R10P2G12 beta chain | MGIRLLCRVAFCFLAVGLVDVKVTQSSRYLVKRTGEKV FLECVQDMDHENMFWYRQDPGLGLRLIYFSYDVKMKE KGDIPEGYSVSREKKERFSLILESASTNQTSMYLCASSLS SGSHQETQYFGPGTRLLVLEDLKNVFPPEVAVFEPSEAE ISHTQKATLVCLATGFYPDHVELSWWVNGKEVHSGVS TDPQPLKEQPALNDSRYCLSSRLRVSATFWQNPRNHFR CQVQFYGLSENDEWTQDRAKPVTQIVSAEAWGRADCG FTSESYQQGVLSATILYEILLGKATLYAVLVSALVLMA MVKRKDSRG |
| 23 | R10P1A7 alpha chain | MKTFAGFSFLFLWLQLDCMSRGEDVEQSLFLSVREGDS SVINCTYTDSSSTYLYWYKQEPGAGLQLLTYIFSNMDM KQDQRLTVLLNKKDKHLSLRIADTQTGDSAIYFCAESK ETRLMFGDGTQLVVKPNIQNPDPAVYQLRDSKSSDKSV CLFTDFDSQTNVSQSKDSDVYITDKTVLDMRSMDFKSN SAVAWSNKSDFACANAFNNSIIPEDTFFPSPESSCDVKL VEKSFETDTNLNFQNLSVIGFRILLLKVAGFNLLMTLRL WSS |

TABLE 3-continued

Representative Protein and DNA sequences

| SEQ ID NO: | Description | Sequence |
|---|---|---|
| 24 | R10P1A7 beta chain | MLLLLLLLGPGISLLLPGSLAGSGLGAWSQHPSVWICKS GTSVKIECRSLDFQATTMFWYRQFPKQSLMLMATSNEG SKATYEQGVEKDKFLINHASLTLSTLTVTSAHPEDSSFYI CSARAGGHEQFFGPGTRLTVLEDLKNVFPPEVAVFEPSE AEISHTQKATLVCLATGFYPDHVELSWWVNGKEVHSG VSTDPQPLKEQPALNDSRYCLSSRLRVSATFWQNPRNH FRCQVQFYGLSENDEWTQDRAKPVTQIVSAEAWGRAD CGFTSESYQQGVLSATILYEILLGKATLYAVLVSALVLM AMVKRKDSRG |
| 25 | R4P1D10 alpha chain | MKSLRVLLVILWLQLSWVWSQQKEVEQNSGPLSVPEG AIASLNCTYSDRGSQSFFWYRQYSGKSPELIMFIYSNGD KEDGRFTAQLNKASQYVSLLIRDSQPSDSATYLCAVNF HDKIIFGKGTRLHILPNIQNPDAVYQLRDSKSSDKSVCL FTDFDSQTNVSQSKDSDVYITDKTVLDMRSMDFKSNSA VAWSNKSDFACANAFNNSIIPEDTFFPSPESSCDVKLVE KSFETDTNLNFQNLSVIGFRILLLKVAGFNLLMTLRLWS S |
| 26 | R4P1D10 beta chain | MGFRLLCCVAFCLLGAGPVDSGVTQTPKHLITATGQRV TLRCSPRSGDLSVYWYQQSLDQGLQFLIHYYNGEERAK GNILERFSAQQFPDLHSELNLSSLELGDSALYFCASSVAS AYGYTFGSGTRLTVVEDLNKVFPPEVAVFEPSEAEISHT QKATLVCLATGFFPDHVELSWWVNGKEVHSGVSTDPQ PLKEQPALNDSRYCLSSRLRVSATFWQNPRNHFRCQVQ FYGLSENDEWTQDRAKPVTQIVSAEAWGRADCGFTSV SYQQGVLSATILYEILLGKATLYAVLVSALVLMAMVKR KDF |
| 27 | R4P3F9 alpha chain | MKSLRVLLVILWLQLSWVWSQQKEVEQNSGPLSVPEG AIASLNCTYSDRGSQSFFWYRQYSGKSPELIMFIYSNGD KEDGRFTAQLNKASQYVSLLIRDSQPSDSATYLCAAYS GAGSYQLTFGKGTKLSVIPNIQNPDPAVYQLRDSKSSDK SVCLFTDFDSQTNVSQSKDSDVYITDKTVLDMRSMDFK SNSAVAWSNKSDFACANAFNNSIIPEDTFFPSPESSCDV KLVEKSFETDTNLNFQNLSVIGFRILLLKVAGFNLLMTL RLWSS |
| 28 | R4P3F9 beta chain | MGFRLLCCVAFCLLGAGPVDSGVTQTPKHLITATGQRV TLRCSPRSGDLSVYWYQQSLDQGLQFLIQYYNGEERAK GNILERFSAQQFPDLHSELNLSSLELGDSALYFCASSVES SYGYTFGSGTRLTVVEDLNKVFPPEVAVFEPSEAEISHT QKATLVCLATGFFPDHVELSWWVNGKEVHSGVSTDPQ PLKEQPALNDSRYCLSSRLRVSATFWQNPRNHFRCQVQ FYGLSENDEWTQDRAKPVTQIVSAEAWGRADCGFTSV SYQQGVLSATILYEILLGKATLYAVLVSALVLMAMVKR KDF |
| 29 | R4P3H3 alpha chain | MKSLRVLLVILWLQLSWVWSQQKEVEQNSGPLSVPEG AIASLNCTYSDRGSQSFFWYRQYSGKSPELIMFIYSNGD KEDGRFTAQLNKASQYVSLLIRDSQPSDSATYLCAVKA GNQFYFGTGTSLTVIPNIQNPDPAVYQLRDSKSSDKSVC LFTDFDSQTNVSQSKDSDVYITDKTVLDMRSMDFKSNS AVAWSNKSDFACANAFNNSIIPEDTFFPSPESSCDVKLV EKSFETDTNLNFQNLSVIGFRILLLKVAGFNLLMTLRLW SS |
| 30 | R4P3H3 beta chain | MGTRLLCWVVLGFLGTDHTGAGVSQSPRYKVAKRGQ DVALRCDPISGHVSLFWYQQALGQGPEFLTYFQNEAQL DKSGLPSDRFFAERPEGSVSTLKIQRTQQEDSAVYLCAS SLLTSGGDNEQFFGPGTRLTVLEDLKNVFPPEVAVFEPS EAEISHTQKATLVCLATGFYPDHVELSWWVNGKEVHS GVSTDPQPLKEQPALNDSRYCLSSRLRVSATFWQNPRN HFRCQVQFYGLSENDEWTQDRAKPVTQIVSAEAWGRA DCGFTSESYQQGVLSATILYEILLGKATLYAVLVSALVL MAMVKRKDSRG |
| 31 | R36P3F9 alpha chain | METLLGVSLVILWLQLARVNSQQGEEDPQALSIQEGEN ATMNCSYKTSINNLQWYRQNSGRGLVHLILIRSNEREK HSGRLRVTLDTSKKSSSLLITASRAADTASYFCATVSNY QLIWGAGTKLIIKPDIQNPDPAVYQLRDSKSSDKSVCLF TDFDSQTNVSQSKDSDVYITDKTVLDMRSMDFKSNSAV AWSNKSDFACANAFNNSIIPEDTFFPSPESSCDVKLVEKS FETDTNLNFQNLSVIGFRILLLKVAGFNLLMTLRLWSS |

TABLE 3-continued

Representative Protein and DNA sequences

| SEQ ID NO: | Description | Sequence |
|---|---|---|
| 32 | R36P3F9 beta chain | MGPQLLGYVVLCLLGAGPLEAQVTQNPRYLITVTGKKL TVTCSQNMNHEYMSWYRQDPGLGLRQIYYSMNVEVT DKGDVPEGYKVSRKEKRNFPLILESPSPNQTSLYFCASS STSGGLSGETQYFGPGTRLLVLEDLKNVFPPEVAVFEPS EAEISHTQKATLVCLATGFYPDHVELSWWVNGKEVHS GVSTDPQPLKEQPALNDSRYCLSSRLRVSATFWQNPRN HFRCQVQFYGLSENDEWTQDRAKPVTQIVSAEAWGRA DCGFTSESYQQGVLSATILYEILLGKATLYAVLVSALVL MAMVKRKDSRG |
| 33 | R52P2G11 alpha chain | MKKHLTTFLVILWLYFYRGNGKNQVEQSPQSLIILEGK NCTLQCNYTVSPFSNLRWYKQDTGRGPVSLTIMTFSEN TKSNGRYTATLDADTKQSSLHITASQLSDSASYICVVSA YGKLQFGAGTQVVVTPDIQNPDPAVYQLRDSKSSDKSV CLFTDFDSQTNVSQSKDSDVYITDKTVLDMRSMDFKSN SAVAWSNKSDFACANAFNNSIIPEDTFFPSPESSCDVKL VEKSFETDTNLNFQNLSVIGFRILLLKVAGFNLLMTLRL WSS |
| 34 | R52P2G11 beta chain | MDSWTFCCVSLCILVAKHTDAGVIQSPRHEVTEMGQEV TLRCKPISGHNSLFWYRQTMMRGLELLIYFNNNVPIDDS GMPEDRFSAKMPNASFSTLKIQPSEPRDSAVYFCASSLG SPDGNQPQHFGDGTRLSILEDLNKVFPPEVAVFEPSEAEI SHTQKATLVCLATGFFPDHVELSWWVNGKEVHSGVST DPQPLKEQPALNDSRYCLSSRLRVSATFWQNPRNHFRC QVQFYGLSENDEWTQDRAKPVTQIVSAEAWGRADCGF TSVSYQQGVLSATILYEILLGKATLYAVLVSALVLMAM VKRKDF |
| 35 | R53P2A9 alpha chain | MACPGFLWALVISTCLEFSMAQTVTQSQPEMSVQEAET VTLSCTYDTSESDYYLFWYKQPPSRQMILVIRQEAYKQ QNATENRFSVNFQKAAKSFSLKISDSQLGDAAMYFCAY NSYAGGTSYGKLTFGQGTILTVHPNIQNPDPAVYQLRD SKSSDKSVCLFTDFDSQTNVSQSKDSDVYITDKTVLDM RSMDFKSNSAVAWSNKSDFACANAFNNSIIPEDTFFPSP ESSCDVKLVEKSFETDTNLNFQNLSVIGFRILLLKVAGF NLLMTLRLWSS |
| 36 | R53P2A9 beta chain | MGPGLLCWVLLCLLGAGPVDAGVTQSPTHLIKTRGQQ VTLRCSPISGHKSVSWYQQVLGQGPQFIFQYYEKEERG RGNFPDRFSARQFPNYSSELNVNALLLGDSALYLCASSL DGTSEQYFGPGTRLTVTEDLKNVFPPEVAVFEPSEAEIS HTQKATLVCLATGFYPDHVELSWWVNGKEVHSGVSTD PQPLKEQPALNDSRYCLSSRLRVSATFWQNPRNHFRCQ VQFYGLSENDEWTQDRAKPVTQIVSAEAWGRADCGFT SESYQQGVLSATILYEILLGKATLYAVLVSALVLMAMV KRKDSRG |
| 37 | R26P1A9 alpha chain | METLLGVSLVILWLQLARVNSQQGEEDPQALSIQEGEN ATMNCSYKTSINNLQWYRQNSGRGLVHLILIRSNEREK HSGRLRVTLDTSKKSSSLLITASRAADTASYFCLIGASGS RLTFGEGTQLTVNPDIQNPDPAVYQLRDSKSSDKSVCLF TDFDSQTNVSQSKDSDVYITDKTVLDMRSMDFKSNSAV AWSNKSDFACANAFNNSIIPEDTFFPSPESSCDVKLVEKS FETDTNLNFQNLSVIGFRILLLKVAGFNLLMTLRLWSS |
| 38 | R26P1A9 beta chain | MGSWTLCCVSLCILVAKHTDAGVIQSPRHEVTEMGQEV TLRCKPISGHDYLFWYRQTMMRGLELLIYFNNNVPIDD SGMPEDRFSAKMPNASFSTLKIQPSEPRDSAVYFCASSY FGWNEKLFFGSGTQLSVLEDLNKVFPPEVAVFEPSEAEI SHTQKATLVCLATGFFPDHVELSWWVNGKEVHSGVST DPQPLKEQPALNDSRYCLSSRLRVSATFWQNPRNHFRC QVQFYGLSENDEWTQDRAKPVTQIVSAEAWGRADCGF TSVSYQQGVLSATILYEILLGKATLYAVLVSALVLMAM VKRKDF |
| 39 | R26P2A6 alpha chain | MMKSLRVLLVILWLQLSWVWSQQKEVEQDPGPLSVPE GAIVSLNCTYSNSAFQYFMWYRQYSRKGPELLMYTYSS GNKEDGRFTAQVDKSSKYISLFIRDSQPSDSATYLCAMS DVSGGYNKLIFGAGTRLAVHPYIQNPDPAVYQLRDSKS SDKSVCLFTDFDSQTNVSQSKDSDVYITDKTVLDMRSM DFKSNSAVAWSNKSDFACANAFNNSIIPEDTFFPSPESSC DVKLVEKSFETDTNLNFQNLSVIGFRILLLKVAGFNLLM TLRLWSS |

TABLE 3-continued

Representative Protein and DNA sequences

| SEQ ID NO: | Description | Sequence |
|---|---|---|
| 40 | R26P2A6 beta chain | MGPQLLGYVVLCLLGAGPLEAQVTQNPRYLITVTGKKL TVTCSQNMNHEYMSWYRQDPGLGLRQIYYSMNVEVT DKGDVPEGYKVSRKEKRNFPLILESPSPNQTSLYFCAST TPDGTDEQFFGPGTRLTVLEDLKNVFPPEVAVFEPSEAEI SHTQKATLVCLATGFYPDHVELSWWVNGKEVHSGVST DPQPLKEQPALNDSRYCLSSRLRVSATFWQNPRNHFRC QVQFYGLSENDEWTQDRAKPVTQIVSAEAWGRADCGF TSESYQQGVLSATILYEILLGKATLYAVLVSALVLMAM VKRKDSRG |
| 41 | R26P3H1 alpha chain | MASAPISMLAMLFTLSGLRAQSVAQPEDQVNVAEGNPL TVKCTYSVSGNPYLFWYVQYPNRGLQFLLKYITGDNLV KGSYGFEAEFNKSQTSFHLKKPSALVSDSALYFCAVRD MNRDDKIIFGKGTRLHILPNIQNPDPAVYQLRDSKSSDK SVCLFTDFDSQTNVSQSKDSDVYITDKTVLDMRSMDFK SNSAVAWSNKSDFACANAFNNSIIPEDTFFPSPESSCDV KLVEKSFETDTNLNFQNLSVIGFRILLLKVAGFNLLMTL RLWSS |
| 42 | R26P3H1 beta chain | MSNQVLCCVVLCFLGANTVDGGITQSPKYLFRKEGQN VTLSCEQNLNHDAMYWYRQDPGQGLRLIYYSQIVNDF QKGDIAEGYSVSREKKESFPLTVTSAQKNPTAFYLCASS RAEGGEQYFGPGTRLTVTEDLKNVFPPEVAVFEPSEAEI SHTQKATLVCLATGFYPDHVELSWWVNGKEVHSGVST DPQPLKEQPALNDSRYCLSSRLRVSATFWQNPRNHFRC QVQFYGLSENDEWTQDRAKPVTQIVSAEAWGRADCGF TSESYQQGVLSATILYEILLGKATLYAVLVSALVLMAM VKRKDSRG |
| 43 | R35P3A4 alpha chain | MTSIRAVFIFLWLQLDLVNGENVEQHPSTLSVQEGDSA VIKCTYSDSASNYFPWYKQELGKRPQLIIDIRSNVGEKK DQRIAVTLNKTAKHFSLHITETQPEDSAVYFCAASPTGG YNKLIFGAGTRLAVHPYIQNPDPAVYQLRDSKSSDKSV CLFTDFDSQTNVSQSKDSDVYITDKTVLDMRSMDFKSN SAVAWSNKSDFACANAFNNSIIPEDTFFPSPESSCDVKL VEKSFETDTNLNFQNLSVIGFRILLLKVAGFNLLMTLRL WSS |
| 44 | R35P3A4 beta chain | MSIGLLCCAALSLLWAGPVNAGVTQTPKFQVLKTGQS MTLQCAQDMNHEYMSWYRQDPGMGLRLIHYSVGAGI TDQGEVPNGYNVSRSTTEDFPLRLLSAAPSQTSVYFCAS SLGGASQEQYFGPGTRLTVTEDLKNVFPPEVAVFEPSEA EISHTQKATLVCLATGFYPDHVELSWWVNGKEVHSGV STDPQPLKEQPALNDSRYCLSSRLRVSATFWQNPRNHF RCQVQFYGLSENDEWTQDRAKPVTQIVSAEAWGRADC GFTSESYQQGVLSATILYEILLGKATLYAVLVSALVLMA MVKRKDSRG |
| 45 | R37P1C9 alpha chain | MKLVTSITVLLSLGIMGDAKTTQPNSMESNEEEPVHLPC NHSTISGTDYIHWYRQLPSQGPEYVIHGLTSNVNNRMA SLAIAEDRKSSTLILHRATLRDAAVYYCILFNFNKFYFGS GTKLNVKPNIQNPDPAVYQLRDSKSSDKSVCLFTDFDS QTNVSQSKDSDVYITDKTVLDMRSMDFKSNSAVAWSN KSDFACANAFNNSIIPEDTFFPSPESSCDVKLVEKSFETD TNLNFQNLSVIGFRILLLKVAGFNLLMTLRLWSS |
| 46 | R37P1C9 beta chain | MGPGLLHWMALCLLGTGHGDAMVIQNPRYQVTQFGK PVTLSCSQTLNHNVMYWYQQKSSQAPKLLFHYYDKDF NNEADTPDNFQSRRPNTSFCFLDIRSPGLGDAAMYLCA TSSGETNEKLFFGSGTQLSVLEDLNKVFPPEVAVFEPSE AEISHTQKATLVCLATGFFPDHVELSWWVNGKEVHSG VSTDPQPLKEQPALNDSRYCLSSRLRVSATFWQNPRNH FRCQVQFYGLSENDEWTQDRAKPVTQIVSAEAWGRAD CGFTSVSYQQGVLSATILYEILLGKATLYAVLVSALVLM AMVKRKDF |
| 47 | R37P1H1 alpha chain | MTRVSLLWAVVVSTCLESGMAQTVTQSQPEMSVQEAE TVTLSCTYDTSESNYYLFWYKQPPSRQMILVIRQEAYK QQNATENRFSVNFQKAAKSFSLKISDSQLGDTAMYFCA FGYSGGGADGLTFGKGTHLIIQPYIQNPDPAVYQLRDSK SSDKSVCLFTDFDSQTNVSQSKDSDVYITDKTVLDMRS MDFKSNSAVAWSNKSDFACANAFNNSIIPEDTFFPSPES SCDVKLVEKSFETDTNLNFQNLSVIGFRILLLKVAGFNL LMTLRLWSS |

TABLE 3-continued

Representative Protein and DNA sequences

| SEQ ID NO: | Description | Sequence |
|---|---|---|
| 48 | R37P1H1 beta chain | MGPGLLCWALLCLLGAGLVDAGVTQSPTHLIKTRGQQ VTLRCSPKSGHDTVSWYQQALGQGPQFIFQYYEEERQ RGNFPDRFSGHQFPNYSSELNVNALLLGDSALYLCASS NEGQGWEAEAFFGQGTRLTVVEDLNKVFPPEVAVFEPS EAEISHTQKATLVCLATGFFPDHVELSWWVNGKEVHSG VSTDPQPLKEQPALNDSRYCLSSRLRVSATFWQNPRNH FRCQVQFYGLSENDEWTQDRAKPVTQIVSAEAWGRAD CGFTSVSYQQGVLSATILYEILLGKATLYAVLVSALVLM AMVKRKDF |
| 49 | R42P3A9 alpha chain | MKRILGALLGLLSAQVCCVRGIQVEQSPPDLILQEGANS TLRCNFSDSVNNLQWFHQNPWGQLINLFYIPSGTKQNG RLSATTVATERYSLLYISSSQTTDSGVYFCAVHNFNKFY FGSGTKLNVKPNIQNPDPAVYQLRDSKSSDKSVCLFTDF DSQTNVSQSKDSDVYITDKTVLDMRSMDFKSNSAVAW SNKSDFACANAFNNSIIPEDTFFPSPESSCDVKLVEKSFE TDTNLNFQNLSVIGFRILLLKVAGFNLLMTLRLWSS |
| 50 | R42P3A9 beta chain | MLSPDLPDSAWNTRLLCHVMLCLLGAVSVAAGVIQSPR HLIKEKRETATLKCYPIPRHDTVYWYQQGPGQDPQFLIS FYEKMQSDKGSIPDRFSAQQFSDYHSELNMSSLELGDS ALYFCASSLLGQGYNEQFFGPGTRLTVEDLKNVFPPEV AVFEPSEAEISHTQKATLVCLATGFYPDHVELSWWVNG KEVHSGVSTDPQPLKEQPALNDSRYCLSSRLRVSATFW QNPRNHFRCQVQFYGLSENDEWTQDRAKPVTQIVSAE AWGRADCGFTSESYQQGVLSATILYEILLGKATLYAVL VSALVLMAMVKRKDSRG |
| 51 | R43P3F2 alpha chain | MLTASLLRAVIASICVVSSMAQKVTQAQTEISVVEKED VTLDCVYETRDTTYYLFWYKQPPSGELVFLIRRNSFDE QNEISGRYSWNFQKSTSSFNFTITASQVVDSAVYFCALS NNNAGNMLTFGGGTRLMVKPHIQNPDPAVYQLRDSKS SDKSVCLFTDFDSQTNVSQSKDSDVYITDKTVLDMRSM DFKSNSAVAWSNKSDFACANAFNNSIIPEDTFFPSPESSC DVKLVEKSFETDTNLNFQNLSVIGFRILLLKVAGFNLLM TLRLWSS |
| 52 | R43P3F2 beta chain | MLSPDLPDSAWNTRLLCHVMLCLLGAVSVAAGVIQSPR HLIKEKRETATLKCYPIPRHDTVYWYQQGPGQDPQFLIS FYEKMQSDKGSIPDRFSAQQFSDYHSELNMSSLELGDS ALYFCASSPTGTSGYNEQFFGPGTRLTVEDLKNVFPPE VAVFEPSEAEISHTQKATLVCLATGFYPDHVELSWWVN GKEVHSGVSTDPQPLKEQPALNDSRYCLSSRLRVSATF WQNPRNHFRCQVQFYGLSENDEWTQDRAKPVTQIVSA EAWGRADCGFTSESYQQGVLSATILYEILLGKATLYAV LVSALVLMAMVKRKDSRG |
| 53 | R43P3 G5 alpha chain | MEKNPLAAPLLILWFHLDCVSSILNVEQSPQSLHVQEGD STNFTCSFPSSNFYALHWYRWETAKSPEALFVMTLNGD EKKKGRISATLNTKEGYSYLYIKGSQPEDSATYLCALNR DDKIIFGKGTRLHILPNIQNPDPAVYQLRDSKSSDKSVCL FTDFDSQTNVSQSKDSDVYITDKTVLDMRSMDFKSNSA VAWSNKSDFACANAFNNSIIPEDTFFPSPESSCDVKLVE KSFETDTNLNFQNLSVIGFRILLLKVAGFNLLMTLRLWS S |
| 54 | R43P3G5 beta chain | MGIRLLCRVAFCFLAVGLVDVKVTQSSRYLVKRTGEKV FLECVQDMDHENMFWYRQDPGLGLRLIYFSYDVKMKE KGDIPEGYSVSREKKERFSLILESASTNQTSMYLCASRLP SRTYEQYFGPGTRLTVTEDLKNVFPPEVAVFEPSEAEIS HTQKATLVCLATGFYPDHVELSWWVNGKEVHSGVSTD PQPLKEQPALNDSRYCLSSRLRVSATFWQNPRNHFRCQ VQFYGLSENDEWTQDRAKPVTQIVSAEAWGRADCGFT SESYQQGVLSATILYEILLGKATLYAVLVSALVLMAMV KRKDSRG |
| 55 | R59P2E7 alpha chain | METLLGLLILWLQLQWVSSKQEVTQIPAALSVPEGENL VLNCSFTDSAIYNLQWFRQDPGKGLTSLLLIQSSQREQT SGRLNASLDKSSGRSTLYIAASQPGDSATYLCAVNSDY KLSFGAGTTVTVRANIQNPDPAVYQLRDSKSSDKSVCL FTDFDSQTNVSQSKDSDVYITDKTVLDMRSMDFKSNSA VAWSNKSDFACANAFNNSIIPEDTFFPSPESSCDVKLVE KSFETDTNLNFQNLSVIGFRILLLKVAGFNLLMTLRLWS S |

TABLE 3-continued

Representative Protein and DNA sequences

| SEQ ID NO: | Description | Sequence |
|---|---|---|
| 56 | R59P2E7 beta chain | MLSPDLPDSAWNTRLLCHVMLCLLGAVSVAAGVIQSPR HLIKEKRETATLKCYPIPRHDTVYWYQQGPGQDPQFLIS FYEKMQSDKGSIPDRFSAQQFSDYHSELNMSSLELGDS ALYFCASSLGLGTGDYGYTFGSGTRLTVVEDLNKVFPP EVAVFEPSEAEISHTQKATLVCLATGFFPDHVELSWWV NGKEVHSGVSTDPQPLKEQPALNDSRYCLSSRLRVSAT FWQNPRNHFRCQVQFYGLSENDEWTQDRAKPVTQIVS AEAWGRADCGFTSVSYQQGVLSATILYEILLGKATLYA VLVSALVLMAMVKRKDF |
| 57 | R11P3D3 alpha chain | MEKNPLAAPLLILWFHLDCVSSILNVEQSPQSLHVQEGD STNFTCSFPSSNFYALHWYRWETAKSPEALFVMTLNGD EKKKGRISATLNTKEGYSYLYIKGSQPEDSATYLCALYN NNDMRFGAGTRLTVKPNIQNPDAVYQLRDSKSSDKSV CLFTDFDSQTNVSQSKDSDVYITDKTVLDMRSMDFKSN SAVAWSNKSDFACANAFNNSIIPEDTFFPSPESSCDVKL VEKSFETDTNLNFQNLSVIGFRILLLKVAGFNLLMTLRL WSS |
| 58 | R11P3D3 beta chain | MDSWTFCCVSLCILVAKHTDAGVIQSPRHEVTEMGQEV TLRCKPISGHNSLFWYRQTMMRGLELLIYFNNNVPIDDS GMPEDRFSAKMPNASFSTLKIQPSEPRDSAVYFCASSPG STDTQYFGPGTRLTVEDLKNVFPPEVAVFEPSEAEISHT QKATLVCLATGFYPDHVELSWWVNGKEVHSGVSTDPQ PLKEQPALNDSRYCLSSRLRVSATFWQNPRNHFRCQVQ FYGLSENDEWTQDRAKPVTQIVSAEAWGRADCGFTSES YQQGVLSATILYEILLGKATLYAVLVSALVLMAMVKRK DSRG |
| 59 | R16P1C10 alpha chain | MKSLRVLLVILWLQLSWVWSQQKEVEQNSGPLSVPEG AIASLNCTYSDRGSQSFFWYRQYSGKSPELIMFIYSNGD KEDGRFTAQLNKASQYVSLLIRDSQPSDSATYLCAAVIS NFGNEKLTFGTGTRLTIIPNIQNPDAVYQLRDSKSSDKS VCLFTDFDSQTNVSQSKDSDVYITDKTVLDMRSMDFKS NSAVAWSNKSDFACANAFNNSIIPEDTFFPSPESSCDVK LVEKSFETDTNLNFQNLSVIGFRILLLKVAGFNLLMTLR LWSS |
| 60 | R16P1C10 beta chain | MGSRLLCWVLLCLLGAGPVKAGVTQTPRYLIKTRGQQ VTLSCSPISGHRSVSWYQQTPGQGLQFLFEYFSETQRNK GNFPGRFSGRQFSNSRSEMNVSTLELGDSALYLCASSP WDSPNEQYFGPGTRLTVTEDLKNVFPPEVAVFEPSEAEI SHTQKATLVCLATGFYPDHVELSWWVNGKEVHSGVST DPQPLKEQPALNDSRYCLSSRLRVSATFWQNPRNHFRC QVQFYGLSENDEWTQDRAKPVTQIVSAEAWGRADCGF TSESYQQGVLSATILYEILLGKATLYAVLVSALVLMAM VKRKDSRG |
| 61 | R16P1E8 alpha chain | MMKSLRVLLVILWLQLSWVWSQQKEVEQDPGPLSVPE GAIVSLNCTYSNSAFQYFMWYRQYSRKGPELLMYTYSS GNKEDGRFTAQVDKSSKYISLFIRDSQPSDSATYLCAMS EAAGNKLTFGGGTRVLVKPNIQNPDAVYQLRDSKSSD KSVCLFTDFDSQTNVSQSKDSDVYITDKTVLDMRSMDF KSNSAVAWSNKSDFACANAFNNSIIPEDTFFPSPESSCD VKLVEKSFETDTNLNFQNLSVIGFRILLLKVAGFNLLMT LRLWSS |
| 62 | R16P1E8 beta chain | MGTRLLCWAALCLLGAELTEAGVAQSPRYKIIEKRQSV AFWCNPISGHATLYWYQQILGQGPKLLIQFQNNGVVDD SQLPKDRFSAERLKGVDSTLKIQPAKLEDSAVYLCASSY TNQGEAFFGQGTRLTVVEDLNKVFPPEVAVFEPSEAEIS HTQKATLVCLATGFFPDHVELSWWVNGKEVHSGVSTD PQPLKEQPALNDSRYCLSSRLRVSATFWQNPRNHFRCQ VQFYGLSENDEWTQDRAKPVTQIVSAEAWGRADCGFT SVSYQQGVLSATILYEILLGKATLYAVLVSALVLMAMV KRKDF |
| 63 | R17P1A9 alpha chain | MKSLRVLLVILWLQLSWVWSQQKEVEQNSGPLSVPEG AIASLNCTYSDRGSQSFFWYRQYSGKSPELIMSIYSNGD KEDGRFTAQLNKASQYVSLLIRDSQPSDSATYLCAVLN QAGTALIFGKGTTLSVSSNIQNPDAVYQLRDSKSSDKS |

TABLE 3-continued

Representative Protein and DNA sequences

| SEQ ID NO: | Description | Sequence |
|---|---|---|
| | | VCLFTDFDSQTNVSQSKDSDVYITDKTVLDMRSMDFKS NSAVAWSNKSDFACANAFNNSIIPEDTFFPSPESSCDVK LVEKSFETDTNLNFQNLSVIGFRILLLKVAGFNLLMTLR LWSS |
| 64 | R17P1A9 beta chain | MGFRLLCCVAFCLLGAGPVDSGVTQTPKHLITATGQRV TLRCSPRSGDLSVYWYQQSLDQGLQFLIQYYNGEERAK GNILERFSAQQFPDLHSELNLSSLELGDSALYFCASSAET GPWLGNEQFFGPGTRLTVLEDLKNVFPPEVAVFEPSEAE ISHTQKATLVCLATGFYPDHVELSWWVNGKEVHSGVS TDPQPLKEQPALNDSRYCLSSRLRVSATFWQNPRNHFR CQVQFYGLSENDEWTQDRAKPVTQIVSAEAWGRADCG FTSESYQQGVLSATILYEILLGKATLYAVLVSALVLMA MVKRKDSRG |
| 65 | R17P1D7 alpha chain | MACPGFLWALVISTCLEFSMAQTVTQSQPEMSVQEAET VTLSCTYDTSESDYYLFWYKQPPSRQMILVIRQEAYKQ QNATENRFSVNFQKAAKSFSLKISDSQLGDAAMYFCAY RWAQGGSEKLVFGKGTKLTVNPYIQKPDPAVYQLRDS KSSDKSVCLFTDFDSQTNVSQSKDSDVYITDKTVLDMR SMDFKSNSAVAWSNKSDFACANAFNNSIIPEDTFFPSPE SSCDVKLVEKSFETDTNLNFQNLSVIGFRILLLKVAGFN LLMTLRLWSS |
| 66 | R17P1D7 beta chain | MTIRLLCYMGFYFLGAGLMEADIYQTPRYLVIGTGKKIT LECSQTMGHDKMYWYQQDPGMELHLIHYSYGVNSTE KGDLSSESTVSRIRTEHFPLTLESARPSHTSQYLCATELW SSGGTGELFFGEGSRLTVLEDLKNVFPPEVAVFEPSEAEI SHTQKATLVCLATGFYPDHVELSWWVNGKEVHSGVST DPQPLKEQPALNDSRYCLSSRLRVSATFWQNPRNHFRC QVQFYGLSENDEWTQDRAKPVTQIVSAEAWGRADCGF TSESYQQGVLSATILYEILLGKATLYAVLVSALVLMAM VKRKDSRG |
| 67 | R17P1G3 alpha chain | MKSLRVLLVILWLQLSWVWSQQKEVEQNSGPLSVPEG AIASLNCTYSDRGSQSFFWYRQYSGKSPELIMSIYSNGD KEDGRFTAQLNKASQYVSLLIRDSQPSDSATYLCAVGPS GTYKYIFGTGTRLKVLANIQNPDPAVYQLRDSKSSDKS VCLFTDFDSQTNVSQSKDSDVYITDKTVLDMRSMDFKS NSAVAWSNKSDFACANAFNNSIIPEDTFFPSPESSCDVK LVEKSFETDTNLNFQNLSVIGFRILLLKVAGFNLLMTLR LWSS |
| 68 | R17P1G3 beta chain | MGPQLLGYVVLCLLGAGPLEAQVTQNPRYLITVTGKKL TVTCSQNMNHEYMSWYRQDPGLGLRQIYYSMNVEVT DKGDVPEGYKVSRKEKRNFPLILESPSPNQTSLYFCASS PGGSGNEQFFGPGTRLTVLEDLKNVFPPEVAVFEPSEAE ISHTQKATLVCLATGFYPDHVELSWWVNGKEVHSGVS TDPQPLKEQPALNDSRYCLSSRLRVSATFWQNPRNHFR CQVQFYGLSENDEWTQDRAKPVTQIVSAEAWGRADCG FTSESYQQGVLSATILYEILLGKATLYAVLVSALVLMA MVKRKDSRG |
| 69 | R17P2B6 alpha chain | MKSLRVLLVILWLQLSWVWSQQKEVEQNSGPLSVPEG AIASLNCTYSDRGSQSFFWYRQYSGKSPELIMFIYSNGD KEDGRFTAQLNKASQYVSLLIRDSQPSDSATYLCAVVS GGGADGLTFGKGTHLIIQPYIQKPDPAVYQLRDSKSSDK SVCLFTDFDSQTNVSQSKDSDVYITDKTVLDMRSMDFK SNSAVAWSNKSDFACANAFNNSIIPEDTFFPSPESSCDV KLVEKSFETDTNLNFQNLSVIGFRILLLKVAGFNLLMTL RLWSS |
| 70 | R17P2B6 beta chain | MLSPDLPDSAWNTRLLCHVMLCLLGAVSVAAGVIQSPR HLIKEKRETATLKCYPIPRHDTVYWYQQGPGQDPQFLIS FYEKMQSDKGSIPDRFSAQQFSDYHSELNMSSLELGDS ALYFCASSLGRGGQPQHFGDGTRLSILEDLNKVFPPEVA VFEPSEAEISHTQKATLVCLATGFFPDHVELSWWVNGK EVHSGVSTDPQPLKEQPALNDSRYCLSSRLRVSATFWQ NPRNHFRCQVQFYGLSENDEWTQDRAKPVTQIVSAEA WGRADCGFTSVSYQQGVLSATILYEILLGKATLYAVLV SALVLMAMVKRKDF |
| 71 | R11P3D3KE alpha chain | MEKNPLAAPLLILWFHLDCVSSILNVEQSPQSLHVQEGD STNFTCSFPSSNFYALHWYRKETAKSPEALFVMTLNGD EKKKGRISATLNTKEGYSYLYIKGSQPEDSATYLCALYN |

TABLE 3-continued

Representative Protein and DNA sequences

| SEQ ID NO: | Description | Sequence |
|---|---|---|
| | | NNDMRFGAGTRLTVKPNIQNPDPAVYQLRDSKSSDKSV CLFTDFDSQTNVSQSKDSDVYITDKTVLDMRSMDFKSN SAVAWSNKSDFACANAFNNSIIPEDTFFPSPESSCDVKL VEKSFETDTNLNFQNLSVIGFRILLLKVAGFNLLMTLRL WSS |
| 72 | R11P3D3KE beta chain | NNNVPIDDSGMPEDRFSAKMPNASFSTLKIQPSEPRDSA VYFCASSPGSTDTQYFGPGTRLTVEDLKNVFPPEVAVF EPSEAEISHTQKATLVCLATGFYPDHVELSWWVNGKEV HSGVSTDPQPLKEQPALNDSRYCLSSRLRVSATFWQNP RNHFRCQVQFYGLSENDEWTQDRAKPVTQIVSAEAWG RADCGFTSESYQQGVLSATILYEILLGKATLYAVLVSAL VLMAMVKRKDSRG |
| 73 | R39P1C12 alpha chain | TYLYWYKQEPGAGLQLLTYIFSNMDMKQDQRLTVLLN KKDKHLSLRIADTQTGDSAIYFCAEIDNQGGKLIFGQGT ELSVKPNIQNPDPAVYQLRDSKSSDKSVCLFTDFDSQTN VSQSKDSDVYITDKTVLDMRSMDFKSNSAVAWSNKSD FACANAFNNSIIPEDTFFPSPESSCDVKLVEKSFETDTNL NFQNLSVIGFRILLLKVAGFNLLMTLRLWSS |
| 74 | R39P1C12 beta chain | MGPGLLCWALLCLLGAGLVDAGVTQSPTHLIKTRGQQ VTLRCSPKSGHDTVSWYQQALGQGPQFIFQYYEEEERQ RGNFPDRFSGHQFPNYSSELNVNALLLGDSALYLCASS QLNTEAFFGQGTRLTVVEDLNKVFPPEVAVFEPSEAEIS HTQKATLVCLATGFFPDHVELSWWVNGKEVHSGVSTD PQPLKEQPALNDSRYCLSSRLRVSATFWQNPRNHFRCQ VQFYGLSENDEWTQDRAKPVTQIVSAEAWGRADCGFT SVSYQQGVLSATILYEILLGKATLYAVLVSALVLMAMV KRKDF |
| 75 | R39P1F5 alpha chain | MKSLRVLLVILWLQLSWVWSQQKEVEQNSGPLSVPEG AIASLNCTYSDRGSQSFFWYRQYSGKSPELIMFIYSNGD KEDGRFTAQLNKASQYVSLLIRDSQPSDSATYLCAVNN ARLMFGDGTQLVVKPNIQNPDPAVYQLRDSKSSDKSVC LFTDFDSQTNVSQSKDSDVYITDKTVLDMRSMDFKSNS AVAWSNKSDFACANAFNNSIIPEDTFFPSPESSCDVKLV EKSFETDTNLNFQNLSVIGFRILLLKVAGFNLLMTLRLW SS |
| 76 | R39P1F5 beta chain | MDTWLVCWAIFSLLKAGLTEPEVTQTPSHQVTQMGQE VILRCVPISNHLYFYWYRQILGQKVEFLVSFYNNEISEKS EIFDDQFSVERPDGSNFTLKIRSTKLEDSAMYFCASSGQ GANEQYFGPGTRLTVTEDLKNVFPPEVAVFEPSEAEISH TQKATLVCLATGFYPDHVELSWWVNGKEVHSGVSTDP QPLKEQPALNDSRYCLSSRLRVSATFWQNPRNHFRCQV QFYGLSENDEWTQDRAKPVTQIVSAEAWGRADCGFTS ESYQQGVLSATILYEILLGKATLYAVLVSALVLMAMVK RKDSRG |
| 77 | R40P1C2 alpha chain | MACPGFLWALVISTCLEFSMAQTVTQSQPEMSVQEAET VTLSCTYDTSESDYYLFWYKQPPSRQMILVIRQEAYKQ QNATENRFSVNFQKAAKSFSLKISDSQLGDAAMYFCAY LNYQLIWGAGTKLIIKPDIQNPDPAVYQLRDSKSSDKSV CLFTDFDSQTNVSQSKDSDVYITDKTVLDMRSMDFKSN SAVAWSNKSDFACANAFNNSIIPEDTFFPSPESSCDVKL VEKSFETDTNLNFQNLSVIGFRILLLKVAGFNLLMTLRL WSS |
| 78 | R40P1C2 beta chain | MDTWLVCWAIFSLLKAGLTEPEVTQTPSHQVTQMGQE VILRCVPISNHLYFYWYRQILGQKVEFLVSFYNNEISEKS EIFDDQFSVERPDGSNFTLKIRSTKLEDSAMYFCASSEM TAVGQYFGPGTRLTVTEDLKNVFPPEVAVFEPSEAEISH TQKATLVCLATGFYPDHVELSWWVNGKEVHSGVSTDP QPLKEQPALNDSRYCLSSRLRVSATFWQNPRNHFRCQV QFYGLSENDEWTQDRAKPVTQIVSAEAWGRADCGFTS ESYQQGVLSATILYEILLGKATLYAVLVSALVLMAMVK RKDSRG |
| 79 | R41P3E6 alpha chain | MKSLRVLLVILWLQLSWVWSQQKEVEQNSGPLSVPEG AIASLNCTYSDRGSQSFFWYRQYSGKSPELIMFIYSNGD KEDGRFT AQLNKASQYVSLLIRDSQPSDSATYLCAAFSGYALNFG KGTSLLVTPHIQNPDPAVYQLRDSKSSDKSVCLFTDFDS QTNVSQSKDSDVYITDKTVLDMRSMDFKSNSAVAWSN |

TABLE 3-continued

Representative Protein and DNA sequences

| SEQ ID NO: | Description | Sequence |
|---|---|---|
| | | KSDFACANAFNNSIIPEDTFFPSPESSCDVKLVEKSFETD TNLNFQNLSVIGFRILLLKVAGFNLLMTLRLWSS |
| 80 | R41P3E6 beta chain | MDTWLVCWAIFSLLKAGLTEPVTQTPSHQVTQMGQE VILRCVPISNHLYFYWYRQILGQKVEFLVSFYNNEISEKS EIFDDQFSVERPDGSNFTLKIRSTKLEDSAMYFCASSQY TGELFFGEGSRLTVLEDLKNVFPPEVAVFEPSEAEISHTQ KATLVCLATGFYPDHVELSWWVNGKEVHSGVSTDPQP LKEQPALNDSRYCLSSRLRVSATFWQNPRNHFRCQVQF YGLSENDEWTQDRAKPVTQIVSAEAWGRADCGFTSES YQQGVLSATILYEILLGKATLYAVLVSALVLMAMVKR KDSRG |
| 81 | R43P3G4 alpha chain | MKSLRVLLVILWLQLSWVWSQQKEVEQNSGPLSVPEG AIASLNCTYSDRGSQSFFWYRQYSGKSPELIMFIYSNGD KEDGRFTAQLNKASQYVSLLIRDSQPSDSATYLCAVNG GDMRFGAGTRLTVKPNIQNPDPAVYQLRDSKSSDKSVC LFTDFDSQTNVSQSKDSDVYITDKTVLDMRSMDFKSNS AVAWSNKSDFACANAFNNSIIPEDTFFPSPESSCDVKLV EKSFETDTNLNFQNLSVIGFRILLLKVAGFNLLMTLRLW SS |
| 82 | R43P3G4 beta chain | MDTWLVCWAIFSLLKAGLTEPVTQTPSHQVTQMGQE VILRCVPISNHLYFYWYRQILGQKVEFLVSFYNNEISEKS EIFDDQFSVERPDGSNFTLKIRSTKLEDSAMYFCASSGQ GALEQYFGPGTRLTVTEDLKNVFPPEVAVFEPSEAEISH TQKATLVCLATGFYPDHVELSWWVNGKEVHSGVSTDP QPLKEQPALNDSRYCLSSRLRVSATFWQNPRNHFRCQV QFYGLSENDEWTQDRAKPVTQIVSAEAWGRADCGFTS ESYQQGVLSATILYEILLGKATLYAVLVSALVLMAMVK RKDSRG |
| 83 | R44P3B3 alpha chain | MAMLLGASVLILWLQPDWVNSQQKNDDQQVKQNSPS LSVQEGRISILNCDYTNSMFDYFLWYKKYPAEGPTFLISI SSIKDKNEDGRFTVFLNKSAKHLSLHIVPSQPGDSAVYF CAASGLYNQGGKLIFGQGTELSVKPNIQNPDPAVYQLR DSKSSDKSVCLFTDFDSQTNVSQSKDSDVYITDKTVLD MRSMDFKSNSAVAWSNKSDFACANAFNNSIIPEDTFFPS PESSCDVKLVEKSFETDTNLNFQNLSVIGFRILLLKVAGF NLLMTLRLWSS |
| 84 | R44P3B3 beta chain | MGCRLLCCVVFCLLQAGPLDTAVSQTPKYLVTQMGND KSIKCEQNLGHDTMYWYKQDSKKFLKIMFSYNNKELII NETVPNRFSPKSPDKAHLNLHINSLELGDSAVYFCASSL GDRGYEQYFGPGTRLTVTEDLKNVFPPEVAVFEPSEAEI SHTQKATLVCLATGFYPDHVELSWWVNGKEVHSGVST DPQPLKEQPALNDSRYCLSSRLRVSATFWQNPRNHFRC QVQFYGLSENDEWTQDRAKPVTQIVSAEAWGRADCGF TSESYQQGVLSATILYEILLGKATLYAVLVSALVLMAM VKRKDSRG |
| 85 | R44P3E7 alpha chain | MKTFAGFSFLFLWLQLDCMSRGEDVEQSLFLSVREGDS SVINCTYTDSSSTYLYWYKQEPGAGLQLLTYIFSNMDM KQDQRLTVLLNKKDKHLSLRIADTQTGDSAIYFCAEINN NARLMFGDGTQLVVKPNIQNPDPAVYQLRDSKSSDKSV CLFTDFDSQTNVSQSKDSDVYITDKTVLDMRSMDFKSN SAVAWSNKSDFACANAFNNSIIPEDTFFPSPESSCDVKL VEKSFETDTNLNFQNLSVIGFRILLLKVAGFNLLMTLRL WSS |
| 86 | R44P3E7 beta chain | MLSPDLPDSAWNTRLLCHVMLCLLGAVSVAAGVIQSPR HLIKEKRETATLKCYPIPRHDTVYWYQQGPGQDPQFLIS FYEKMQSDKGSIPDRFSAQQFSDYHSELNMSSLELGDS ALYFCASSPPDQNTQYFGPGTRLTVLEDLKNVFPPEVA VFEPSEAEISHTQKATLVCLATGFYPDHVELSWWVNGK EVHSGVSTDPQPLKEQPALNDSRYCLSSRLRVSATFWQ NPRNHFRCQVQFYGLSENDEWTQDRAKPVTQIVSAEA WGRADCGFTSESYQQGVLSATILYEILLGKATLYAVLV SALVLMAMVKRKDSRG |
| 87 | R49P2B7 alpha chain | MLLLLVPVLEVIFTLGGTRAQSVTQLGSHVSVSEGALVL LRCNYSSSVPPYLFWYVQYPNQGLQLLLKYTTGATLVK GINGFEAEFKKSETSFHLTKPSAHMSDAAEYFCAVRIFG NEKLTFGTGTRLTIIPNIQNPDPAVYQLRDSKSSDKSVCL FTDFDSQTNVSQSKDSDVYITDKTVLDMRSMDFKSNSA |

TABLE 3-continued

Representative Protein and DNA sequences

| SEQ ID NO: | Description | Sequence |
|---|---|---|
| | | VAWSNKSDFACANAFNNSIIPEDTFFPSPESSCDVKLVE KSFETDTNLNFQNLSVIGFRILLLKVAGFNLLMTLRLWS S |
| 88 | R49P2B7 beta chain | MGIRLLCRVAFCFLAVGLVDVKVTQSSRYLVKRTGEKV FLECVQDMDHENMFWYRQDPGLGLRLIYFSYDVKMKE KGDIPEGYSVSREKKERFSLILESASTNQTSMYLCASSL MGELTGELFFGEGSRLTVLEDLKNVFPPEVAVFEPSEAE ISHTQKATLVCLATGFYPDHVELSWWVNGKEVHSGVS TDPQPLKEQPALNDSRYCLSSRLRVSATFWQNPRNHFR CQVQFYGLSENDEWTQDRAKPVTQIVSAEAWGRADCG FTSESYQQGVLSATILYEILLGKATLYAVLVSALVLMA MVKRKDSRG |
| 89 | R55P1G7 alpha chain | MMKSLRVLLVILWLQLSWVWSQQKEVEQDPGPLSVPE GAIVSLNCTYSNSAFQYFMWYRQYSRKGPELLMYTYSS GNKEDGRFTAQVDKSSKYISLFIRDSQPSDSATYLCAM MGDTGTASKLTFGTGTRLQVTLDIQNPDPAVYQLRDSK SSDKSVCLFTDFDSQTNVSQSKDSDVYITDKTVLDMRS MDFKSNSAVAWSNKSDFACANAFNNSIIPEDTFFPSPES SCDVKLVEKSFETDTNLNFQNLSVIGFRILLLKVAGFNL LMTLRLWSS |
| 90 | R55P1G7 beta chain | MGIRLLCRVAFCFLAVGLVDVKVTQSSRYLVKRTGEKV FLECVQDMDHENMFWYRQDPGLGLRLIYFSYDVKMKE KGDIPEGYSVSREKKERFSLILESASTNQTSMYLCASSFG GYEQYFGPGTRLTVTEDLKNVFPPEVAVFEPSEAEISHT QKATLVCLATGFYPDHVELSWWVNGKEVHSGVSTDPQ PLKEQPALNDSRYCLSSRLRVSATFWQNPRNHFRCQVQ FYGLSENDEWTQDRAKPVTQIVSAEAWGRADCGFTSES YQQGVLSATILYEILLGKATLYAVLVSALVLMAMVKR KDSRG |
| 91 | R59P2A7 alpha chain | MKSLRVLLVILWLQLSWVWSQQKEVEQNSGPLSVPEG AIASLNCTYSDRGSQSFFWYRQYSGKSPELIMSIYSNGD KEDGRFTAQLNKASQYVSLLIRDSQPSDSATYLCAVQP HDMRFGAGTRLTVKPNIQNPDPAVYQLRDSKSSDKSVC LFTDFDSQTNVSQSKDSDVYITDKTVLDMRSMDFKSNS AVAWSNKSDFACANAFNNSIIPEDTFFPSPESSCDVKLV EKSFETDTNLNFQNLSVIGFRILLLKVAGFNLLMTLRLW SS |
| 92 | R59P2A7 beta chain | MLCSLLALLLGTFFGVRSQTIHQWPATLVQPVGSPLSLE CTVEGTSNPNLYWYRQAAGRGLQLLFYSVGIGQISSEV PQNLSASRPQDRQFILSSKKLLLSDSGFYLCAWSGLVAE QFFGPGTRLTVLEDLKNVFPPEVAVFEPSEAEISHTQKA TLVCLATGFYPDHVELSWWVNGKEVHSGVSTDPQPLK EQPALNDSRYCLSSRLRVSATFWQNPRNHFRCQVQFYG LSENDEWTQDRAKPVTQIVSAEAWGRADCGFTSESYQ QGVLSATILYEILLGKATLYAVLVSALVLMAMVKRKDS RG |
| 93 | P2A | ATNFSLLKQAGDVEENPGP |
| 94 | T2A | EGRGSLLTCGDVEENPGP |
| 95 | E2A | QCTNYALLKLAGDVESNPGP |
| 96 | F2A | VKQTLNFDLLKLAGDVESNPGP |
| 97 | RD114TR | MKLPTGMVILCSLIIVRAGFDDPRKAIALVQKQHGKPCE CSGGQVSEAPPNSIQQVTCPGKTAYLMTNQKWKCRVT PKISPSGGELQNCPCNTFQDSMHSSCYTEYRQCRRINKT YYTATLLKIRSGSLNEVQILQNPNQLLQSPCRGSINQVC WSATAPIHISDGGGPLDTKRVWTVQKRLEQIHKAMTPE LQYHPLALPKVRDDLSLDARTFDILNTTFRLLQMSNFSL AQDCWLCLKLGTPTPLAIPTPSLTYSLADSLANASCQIIP PLLVQPMQFSNSSCLSSPFINDTEQIDLGAVTFTNCTSVA NVSSPLCALNGSVFLCGNNMAYTYLPQNWTRLCVQAS LLPDIDINPGDEPVPIPAIDHYIHRPKRAVQFIPLLAGLGI TAAFTTGATGLGVSVTQYTKLSHQLISDVQVLSGTIQDL QDQVDSLAEVVLQNRRGLDLLTAEQGGICLALQEKCCF YANKSGIVRNKIRTLQEELKRRESLASNPLWTGLQGFL PYLLPLLGPLLTLLLILTIGPCVFNRLVQFVKDRISVVQA LVLTQQYHQLKPL |

TABLE 3-continued

Representative Protein and DNA sequences

| SEQ ID NO: | Description | Sequence |
|---|---|---|
| 256 | WPREmut1 | cagtctgacgtacgcgtaatcaacctctggattacaaaatttgtgaaagattgactggtatt cttaactatgttgctccttttacgctatgtggatacgctgctttaatgcctttgtatcatgctatt gcttcccgtatggctttcattttctcctccttgtataaatcctggttgctgtctctttatgagga gttgtggcccgttgtcaggcaacgtggcgtggtgtgcactgtgtttgctgacgcaacccc cactggttggggcattgccaccacctgtcagctcctttccgggactttcgctttcccctcc ctattgccacggcggaactcatcgccgcctgccttgcccgctgctggacaggggctcg gctgttgggcactgacaattccgtggtgttgtcggggaaatcatcgtccttccttggctgc tcgcctgtgttgccacctggattctgcgcgggacgtccttctgctacgtcccttcggccct caatccagcggaccttccttcccgcggcctgctgccggctctgcggcctcttccgcgtct tcgccttcgccctcagacgagtcggatctcccctttgggccgcctccccgcc |
| 257 | WPREmut2 | Gagcatcttaccgccatttatacccatatttgactgtttttcttgatttgggtatacatttaaat gttaataaaacaaaatggtggggcaatcatttacatttttgggatatgtaattactagttcag gtgtattgccacaagacaaacttgttaagaaactttcccgttatttacgctctgttcctgttaa tcaacctctggattacaaaatttgtgaaagattgactgatattcttaactttgttgctccttttac gctgtgtggatttgctgctttattgcctctgtatcttgctattgcttcccgtacggctttcgtttt ctcctccttgtataaatcctggttgctgtctctttttgaggagttgtggcccgttgtccgtcaa cgtggcgtggtgtgctctgtgtttgctgacgcaacccccactggctggggcattgccacc acctgtcaactcctttctggactttcgctttcccctcccgatcgccacggcagaactcat cgccgcctgcccgctgctggacaggggctaggttgctgggcactgataaattccg tggtgttgtc |
| 258 | CD8α1 | MALPVTALLLPLALLLHAARPSQFRVSPLDRTWNLGET VELKCQVLLSNPTSGCSWLFQPRGAAASPTFLLYLSQN KPKAAEGLDTQRFSGKRLGDTFVLTLSDFRRENEGYYF CSALSNSIMYFSHFVPVFLPAKPTTTPAPRPPTPAPTIASQ PLSLRPEACRPAAGGAVHTRGLDFACDIYIWAPLAGTC GVLLLSLVITLYCNHRNRRRVCKCPRPVVKSGDKPSLS ARYV |
| 259 | CD8α2 | MALPVTALLLPLALLLHAARPSQFRVSPLDRTWNLGET VELKCQVLLSNPTSGCSWLFQPRGAAASPTFLLYLSQN KPKAAEGLDTQRFSGKRLGDTFVLTLSDFRRENEGCYF CSALSNSIMYFSHFVPVFLPAKPTTTPAPRPPTPAPTIASQ PLSLRPEACRPAAGGAVHTRGLDFACDIYIWAPLAGTC GVLLLSLVITLYCNHRNRRRVCKCPRPVVKSGDKPSLS ARYV |
| 260 | CD8α stalk | KPTTTPAPRPPTPAPTIASQPLSLRPEACRPAAGGAVHTR GLDFACD |
| 261 | CD8α Ig-like domain-2 | SQFRVSPLDRTWNLGETVELKCQVLLSNPTSGCSWLFQ PRGAAASPTFLLYLSQNKPKAAEGLDTQRFSGKRLGDT FVLTLSDFRRENEGCYFCS2ALSNSIMYFSHFVPVFLPA |
| 262 | m2CD8α | MALPVTALLLPLALLLHAARPSQFRVSPLDRTWNLGET VELKCQVLLSNPTSGCSWLFQPRGAAASPTFLLYLSQN KPKAAEGLDTQRFSGKRLGDTFVLTLSDFRRENEGCYF CSALSNSIMYFSHFVPVFLPASVVDFLPTTAQPTKKSTL KKRVCRLPRPETQKGPLCSPIYIWAPLAGTCGVLLLSLVI TLYCNHRNRRRVCKCPRPVVKSGDKPSLSARYV |
| 263 | MSCV promoter | Tgaaagaccccacctgtaggtttggcaagctagcttaagtaacgccattttgcaaggcat ggaaaatacataactgagaatagagaagttcagatcaaggttaggaacagagagacag cagaatatgggccaaacaggatatctgtggtaagcagttcctgccccggctcagggcca agaacagatggtccccagatgcggtcccgccctcagcagtttctagagaaccatcagat gttttccagggtgccccaaggacctgaaaatgaccctgtgccttatttgaactaaccaatca gttcgcttctcgcttctgttcgcgcgcttctgctccccgagctcaataaaagagcccacaa cccctcact |
| 264 | WPRE | cagtctgacgtacgcgtaatcaacctctggattacaaaatttgtgaaagattgactggtatt cttaactatgttgctccttttacgctatgtggatacgctgctttaatgcctttgtatcatgctatt gcttcccgtatggctttcattttctcctccttgtataaatcctggttgctgtctctttatgagga gttgtggcccgttgtcaggcaacgtggcgtggtgtgcactgtgtttgctgacgcaacccc cactggttggggcattgccaccacctgtcagctcctttccgggactttcgctttcccctcc ctattgccacgcggaactcatcgccgcctgccttgcccgctgctggacaggggctcg gctgttgggcactgacaattccgtggtgttgtcggggaagctgacgtccttccatggctg ctcgcctgtgttgccacctggattctgcgcgggacgtccttctgctacgtcccttcggccc tcaatccagcggaccttccttcccgcggcctgctgccggctctgcggcctcttccgcgtc ttcgccttcgccctcagacgagtcggatctccctttgggccgcctccccgcc |
| 265 | Furin consensus | RXXR |
| 266 | Linker | SGSG |

TABLE 3-continued

Representative Protein and DNA sequences

| SEQ ID NO: | Description | Sequence |
|---|---|---|
| 293 | CD8β Signal peptide | MRPRLWLLLAAQLTVLHGNSV |
| 294 | S19 Signal peptide | MEFGLSWLFLVAILKGVQC |
| 303 | R11P3D3KE beta chain | MDSWTFCCVSLCILVAKHTDAGVIQSPRHEVTEMGQEV TLRCKPISGHNSLFWYRETMMRGLELLIYFNNNVPIDDS GMPEDRFSAKMPNASFSTLKIQPSEPRDSAVYFCASSPG STDTQYFGPGTRLTVLEDLKNVFPPEVAVFEPSEAEISHT QKATLVCLATGFYPDHVELSWWVNGKEVHSGVSTDPQ PLKEQPALNDSRYCLSSRLRVSATFWQNPRNHFRCQVQ FYGLSENDEWTQDRAKPVTQIVSAEAWGRADCGFTSES YQQGVLSATILYEILLGKATLYAVLVSALVLMAMVKR KDSRG |
| 304 | R39P1C12 alpha chain | MKTFAGFSFLFLWLQLDCMSRGEDVEQSLFLSVREGDS SVINCTYTDSSSTYLYWYKQEPGAGLQLLTYIFSNMDM KQDQRLTVLLNKKDKHLSLRIADTQTGDSAIYFCAEIDN QGGKLIFGQGTELSVKPNIQNPDPAVYQLRDSKSSDKSV CLFTDFDSQTNVSQSKDSDVYITDKTVLDMRSMDFKSN SAVAWSNKSDFACANAFNNSIIPEDTFFPSPESSCDVKL VEKSFETDTNLNFQNLSVIGFRILLLKVAGFNLLMTLRL WSS |

The constructs in Table 2 may be assemblages of the individual components described in Table 3. The inventors found that the combination, order, and inclusion of transcription enhancers from Table 3 as described in Table 2 provided unexpected improvements in transfection efficiency, expression levels, and induction of cytotoxic T-cell activities, e.g., IL-12 secretion, IFN-γ secretion, TNF-α secretion, granzyme A secretion, MIP-1a secretion, IP-10 secretion, granzyme B secretion, and combinations thereof.

Tumor Associated Antigens (TAA)

In the MHC class I dependent immune reaction, peptides not only have to be able to bind to certain MHC class I molecules expressed by tumor cells, they subsequently also have to be recognized by T cells bearing specific T cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (e.g., copy numbers of the respective peptide per cell). Tumor-specific and tumor-associated antigens are often derived from proteins directly involved in transformation of a normal cell to a tumor cell due to their function, e.g., in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach. Singh-Jasuja et al. Cancer Immunol. Immunother. 53 (2004): 187-195. Epitopes are present in the amino acid sequence of the antigen, making the peptide an "immunogenic peptide", and being derived from a tumor associated antigen, leads to a T-cell-response, both in vitro and in vivo.

Any peptide able to bind an MHC molecule may function as a T-cell epitope. For the induction of a T-cell-response, the TAA must be presented a T cell having a corresponding TCR and the host must not have immunological tolerance for this particular epitope. Exemplary Tumor Associated Antigens (TAA) that may be used with the CD8 polypeptides described herein are disclosed herein.

TABLE 4

TAA Peptide sequences

| SEQ ID NO: | Amino Acid Sequence |
|---|---|
| 98 | YLYDSETKNA |
| 99 | HLMDQPLSV |
| 100 | GLLKKINSV |
| 101 | FLVDGSSAL |
| 102 | FLFDGSANLV |
| 103 | FLYKIIDEL |
| 104 | FILDSAETTTL |
| 105 | SVDVSPPKV |
| 106 | VADKIHSV |
| 107 | IVDDLTINL |
| 108 | GLLEELVTV |
| 109 | TLDGAAVNQV |
| 110 | SVLEKEIYSI |
| 111 | LLDPKTIFL |
| 112 | YTFSGDVQL |

TABLE 4-continued

TAA Peptide sequences

| SEQ ID NO: | Amino Acid Sequence |
|---|---|
| 113 | YLMDDFSSL |
| 114 | KVWSDVTPL |
| 115 | LLWGHPRVALA |
| 116 | KIWEELSVLEV |
| 117 | LLIPFTIFM |
| 118 | FLIENLLAA |
| 119 | LLWGHPRVALA |
| 120 | FLLEREQLL |
| 121 | SLAETIFIV |
| 122 | TLLEGISRA |
| 123 | KIQEILTQV |
| 124 | VIFEGEPMYL |
| 125 | SLFESLEYL |
| 126 | SLLNQPKAV |
| 127 | GLAEFQENV |
| 128 | KLLAVIHEL |
| 129 | TLHDQVHLL |
| 130 | TLYNPERTITV |
| 131 | KLQEKIQEL |
| 132 | SVLEKEIYSI |
| 133 | RVIDDSLVVGV |
| 134 | VLFGELPAL |
| 135 | GLVDIMVHL |
| 136 | FLNAIETAL |
| 137 | ALLQALMEL |
| 138 | ALSSSQAEV |
| 139 | SLITGQDLLSV |
| 140 | QLIEKNWLL |
| 141 | LLDPKTIFL |
| 142 | RLHDENILL |
| 143 | YTFSGDVQL |
| 144 | GLPSATTTV |
| 145 | GLLPSAESIKL |
| 146 | KTASINQNV |
| 147 | SLLQHLIGL |
| 148 | YLMDDFSSL |
| 149 | LMYPYIYHV |
| 150 | KVWSDVTPL |

TABLE 4-continued

TAA Peptide sequences

| SEQ ID NO: | Amino Acid Sequence |
|---|---|
| 151 | LLWGHPRVALA |
| 152 | VLDGKVAVV |
| 153 | GLLGKVTSV |
| 154 | KMISAIPTL |
| 155 | GLLETTGLLAT |
| 156 | TLNTLDINL |
| 157 | VIIKGLEEI |
| 158 | YLEDGFAYV |
| 159 | KIWEELSVLEV |
| 160 | LLIPFTIFM |
| 161 | ISLDEVAVSL |
| 162 | KISDFGLATV |
| 163 | KLIGNIHGNEV |
| 164 | ILLSVLHQL |
| 165 | LDSEALLTL |
| 166 | VLQENSSDYQSNL |
| 167 | HLLGEGAFAQV |
| 168 | SLVENIHVL |
| 169 | YTFSGDVQL |
| 170 | SLSEKSPEV |
| 171 | AMFPDTIPRV |
| 172 | FLIENLLAA |
| 173 | FTAEFLEKV |
| 174 | ALYGNVQQV |
| 175 | LFQSRIAGV |
| 176 | ILAEEPIYIRV |
| 177 | FLLEREQLL |
| 178 | LLLPLELSLA |
| 179 | SLAETIFIV |
| 180 | AILNVDEKNQV |
| 181 | RLFEEVLGV |
| 182 | YLDEVAFML |
| 183 | KLIDEDEPLFL |
| 184 | KLFEKSTGL |
| 185 | SLLEVNEASSV |
| 186 | GVYDGREHTV |
| 187 | GLYPVTLVGV |

TABLE 4-continued

TAA Peptide sequences

| SEQ ID NO: | Amino Acid Sequence |
|---|---|
| 188 | ALLSSVAEA |
| 189 | TLLEGISRA |
| 190 | SLIEESEEL |
| 191 | ALYVQAPTV |
| 192 | KLIYKDLVSV |
| 193 | ILQDGQFLV |
| 194 | SLLDYEVSI |
| 195 | LLGDSSFFL |
| 196 | VIFEGEPMYL |
| 197 | ALSYILPYL |
| 198 | FLFVDPELV |
| 199 | SEWGSPHAAVP |
| 200 | ALSELERVL |
| 201 | SLFESLEYL |
| 202 | KVLEYVIKV |
| 203 | VLLNEILEQV |
| 204 | SLLNQPKAV |
| 205 | KMSELQTYV |
| 206 | ALLEQTGDMSL |
| 207 | VIIKGLEEITV |
| 208 | KQFEGTVEI |
| 209 | KLQEEIPVL |
| 210 | GLAEFQENV |
| 211 | NVAEIVIHI |
| 212 | ALAGIVTNV |
| 213 | NLLIDDKGTIKL |
| 214 | VLMQDSRLYL |
| 215 | KVLEHVVRV |
| 216 | LLWGNLPEI |
| 217 | SLMEKNQSL |
| 218 | KLLAVIHEL |
| 219 | ALGDKFLLRV |
| 220 | FLMKNSDLYGA |
| 221 | KLIDHQGLYL |
| 222 | GPGIFPPPPPQP |
| 223 | ALNESLVEC |
| 224 | GLAALAVHL |
| 225 | LLLEAVWHL |
| 226 | SIIEYLPTL |
| 227 | TLHDQVHLL |
| 228 | SLLMWITQC |
| 229 | FLLDKPQDLSI |
| 230 | YLLDMPLWYL |
| 231 | GLLDCPIFL |
| 232 | VLIEYNFSI |
| 233 | TLYNPERTITV |
| 234 | AVPPPPSSV |
| 235 | KLQEELNKV |
| 236 | KLMDPGSLPPL |
| 237 | ALIVSLPYL |
| 238 | FLLDGSANV |
| 239 | ALDPSGNQLI |
| 240 | ILIKHLVKV |
| 241 | VLLDTILQL |
| 242 | HLIAEIHTA |
| 243 | SMNGGVFAV |
| 244 | MLAEKLLQA |
| 245 | YMLDIFHEV |
| 246 | ALWLPTDSATV |
| 247 | GLASRILDA |
| 248 | ALSVLRLAL |
| 249 | SYVKVLHHL |
| 250 | VYLPKIPSW |
| 251 | NYEDHFPLL |
| 252 | VYIAELEKI |
| 253 | VHFEDTGKTLLF |
| 254 | VLSPFILTL |
| 255 | HLLEGSVGV |

Example 2

CD8α Molecules

CD8α homodimer (CD8αα) may be composed of two a subunits held together by two disulfide bonds at the stalk regions. FIG. 1 shows a CD8α polypeptide, e.g., SEQ ID NO: 258 (CD8α1), that includes five domains: (1) one signal peptide (from −21 to −1), e.g., SEQ ID NO: 6, (2) one Ig-like domain-1 (from 1 to 115), e.g., SEQ ID NO: 1, (3) one stalk region (from 116 to 160), e.g., SEQ ID NO: 260, (4) one transmembrane (TM) domain (from 161-188), e.g., SEQ ID NO: 3, and (5) one cytoplasmic tail (Cyto) comprising a lck-binding motif (from 189 to 214), e.g., SEQ ID NO: 4. Another example of CD8α subunit, e.g., CD8α2 (SEQ ID NO: 259), differs from CD8α1 at position 112, at which CD8α2 contains a cysteine (C), whereas CD8α1 contains a tyrosine (Y).

Modified CD8 Polypeptides

Different from CD8α polypeptide, e.g., CD8α1 (SEQ ID NO: 258) and CD8α2 (SEQ ID NO: 259), a modified CD8α polypeptide, e.g., m1CD8α (SEQ ID NO: 7) and m2CD8α (SEQ ID NO: 262), may contain additional regions, such as sequence stretches from a CD8β polypeptide. In an embodiment, SEQ ID NO: 2 or variants thereof are used with a CD8α polypeptide. In other embodiments, a portion of a CD8α polypeptide, e.g., SEQ ID NO: 260, is removed or not included in modified CD8 polypeptides described herein. FIG. 2 shows a sequence alignment between CD8α1 (SEQ ID NO: 258) and m1CD8α (SEQ ID NO: 7). FIG. 3 shows a sequence alignment between CD8α2 (SEQ ID NO: 259) and m2CD8α (SEQ ID NO: 262), in which the cysteine substitution is indicated by an arrow. The stalk regions are shown within the boxes.

Modified CD8 expressing cells showed improved functionality in terms of cytotoxicity and cytokine response as compared to original CD8 expressing T cells transduced with the TCR.

Example 3

Lentiviral Viral Vectors

The lentiviral vectors used herein contain several elements that enhance vector function, including a central polypurine tract (cPPT) for improved replication and nuclear import, a promoter from the murine stem cell virus (MSCV) (SEQ ID NO: 263), which lessens vector silencing in some cell types, a woodchuck hepatitis virus posttranscriptional responsive element (WPRE) (SEQ ID NO: 264) for improved transcriptional termination, and the backbone was a deleted 3'-LTR self-inactivating (SIN) vector design that improves safety, sustained gene expression and anti-silencing properties. Yang et al. *Gene Therapy* (2008) 15, 1411-1423.

In an embodiment, vectors, constructs, or sequences described herein comprise mutated forms of WPRE. In an embodiment, sequences or vectors described herein comprise mutations in WPRE version 1, e.g., WPREmut1 (SEQ ID NO: 256), or WPRE version 2, e.g., WPREmut2 (SEQ ID NO: 257). Construct #9 and Construct #9b represent two LV production batches with the same construct containing SEQ ID NO: 257 as WPREmut2, with the difference between Construct #9 and Construct #9b being the titer consistent with Table 4. In an embodiment, WPRE mutants comprise at most one mutation, at most two mutations, at most three mutations, at least four mutations, or at most five mutations. In an embodiment, vectors, constructs, or sequences described herein do not comprise WPRE. In an aspect, WPRE sequences described in U.S. 2021/0285011, the content of which is incorporated by reference in its entirety, may be used together with vectors, sequences, or constructs described herein.

In an embodiment, vectors, constructs, or sequences described herein do not include an X protein promoter. The WPRE mutants described herein do not express an X protein. WPRE promotes accumulation of mRNA, theorized to promote export of mRNA from nucleosome to cytoplasm to promote translation of the transgene mRNA.

To obtain optimal co-expression levels of TCRαβ, mCD8α (e.g., m1CD8α (SEQ ID NO: 7) and m2CD8α (SEQ ID NO: 262)) and CD8β (e.g., any one of CD8β1-7 (SEQ ID NO: 8-14)) in the transduced CD4+ T cells, CD8+ T cells, and/or γδ T cells, lentiviral vectors with various designs were generated. T cells may be transduced with two separate lentiviral vectors (2-in-1), e.g., one expressing TCRα and TCRβ and the other expressing mCD8α and CD8β, for co-expression of TCRαβ and CD8αβ heterodimer, or one expressing TCRα and TCRβ and the other expressing mCD8α for co-expression of TCRαβ and mCD8α homodimer. Alternatively, T cells may be transduced with a single lentiviral vector (4-in-1) co-expressing TCRα, TCRβ, mCD8α, and CD8β for co-expression of TCRαβ and CD8αβ heterodimer. In the 4-in-1 vector, the nucleotides encoding TCRα chain, TCRβ chain, mCD8α chain, and CD8β chain may be shuffled in various orders, e.g., from 5' to 3' direction, TCRα-TCRβ-mCD8α-CD8β, TCRα-TCRβ-CD8β-mCD8α, TCRβ-TCRα-mCD8α-CD8β, TCRβ-TCRα-CD8β-mCD8α, mCD8α-CD8β-TCRα-TCRβ, mCD8α-CD8β-TCRβ-TCRα, CD8β-mCD8α-TCRα-TCRβ, and CD8β-mCD8α-TCRβ-TCRα. Various 4-in-1 vectors, thus generated, may be used to transduce CD4+ T cells, CD8+ T cells, and/or γδ T cells, followed by measuring TCRαβ/mCD8α/CD8β co-expression levels of the transduced cells using techniques known in the art, e.g., flow cytometry. Similarly, T cells may be transduced with a single lentiviral vector (3-in-1) co-expressing TCRα, TCRβ, and mCD8α (e.g., m1CD8α and m2CD8α) for co-expression of TCRαβ and mCD8α homodimer. In the 3-in-1 vector, the nucleotides encoding TCRα chain, TCRβ chain, mCD8α chain may be shuffled in various orders, e.g., TCRα-TCRβ-mCD8α, TCRβ-TCRα-mCD8α, mCD8α-TCRα-TCRβ, and mCD8α-TCRβ-TCRα. Various 3-in-1 vectors, thus generated, may be used to transduce CD4+ T cells, CD8+ T cells, and/or γδ T cells, followed by measuring TCRαβ/mCD8α co-expression levels of the transduced cells using techniques known in the art.

To generate lentiviral vectors co-expressing TCRαβ and mCD8α and/or CD8β, a nucleotide encoding furin-linker (GSG or SGSG (SEQ ID NO: 266))-2A peptide may be positioned between TCRα chain and TCRβ chain, between mCD8α chain and CD8β chain, and between a TCR chain and a CD8 chain to enable highly efficient gene expression. The 2A peptide may be selected from P2A (SEQ ID NO: 93), T2A (SEQ ID NO: 94), E2A (SEQ ID NO: 95), or F2A (SEQ ID NO: 96).

Lentiviral viral vectors may also contain post-transcriptional regulatory element (PRE), such as WPRE (SEQ ID NO: 264), WPREmut1 (SEQ ID NO: 256), or WPREmut2 (SEQ ID NO: 257), to enhance the expression of the transgene by increasing both nuclear and cytoplasmic mRNA levels. One or more regulatory elements including mouse RNA transport element (RTE), the constitutive transport element (CTE) of the simian retrovirus type 1 (SRV-1), and the 5' untranslated region of the human heat shock protein 70 (Hsp70 5'UTR) may also be used and/or in combination with WPRE to increase transgene expression. The WPREmut1 and WPREmut2 do not express an X protein, but still act to enhance translation of the transgene mRNA.

Lentiviral vectors may be pseudotyped with RD114TR (for example, SEQ ID NO: 97), which is a chimeric glycoprotein comprising an extracellular and transmembrane domain of feline endogenous virus (RD114) fused to cytoplasmic tail (TR) of murine leukemia virus. Other viral envelop proteins, such as VSV-G env, MLV 4070A env, RD114 env, chimeric envelope protein RD114pro, baculovirus GP64 env, or GALV env, or derivatives thereof, may also be used. RD114TR variants comprising at least 85%, at least 90%, at least 95%, at least 98%, at least 99%, or 100% to SEQ ID NO: 97 also provided for.

Figure 4:
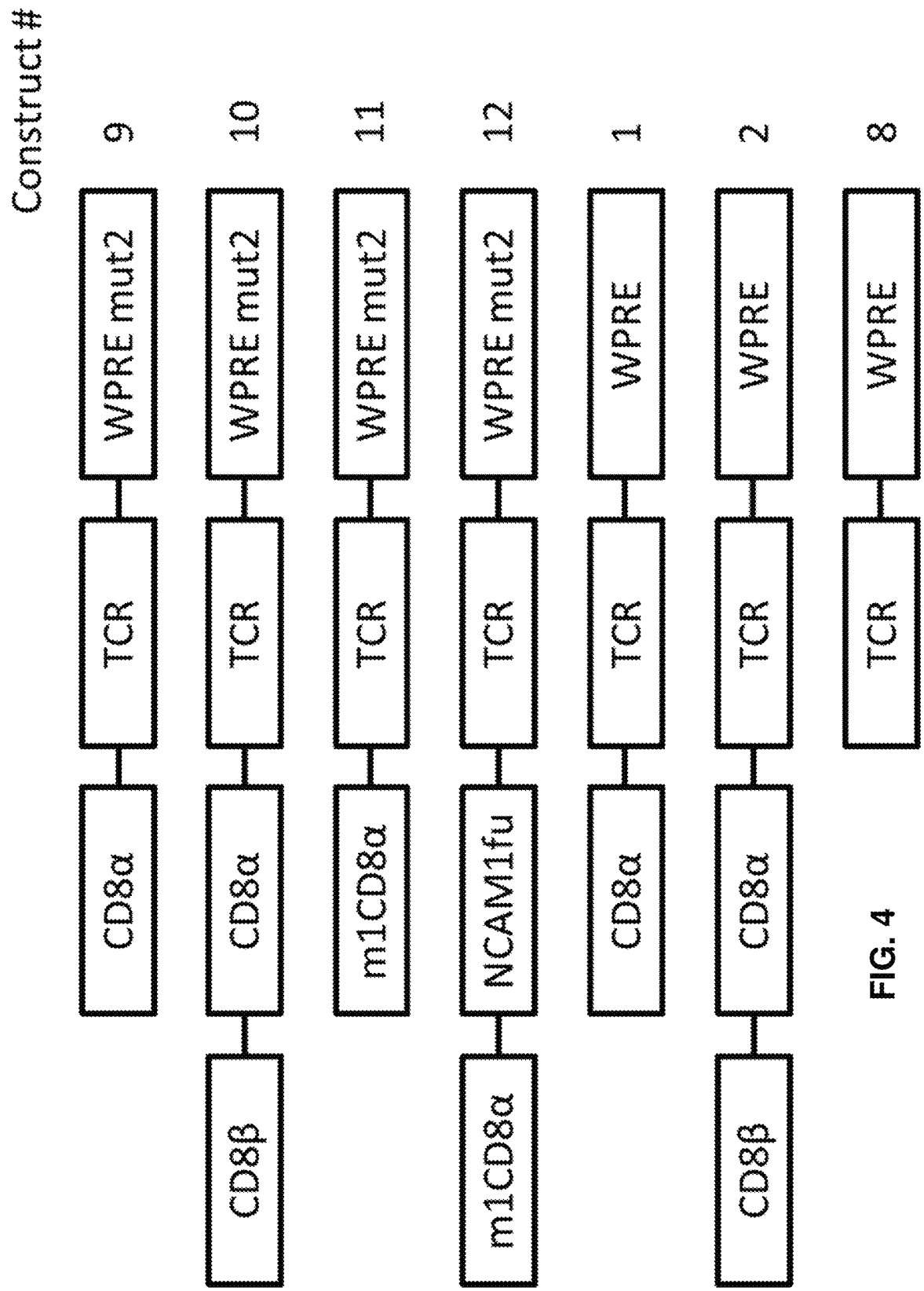
FIG. 4 shows vectors according to an aspect of the disclosure.

For example, FIG. 4 shows exemplary vectors, which include two 4-in-1 vectors, e.g., Constructs #10 and #2, co-expressing TCR (TCRα chain and TCRβ chain), CD8α, and CD8β; three 3-in-1 vectors expressing TCR and CD8α, e.g., Constructs #1 and #9, two 3-in-1 vectors expressing TCR and m1CD8α (SEQ ID NO: 7), e.g., Constructs #11 and #12, and Construct #8 expressing TCR only. To improve transcriptional termination, wild type WPRE (WPRE) (SEQ ID NO: 264) is included in Constructs #1, #2, and #8; WPREmut (SEQ ID NO: 257) is included in Constructs #9, #10, #11, and #12.

Further exemplary constructs (Constructs #13-#19 and #21-#26) are described in Table 2 above. In particular, Constructs #13, #14, and #16 are 4-in-1 constructs co-expressing TCR, CD8α, and CD8β3 with various combinations of signal peptides (SEQ ID NO: 6 [WT CD8α signal peptide]; SEQ ID NO: 293 [WT CD8β signal peptide]; and SEQ ID NO: 294 [S19 signal peptide]) and differing element order. Constructs #15 and #17 are 4-in-1 constructs co-expressing TCR, CD8α, and CD8β5. Construct #15 comprises the WT CD8α signal peptide (SEQ ID NO: 6) and WT CD8β signal peptide (SEQ ID NO: 293), whereas Construct #17 comprises the S19 signal peptide (SEQ ID NO: 294) at the N-terminal end of both CD8α and CD8β5. Construct #21 is a 4-in-1 constructs co-expressing TCR, CD8α, and CD8β2 comprising WT CD8α signal peptide (SEQ ID NO: 6) and WT CD8β signal peptide (SEQ ID NO: 293). Construct #18 is a variant of Construct #10 in which the WT signal peptides for CD8α and CD8β1 (SEQ ID NOs: 6 and 293, respectively) were replaced with S19 signal peptide (SEQ ID NO: 294). Construct #19 is a variant of Construct #11 in which the WT CD8α signal peptide (SEQ ID NO: 6) was replaced with the S19 signal peptide (SEQ ID NO: 294). Construct #22 is a variant of Construct #11 in which the CD4 transmembrane and intracellular domains are fused to the C-terminus of the CD8β stalk sequence in place of the CD8α transmembrane and intracellular domains. Construct #25 is a variant of Construct #22 in which the CD8β stalk sequence (SEQ ID NO: 2) is replaced with the CD8α stalk sequence (SEQ ID NO: 260).

Example 4

Vector Screening (Constructs #1, #2, #8, #9, #10, #11, and #12)

Viral Titers

Figure 5A:
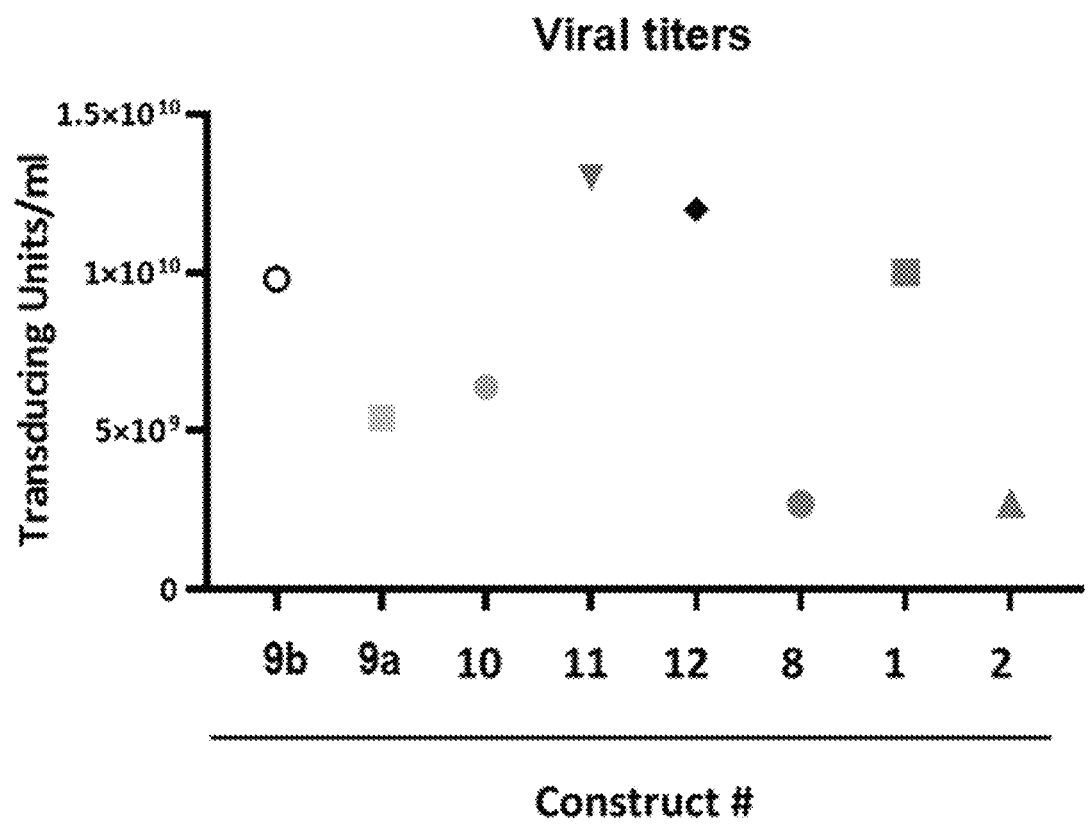
FIG. 5A shows titers of viral vectors shown in FIG. 4.

FIG. 5A shows viral titer of Constructs #1, #2, #8, #9, #10, #11, and #12. Table 5 shows viral titers and lentiviral P24 ELISA data for Constructs #9, #10, #11, and #12.

TABLE 5

| Constructs # | Titer | Lentiviral P24 |
|---|---|---|
| 9 | 5.40 × 10$^9$ | 6556 |
| 9b | 9.80 × 10$^9$ | 16196 |
| 10 | 6.40 × 10$^9$ | 9525 |

TABLE 5-continued

| Constructs # | Titer | Lentiviral P24 |
|---|---|---|
| 11 | 1.30 × 10$^{10}$ | 16797 |
| 12 | 1.20 × 10$^{10}$ | 17996 |

For construct 12, NCAMfu refers to NCAMFusion protein expressing modified CD8α extracellular and Neural cell adhesion molecule 1 (CD56) intracellular domain.

For Table 5, the WPREmut2 portion refers to SEQ ID NO: 257.

T Cell Manufacturing

Activation

Figure 6:
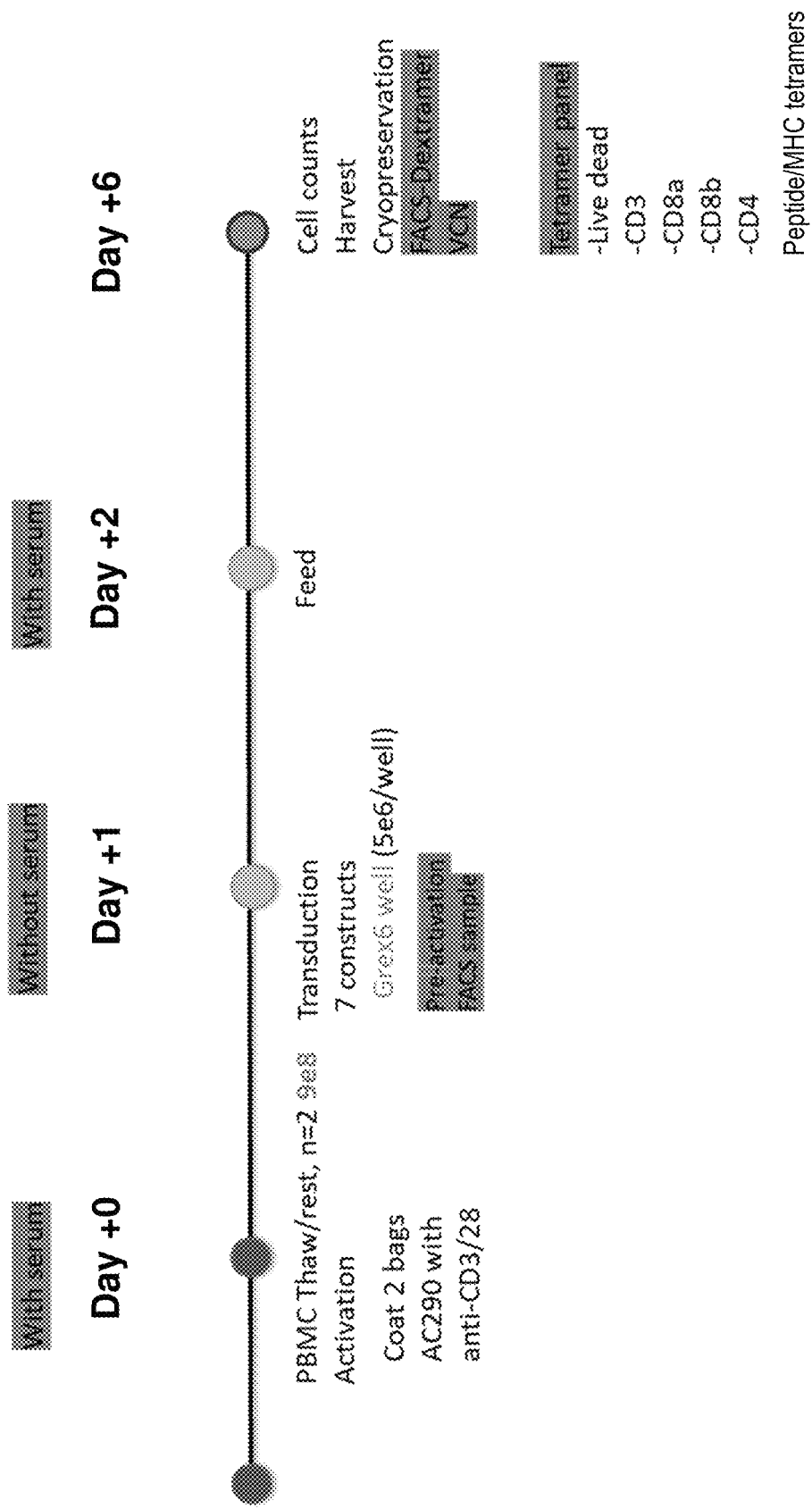
FIG. 6 shows T cell manufacturing.
Figure 7A:
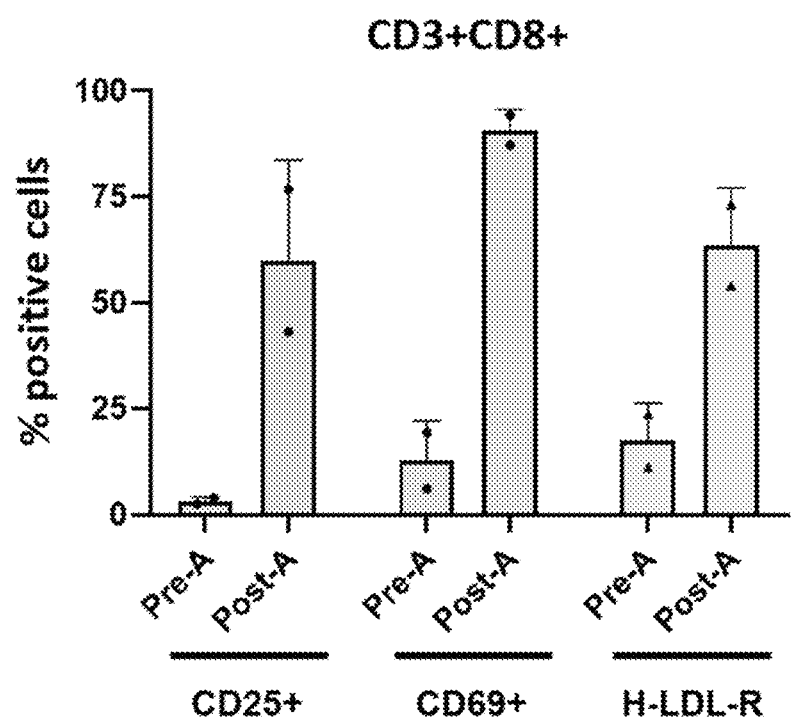
FIG. 7A shows expression of activation markers before and after activation in CD3+CD8+ cells.
Figure 7B:
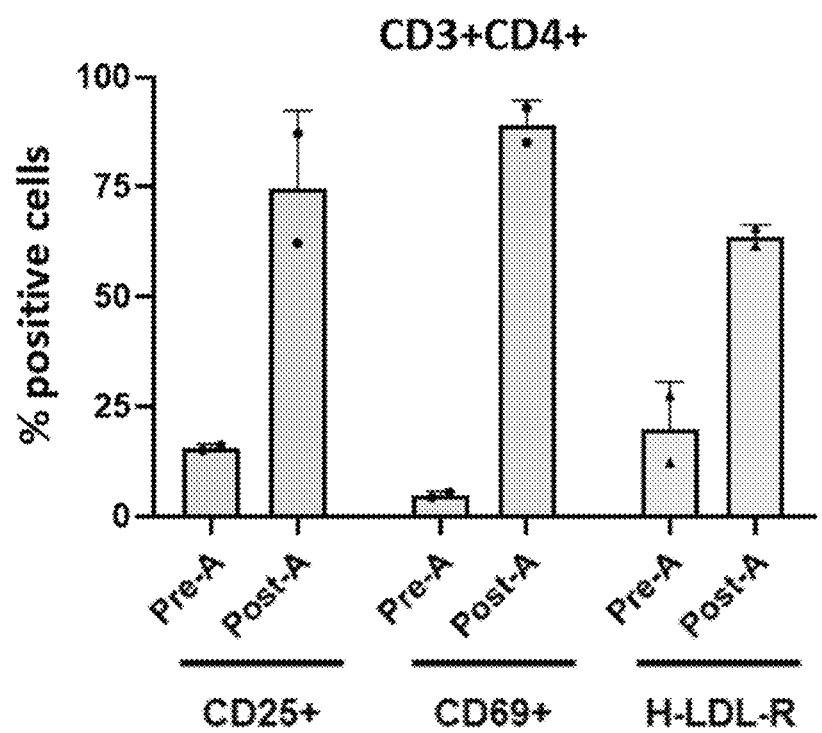
FIG. 7B shows expression of activation markers before and after activation in CD3+CD4+ cells.

FIG. 6 shows that, on Day +0, PBMCs (about 9×10$^8$ cells) obtained from two donors (Donor #1 and Donor #2) were thawed and rested. Cells were activated in bags (AC290) coated with anti-CD3 and anti-CD28 antibodies in the presence of serum. Activation markers, e.g., CD25, CD69, and human low density lipoprotein receptor (H-LDL-R) are in CD8+ and CD4+ cells, were subsequently measured. FIG. 7A shows that % CD3+CD8+CD25+ cells, % CD3+CD8+ CD69+ cells, and % CD3+CD8+H-LDL-R+ cells increase after activation (Post-A) as compared with that before activation (Pre-A). Similarly, FIG. 7B shows that % CD3+ CD4+CD25+ cells, % CD3+CD4+CD69+ cells, and % CD3+CD4+H-LDL-R+ cells increase after activation (Post-A) as compared with that before activation (Pre-A). These results support the activation of PBMCs.

Transduction

FIG. 6 shows that, on Day +1, activated PBMCs were transduced with viral vectors, e.g., Constructs #1, #2, #8, #9, #10, #11, and #12, in G-Rex® 6 well plates at about 5×10$^6$ cells/well in the absence of serum. The amounts of virus used for transduction are shown in Table 6.

TABLE 6

| Constructs | Virus Volume/1 × 10$^6$ cells |
|---|---|
| #9, #10, #11, #12 | 1.25 µl, 2.5 µl, 5 µl |
| #1 | 1.25 µl |
| #2 | 5 µl |
| #8 (TCR) | 2.5 µl |

Expansion

Figure 8A:
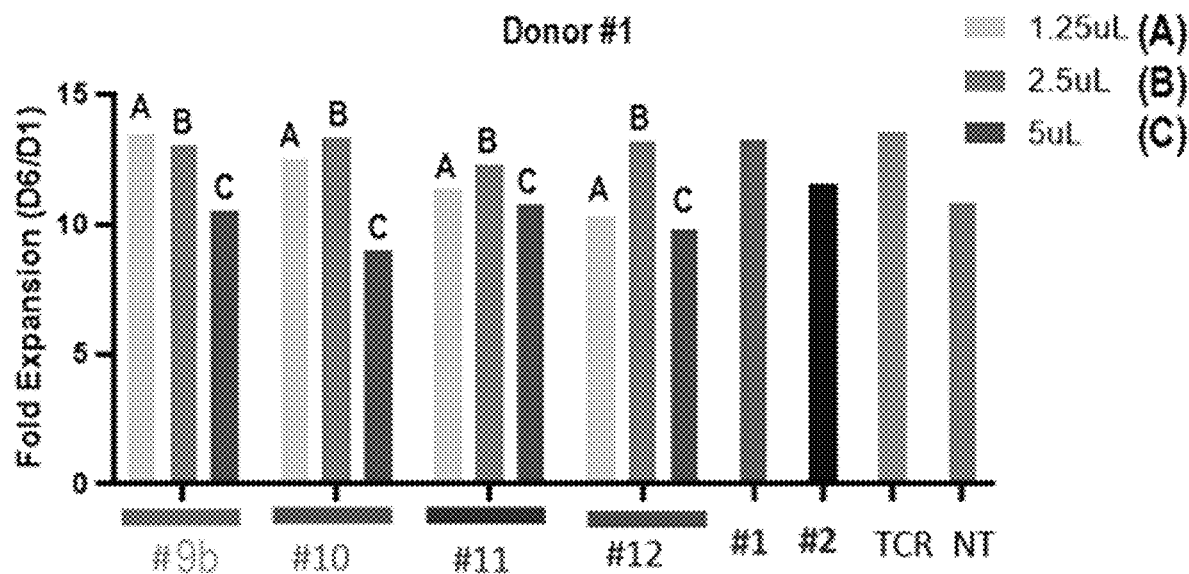
FIG. 8A shows fold expansion of cells transduced with various constructs from Donor #1. The constructs are as follows: Construct #9b; Construct #10; Construct #11; Construct #12; Construct #1; Construct #2; TCR=R11KEA.WPRE$^{wt}$ (TCR with wild type WPRE); NT=Non-transduced T cells (as a negative control). Note that Constructs #9 and #9b are different batches of the same construct (SEQ ID NO: 287 and 288).
Figure 8B:
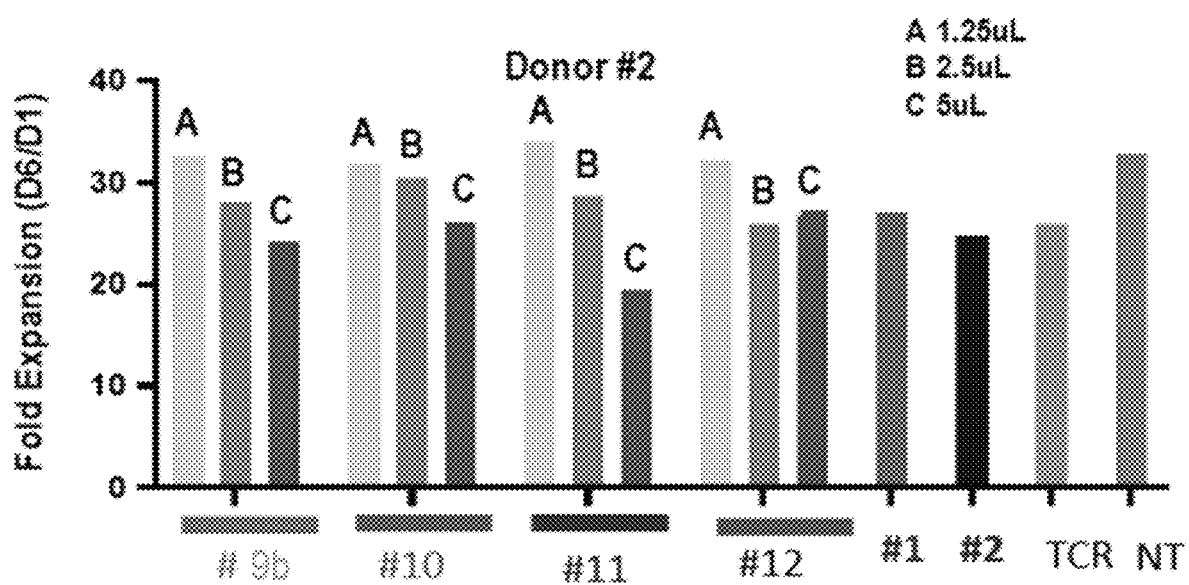
FIG. 8B shows fold expansion of cells transduced with various constructs from Donor #2. The constructs are as follows: Construct #9b; Construct #10; Construct #11; Construct #12; Construct #1; Construct #2; TCR=R11KEA.WPRE$^{wt}$ (TCR with wild type WPRE) (Construct #8); NT=Non-transduced T cells (as a negative control).

FIG. 6 shows that, on Day +2, transduced PBMCs were expanded in the presence of serum. On Day +6, cells were harvested for subsequent analysis, e.g., FACS-Dextramer and vector copy number (VCN) and were cryopreserved. FIGS. 8A and 8B show fold expansion on Day +6 of transduced T cell products obtained from Donor #1 and donor #2, respectively. Viabilities of cells is greater than 90% on Day +6.

Characterization of T Cell Products

Cell counts, FACS-dextramers, and vector copy numbers (VCN) were determined. Tetramer panels may comprise live/dead cells, CD3, CD8α, CD8β, CD4, and peptide/MHC tetramers, e.g., PRAME-004 (SLLQHLIGL) (SEQ ID NO: 147)/MHC tetramers. FACS analysis was gated on live singlets, followed by CD3+, followed by CD4+CD8+, followed by CD4+CD8+Tetramer(Tet)+ and CD8+Tet+.

FIGS. 9A, 9B, 9C, and 9D show representative flow plots of cells obtained from Donor #1 indicating % CD8, CD4, and PRAME-004/MHC tetramer (Tet) of cells transduced with Construct #9b, #10, #11, or #12, respectively.

Figure 10:
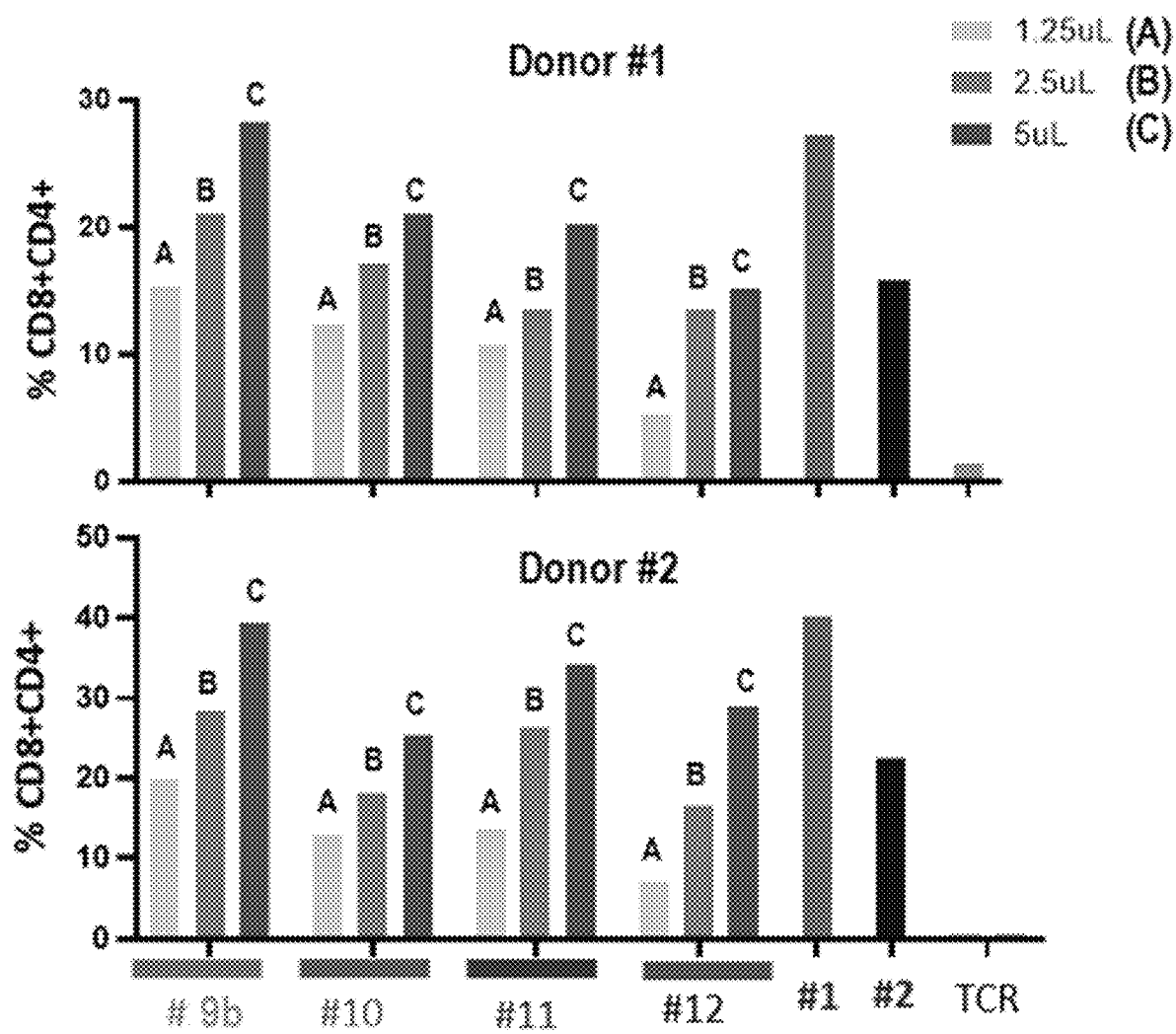
FIG. 10 shows % CD8+CD4+ of cells transduced with various constructs for Donor #1 and Donor #2. The constructs are as follows: Construct #9b; Construct #10; Construct #11; Construct #12; Construct #1; Construct #2; TCR=R11KEA.WPRE$^{wt}$ TCR with wild type WPRE); NT=Non-transduced T cells (as a negative control).
Figure 11:
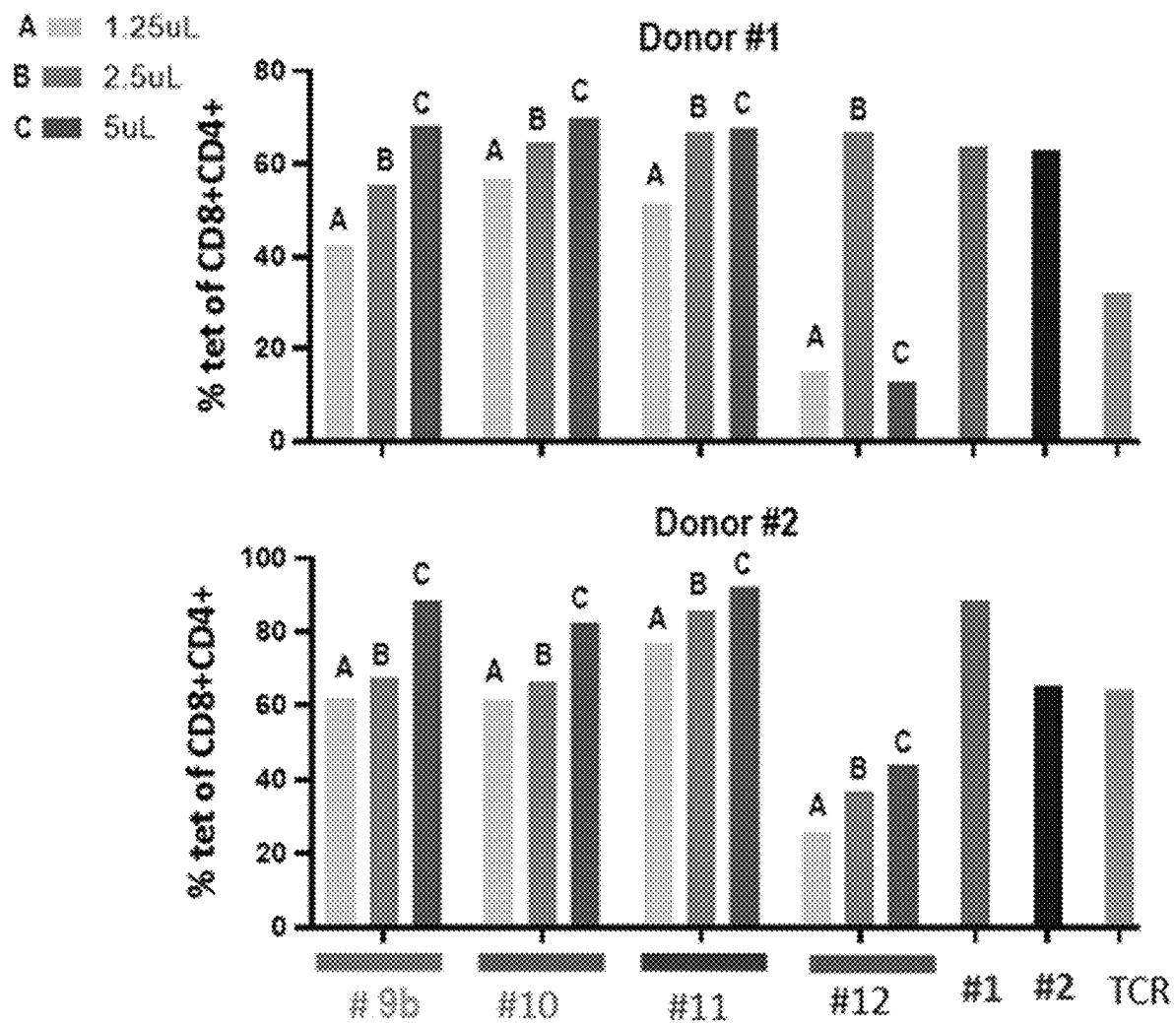
FIG. 11 shows % Tet of CD8+CD4+ of cells transduced with various constructs. The constructs are as follows: Construct #9b; Construct #10; Construct #11; Construct #12; Construct #1; Construct #2; TCR=R11KEA.WPRE$^{wt}$ (TCR with wild type WPRE); NT=Non-transduced T cells (as a negative control).

FIG. 10 shows % CD8+CD4+ cells from Donor #1 (upper panel) and Donor #2 (lower panel) transduced with Construct #1, #2, #8 (TCR), #9, #10, #11, or #12 at 1.25 µl, 2.5 µl, or 5 µl per 1×10⁶ cells. These results show that higher % CD8+CD4+ cells are obtained by transduction with vectors expressing CD8α and TCR with wild type WPRE (Construct #1) and WPREmut2 (Construct #9) than that transduced with Constructs #10, #11, or #12. Construct #8 (TCR only) serves as negative control. FIG. 11 shows % Tet of CD8+CD4+ cells from Donor #1 (upper panel) and Donor #2 (lower panel) transduced with Constructs #1, #2, #8 (TCR), #9, #10, #11, and #12 at 1.25 µl, 2.5 µl, or 5 µl per 1×10⁶ cells. These results show that % Tet of CD8+CD4+ cells appear comparable among cells transduced with Constructs #9, #10, and #11, and seems greater than that transduced with Construct #12. FACS analysis was gated on live singlets, followed by CD3+, followed by CD4+CD8+, and followed by CD4+CD8+Tet+.

Figure 12:
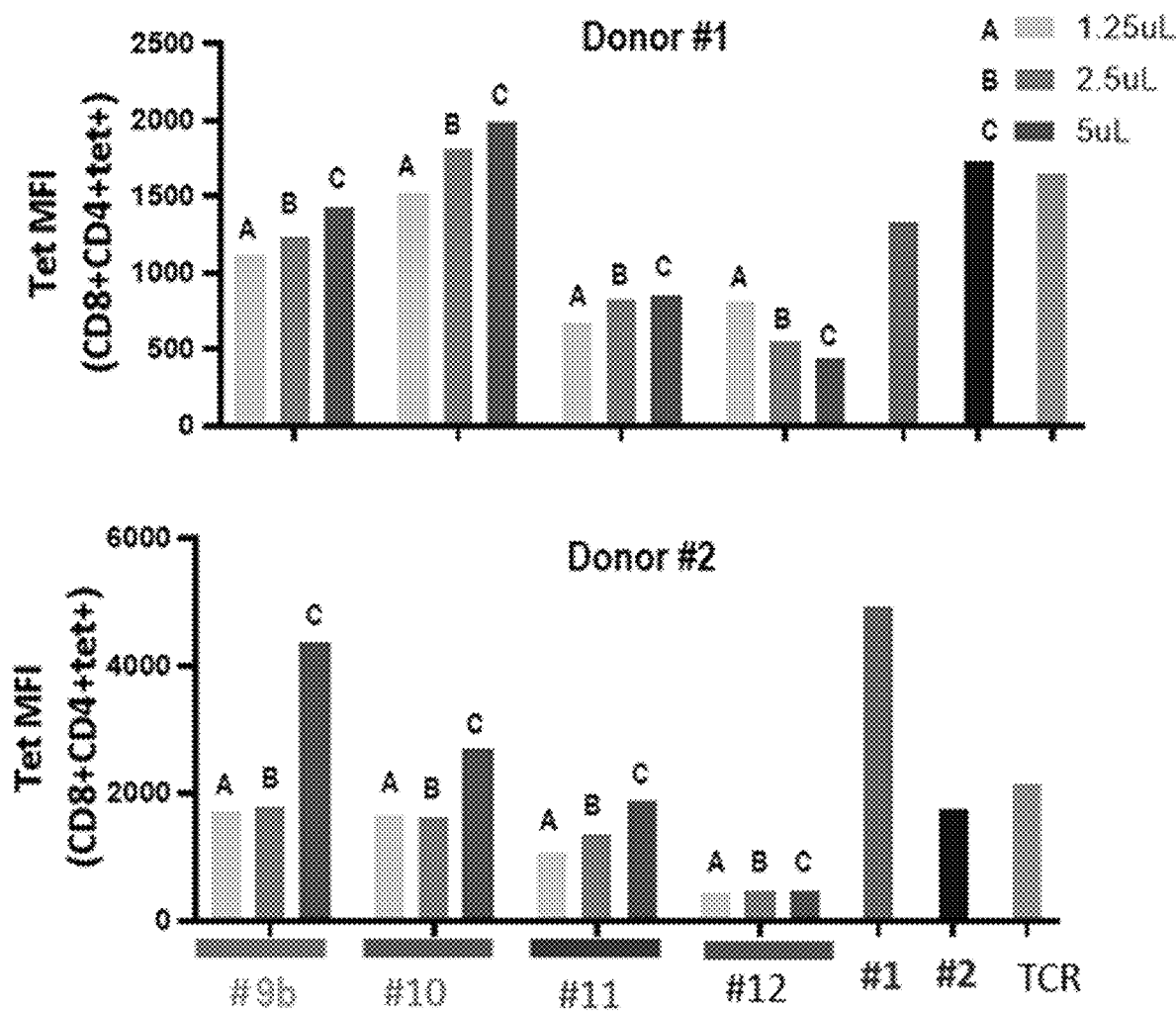
FIG. 12 shows Tet MFI (CD8+CD4+Tet+) of cells transduced with various constructs. The constructs are as follows: Construct #9b; Construct #10; Construct #11; Construct #12; Construct #1; Construct #2; TCR=R11KEA.WPRE$^{wt}$ (TCR with wild type WPRE); NT=Non-transduced T cells (as a negative control).
Figure 13:
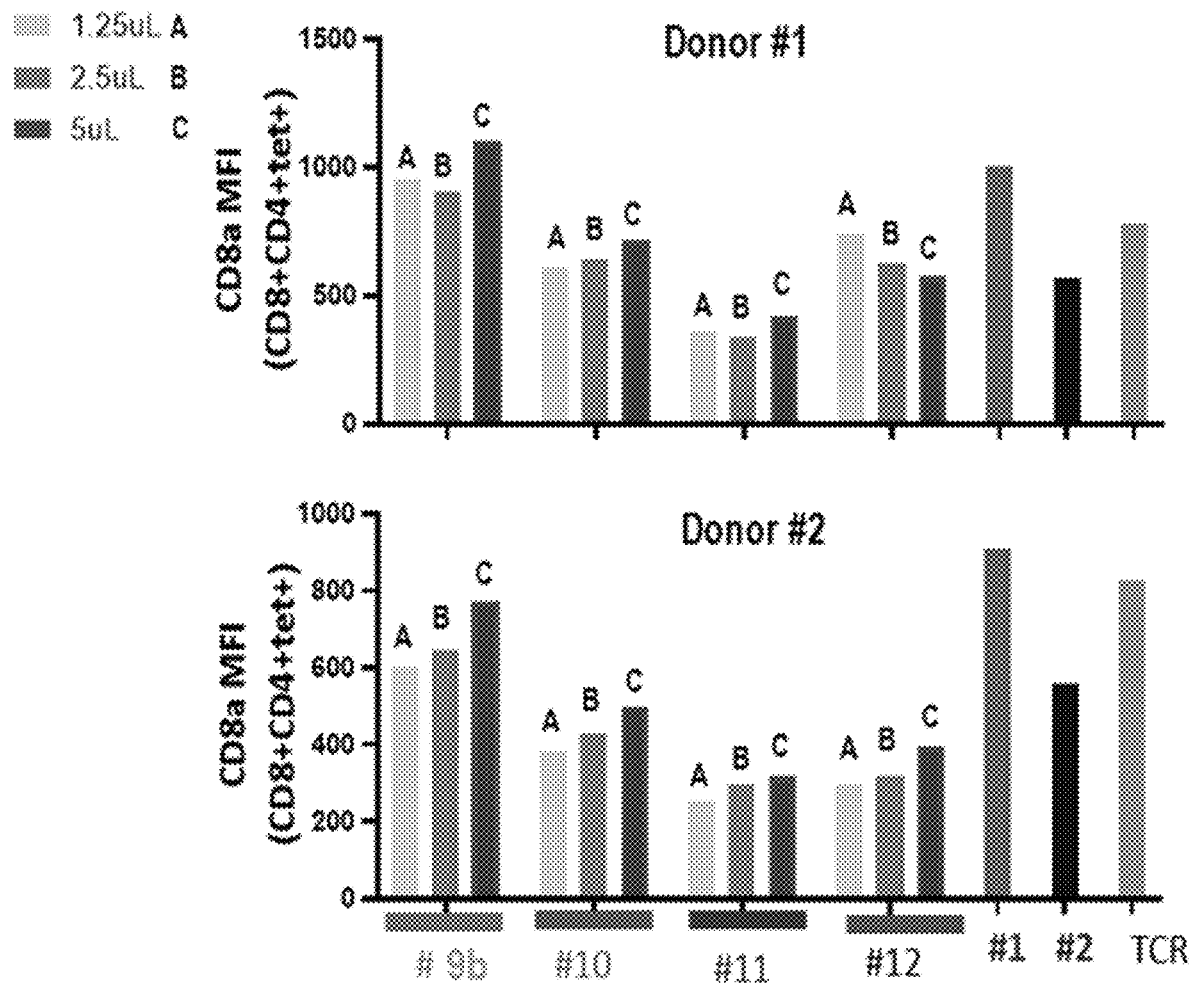
FIG. 13 shows CD8α MFI (CD8+CD4+Tet+) of cells transduced with various constructs. The constructs are as follows: Construct #9b; Construct #10; Construct #11; Construct #12; Construct #1; Construct #2; TCR=R11KEA.WPRE$^{wt}$ (TCR with wild type WPRE); NT=Non-transduced T cells (as a negative control).

FIG. 12 shows Tet MFI of CD8+CD4+Tet+ cells from Donor #1 (upper panel) and Donor #2 (lower panel) transduced with Construct #1, #2, #8 (TCR), #9, #10, #11, or #12 at 1.25 µl, 2.5 µl, or 5 µl per 1×10⁶ cells. These results show that tetramer MFI on CD4+CD8+Tet+ varies among donors. FIG. 13 shows CD8α MFI of CD8+CD4+Tet+ cells from Donor #1 (upper panel) and Donor #2 (lower panel) transduced with Construct #1, #2, #8 (TCR), #9, #10, #11, or #12 at 1.25 µl, 2.5 µl, or 5 µl per 1×10⁶ cells. These results show higher CD8α MFI in cells transduced with vectors expressing CD8α and TCR with wild type WPRE (Construct #1) and WPREmut2 (Construct #9) than that transduced with the other constructs. Transduction volume of 5 µl/10⁶ appears to yield better results than 1.25 µl/10⁶ and 2.5 µl/10⁶. FACS analysis was gated on live singlets, followed by CD3+, followed by CD4+CD8+, followed by CD4+CD8+Tet+, and followed by Tet MFI/CD8α MFI.

Figure 14:
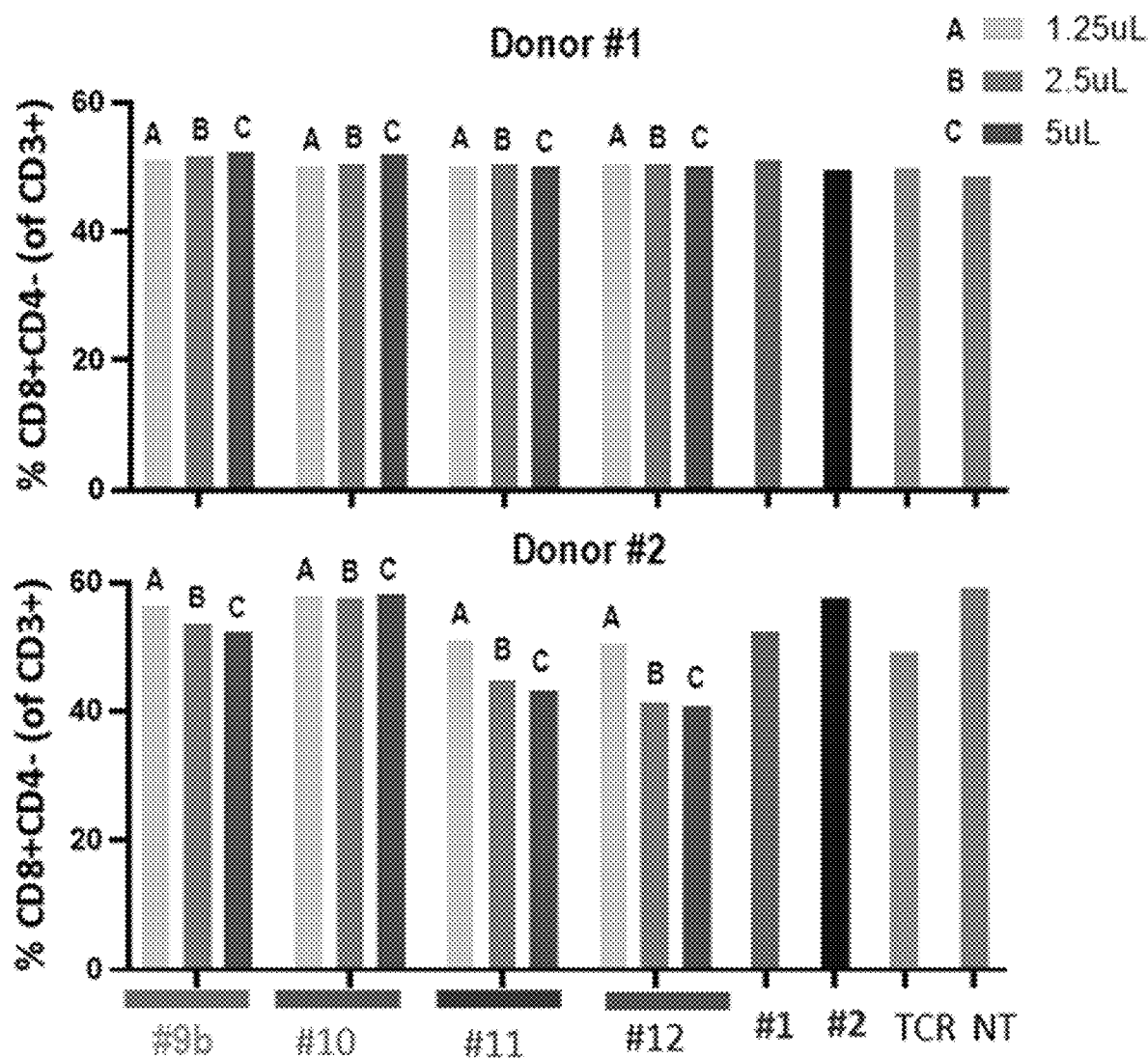
FIG. 14 shows % CD8+CD4 (of CD3+) of cells transduced with various constructs. The constructs are as follows: Construct #9b; Construct #10; Construct #11; Construct #12; Construct #1; Construct #2; TCR=R11KEA.WPRE$^{wt}$ (TCR with wild type WPRE); NT=Non-transduced T cells (as a negative control).
Figure 15:
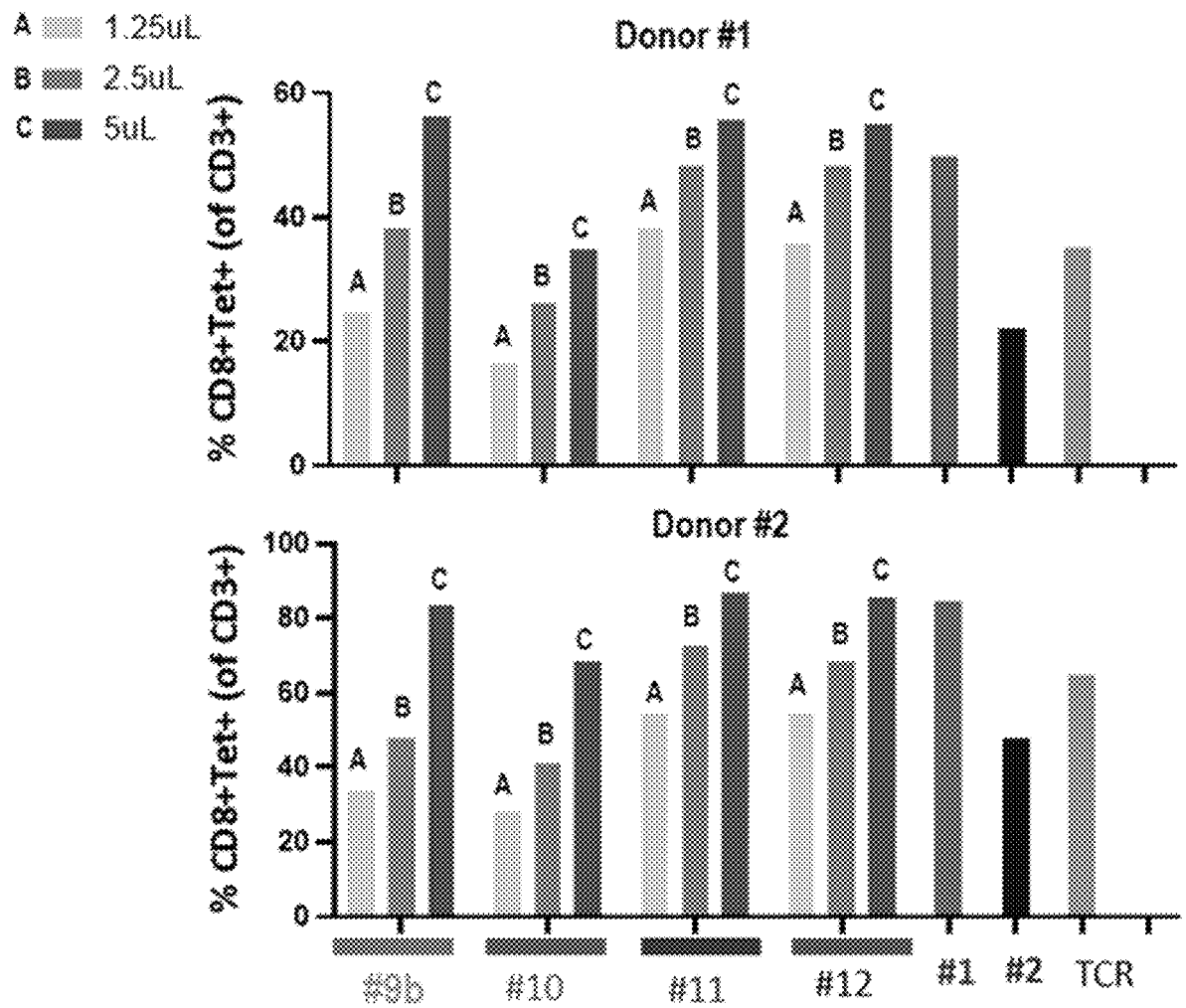
FIG. 15 shows % CD8+Tet+(of CD3+) of cells transduced with various constructs. The constructs are as follows: Construct #9b; Construct #10; Construct #11; Construct #12; Construct #1; Construct #2; TCR=R11KEA.WPRE$^{wt}$ TCR with wild type WPRE); NT=Non-transduced T cells (as a negative control).

FIG. 14 shows CD8 frequencies (% CD8+CD4− of CD3+) in cells from Donor #1 (upper panel) and Donor #2 (lower panel) transduced with Construct #1, #2, #8 (TCR), #9, #10, #11, or #12 at 1.25 µl, 2.5 µl, or 5 µl per 1×10⁶ cells. These results show no difference in the CD8 frequencies among the constructs. Non-transduction (NT) serves as negative control. FIG. 15 shows % CD8+Tet+(of CD3+) cells from Donor #1 (upper panel) and Donor #2 (lower panel) transduced with Construct #1, #2, #8 (TCR), #9, #10, #11, or #12 at 1.25 µl, 2.5 µl, or 5 µl per 1×10⁶ cells. These results show higher frequencies of CD8+Tet+(of CD3+) in cells transduced with Constructs #9, #11, and #12 than that transduced with Construct #10. FACS analysis was gated on live singlets, followed by CD3+, followed by CD8+CD4−, and followed by CD8+Tet+.

Figure 16:
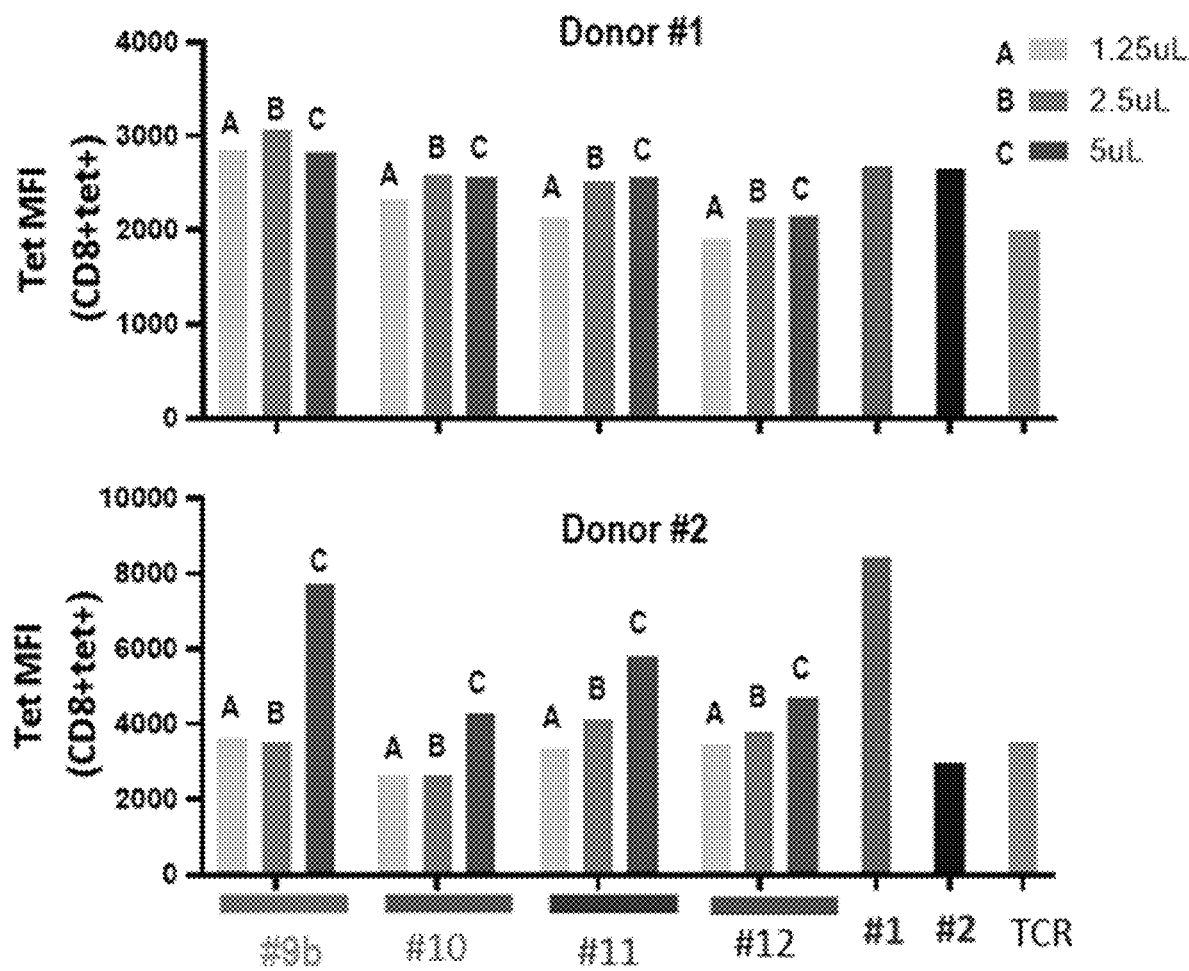
FIG. 16 shows Tet MFI (CD8+Tet+) of cells transduced with various constructs. The constructs are as follows: Construct #9b; Construct #10; Construct #11; Construct #12; Construct #1; Construct #2; TCR=R11KEA.WPRE$^{wt}$ (TCR with wild type WPRE); NT=Non-transduced T cells (as a negative control).
Figure 17:
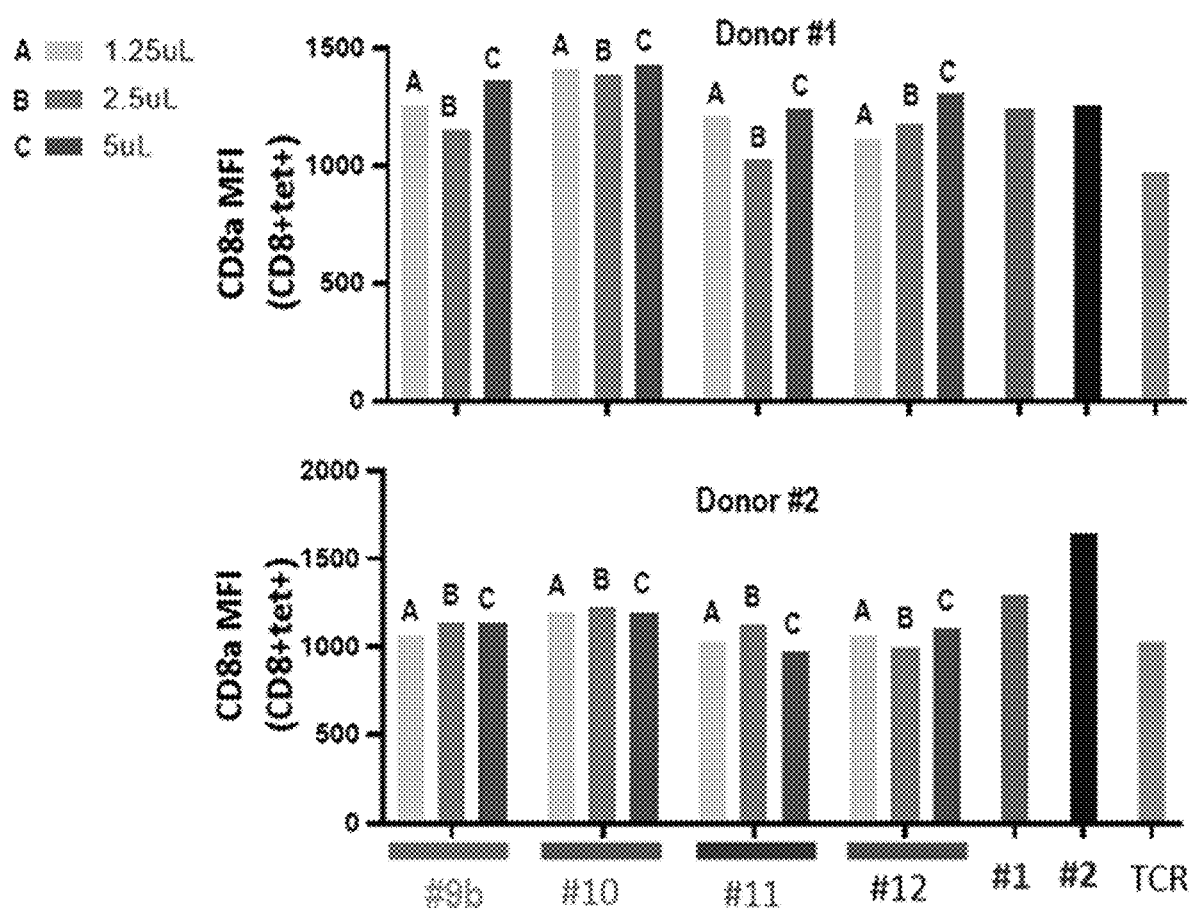
FIG. 17 shows CD8α MFI (CD8+Tet+) of cells transduced with various constructs. The constructs are as follows: Construct #9b; Construct #10; Construct #11; Construct #12; Construct #1; Construct #2; TCR=R11KEA.WPRE$^{wt}$ (TCR with wild type WPRE); NT=Non-transduced T cells (as a negative control).

FIG. 16 shows Tet MFI of CD8+Tet+ cells from Donor #1 (upper panel) and Donor #2 (lower panel) transduced with Construct #1, #2, #8 (TCR), #9, #10, #11, or #12 at 1.25 µl, 2.5 µl, or 5 µl per 1×10⁶ cells. These results show tetramer MFI of CD8+tet+ cells varies among donors. FIG. 17 shows CD8α MFI of CD8+Tet+ cells from Donor #1 (upper panel) and Donor #2 (lower panel) transduced with Construct #1, #2, #8 (TCR), #9, #10, #11, or #12 at 1.25 µl, 2.5 µl, or 5 µl per 1×10⁶ cells. These results show that CD8α MFI of CD8+Tet+ are comparable among cells transduced with different constructs. FACS analysis was gated on live singlets, followed by CD3+, followed by CD4+CD8+, followed by CD4+CD8+Tet+, and followed by Tet MFI/CD8α MFI.

FIG. 18 shows % Tet+ of CD3+ cells from Donor #1 (upper panel) and Donor #2 (lower panel) transduced with Construct #1, #2, #8 (TCR), #9, #10, #11, or #12 at 1.25 µl, 2.5 µl, or 5 µl per 1×10⁶ cells. These results show higher frequencies of CD3+Tet+ in cells transduced with Construct #9 or #11 than that transduced with Construct #10 or #12. It appears more % Tet+CD3+ cells in cells transduced with Construct #9 (WPREmut2) than that transduced with Construct #2 (wild type WPRE) at 5 µl per 1×10⁶ cells. FACS analysis was gated on live singlets, followed by CD3+, followed by CD3+, and followed by Tet+.

Figure 19:
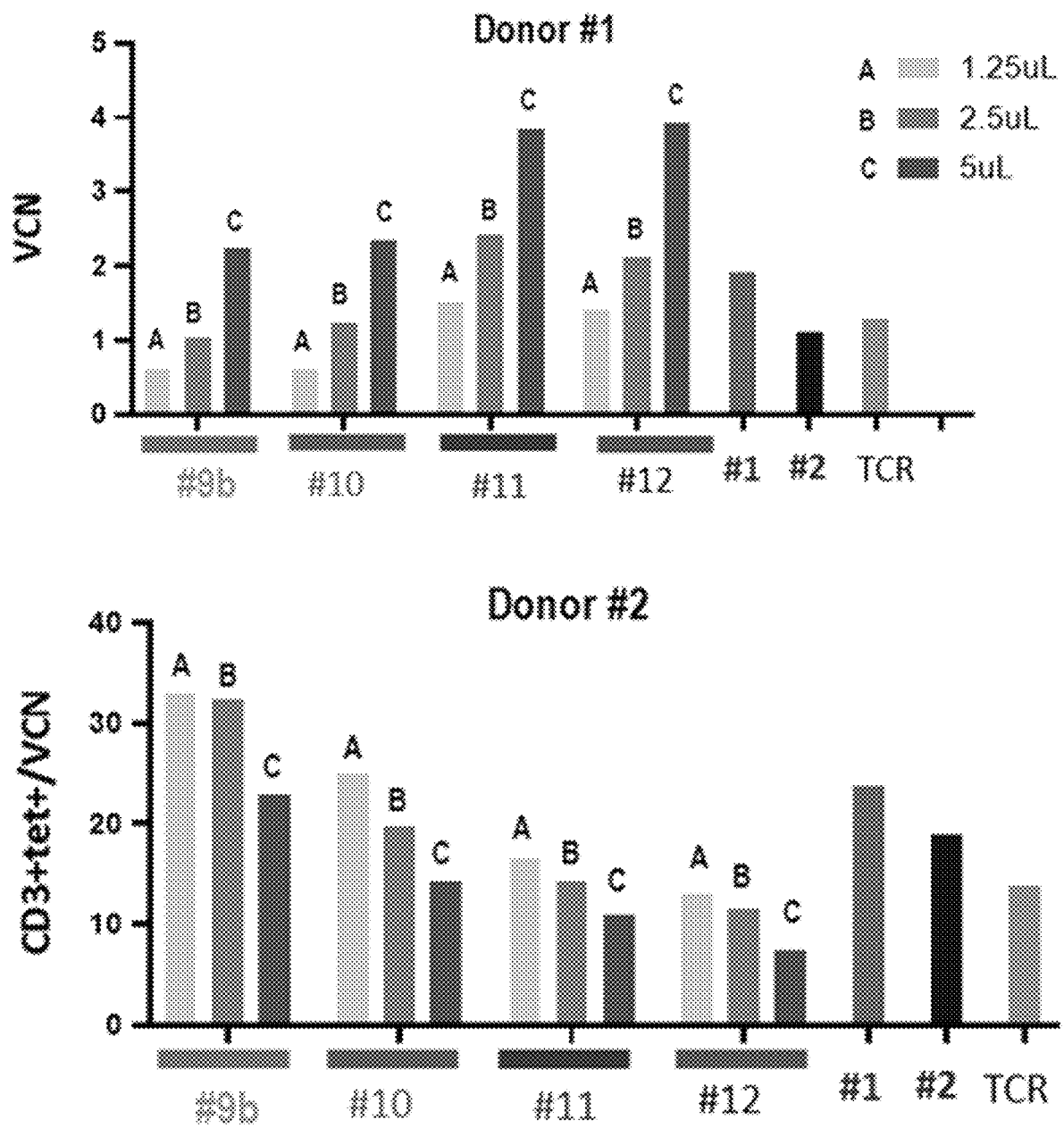
FIG. 19 shows VCN (upper panel) and CD3+Tet+/VCN (lower panel) of cells transduced with various constructs. The constructs are as follows: Construct #9b; Construct #10; Construct #11; Construct #12; Construct #1; Construct #2; TCR=R11KEA.WPRE$^{wt}$ (TCR with wild type WPRE); NT=Non-transduced T cells (as a negative control).

FIG. 19 (upper panel) shows vector copy number (VCN) of cells from Donor #1 transduced with Construct #1, #2, #8 (TCR), #9, #10, #11, or #12 at 1.25 µl, 2.5 µl, or 5 µl per 1×10⁶ cells. These results show higher VCN for cells transduced with Constructs #11 or #12 (may be due to higher titers) than that transduced with Construct #9 or #10. FIG. 19 (lower panel) shows CD3+Tet+/VCN of cells from Donor #1 transduced with Construct #1, #2, #8 (TCR), #9, #10, #11, or #12 at 1.25 µl, 2.5 µl, or 5 µl per 1×10⁶ cells. These results show higher CD3+Tet+/VCN in cells transduced with Construct #9 than that transduced with Construct #10, #11, or #12.

In sum, these results show (1) higher % CD8+CD4+ cells obtained by transducing cells with vectors expressing CD8α and TCR with wild type WPRE (Construct #1) and WPREmut2 (Construct #9) than that transduced with Construct #10, #11 or #12; (2) % CD8+CD4+Tet+ cells was comparable among cells transduced with different constructs; (3) dose dependent increase in % tetramer, e.g., 5 µl per 1×10⁶ cells showed better results than 1.25 µl and 2.5 µl per 1×10⁶ cells; (4) % CD8+ cells comparable among cells transduced with different constructs; (5) higher frequencies of CD8+Tet+ in cells transduced with Construct #9, #11, or #12 than that transduced with Construct #10; (6) higher frequencies of CD3+Tet+ in cells transduced with Construct #9 or #11 than that transduced with Construct #10 or #12; (7) higher VCN in cells transduced with Construct #11 or #12 than that transduced with Construct #9 or #10; and (8) higher CD3+tet+/VCN in cells transduced with Construct #9 than that transduced with Construct #10, #11, or #12.

T cell products transduced with viral vector expressing a transgenic TCR and modified CD8 co-receptor showed superior cytotoxicity and increased cytokine production against target positive cell lines.

Example 5

Tumor Death Assay

Figure 20A:
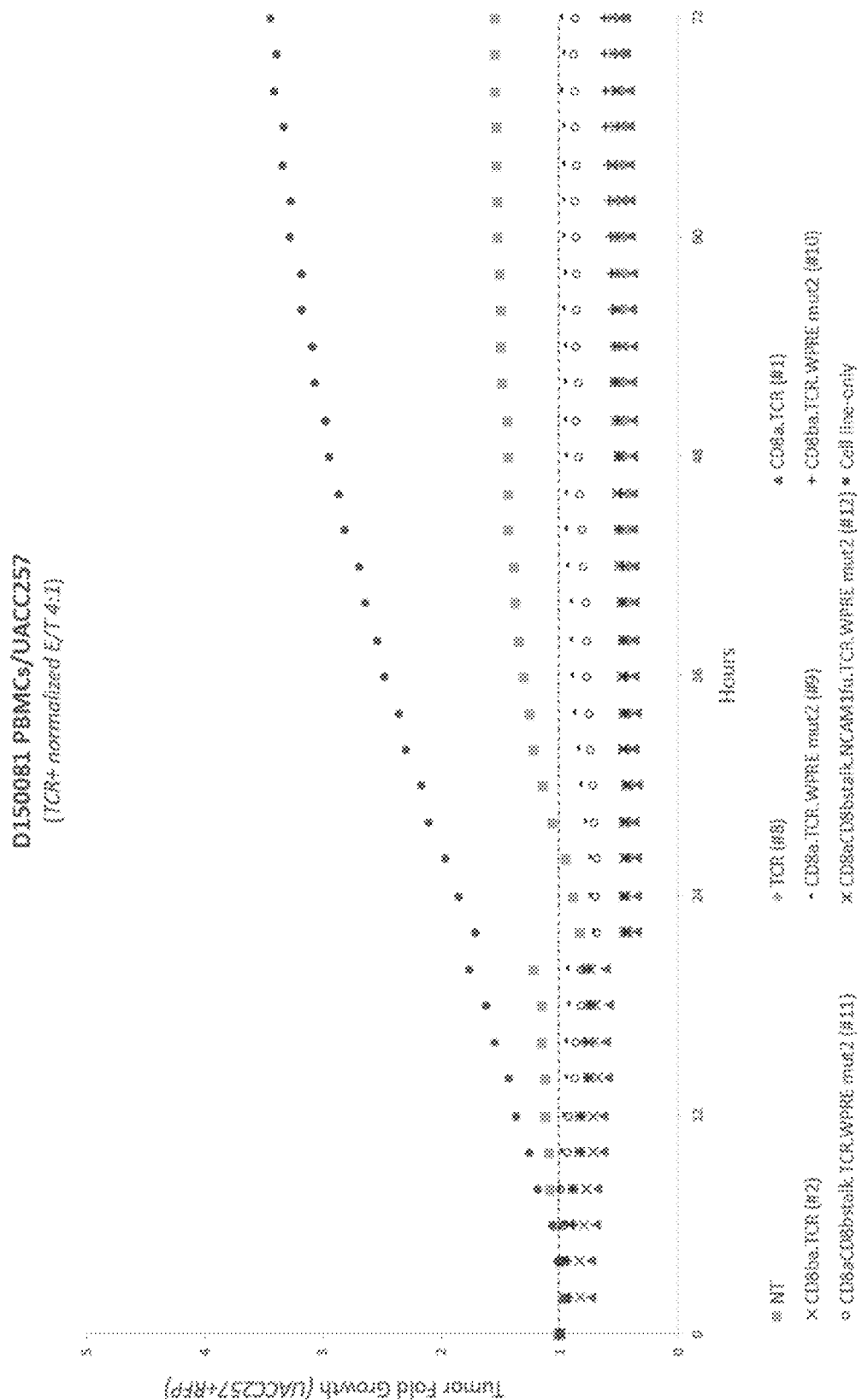
FIG. 20A-20C depicts data showing that constructs (#10, #11, & #12) are comparable to TCR-only in mediating cytotoxicity against target positive cells lines expressing antigen at different levels (UACC257 at 1081 copies per cell and A375 at 50 copies per cell).
Figure 20B:
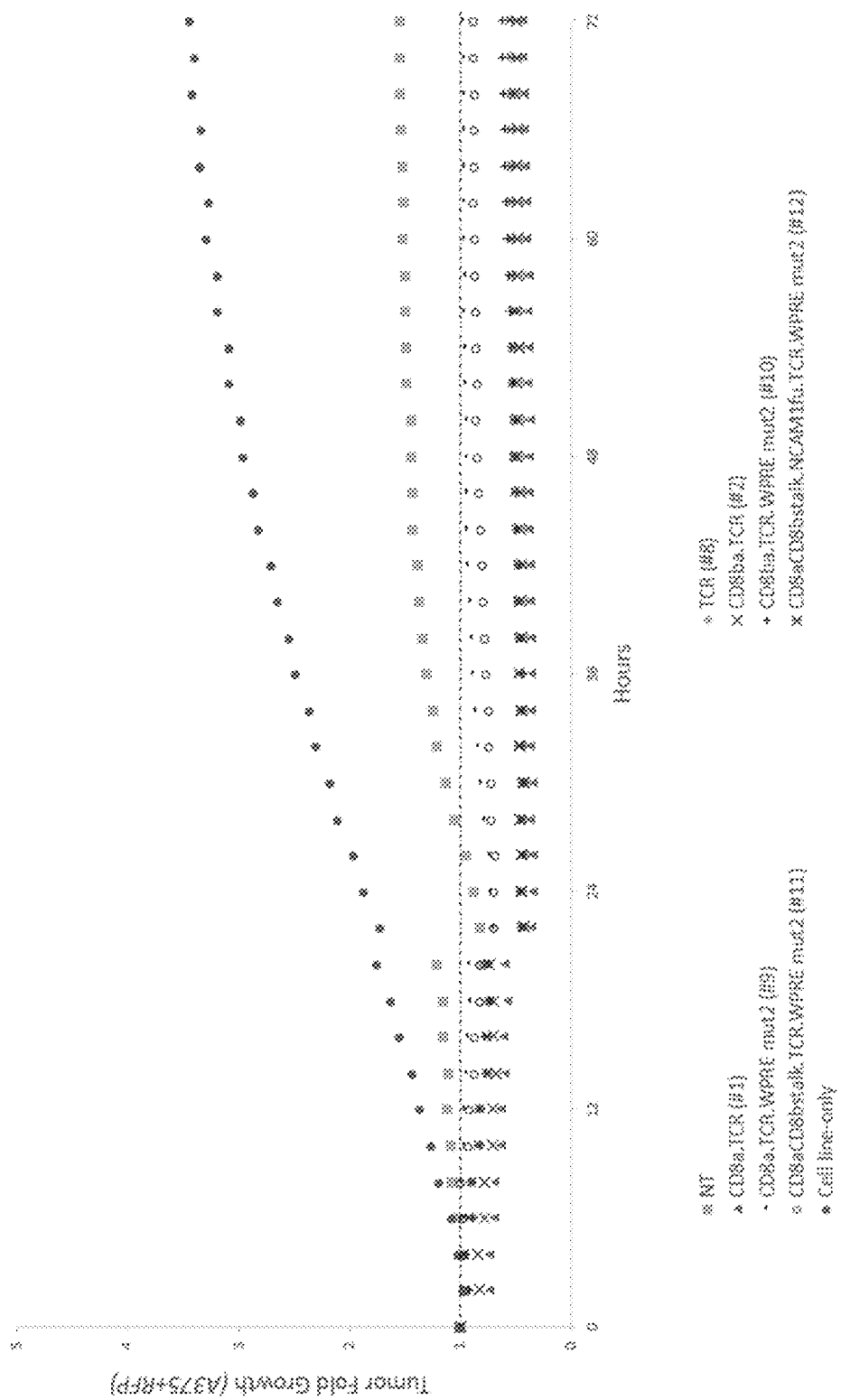
Figure 20C:
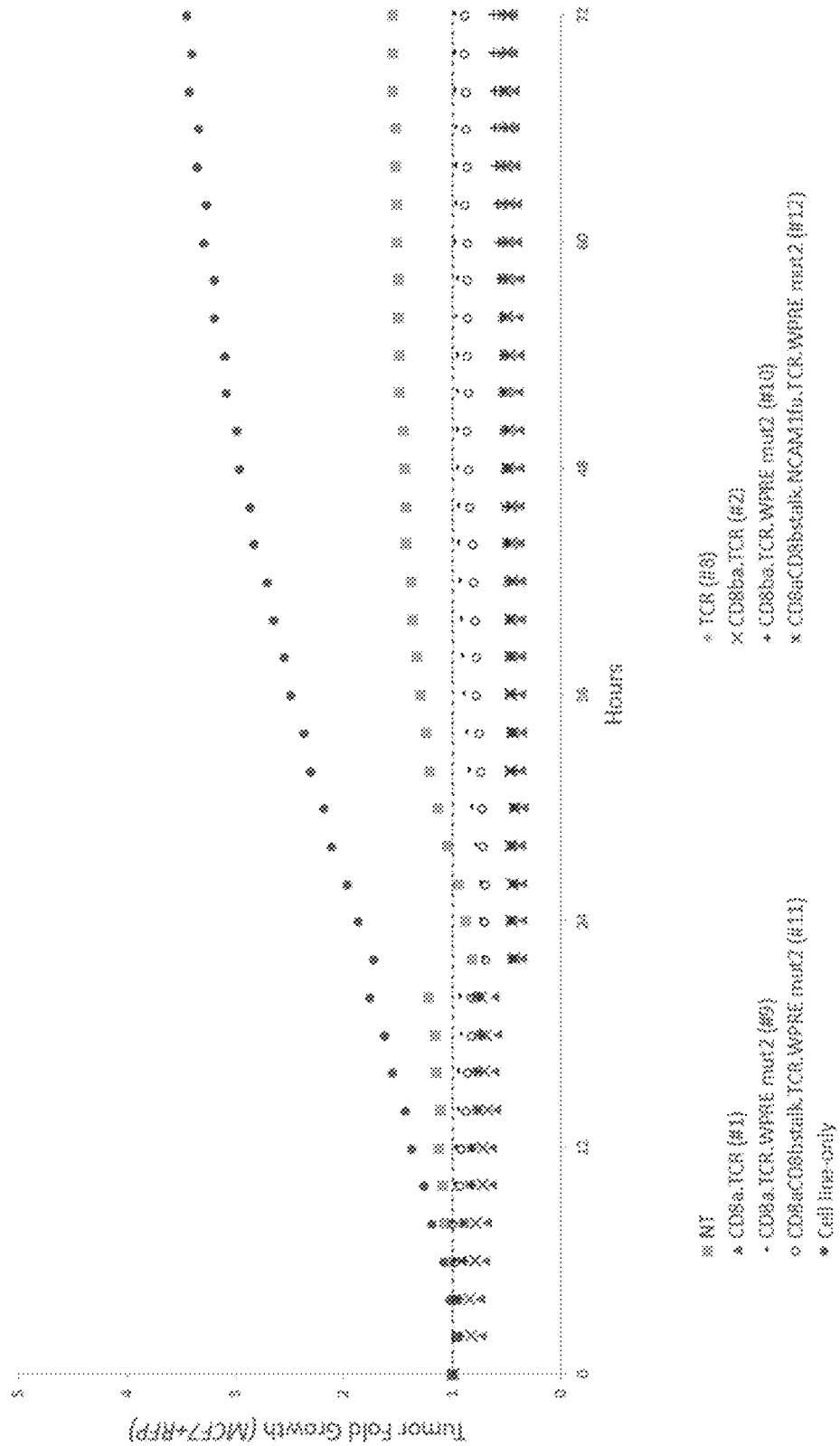

FIG. 20A-C depicts data showing that constructs (#10, #11, & #12) are comparable to TCR-only in mediating cytotoxicity against target positive cells lines expressing antigen at different levels (UACC257 at 1081 copies per cell and A375 at 50 copies per cell).

TABLE 7

| Tumor Cell Line | Antigen Positivity |
|---|---|
| UACC257 | High |
| A375 | Low |
| MCF7 | Negative |

Construct #9 loses tumor control over time against the low target antigen expressing A375 cell line.

Example 6

IFNγ Secretion Assay

Figure 21A:
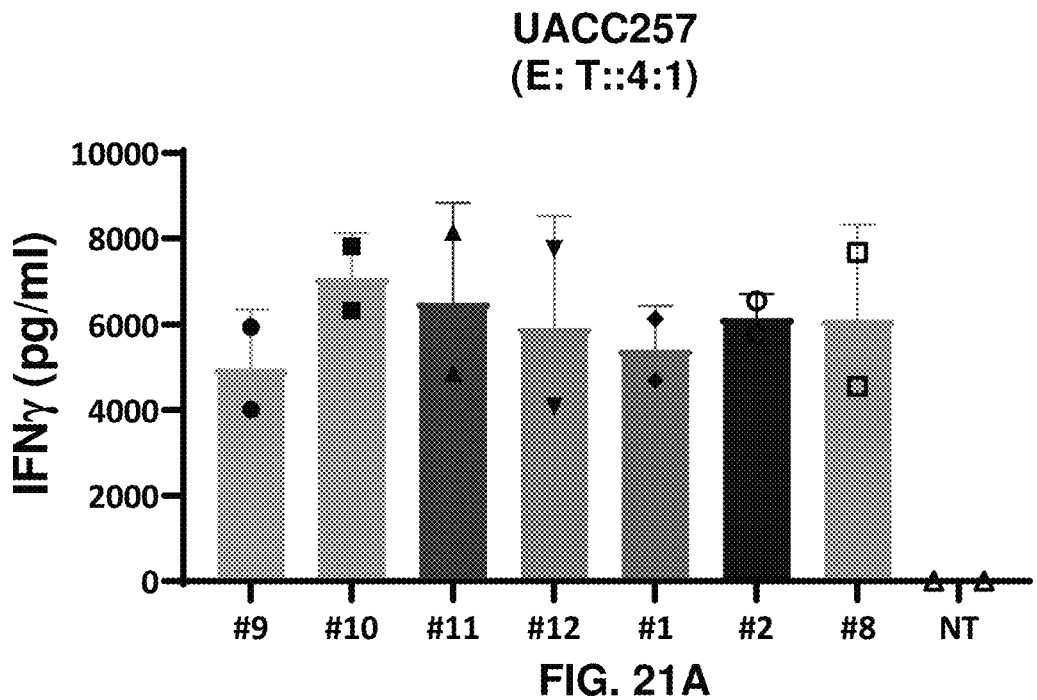
FIG. 21A-21B depict data showing that IFNγ secretion in response to UACC257 is comparable among constructs, however with A375, #10 expressing is the highest among all constructs. However, comparing #9 with #11 expressing wild type and modified CD8 coreceptor sequences respectively, T cells transduced with #11 induced stronger cytokine response measured as IFNγ quantified in the supernatants from Incucyte plates. Construct #9; Construct #10; Construct #11; Construct #12; Construct #1; Construct #2; Construct #8=R11KEA TCR only.
Figure 21B:
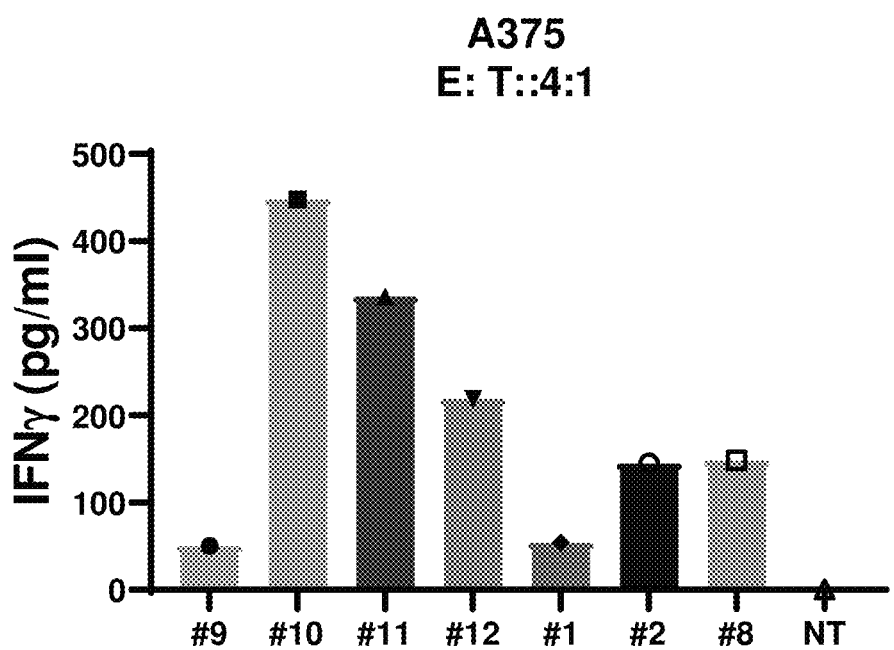

IFNγ secretion was measured in UACC257 and A375 cells lines. IFNγ secretion in response in UACC257 cell line was comparable among constructs. However, in the A375 cell line, Construct #10 showed higher IFNγ secretion than other constructs. IFNγ quantified in the supernatants from Incucyte plates. FIG. 21A-B.

Figure 22:
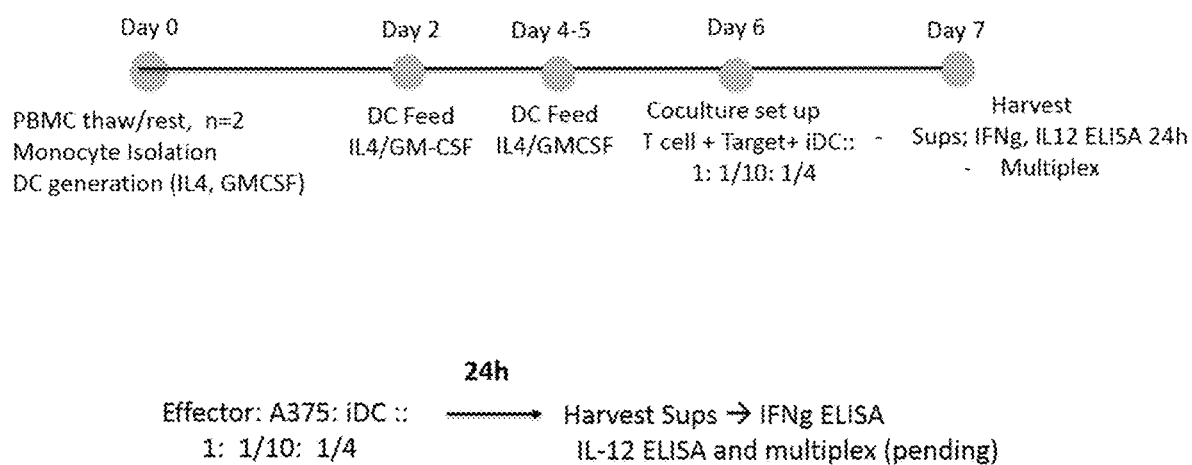
FIG. 22 depicts an exemplary experiment design to assess DC maturation and cytokine secretion by PBMC-derived product in response to UACC257 and A375 targets. N=2.

FIG. 22 depicts an exemplary experiment design to assess Dendritic Cell (DC) maturation and cytokine secretion by PBMC-derived T cell products in response to exposure to target positive tumor cell lines UACC257 and A375.

Figure 23A:
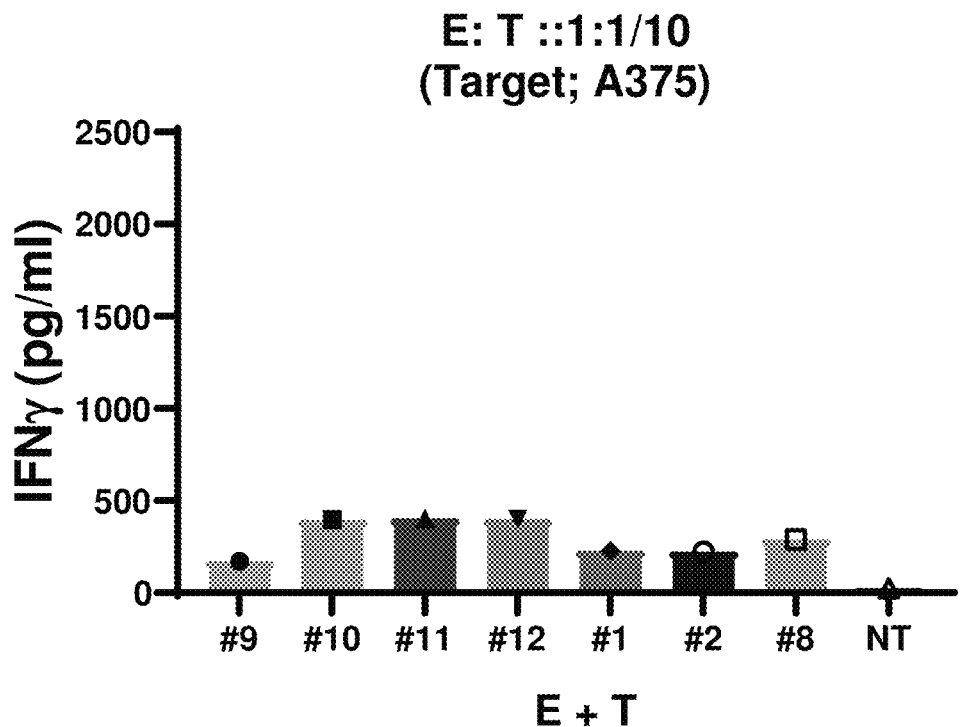
FIG. 23A-23B depicts data showing that the IFNγ secretion in response to A375 increases in the presence of iDCs. In the tri-cocultures with iDCs, IFNγ secretion is higher in Construct #10 compared to the other constructs. However, comparing Construct #9 with Construct #11 expressing wild type and modified CD8 coreceptor sequences respectively, T cells transduced with #11 induced stronger cytokine response measured as IFNγ quantified in the culture supernatants of three-way cocultures using donor D600115, E:T: iDC::1:1/10:1/4. Construct #9; Construct #10; Construct #11; Construct #12; Construct #1; Construct #2; Construct #8=R11KEA TCR only.
Figure 23B:
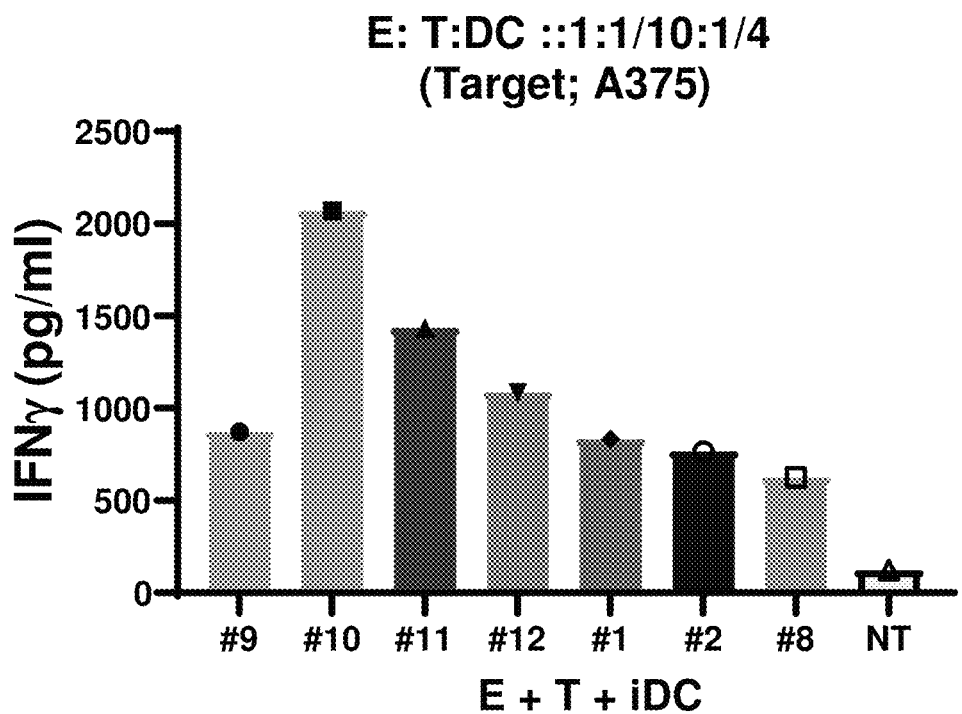

IFNγ secretion in response to A375 increases in the presence of immature DC (iDCs). In the tri-cocultures with iDCs, IFNγ secretion is higher in Construct #10 compared to the other constructs. However, comparing Construct #9 with Construct #11 expressing wild type and modified CD8 coreceptor sequences respectively, T cells transduced with #11 induced stronger cytokine response measured as IFNγ quantified in the culture supernatants of three-way cocultures using donor D600115, E:T:iDC::1:1/10:1/4. FIG. 23A-B.

Figure 24A:
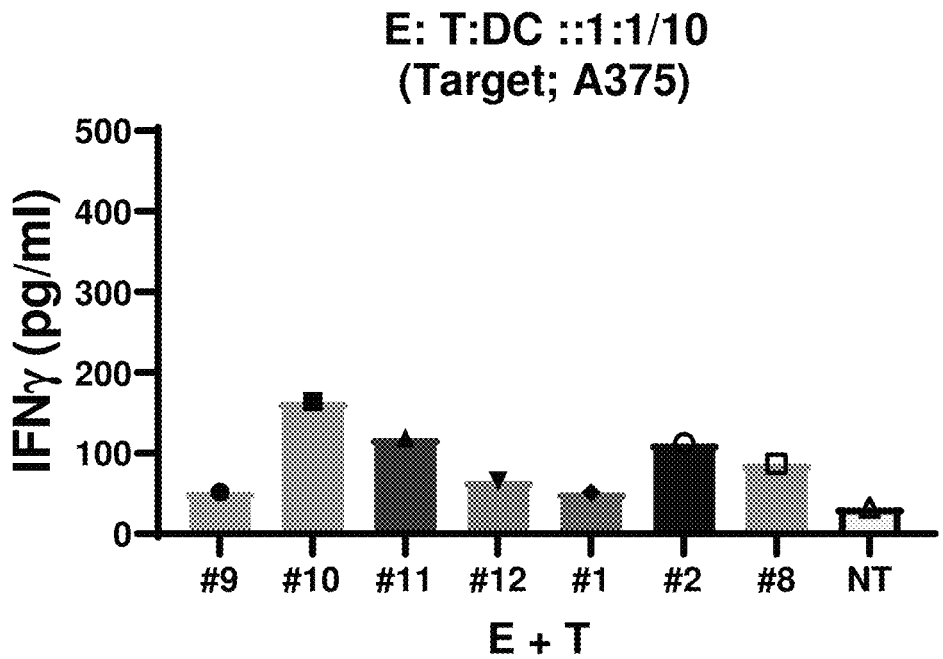
FIG. 24A-24B depicts data showing that IFNγ secretion in response to A375 increases in the presence of iDCs. In the tri-cocultures with iDCs, IFNγ secretion was higher in Construct #10 compared to the other constructs. IFNγ quantified in the culture supernatants of three-way cocultures using donor D150081, E:T:iDC::1:1/10:1/4. Construct #9; Construct #10; Construct #11; Construct #12; Construct #1; Construct #2; Construct #8=R11KEA TCR only.
Figure 24B:
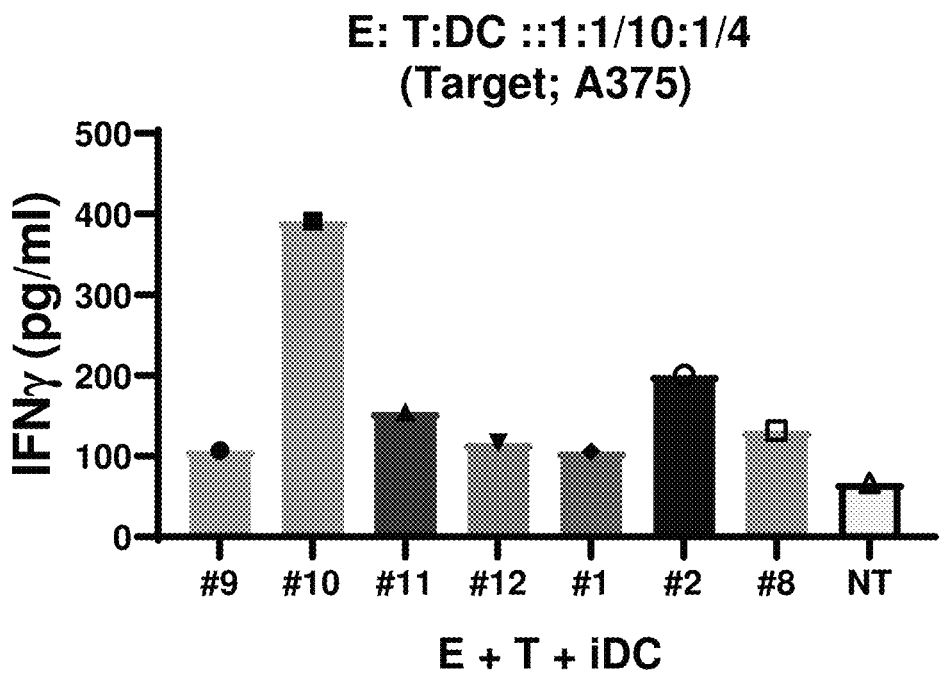
Figure 25A:
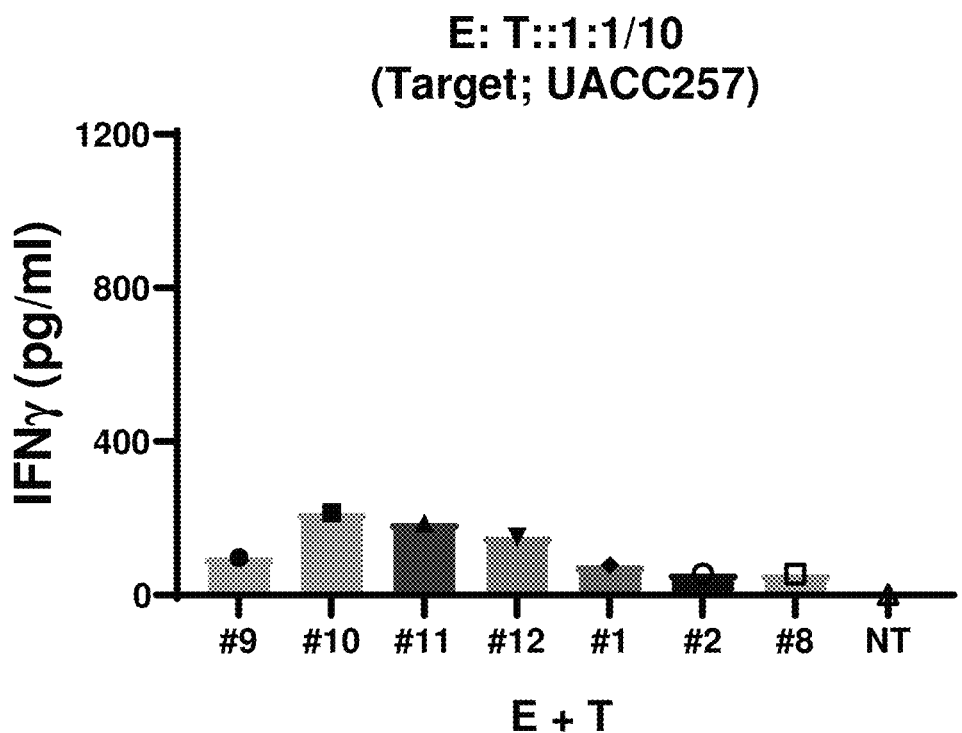
FIG. 25A-25B depicts data showing that IFNγ secretion in response to UACC257 increases in the presence of iDCs. In the tri-cocultures with iDCs, IFNγ secretion is higher in Construct #10 compared to the other constructs. However, comparing Construct #9 with Construct #11 expressing wild type and modified CD8 coreceptor sequences respectively, T cells transduced with Construct #11 induced stronger cytokine response measured as IFNγ quantified in the culture supernatants of three-way cocultures using donor D600115, E:T:iDC::1:1/10:1/4. Construct #9; Construct #10; Construct #11; Construct #12; Construct #1; Construct #2; Construct #8=R11KEA TCR only.
Figure 25B:
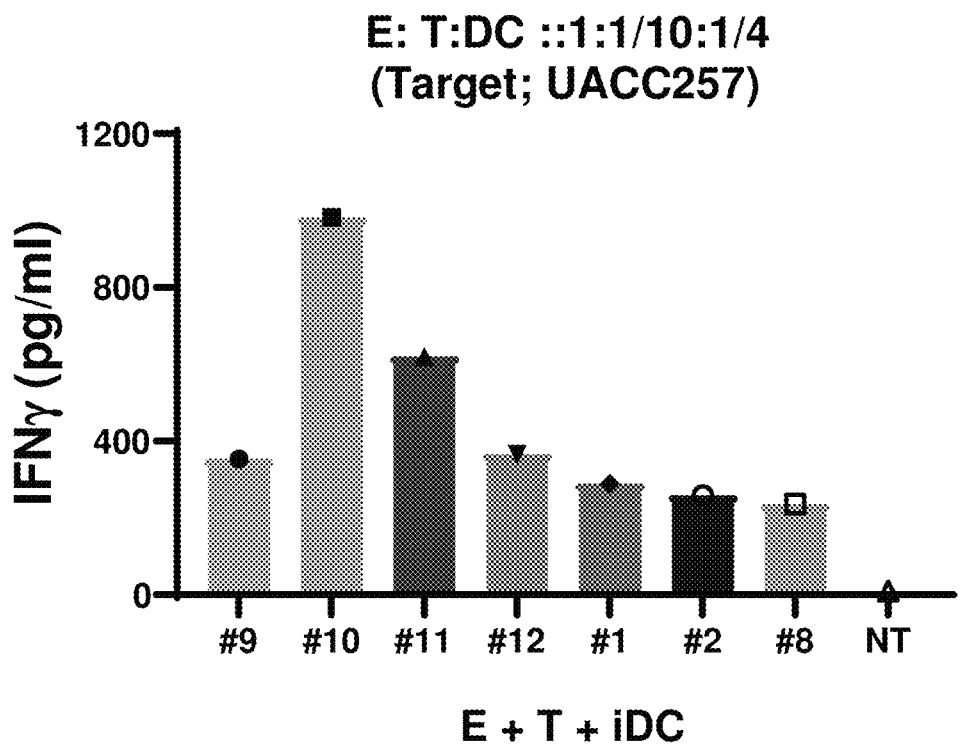

IFNγ secretion in response to A375 increases in the presence of iDCs. In the tri-cocultures with iDCs, IFNγ secretion was higher in Construct #10 compared to the other constructs. IFNγ quantified in the supernatants from DC cocultures D150081, E:T:iDC::1:1/10:1/4. FIG. 24A-B IFNγ secretion in response to UACC257 increases in the presence of iDCs. In the tri-cocultures with iDCs, IFNγ secretion is higher in Construct #10 compared to the other constructs. However, comparing Construct #9 with Construct #11 expressing wild type and modified CD8 coreceptor sequences respectively, T cells transduced with Construct #11 induced stronger cytokine response measured as IFNγ quantified in the culture supernatants of three-way cocultures using donor D600115, E:T:iDC::1:1/10:1/4. FIG. 25A-B. These results demonstrate that T cell products co-expressing a transgenic TCR and CD8 co-receptor (αβ heterodimer or modified CD8α homodimer) are able to license DCs in the microenvironment through antigen cross presentation and therefore hold the potential to mount a stronger anti-tumor response and modulate the tumor microenvironment.

Example 7

Vector Screening (Constructs #13-#21)

Viral Titers

Figure 5B:
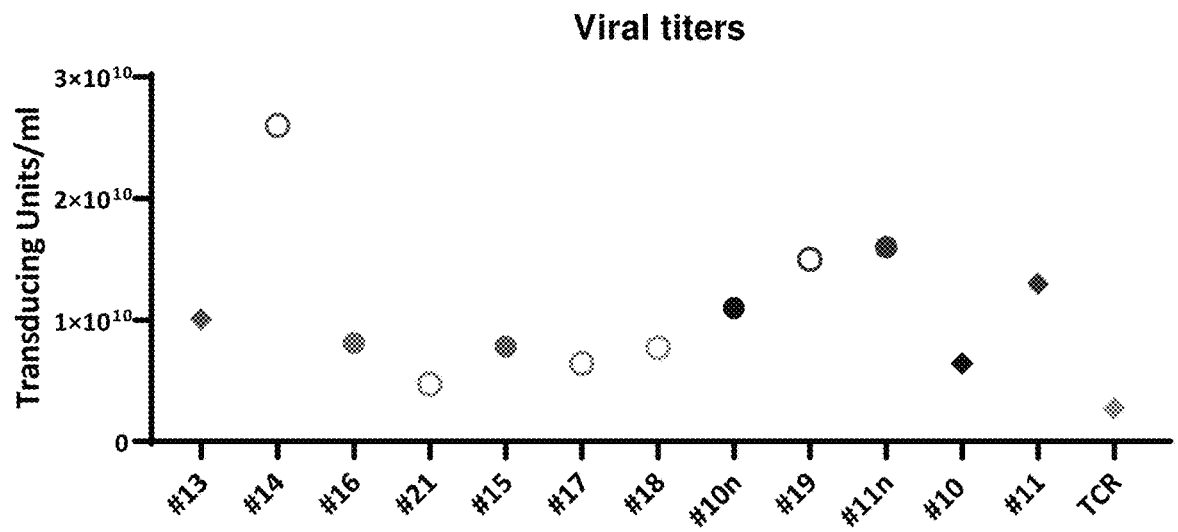
FIG. 5B shows titers of further viral vectors in accordance with an embodiment of the present disclosure. Construct #13; Construct #14; Construct #15; Construct #16; Construct #17; Construct #18; Construct #19; Construct #21; Construct #10n; Construct #11n; and TCR: R11KEA (SEQ ID NO: 15 and SEQ ID NO: 16) (Construct #8), which binds PRAME-004 (SLLQHLIGL) (SEQ ID NO: 147). Note that Constructs #10 and #10n are different batches of the same construct (SEQ ID NO: 291 and 292) and Constructs #11 and #11n are different batches of the same construct (SEQ ID NO: 285 and 286).

FIG. 5B shows viral titer of Constructs #10, #10n (new batch), #11, #11n (new batch), #13-#21, and TCR only as a control.

T Cell Manufacturing

Activation

Figure 26:
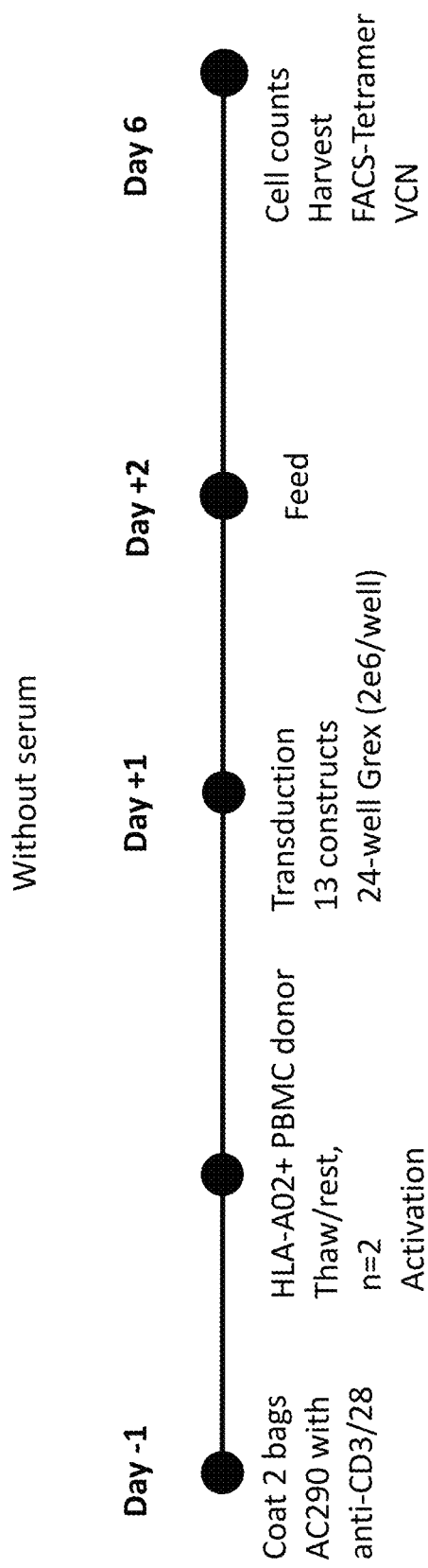
FIG. 26 shows T cell manufacturing in accordance with one embodiment of the present disclosure.
Figure 27A:
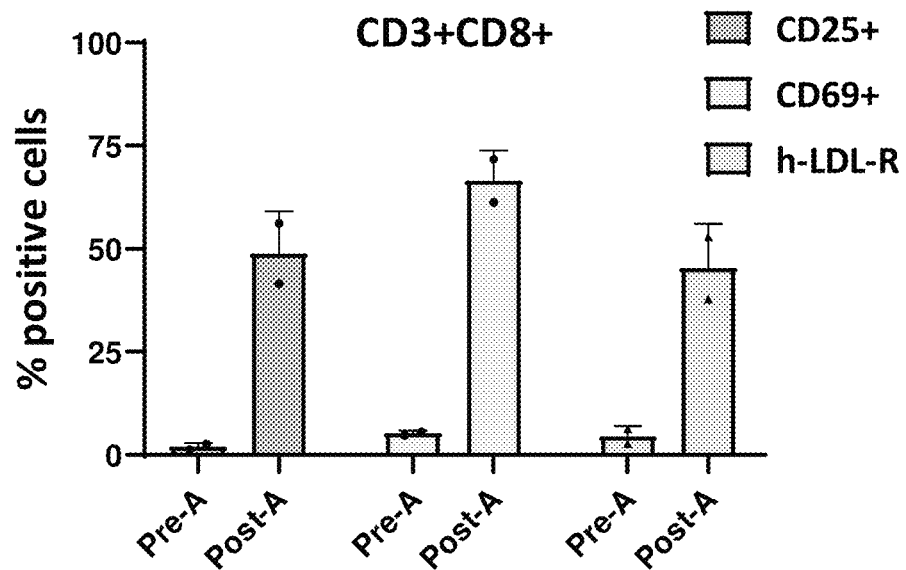
FIG. 27A shows expression of activation markers before and after activation in CD3+CD8+ cells.
Figure 27B:
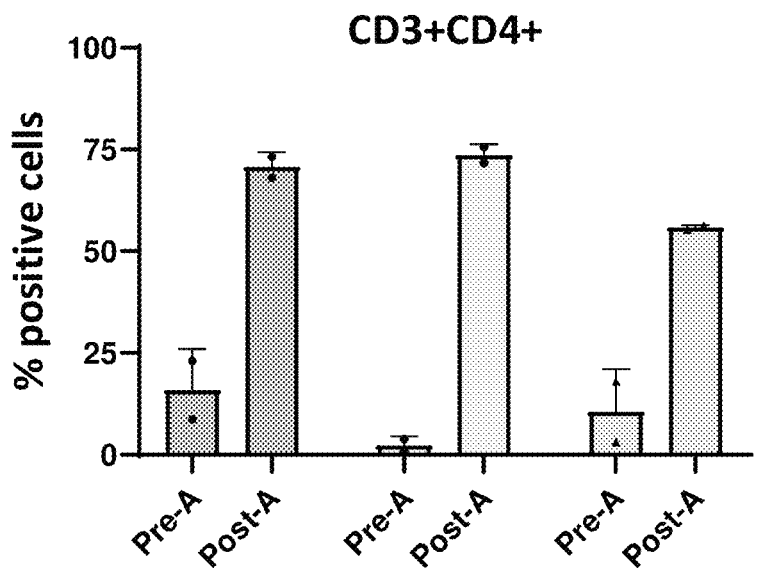
FIG. 27B shows expression of activation markers before and after activation in CD3+CD4+ cells in accordance with one embodiment of the present disclosure.

FIG. 26 shows that, on Day +0, PBMCs obtained from two HLA-A02+ donors (Donor #1 and Donor #2) were thawed and rested. Cells were activated in bags (AC290) coated with anti-CD3 and anti-CD28 antibodies in the absence of serum. Activation markers, e.g., CD25, CD69, and human low density lipoprotein receptor (H-LDL-R) are in CD8+ and CD4+ cells, were subsequently measured. FIG. 27A shows that % CD3+CD8+CD25+ cells, % CD3+CD8+ CD69+ cells, and % CD3+CD8+H-LDL-R+ cells increase after activation (Post-A) as compared with that before activation (Pre-A). Similarly, FIG. 27B shows that % CD3+ CD4+CD25+ cells, % CD3+CD4+CD69+ cells, and % CD3+CD4+H-LDL-R+ cells increase after activation (Post-A) as compared with that before activation (Pre-A). These results support the activation of PBMCs.

Transduction

FIG. 26 shows that, on Day +1, activated PBMCs were transduced with viral vectors, e.g., Constructs #8, #10, #10n, #11, #11n, and #13-#21, in G-Rex® 24-well plates at about $2 \times 10^6$ cells/well in the absence of serum. The amounts of virus used for transduction are shown in Table 8.

TABLE 8

| Constructs | Virus Volume/1 × 10⁶ cells |
|---|---|
| #10n, #11n, #13-#21 | 0.3 µl, 1.1 µl, 3.3 µl, 10 µl, 30 µl |
| #8 (TCR), #10 | 2.5 µl |
| #11 | 1.25 µl |
| NT | — |

Expansion

Figure 28:
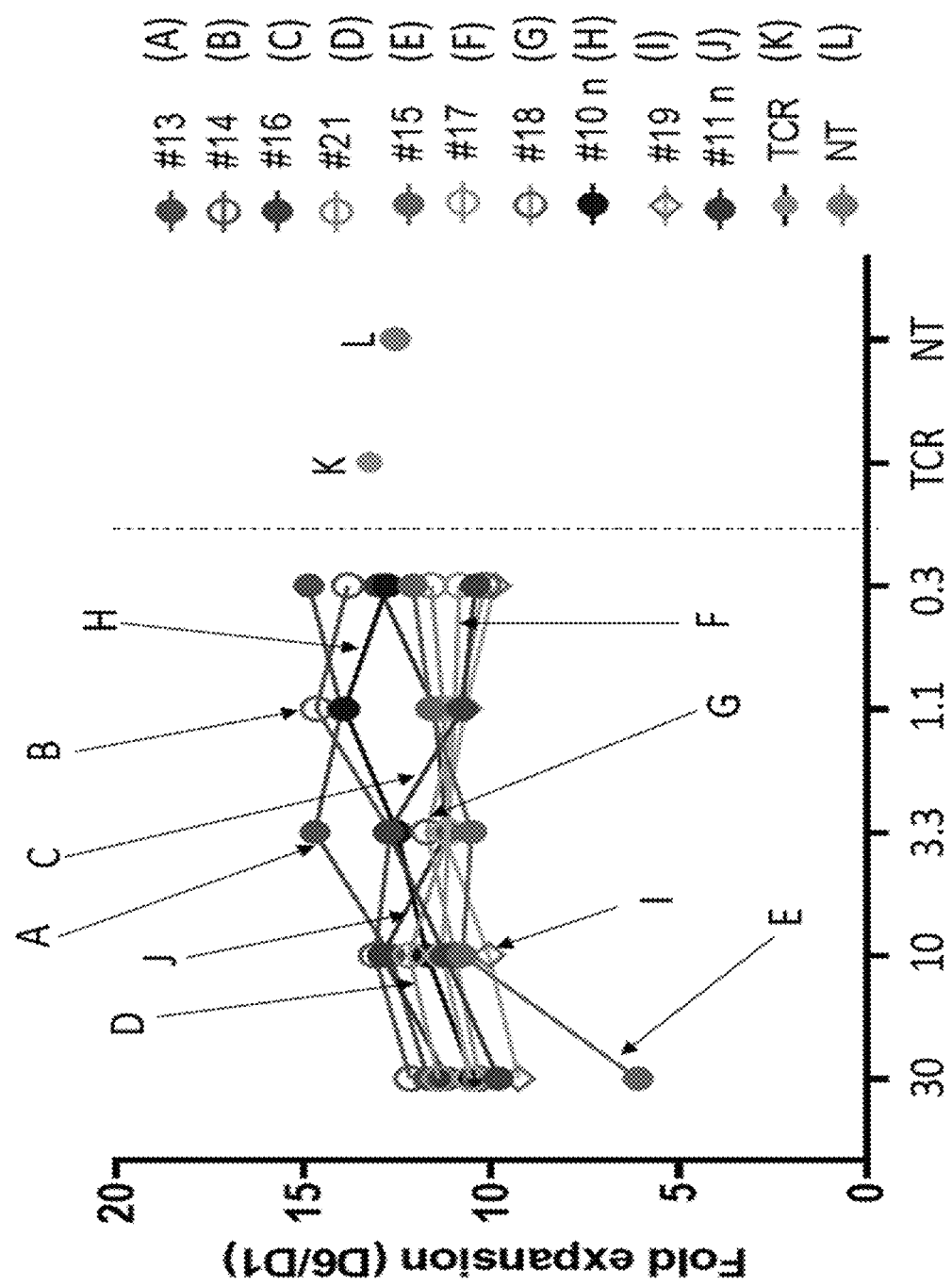
FIG. 28 shows fold expansion of cells transduced with various constructs.

FIG. 26 shows that, on Day +2, transduced PBMCs were expanded in the absence of serum. On Day +6, cells were harvested for subsequent analysis, e.g., FACS-Tetramer and vector copy number (VCN) and were cryopreserved. FIG. 28 shows fold expansion on Day +6 of transduced T cell products. Viabilities of cells is greater than 90% on Day +6.

Characterization of T Cell Products

Cell counts, FACS-dextramers, and vector copy numbers (VCN) were determined. Tetramer panels may comprise live/dead cells, CD3, CD8α, CD8β, CD4, and peptide/MHC tetramers, e.g., PRAME-004 (SLLQHLIGL) (SEQ ID NO: 147)/MHC tetramers. FACS analysis was gated on live singlets, followed by CD3+, followed by CD4+CD8+, followed by CD4+CD8+Tetramer(Tet)+ and CD8+Tet+.

Figure 29A:
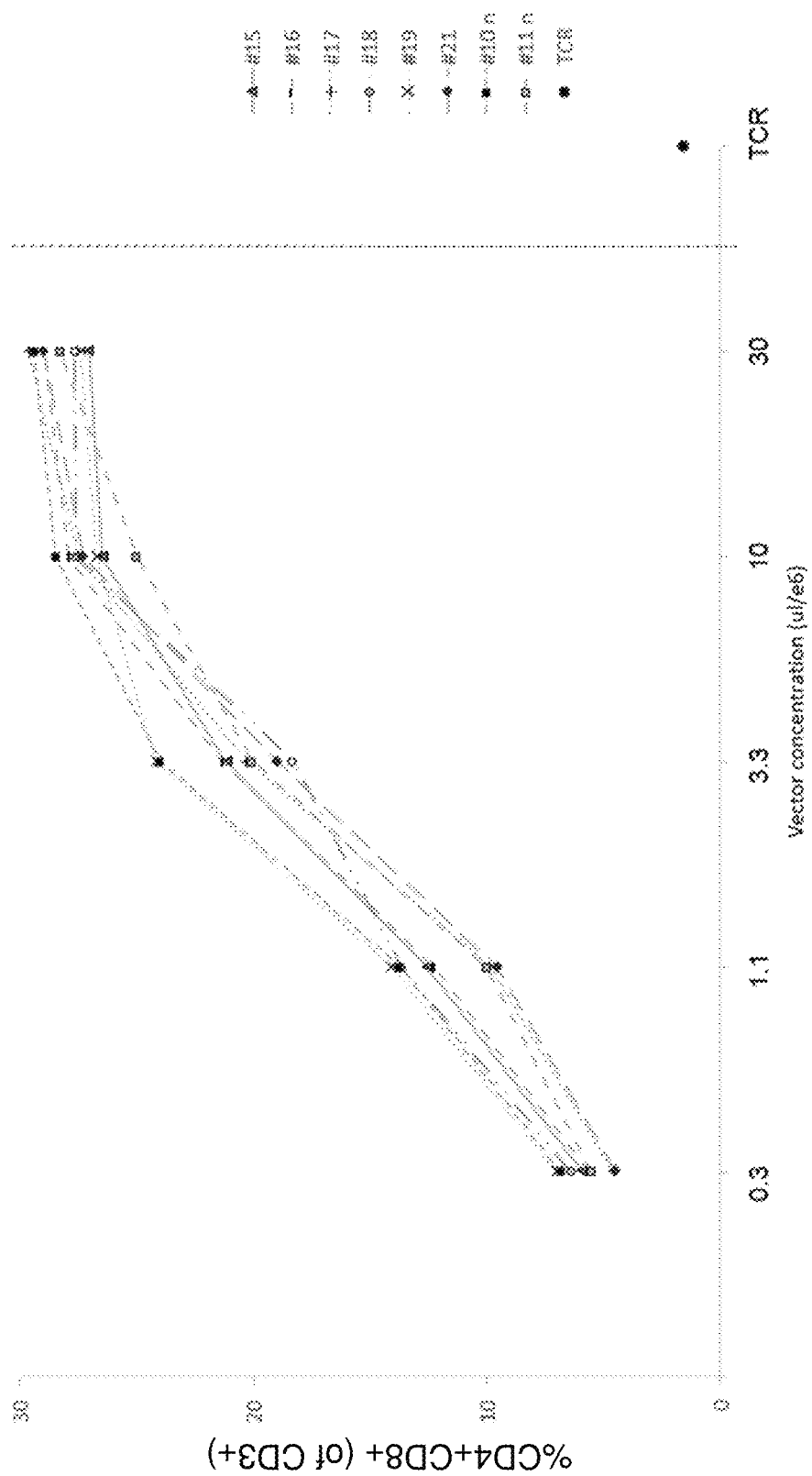
FIGS. 29A & 29B show % CD8+CD4+ of cells transduced with various constructs in accordance with one embodiment of the present disclosure.
Figure 29B:
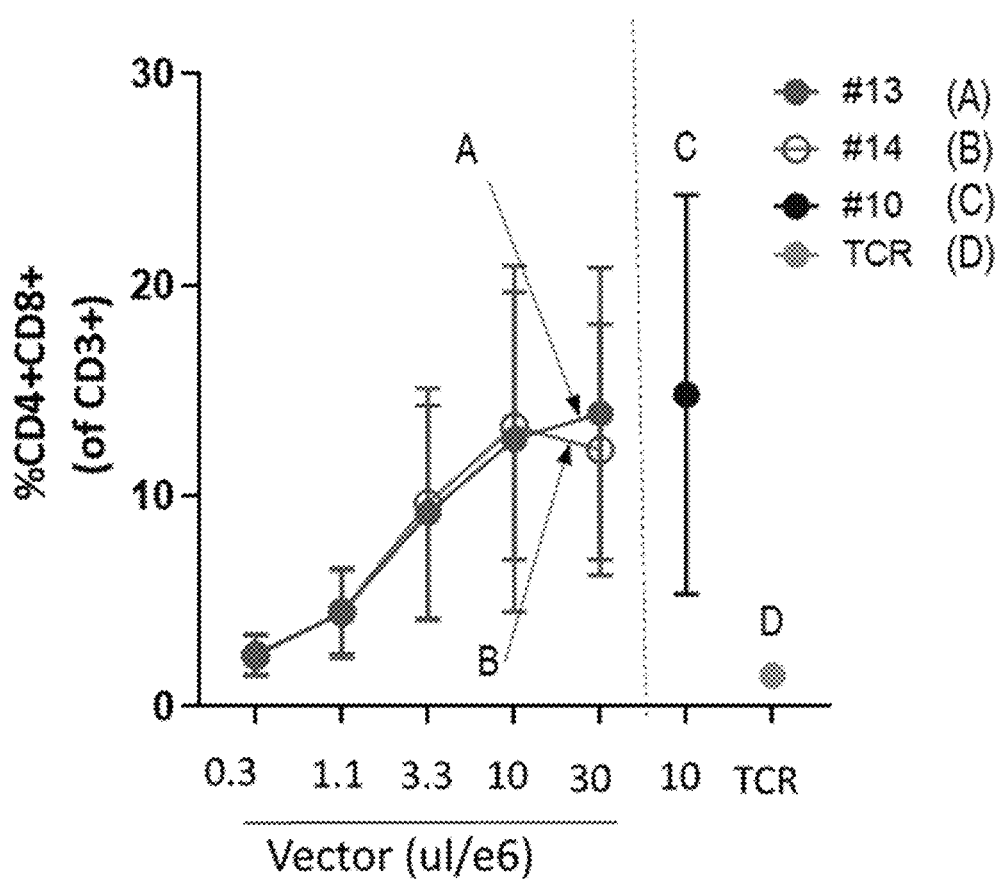
Figure 30A:
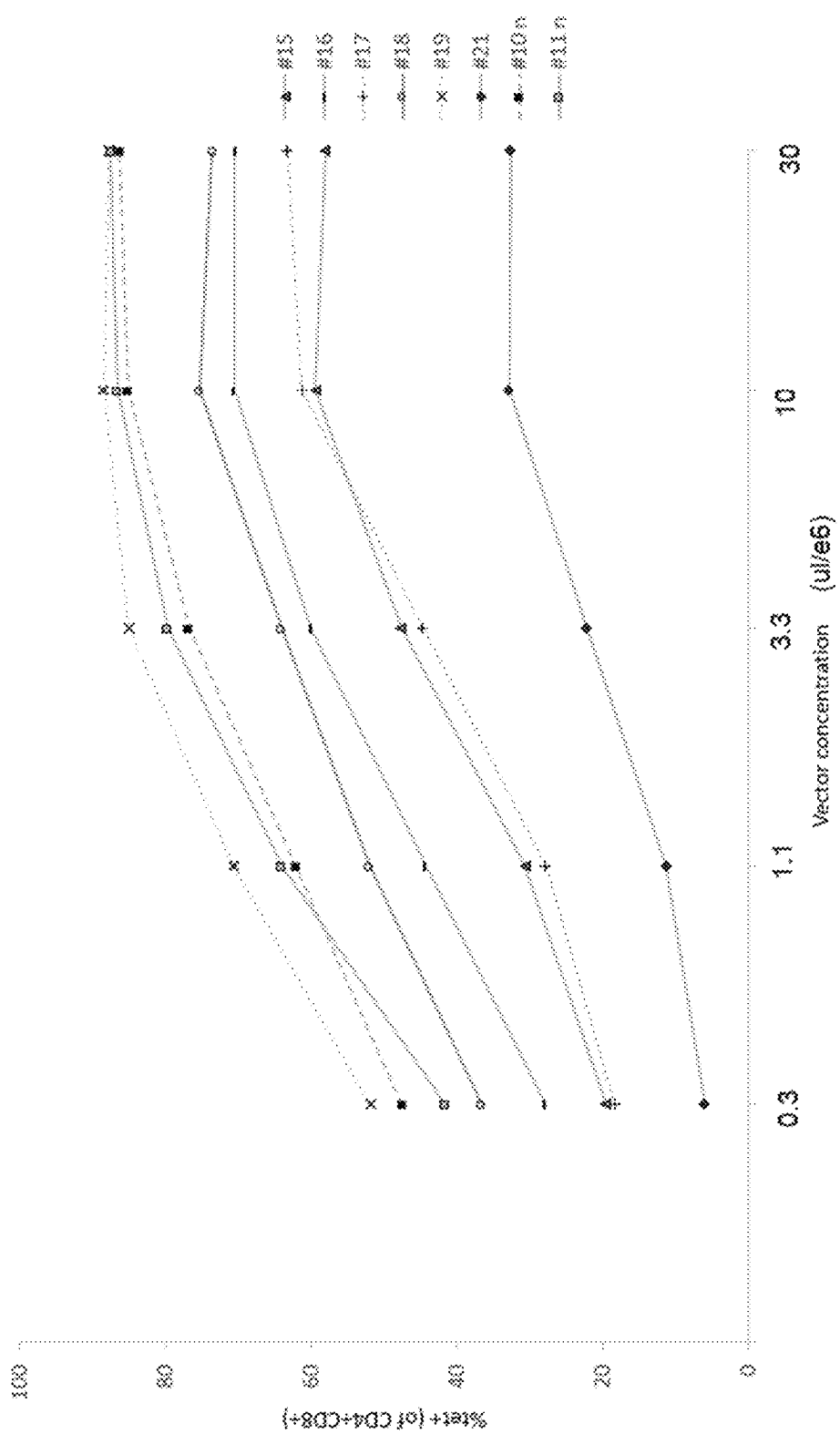
FIGS. 30A & 30B show % Tet of CD8+CD4+ of cells transduced with various constructs in accordance with one embodiment of the present disclosure.
Figure 30B:
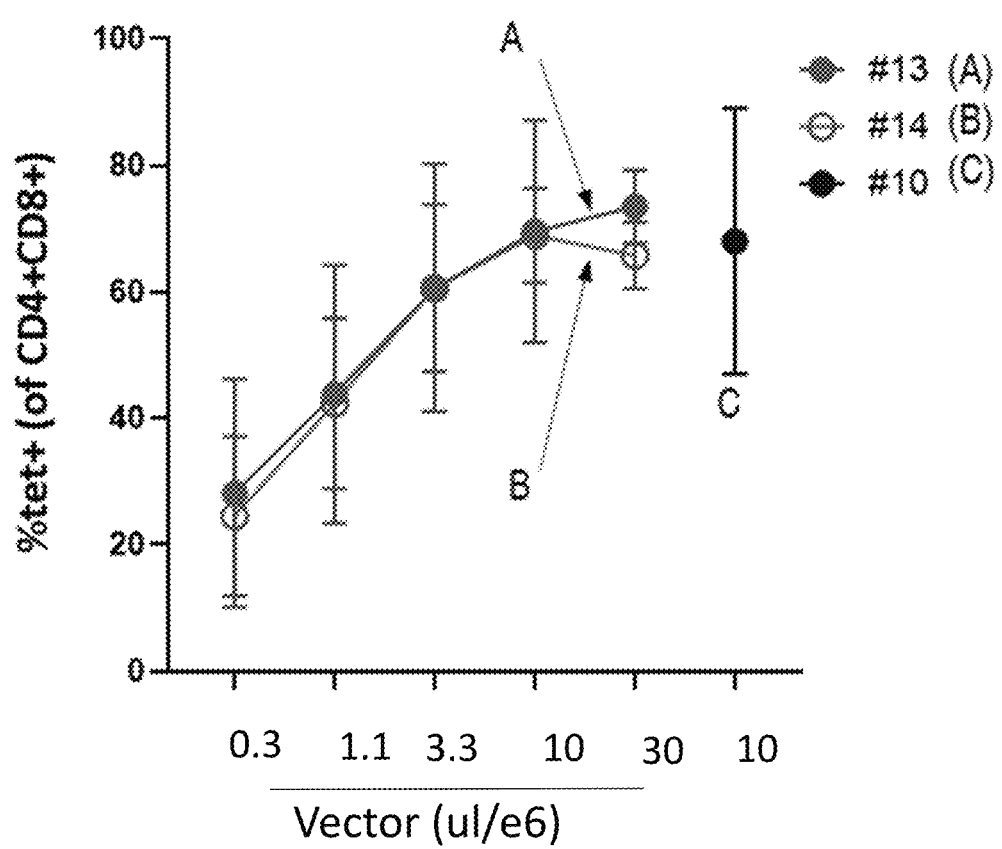

FIG. 29A and FIG. 29B shows % CD8+CD4+ cells transduced with Construct #10, #10n, #11, #13-#21 at 0.3 µl, 1.1 µl, 3.3 µl, 10 µl or 30 µl per 1×10⁶ cells. These results show comparable frequencies of CD8+CD4+ cells obtained by transduction with all vectors tested. Construct #8 (TCR only) serves as negative control. FIG. 30A and FIG. 30B shows % Tet of CD8+CD4+ cells from transduced with Construct #10, #10n, #11, #13-#21 at 0.3 µl, 1.1 µl, 3.3 µl, 10 µl or 30 µl per 1×10⁶ cells. These results show that there was a trend towards higher frequencies of CD4+CD8+tet+ in CD8β1 isoforms (Constructs #10 and #18) compared to CD8β3 isoforms (Construct #16) and CD8β5 isoforms (Constructs #15 and #17). FACS analysis was gated on live singlets, followed by CD3+, followed by CD4+CD8+, and followed by CD4+CD8+Tet+.

Figure 31A:
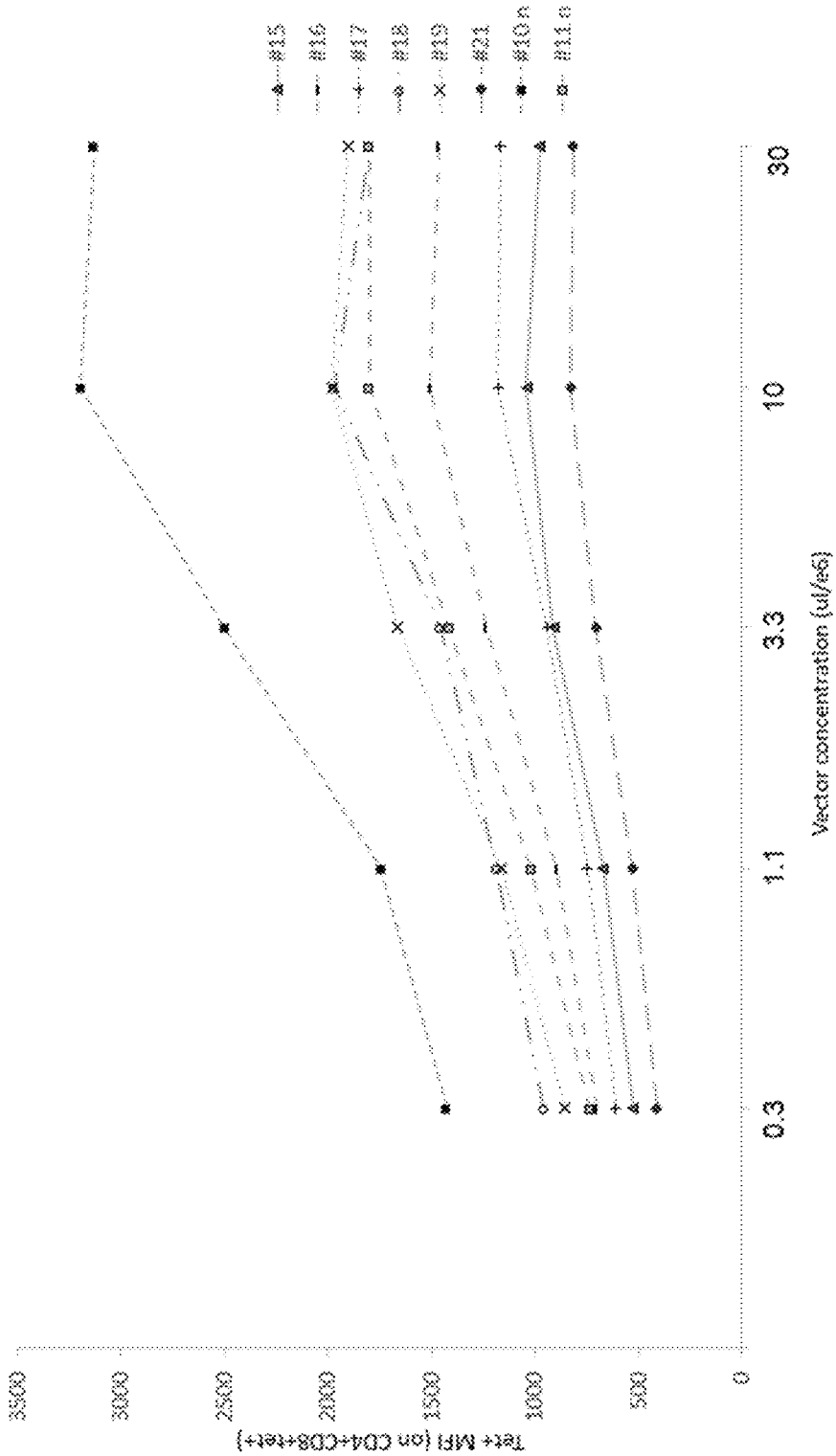
FIGS. 31A & 31B show Tet MFI (CD8+CD4+Tet+) of cells transduced with various constructs in accordance with one embodiment of the present disclosure.
Figure 31B:
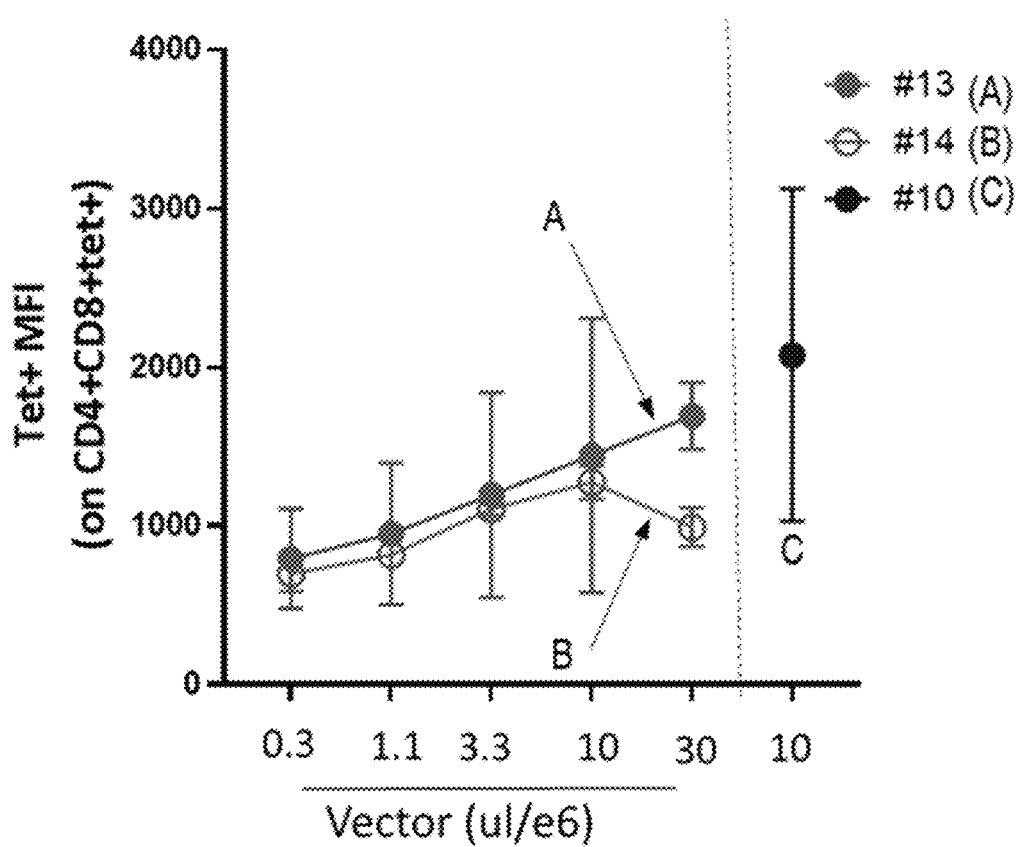

FIG. 31A and FIG. 31B shows Tet MFI of CD8+CD4+ Tet+ cells from transduced with Construct #10, #10n, #11, #13-#21 at 0.3 µl, 1.1 µl, 3.3 µl, 10 µl or 30 µl per 1×10⁶ cells. These results show a trend towards higher tetramer MFI on CD4+CD8+Tet+ population in CD8β1 isoforms (Constructs #10 and #18) compared to CD8β3 isoforms (Construct #16) and CD8β5 isoforms (Constructs #15 and #17).

Figure 32A:
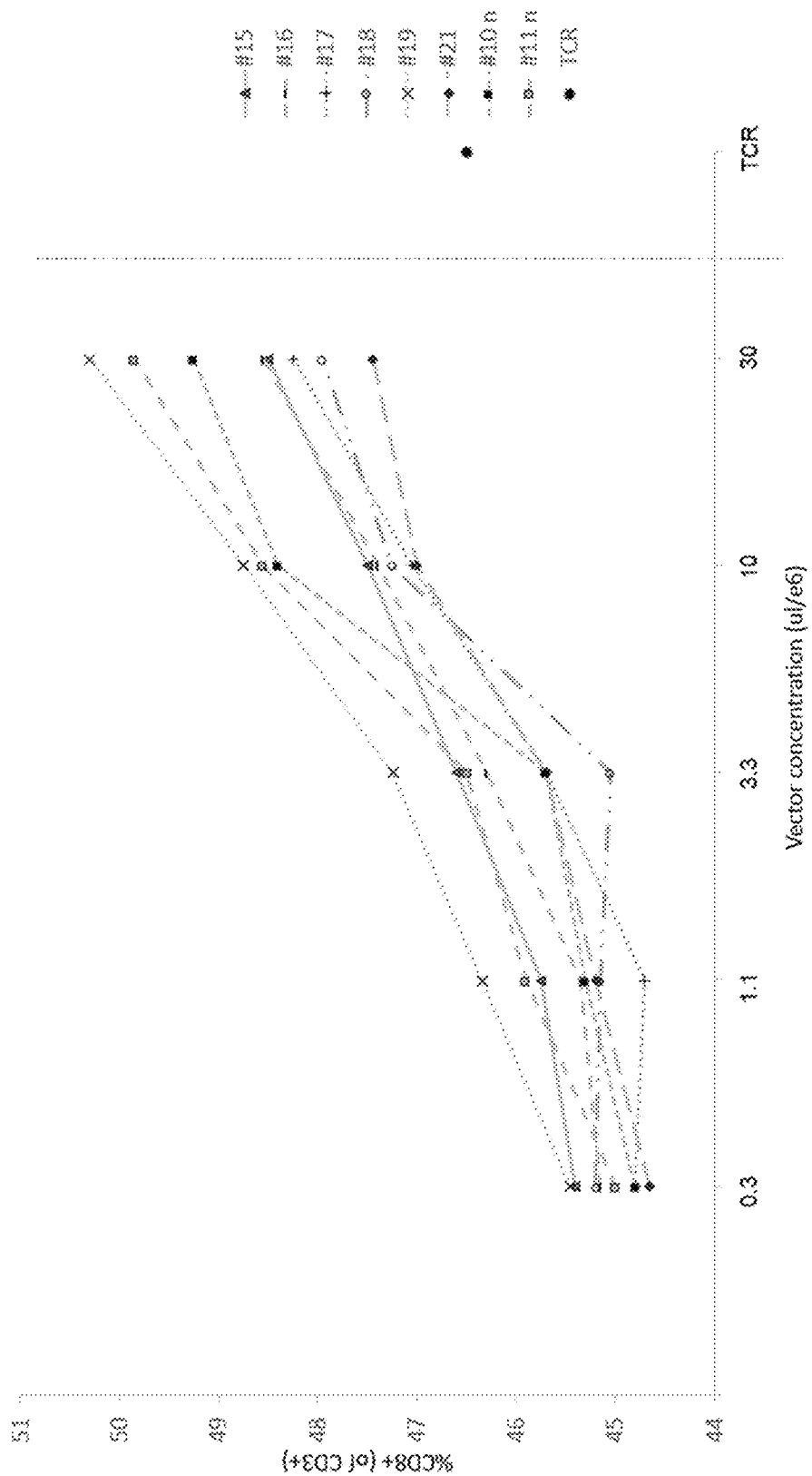
FIGS. 32A & 32B show % CD8+CD4− (of CD3+) of cells transduced with various constructs in accordance with one embodiment of the present disclosure.
Figure 32B:
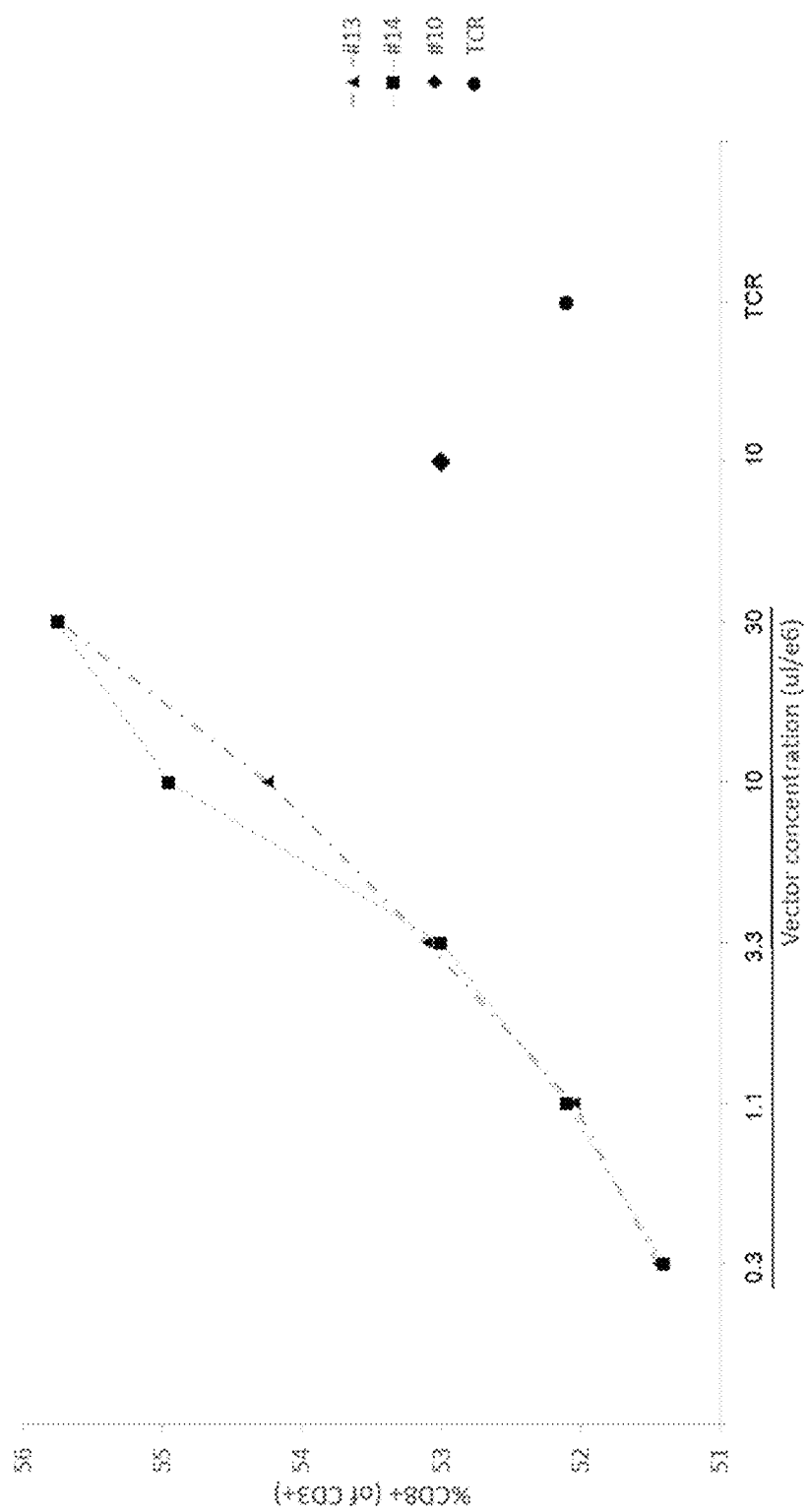
Figure 33A:
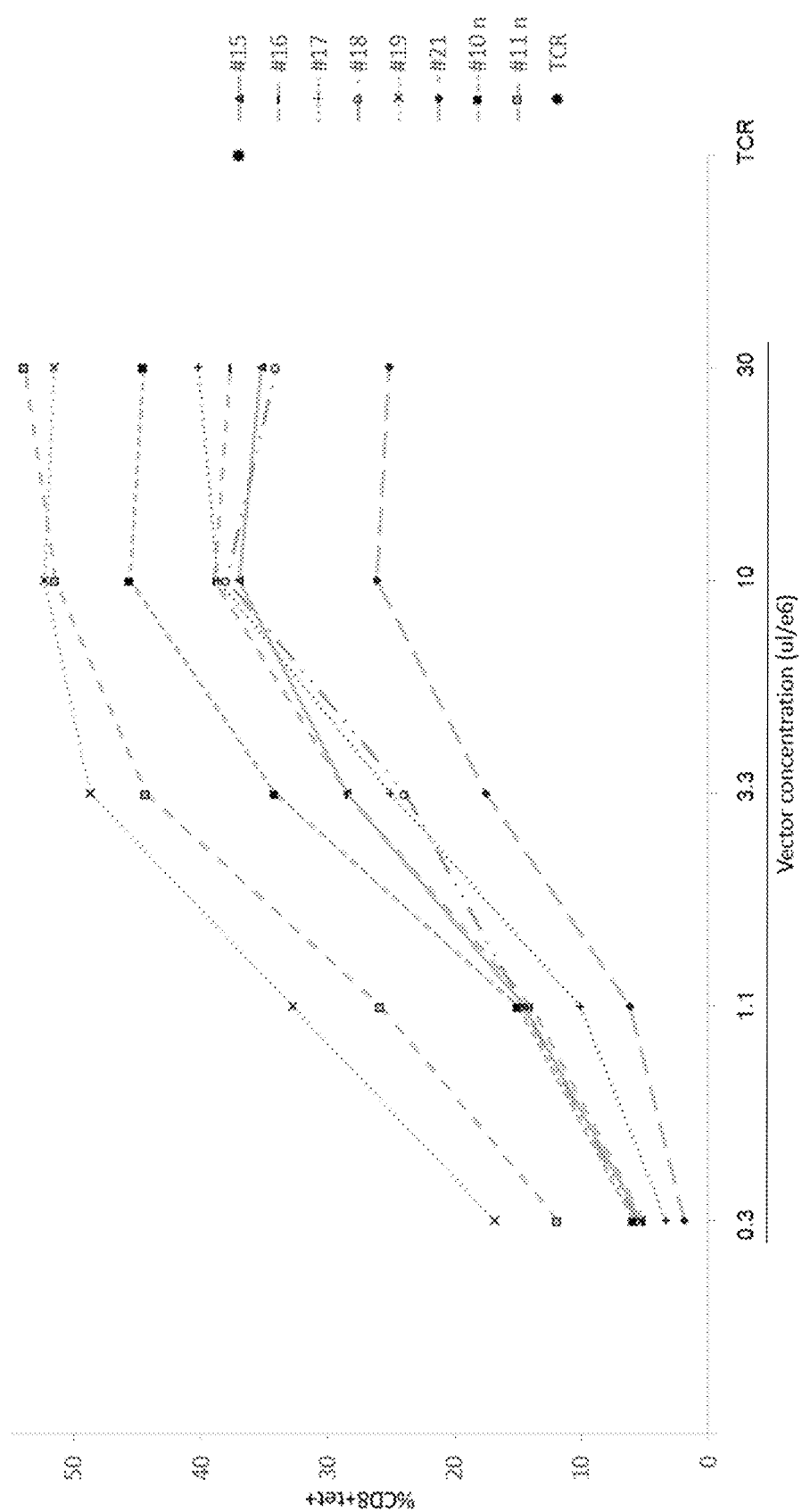
FIGS. 33A & 33B show % CD8+Tet+(of CD3+) of cells transduced with various constructs in accordance with one embodiment of the present disclosure.
Figure 33B:
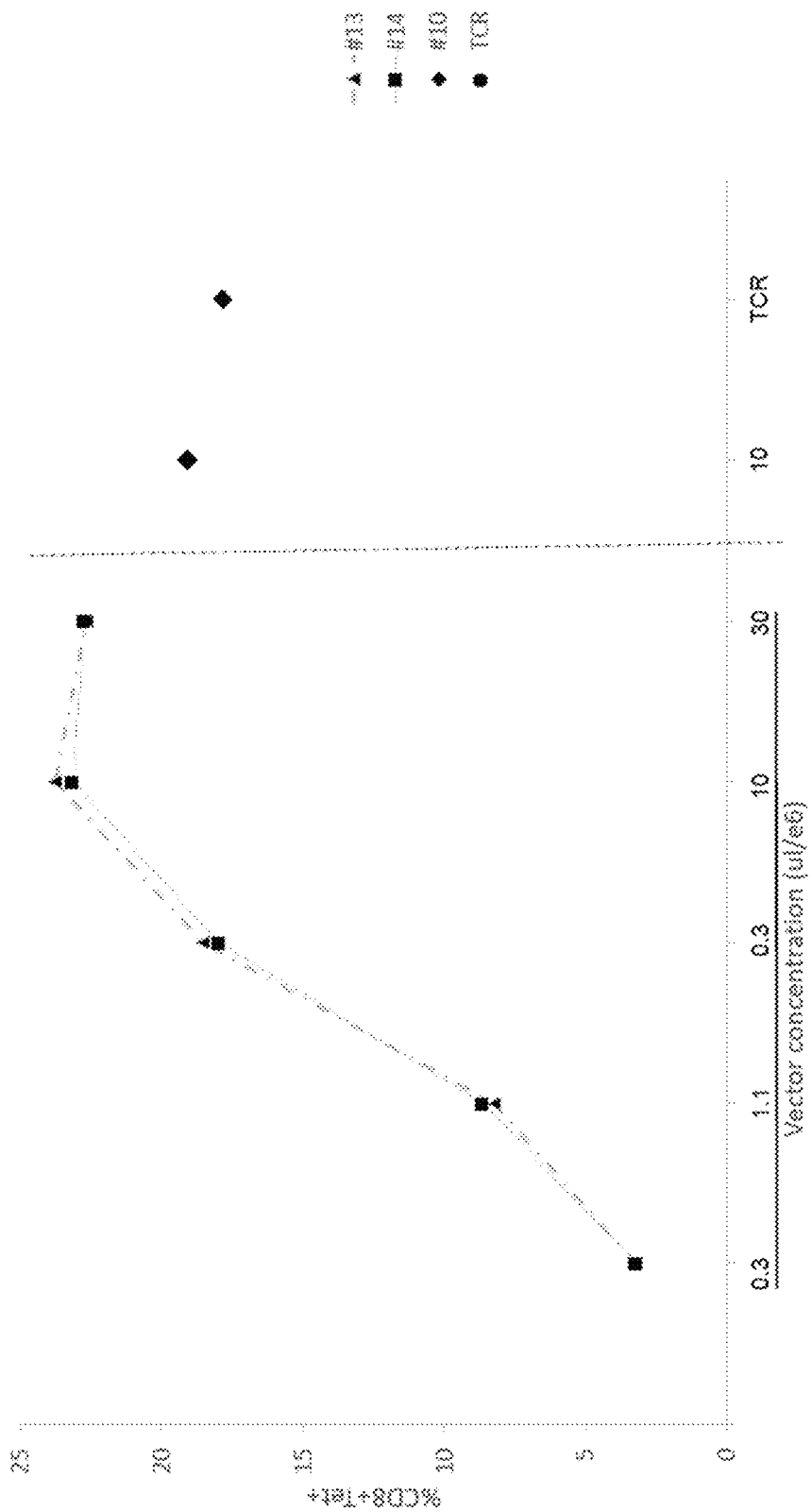

FIG. 32A and FIG. 32B show CD8 frequencies (% CD8+CD4− of CD3+) in cells transduced with Construct #10, #10n, #11, #13-#21 at 0.3 µl, 1.1 µl, 3.3 µl, 10 µl or 30 µl per 1×10⁶ cells. These results show no difference in the CD8 frequencies among the constructs. FIG. 33A and FIG. 33B shows % CD8+Tet+(of CD3+) cells transduced with Construct #10, #10n, #11, #13-#21 at 0.3 µl, 1.1 µl, 3.3 µl, 10 µl or 30 µl per 1×10⁶ cells. These results show slightly higher frequencies of CD8+Tet+(of CD3+) in cells transduced with Construct #10 than those transduced with the other constructs. FACS analysis was gated on live singlets, followed by CD3+, followed by CD8+CD4−, and followed by Tet+.

Figure 34A:
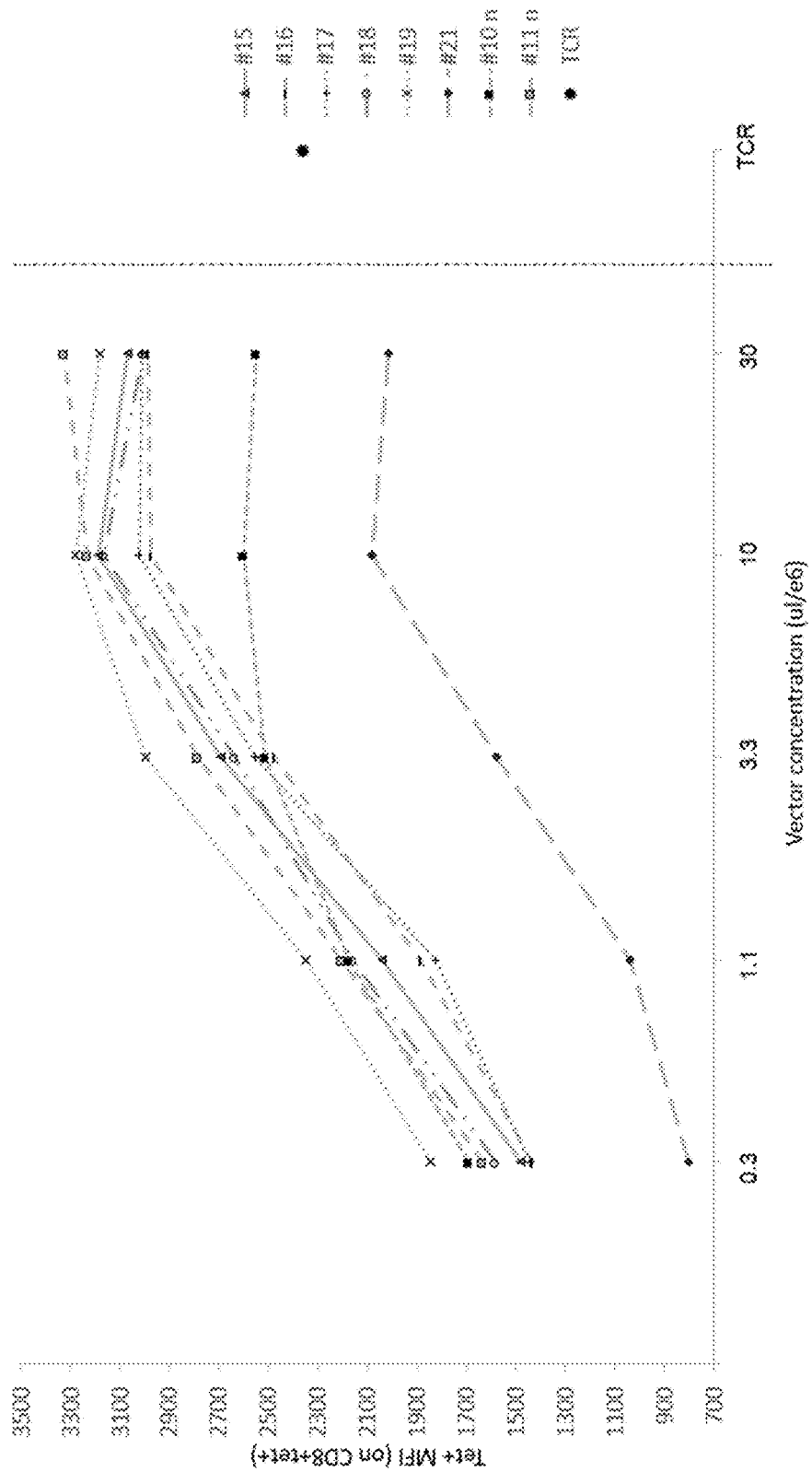
FIGS. 34A & 34B show Tet MFI (CD8+Tet+) of cells transduced with various constructs in accordance with one embodiment of the present disclosure.
Figure 34B:
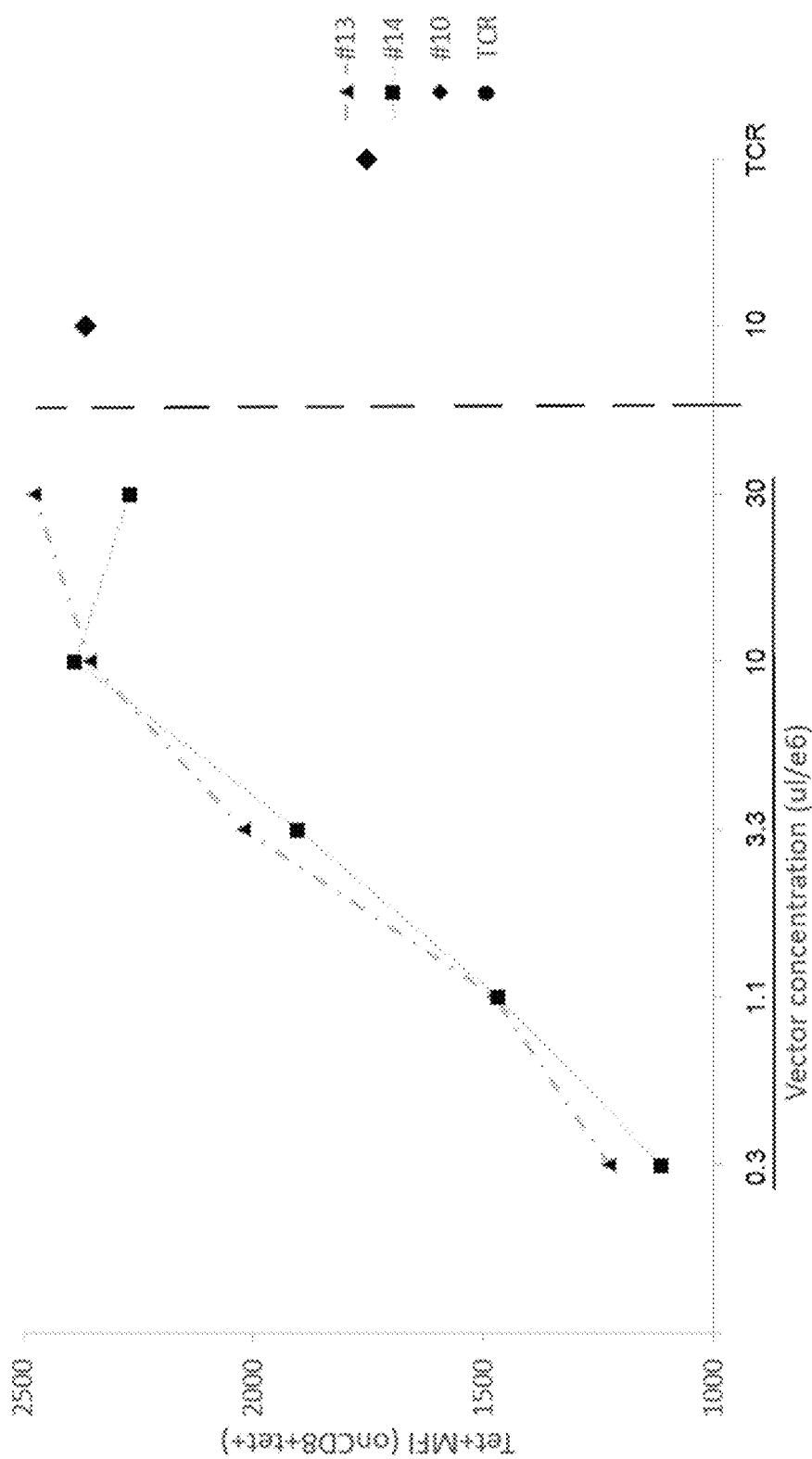

FIG. 34A and FIG. 34B shows Tet MFI of CD8+Tet+ cells transduced with Construct #10, #10n, #11, #13-#21 at 0.3 µl, 1.1 μl, 3.3 μl, 10 μl or 30 μl per 1×10⁶ cells. These results show tetramer MFI of CD8+tet+ cells was comparable among CD8β1 (Constructs #18 and #10), CD8β5 (Constructs #15 and #17), and CD8β3 (Construct #16) isoforms, while Construct #21 expressed lower tetramer MFI.

Figure 35A:
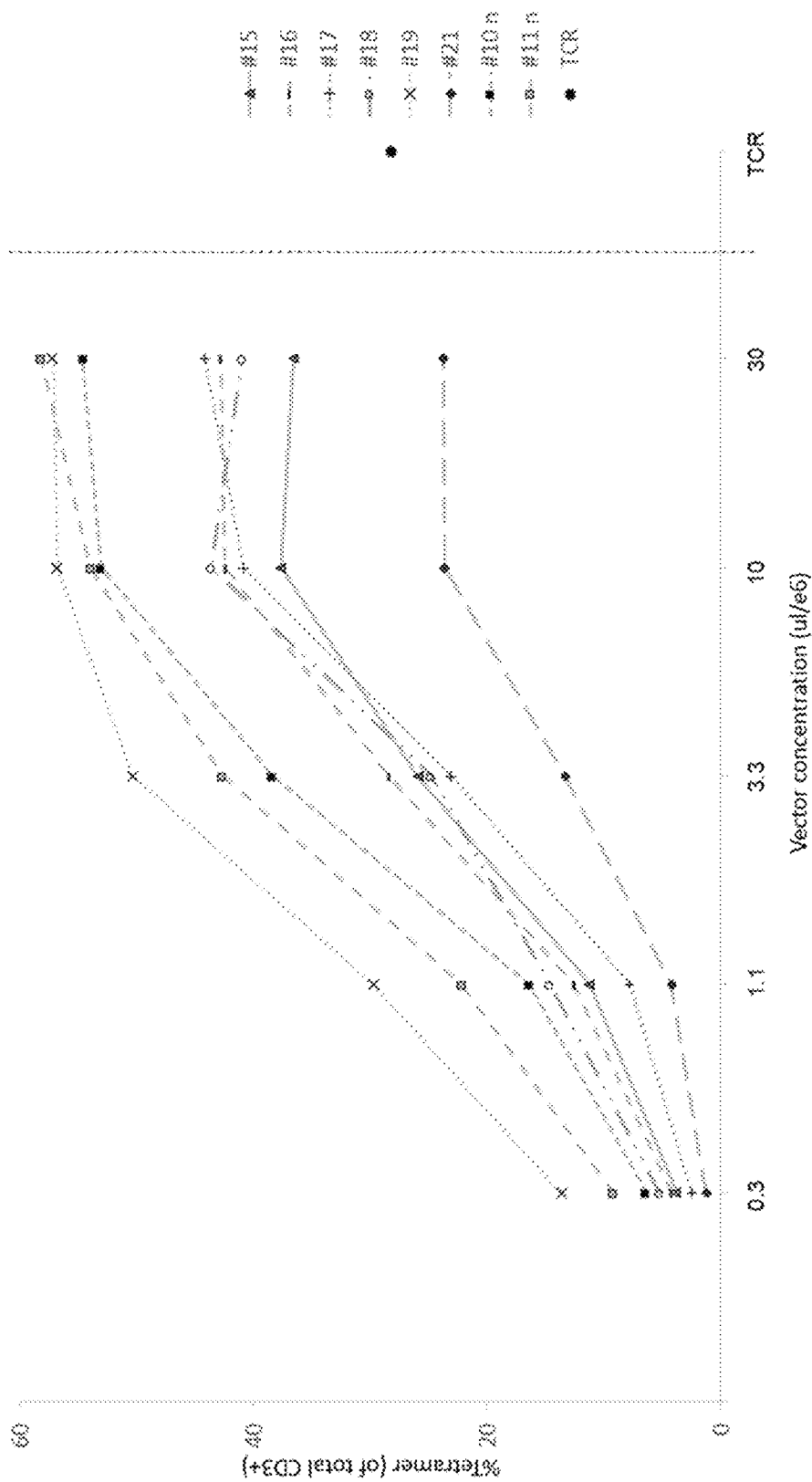
FIGS. 35A & 35B show % Tet+(of CD3+) of cells transduced with various constructs in accordance with one embodiment of the present disclosure.
Figure 35B:
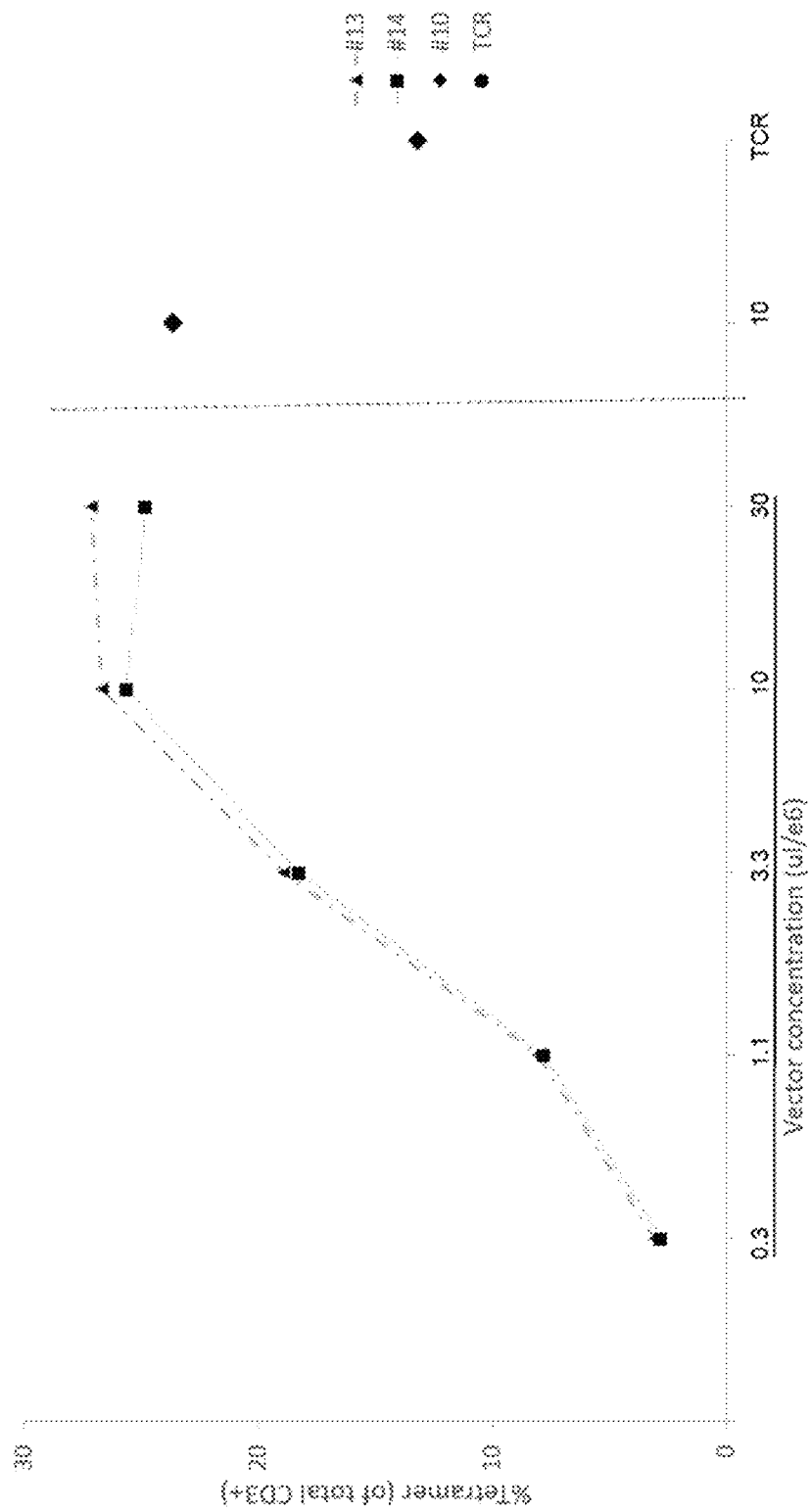

FIG. 35A and FIG. 35B shows % Tet+ of CD3+ cells transduced with Construct #10, #10n, #11, #13-#21 at 0.3 μl, 1.1 μl, 3.3 μl, 10 μl or 30 μl per 1×10⁶ cells. These results show higher frequencies of CD3+Tet+ in cells transduced with Construct #10 (CD8β1) compared to those transduced with CD8β3 (Construct #16) and CD8β5 (Constructs #15 and #17). FACS analysis was gated on live singlets, followed by CD3+, and followed by Tet+.

Figure 36A:
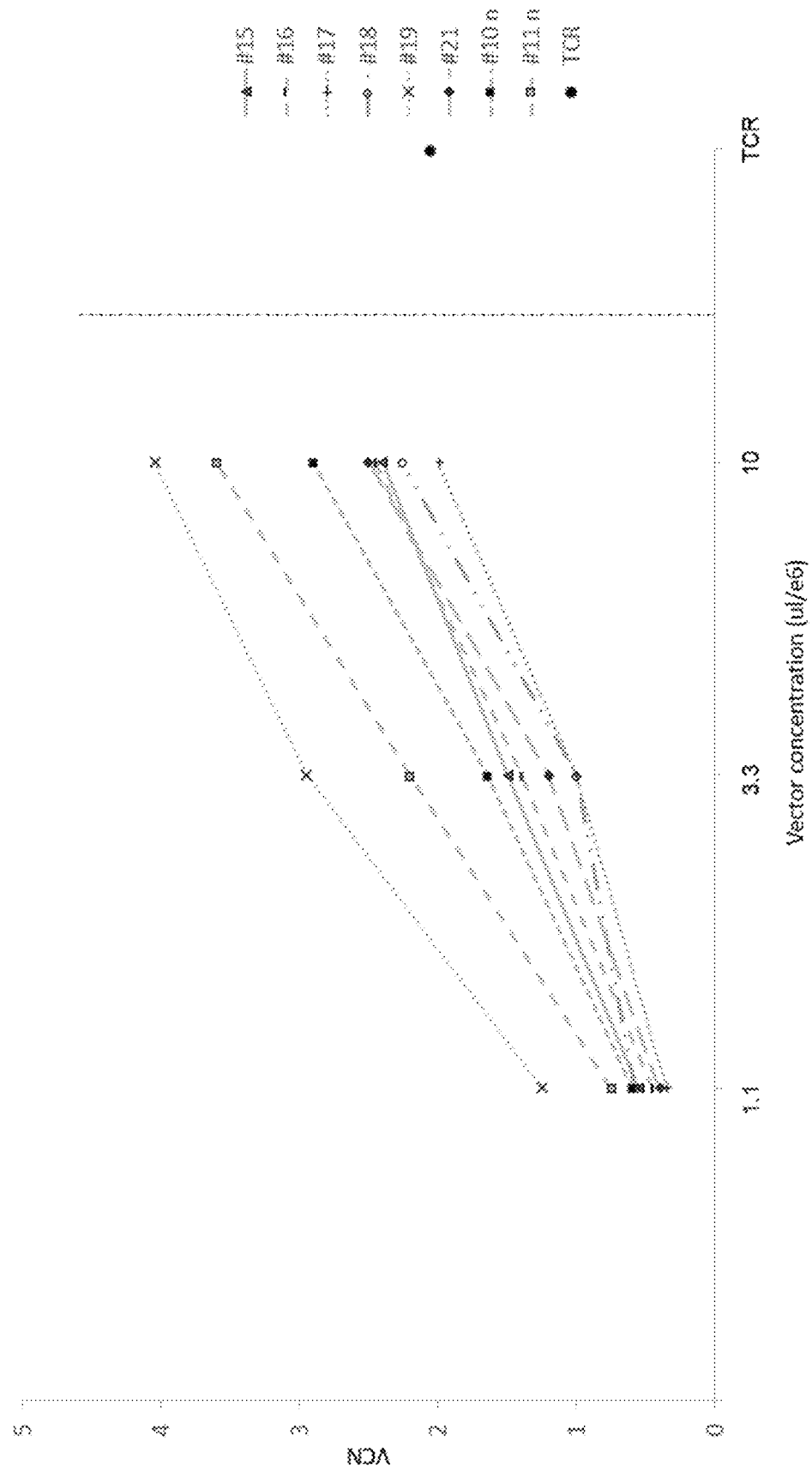
FIGS. 36A & 36B show VCN of cells transduced with various constructs in accordance with one embodiment of the present disclosure.
Figure 36B:
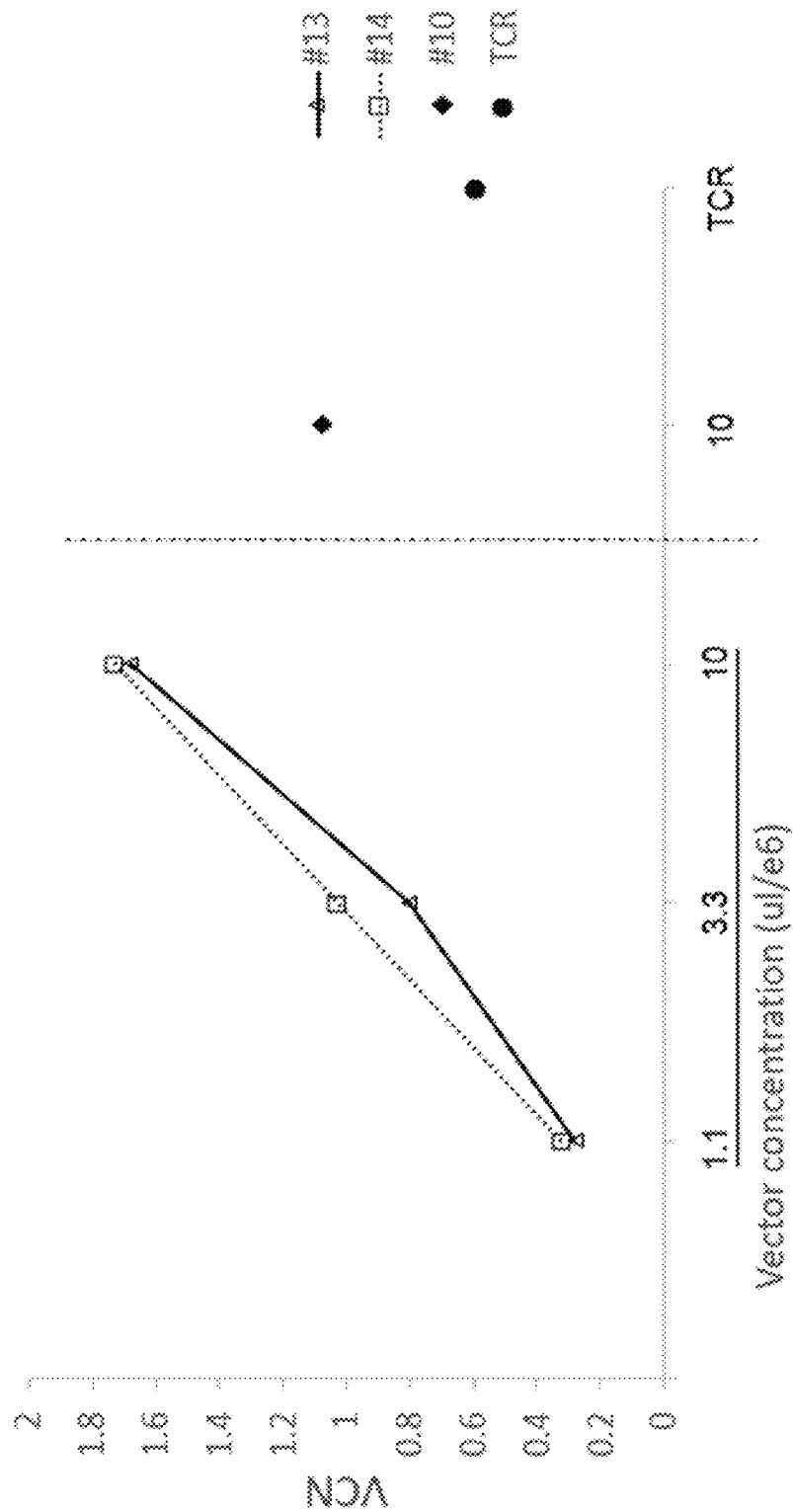

FIG. 36A and FIG. 36B shows vector copy number (VCN) of cells transduced with Construct #10, #10n, #11, #13-#21 at 0.3 μl, 1.1 μl, 3.3 μl, 10 μl or 30 μl per 1×10⁶ cells. These results show comparable ability of all constructs to integrate and express CD8/TCR genes.

In sum, these results show (1) viral vectors with CD8β1, CD8β3 and CD8β5 isoforms had good transducing titers; (2) all constructs were capable of successful manufacturing (e.g., high viability, fold expansions in the range of 6-12); (3) frequencies of CD3+tet+ among CD8β isoforms: CD8β1 (Construct #10) was greater than CD8β3 (Construct #16) and CD8β5 (Constructs #15 and #17), with Construct #21 showing the lowest values; (4) frequency of CD3+tet+ in Constructs #11 and #19 (m1CD8α (SEQ ID NO: 7)) showed the highest values; and (5) saturation in % CD3+tet+, % CD8+tet+ and % CD4+CD8+tet+ observed at 10 μl/e6. Optimal vector dose ranges between 3.3-10 μl/e6 for all constructs.

Example 7

Mid-Scale Vector Screening (Constructs #13-#19)

T Cell Manufacturing
Activation/Transduction

Figure 37:
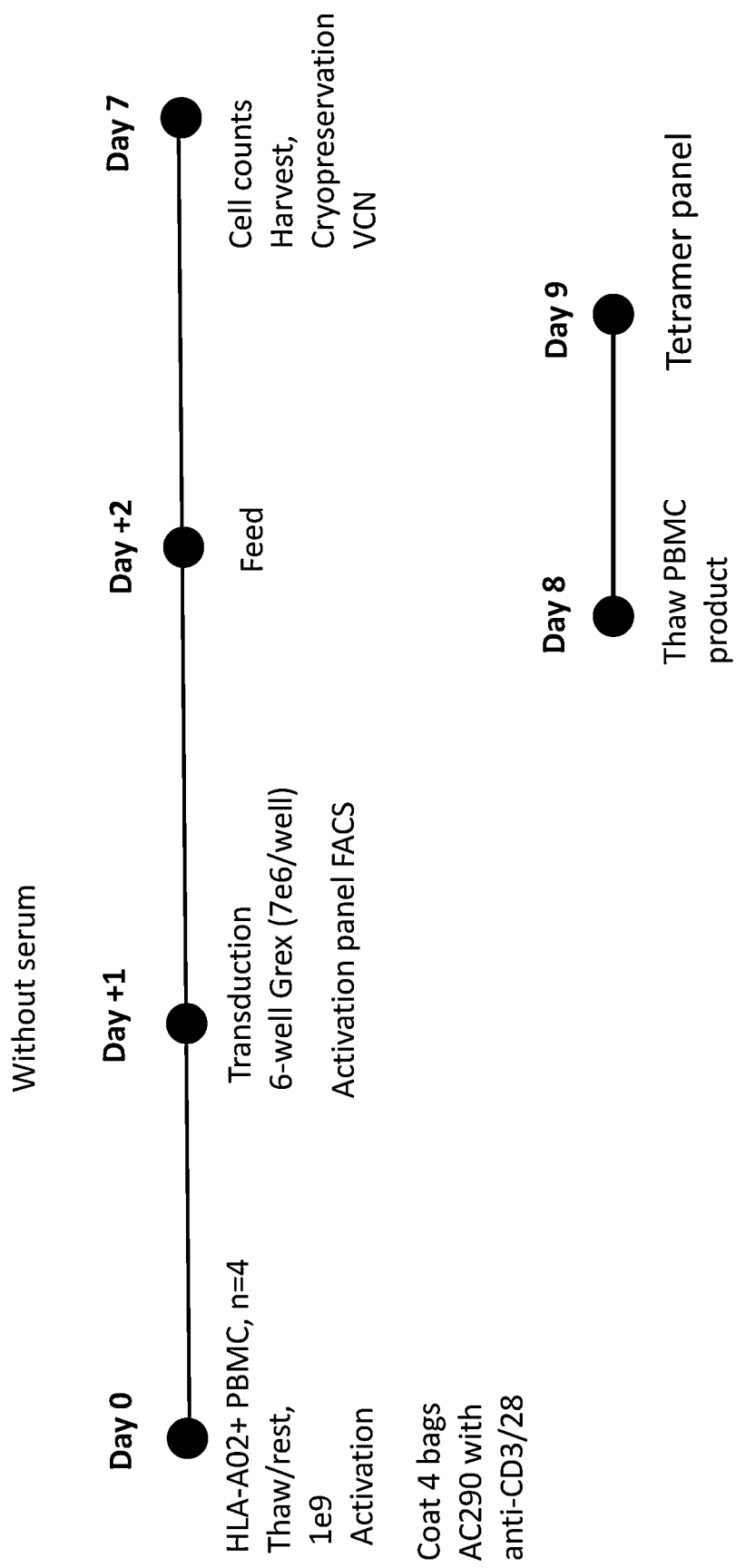
FIG. 37 shows T cell manufacturing in accordance with one embodiment of the present disclosure.

FIG. 37 shows that, on Day +0, PBMCs obtained from four HLA-A02+ donors were thawed and rested. Cells were activated in bags (AC290) coated with anti-CD3 and anti-CD28 antibodies in the absence of serum. On Day +1, activated PBMCs were transduced with viral vectors, e.g., Constructs #8, #10n, #11n, and #13-#19, in G-Rex® 6-well plates at about 7×10⁶ cells/well in the absence of serum. The amounts of virus used for transduction are shown in Table 9.

TABLE 9

| Constructs | Virus Volume/1 × 10⁶ cells |
|---|---|
| #13-19 | 2.5 μl and 5 μl |
| #10n and #11n | 2.5 μl and 5 μl |
| #8 (TCR) | 2.5 μl |
| NT | — |

Expansion

FIG. 37 shows that, on Day +2, transduced PBMCs were expanded in the absence of serum. On Day +7, cells were harvested for subsequent analysis, e.g., FACS-Tetramer and vector copy number (VCN) and were cryopreserved. Fold expansion on Day +7 was comparable for all constructs (approximately 30-fold expansion). Viabilities of cells is greater than 90% on Day +7.
Characterization of T Cell Products Cell counts, FACS-dextramers, and vector copy numbers (VCN) were determined. Tetramer panels may comprise live/dead cells, CD3, CD8α, CD8β, CD4, and peptide/MHC tetramers, e.g., PRAME-004 (SLLQHLIGL) (SEQ ID NO: 147)/MHC tetramers. FACS analysis was gated on live singlets, followed by CD3+, followed by CD4+CD8+, followed by CD4+CD8+Tetramer(Tet)+ and CD8+Tet+.

Figure 38:
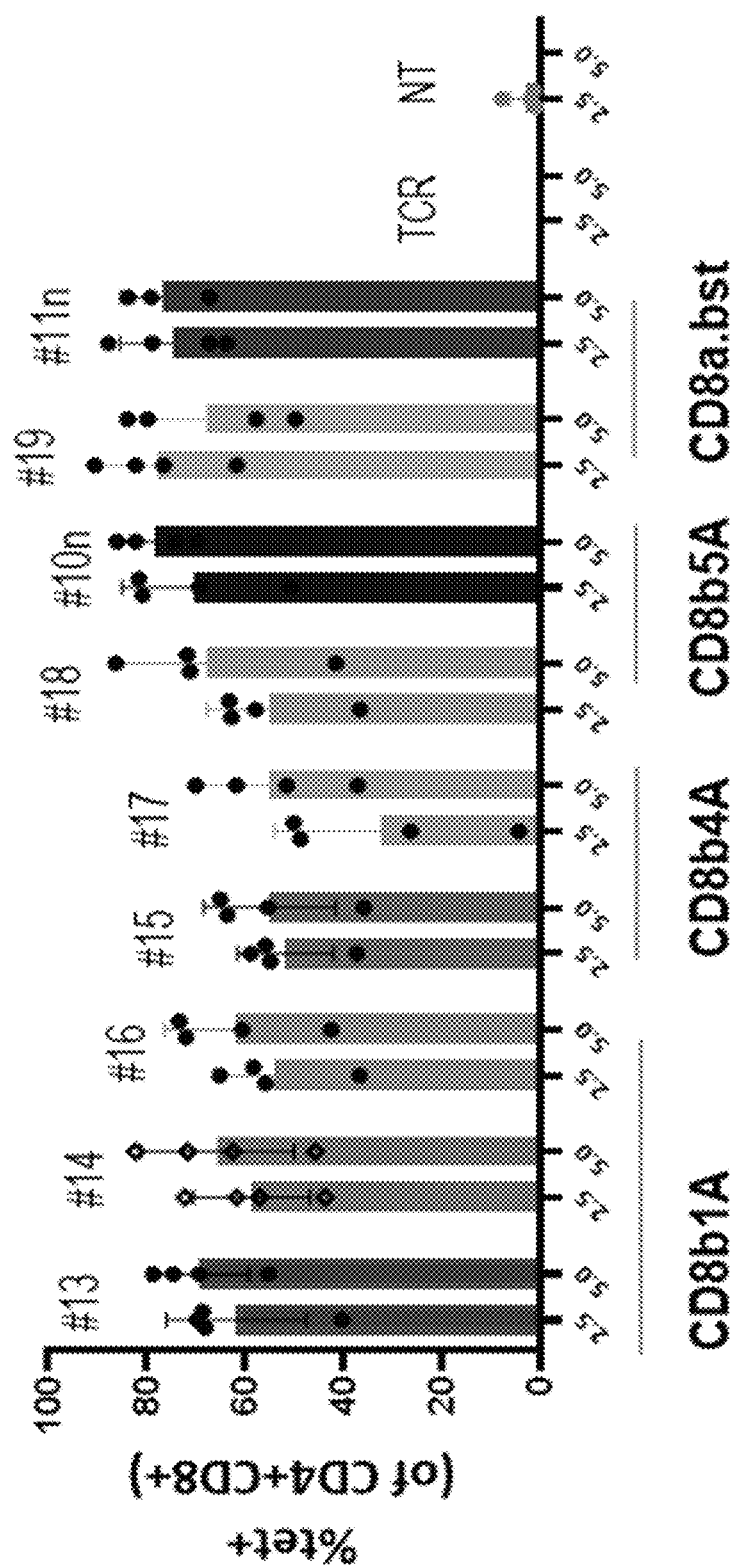
FIG. 38 shows % Tet of CD8+CD4+ of cells transduced with various constructs.

Similar to results described in Example 6, comparable frequencies of CD8+CD4+ cells were obtained by transduction with Construct #10n, #11n, #13-#19 at 2.5 μl or 5.0 μl per 1×10⁶ cells. Construct #8 (TCR only) serves as negative control. FIG. 38 shows % Tet of CD8+CD4+ cells transduced with Construct #10n, #11n, #13-#19 at 2.5 μl or 5.0 μl per 1×10⁶ cells. Similar to results described in Example 6, these results show that there was a trend towards higher frequencies of CD4+CD8+tet+ in CD8β1 isoforms (Construct #10n) compared to CD8β3 isoforms (Constructs #13, #14, #16) and CD8β5 isoforms (Constructs #15 and #17). FACS analysis was gated on live singlets, followed by CD3+, followed by CD4+CD8+, and followed by Tet+.

Figure 39:
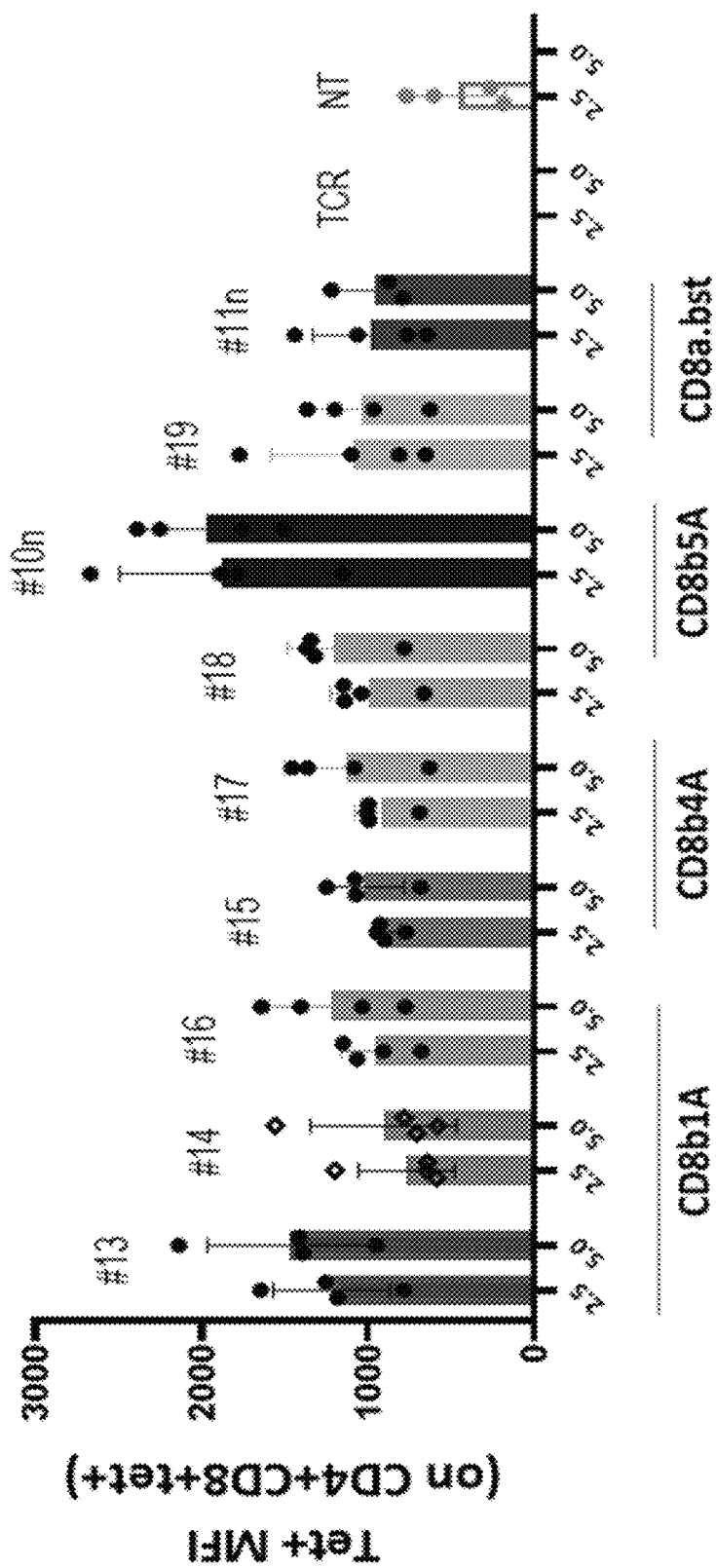
FIG. 39 shows Tet MFI of CD8+CD4+Tet+ of cells transduced with various constructs.

FIG. 39 shows Tet MFI of CD8+CD4+Tet+ cells from transduced with Construct #10n, #11n, #13-#19 at 2.5 μl or 5.0 μl per 1×10⁶ cells. These results show higher tetramer MFIs on CD4+CD8+Tet+ population in CD8β1 isoforms (Construct #10n) compared to CD8β3 isoforms (Construct #13) and CD8β5 isoforms (Constructs #15 and #17).

Similar to results described in Example 6, results show no difference in the CD8 frequencies (% CD8+CD4− of CD3+) in cells transduced with Construct #10n, #11n, #13-#19 at 2.5 μl or 5.0 μl per 1×10⁶ cells among the constructs (data not shown). Comparable frequencies of CD8+Tet+(of CD3+) in cells transduced with Construct #10n, #11n, #13-#19 at 2.5 μl or 5.0 μl per 1×10⁶ cells (data not shown). FACS analysis was gated on live singlets, followed by CD3+, followed by CD8+CD4−, and followed by Tet+.

Figure 40:
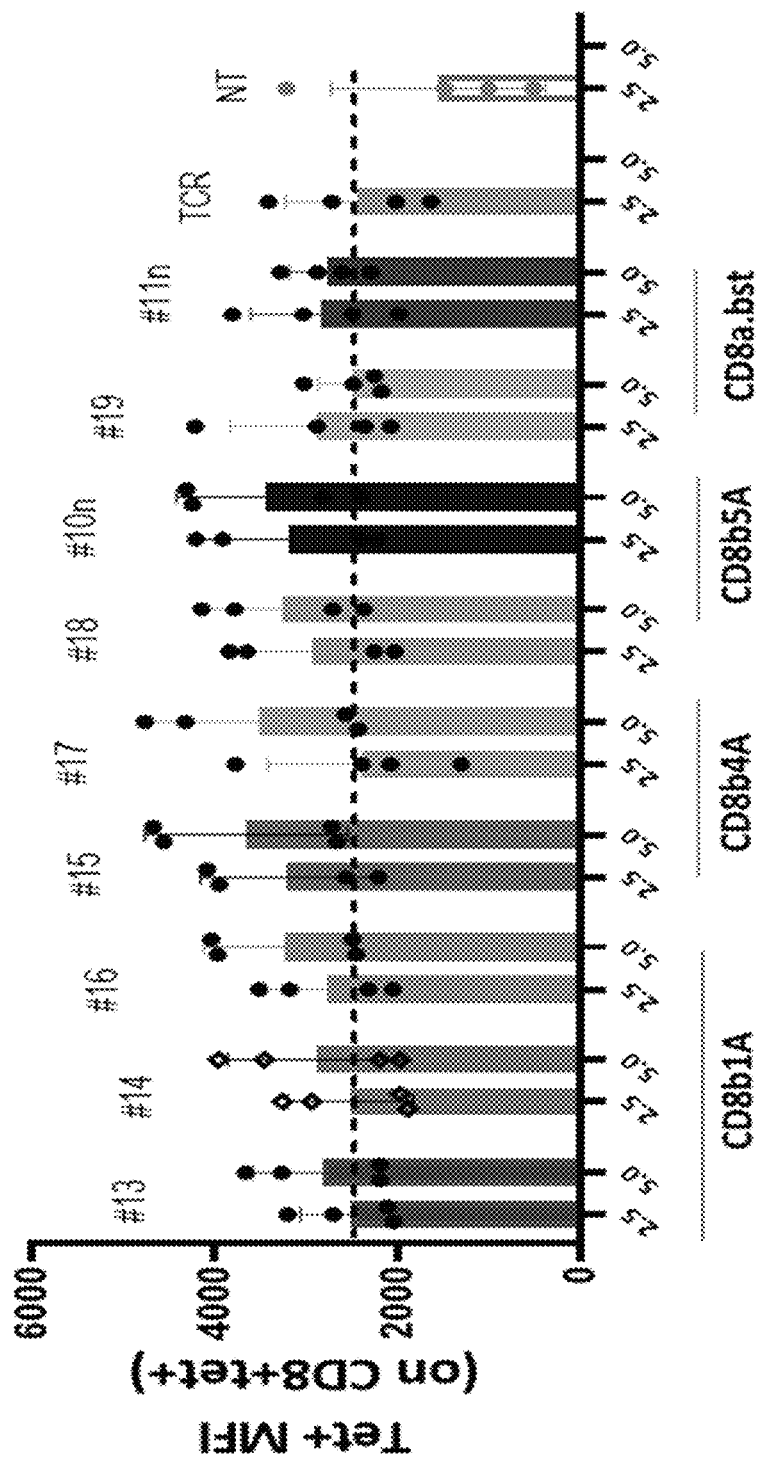
FIG. 40 shows Tet MFI of CD8+Tet+ of cells transduced with various constructs.

FIG. 40 shows Tet MFI of CD8+Tet+ cells transduced with Construct #10n, #11n, #13-#19 at 2.5 μl or 5.0 μl per 1×10⁶ cells. These results show tetramer MFI of CD8+tet+ cells was comparable among CD8β1 (Constructs #18 and #10) and CD8β5 (Construct #15) isoforms, while CD8β3 (Constructs #13, #14, and #16) isoforms expressed lower tetramer MFI.

Figure 41:
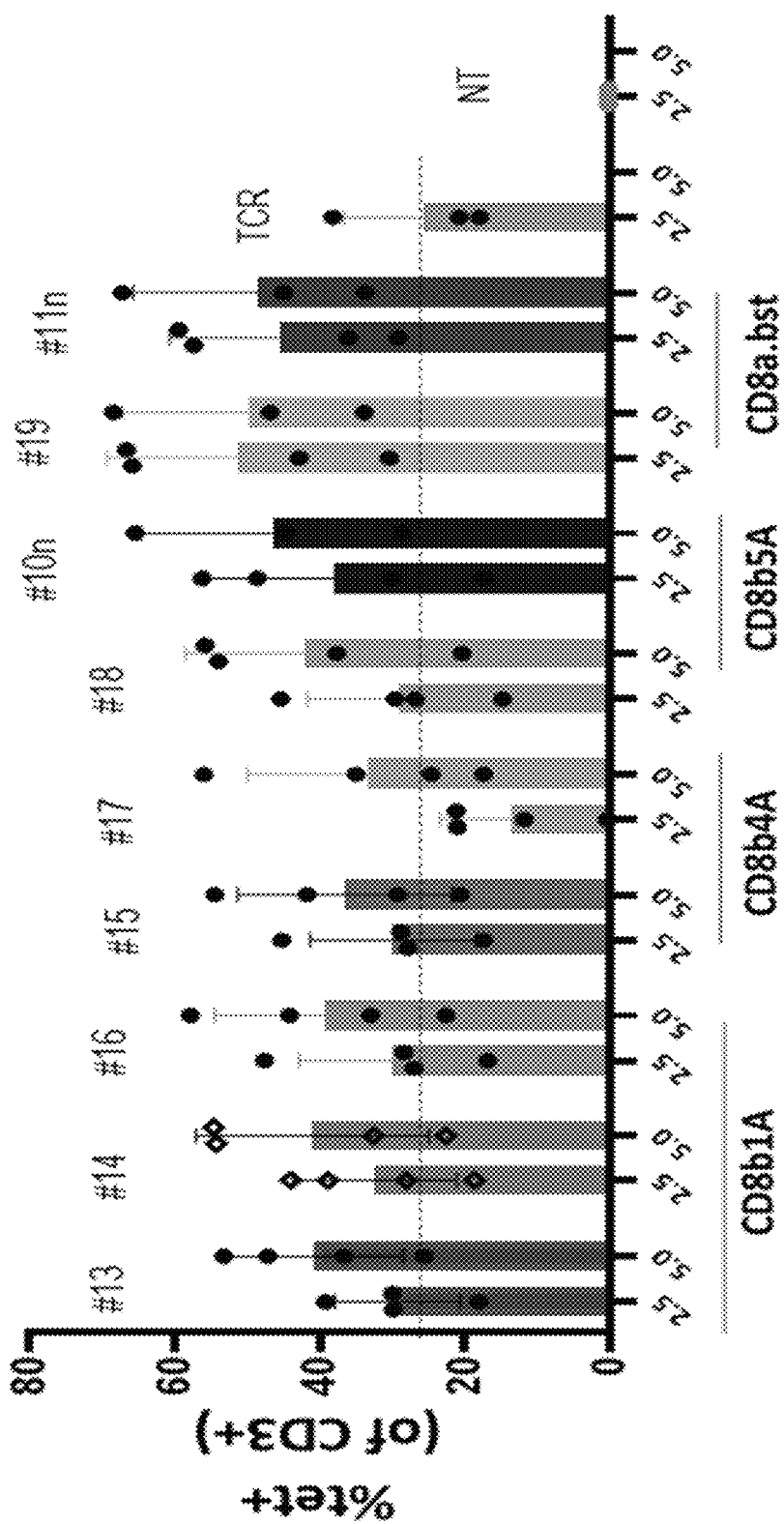
FIG. 41 shows % Tet+ of CD3+ cells transduced with various constructs.

FIG. 41 shows % Tet+ of CD3+ cells transduced with Construct #10n, #11n, #13-#19 at 2.5 μl or 5.0 μl per 1×10⁶ cells. These results show slightly higher frequencies of CD3+Tet+ in cells transduced with Construct #10 (CD8β1) compared to those transduced with CD8β3 (Constructs #13, #14, and #16) and CD8β5 (Construct #15). FACS analysis was gated on live singlets, followed by CD3+, and followed by Tet+. Slightly higher total CD3+tet+ cell counts were observed in PBMC transduced with Construct #10 CD8β1) compared to those transduced with CD8β3 (Constructs #13, #14, and #16) and CD8β5 (Construct #15) (data not shown).

Figure 42:
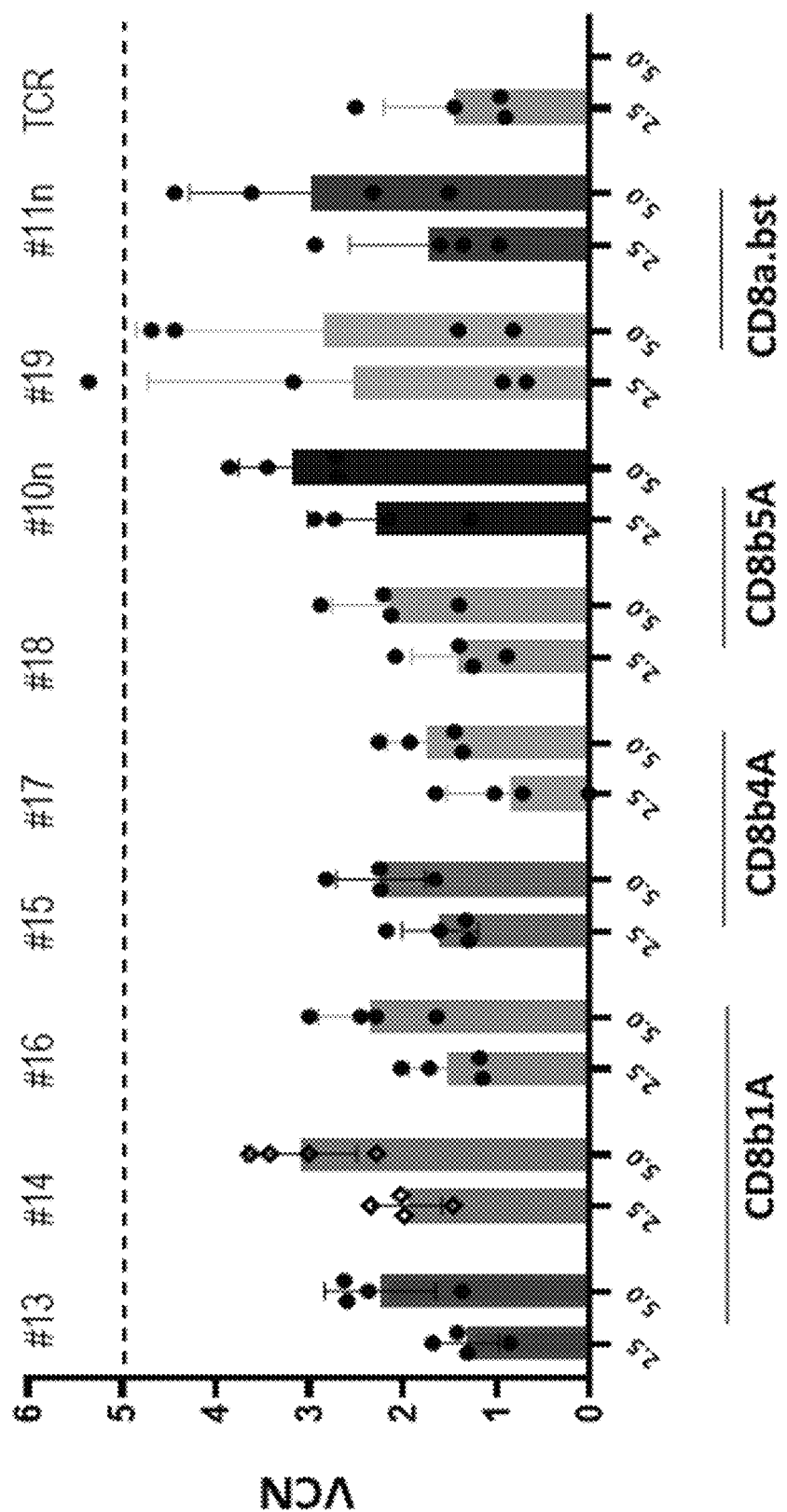
FIG. 42 shows vector copy number (VCN) of cells transduced with various constructs.

FIG. 42 shows vector copy number (VCN) of cells transduced with Construct #10n, #11n, #13-#19 at 2.5 μl or 5.0 μl per 1×10⁶ cells. These results show vector copies per cell remained below 5 in PBMC product derived using each individual construct at vector dose of 2.5 μl or 5.0 μl per 1×10⁶ cells.

Figure 43:
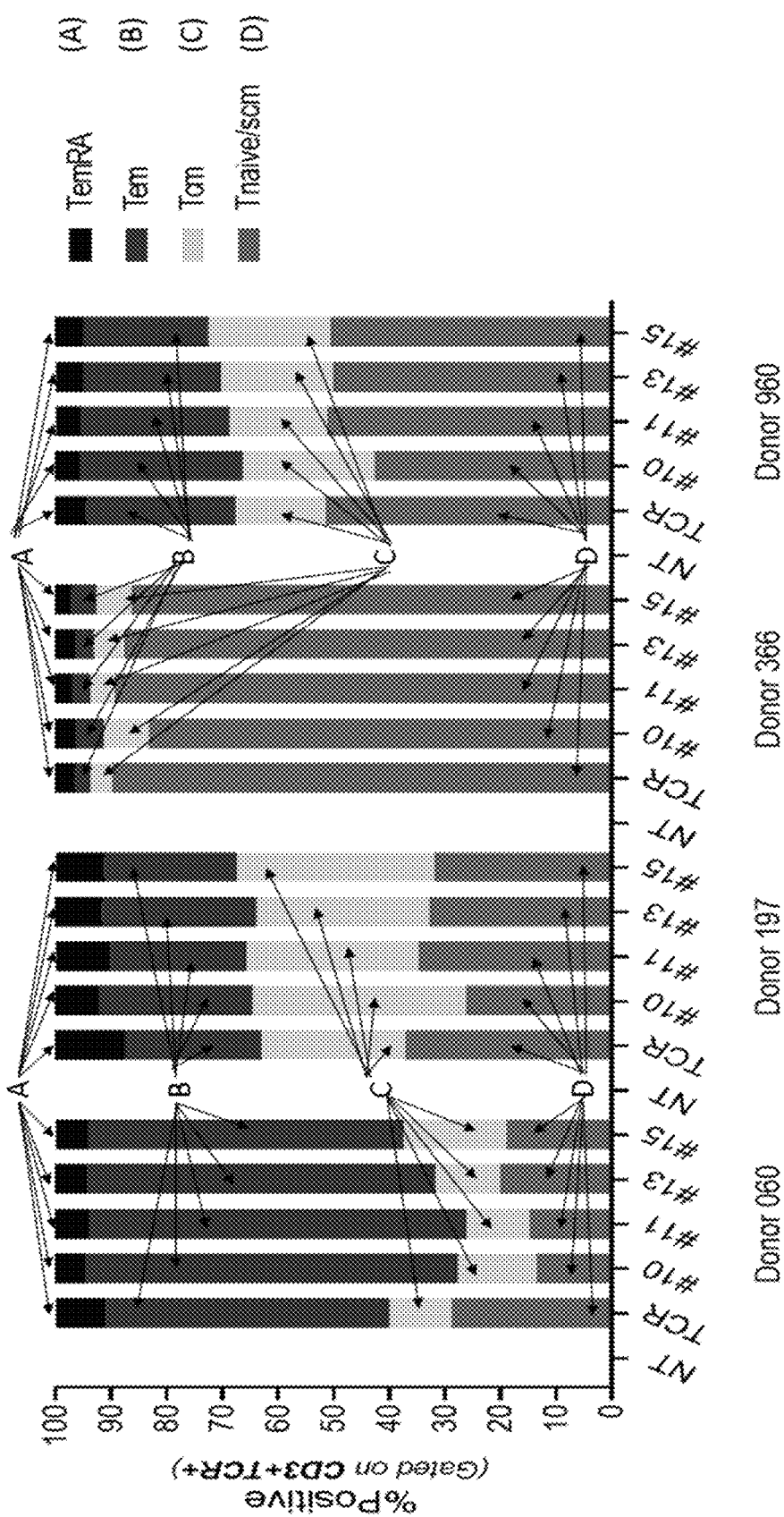
FIG. 43 shows the % T cell subsets in cells transduced with various constructs. FACS analysis was gated on CD3+ TCR+.
Figure 44A:
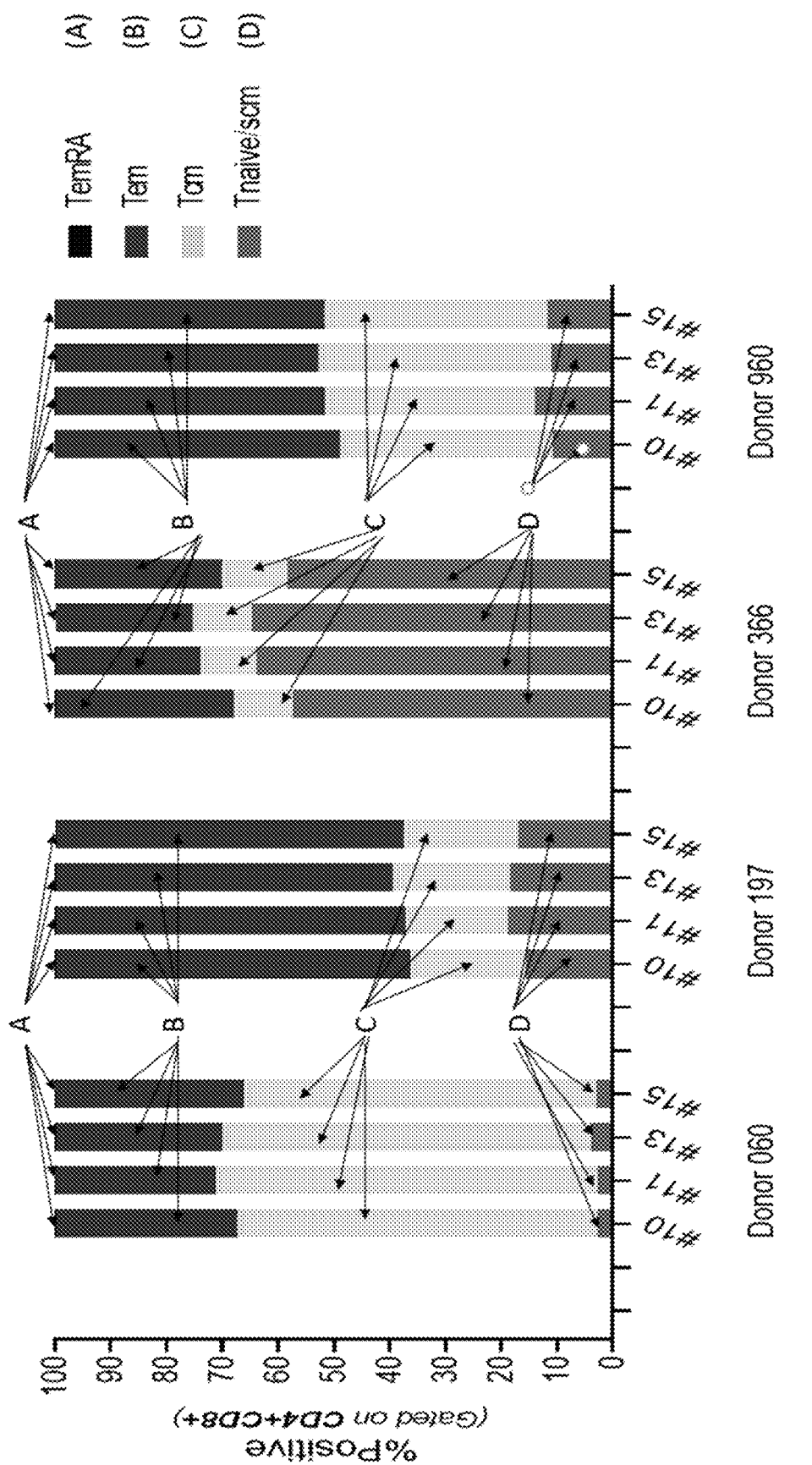
FIG. 44A and FIG. 44B shows % T cell subsets in cells transduced with various constructs. FACS analysis was gated on CD4+CD8+ for FIG. 44A and on CD4−CD8+ TCR+ for FIG. 44B.
Figure 44B:
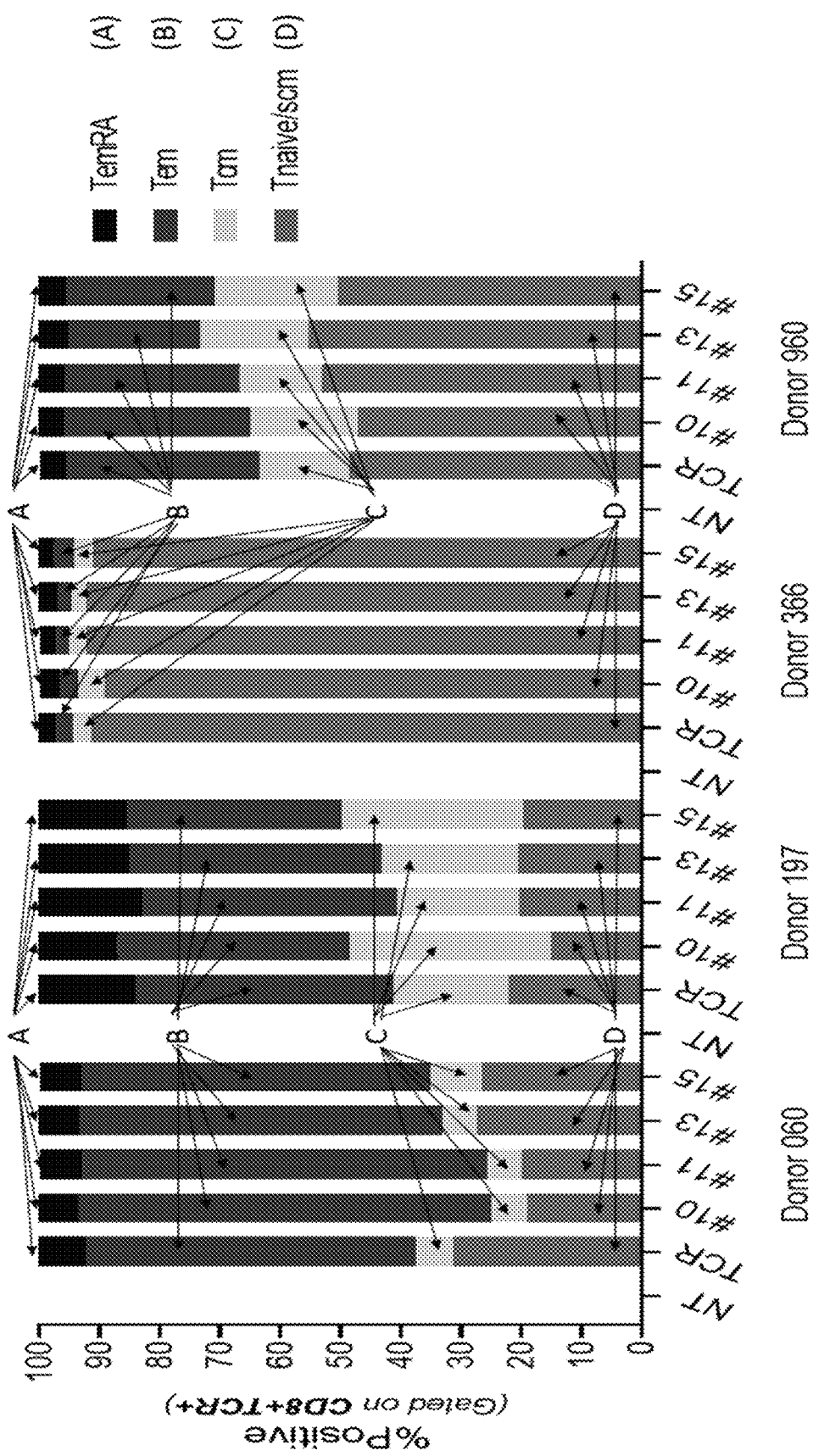

FIG. 43 shows the % T cell subsets in cells transduced with Construct #10, #11, #13, and #15 for each donor. Construct #8 (TCR only) and non-transduced cells were used as controls. These results show that TCR-only condition has slightly more naïve cells compared to the other constructs, consistent with lower fold-expansion. FIG. 44A and FIG. 44B shows % T cell subsets in cells transduced with Construct #10, #11, #13, and #15 for each donor. Construct #8 (TCR only) and non-transduced cells were used as controls. FACS analysis was gated on CD4+CD8+ for FIG. 44A and on CD4−CD8+TCR+ for FIG. 44B. These results show donor-to-donor variability between frequencies of T cell memory subsets but little difference in the frequencies of $T_{naive}$ and $T_{cm}$ between constructs.

In sum, these results show (1) viability and fold expansions were comparable among all constructs at day 7; (2) slightly higher frequency of CD3+tet+ observed in CD8β1 (Construct #10) compared to CD8β3 (Constructs #13, #14, and #16) and CD8β5 (Constructs #15 and #17); (3) vector copies per cell <5 for majority of the constructs at 2.5-5 ul/$10^6$ dose; and (4) donor-to-donor variability between frequencies of T cell memory subsets but generally, Construct #10 has less naïve but more Tcm cells than the other β isoform constructs.

Example 8

Tumor Death Assay—Constructs #10, #11, #13 & #15

Figure 45A:
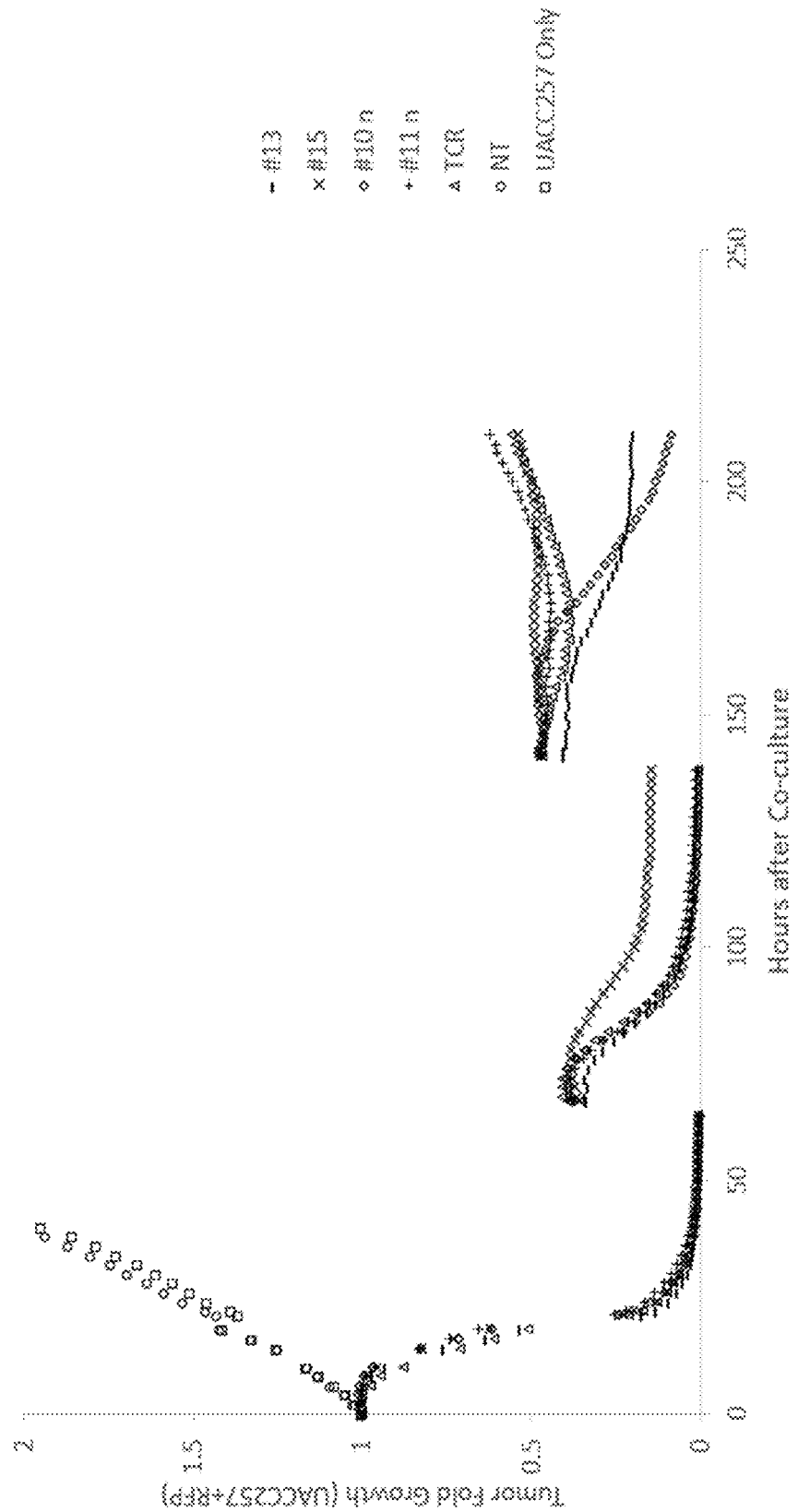
FIGS. 45A and 45B depicts data showing that Constructs #13 and #10 are comparable to TCR-only in mediating cytotoxicity against UACC257 target positive cells lines expressing high levels of antigen (1081 copies per cell). Construct #15 was also effective but slower in killing compared to Constructs #13 and #10. The effector:target ratio used to generate these results was 4:1.
Figure 45B:
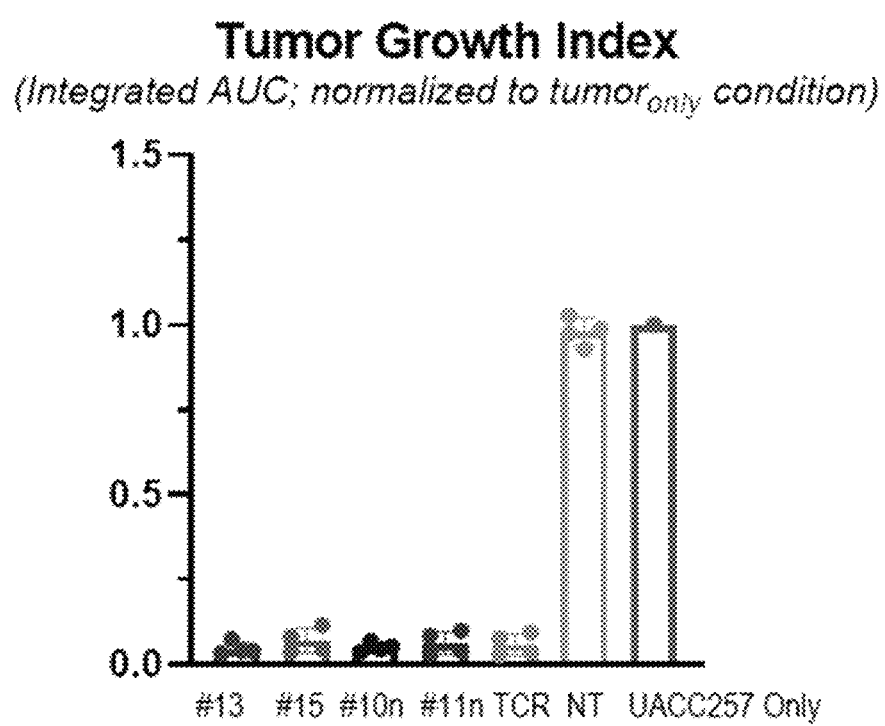

FIGS. 45A and 45B depicts data showing that Constructs #13 and #10 are comparable to TCR-only in mediating cytotoxicity against UACC257 target positive cells lines expressing high levels of antigen (1081 copies per cell). Construct #15 was also effective but slower in killing compared to Constructs #13 and #10. The effector:target ratio used to generate these results was 4:1. Similar results were obtained with a 2:1 effector:target ratio (data not shown).

Example 9

IFNγ Secretion Assay—Constructs #10, #11, #13 & #15

Figure 46:
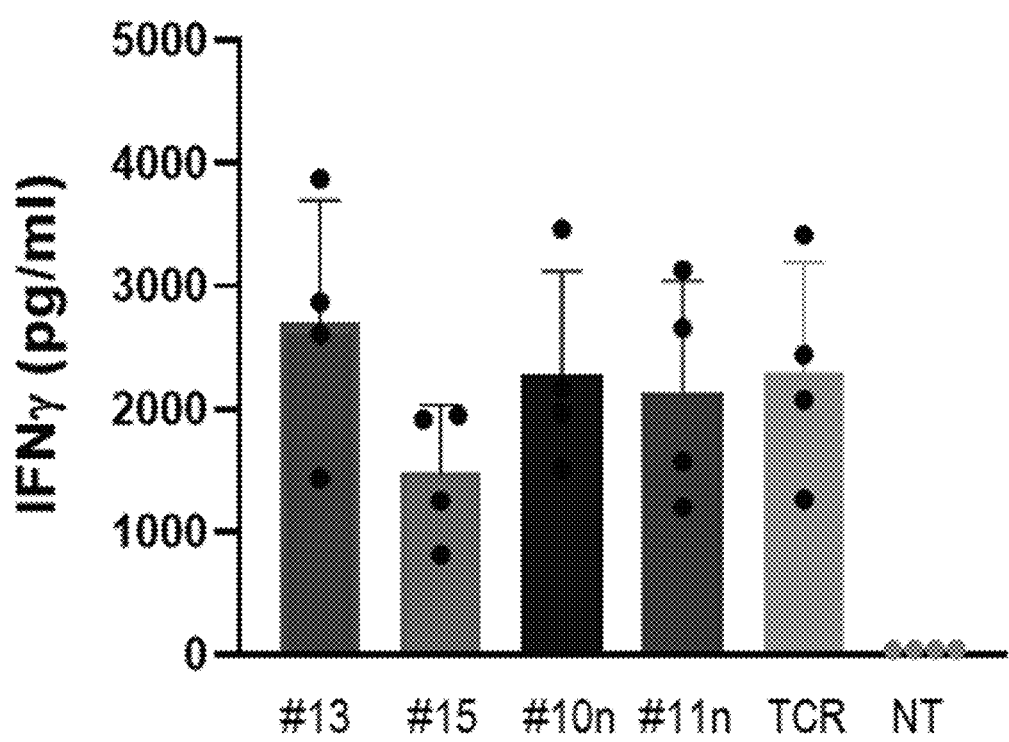
FIG. 46 shows IFNγ secretion in response in UACC257 cell line was higher with Construct #13 compared to Construct #10. IFNγ quantified in the supernatants from Incucyte plates. The effector:target ratio used to generate these results was 4:1.

IFNγ secretion was measured in the UACC257 cells line. FIG. 46 shows IFNγ secretion in response in UACC257 cell line was higher with Construct #13 compared to Construct #10. IFNγ quantified in the supernatants from Incucyte plates. The effector:target ratio used to generate these results was 4:1. Similar results were obtained with a 2:1 effector:target ratio (data not shown).

Example 10

ICI Marker Expression—Constructs #10, #11, #13 & #15

Figure 47:
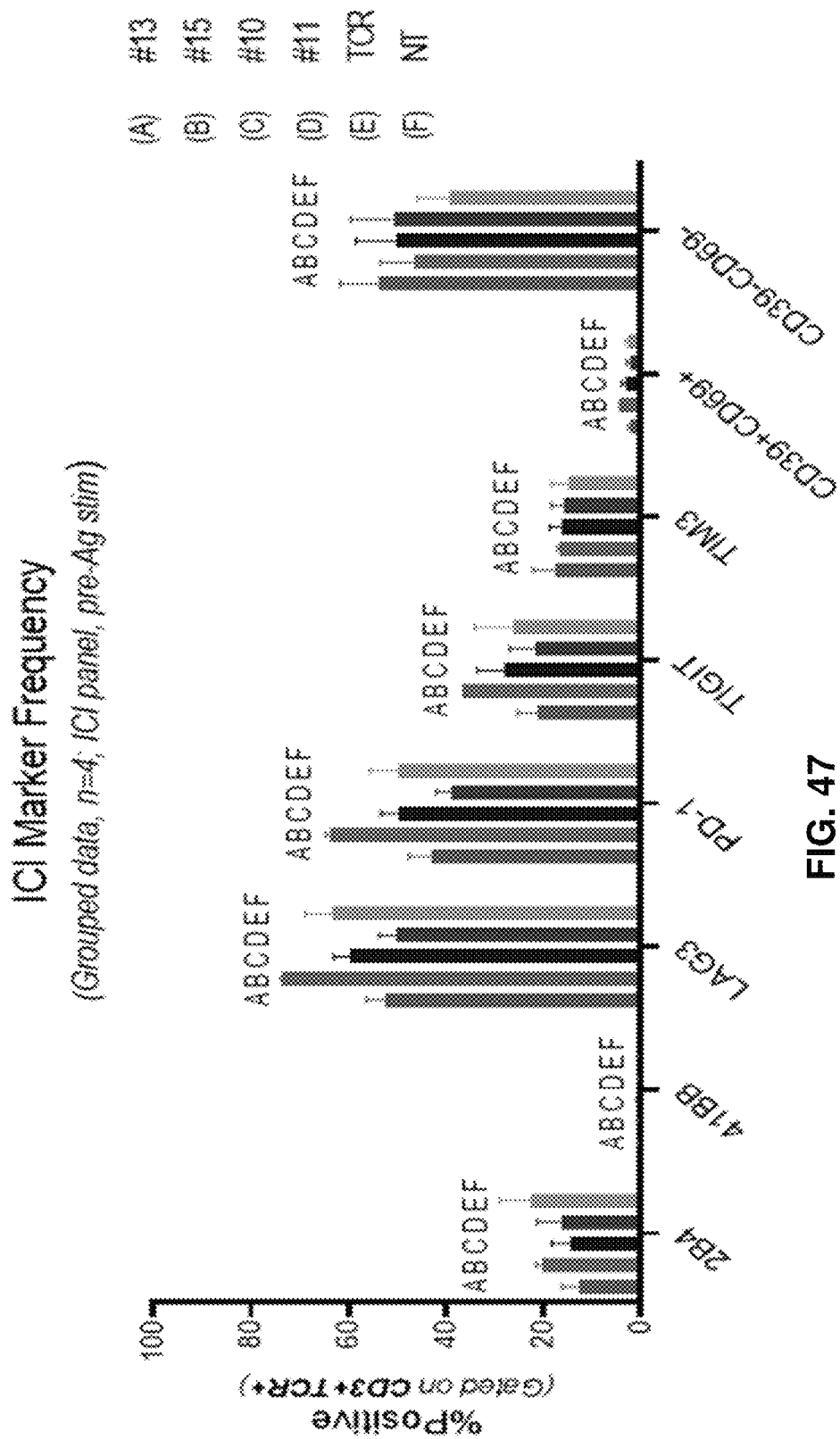
FIG. 47 shows ICI marker frequency (2B4, 41BB, LAG3, PD-1, TIGIT, TIM3, CD39+CD69+, and CD39−CD69−).
Figure 48A:
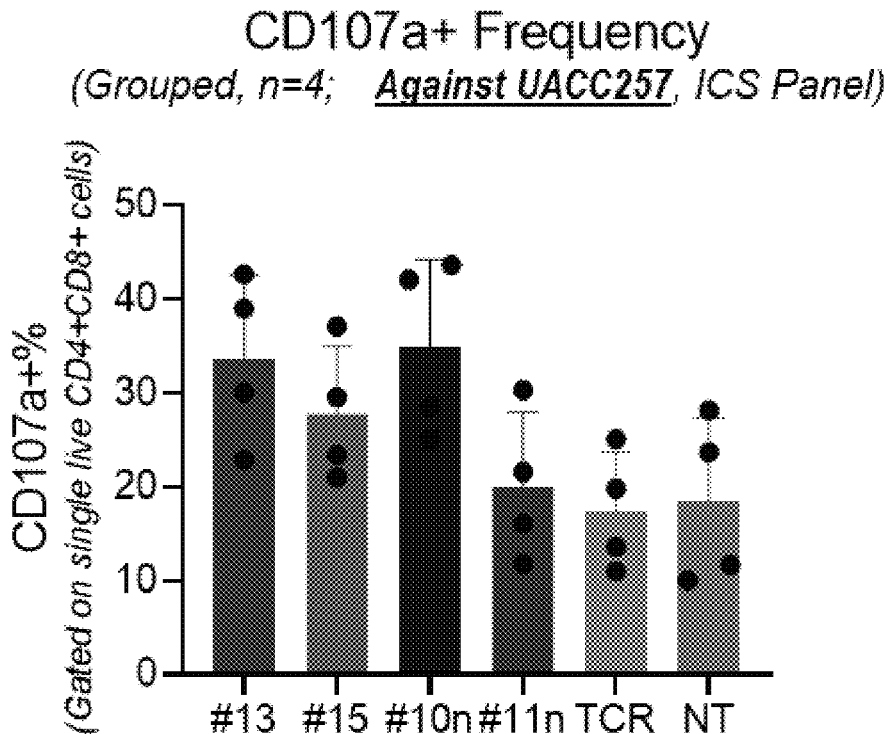
FIG. 48A-48G show increased expression of IFNγ, IL-2, and TNFα with CD4+CD8+ cells transduced with Construct #10 (WT signal peptide, CD8β1) compared to other constructs. FACS analysis was gated on CD3+CD4+CD8+ cells against UACC257, 4:1 E:T.
Figure 48B:
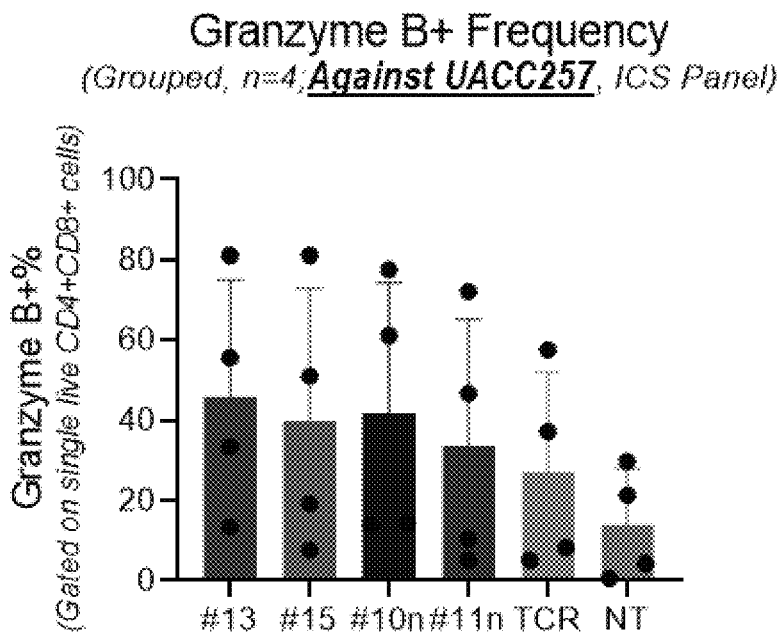
Figure 48C:
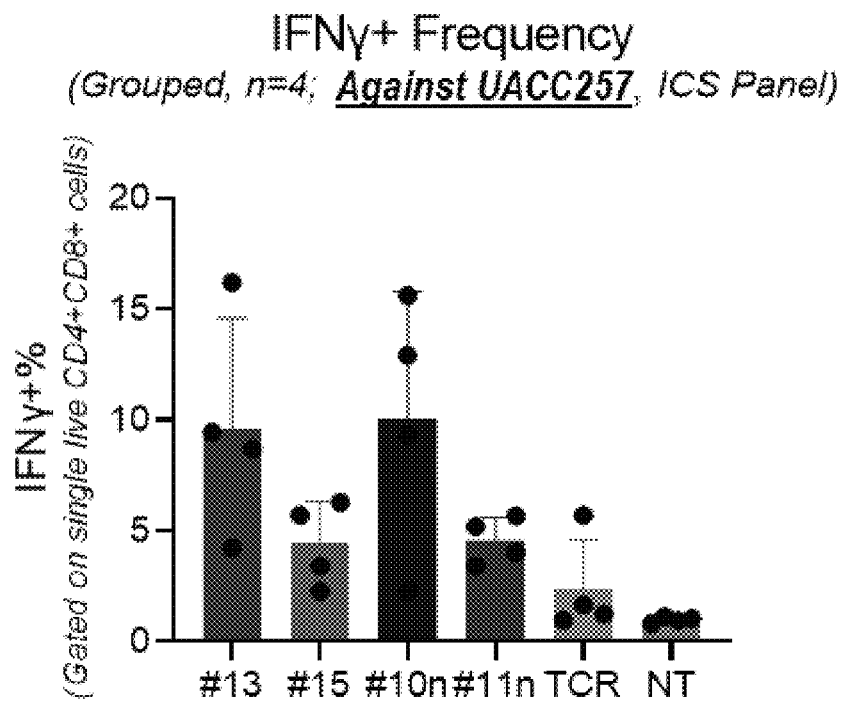
Figure 48D:
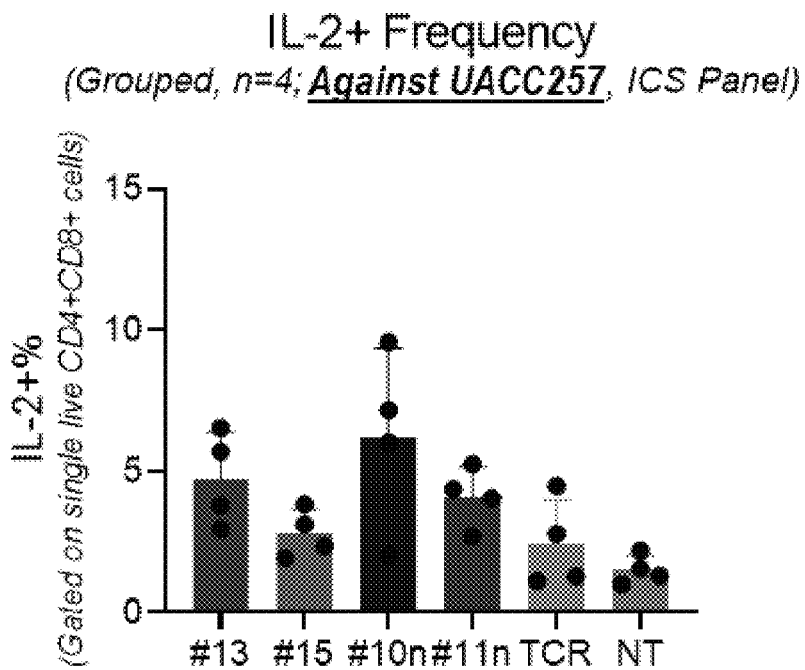
Figure 48E:
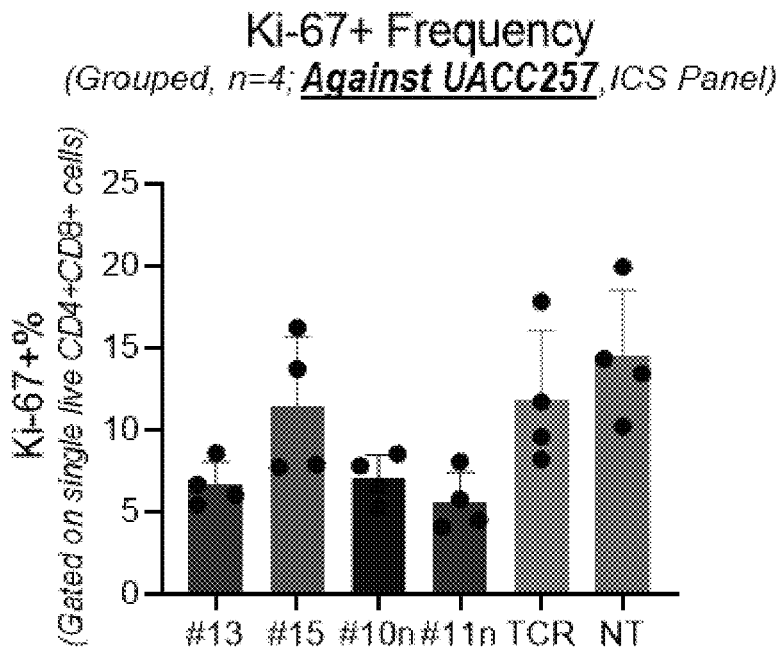
Figure 48F:
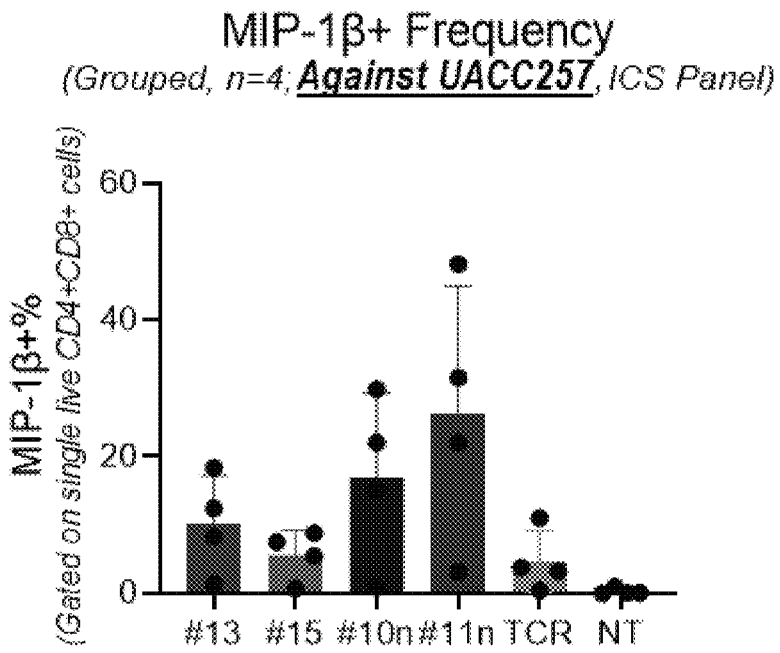
Figure 48G:
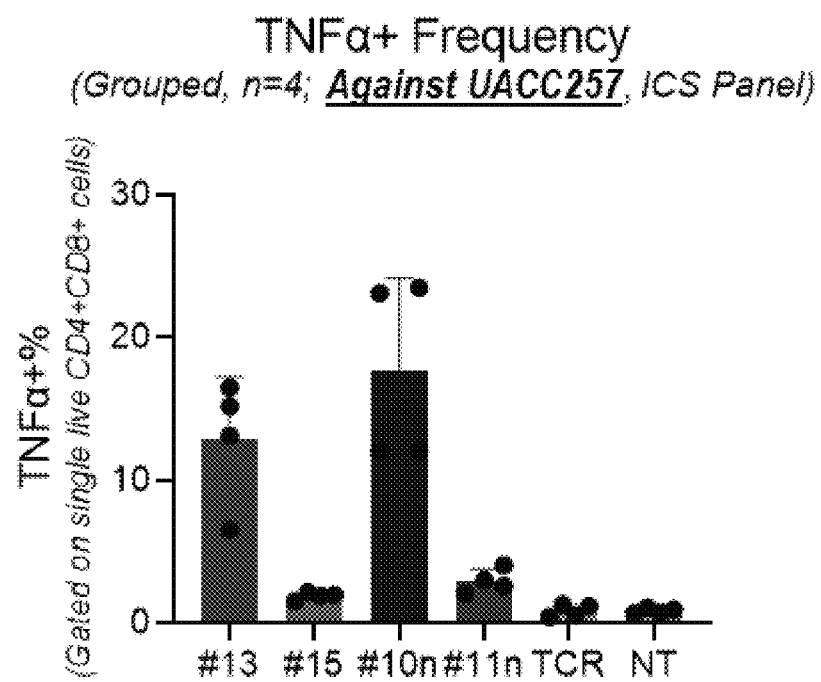
Figure 49A:
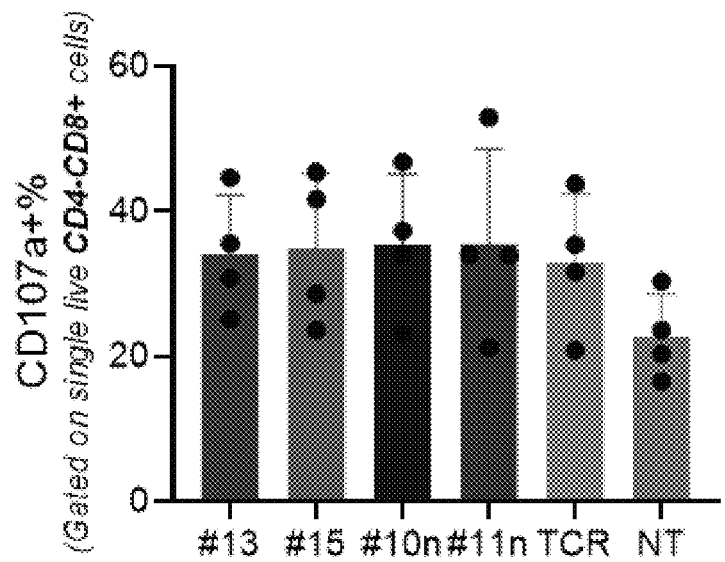
FIG. 49A-49G show increased expression of IFNγ, IL-2, MIP-10, and TNFα with CD4− CD8+ cells transduced with Construct #10 (WT signal peptide, CD8β1) compared to other constructs. FACS analysis was gated on CD3+CD4− CD8+ cells against UACC257, 4:1 E:T.
Figure 49B:
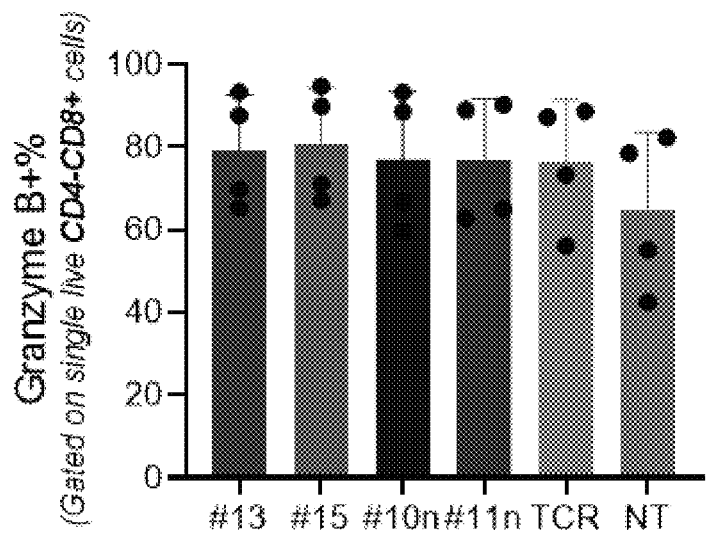
Figure 49C:
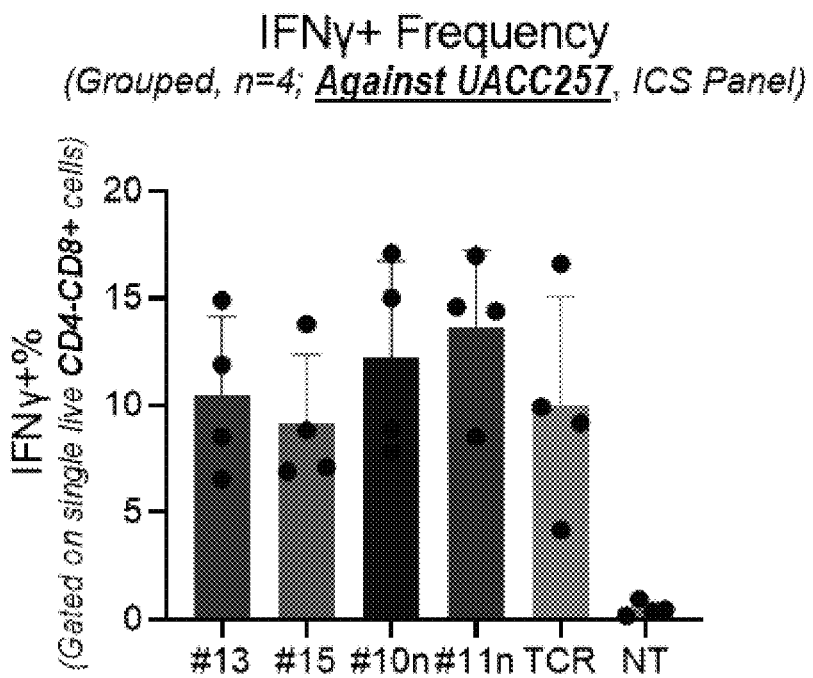
Figure 49D:
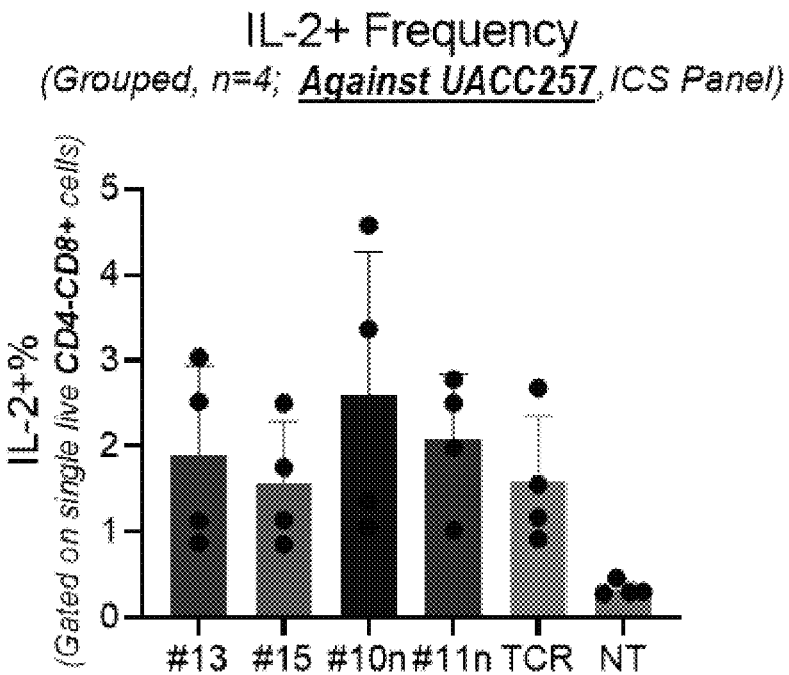
Figure 49E:
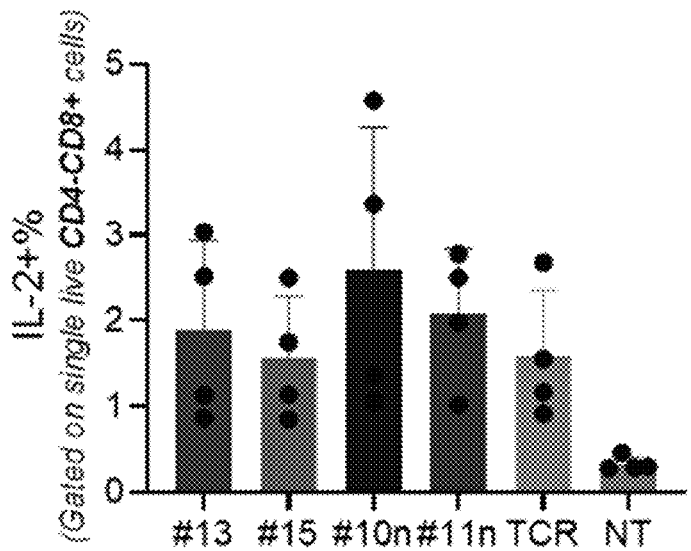
Figure 49F:
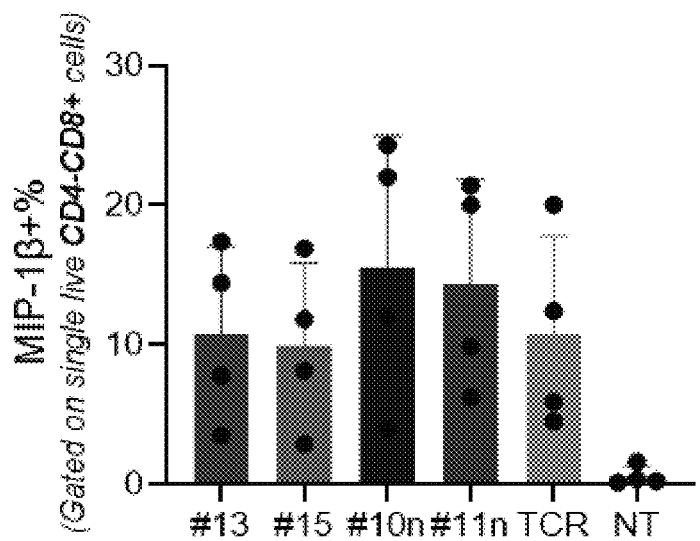
Figure 49G:
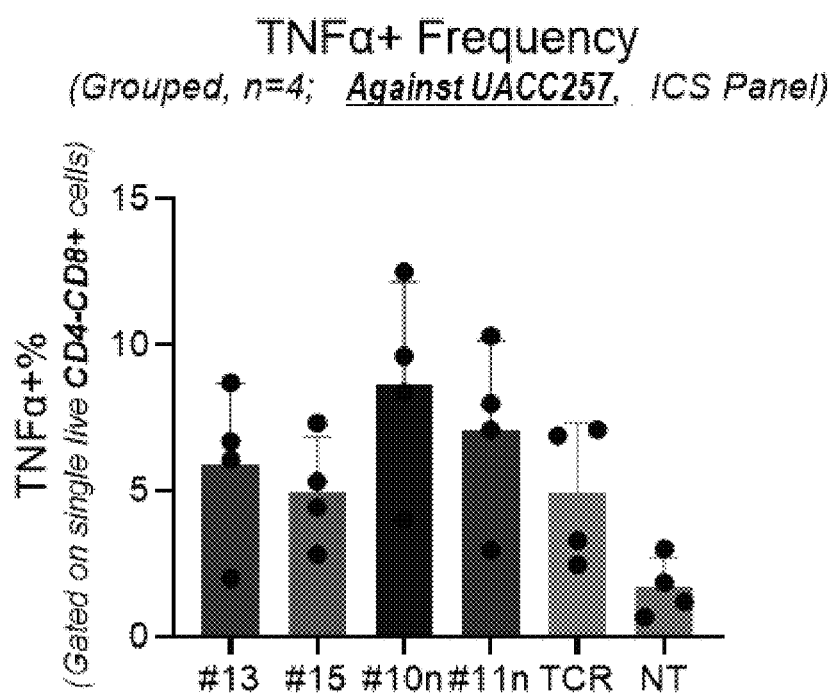
Figure 50A:
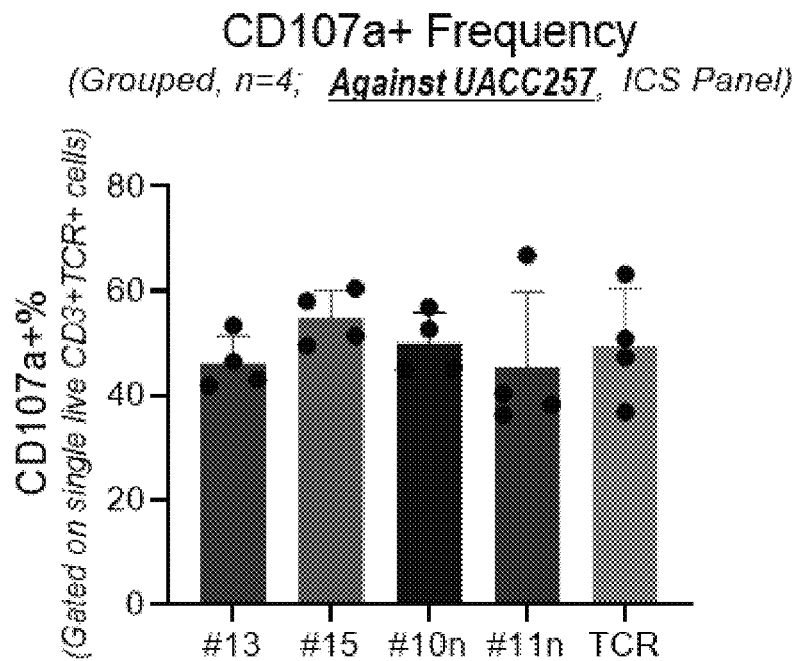
FIG. 50A-50G show increased expression of IL-2 and TNFα with CD3+TCR+ cells transduced with Construct #10 (WT signal peptide, CD8β1) compared to other constructs. FACS analysis was gated on CD3+TCR+ cells against UACC257, 4:1 E:T.
Figure 50B:
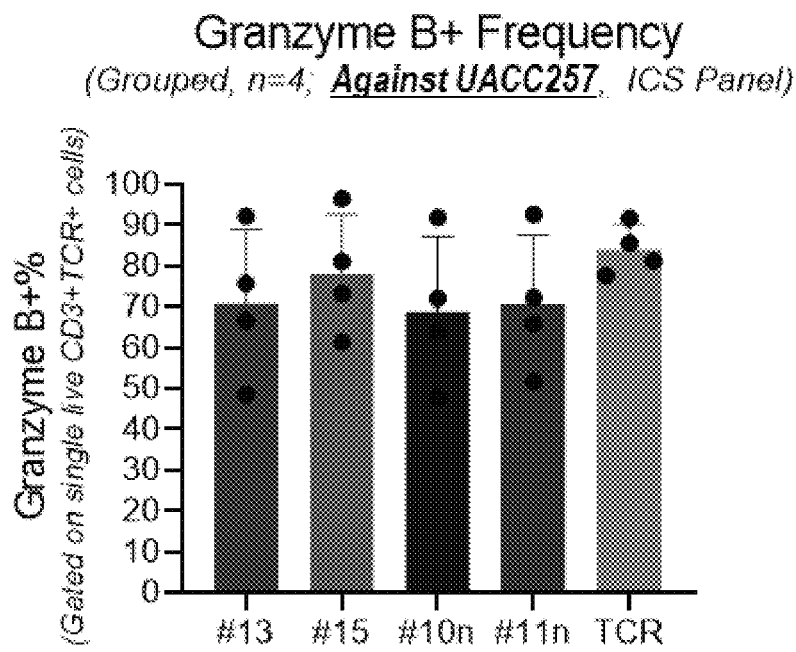
Figure 50C:
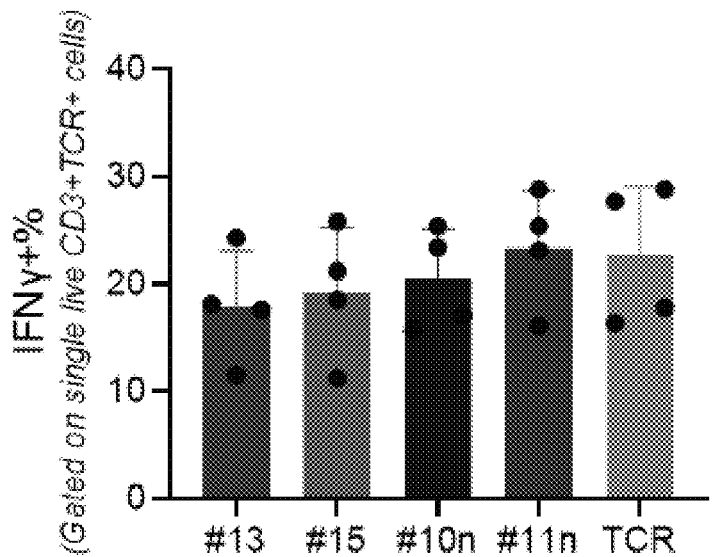
Figure 50D:
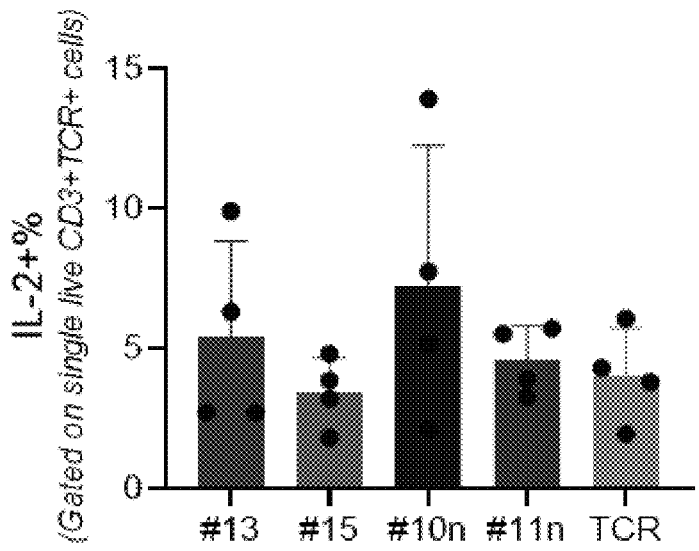
Figure 50E:
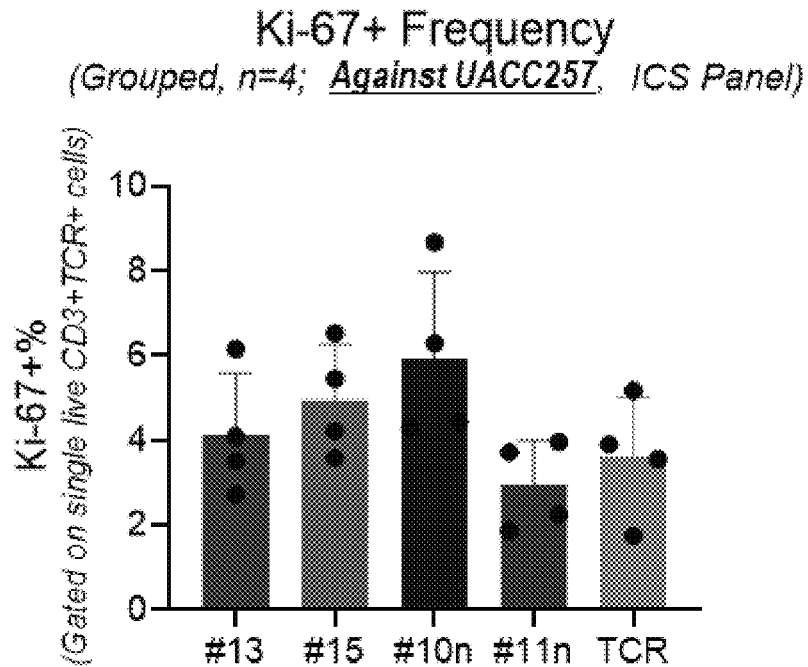
Figure 50F:
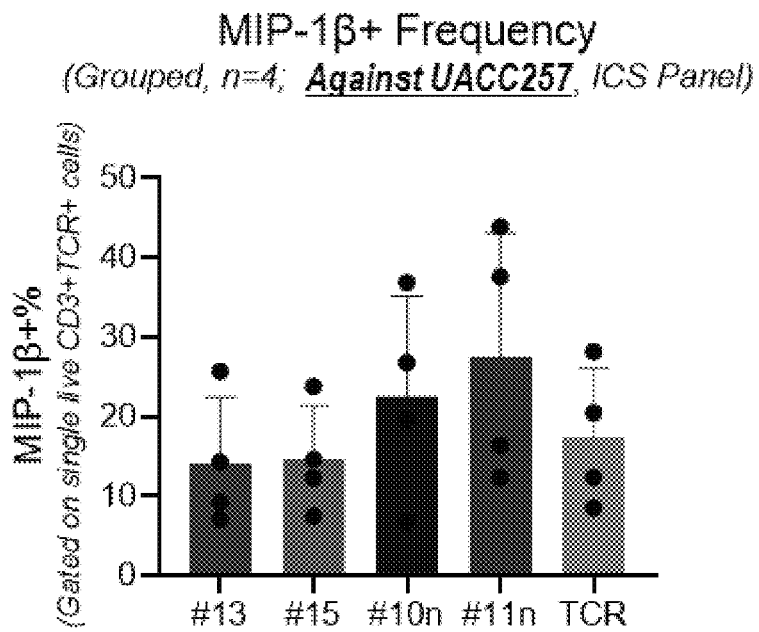
Figure 50G:
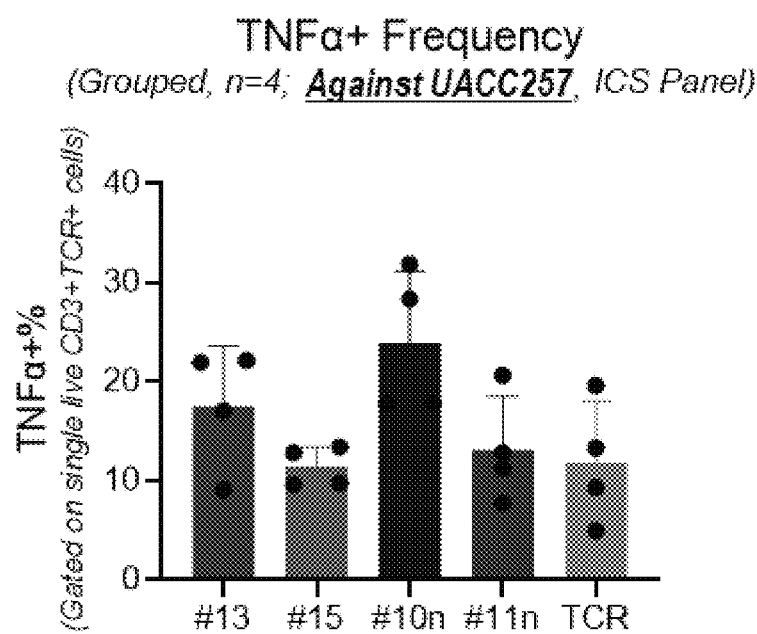

ICI marker frequency (2B4, 41BB, LAG3, PD-1, TIGIT, TIM3, CD39+CD69+, and CD39−CD69−) was measured. FIG. 47 shows Construct #15 has higher expression of LAG3, PD-1, and TIGIT compared to other constructs, followed by Construct #10.

Example 11

Cytokine Expression—Constructs #10, #11, #13 & #15

Expression of various cytokines was measured in UACC257 cells co-cultured at a 4:1 E:T ratio with PBMC transduced with Constructs #10, #11, #13, and #15. FIG. 48A-48G show increased expression of IFNγ, IL-2, and TNFα with CD4+CD8+ cells transduced with construct #10 (WT signal peptide, CD8β1) compared to other constructs. FACS analysis was gated on CD3+CD4+CD8+ cells against UACC257, 4:1 E:T. FIG. 49A-49G show increased expression of IFNγ, IL-2, MIP-10, and TNFα with CD4−CD8+ cells transduced with construct #10 (WT signal peptide, CD8β1) compared to other constructs. FACS analysis was gated on CD3+CD4−CD8+ cells against UACC257, 4:1 E:T. FIG. 50A-50G show increased expression of IL-2 and TNFα with CD3+TCR+ cells transduced with construct #10 (WT signal peptide, CD8β1) compared to other constructs. MIP-10 expression is highest in Construct #11 (similar results when gated on CD4+CD8+ cells). FACS analysis was gated on CD3+TCR+ cells against UACC257, 4:1 E:T.

Figure 51A:
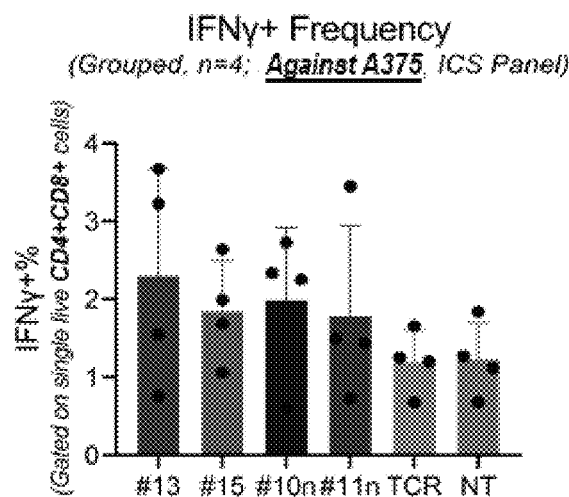
FIG. 51A-51C show results from FACS analysis gated on CD4+CD8+ cells against A375, 4:1 E:T.
Figure 51B:
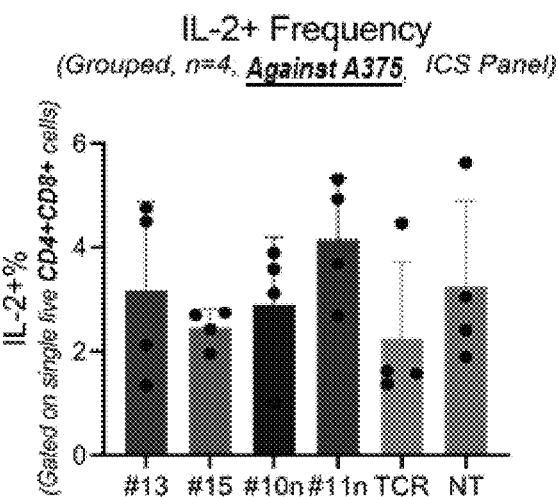
Figure 51C:
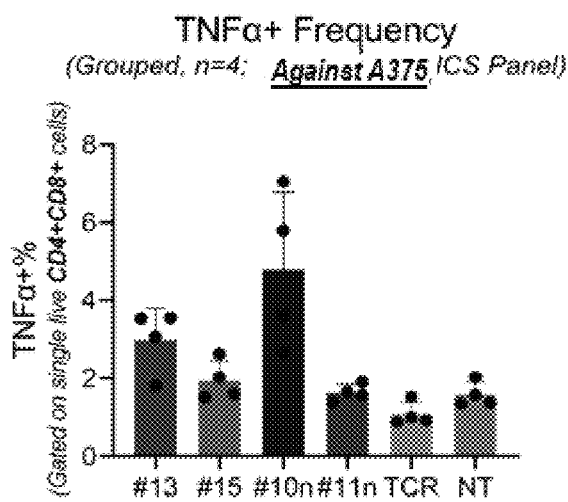
Figure 52A:
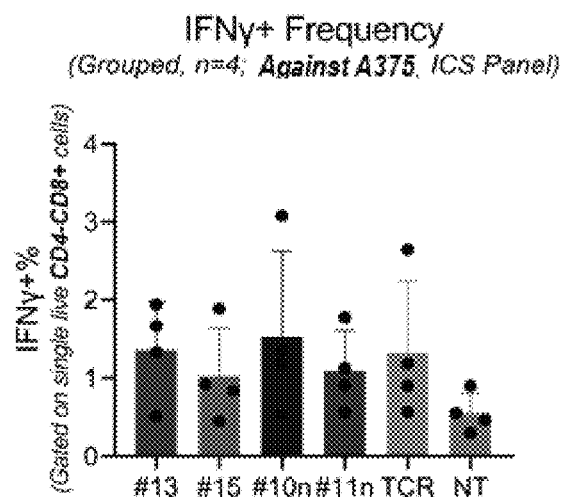
FIG. 52A-52C show results from FACS analysis gated on CD4−CD8+ cells against A375, 4:1 E:T.
Figure 52B:
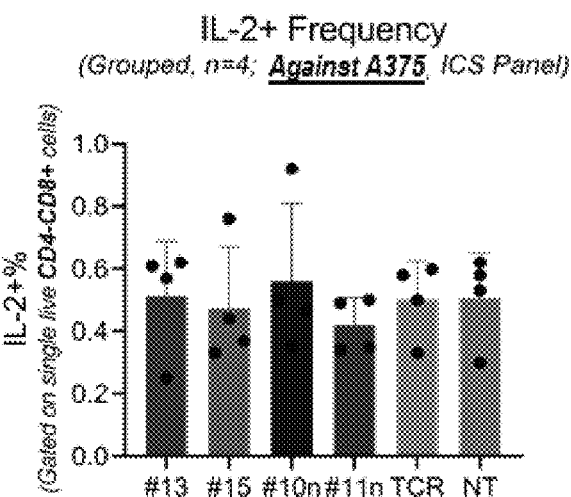
Figure 52C:
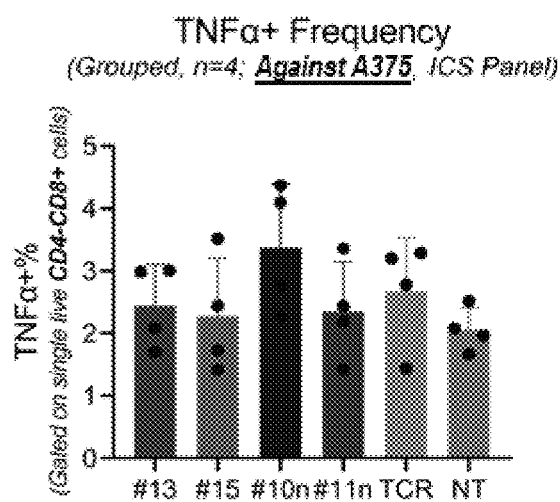
Figure 53A:
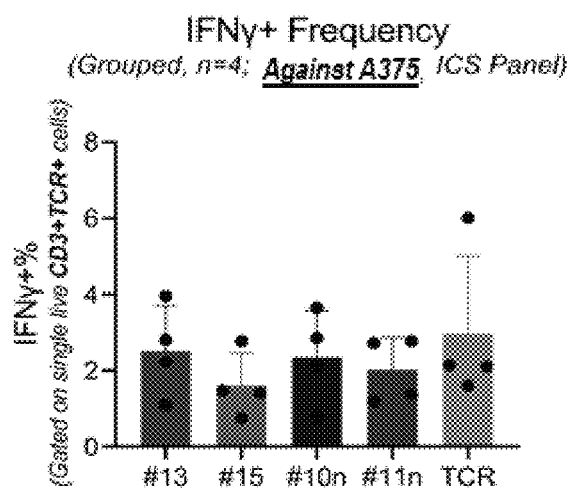
FIG. 53A-53C show results from FACS analysis gated on CD3+TCR+ cells against A375, 4:1 E:T.
Figure 53B:
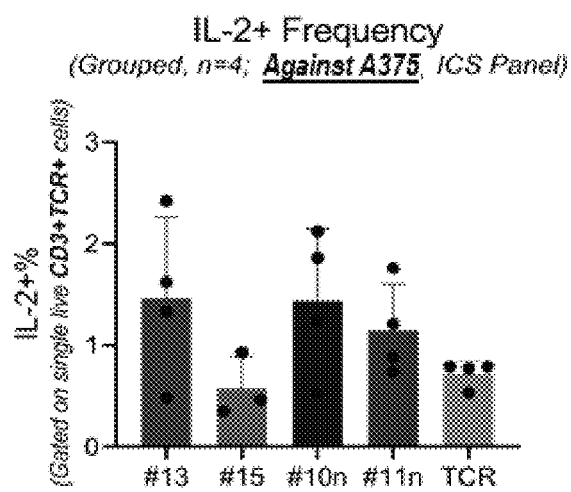
Figure 53C:
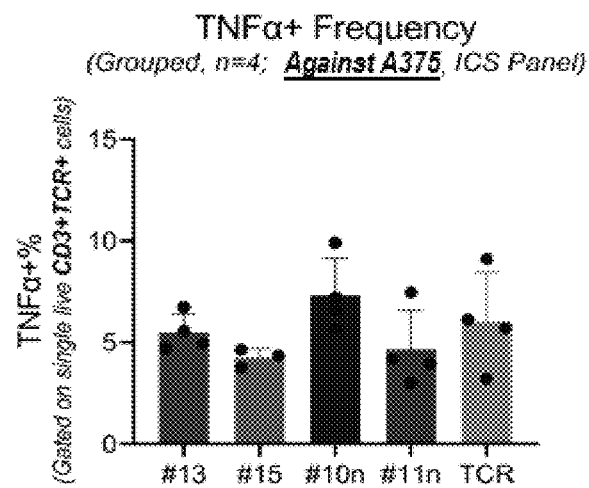

Expression of various cytokines was measured in A375 cells co-cultured at a 4:1 E:T ratio with PBMC transduced with Constructs #10, #11, #13, and #15. FIG. 51A-51C show results from FACS analysis gated on CD4+CD8+ cells against A375, 4:1 E:T. FIG. 52A-52C show results from FACS analysis gated on CD4−CD8+ cells against A375, 4:1 E:T. FIG. 53A-53C show results from FACS analysis gated on CD3+TCR+ cells against A375, 4:1 E:T. Overall, results were more variable when cells are co-cultured with A375+RFP, but similar trends are observed compared to activation by UACC257+RFP.

Example 12

Large-Scale Vector Screening (Constructs #10, #11, #13, #16, #18, #19)

T Cell Manufacturing
Activation/Transduction

Figure 54:
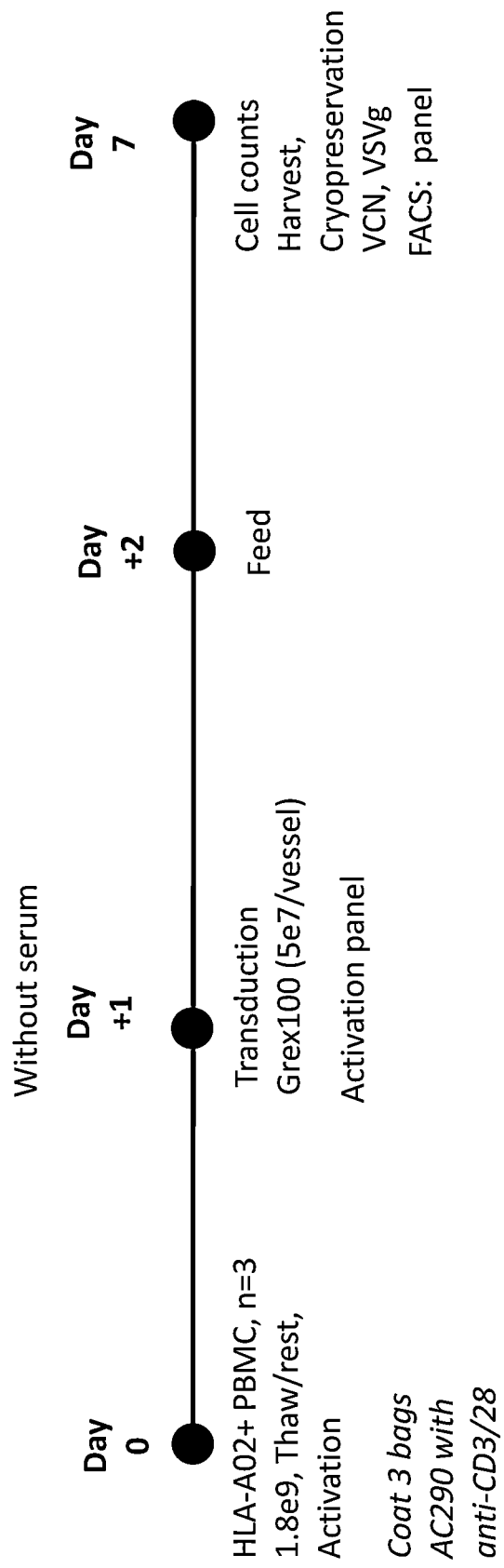
FIG. 54 shows T cell manufacturing in accordance with one embodiment of the present disclosure.
Figure 55:
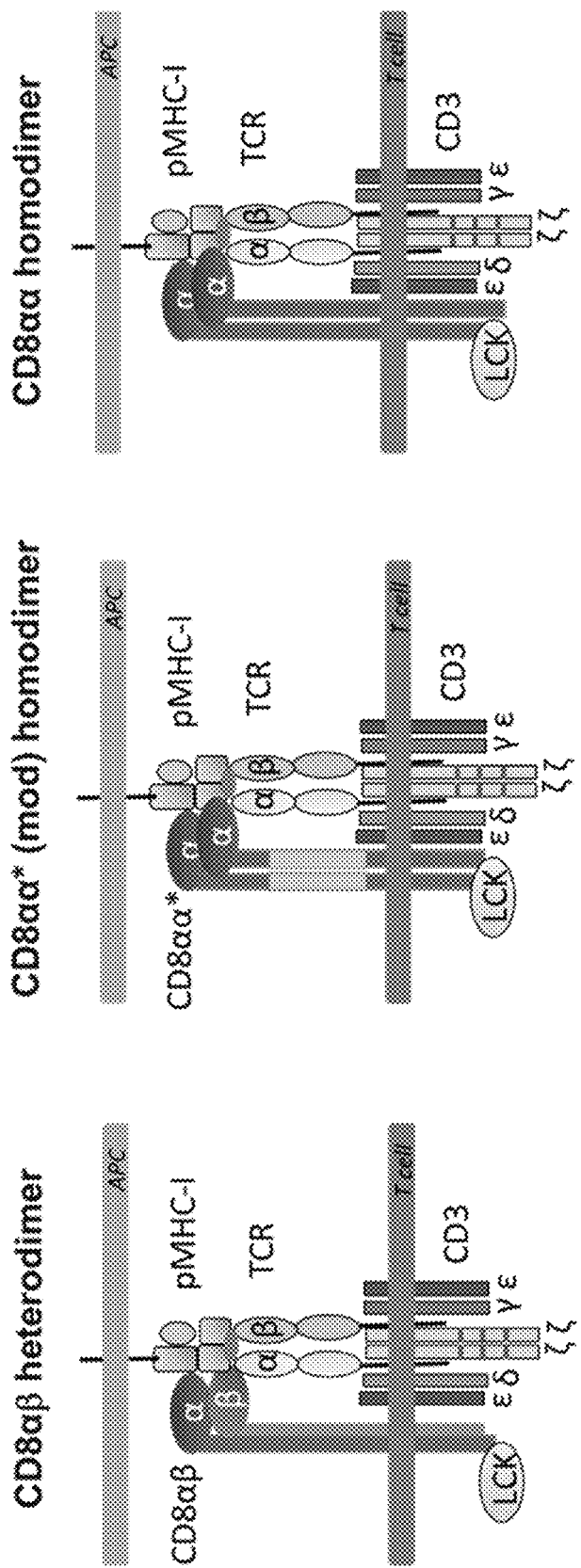
FIG. 55A-55C show interaction between peptide/MHC complex of antigen-presenting cell (APC) with T cell by binding a complex of TCR and CD8αβ heterodimer (FIG. 55A, e.g., produced by transducing T cells with Constructs #2, #3, #4, #10, #13, #14, #15, #16, #17, #18, or #21), a complex of TCR and homodimer CD8α having its stalk region replaced with CD8β stalk region (CD8αα*) (FIG. 55B, e.g., produced by transducing T cells with Construct #11, #12, or #19), and a complex of TCR and CD8α homodimer (FIG. 55C, e.g., produced by transducing T cells with Constructs #1, #5, #6, #7, or #9).

FIG. 54 shows that, on Day +0, PBMCs obtained from three HLA-A02+ donors were thawed and rested. Cells were activated in bags (AC290) coated with anti-CD3 and anti-CD28 antibodies in the absence of serum. On Day +1, activated PBMCs were transduced with viral vectors, e.g., Constructs #8, #10n, #11n, #13, #16, #18, and #19 in G-Rex® 100 cell culture vessels at about $5 \times 10^7$ cells/vessel in the absence of serum. The amounts of virus used for transduction are shown in Table 10.

TABLE 10

| Constructs | Virus Volume/$1 \times 10^6$ cells |
| --- | --- |
| #13, #16, #18, #10n | 5 μl |
| #19 and #11n | 2.5 μl |
| #8 (TCR) | 2.5 μl |
| NT | — |

Expansion

FIG. 54 shows that, on Day +2, transduced PBMCs were expanded in the absence of serum. On Day +7, cells were harvested for subsequent analysis, e.g., FACS-Tetramer and vector copy number (VCN) and were cryopreserved. Fold expansion on Day +7 was comparable for all constructs (approximately 30-fold expansion). Viabilities of cells is greater than 90% on Day +7.

Characterization of T Cell Products

Cell counts, FACS-dextramers, and vector copy numbers (VCN) were determined. Tetramer panels may comprise live/dead cells, CD3, CD8α, CD8β, CD4, and peptide/MHC tetramers, e.g., PRAME-004 (SLLQHLIGL) (SEQ ID NO: 147)/MHC tetramers. FACS analysis was gated on live singlets, followed by CD3+, followed by CD4+CD8+, followed by CD4+CD8+Tetramer(Tet)+ and CD8+Tet+.

Tumor death assays and cytokine expression in the presence and absence of autologous immature dendritic cells was also measured.

The results were consistent with the prior examples and are summarized in Table 11.

TABLE 11

| Parameters | | Construct #10 | Construct #13 | Construct #11 | Construct #19 | TCR only Construct #8 |
|---|---|---|---|---|---|---|
| Manufacturing | Viabilities | >90% | >90% | >90% | >90% | >90% |
| | Fold Expansion d7 | 28.7 ± 11% | 28.6 ± 11% | 31.6 ± 13% | 29.6 ± 13% | 30.1 ± 11% |
| | Transgene expression (% CD3+Tet+), mean ± SD | 46.9 ± 12% | 42 ± 9.8% | 41 ± 12% | 48.2 ± 14% | 22.8 ± 8% |
| | Vector Copy Number | 3.3 ± 0.6% | 2.6 ± 0.7% | 2.0 ± 0.8% | 3.1 ± 1.8% | 1.7 ± 0.7% |
| Functionality | Multiple rounds of killing with UACC | +++ | +++ | +++ | +++ | +++ |
| | Cytokine secretion (24 h, with UACC); IFN-g, TNF-a, IL-2 | +++ | +++ | ++ | ++ | ++ |
| | Cytokine secretion; CD4+CD8+TCR+ (16 h, UACC); ICS | +++ | +++ | + | + | +/− |
| | DC licensing assay (PBMC product) IL-12, TNF-a & IL-6 | +++ | +++ | + | + | + |
| | 3D Spheroid Assay | +++ | N/A | +++ | N/A | ++ |

Example 13

DC Licensing by CD4 Cells Expressing Constructs of the Present Disclosure

Figure 59:
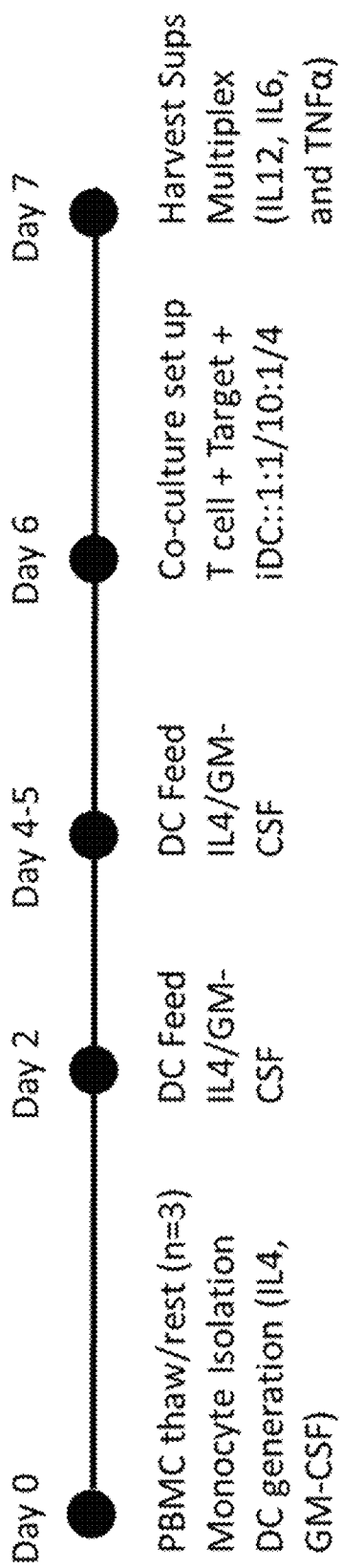
FIG. 59 shows a scheme of determining the levels of cytokine secretion by dendritic cells (DC) in the presence of PBMCs transduced with various constructs and target cells in accordance with one embodiment of the present disclosure.

FIG. 59 shows a scheme of determining the levels of cytokine secretion by dendritic cells (DC) in the presence of PBMCs transduced with constructs of the present disclosure and in the presence of target cells, e.g., UACC257 cells. Briefly, Day 0, PBMCs (n=3) were thawed and rested, followed by monocyte isolation and autologous immature DCs (iDC) generation in the presence of IL-4 and GM-CSF; Day 2 and Day 4-5, DC were fed in the presence of IL-4 and GM-CSF; Day 6, iDC (+DC) were co-cultured with PBMC transduced with Construct #13, #16, #10n, #18, #11n, or #19 (Effector) and UACC257 cells (Target) at a ratio of Effector: Target:iDC=1:1/10:1/4 or without iDC (−DC), PBMCs transduced with TCR only, PBMCs without transduction (NT), PBMCs treated with iDC and LPS, and iDC only serve as controls; and Day 7 (after co-culturing for 24 hours), supernatants from the co-cultures were harvested, followed by cytokine profiling including, e.g., IL-12, IL-6, and TNF-α, using Multiplex.

Increased secretion of pro-inflammatory cytokines in tri-cocultures of autologous immature dendritic cells, UACC257 tumor cell line, and CD4+ T cell product expressing CD8αβ heterodimer and TCR (Construct #10) compared with that expressing CD8α* homodimer, in which the stalk region is replaced with CD8β stalk region, and TCR (Construct #11).

To determine the ability of CD4+ T cells expressing Constructs #10 or #11 to license DC, bulk PBMCs were transduced with Constructs #10 or #11, followed by selection of CD8+ and CD4+ cells from the product. Tri-cocultures of PBMCs, CD8+CD4− selected-product, or CD4+CD8+ selected-product with UACC257 tumor cell line in the presence or absence of autologous immature dendritic cells (iDCs) for 24 h followed by cytokine quantification of IL-12, TNF-α and IL-6 using Multiplex; iDCs alone or with LPS as controls, N=4-7, mean±SD, P values based on 2way ANOVA.

Figure 56:
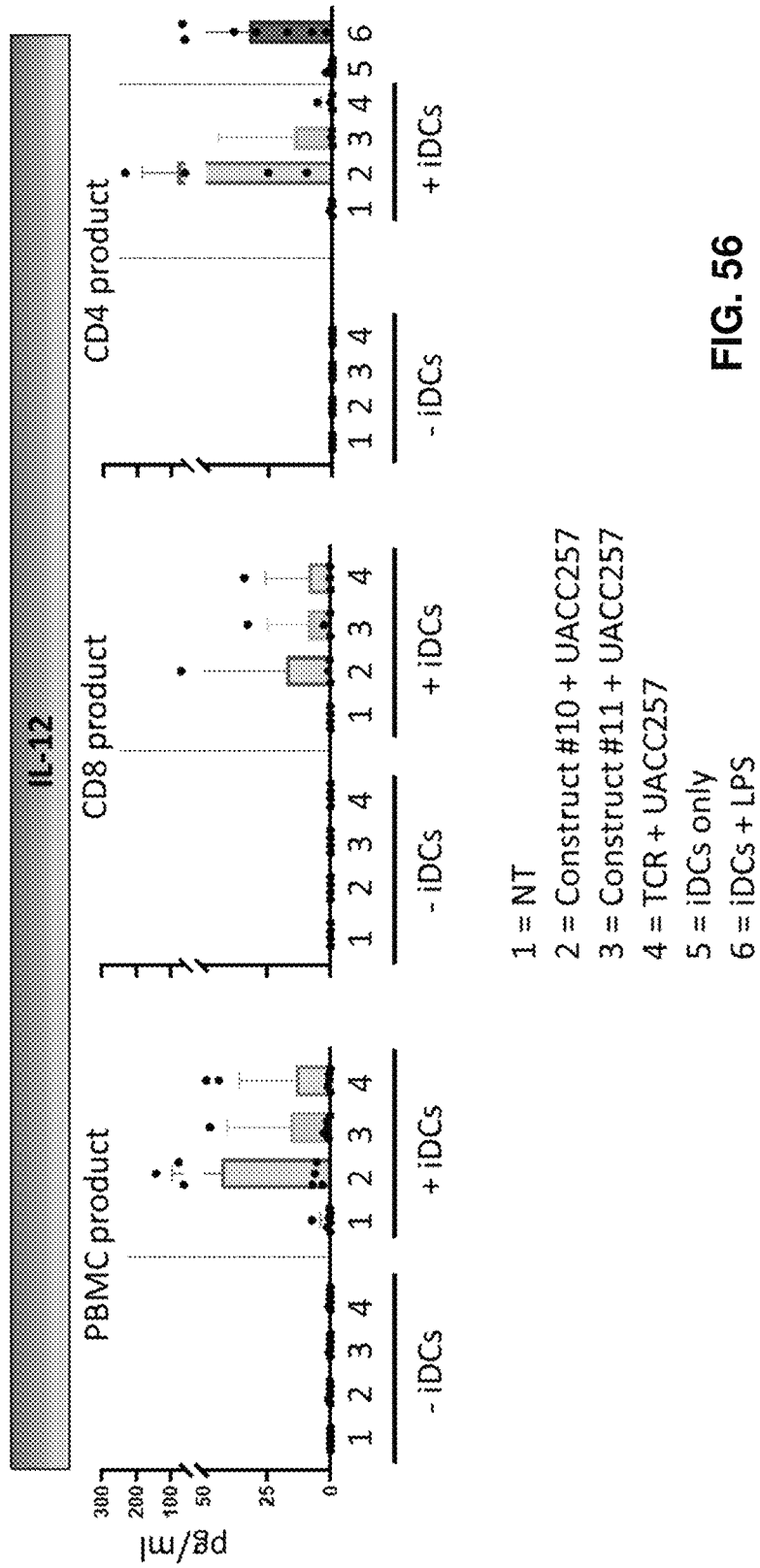
FIG. 56 shows the levels of IL-12 secretion by dendritic cells (DC) in the presence of CD4+ T cells transduced with Construct #10 or #11 and immature dendritic cells (iDCs) in accordance with one embodiment of the present disclosure.
Figure 57:
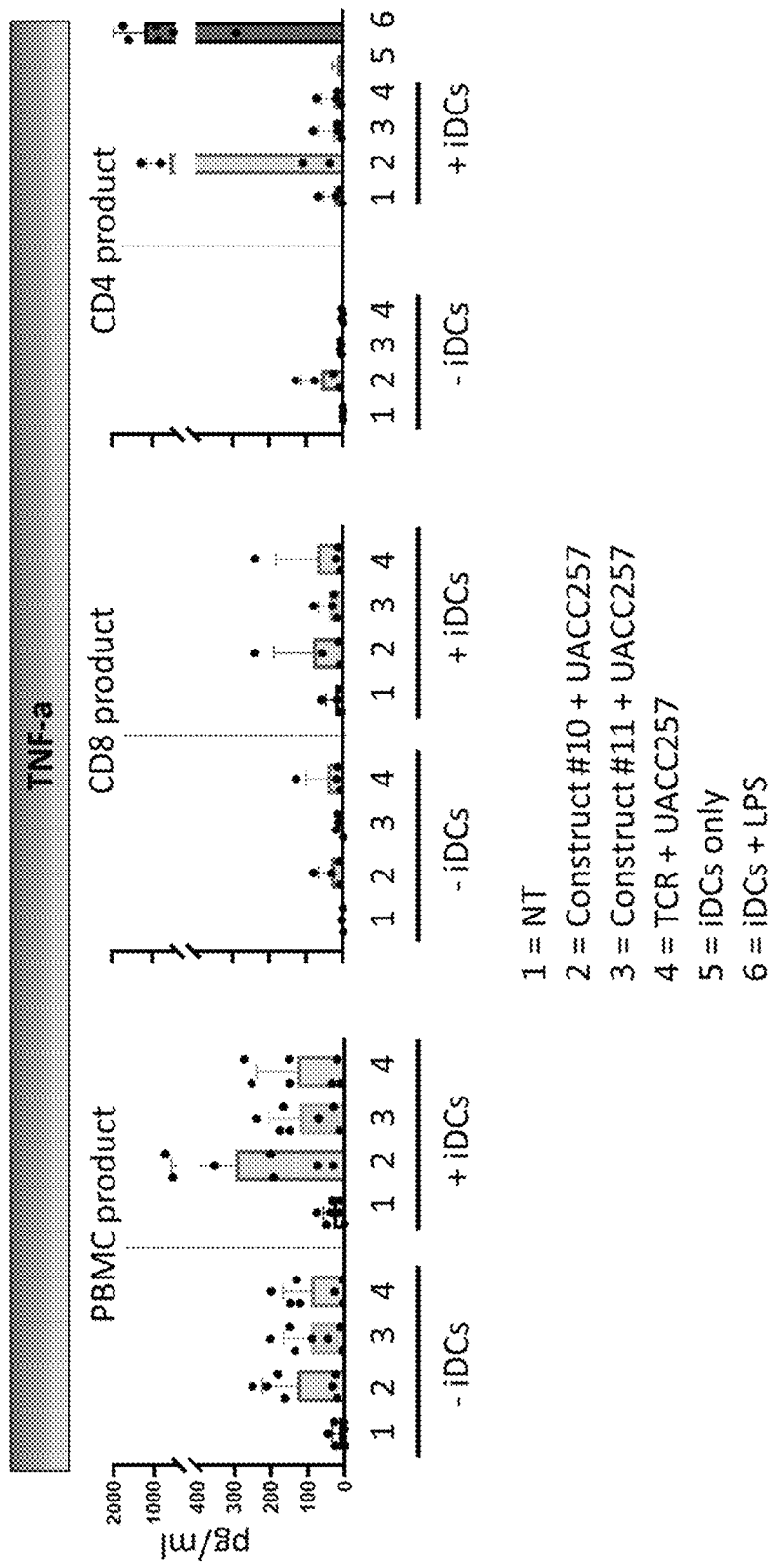
FIG. 57 shows the levels of TNF-α secretion by dendritic cells (DC) in the presence of CD4+ T cells transduced with Construct #10 or #11 and immature dendritic cells (iDCs) in accordance with one embodiment of the present disclosure.
Figure 58:
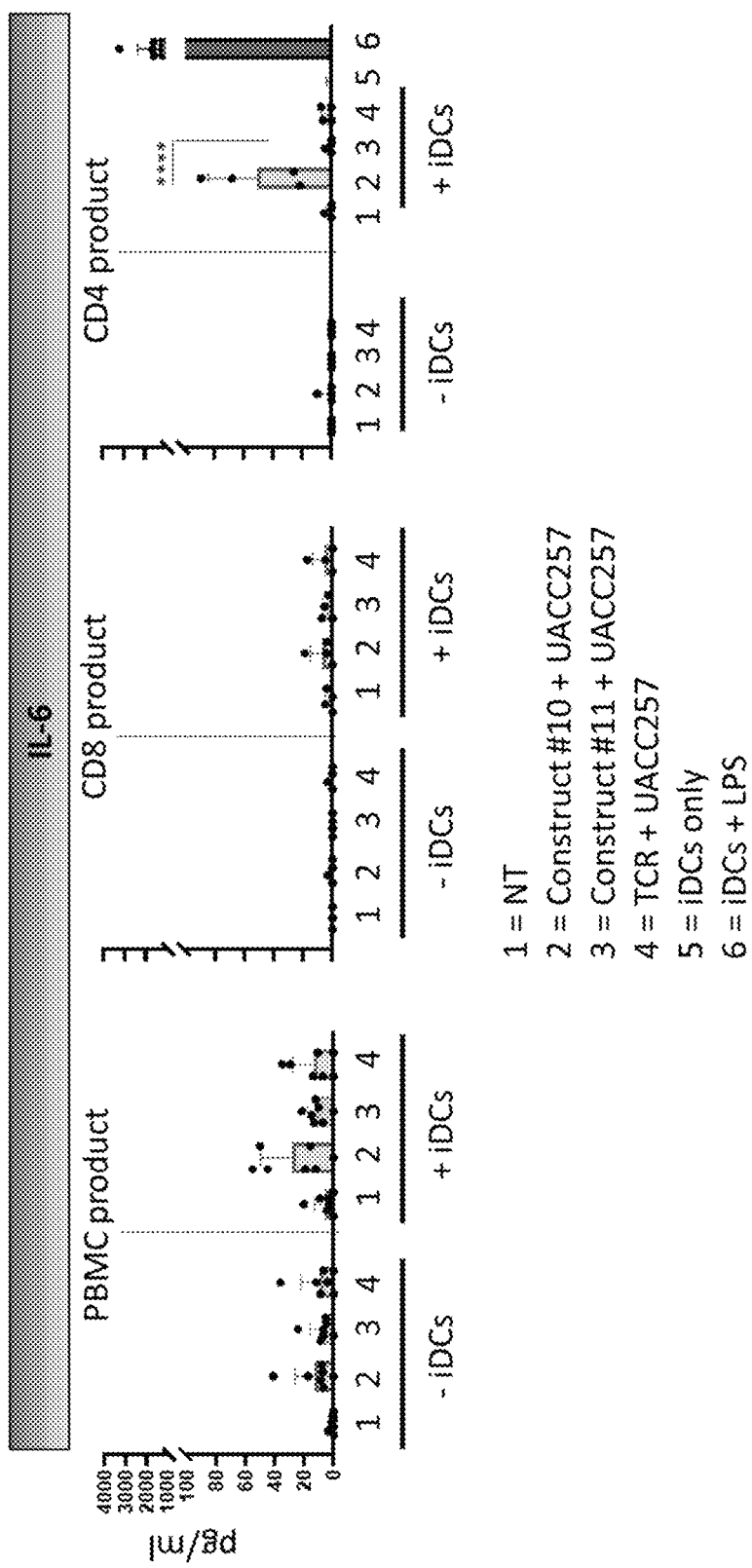
FIG. 58 shows the levels of IL-6 secretion by dendritic cells (DC) in the presence of CD4+ T cells transduced with Construct #10 or #11 and immature dendritic cells (iDCs) in accordance with one embodiment of the present disclosure.

In the presence of immature dendritic cells (iDCs) and UACC257 cells, CD4+ T cells expressing Construct #10 (CD4+CD8+ T cells) performed better by inducing higher levels of IL-12 (FIG. 56), TNF-α (FIG. 57), and IL-6 (FIG. 58) secreted by dendritic cells (DC) than CD4+ T cells expressing Construct #11. On the other hand, the levels of IL-12, TNF-α, and IL-6 were comparable between CD8+ T cells expressing Constructs #10 and #11 (CD8+CD4− T cells). These results suggest that CD4+ T cells expressing CD8αβ heterodimer and TCR (Construct #10) may be a better product than CD4+ T cells expressing CD8α* homodimer and TCR (Construct #11) in DC licensing. The negative controls include the cytokine levels obtained (1) in the absence of iDCs (−iDCs), (2) in the presence of non-transduced T cells (NT)+UACC257 cells, and (3) in the presence of T cells transduced with TCR only (TCR)+UACC257 cells. The positive control includes the cytokine levels obtained from iDCs treated with lipopolysaccharide (LPS), which can activate DC.

Example 14

Figure 60:
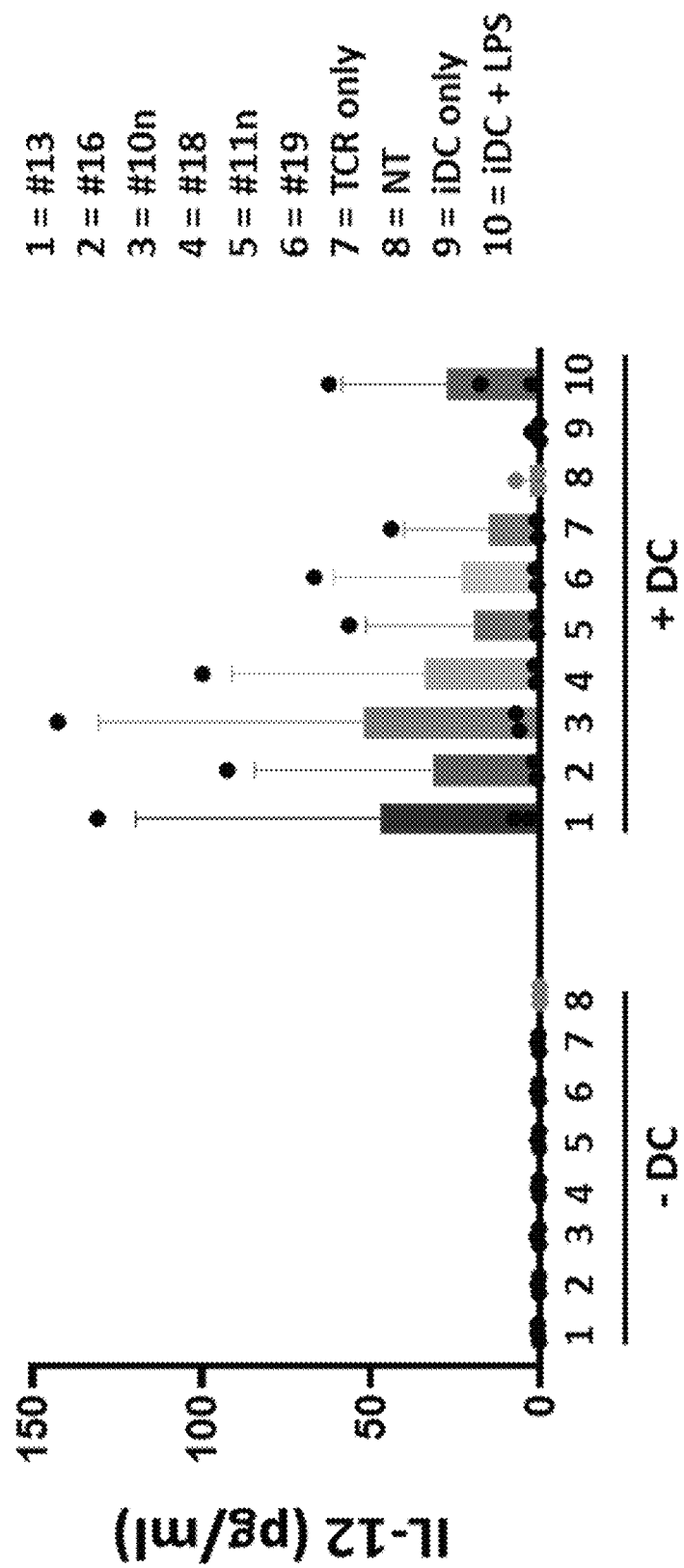
FIG. 60 shows the levels of IL-12 secretion by dendritic cells (DC) in the presence of PBMCs transduced with various constructs and target cells in accordance with one embodiment of the present disclosure.

Assessment of DC Maturation and Cytokine Secretion by PBMC Products in Response to UACC257 Targets FIG. 60 shows IL-12 secretion levels induced by co-culturing PBMCs transduced with constructs of the present disclosure in the presence or absence of iDC and target cells, e.g., UACC257 cells. For example, IL-12 secretion was increased by co-culturing PBMCs transduced with Constructs #10 and 13 in the presence of iDC (+DC) and UACC257, as compared with that by co-culturing PBMCs transduced with TCR only. Increase of IL-12 secretion suggests (1) polarization towards Th1 cell-mediated immunity including TNF-α production (see, FIG. 61), (2) T cell proliferation, (3) IFN-γ production, and (4) cytolytic activity of cytotoxic T lymphocytes (CTLs).

Figure 61:
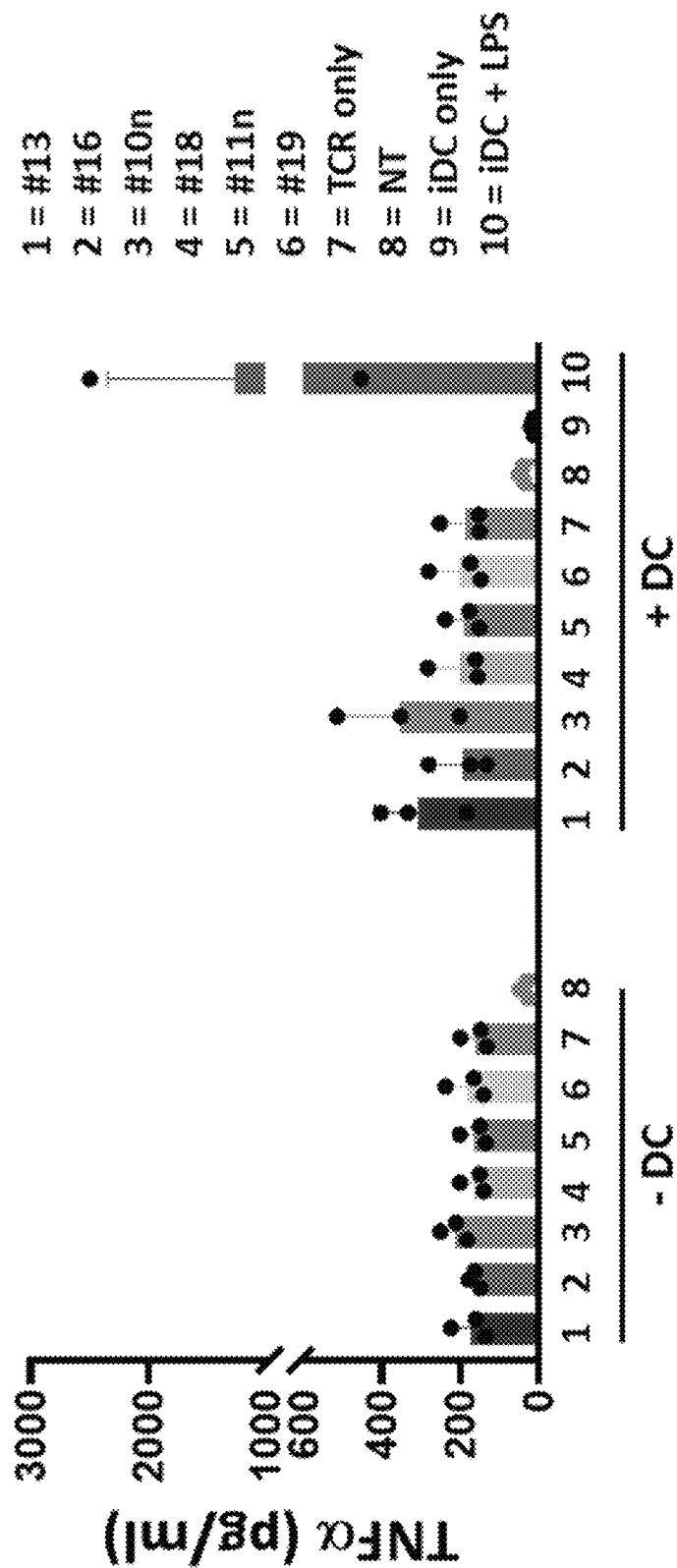
FIG. 61 shows the levels of TNF-α secretion by dendritic cells (DC) in the presence of PBMCs transduced with various constructs and target cells in accordance with one embodiment of the present disclosure

FIG. 61 shows TNF-α secretion levels induced by co-culturing PBMCs transduced with constructs of the present disclosure in the presence or absence of iDC and target cells, e.g., UACC257 cells. For example, TNF-α secretion was increased by co-culturing PBMCs transduced with Constructs #10 and 13 in the presence of iDC (+DC) and UACC257, as compared with that by co-culturing PBMCs transduced with TCR only.

The increased IL-6 secretion (in addition to IL-12, TNF-α) may signify dendritic cell maturation, which may be augmented by CD40–CD40L interactions between CD4+ T cells and DCs. DC maturation and subsequent cytokine secretion may aid in modulation of the proinflammatory environment.

Figure 62:
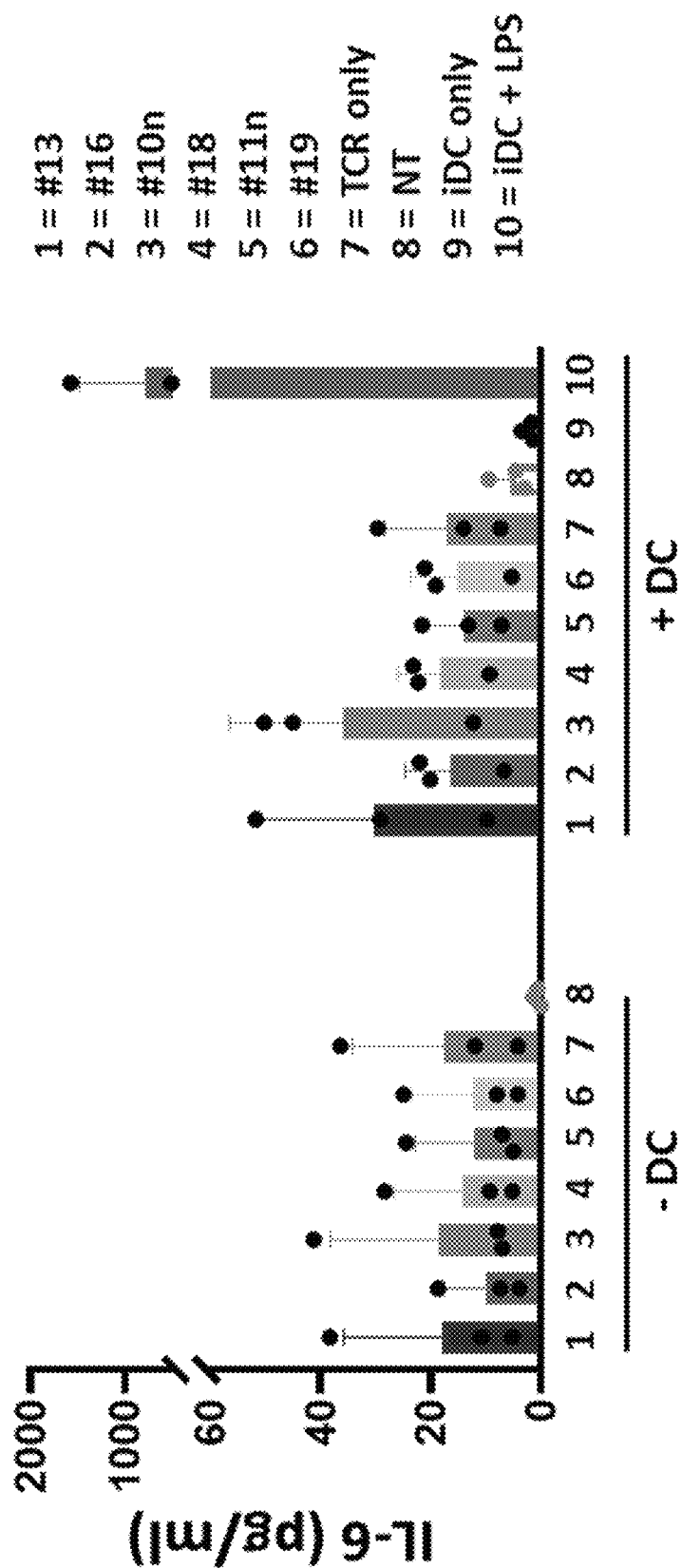
FIG. 62 shows the levels of IL-6 secretion by dendritic cells (DC) in the presence of PBMCs transduced with various constructs and target cells in accordance with one embodiment of the present disclosure.

FIG. 62 shows IL-6 secretion levels induced by co-culturing PBMCs transduced with constructs of the present disclosure in the presence or absence of iDC and target cells, e.g., UACC257 cells. For example, IL-6 secretion was increased by co-culturing PBMCs transduced with Constructs #10 and 13 in the presence of iDC (+DC) and UACC257, as compared with that by co-culturing PBMCs transduced with TCR only.

These results show that PBMC products containing CD4+ T cells co-expressing transgenic TCR and CD8 co-receptor (CD8αβ heterodimer or CD8α homodimer) may license DCs in the microenvironment through antigen cross presentation to modulate the tumor microenvironment by, e.g., increasing IL-12, IL-6, and TNF-α secretion.

Table 12 shows comparison between constructs based on manufacturability and functionality.

TABLE 12

| | Parameters | Construct #10 | Construct #13 | Construct #11 | Construct #19 | TCR only |
|---|---|---|---|---|---|---|
| Manufacturability | Viabilities | >90% | >90% | >90% | >90% | >90% |
| | Fold expansion on Day 7 | 28.7 ± 11% | 28.6 ± 11% | 31.6 ± 13% | 29.6 ± 13% | 30.1 ± 11% |
| | Transgene expression (% CD3+Tet+) mean ± SD | 46.9 ± 12% | 42 ± 9.8% | 41 ± 12% | 48.2 ± 14% | 22.8 ± 8% |
| | Vector copy number | 3.3 ± 0.6% | 2.6 ± 0.7% | 2.0 ± 0.8% | 3.1 ± 1.8% | 1.7 ± 0.7% |
| Functionality | Multiple rounds of killing with UACC257 cells | +++ | +++ | +++ | +++ | +++ |
| | Cytokine secretion (24 h, with UACC257 cells); IFN-γ, TNF-α, IL-2 | +++ | +++ | ++ | ++ | ++ |
| | Cytokine secretion; CD4+CD8+TCR+ (16 h with UACC257 cells); ICS | +++ | +++ | + | + | +/− |
| | DC licensing assay (PBMC product) IL-12, TNF-α, and IL-6 | +++ | +++ | + | + | + |
| | 3D spheroid assay | +++ | N/A | +++ | N/A | ++ |

Notes:
"+++" = best response; "++" = good response; "+" = average response; "+/−" = poor response.

TABLE 13 shows construct comparison and ranking (the smaller the number the better).

| Parameters | Construct #10 | Construct #13 | Construct #11 | Construct #19 |
|---|---|---|---|---|
| Manufacturability | 1 | 1 | 1 | 1 |
| Functionality PBMC | 1 | 1 | 2 | 2 |
| Functionality CD8 | 1 | 1 | 1 | 1 |
| Functionality CD4 | 1 | 1 | 3 | 3 |
| Time delay* | 1 | 1 | 1 | 1 |
| Total | 5 | 5 | 8 | 8 |

*Time delay here refers to any delay from, for example, GMP Vector manufacturing or any delay due to incomplete data set, which may add delay in implementation of constructs in clinical trials.

In sum, while manufacturability in terms of, e.g., viability, fold expansion, transgene expression, and vector copy number, may be equally good, as ranked 1, among cells transduced with Construct #10, #11, #13, or #19, functionality in terms of, e.g., cell killing, cytokine secretion, DC licensing, and 3D spheroid forming ability, of cells transduced with Construct #10 and #13 may be better, as ranked 1, than those transduced with Construct #11 and #19, as ranked 1-3.

Example 15

EC50 Assays

To determine the efficacy of T cells transduced with constructs of the present disclosure, e.g., Constructs #10 and #11, against target cells, EC50s were determined based on the levels of IFNγ produced by the transduced cells in the presence of PRAME peptide-pulsed T2 cells.

Figure 63A:
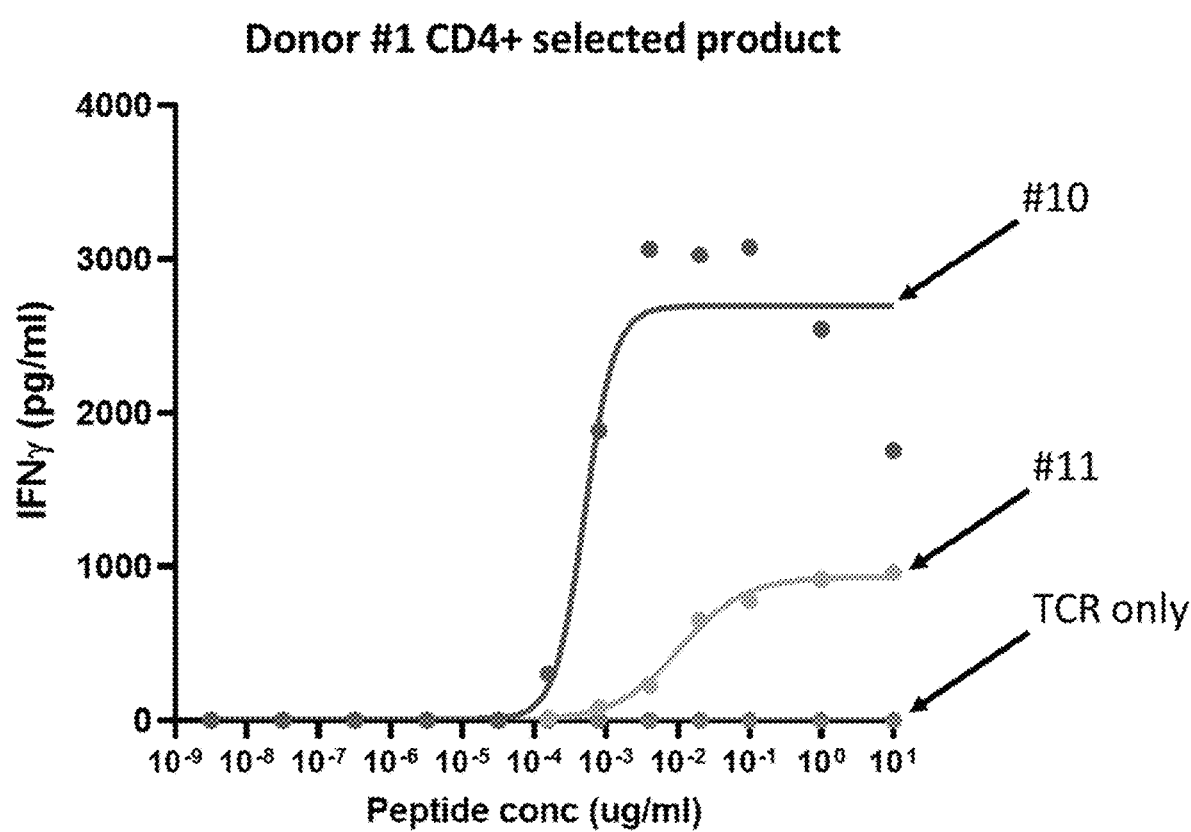
FIG. 63A-63C show IFNγ production from the transduced CD4+ selected T cells obtained from Donor #1 (FIG. 63A), Donor #2 (FIG. 63B), and Donor #3 (FIG. 63C) in accordance to one embodiment of the present disclosure.
Figure 63B:
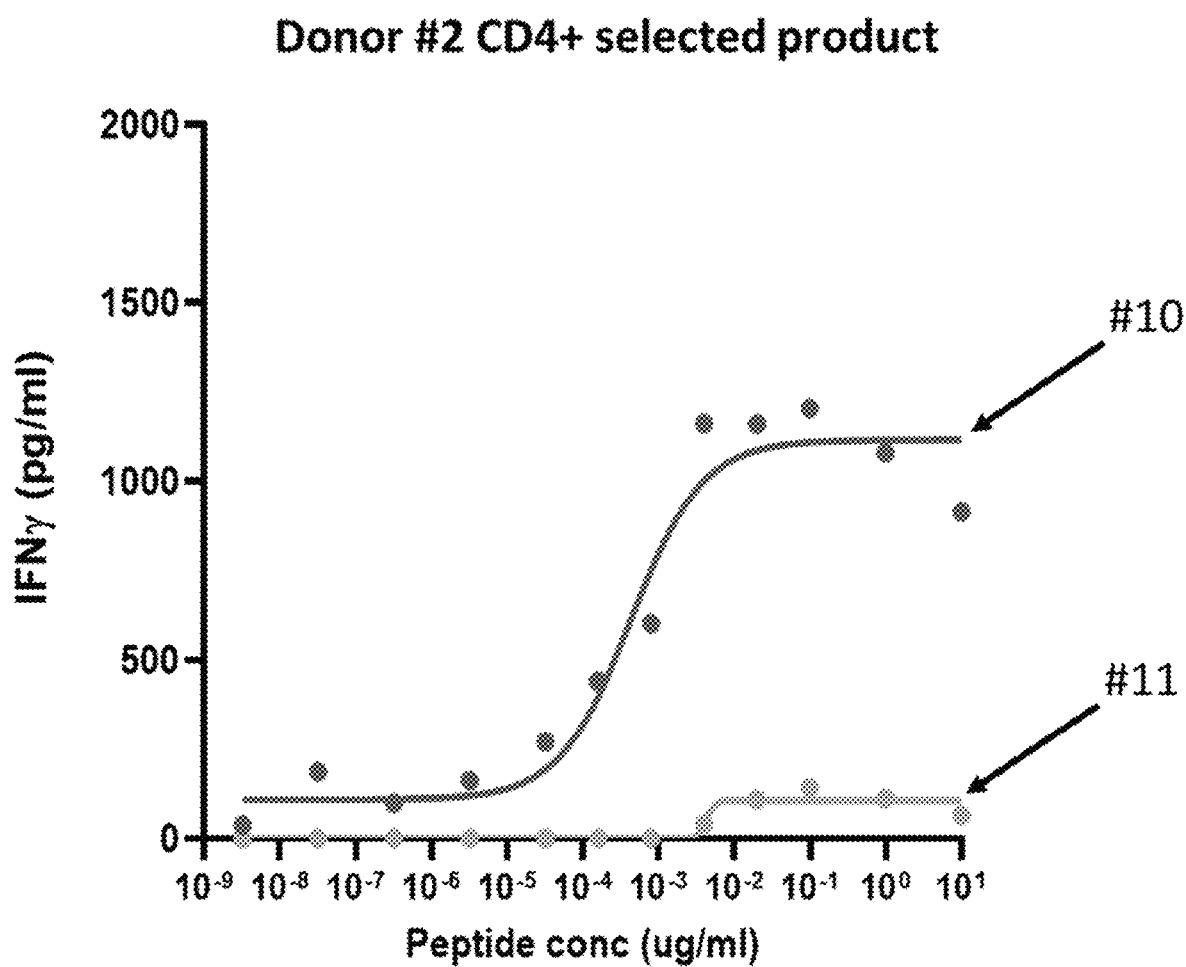
Figure 63C:
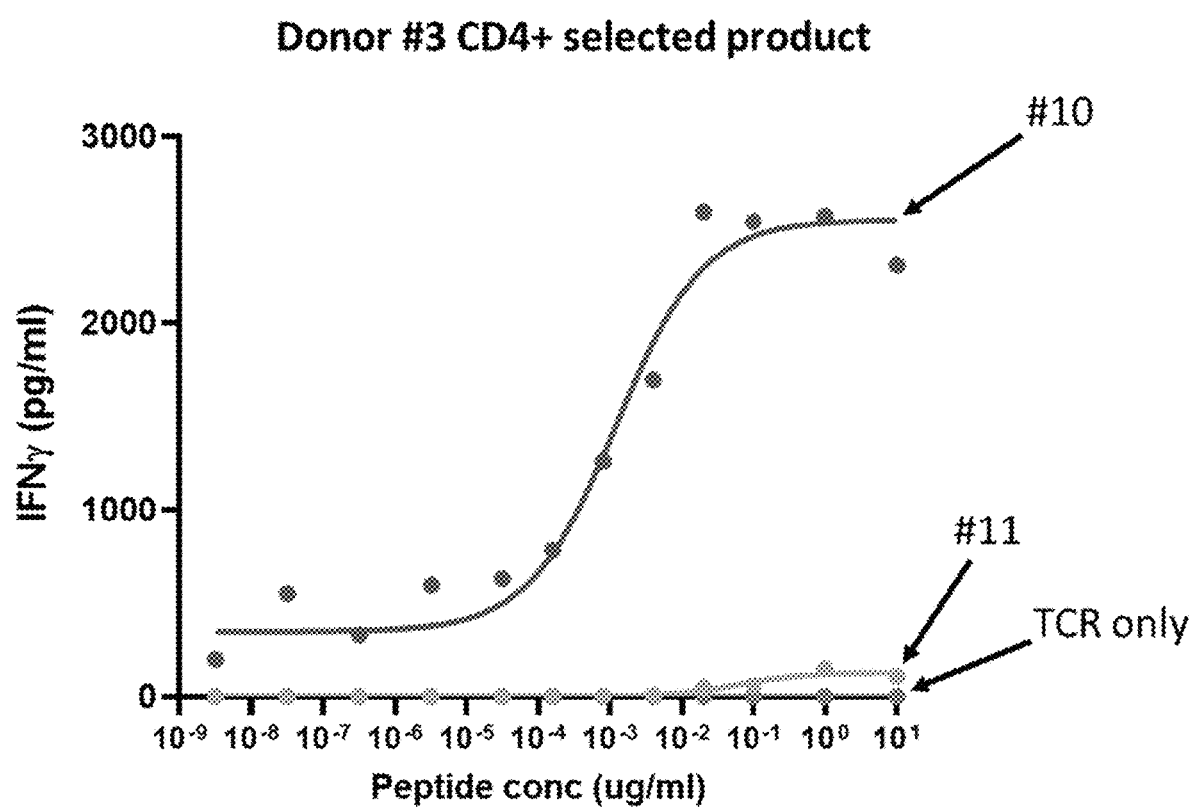

For example, to compare EC50s of CD4+ selected T cells transduced with Construct #10 (CD8αβ-TCR), Construct #11 (m1CD8α-TCR), or Construct #8 (TCR only), CD4+ selected products (TCR+ normalized) were co-cultured with PRAME peptide-pulsed T2 cells at defined concentrations at E:T ratio of 1:1 for 24 h. IFNγ levels were quantified in the supernatants after 24 h. FIGS. 63A-63C show IFNγ levels produced by the transduced CD4+ selected T cells obtained from Donor #1, #2, and #3, respectively. In general, CD4+ selected T cells transduced with Construct #10 were more sensitive to PRAME antigen as compared with that transduced with Construct #11 (m1CD8α TCR+ CD4 T cells), as indicated by lower EC50 values (ng/ml) of CD4+ selected T cells transduced with Construct #10 than that transduced with Construct #11 (FIG. 63D). No response was observed among TCR+ CD4+ cells (FIGS. 63A-63D). These results suggest that CD8αβ heterodimer may impart increased avidity to CD8αβ TCR+ CD4+ T cells as compared to m1CD8α homodimer, leading to better efficacy against target cells.

Figure 64A:
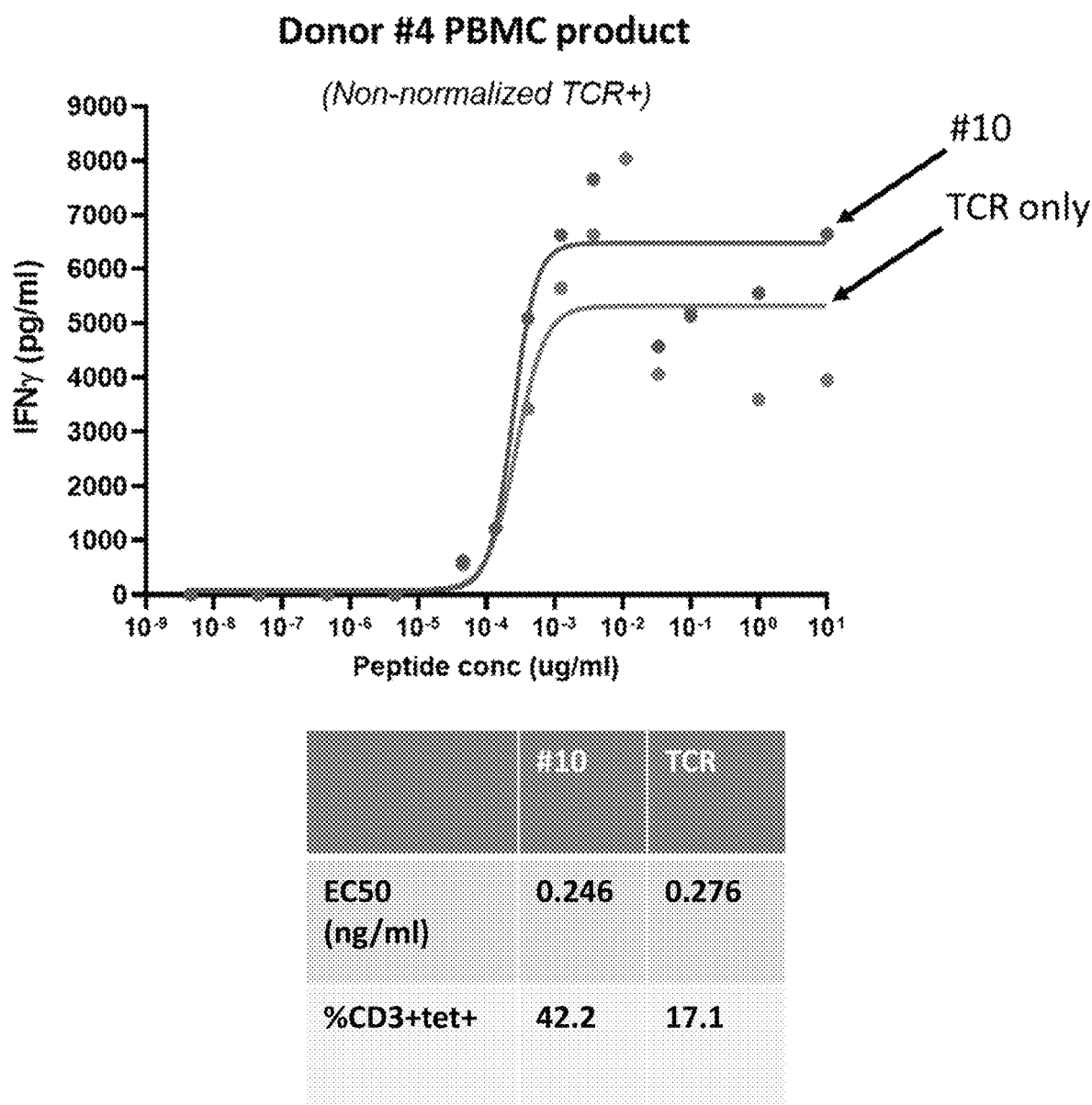
FIG. 64A-64C show IFNγ production from the transduced PBMC obtained from Donor #4 (FIG. 64A), Donor #1 (FIG. 64B), and Donor #3 (FIG. 64C) and their respective EC50 values (ng/ml) in accordance to one embodiment of the present disclosure.
Figure 64B:
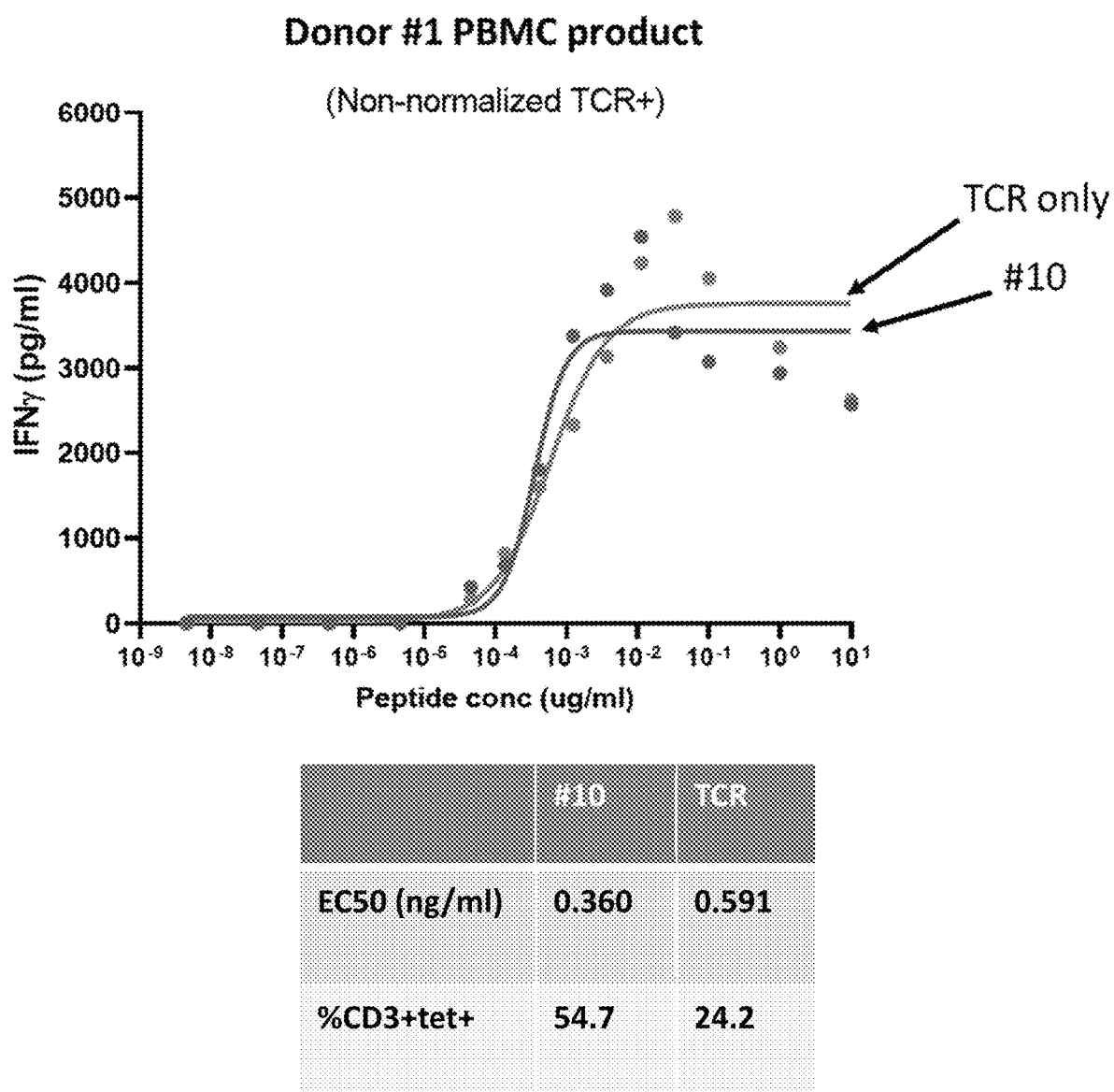
Figure 64C:
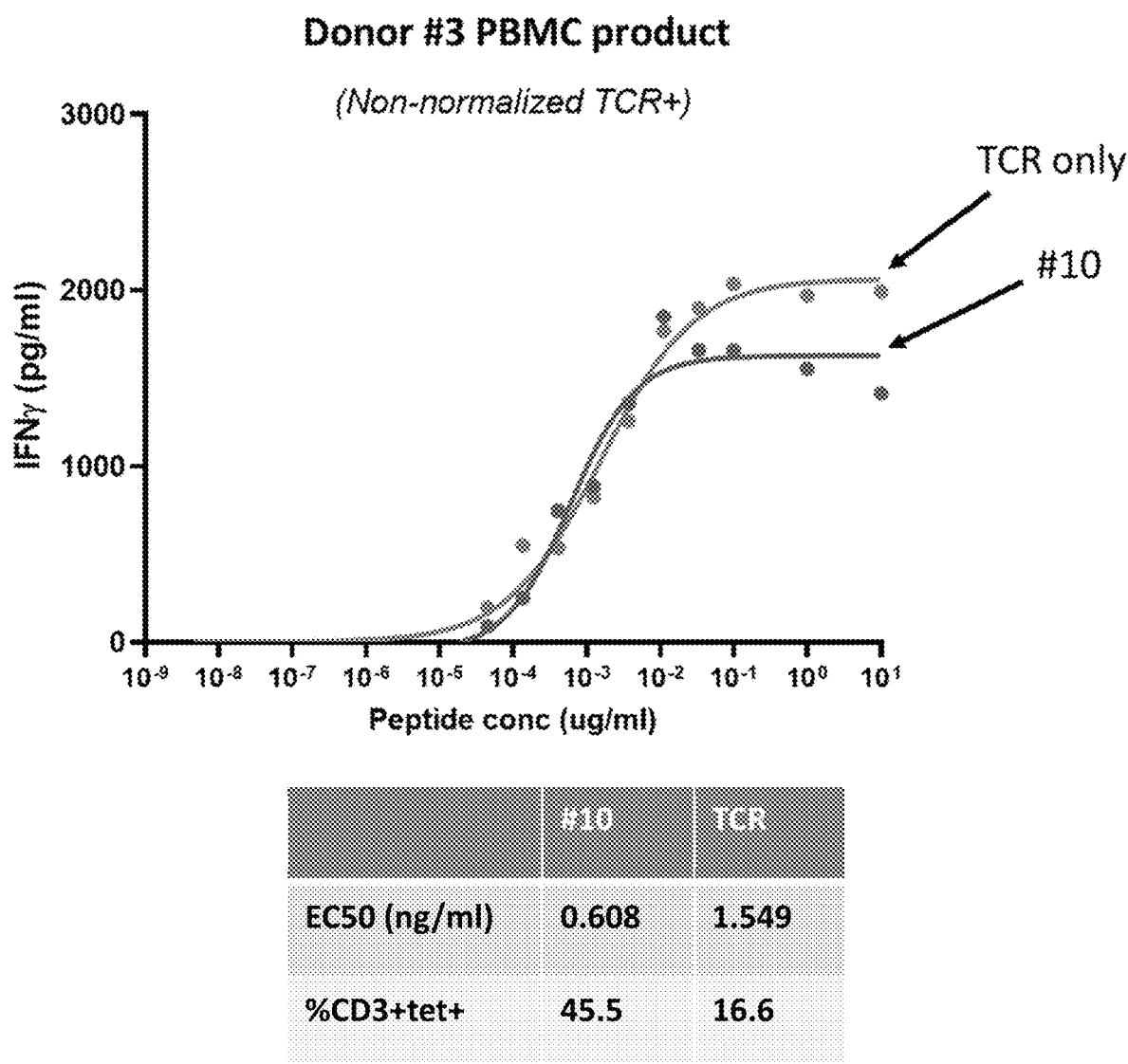
Figure 64D:
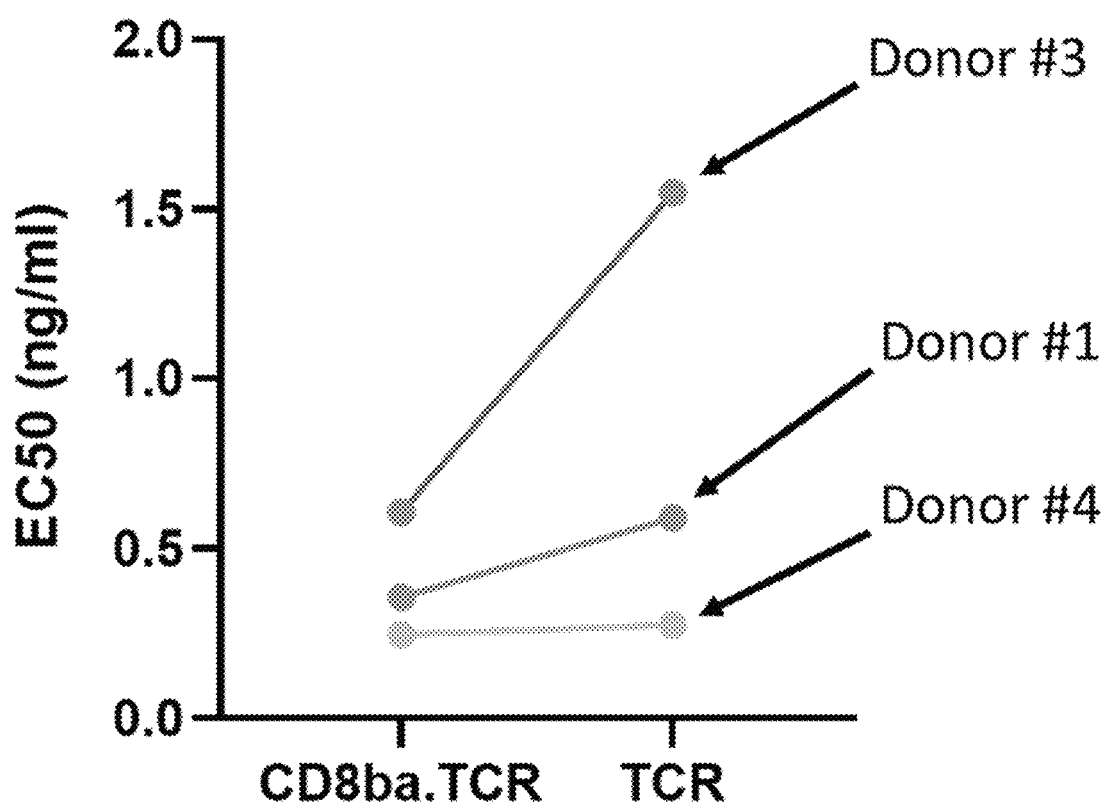
FIG. 64D shows comparison of EC50 values (ng/ml) among different donors in FIG. 64A-64C.

Similar experiments were performed using PBMC obtained from Donor #1, #3, and #4. Briefly, PBMC products (TCR+ non-normalized) were co-cultured with PRAME peptide-pulsed T2 cells at defined concentrations at E:T ratio of 1:1 for 24 h. IFNγ levels were quantified in the supernatants after 24 h. FIGS. 64A-64C show IFNγ levels produced by the transduced PBMC obtained from Donor #4, #1, and #3, respectively. Donor-to-donor variability was observed in the EC50 values. For example, while Donor #3 (FIGS. 64C and 64D) shows lower EC50 of PBMC transduced with Construct #10 as compared with that transduced with TCR only, Donors #1 (FIG. 64B) and #4 (FIG. 64A) show comparable EC50s between Construct #10 and TCR only (FIG. 64D). Thus, the increased avidity and efficacy observed in CD4+ selected T cell products expressing TCR and CD8αβ heterodimer as compared with that expressing TCR only may be obtained but to lesser extent when using PBMC products.

Figure 65A:
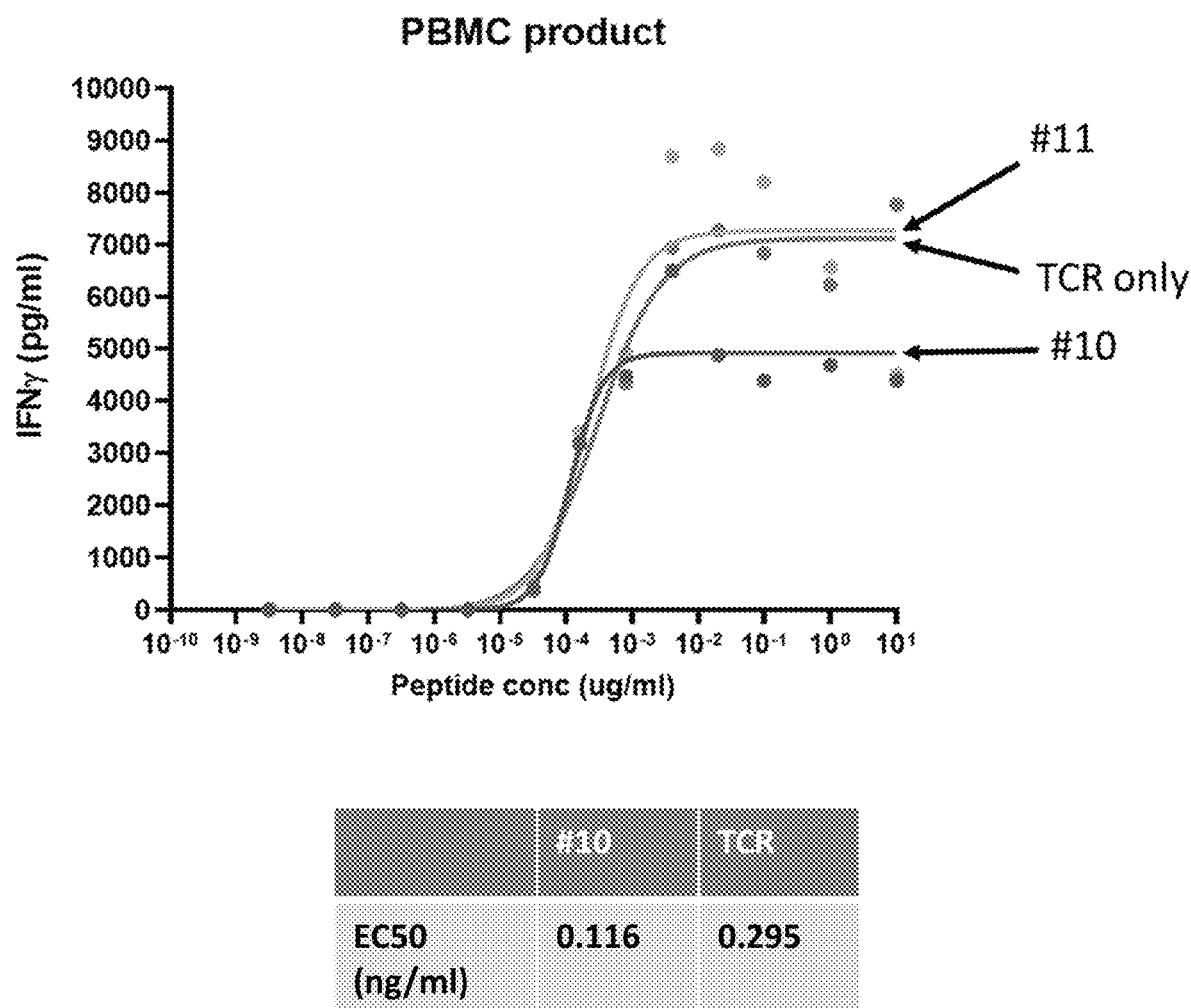
FIG. 65A-65C show IFNγ production from the transduced PBMC (FIG. 65A), CD8+ selected T cells (FIG. 65B), and CD4+ selected T cells (FIG. 65C) and their respective EC50 values (ng/ml) from a single donor in accordance to one embodiment of the present disclosure.
Figure 65B:
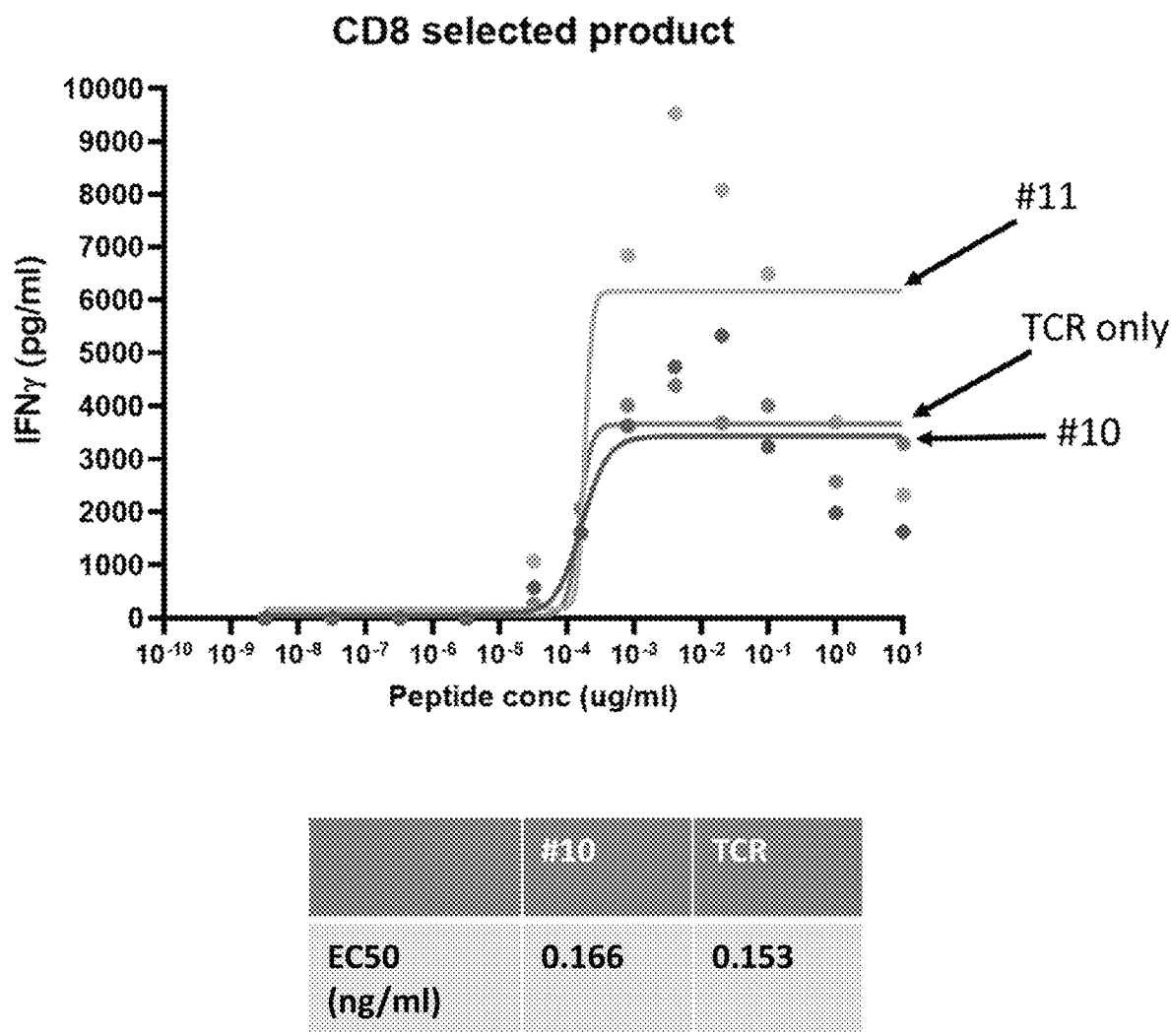
Figure 65C:
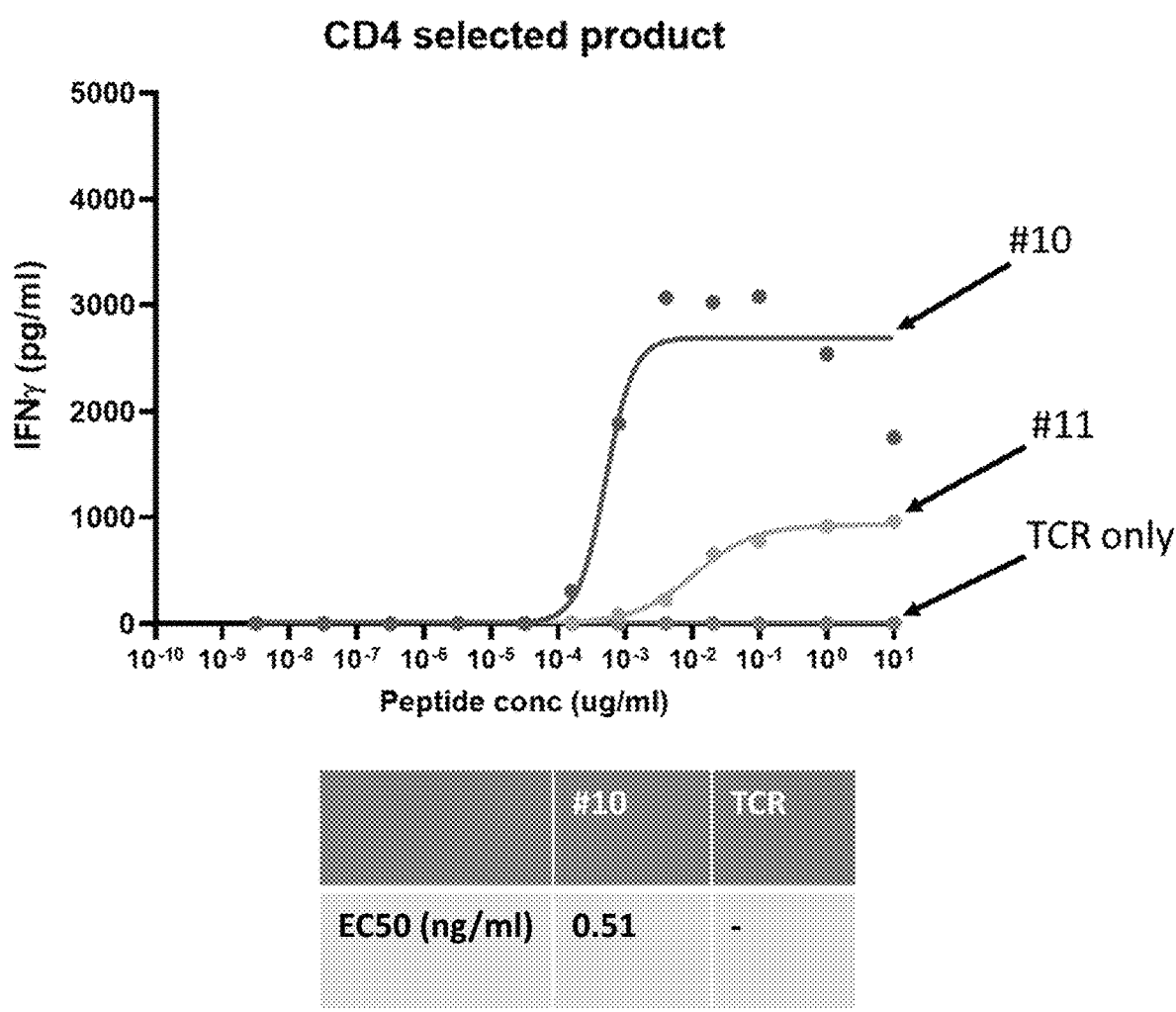

To compare EC50s of different T cell products obtained from the same donor, PBMC products, CD8+ selected products, and CD4+ selected products obtained from a single donor were co-cultured with PRAME peptide-pulsed T2 cells (TCR+ normalized) at defined concentrations at E:T ratio of 1:1 for 24 h. IFNγ levels were quantified in the supernatants after 24 h.. FIGS. 65A-65C show that IFNγ levels produced by PBMC products (FIG. 65A), CD8+ selected products (FIG. 65B), and CD4+ selected products (FIG. 65C), respectively. Consistently, EC50 of CD4+ selected T cells transduced with Construct #10 was lower than that transduced with Construct #11 or TCR only (FIG. 65C), while EC50s of the transduced PBMC and CD8+ selected T cells were comparable between Construct #10 and TCR only transduction. Thus, the increased avidity and efficacy observed in CD4+ selected T cell products expressing TCR and CD8αβ heterodimer as compared with that expressing TCR and m1CD8α homodimer or with that expressing TCR only may be obtained but to lesser extent when using PBMC products or CD8+ selected T cell products.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific embodiments of this disclosure set forth in the appended claims. The foregoing embodiments are presented by way of example only; the scope of the present disclosure is to be limited only by the following claims.

What is claimed is:

1. A nucleic acid encoding a T-cell receptor (TCR) comprising an α chain and a β chain and a CD8 α chain, wherein the CD8 α chain comprises the amino acid sequence with at least 98% identity to SEQ ID NO: 5.

2. A polypeptide encoded by the nucleic acid of claim 1.

3. A vector comprising the nucleic acid of claim 1.

4. The vector of claim 3, wherein the vector further comprises a nucleic acid encoding a 2A peptide or an IRES positioned between the nucleic acid encoding the TCR α chain and the nucleic acid encoding the TCR β chain.

5. The vector of claim 4, wherein the 2A peptide is P2A (SEQ ID NO: 93), T2A (SEQ ID NO: 94), E2A (SEQ ID NO: 95), or F2A (SEQ ID NO: 96).

6. The vector of claim 5, wherein the vector further comprises a post-transcriptional regulatory element (PRE) selected from a Woodchuck PRE (WPRE), Woodchuck PRE (WPRE) mutant 1, Woodchuck PRE (WPRE) mutant 2, or hepatitis B virus (HBV) PRE (HPRE).

7. The vector of claim 6, wherein the WPRE mutant 1 comprises SEQ ID NO: 256.

8. The vector of claim 6, wherein the WPRE mutant 2 comprises SEQ ID NO: 257.

9. The nucleic acid of claim 1, wherein the nucleic acid encodes a signal peptide comprising SEQ ID NO: 294, wherein the signal peptide is fused with the CD8 α chain.

10. A method of preparing T cells for immunotherapy comprising
isolating T cells from a blood sample of a human subject,
activating the isolated T cells,
transducing the activated T cells with the nucleic acid of claim 1, and
expanding the transduced T cells.

11. The method of claim 10, wherein the blood sample comprises peripheral blood mononuclear cells (PMBC).

12. A nucleic acid encoding a CD8 α chain comprises the amino acid sequence with at least 98% identity to SEQ ID NO: 5.

* * * * *

SEQUENCE LISTING

```
<160> NUMBER OF SEQ ID NOS: 304

<210> SEQ ID NO 1
<211> LENGTH: 114
<212> TYPE: PRT
<213> ORGANISM: Artificial Sequence
<220> FEATURE:
<223> OTHER INFORMATION: CD8alpha Ig-like domain-1

<400> SEQUENCE: 1

Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
            20                  25                  30

Cys Ser Trp Leu Phe Gln Pro Arg Gly Ala Ala Ala Ser Pro Thr Phe
        35                  40                  45

Leu Leu Tyr Leu Ser Gln Asn Lys Pro Lys Ala Ala Glu Gly Leu Asp
    50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
```

Pro Ala

<210> SEQ ID NO 2
<211> LENGTH: 38
<212> TYPE: PRT
<213> ORGANISM: Artificial Sequence
<220> FEATURE:
<223> OTHER INFORMATION: CD8beta stalk region

<400> SEQUENCE: 2

Ser Val Val Asp Phe Leu Pro Thr Thr Ala Gln Pro Thr Lys Lys Ser
1               5                   10                  15

Thr Leu Lys Lys Arg Val Cys Arg Leu Pro Arg Pro Glu Thr Gln Lys
            20                  25                  30

Gly Pro Leu Cys Ser Pro
        35

<210> SEQ ID NO 3
<211> LENGTH: 21
<212> TYPE: PRT
<213> ORGANISM: Artificial Sequence
<220> FEATURE:
<223> OTHER INFORMATION: CD8alpha transmembrane domain

<400> SEQUENCE: 3

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 4
<211> LENGTH: 32
<212> TYPE: PRT
<213> ORGANISM: Artificial Sequence
<220> FEATURE:
<223> OTHER INFORMATION: CD8alpha cytoplasmic tail

<400> SEQUENCE: 4

Leu Tyr Cys Asn His Arg Asn Arg Arg Arg Val Cys Lys Cys Pro Arg
1               5                   10                  15

Pro Val Val Lys Ser Gly Asp Lys Pro Ser Leu Ser Ala Arg Tyr Val
            20                  25                  30

<210> SEQ ID NO 5
<211> LENGTH: 205
<212> TYPE: PRT
<213> ORGANISM: Artificial Sequence
<220> FEATURE:
<223> OTHER INFORMATION: m1CD8alpha (signal-less)

<400> SEQUENCE: 5

Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
            20                  25                  30

Cys Ser Trp Leu Phe Gln Pro Arg Gly Ala Ala Ala Ser Pro Thr Phe
        35                  40                  45

Leu Leu Tyr Leu Ser Gln Asn Lys Pro Lys Ala Ala Glu Gly Leu Asp
    50                  55                  60

Thr Gln Arg Phe Ser Gly Lys Arg Leu Gly Asp Thr Phe Val Leu Thr
65                  70                  75                  80

```
Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
            100                 105                 110

Pro Ala Ser Val Val Asp Phe Leu Pro Thr Thr Ala Gln Pro Thr Lys
        115                 120                 125

Lys Ser Thr Leu Lys Lys Arg Val Cys Arg Leu Pro Arg Pro Glu Thr
    130                 135                 140

Gln Lys Gly Pro Leu Cys Ser Pro Ile Tyr Ile Trp Ala Pro Leu Ala
145                 150                 155                 160

Gly Thr Cys Gly Val Leu Leu Leu Ser Leu Val Ile Thr Leu Tyr Cys
                165                 170                 175

Asn His Arg Asn Arg Arg Val Cys Lys Cys Pro Arg Pro Val Val
            180                 185                 190

Lys Ser Gly Asp Lys Pro Ser Leu Ser Ala Arg Tyr Val
            195                 200                 205

<210> SEQ ID NO 6
<211> LENGTH: 21
<212> TYPE: PRT
<213> ORGANISM: Artificial Sequence
<220> FEATURE:
<223> OTHER INFORMATION: Signal peptide

<400> SEQUENCE: 6

Met Ala Leu Pro Val Thr Ala Leu Leu Leu Pro Leu Ala Leu Leu Leu
1               5                   10                  15

His Ala Ala Arg Pro
            20

<210> SEQ ID NO 7
<211> LENGTH: 226
<212> TYPE: PRT
<213> ORGANISM: Artificial Sequence
<220> FEATURE:
<223> OTHER INFORMATION: m1CD8alpha

<400> SEQUENCE: 7

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Ser Val Val Asp Phe Leu Pro Thr Thr
    130                 135                 140

Ala Gln Pro Thr Lys Lys Ser Thr Leu Lys Lys Arg Val Cys Arg Leu
```

```
            145                 150                 155                 160
        Pro Arg Pro Glu Thr Gln Lys Gly Pro Leu Cys Ser Pro Ile Tyr Ile
                        165                 170                 175

Trp Ala Pro Leu Ala Gly Thr Cys Gly Val Leu Leu Ser Leu Val
                    180                 185                 190

Ile Thr Leu Tyr Cys Asn His Arg Asn Arg Arg Val Cys Lys Cys
                    195                 200                 205

Pro Arg Pro Val Val Lys Ser Gly Asp Lys Pro Ser Leu Ser Ala Arg
                    210                 215                 220

Tyr Val
        225

<210> SEQ ID NO 8
<211> LENGTH: 243
<212> TYPE: PRT
<213> ORGANISM: Homo sapiens

<400> SEQUENCE: 8

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
                20                  25                  30

Thr Asn Lys Met Val Met Leu Ser Cys Glu Ala Lys Ile Ser Leu Ser
            35                  40                  45

Asn Met Arg Ile Tyr Trp Leu Arg Gln Arg Gln Ala Pro Ser Ser Asp
        50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Val Ser Leu Gly Val Ala Ile His
            180                 185                 190

Leu Cys Cys Arg Arg Arg Arg Ala Arg Leu Arg Phe Met Lys Gln Pro
        195                 200                 205

Gln Gly Glu Gly Ile Ser Gly Thr Phe Val Pro Gln Cys Leu His Gly
    210                 215                 220

Tyr Tyr Ser Asn Thr Thr Thr Ser Gln Lys Leu Leu Asn Pro Trp Ile
225                 230                 235                 240

Leu Lys Thr

<210> SEQ ID NO 9
<211> LENGTH: 198
<212> TYPE: PRT
<213> ORGANISM: Homo sapiens

<400> SEQUENCE: 9
```

```
Met Arg Pro Arg Leu Trp Leu Leu Ala Gln Leu Thr Val Leu
1               5                   10                  15

His Gly Asn Ser Val Leu Gln Gln Thr Pro Ala Tyr Ile Lys Val Gln
                20                  25                  30

Thr Asn Lys Met Val Met Leu Ser Cys Glu Ala Lys Ile Ser Leu Ser
            35                  40                  45

Asn Met Arg Ile Tyr Trp Leu Arg Gln Arg Gln Ala Pro Ser Ser Asp
50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
                100                 105                 110

Ile Tyr Phe Cys Met Ile Val Gly Ser Pro Glu Leu Thr Phe Gly Lys
            115                 120                 125

Gly Thr Gln Leu Ser Val Val Asp Phe Leu Pro Thr Thr Ala Gln Pro
130                 135                 140

Thr Lys Lys Ser Thr Leu Lys Lys Arg Val Cys Arg Leu Pro Arg Pro
145                 150                 155                 160

Glu Thr Gln Lys Gly Leu Lys Gly Lys Val Tyr Gln Glu Pro Leu Ser
                165                 170                 175

Pro Asn Ala Cys Met Asp Thr Thr Ala Ile Leu Gln Pro His Arg Ser
                180                 185                 190

Cys Leu Thr His Gly Ser
            195

<210> SEQ ID NO 10
<211> LENGTH: 189
<212> TYPE: PRT
<213> ORGANISM: Homo sapiens

<400> SEQUENCE: 10

Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
                20                  25                  30

Trp Leu Arg Gln Arg Gln Ala Pro Ser Ser Asp Ser His His Glu Phe
                35                  40                  45

Leu Ala Leu Trp Asp Ser Ala Lys Gly Thr Ile His Gly Glu Glu Val
    50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
                100                 105                 110

Val Val Asp Phe Leu Pro Thr Thr Ala Gln Pro Thr Lys Lys Ser Thr
            115                 120                 125

Leu Lys Lys Arg Val Cys Arg Leu Pro Arg Pro Glu Thr Gln Lys Gly
            130                 135                 140

Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
```

```
                            165                 170                 175
Arg Arg Ala Arg Leu Arg Phe Met Lys Gln Phe Tyr Lys
            180                 185

<210> SEQ ID NO 11
<211> LENGTH: 200
<212> TYPE: PRT
<213> ORGANISM: Homo sapiens

<400> SEQUENCE: 11

Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
        35                  40                  45

Leu Ala Leu Trp Asp Ser Ala Lys Gly Thr Ile His Gly Glu Glu Val
    50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
            100                 105                 110

Val Val Asp Phe Leu Pro Thr Thr Ala Gln Pro Thr Lys Lys Ser Thr
        115                 120                 125

Leu Lys Lys Arg Val Cys Arg Leu Pro Arg Pro Glu Thr Gln Lys Gly
    130                 135                 140

Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
                165                 170                 175

Arg Arg Ala Arg Leu Arg Phe Met Lys Gln Leu Arg Leu His Pro Leu
            180                 185                 190

Glu Lys Cys Ser Arg Met Asp Tyr
        195                 200

<210> SEQ ID NO 12
<211> LENGTH: 225
<212> TYPE: PRT
<213> ORGANISM: Homo sapiens

<400> SEQUENCE: 12

Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
        35                  40                  45

Leu Ala Leu Trp Asp Ser Ala Lys Gly Thr Ile His Gly Glu Glu Val
    50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
```

```
                    100                 105                 110
Val Val Asp Phe Leu Pro Thr Thr Ala Gln Pro Thr Lys Lys Ser Thr
                115                 120                 125

Leu Lys Lys Arg Val Cys Arg Leu Pro Arg Pro Glu Thr Gln Lys Gly
            130                 135                 140

Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
                165                 170                 175

Arg Arg Ala Arg Leu Arg Phe Met Lys Gln Lys Phe Asn Ile Val Cys
            180                 185                 190

Leu Lys Ile Ser Gly Phe Thr Thr Cys Cys Cys Phe Gln Ile Leu Gln
                195                 200                 205

Ile Ser Arg Glu Tyr Gly Phe Gly Val Leu Leu Gln Lys Asp Ile Gly
            210                 215                 220

Gln
225

<210> SEQ ID NO 13
<211> LENGTH: 225
<212> TYPE: PRT
<213> ORGANISM: Homo sapiens

<400> SEQUENCE: 13

Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
                20                  25                  30

Trp Leu Arg Gln Arg Gln Ala Pro Ser Ser Asp Ser His His Glu Phe
            35                  40                  45

Leu Ala Leu Trp Asp Ser Ala Lys Gly Thr Ile His Gly Glu Glu Val
        50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
                100                 105                 110

Val Val Asp Phe Leu Pro Thr Thr Ala Gln Pro Thr Lys Lys Ser Thr
                115                 120                 125

Leu Lys Lys Arg Val Cys Arg Leu Pro Arg Pro Glu Thr Gln Lys Gly
            130                 135                 140

Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
                165                 170                 175

Arg Arg Ala Arg Leu Arg Phe Met Lys Gln Lys Phe Asn Ile Val Cys
            180                 185                 190

Leu Lys Ile Ser Gly Phe Thr Thr Cys Cys Cys Phe Gln Ile Leu Gln
                195                 200                 205

Ile Ser Arg Glu Tyr Gly Phe Gly Val Leu Leu Gln Lys Asp Ile Gly
            210                 215                 220

Gln
225
```

<210> SEQ ID NO 14
<211> LENGTH: 222
<212> TYPE: PRT
<213> ORGANISM: Homo sapiens

<400> SEQUENCE: 14

```
Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
        35                  40                  45

Leu Ala Leu Trp Asp Ser Ala Lys Gly Thr Ile His Gly Glu Glu Val
    50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
            100                 105                 110

Val Val Asp Phe Leu Pro Thr Thr Ala Gln Pro Thr Lys Lys Ser Thr
        115                 120                 125

Leu Lys Lys Arg Val Cys Arg Leu Pro Arg Pro Glu Thr Gln Lys Gly
    130                 135                 140

Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
                165                 170                 175

Arg Arg Ala Arg Leu Arg Phe Met Lys Gln Pro Gln Gly Glu Gly Ile
            180                 185                 190

Ser Gly Thr Phe Val Pro Gln Cys Leu His Gly Tyr Tyr Ser Asn Thr
        195                 200                 205

Thr Thr Ser Gln Lys Leu Leu Asn Pro Trp Ile Leu Lys Thr
    210                 215                 220
```

<210> SEQ ID NO 15
<211> LENGTH: 273
<212> TYPE: PRT
<213> ORGANISM: Artificial Sequence
<220> FEATURE:
<223> OTHER INFORMATION: R11KEA alpha chain

<400> SEQUENCE: 15

```
Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
            20                  25                  30

Leu His Val Gln Glu Gly Asp Ser Thr Asn Phe Thr Cys Ser Phe Pro
        35                  40                  45

Ser Ser Asn Phe Tyr Ala Leu His Trp Tyr Arg Lys Glu Thr Ala Lys
    50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
                85                  90                  95

Leu Tyr Ile Lys Gly Ser Gln Pro Glu Asp Ser Ala Thr Tyr Leu Cys
```

```
            100                 105                 110
Ala Leu Tyr Asn Asn Asp Met Arg Phe Gly Ala Gly Thr Arg Leu
        115                 120                 125

Thr Val Lys Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 16
<211> LENGTH: 311
<212> TYPE: PRT
<213> ORGANISM: Artificial Sequence
<220> FEATURE:
<223> OTHER INFORMATION: R11KE beta chain

<400> SEQUENCE: 16

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Glu Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Pro Gly Ser Thr Asp Thr Gln Tyr Phe Gly Pro Gly Thr Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190
```

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
            290                 295                 300

Lys Arg Lys Asp Ser Arg Gly
305                 310

<210> SEQ ID NO 17
<211> LENGTH: 274
<212> TYPE: PRT
<213> ORGANISM: Artificial Sequence
<220> FEATURE:
<223> OTHER INFORMATION: R20P1H7 alpha chain

<400> SEQUENCE: 17

Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Leu Asn Cys Ser Tyr Thr Val
            35                  40                  45

Ser Gly Leu Arg Gly Leu Phe Trp Tyr Arg Gln Asp Pro Gly Lys Gly
50                  55                  60

Pro Glu Phe Leu Phe Thr Leu Tyr Ser Ala Gly Glu Glu Lys Glu Lys
65                  70                  75                  80

Glu Arg Leu Lys Ala Thr Leu Thr Lys Lys Glu Ser Phe Leu His Ile
            85                  90                  95

Thr Ala Pro Lys Pro Glu Asp Ser Ala Thr Tyr Leu Cys Ala Val Gln
            100                 105                 110

Gly Glu Asn Ser Gly Tyr Ser Thr Leu Thr Phe Gly Lys Gly Thr Met
            115                 120                 125

Leu Leu Val Ser Pro Asp Ile Gln Asn Pro Asp Pro Ala Val Tyr Gln
130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
            165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
            195                 200                 205

Ala Phe Asn Asn Ser Ile Ile Pro Glu Asp Thr Phe Phe Pro Ser Pro
            210                 215                 220

Glu Ser Ser Cys Asp Val Lys Leu Val Glu Lys Ser Phe Glu Thr Asp
225                 230                 235                 240

-continued

```
Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 18
<211> LENGTH: 314
<212> TYPE: PRT
<213> ORGANISM: Artificial Sequence
<220> FEATURE:
<223> OTHER INFORMATION: R20P1H7 beta chain

<400> SEQUENCE: 18

Met Gly Pro Gln Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
            35                  40                  45

Glu Tyr Met Ser Trp Tyr Arg Gln Asp Pro Gly Leu Gly Leu Arg Gln
50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Leu Gly Pro Gly Leu Ala Ala Tyr Asn Glu Gln Phe Phe Gly Pro
            115                 120                 125

Gly Thr Arg Leu Thr Val Leu Glu Asp Leu Lys Asn Val Phe Pro Pro
            130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
            195                 200                 205

Tyr Cys Leu Ser Ser Arg Leu Arg Val Ser Ala Thr Phe Trp Gln Asn
            210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
            275                 280                 285

Gly Lys Ala Thr Leu Tyr Ala Val Leu Val Ser Ala Leu Val Leu Met
            290                 295                 300

Ala Met Val Lys Arg Lys Asp Ser Arg Gly
305                 310
```

```
<210> SEQ ID NO 19
<211> LENGTH: 272
<212> TYPE: PRT
<213> ORGANISM: Artificial Sequence
<220> FEATURE:
<223> OTHER INFORMATION: R7P1D5 alpha chain

<400> SEQUENCE: 19

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
    50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Tyr Ser Ser Ala Ser Lys Ile Ile Phe Gly Ser Gly Thr Arg Leu Ser
        115                 120                 125

Ile Arg Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 20
<211> LENGTH: 310
<212> TYPE: PRT
<213> ORGANISM: Artificial Sequence
<220> FEATURE:
<223> OTHER INFORMATION: R7P1D5 beta chain

<400> SEQUENCE: 20

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45
```

Asp Tyr Leu Phe Trp Tyr Arg Gln Thr Met Met Arg Gly Leu Glu Leu
            50                  55                  60

Leu Ile Tyr Phe Asn Asn Val Pro Ile Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Arg Ala Asn Thr Gly Glu Leu Phe Phe Gly Gly Ser Arg Leu
            115                 120                 125

Thr Val Leu Glu Asp Leu Lys Asn Val Phe Pro Pro Glu Val Ala Val
            130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
                180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
                260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
            290                 295                 300

Arg Lys Asp Ser Arg Gly
305                 310

<210> SEQ ID NO 21
<211> LENGTH: 277
<212> TYPE: PRT
<213> ORGANISM: Artificial Sequence
<220> FEATURE:
<223> OTHER INFORMATION: R10P2G12 alpha chain

<400> SEQUENCE: 21

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
            50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

```
Phe Thr Ile Thr Ala Ser Gln Val Val Asp Ser Ala Val Tyr Phe Cys
            100                 105                 110

Ala Leu Ser Glu Gly Asn Ser Gly Asn Thr Pro Leu Val Phe Gly Lys
            115                 120                 125

Gly Thr Arg Leu Ser Val Ile Ala Asn Ile Gln Asn Pro Asp Pro Ala
        130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
            275

<210> SEQ ID NO 22
<211> LENGTH: 313
<212> TYPE: PRT
<213> ORGANISM: Artificial Sequence
<220> FEATURE:
<223> OTHER INFORMATION: R10P2G12 beta chain

<400> SEQUENCE: 22

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Leu Ser Ser Gly Ser His Gln Glu Thr Gln Tyr Phe Gly Pro Gly
        115                 120                 125

Thr Arg Leu Leu Val Leu Glu Asp Leu Lys Asn Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175
```

```
Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
            245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
            290                 295                 300

Met Val Lys Arg Lys Asp Ser Arg Gly
305                 310

<210> SEQ ID NO 23
<211> LENGTH: 271
<212> TYPE: PRT
<213> ORGANISM: Artificial Sequence
<220> FEATURE:
<223> OTHER INFORMATION: R10P1A7 alpha chain

<400> SEQUENCE: 23

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
            35                  40                  45

Ser Ser Thr Tyr Leu Tyr Trp Tyr Lys Gln Glu Pro Gly Ala Gly Leu
50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
            85                  90                  95

Ile Ala Asp Thr Gln Thr Gly Asp Ser Ala Ile Tyr Phe Cys Ala Glu
            100                 105                 110

Ser Lys Glu Thr Arg Leu Met Phe Gly Asp Gly Thr Gln Leu Val Val
            115                 120                 125

Lys Pro Asn Ile Gln Asn Pro Asp Pro Ala Val Tyr Gln Leu Arg Asp
            130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
            165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
            195                 200                 205

Asn Ser Ile Ile Pro Glu Asp Thr Phe Phe Pro Ser Pro Glu Ser Ser
210                 215                 220
```

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
            245                 250                 255

Val Ala Gly Phe Asn Leu Leu Met Thr Leu Arg Leu Trp Ser Ser
        260                 265                 270

<210> SEQ ID NO 24
<211> LENGTH: 317
<212> TYPE: PRT
<213> ORGANISM: Artificial Sequence
<220> FEATURE:
<223> OTHER INFORMATION: R10P1A7 beta chain

<400> SEQUENCE: 24

Met Leu Leu Leu Leu Leu Leu Gly Pro Gly Ile Ser Leu Leu Leu
1               5                   10                  15

Pro Gly Ser Leu Ala Gly Ser Gly Leu Gly Ala Trp Ser Gln His Pro
                20                  25                  30

Ser Val Trp Ile Cys Lys Ser Gly Thr Ser Val Lys Ile Glu Cys Arg
            35                  40                  45

Ser Leu Asp Phe Gln Ala Thr Thr Met Phe Trp Tyr Arg Gln Phe Pro
        50                  55                  60

Lys Gln Ser Leu Met Leu Met Ala Thr Ser Asn Glu Gly Ser Lys Ala
65                  70                  75                  80

Thr Tyr Glu Gln Gly Val Glu Lys Asp Lys Phe Leu Ile Asn His Ala
                85                  90                  95

Ser Leu Thr Leu Ser Thr Leu Thr Val Thr Ser Ala His Pro Glu Asp
            100                 105                 110

Ser Ser Phe Tyr Ile Cys Ser Ala Arg Ala Gly Gly His Glu Gln Phe
        115                 120                 125

Phe Gly Pro Gly Thr Arg Leu Thr Val Leu Glu Asp Leu Lys Asn Val
    130                 135                 140

Phe Pro Pro Glu Val Ala Val Phe Glu Pro Ser Glu Ala Glu Ile Ser
145                 150                 155                 160

His Thr Gln Lys Ala Thr Leu Val Cys Leu Ala Thr Gly Phe Tyr Pro
                165                 170                 175

Asp His Val Glu Leu Ser Trp Trp Asn Gly Lys Glu Val His Ser
            180                 185                 190

Gly Val Ser Thr Asp Pro Gln Pro Leu Lys Glu Gln Pro Ala Leu Asn
        195                 200                 205

Asp Ser Arg Tyr Cys Leu Ser Ser Arg Leu Arg Val Ser Ala Thr Phe
210                 215                 220

Trp Gln Asn Pro Arg Asn His Phe Arg Cys Gln Val Gln Phe Tyr Gly
225                 230                 235                 240

Leu Ser Glu Asn Asp Glu Trp Thr Gln Asp Arg Ala Lys Pro Val Thr
                245                 250                 255

Gln Ile Val Ser Ala Glu Ala Trp Gly Arg Ala Asp Cys Gly Phe Thr
            260                 265                 270

Ser Glu Ser Tyr Gln Gln Gly Val Leu Ser Ala Thr Ile Leu Tyr Glu
        275                 280                 285

Ile Leu Leu Gly Lys Ala Thr Leu Tyr Ala Val Leu Val Ser Ala Leu
    290                 295                 300

Val Leu Met Ala Met Val Lys Arg Lys Asp Ser Arg Gly
305                 310                 315

<210> SEQ ID NO 25
<211> LENGTH: 271
<212> TYPE: PRT
<213> ORGANISM: Artificial Sequence
<220> FEATURE:
<223> OTHER INFORMATION: R4P1D10 alpha chain

<400> SEQUENCE: 25

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn Phe His Asp Lys Ile Ile Phe Gly Lys Gly Thr Arg Leu His Ile
        115                 120                 125

Leu Pro Asn Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 26
<211> LENGTH: 308
<212> TYPE: PRT
<213> ORGANISM: Artificial Sequence
<220> FEATURE:
<223> OTHER INFORMATION: R4P1D10 beta chain

<400> SEQUENCE: 26

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp

```
                35                  40                  45
Leu Ser Val Tyr Trp Tyr Gln Gln Ser Leu Asp Gln Gly Leu Gln Phe
 50                  55                  60
Leu Ile His Tyr Tyr Asn Gly Glu Glu Arg Ala Lys Gly Asn Ile Leu
 65                  70                  75                  80
Glu Arg Phe Ser Ala Gln Gln Phe Pro Asp Leu His Ser Glu Leu Asn
                 85                  90                  95
Leu Ser Ser Leu Glu Leu Gly Asp Ser Ala Leu Tyr Phe Cys Ala Ser
                100                 105                 110
Ser Val Ala Ser Ala Tyr Gly Tyr Thr Phe Gly Ser Gly Thr Arg Leu
            115                 120                 125
Thr Val Val Glu Asp Leu Asn Lys Val Phe Pro Pro Glu Val Ala Val
        130                 135                 140
Phe Glu Pro Ser Glu Ala Glu Ile Ser His Thr Gln Lys Ala Thr Leu
145                 150                 155                 160
Val Cys Leu Ala Thr Gly Phe Phe Pro Asp His Val Glu Leu Ser Trp
                165                 170                 175
Trp Val Asn Gly Lys Glu Val His Ser Gly Val Ser Thr Asp Pro Gln
            180                 185                 190
Pro Leu Lys Glu Gln Pro Ala Leu Asn Asp Ser Arg Tyr Cys Leu Ser
        195                 200                 205
Ser Arg Leu Arg Val Ser Ala Thr Phe Trp Gln Asn Pro Arg Asn His
210                 215                 220
Phe Arg Cys Gln Val Gln Phe Tyr Gly Leu Ser Glu Asn Asp Glu Trp
225                 230                 235                 240
Thr Gln Asp Arg Ala Lys Pro Val Thr Gln Ile Val Ser Ala Glu Ala
                245                 250                 255
Trp Gly Arg Ala Asp Cys Gly Phe Thr Ser Val Ser Tyr Gln Gln Gly
            260                 265                 270
Val Leu Ser Ala Thr Ile Leu Tyr Glu Ile Leu Leu Gly Lys Ala Thr
        275                 280                 285
Leu Tyr Ala Val Leu Val Ser Ala Leu Val Leu Met Ala Met Val Lys
290                 295                 300
Arg Lys Asp Phe
305

<210> SEQ ID NO 27
<211> LENGTH: 274
<212> TYPE: PRT
<213> ORGANISM: Artificial Sequence
<220> FEATURE:
<223> OTHER INFORMATION: R4P3F9 alpha chain

<400> SEQUENCE: 27

Met Lys Ser Leu Arg Val Leu Leu Val Ile Leu Trp Leu Gln Leu Ser
 1               5                  10                  15
Trp Val Trp Ser Gln Gln Lys Glu Val Glu Gln Asn Ser Gly Pro Leu
                20                  25                  30
Ser Val Pro Glu Gly Ala Ile Ala Ser Leu Asn Cys Thr Tyr Ser Asp
            35                  40                  45
Arg Gly Ser Gln Ser Phe Phe Trp Tyr Arg Gln Tyr Ser Gly Lys Ser
        50                  55                  60
Pro Glu Leu Ile Met Phe Ile Tyr Ser Asn Gly Asp Lys Glu Asp Gly
 65                  70                  75                  80
Arg Phe Thr Ala Gln Leu Asn Lys Ala Ser Gln Tyr Val Ser Leu Leu
```

-continued

```
                85                  90                  95
Ile Arg Asp Ser Gln Pro Ser Asp Ser Ala Thr Tyr Leu Cys Ala Ala
            100                 105                 110

Tyr Ser Gly Ala Gly Ser Tyr Gln Leu Thr Phe Gly Lys Gly Thr Lys
        115                 120                 125

Leu Ser Val Ile Pro Asn Ile Gln Asn Pro Asp Pro Ala Val Tyr Gln
130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 28
<211> LENGTH: 308
<212> TYPE: PRT
<213> ORGANISM: Artificial Sequence
<220> FEATURE:
<223> OTHER INFORMATION: R4P3F9 beta chain

<400> SEQUENCE: 28

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Val Glu Ser Ser Tyr Gly Tyr Thr Phe Gly Ser Gly Thr Arg Leu
        115                 120                 125

Thr Val Val Glu Asp Leu Asn Lys Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175
```

```
Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
                260                 265                 270

Val Leu Ser Ala Thr Ile Leu Tyr Glu Ile Leu Leu Gly Lys Ala Thr
                275                 280                 285

Leu Tyr Ala Val Leu Val Ser Ala Leu Val Leu Met Ala Met Val Lys
            290                 295                 300

Arg Lys Asp Phe
305

<210> SEQ ID NO 29
<211> LENGTH: 271
<212> TYPE: PRT
<213> ORGANISM: Artificial Sequence
<220> FEATURE:
<223> OTHER INFORMATION: R4P3H3 alpha chain

<400> SEQUENCE: 29

Met Lys Ser Leu Arg Val Leu Val Ile Leu Trp Leu Gln Leu Ser
1               5                   10                  15

Trp Val Trp Ser Gln Gln Lys Glu Val Glu Gln Asn Ser Gly Pro Leu
                20                  25                  30

Ser Val Pro Glu Gly Ala Ile Ala Ser Leu Asn Cys Thr Tyr Ser Asp
            35                  40                  45

Arg Gly Ser Gln Ser Phe Phe Trp Tyr Arg Gln Tyr Ser Gly Lys Ser
        50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Lys Ala Gly Asn Gln Phe Tyr Phe Gly Thr Gly Thr Ser Leu Thr Val
        115                 120                 125

Ile Pro Asn Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220
```

```
Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
            245                 250                 255

Val Ala Gly Phe Asn Leu Leu Met Thr Leu Arg Leu Trp Ser Ser
        260                 265                 270

<210> SEQ ID NO 30
<211> LENGTH: 314
<212> TYPE: PRT
<213> ORGANISM: Artificial Sequence
<220> FEATURE:
<223> OTHER INFORMATION: R4P3H3 beta chain

<400> SEQUENCE: 30

Met Gly Thr Arg Leu Leu Cys Trp Val Val Leu Gly Phe Leu Gly Thr
1               5                   10                  15

Asp His Thr Gly Ala Gly Val Ser Gln Ser Pro Arg Tyr Lys Val Ala
            20                  25                  30

Lys Arg Gly Gln Asp Val Ala Leu Arg Cys Asp Pro Ile Ser Gly His
        35                  40                  45

Val Ser Leu Phe Trp Tyr Gln Gln Ala Leu Gly Gln Gly Pro Glu Phe
50                  55                  60

Leu Thr Tyr Phe Gln Asn Glu Ala Gln Leu Asp Lys Ser Gly Leu Pro
65                  70                  75                  80

Ser Asp Arg Phe Phe Ala Glu Arg Pro Glu Gly Ser Val Ser Thr Leu
                85                  90                  95

Lys Ile Gln Arg Thr Gln Gln Glu Asp Ser Ala Val Tyr Leu Cys Ala
            100                 105                 110

Ser Ser Leu Leu Thr Ser Gly Gly Asp Asn Glu Gln Phe Phe Gly Pro
        115                 120                 125

Gly Thr Arg Leu Thr Val Leu Glu Asp Leu Lys Asn Val Phe Pro Pro
130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
290                 295                 300

Ala Met Val Lys Arg Lys Asp Ser Arg Gly
305                 310
```

<210> SEQ ID NO 31
<211> LENGTH: 270
<212> TYPE: PRT
<213> ORGANISM: Artificial Sequence
<220> FEATURE:
<223> OTHER INFORMATION: R36P3F9 alpha chain

<400> SEQUENCE: 31

```
Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Val
            100                 105                 110

Ser Asn Tyr Gln Leu Ile Trp Gly Ala Gly Thr Lys Leu Ile Ile Lys
        115                 120                 125

Pro Asp Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270
```

<210> SEQ ID NO 32
<211> LENGTH: 314
<212> TYPE: PRT
<213> ORGANISM: Artificial Sequence
<220> FEATURE:
<223> OTHER INFORMATION: R36P3F9 beta chain

<400> SEQUENCE: 32

```
Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
```

```
                35                  40                  45
Glu Tyr Met Ser Trp Tyr Arg Gln Asp Pro Gly Leu Gly Leu Arg Gln
 50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Ser Thr Ser Gly Gly Leu Ser Gly Glu Thr Gln Tyr Phe Gly Pro
        115                 120                 125

Gly Thr Arg Leu Leu Val Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly
305                 310

<210> SEQ ID NO 33
<211> LENGTH: 272
<212> TYPE: PRT
<213> ORGANISM: Artificial Sequence
<220> FEATURE:
<223> OTHER INFORMATION: R52P2G11 alpha chain

<400> SEQUENCE: 33

Met Lys Lys His Leu Thr Thr Phe Leu Val Ile Leu Trp Leu Tyr Phe
1               5                   10                  15

Tyr Arg Gly Asn Gly Lys Asn Gln Val Glu Gln Ser Pro Gln Ser Leu
            20                  25                  30

Ile Ile Leu Glu Gly Lys Asn Cys Thr Leu Gln Cys Asn Tyr Thr Val
        35                  40                  45

Ser Pro Phe Ser Asn Leu Arg Trp Tyr Lys Gln Asp Thr Gly Arg Gly
    50                  55                  60

Pro Val Ser Leu Thr Ile Met Thr Phe Ser Glu Asn Thr Lys Ser Asn
65                  70                  75                  80

Gly Arg Tyr Thr Ala Thr Leu Asp Ala Asp Thr Lys Gln Ser Ser Leu
```

```
                    85                  90                  95
His Ile Thr Ala Ser Gln Leu Ser Asp Ser Ala Ser Tyr Ile Cys Val
                100                 105                 110

Val Ser Ala Tyr Gly Lys Leu Gln Phe Gly Ala Gly Thr Gln Val Val
            115                 120                 125

Val Thr Pro Asp Ile Gln Asn Pro Asp Pro Ala Val Tyr Gln Leu Arg
        130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
        210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 34
<211> LENGTH: 312
<212> TYPE: PRT
<213> ORGANISM: Artificial Sequence
<220> FEATURE:
<223> OTHER INFORMATION: R52P2G11 beta chain

<400> SEQUENCE: 34

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Leu Gly Ser Pro Asp Gly Asn Gln Pro Gln His Phe Gly Asp
        115                 120                 125

Gly Thr Arg Leu Ser Ile Leu Glu Asp Leu Asn Lys Val Phe Pro Pro
        130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Ser
```

```
                180                 185                 190
Thr Asp Pro Gln Pro Leu Lys Glu Gln Pro Ala Leu Asn Asp Ser Arg
        195                 200                 205
Tyr Cys Leu Ser Ser Arg Leu Arg Val Ser Ala Thr Phe Trp Gln Asn
        210                 215                 220
Pro Arg Asn His Phe Arg Cys Gln Val Gln Phe Tyr Gly Leu Ser Glu
225                 230                 235                 240
Asn Asp Glu Trp Thr Gln Asp Arg Ala Lys Pro Val Thr Gln Ile Val
                245                 250                 255
Ser Ala Glu Ala Trp Gly Arg Ala Asp Cys Gly Phe Thr Ser Val Ser
        260                 265                 270
Tyr Gln Gln Gly Val Leu Ser Ala Thr Ile Leu Tyr Glu Ile Leu Leu
        275                 280                 285
Gly Lys Ala Thr Leu Tyr Ala Val Leu Val Ser Ala Leu Val Leu Met
        290                 295                 300
Ala Met Val Lys Arg Lys Asp Phe
305                 310

<210> SEQ ID NO 35
<211> LENGTH: 279
<212> TYPE: PRT
<213> ORGANISM: Artificial Sequence
<220> FEATURE:
<223> OTHER INFORMATION: R53P2A9 alpha chain

<400> SEQUENCE: 35

Met Ala Cys Pro Gly Phe Leu Trp Ala Leu Val Ile Ser Thr Cys Leu
1               5                   10                  15
Glu Phe Ser Met Ala Gln Thr Val Thr Gln Ser Gln Pro Glu Met Ser
                20                  25                  30
Val Gln Glu Ala Glu Thr Val Thr Leu Ser Cys Thr Tyr Asp Thr Ser
        35                  40                  45
Glu Ser Asp Tyr Tyr Leu Phe Trp Tyr Lys Gln Pro Pro Ser Arg Gln
    50                  55                  60
Met Ile Leu Val Ile Arg Gln Glu Ala Tyr Lys Gln Gln Asn Ala Thr
65                  70                  75                  80
Glu Asn Arg Phe Ser Val Asn Phe Gln Lys Ala Ala Lys Ser Phe Ser
                85                  90                  95
Leu Lys Ile Ser Asp Ser Gln Leu Gly Asp Ala Ala Met Tyr Phe Cys
                100                 105                 110
Ala Tyr Asn Ser Tyr Ala Gly Gly Thr Ser Tyr Gly Lys Leu Thr Phe
        115                 120                 125
Gly Gln Gly Thr Ile Leu Thr Val His Pro Asn Ile Gln Asn Pro Asp
    130                 135                 140
Pro Ala Val Tyr Gln Leu Arg Asp Ser Lys Ser Ser Asp Lys Ser Val
145                 150                 155                 160
Cys Leu Phe Thr Asp Phe Asp Ser Gln Thr Asn Val Ser Gln Ser Lys
                165                 170                 175
Asp Ser Asp Val Tyr Ile Thr Asp Lys Thr Val Leu Asp Met Arg Ser
                180                 185                 190
Met Asp Phe Lys Ser Asn Ser Ala Val Ala Trp Ser Asn Lys Ser Asp
        195                 200                 205
Phe Ala Cys Ala Asn Ala Phe Asn Asn Ser Ile Ile Pro Glu Asp Thr
    210                 215                 220
Phe Phe Pro Ser Pro Glu Ser Ser Cys Asp Val Lys Leu Val Glu Lys
```

```
225                 230                 235                 240
Ser Phe Glu Thr Asp Thr Asn Leu Asn Phe Gln Asn Leu Ser Val Ile
                245                 250                 255
Gly Phe Arg Ile Leu Leu Lys Val Ala Gly Phe Asn Leu Leu Met
            260                 265                 270
Thr Leu Arg Leu Trp Ser Ser
            275

<210> SEQ ID NO 36
<211> LENGTH: 310
<212> TYPE: PRT
<213> ORGANISM: Artificial Sequence
<220> FEATURE:
<223> OTHER INFORMATION: R53P2A9 beta chain

<400> SEQUENCE: 36

Met Gly Pro Gly Leu Leu Cys Trp Val Leu Leu Cys Leu Leu Gly Ala
1               5                   10                  15
Gly Pro Val Asp Ala Gly Val Thr Gln Ser Pro Thr His Leu Ile Lys
            20                  25                  30
Thr Arg Gly Gln Gln Val Thr Leu Arg Cys Ser Pro Ile Ser Gly His
        35                  40                  45
Lys Ser Val Ser Trp Tyr Gln Gln Val Leu Gly Gln Gly Pro Gln Phe
    50                  55                  60
Ile Phe Gln Tyr Tyr Glu Lys Glu Arg Gly Arg Gly Asn Phe Pro
65                  70                  75                  80
Asp Arg Phe Ser Ala Arg Gln Phe Pro Asn Tyr Ser Ser Glu Leu Asn
                85                  90                  95
Val Asn Ala Leu Leu Leu Gly Asp Ser Ala Leu Tyr Leu Cys Ala Ser
            100                 105                 110
Ser Leu Asp Gly Thr Ser Glu Gln Tyr Phe Gly Pro Gly Thr Arg Leu
        115                 120                 125
Thr Val Thr Glu Asp Leu Lys Asn Val Phe Pro Pro Glu Val Ala Val
    130                 135                 140
Phe Glu Pro Ser Glu Ala Glu Ile Ser His Thr Gln Lys Ala Thr Leu
145                 150                 155                 160
Val Cys Leu Ala Thr Gly Phe Tyr Pro Asp His Val Glu Leu Ser Trp
                165                 170                 175
Trp Val Asn Gly Lys Glu Val His Ser Gly Val Ser Thr Asp Pro Gln
            180                 185                 190
Pro Leu Lys Glu Gln Pro Ala Leu Asn Asp Ser Arg Tyr Cys Leu Ser
        195                 200                 205
Ser Arg Leu Arg Val Ser Ala Thr Phe Trp Gln Asn Pro Arg Asn His
    210                 215                 220
Phe Arg Cys Gln Val Gln Phe Tyr Gly Leu Ser Glu Asn Asp Glu Trp
225                 230                 235                 240
Thr Gln Asp Arg Ala Lys Pro Val Thr Gln Ile Val Ser Ala Glu Ala
                245                 250                 255
Trp Gly Arg Ala Asp Cys Gly Phe Thr Ser Glu Ser Tyr Gln Gln Gly
            260                 265                 270
Val Leu Ser Ala Thr Ile Leu Tyr Glu Ile Leu Leu Gly Lys Ala Thr
        275                 280                 285
Leu Tyr Ala Val Leu Val Ser Ala Leu Val Leu Met Ala Met Val Lys
    290                 295                 300
Arg Lys Asp Ser Arg Gly
```

<210> SEQ ID NO 37
<211> LENGTH: 271
<212> TYPE: PRT
<213> ORGANISM: Artificial Sequence
<220> FEATURE:
<223> OTHER INFORMATION: R26P1A9 alpha chain

<400> SEQUENCE: 37

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Leu Ile Gly
            100                 105                 110

Ala Ser Gly Ser Arg Leu Thr Phe Gly Glu Gly Thr Gln Leu Thr Val
        115                 120                 125

Asn Pro Asp Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 38
<211> LENGTH: 310
<212> TYPE: PRT
<213> ORGANISM: Artificial Sequence
<220> FEATURE:
<223> OTHER INFORMATION: R26P1A9 beta chain

<400> SEQUENCE: 38

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
35                  40                  45

Asp Tyr Leu Phe Trp Tyr Arg Gln Thr Met Met Arg Gly Leu Glu Leu
50                  55                  60

Leu Ile Tyr Phe Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
                100                 105                 110

Ser Ser Tyr Phe Gly Trp Asn Glu Lys Leu Phe Phe Gly Ser Gly Thr
                115                 120                 125

Gln Leu Ser Val Leu Glu Asp Leu Asn Lys Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
                180                 185                 190

Pro Gln Pro Leu Lys Glu Gln Pro Ala Leu Asn Asp Ser Arg Tyr Cys
                195                 200                 205

Leu Ser Ser Arg Leu Arg Val Ser Ala Thr Phe Trp Gln Asn Pro Arg
210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
                260                 265                 270

Gln Gly Val Leu Ser Ala Thr Ile Leu Tyr Glu Ile Leu Leu Gly Lys
                275                 280                 285

Ala Thr Leu Tyr Ala Val Leu Val Ser Ala Leu Val Leu Met Ala Met
290                 295                 300

Val Lys Arg Lys Asp Phe
305                 310

<210> SEQ ID NO 39
<211> LENGTH: 276
<212> TYPE: PRT
<213> ORGANISM: Artificial Sequence
<220> FEATURE:
<223> OTHER INFORMATION: R26P2A6 alpha chain

<400> SEQUENCE: 39

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
                20                  25                  30

Leu Ser Val Pro Glu Gly Ala Ile Val Ser Leu Asn Cys Thr Tyr Ser
                35                  40                  45

Asn Ser Ala Phe Gln Tyr Phe Met Trp Tyr Arg Gln Tyr Ser Arg Lys
                50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Lys Tyr Ile Ser Leu
               85                  90                  95

Phe Ile Arg Asp Ser Gln Pro Ser Asp Ser Ala Thr Tyr Leu Cys Ala
            100                 105                 110

Met Ser Asp Val Ser Gly Gly Tyr Asn Lys Leu Ile Phe Gly Ala Gly
            115                 120                 125

Thr Arg Leu Ala Val His Pro Tyr Ile Gln Asn Pro Asp Pro Ala Val
            130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
                180                 185                 190

Lys Ser Asn Ser Ala Val Ala Trp Ser Asn Lys Ser Asp Phe Ala Cys
            195                 200                 205

Ala Asn Ala Phe Asn Asn Ser Ile Ile Pro Glu Asp Thr Phe Phe Pro
            210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
            275

<210> SEQ ID NO 40
<211> LENGTH: 311
<212> TYPE: PRT
<213> ORGANISM: Artificial Sequence
<220> FEATURE:
<223> OTHER INFORMATION: R26P2A6 beta chain

<400> SEQUENCE: 40

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
            35                  40                  45

Glu Tyr Met Ser Trp Tyr Arg Gln Asp Pro Gly Leu Gly Leu Arg Gln
        50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Thr Thr Pro Asp Gly Thr Asp Glu Gln Phe Phe Gly Pro Gly Thr Arg
            115                 120                 125

Leu Thr Val Leu Glu Asp Leu Lys Asn Val Phe Pro Pro Glu Val Ala
            130                 135                 140

Val Phe Glu Pro Ser Glu Ala Glu Ile Ser His Thr Gln Lys Ala Thr
145                 150                 155                 160

```
Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Glu Ser Tyr Gln Gln
        260                 265                 270

Gly Val Leu Ser Ala Thr Ile Leu Tyr Glu Ile Leu Leu Gly Lys Ala
    275                 280                 285

Thr Leu Tyr Ala Val Leu Val Ser Ala Leu Val Leu Met Ala Met Val
        290                 295                 300

Lys Arg Lys Asp Ser Arg Gly
305                 310

<210> SEQ ID NO 41
<211> LENGTH: 274
<212> TYPE: PRT
<213> ORGANISM: Artificial Sequence
<220> FEATURE:
<223> OTHER INFORMATION: R26P3H1 alpha chain

<400> SEQUENCE: 41

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Met Asn Arg Asp Asp Lys Ile Ile Phe Gly Lys Gly Thr Arg
        115                 120                 125

Leu His Ile Leu Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205
```

```
Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
                260                 265                 270

Ser Ser

<210> SEQ ID NO 42
<211> LENGTH: 310
<212> TYPE: PRT
<213> ORGANISM: Artificial Sequence
<220> FEATURE:
<223> OTHER INFORMATION: R26P3H1 beta chain

<400> SEQUENCE: 42

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Arg Ala Glu Gly Gly Glu Gln Tyr Phe Gly Pro Gly Thr Arg Leu
        115                 120                 125

Thr Val Thr Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
```

```
                290                 295                 300

Arg Lys Asp Ser Arg Gly
305                 310

<210> SEQ ID NO 43
<211> LENGTH: 273
<212> TYPE: PRT
<213> ORGANISM: Artificial Sequence
<220> FEATURE:
<223> OTHER INFORMATION: R35P3A4 alpha chain

<400> SEQUENCE: 43

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Pro Thr Gly Gly Tyr Asn Lys Leu Ile Phe Gly Ala Gly Thr Arg Leu
        115                 120                 125

Ala Val His Pro Tyr Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 44
<211> LENGTH: 311
<212> TYPE: PRT
<213> ORGANISM: Artificial Sequence
<220> FEATURE:
<223> OTHER INFORMATION: R35P3A4 beta chain

<400> SEQUENCE: 44

Met Ser Ile Gly Leu Leu Cys Cys Ala Ala Leu Ser Leu Leu Trp Ala
```

```
                1               5                  10                 15
        Gly Pro Val Asn Ala Gly Val Thr Gln Thr Pro Lys Phe Gln Val Leu
                        20                  25                  30
        Lys Thr Gly Gln Ser Met Thr Leu Gln Cys Ala Gln Asp Met Asn His
                        35                  40                  45
        Glu Tyr Met Ser Trp Tyr Arg Gln Asp Pro Gly Met Gly Leu Arg Leu
                50                  55                  60
        Ile His Tyr Ser Val Gly Ala Gly Ile Thr Asp Gln Gly Glu Val Pro
        65                  70                  75                  80
        Asn Gly Tyr Asn Val Ser Arg Ser Thr Thr Glu Asp Phe Pro Leu Arg
                        85                  90                  95
        Leu Leu Ser Ala Ala Pro Ser Gln Thr Ser Val Tyr Phe Cys Ala Ser
                        100                 105                 110
        Ser Leu Gly Gly Ala Ser Gln Glu Gln Tyr Phe Gly Pro Gly Thr Arg
                        115                 120                 125
        Leu Thr Val Thr Glu Asp Leu Lys Asn Val Phe Pro Pro Glu Val Ala
                        130                 135                 140
        Val Phe Glu Pro Ser Glu Ala Glu Ile Ser His Thr Gln Lys Ala Thr
        145                 150                 155                 160
        Leu Val Cys Leu Ala Thr Gly Phe Tyr Pro Asp His Val Glu Leu Ser
                        165                 170                 175
        Trp Trp Val Asn Gly Lys Glu Val His Ser Gly Val Ser Thr Asp Pro
                        180                 185                 190
        Gln Pro Leu Lys Glu Gln Pro Ala Leu Asn Asp Ser Arg Tyr Cys Leu
                        195                 200                 205
        Ser Ser Arg Leu Arg Val Ser Ala Thr Phe Trp Gln Asn Pro Arg Asn
                210                 215                 220
        His Phe Arg Cys Gln Val Gln Phe Tyr Gly Leu Ser Glu Asn Asp Glu
        225                 230                 235                 240
        Trp Thr Gln Asp Arg Ala Lys Pro Val Thr Gln Ile Val Ser Ala Glu
                        245                 250                 255
        Ala Trp Gly Arg Ala Asp Cys Gly Phe Thr Ser Glu Ser Tyr Gln Gln
                        260                 265                 270
        Gly Val Leu Ser Ala Thr Ile Leu Tyr Glu Ile Leu Leu Gly Lys Ala
                        275                 280                 285
        Thr Leu Tyr Ala Val Leu Val Ser Ala Leu Val Leu Met Ala Met Val
                        290                 295                 300
        Lys Arg Lys Asp Ser Arg Gly
        305                 310

<210> SEQ ID NO 45
<211> LENGTH: 266
<212> TYPE: PRT
<213> ORGANISM: Artificial Sequence
<220> FEATURE:
<223> OTHER INFORMATION: R37P1C9 alpha chain

<400> SEQUENCE: 45

Met Lys Leu Val Thr Ser Ile Thr Val Leu Leu Ser Leu Gly Ile Met
        1               5                   10                  15
        Gly Asp Ala Lys Thr Thr Gln Pro Asn Ser Met Glu Ser Asn Glu Glu
                        20                  25                  30
        Glu Pro Val His Leu Pro Cys Asn His Ser Thr Ile Ser Gly Thr Asp
                        35                  40                  45
        Tyr Ile His Trp Tyr Arg Gln Leu Pro Ser Gln Gly Pro Glu Tyr Val
```

```
                50                  55                  60
Ile His Gly Leu Thr Ser Asn Val Asn Arg Met Ala Ser Leu Ala
 65                  70                  75                  80

Ile Ala Glu Asp Arg Lys Ser Ser Thr Leu Ile Leu His Arg Ala Thr
                     85                  90                  95

Leu Arg Asp Ala Ala Val Tyr Tyr Cys Ile Leu Phe Asn Phe Asn Lys
                100                 105                 110

Phe Tyr Phe Gly Ser Gly Thr Lys Leu Asn Val Lys Pro Asn Ile Gln
                115                 120                 125

Asn Pro Asp Pro Ala Val Tyr Gln Leu Arg Asp Ser Lys Ser Ser Asp
                130                 135                 140

Lys Ser Val Cys Leu Phe Thr Asp Phe Asp Ser Gln Thr Asn Val Ser
145                 150                 155                 160

Gln Ser Lys Asp Ser Asp Val Tyr Ile Thr Asp Lys Thr Val Leu Asp
                165                 170                 175

Met Arg Ser Met Asp Phe Lys Ser Asn Ser Ala Val Ala Trp Ser Asn
                180                 185                 190

Lys Ser Asp Phe Ala Cys Ala Asn Ala Phe Asn Asn Ser Ile Ile Pro
                195                 200                 205

Glu Asp Thr Phe Phe Pro Ser Pro Glu Ser Ser Cys Asp Val Lys Leu
                210                 215                 220

Val Glu Lys Ser Phe Glu Thr Asp Thr Asn Leu Asn Phe Gln Asn Leu
225                 230                 235                 240

Ser Val Ile Gly Phe Arg Ile Leu Leu Leu Lys Val Ala Gly Phe Asn
                245                 250                 255

Leu Leu Met Thr Leu Arg Leu Trp Ser Ser
                260                 265

<210> SEQ ID NO 46
<211> LENGTH: 309
<212> TYPE: PRT
<213> ORGANISM: Artificial Sequence
<220> FEATURE:
<223> OTHER INFORMATION: R37P1C9 beta chain

<400> SEQUENCE: 46

Met Gly Pro Gly Leu Leu His Trp Met Ala Leu Cys Leu Leu Gly Thr
 1               5                  10                  15

Gly His Gly Asp Ala Met Val Ile Gln Asn Pro Arg Tyr Gln Val Thr
                20                  25                  30

Gln Phe Gly Lys Pro Val Thr Leu Ser Cys Ser Gln Thr Leu Asn His
            35                  40                  45

Asn Val Met Tyr Trp Tyr Gln Gln Lys Ser Ser Gln Ala Pro Lys Leu
        50                  55                  60

Leu Phe His Tyr Tyr Asp Lys Asp Phe Asn Asn Glu Ala Asp Thr Pro
 65                  70                  75                  80

Asp Asn Phe Gln Ser Arg Arg Pro Asn Thr Ser Phe Cys Phe Leu Asp
                 85                  90                  95

Ile Arg Ser Pro Gly Leu Gly Asp Ala Ala Met Tyr Leu Cys Ala Thr
                100                 105                 110

Ser Ser Gly Glu Thr Asn Glu Lys Leu Phe Phe Gly Ser Gly Thr Gln
                115                 120                 125

Leu Ser Val Leu Glu Asp Leu Asn Lys Val Phe Pro Pro Glu Val Ala
                130                 135                 140

Val Phe Glu Pro Ser Glu Ala Glu Ile Ser His Thr Gln Lys Ala Thr
```

```
            145                 150                 155                 160
Leu Val Cys Leu Ala Thr Gly Phe Phe Pro Asp His Val Glu Leu Ser
                165                 170                 175
Trp Trp Val Asn Gly Lys Glu Val His Ser Gly Val Ser Thr Asp Pro
                180                 185                 190
Gln Pro Leu Lys Glu Gln Pro Ala Leu Asn Asp Ser Arg Tyr Cys Leu
                195                 200                 205
Ser Ser Arg Leu Arg Val Ser Ala Thr Phe Trp Gln Asn Pro Arg Asn
                210                 215                 220
His Phe Arg Cys Gln Val Gln Phe Tyr Gly Leu Ser Glu Asn Asp Glu
225                 230                 235                 240
Trp Thr Gln Asp Arg Ala Lys Pro Val Thr Gln Ile Val Ser Ala Glu
                245                 250                 255
Ala Trp Gly Arg Ala Asp Cys Gly Phe Thr Ser Val Ser Tyr Gln Gln
                260                 265                 270
Gly Val Leu Ser Ala Thr Ile Leu Tyr Glu Ile Leu Leu Gly Lys Ala
                275                 280                 285
Thr Leu Tyr Ala Val Leu Val Ser Ala Leu Val Leu Met Ala Met Val
                290                 295                 300
Lys Arg Lys Asp Phe
305

<210> SEQ ID NO 47
<211> LENGTH: 277
<212> TYPE: PRT
<213> ORGANISM: Artificial Sequence
<220> FEATURE:
<223> OTHER INFORMATION: R37P1H1 alpha chain

<400> SEQUENCE: 47

Met Thr Arg Val Ser Leu Leu Trp Ala Val Val Ser Thr Cys Leu
1               5                   10                  15
Glu Ser Gly Met Ala Gln Thr Val Thr Gln Ser Gln Pro Glu Met Ser
                20                  25                  30
Val Gln Glu Ala Glu Thr Val Thr Leu Ser Cys Thr Tyr Asp Thr Ser
                35                  40                  45
Glu Ser Asn Tyr Tyr Leu Phe Trp Tyr Lys Gln Pro Pro Ser Arg Gln
                50                  55                  60
Met Ile Leu Val Ile Arg Gln Glu Ala Tyr Lys Gln Gln Asn Ala Thr
65                  70                  75                  80
Glu Asn Arg Phe Ser Val Asn Phe Gln Lys Ala Ala Lys Ser Phe Ser
                85                  90                  95
Leu Lys Ile Ser Asp Ser Gln Leu Gly Asp Thr Ala Met Tyr Phe Cys
                100                 105                 110
Ala Phe Gly Tyr Ser Gly Gly Ala Asp Gly Leu Thr Phe Gly Lys
                115                 120                 125
Gly Thr His Leu Ile Ile Gln Pro Tyr Ile Gln Asn Pro Asp Pro Ala
                130                 135                 140
Val Tyr Gln Leu Arg Asp Ser Lys Ser Ser Asp Lys Ser Val Cys Leu
145                 150                 155                 160
Phe Thr Asp Phe Asp Ser Gln Thr Asn Val Ser Gln Ser Lys Asp Ser
                165                 170                 175
Asp Val Tyr Ile Thr Asp Lys Thr Val Leu Asp Met Arg Ser Met Asp
                180                 185                 190
Phe Lys Ser Asn Ser Ala Val Ala Trp Ser Asn Lys Ser Asp Phe Ala
```

```
              195                 200                 205
Cys Ala Asn Ala Phe Asn Asn Ser Ile Ile Pro Glu Asp Thr Phe Phe
    210                 215                 220
Pro Ser Pro Glu Ser Ser Cys Asp Val Lys Leu Val Glu Lys Ser Phe
225                 230                 235                 240
Glu Thr Asp Thr Asn Leu Asn Phe Gln Asn Leu Ser Val Ile Gly Phe
                245                 250                 255
Arg Ile Leu Leu Leu Lys Val Ala Gly Phe Asn Leu Leu Met Thr Leu
            260                 265                 270
Arg Leu Trp Ser Ser
            275

<210> SEQ ID NO 48
<211> LENGTH: 311
<212> TYPE: PRT
<213> ORGANISM: Artificial Sequence
<220> FEATURE:
<223> OTHER INFORMATION: R37P1H1 beta chain

<400> SEQUENCE: 48

Met Gly Pro Gly Leu Leu Cys Trp Ala Leu Leu Cys Leu Leu Gly Ala
1               5                   10                  15
Gly Leu Val Asp Ala Gly Val Thr Gln Ser Pro Thr His Leu Ile Lys
            20                  25                  30
Thr Arg Gly Gln Gln Val Thr Leu Arg Cys Ser Pro Lys Ser Gly His
        35                  40                  45
Asp Thr Val Ser Trp Tyr Gln Gln Ala Leu Gly Gln Gly Pro Gln Phe
    50                  55                  60
Ile Phe Gln Tyr Tyr Glu Glu Glu Arg Gln Arg Gly Asn Phe Pro
65                  70                  75                  80
Asp Arg Phe Ser Gly His Gln Phe Pro Asn Tyr Ser Ser Glu Leu Asn
                85                  90                  95
Val Asn Ala Leu Leu Leu Gly Asp Ser Ala Leu Tyr Leu Cys Ala Ser
            100                 105                 110
Ser Asn Glu Gly Gln Gly Trp Glu Ala Glu Ala Phe Phe Gly Gln Gly
        115                 120                 125
Thr Arg Leu Thr Val Val Glu Asp Leu Asn Lys Val Phe Pro Pro Glu
    130                 135                 140
Val Ala Val Phe Glu Pro Ser Glu Ala Glu Ile Ser His Thr Gln Lys
145                 150                 155                 160
Ala Thr Leu Val Cys Leu Ala Thr Gly Phe Phe Pro Asp His Val Glu
                165                 170                 175
Leu Ser Trp Trp Val Asn Gly Lys Glu Val His Ser Gly Val Ser Thr
            180                 185                 190
Asp Pro Gln Pro Leu Lys Glu Gln Pro Ala Leu Asn Asp Ser Arg Tyr
        195                 200                 205
Cys Leu Ser Ser Arg Leu Arg Val Ser Ala Thr Phe Trp Gln Asn Pro
    210                 215                 220
Arg Asn His Phe Arg Cys Gln Val Gln Phe Tyr Gly Leu Ser Glu Asn
225                 230                 235                 240
Asp Glu Trp Thr Gln Asp Arg Ala Lys Pro Val Thr Gln Ile Val Ser
                245                 250                 255
Ala Glu Ala Trp Gly Arg Ala Asp Cys Gly Phe Thr Ser Val Ser Tyr
            260                 265                 270
Gln Gln Gly Val Leu Ser Ala Thr Ile Leu Tyr Glu Ile Leu Leu Gly
```

```
                275                 280                 285
Lys Ala Thr Leu Tyr Ala Val Leu Val Ser Ala Leu Val Leu Met Ala
    290                 295                 300

Met Val Lys Arg Lys Asp Phe
305                 310

<210> SEQ ID NO 49
<211> LENGTH: 268
<212> TYPE: PRT
<213> ORGANISM: Artificial Sequence
<220> FEATURE:
<223> OTHER INFORMATION: R42P3A9 alpha chain

<400> SEQUENCE: 49

Met Lys Arg Ile Leu Gly Ala Leu Leu Gly Leu Leu Ser Ala Gln Val
1               5                   10                  15

Cys Cys Val Arg Gly Ile Gln Val Glu Gln Ser Pro Pro Asp Leu Ile
            20                  25                  30

Leu Gln Glu Gly Ala Asn Ser Thr Leu Arg Cys Asn Phe Ser Asp Ser
        35                  40                  45

Val Asn Asn Leu Gln Trp Phe His Gln Asn Pro Trp Gly Gln Leu Ile
    50                  55                  60

Asn Leu Phe Tyr Ile Pro Ser Gly Thr Lys Gln Asn Gly Arg Leu Ser
65                  70                  75                  80

Ala Thr Thr Val Ala Thr Glu Arg Tyr Ser Leu Leu Tyr Ile Ser Ser
                85                  90                  95

Ser Gln Thr Thr Asp Ser Gly Val Tyr Phe Cys Ala Val His Asn Phe
            100                 105                 110

Asn Lys Phe Tyr Phe Gly Ser Gly Thr Lys Leu Asn Val Lys Pro Asn
        115                 120                 125

Ile Gln Asn Pro Asp Pro Ala Val Tyr Gln Leu Arg Asp Ser Lys Ser
    130                 135                 140

Ser Asp Lys Ser Val Cys Leu Phe Thr Asp Phe Asp Ser Gln Thr Asn
145                 150                 155                 160

Val Ser Gln Ser Lys Asp Ser Asp Val Tyr Ile Thr Asp Lys Thr Val
                165                 170                 175

Leu Asp Met Arg Ser Met Asp Phe Lys Ser Asn Ser Ala Val Ala Trp
            180                 185                 190

Ser Asn Lys Ser Asp Phe Ala Cys Ala Asn Ala Phe Asn Asn Ser Ile
        195                 200                 205

Ile Pro Glu Asp Thr Phe Phe Pro Ser Pro Glu Ser Ser Cys Asp Val
    210                 215                 220

Lys Leu Val Glu Lys Ser Phe Glu Thr Asp Thr Asn Leu Asn Phe Gln
225                 230                 235                 240

Asn Leu Ser Val Ile Gly Phe Arg Ile Leu Leu Leu Lys Val Ala Gly
                245                 250                 255

Phe Asn Leu Leu Met Thr Leu Arg Leu Trp Ser Ser
            260                 265

<210> SEQ ID NO 50
<211> LENGTH: 322
<212> TYPE: PRT
<213> ORGANISM: Artificial Sequence
<220> FEATURE:
<223> OTHER INFORMATION: R42P3A9 beta chain

<400> SEQUENCE: 50
```

```
Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
                20                  25                  30

Val Ile Gln Ser Pro Arg His Leu Ile Lys Glu Lys Arg Glu Thr Ala
            35                  40                  45

Thr Leu Lys Cys Tyr Pro Ile Pro Arg His Asp Thr Val Tyr Trp Tyr
        50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Leu Gly Gln Gly
        115                 120                 125

Tyr Asn Glu Gln Phe Phe Gly Pro Gly Thr Arg Leu Thr Val Leu Glu
130                 135                 140

Asp Leu Lys Asn Val Phe Pro Pro Glu Val Ala Val Phe Glu Pro Ser
145                 150                 155                 160

Glu Ala Glu Ile Ser His Thr Gln Lys Ala Thr Leu Val Cys Leu Ala
                165                 170                 175

Thr Gly Phe Tyr Pro Asp His Val Glu Leu Ser Trp Trp Val Asn Gly
            180                 185                 190

Lys Glu Val His Ser Gly Val Ser Thr Asp Pro Gln Pro Leu Lys Glu
        195                 200                 205

Gln Pro Ala Leu Asn Asp Ser Arg Tyr Cys Leu Ser Ser Arg Leu Arg
210                 215                 220

Val Ser Ala Thr Phe Trp Gln Asn Pro Arg Asn His Phe Arg Cys Gln
225                 230                 235                 240

Val Gln Phe Tyr Gly Leu Ser Glu Asn Asp Glu Trp Thr Gln Asp Arg
                245                 250                 255

Ala Lys Pro Val Thr Gln Ile Val Ser Ala Glu Ala Trp Gly Arg Ala
            260                 265                 270

Asp Cys Gly Phe Thr Ser Glu Ser Tyr Gln Gln Gly Val Leu Ser Ala
        275                 280                 285

Thr Ile Leu Tyr Glu Ile Leu Leu Gly Lys Ala Thr Leu Tyr Ala Val
    290                 295                 300

Leu Val Ser Ala Leu Val Leu Met Ala Met Val Lys Arg Lys Asp Ser
305                 310                 315                 320

Arg Gly
```

<210> SEQ ID NO 51
<211> LENGTH: 276
<212> TYPE: PRT
<213> ORGANISM: Artificial Sequence
<220> FEATURE:
<223> OTHER INFORMATION: R43P3F2 alpha chain

<400> SEQUENCE: 51

```
Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
                20                  25                  30

Val Val Glu Lys Glu Asp Val Thr Leu Asp Cys Val Tyr Glu Thr Arg
```

```
            35                  40                  45
Asp Thr Thr Tyr Tyr Leu Phe Trp Tyr Lys Gln Pro Pro Ser Gly Glu
 50                  55                  60

Leu Val Phe Leu Ile Arg Arg Asn Ser Phe Asp Glu Gln Asn Glu Ile
 65                  70                  75                  80

Ser Gly Arg Tyr Ser Trp Asn Phe Gln Lys Ser Thr Ser Ser Phe Asn
                 85                  90                  95

Phe Thr Ile Thr Ala Ser Gln Val Val Asp Ser Ala Val Tyr Phe Cys
                100                 105                 110

Ala Leu Ser Asn Asn Asn Ala Gly Asn Met Leu Thr Phe Gly Gly Gly
                115                 120                 125

Thr Arg Leu Met Val Lys Pro His Ile Gln Asn Pro Asp Pro Ala Val
                130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
                180                 185                 190

Lys Ser Asn Ser Ala Val Ala Trp Ser Asn Lys Ser Asp Phe Ala Cys
                195                 200                 205

Ala Asn Ala Phe Asn Asn Ser Ile Ile Pro Glu Asp Thr Phe Phe Pro
                210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
                260                 265                 270

Leu Trp Ser Ser
            275

<210> SEQ ID NO 52
<211> LENGTH: 323
<212> TYPE: PRT
<213> ORGANISM: Artificial Sequence
<220> FEATURE:
<223> OTHER INFORMATION: R43P3F2 beta chain

<400> SEQUENCE: 52

Met Leu Ser Pro Asp Leu Pro Asp Ser Ala Trp Asn Thr Arg Leu Leu
 1               5                  10                  15

Cys His Val Met Leu Cys Leu Leu Gly Ala Val Ser Val Ala Ala Gly
                 20                  25                  30

Val Ile Gln Ser Pro Arg His Leu Ile Lys Glu Lys Arg Glu Thr Ala
                 35                  40                  45

Thr Leu Lys Cys Tyr Pro Ile Pro Arg His Asp Thr Val Tyr Trp Tyr
 50                  55                  60

Gln Gln Gly Pro Gly Gln Asp Pro Gln Phe Leu Ile Ser Phe Tyr Glu
 65                  70                  75                  80

Lys Met Gln Ser Asp Lys Gly Ser Ile Pro Asp Arg Phe Ser Ala Gln
                 85                  90                  95

Gln Phe Ser Asp Tyr His Ser Glu Leu Asn Met Ser Ser Leu Glu Leu
                100                 105                 110

Gly Asp Ser Ala Leu Tyr Phe Cys Ala Ser Ser Pro Thr Gly Thr Ser
```

```
                     115                 120                 125
Gly Tyr Asn Glu Gln Phe Phe Gly Pro Gly Thr Arg Leu Thr Val Leu
    130                 135                 140

Glu Asp Leu Lys Asn Val Phe Pro Pro Glu Val Ala Val Phe Glu Pro
145                 150                 155                 160

Ser Glu Ala Glu Ile Ser His Thr Gln Lys Ala Thr Leu Val Cys Leu
                165                 170                 175

Ala Thr Gly Phe Tyr Pro Asp His Val Glu Leu Ser Trp Trp Val Asn
            180                 185                 190

Gly Lys Glu Val His Ser Gly Val Ser Thr Asp Pro Gln Pro Leu Lys
        195                 200                 205

Glu Gln Pro Ala Leu Asn Asp Ser Arg Tyr Cys Leu Ser Ser Arg Leu
    210                 215                 220

Arg Val Ser Ala Thr Phe Trp Gln Asn Pro Arg Asn His Phe Arg Cys
225                 230                 235                 240

Gln Val Gln Phe Tyr Gly Leu Ser Glu Asn Asp Glu Trp Thr Gln Asp
                245                 250                 255

Arg Ala Lys Pro Val Thr Gln Ile Val Ser Ala Glu Ala Trp Gly Arg
            260                 265                 270

Ala Asp Cys Gly Phe Thr Ser Glu Ser Tyr Gln Gln Gly Val Leu Ser
        275                 280                 285

Ala Thr Ile Leu Tyr Glu Ile Leu Leu Gly Lys Ala Thr Leu Tyr Ala
    290                 295                 300

Val Leu Val Ser Ala Leu Val Leu Met Ala Met Val Lys Arg Lys Asp
305                 310                 315                 320

Ser Arg Gly

<210> SEQ ID NO 53
<211> LENGTH: 273
<212> TYPE: PRT
<213> ORGANISM: Artificial Sequence
<220> FEATURE:
<223> OTHER INFORMATION: R43P3G5 alpha chain

<400> SEQUENCE: 53

Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
                20                  25                  30

Leu His Val Gln Glu Gly Asp Ser Thr Asn Phe Thr Cys Ser Phe Pro
            35                  40                  45

Ser Ser Asn Phe Tyr Ala Leu His Trp Tyr Arg Trp Glu Thr Ala Lys
50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
                85                  90                  95

Leu Tyr Ile Lys Gly Ser Gln Pro Glu Asp Ser Ala Thr Tyr Leu Cys
            100                 105                 110

Ala Leu Asn Arg Asp Asp Lys Ile Ile Phe Gly Lys Gly Thr Arg Leu
        115                 120                 125

His Ile Leu Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160
```

```
Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser
```

<210> SEQ ID NO 54
<211> LENGTH: 311
<212> TYPE: PRT
<213> ORGANISM: Artificial Sequence
<220> FEATURE:
<223> OTHER INFORMATION: R43P3G5 beta chain

<400> SEQUENCE: 54

```
Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Arg Leu Pro Ser Arg Thr Tyr Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240
```

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
            290                 295                 300

Lys Arg Lys Asp Ser Arg Gly
305                 310

<210> SEQ ID NO 55
<211> LENGTH: 270
<212> TYPE: PRT
<213> ORGANISM: Artificial Sequence
<220> FEATURE:
<223> OTHER INFORMATION: R59P2E7 alpha chain

<400> SEQUENCE: 55

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Asn
            100                 105                 110

Ser Asp Tyr Lys Leu Ser Phe Gly Ala Gly Thr Thr Val Thr Val Arg
            115                 120                 125

Ala Asn Ile Gln Asn Pro Asp Pro Ala Val Tyr Gln Leu Arg Asp Ser
            130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
            195                 200                 205

Ser Ile Ile Pro Glu Asp Thr Phe Phe Pro Ser Pro Glu Ser Ser Cys
            210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 56
<211> LENGTH: 321

```
<212> TYPE: PRT
<213> ORGANISM: Artificial Sequence
<220> FEATURE:
<223> OTHER INFORMATION: R59P2E7 beta chain

<400> SEQUENCE: 56

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65              70                  75                  80

Lys Met Gln Ser Asp Lys Gly Ser Ile Pro Asp Arg Phe Ser Ala Gln
            85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Gly Leu Gly Thr
            115                 120                 125

Gly Asp Tyr Gly Tyr Thr Phe Gly Ser Gly Thr Arg Leu Thr Val Val
130                 135                 140

Glu Asp Leu Asn Lys Val Phe Pro Pro Glu Val Ala Val Phe Glu Pro
145                 150                 155                 160

Ser Glu Ala Glu Ile Ser His Thr Gln Lys Ala Thr Leu Val Cys Leu
                165                 170                 175

Ala Thr Gly Phe Phe Pro Asp His Val Glu Leu Ser Trp Trp Val Asn
            180                 185                 190

Gly Lys Glu Val His Ser Gly Val Ser Thr Asp Pro Gln Pro Leu Lys
        195                 200                 205

Glu Gln Pro Ala Leu Asn Asp Ser Arg Tyr Cys Leu Ser Ser Arg Leu
210                 215                 220

Arg Val Ser Ala Thr Phe Trp Gln Asn Pro Arg Asn His Phe Arg Cys
225                 230                 235                 240

Gln Val Gln Phe Tyr Gly Leu Ser Glu Asn Asp Glu Trp Thr Gln Asp
                245                 250                 255

Arg Ala Lys Pro Val Thr Gln Ile Val Ser Ala Glu Ala Trp Gly Arg
            260                 265                 270

Ala Asp Cys Gly Phe Thr Ser Val Ser Tyr Gln Gln Gly Val Leu Ser
        275                 280                 285

Ala Thr Ile Leu Tyr Glu Ile Leu Leu Gly Lys Ala Thr Leu Tyr Ala
290                 295                 300

Val Leu Val Ser Ala Leu Val Leu Met Ala Met Val Lys Arg Lys Asp
305                 310                 315                 320

Phe

<210> SEQ ID NO 57
<211> LENGTH: 273
<212> TYPE: PRT
<213> ORGANISM: Artificial Sequence
<220> FEATURE:
<223> OTHER INFORMATION: R11P3D3 alpha chain

<400> SEQUENCE: 57
```

Met Glu Lys Asn Pro Leu Ala Ala Pro Leu Ile Leu Trp Phe His
1               5                   10                  15

Leu Asp Cys Val Ser Ser Ile Leu Asn Val Glu Gln Ser Pro Gln Ser
            20                  25                  30

Leu His Val Gln Glu Gly Asp Ser Thr Asn Phe Thr Cys Ser Phe Pro
            35                  40                  45

Ser Ser Asn Phe Tyr Ala Leu His Trp Tyr Arg Trp Glu Thr Ala Lys
50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
            85                  90                  95

Leu Tyr Ile Lys Gly Ser Gln Pro Glu Asp Ser Ala Thr Tyr Leu Cys
            100                 105                 110

Ala Leu Tyr Asn Asn Asn Asp Met Arg Phe Gly Ala Gly Thr Arg Leu
            115                 120                 125

Thr Val Lys Pro Asn Ile Gln Asn Pro Asp Pro Ala Val Tyr Gln Leu
            130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Pro Glu
210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 58
<211> LENGTH: 311
<212> TYPE: PRT
<213> ORGANISM: Artificial Sequence
<220> FEATURE:
<223> OTHER INFORMATION: R11P3D3 beta chain

<400> SEQUENCE: 58

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
            35                  40                  45

Asn Ser Leu Phe Trp Tyr Arg Gln Thr Met Met Arg Gly Leu Glu Leu
50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu

-continued

```
                85                  90                  95
Lys Ile Gln Pro Ser Glu Pro Arg Asp Ser Ala Val Tyr Phe Cys Ala
            100                 105                 110
Ser Ser Pro Gly Ser Thr Asp Thr Gln Tyr Phe Gly Pro Gly Thr Arg
            115                 120                 125
Leu Thr Val Leu Glu Asp Leu Lys Asn Val Phe Pro Pro Glu Val Ala
            130                 135                 140
Val Phe Glu Pro Ser Glu Ala Glu Ile Ser His Thr Gln Lys Ala Thr
145                 150                 155                 160
Leu Val Cys Leu Ala Thr Gly Phe Tyr Pro Asp His Val Glu Leu Ser
                165                 170                 175
Trp Trp Val Asn Gly Lys Glu Val His Ser Gly Val Ser Thr Asp Pro
                180                 185                 190
Gln Pro Leu Lys Glu Gln Pro Ala Leu Asn Asp Ser Arg Tyr Cys Leu
                195                 200                 205
Ser Ser Arg Leu Arg Val Ser Ala Thr Phe Trp Gln Asn Pro Arg Asn
            210                 215                 220
His Phe Arg Cys Gln Val Gln Phe Tyr Gly Leu Ser Glu Asn Asp Glu
225                 230                 235                 240
Trp Thr Gln Asp Arg Ala Lys Pro Val Thr Gln Ile Val Ser Ala Glu
                245                 250                 255
Ala Trp Gly Arg Ala Asp Cys Gly Phe Thr Ser Glu Ser Tyr Gln Gln
                260                 265                 270
Gly Val Leu Ser Ala Thr Leu Leu Tyr Glu Ile Leu Leu Gly Lys Ala
            275                 280                 285
Thr Leu Tyr Ala Val Leu Val Ser Ala Leu Val Leu Met Ala Met Val
            290                 295                 300
Lys Arg Lys Asp Ser Arg Gly
305                 310

<210> SEQ ID NO 59
<211> LENGTH: 275
<212> TYPE: PRT
<213> ORGANISM: Artificial Sequence
<220> FEATURE:
<223> OTHER INFORMATION: R16P1C10 alpha chain

<400> SEQUENCE: 59

Met Lys Ser Leu Arg Val Leu Leu Val Ile Leu Trp Leu Gln Leu Ser
1               5                   10                  15
Trp Val Trp Ser Gln Gln Lys Glu Val Glu Gln Asn Ser Gly Pro Leu
                20                  25                  30
Ser Val Pro Glu Gly Ala Ile Ala Ser Leu Asn Cys Thr Tyr Ser Asp
            35                  40                  45
Arg Gly Ser Gln Ser Phe Phe Trp Tyr Arg Gln Tyr Ser Gly Lys Ser
        50                  55                  60
Pro Glu Leu Ile Met Phe Ile Tyr Ser Asn Gly Asp Lys Glu Asp Gly
65                  70                  75                  80
Arg Phe Thr Ala Gln Leu Asn Lys Ala Ser Gln Tyr Val Ser Leu Leu
                85                  90                  95
Ile Arg Asp Ser Gln Pro Ser Asp Ser Ala Thr Tyr Leu Cys Ala Ala
            100                 105                 110
Val Ile Ser Asn Phe Gly Asn Glu Lys Leu Thr Phe Gly Thr Gly Thr
            115                 120                 125
Arg Leu Thr Ile Ile Pro Asn Ile Gln Asn Pro Asp Pro Ala Val Tyr
```

```
              130                 135                 140
Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
            195                 200                 205

Asn Ala Phe Asn Asn Ser Ile Ile Pro Glu Asp Thr Phe Phe Pro Ser
            210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
            245                 250                 255

Leu Leu Leu Lys Val Ala Gly Phe Asn Leu Leu Met Thr Leu Arg Leu
            260                 265                 270

Trp Ser Ser
      275

<210> SEQ ID NO 60
<211> LENGTH: 311
<212> TYPE: PRT
<213> ORGANISM: Artificial Sequence
<220> FEATURE:
<223> OTHER INFORMATION: R16P1C10 beta chain

<400> SEQUENCE: 60

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
                20                  25                  30

Thr Arg Gly Gln Gln Val Thr Leu Ser Cys Ser Pro Ile Ser Gly His
            35                  40                  45

Arg Ser Val Ser Trp Tyr Gln Gln Thr Pro Gly Gln Gly Leu Gln Phe
        50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Pro Trp Asp Ser Pro Asn Glu Gln Tyr Phe Gly Pro Gly Thr Arg
        115                 120                 125

Leu Thr Val Thr Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
```

-continued

```
                210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
                275                 280                 285

Thr Leu Tyr Ala Val Leu Val Ser Ala Leu Val Leu Met Ala Met Val
                290                 295                 300

Lys Arg Lys Asp Ser Arg Gly
305                 310

<210> SEQ ID NO 61
<211> LENGTH: 274
<212> TYPE: PRT
<213> ORGANISM: Artificial Sequence
<220> FEATURE:
<223> OTHER INFORMATION: R16P1E8 alpha chain

<400> SEQUENCE: 61

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
                20                  25                  30

Leu Ser Val Pro Glu Gly Ala Ile Val Ser Leu Asn Cys Thr Tyr Ser
                35                  40                  45

Asn Ser Ala Phe Gln Tyr Phe Met Trp Tyr Arg Gln Tyr Ser Arg Lys
            50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
                100                 105                 110

Met Ser Glu Ala Ala Gly Asn Lys Leu Thr Phe Gly Gly Gly Thr Arg
                115                 120                 125

Val Leu Val Lys Pro Asn Ile Gln Asn Pro Asp Pro Ala Val Tyr Gln
                130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
                180                 185                 190

Asn Ser Ala Val Ala Trp Ser Asn Lys Ser Asp Phe Ala Cys Ala Asn
                195                 200                 205

Ala Phe Asn Asn Ser Ile Ile Pro Glu Asp Thr Phe Phe Pro Ser Pro
                210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
```

Ser Ser

<210> SEQ ID NO 62
<211> LENGTH: 309
<212> TYPE: PRT
<213> ORGANISM: Artificial Sequence
<220> FEATURE:
<223> OTHER INFORMATION: R16P1E8 beta chain

<400> SEQUENCE: 62

Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Ser Tyr Thr Asn Gln Gly Glu Ala Phe Phe Gly Gln Gly Thr Arg
        115                 120                 125

Leu Thr Val Val Glu Asp Leu Asn Lys Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe
305

<210> SEQ ID NO 63
<211> LENGTH: 273
<212> TYPE: PRT
<213> ORGANISM: Artificial Sequence -continued

```
<220> FEATURE:
<223> OTHER INFORMATION: R17P1A9 alpha chain

<400> SEQUENCE: 63

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Ser Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Leu Asn Gln Ala Gly Thr Ala Leu Ile Phe Gly Lys Gly Thr Thr Leu
        115                 120                 125

Ser Val Ser Ser Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 64
<211> LENGTH: 314
<212> TYPE: PRT
<213> ORGANISM: Artificial Sequence
<220> FEATURE:
<223> OTHER INFORMATION: R17P1A9 beta chain

<400> SEQUENCE: 64

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60
```

-continued

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
            85                  90                  95

Leu Ser Ser Leu Glu Leu Gly Asp Ser Ala Leu Tyr Phe Cys Ala Ser
        100                 105                 110

Ser Ala Glu Thr Gly Pro Trp Leu Gly Asn Glu Gln Phe Phe Gly Pro
    115                 120                 125

Gly Thr Arg Leu Thr Val Leu Glu Asp Leu Lys Asn Val Phe Pro Pro
130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly
305                 310

<210> SEQ ID NO 65
<211> LENGTH: 277
<212> TYPE: PRT
<213> ORGANISM: Artificial Sequence
<220> FEATURE:
<223> OTHER INFORMATION: R17P1D7 alpha chain

<400> SEQUENCE: 65

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
            85                  90                  95

Leu Lys Ile Ser Asp Ser Gln Leu Gly Asp Ala Ala Met Tyr Phe Cys
        100                 105                 110

Ala Tyr Arg Trp Ala Gln Gly Gly Ser Glu Lys Leu Val Phe Gly Lys
            115                 120                 125

Gly Thr Lys Leu Thr Val Asn Pro Tyr Ile Gln Lys Pro Asp Pro Ala
    130                 135                 140

Val Tyr Gln Leu Arg Asp Ser Lys Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
                180                 185                 190

Phe Lys Ser Asn Ser Ala Val Ala Trp Ser Asn Lys Ser Asp Phe Ala
            195                 200                 205

Cys Ala Asn Ala Phe Asn Asn Ser Ile Ile Pro Glu Asp Thr Phe Phe
210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275

<210> SEQ ID NO 66
<211> LENGTH: 313
<212> TYPE: PRT
<213> ORGANISM: Artificial Sequence
<220> FEATURE:
<223> OTHER INFORMATION: R17P1D7 beta chain

<400> SEQUENCE: 66

Met Thr Ile Arg Leu Leu Cys Tyr Met Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
        35                  40                  45

Asp Lys Met Tyr Trp Tyr Gln Gln Asp Pro Gly Met Glu Leu His Leu
    50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Thr
            100                 105                 110

Glu Leu Trp Ser Ser Gly Gly Thr Gly Glu Leu Phe Phe Gly Glu Gly
        115                 120                 125

Ser Arg Leu Thr Val Leu Glu Asp Leu Lys Asn Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

```
Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
        210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
            245                 250                 255

Ala Glu Ala Trp Gly Arg Ala Asp Cys Gly Phe Thr Ser Glu Ser Tyr
        260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
290                 295                 300

Met Val Lys Arg Lys Asp Ser Arg Gly
305                 310

<210> SEQ ID NO 67
<211> LENGTH: 273
<212> TYPE: PRT
<213> ORGANISM: Artificial Sequence
<220> FEATURE:
<223> OTHER INFORMATION: R17P1G3 alpha chain

<400> SEQUENCE: 67

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Ser Ile Tyr Ser Asn Gly Asp Lys Glu Asp Gly
65              70                  75                  80

Arg Phe Thr Ala Gln Leu Asn Lys Ala Ser Gln Tyr Val Ser Leu Leu
            85                  90                  95

Ile Arg Asp Ser Gln Pro Ser Asp Ser Ala Thr Tyr Leu Cys Ala Val
        100                 105                 110

Gly Pro Ser Gly Thr Tyr Lys Tyr Ile Phe Gly Thr Gly Thr Arg Leu
    115                 120                 125

Lys Val Leu Ala Asn Ile Gln Asn Pro Asp Pro Ala Val Tyr Gln Leu
130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
            165                 170                 175

Thr Asp Lys Thr Val Leu Asp Met Arg Ser Met Asp Phe Lys Ser Asn
        180                 185                 190

Ser Ala Val Ala Trp Ser Asn Lys Ser Asp Phe Ala Cys Ala Asn Ala
    195                 200                 205

Phe Asn Asn Ser Ile Ile Pro Glu Asp Thr Phe Phe Pro Ser Pro Glu
210                 215                 220

Ser Ser Cys Asp Val Lys Leu Val Glu Lys Ser Phe Glu Thr Asp Thr
225                 230                 235                 240
```

```
Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 68
<211> LENGTH: 311
<212> TYPE: PRT
<213> ORGANISM: Artificial Sequence
<220> FEATURE:
<223> OTHER INFORMATION: R17P1G3 beta chain

<400> SEQUENCE: 68

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Pro Gly Gly Ser Gly Asn Glu Gln Phe Phe Gly Pro Gly Thr Arg
        115                 120                 125

Leu Thr Val Leu Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
290                 295                 300

Lys Arg Lys Asp Ser Arg Gly
305                 310
```

```
<210> SEQ ID NO 69
<211> LENGTH: 274
<212> TYPE: PRT
<213> ORGANISM: Artificial Sequence
<220> FEATURE:
<223> OTHER INFORMATION: R17P2B6 alpha chain

<400> SEQUENCE: 69

Met Lys Ser Leu Arg Val Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Val Ser Gly Gly Gly Ala Asp Gly Leu Thr Phe Gly Lys Gly Thr His
        115                 120                 125

Leu Ile Ile Gln Pro Tyr Ile Gln Lys Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 70
<211> LENGTH: 319
<212> TYPE: PRT
<213> ORGANISM: Artificial Sequence
<220> FEATURE:
<223> OTHER INFORMATION: R17P2B6 beta chain

<400> SEQUENCE: 70

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30
```

Val Ile Gln Ser Pro Arg His Leu Ile Lys Glu Lys Arg Glu Thr Ala
                35                  40                  45

Thr Leu Lys Cys Tyr Pro Ile Pro Arg His Asp Thr Val Tyr Trp Tyr
 50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Gly Arg Gly Gly
            115                 120                 125

Gln Pro Gln His Phe Gly Asp Gly Thr Arg Leu Ser Ile Leu Glu Asp
            130                 135                 140

Leu Asn Lys Val Phe Pro Pro Glu Val Ala Val Phe Glu Pro Ser Glu
145                 150                 155                 160

Ala Glu Ile Ser His Thr Gln Lys Ala Thr Leu Val Cys Leu Ala Thr
                165                 170                 175

Gly Phe Phe Pro Asp His Val Glu Leu Ser Trp Trp Val Asn Gly Lys
                180                 185                 190

Glu Val His Ser Gly Val Ser Thr Asp Pro Gln Pro Leu Lys Glu Gln
            195                 200                 205

Pro Ala Leu Asn Asp Ser Arg Tyr Cys Leu Ser Ser Arg Leu Arg Val
            210                 215                 220

Ser Ala Thr Phe Trp Gln Asn Pro Arg Asn His Phe Arg Cys Gln Val
225                 230                 235                 240

Gln Phe Tyr Gly Leu Ser Glu Asn Asp Glu Trp Thr Gln Asp Arg Ala
                245                 250                 255

Lys Pro Val Thr Gln Ile Val Ser Ala Glu Ala Trp Gly Arg Ala Asp
                260                 265                 270

Cys Gly Phe Thr Ser Val Ser Tyr Gln Gln Gly Val Leu Ser Ala Thr
                275                 280                 285

Ile Leu Tyr Glu Ile Leu Leu Gly Lys Ala Thr Leu Tyr Ala Val Leu
                290                 295                 300

Val Ser Ala Leu Val Leu Met Ala Met Val Lys Arg Lys Asp Phe
305                 310                 315

```
<210> SEQ ID NO 71
<211> LENGTH: 273
<212> TYPE: PRT
<213> ORGANISM: Artificial Sequence
<220> FEATURE:
<223> OTHER INFORMATION: R11P3D3KE alpha chain

<400> SEQUENCE: 71
```

Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
                20                  25                  30

Leu His Val Gln Glu Gly Asp Ser Thr Asn Phe Thr Cys Ser Phe Pro
            35                  40                  45

Ser Ser Asn Phe Tyr Ala Leu His Trp Tyr Arg Lys Glu Thr Ala Lys
            50                  55                  60

Ser Pro Glu Ala Leu Phe Val Met Thr Leu Asn Gly Asp Glu Lys Lys
65                  70                  75                  80

```
Lys Gly Arg Ile Ser Ala Thr Leu Asn Thr Lys Glu Gly Tyr Ser Tyr
                85                  90                  95

Leu Tyr Ile Lys Gly Ser Gln Pro Glu Asp Ser Ala Thr Tyr Leu Cys
            100                 105                 110

Ala Leu Tyr Asn Asn Asp Met Arg Phe Gly Ala Gly Thr Arg Leu
            115                 120                 125

Thr Val Lys Pro Asn Ile Gln Asn Pro Asp Pro Ala Val Tyr Gln Leu
130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 72
<211> LENGTH: 243
<212> TYPE: PRT
<213> ORGANISM: Artificial Sequence
<220> FEATURE:
<223> OTHER INFORMATION: R11P3D3KE beta chain

<400> SEQUENCE: 72

Asn Asn Asn Val Pro Ile Asp Asp Ser Gly Met Pro Glu Asp Arg Phe
1               5                   10                  15

Ser Ala Lys Met Pro Asn Ala Ser Phe Ser Thr Leu Lys Ile Gln Pro
            20                  25                  30

Ser Glu Pro Arg Asp Ser Ala Val Tyr Phe Cys Ala Ser Ser Pro Gly
            35                  40                  45

Ser Thr Asp Thr Gln Tyr Phe Gly Pro Gly Thr Arg Leu Thr Val Leu
50                  55                  60

Glu Asp Leu Lys Asn Val Phe Pro Pro Glu Val Ala Val Phe Glu Pro
65                  70                  75                  80

Ser Glu Ala Glu Ile Ser His Thr Gln Lys Ala Thr Leu Val Cys Leu
                85                  90                  95

Ala Thr Gly Phe Tyr Pro Asp His Val Glu Leu Ser Trp Trp Val Asn
            100                 105                 110

Gly Lys Glu Val His Ser Gly Val Ser Thr Asp Pro Gln Pro Leu Lys
            115                 120                 125

Glu Gln Pro Ala Leu Asn Asp Ser Arg Tyr Cys Leu Ser Ser Arg Leu
            130                 135                 140

Arg Val Ser Ala Thr Phe Trp Gln Asn Pro Arg Asn His Phe Arg Cys
145                 150                 155                 160

Gln Val Gln Phe Tyr Gly Leu Ser Glu Asn Asp Glu Trp Thr Gln Asp
```

```
                    165                 170                 175
Arg Ala Lys Pro Val Thr Gln Ile Val Ser Ala Glu Ala Trp Gly Arg
                180                 185                 190

Ala Asp Cys Gly Phe Thr Ser Glu Ser Tyr Gln Gln Gly Val Leu Ser
                195                 200                 205

Ala Thr Leu Leu Tyr Glu Ile Leu Leu Gly Lys Ala Thr Leu Tyr Ala
            210                 215                 220

Val Leu Val Ser Ala Leu Val Leu Met Ala Met Val Lys Arg Lys Asp
225                 230                 235                 240

Ser Arg Gly

<210> SEQ ID NO 73
<211> LENGTH: 223
<212> TYPE: PRT
<213> ORGANISM: Artificial Sequence
<220> FEATURE:
<223> OTHER INFORMATION: R39P1C12 alpha chain

<400> SEQUENCE: 73

Thr Tyr Leu Tyr Trp Tyr Lys Gln Glu Pro Gly Ala Gly Leu Gln Leu
1               5                   10                  15

Leu Thr Tyr Ile Phe Ser Asn Met Asp Met Lys Gln Asp Gln Arg Leu
                20                  25                  30

Thr Val Leu Leu Asn Lys Lys Asp Lys His Leu Ser Leu Arg Ile Ala
            35                  40                  45

Asp Thr Gln Thr Gly Asp Ser Ala Ile Tyr Phe Cys Ala Glu Ile Asp
        50                  55                  60

Asn Gln Gly Gly Lys Leu Ile Phe Gly Gln Gly Thr Glu Leu Ser Val
65                  70                  75                  80

Lys Pro Asn Ile Gln Asn Pro Asp Pro Ala Val Tyr Gln Leu Arg Asp
                85                  90                  95

Ser Lys Ser Ser Asp Lys Ser Val Cys Leu Phe Thr Asp Phe Asp Ser
            100                 105                 110

Gln Thr Asn Val Ser Gln Ser Lys Asp Ser Asp Val Tyr Ile Thr Asp
        115                 120                 125

Lys Thr Val Leu Asp Met Arg Ser Met Asp Phe Lys Ser Asn Ser Ala
130                 135                 140

Val Ala Trp Ser Asn Lys Ser Asp Phe Ala Cys Ala Asn Ala Phe Asn
                145                 150                 155                 160

Asn Ser Ile Ile Pro Glu Asp Thr Phe Phe Pro Ser Pro Glu Ser Ser
            165                 170                 175

Cys Asp Val Lys Leu Val Glu Lys Ser Phe Glu Thr Asp Thr Asn Leu
        180                 185                 190

Asn Phe Gln Asn Leu Ser Val Ile Gly Phe Arg Ile Leu Leu Leu Lys
    195                 200                 205

Val Ala Gly Phe Asn Leu Leu Met Thr Leu Arg Leu Trp Ser Ser
    210                 215                 220

<210> SEQ ID NO 74
<211> LENGTH: 307
<212> TYPE: PRT
<213> ORGANISM: Artificial Sequence
<220> FEATURE:
<223> OTHER INFORMATION: R39P1C12 beta chain

<400> SEQUENCE: 74

Met Gly Pro Gly Leu Leu Cys Trp Ala Leu Leu Cys Leu Leu Gly Ala
```

```
            1               5                  10                 15
        Gly Leu Val Asp Ala Gly Val Thr Gln Ser Pro Thr His Leu Ile Lys
                        20                 25                 30

Thr Arg Gly Gln Gln Val Thr Leu Arg Cys Ser Pro Lys Ser Gly His
                    35                 40                 45

Asp Thr Val Ser Trp Tyr Gln Gln Ala Leu Gly Gln Gly Pro Gln Phe
                50                 55                 60

Ile Phe Gln Tyr Tyr Glu Glu Glu Arg Gln Arg Gly Asn Phe Pro
        65                 70                 75                 80

Asp Arg Phe Ser Gly His Gln Phe Pro Asn Tyr Ser Ser Glu Leu Asn
                        85                 90                 95

Val Asn Ala Leu Leu Leu Gly Asp Ser Ala Leu Tyr Leu Cys Ala Ser
                    100                105                110

Ser Gln Leu Asn Thr Glu Ala Phe Phe Gly Gln Gly Thr Arg Leu Thr
                    115                120                125

Val Val Glu Asp Leu Asn Lys Val Phe Pro Pro Glu Val Ala Val Phe
                130                135                140

Glu Pro Ser Glu Ala Glu Ile Ser His Thr Gln Lys Ala Thr Leu Val
        145                150                155                160

Cys Leu Ala Thr Gly Phe Phe Pro Asp His Val Glu Leu Ser Trp Trp
                        165                170                175

Val Asn Gly Lys Glu Val His Ser Gly Val Ser Thr Asp Pro Gln Pro
                    180                185                190

Leu Lys Glu Gln Pro Ala Leu Asn Asp Ser Arg Tyr Cys Leu Ser Ser
                    195                200                205

Arg Leu Arg Val Ser Ala Thr Phe Trp Gln Asn Pro Arg Asn His Phe
                210                215                220

Arg Cys Gln Val Gln Phe Tyr Gly Leu Ser Glu Asn Asp Glu Trp Thr
        225                230                235                240

Gln Asp Arg Ala Lys Pro Val Thr Gln Ile Val Ser Ala Glu Ala Trp
                        245                250                255

Gly Arg Ala Asp Cys Gly Phe Thr Ser Val Ser Tyr Gln Gln Gly Val
                    260                265                270

Leu Ser Ala Thr Ile Leu Tyr Glu Ile Leu Leu Gly Lys Ala Thr Leu
                    275                280                285

Tyr Ala Val Leu Val Ser Ala Leu Val Leu Met Ala Met Val Lys Arg
                290                295                300

Lys Asp Phe
        305

<210> SEQ ID NO 75
<211> LENGTH: 270
<212> TYPE: PRT
<213> ORGANISM: Artificial Sequence
<220> FEATURE:
<223> OTHER INFORMATION: R39P1F5 alpha chain

<400> SEQUENCE: 75

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
                    20                  25                  30

Ser Val Pro Glu Gly Ala Ile Ala Ser Leu Asn Cys Thr Tyr Ser Asp
                35                  40                  45

Arg Gly Ser Gln Ser Phe Phe Trp Tyr Arg Gln Tyr Ser Gly Lys Ser
```

-continued

```
            50                  55                  60
Pro Glu Leu Ile Met Phe Ile Tyr Ser Asn Gly Asp Lys Glu Asp Gly
 65                  70                  75                  80
Arg Phe Thr Ala Gln Leu Asn Lys Ala Ser Gln Tyr Val Ser Leu Leu
                 85                  90                  95
Ile Arg Asp Ser Gln Pro Ser Asp Ser Ala Thr Tyr Leu Cys Ala Val
            100                 105                 110
Asn Asn Ala Arg Leu Met Phe Gly Asp Gly Thr Gln Leu Val Val Lys
        115                 120                 125
Pro Asn Ile Gln Asn Pro Asp Pro Ala Val Tyr Gln Leu Arg Asp Ser
130                 135                 140
Lys Ser Ser Asp Lys Ser Val Cys Leu Phe Thr Asp Phe Asp Ser Gln
145                 150                 155                 160
Thr Asn Val Ser Gln Ser Lys Asp Ser Asp Val Tyr Ile Thr Asp Lys
                165                 170                 175
Thr Val Leu Asp Met Arg Ser Met Asp Phe Lys Ser Asn Ser Ala Val
            180                 185                 190
Ala Trp Ser Asn Lys Ser Asp Phe Ala Cys Ala Asn Ala Phe Asn Asn
        195                 200                 205
Ser Ile Ile Pro Glu Asp Thr Phe Phe Pro Ser Pro Glu Ser Ser Cys
210                 215                 220
Asp Val Lys Leu Val Glu Lys Ser Phe Glu Thr Asp Thr Asn Leu Asn
225                 230                 235                 240
Phe Gln Asn Leu Ser Val Ile Gly Phe Arg Ile Leu Leu Leu Lys Val
                245                 250                 255
Ala Gly Phe Asn Leu Leu Met Thr Leu Arg Leu Trp Ser Ser
            260                 265                 270

<210> SEQ ID NO 76
<211> LENGTH: 311
<212> TYPE: PRT
<213> ORGANISM: Artificial Sequence
<220> FEATURE:
<223> OTHER INFORMATION: R39P1F5 beta chain

<400> SEQUENCE: 76

Met Asp Thr Trp Leu Val Cys Trp Ala Ile Phe Ser Leu Leu Lys Ala
  1               5                  10                  15
Gly Leu Thr Glu Pro Glu Val Thr Gln Thr Pro Ser His Gln Val Thr
                 20                  25                  30
Gln Met Gly Gln Glu Val Ile Leu Arg Cys Val Pro Ile Ser Asn His
             35                  40                  45
Leu Tyr Phe Tyr Trp Tyr Arg Gln Ile Leu Gly Gln Lys Val Glu Phe
         50                  55                  60
Leu Val Ser Phe Tyr Asn Asn Glu Ile Ser Glu Lys Ser Glu Ile Phe
 65                  70                  75                  80
Asp Asp Gln Phe Ser Val Glu Arg Pro Asp Gly Ser Asn Phe Thr Leu
                 85                  90                  95
Lys Ile Arg Ser Thr Lys Leu Glu Asp Ser Ala Met Tyr Phe Cys Ala
            100                 105                 110
Ser Ser Gly Gln Gly Ala Asn Glu Gln Tyr Phe Gly Pro Gly Thr Arg
        115                 120                 125
Leu Thr Val Thr Glu Asp Leu Lys Asn Val Phe Pro Pro Glu Val Ala
130                 135                 140
Val Phe Glu Pro Ser Glu Ala Glu Ile Ser His Thr Gln Lys Ala Thr
```

```
145                 150                 155                 160
Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
                180                 185                 190

Gln Pro Leu Lys Glu Gln Pro Ala Leu Asn Asp Ser Arg Tyr Cys Leu
                195                 200                 205

Ser Ser Arg Leu Arg Val Ser Ala Thr Phe Trp Gln Asn Pro Arg Asn
                210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
                275                 280                 285

Thr Leu Tyr Ala Val Leu Val Ser Ala Leu Val Leu Met Ala Met Val
                290                 295                 300

Lys Arg Lys Asp Ser Arg Gly
305                 310

<210> SEQ ID NO 77
<211> LENGTH: 272
<212> TYPE: PRT
<213> ORGANISM: Artificial Sequence
<220> FEATURE:
<223> OTHER INFORMATION: R40P1C2 alpha chain

<400> SEQUENCE: 77

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
                20                  25                  30

Val Gln Glu Ala Glu Thr Val Thr Leu Ser Cys Thr Tyr Asp Thr Ser
                35                  40                  45

Glu Ser Asp Tyr Tyr Leu Phe Trp Tyr Lys Gln Pro Pro Ser Arg Gln
                50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
                100                 105                 110

Ala Tyr Leu Asn Tyr Gln Leu Ile Trp Gly Ala Gly Thr Lys Leu Ile
                115                 120                 125

Ile Lys Pro Asp Ile Gln Asn Pro Asp Pro Ala Val Tyr Gln Leu Arg
                130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
                180                 185                 190

Ala Val Ala Trp Ser Asn Lys Ser Asp Phe Ala Cys Ala Asn Ala Phe
```

```
            195                 200                 205
Asn Asn Ser Ile Ile Pro Glu Asp Thr Phe Phe Pro Ser Pro Glu Ser
        210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 78
<211> LENGTH: 311
<212> TYPE: PRT
<213> ORGANISM: Artificial Sequence
<220> FEATURE:
<223> OTHER INFORMATION: R40P1C2 beta chain

<400> SEQUENCE: 78

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Glu Met Thr Ala Val Gly Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
```

```
            290                 295                 300

Lys Arg Lys Asp Ser Arg Gly
305                 310

<210> SEQ ID NO 79
<211> LENGTH: 271
<212> TYPE: PRT
<213> ORGANISM: Artificial Sequence
<220> FEATURE:
<223> OTHER INFORMATION: R41P3E6 alpha chain

<400> SEQUENCE: 79

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Ala
            100                 105                 110

Phe Ser Gly Tyr Ala Leu Asn Phe Gly Lys Gly Thr Ser Leu Leu Val
        115                 120                 125

Thr Pro His Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 80
<211> LENGTH: 310
<212> TYPE: PRT
<213> ORGANISM: Artificial Sequence
<220> FEATURE:
<223> OTHER INFORMATION: R41P3E6 beta chain

<400> SEQUENCE: 80

Met Asp Thr Trp Leu Val Cys Trp Ala Ile Phe Ser Leu Leu Lys Ala
1               5                   10                  15
```

Gly Leu Thr Glu Pro Glu Val Thr Gln Thr Pro Ser His Gln Val Thr
                20                  25                  30

Gln Met Gly Gln Glu Val Ile Leu Arg Cys Val Pro Ile Ser Asn His
            35                  40                  45

Leu Tyr Phe Tyr Trp Tyr Arg Gln Ile Leu Gly Gln Lys Val Glu Phe
50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Gln Tyr Thr Gly Glu Leu Phe Phe Gly Glu Gly Ser Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 81
<211> LENGTH: 270
<212> TYPE: PRT
<213> ORGANISM: Artificial Sequence
<220> FEATURE:
<223> OTHER INFORMATION: R43P3G4 alpha chain

<400> SEQUENCE: 81

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
                20                  25                  30

Ser Val Pro Glu Gly Ala Ile Ala Ser Leu Asn Cys Thr Tyr Ser Asp
            35                  40                  45

Arg Gly Ser Gln Ser Phe Phe Trp Tyr Arg Gln Tyr Ser Gly Lys Ser
        50                  55                  60

```
Pro Glu Leu Ile Met Phe Ile Tyr Ser Asn Gly Asp Lys Glu Asp Gly
 65                  70                  75                  80

Arg Phe Thr Ala Gln Leu Asn Lys Ala Ser Gln Tyr Val Ser Leu Leu
                 85                  90                  95

Ile Arg Asp Ser Gln Pro Ser Asp Ser Ala Thr Tyr Leu Cys Ala Val
            100                 105                 110

Asn Gly Gly Asp Met Arg Phe Gly Ala Gly Thr Arg Leu Thr Val Lys
        115                 120                 125

Pro Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 82
<211> LENGTH: 311
<212> TYPE: PRT
<213> ORGANISM: Artificial Sequence
<220> FEATURE:
<223> OTHER INFORMATION: R43P3G4 beta chain

<400> SEQUENCE: 82

Met Asp Thr Trp Leu Val Cys Trp Ala Ile Phe Ser Leu Leu Lys Ala
 1               5                  10                  15

Gly Leu Thr Glu Pro Glu Val Thr Gln Thr Pro Ser His Gln Val Thr
                20                  25                  30

Gln Met Gly Gln Glu Val Ile Leu Arg Cys Val Pro Ile Ser Asn His
            35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Gly Gln Gly Ala Leu Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160
```

```
Leu Val Cys Leu Ala Thr Gly Phe Tyr Pro Asp His Val Glu Leu Ser
            165                 170                 175

Trp Trp Val Asn Gly Lys Glu Val His Ser Gly Val Ser Thr Asp Pro
        180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
            290                 295                 300

Lys Arg Lys Asp Ser Arg Gly
305                 310

<210> SEQ ID NO 83
<211> LENGTH: 281
<212> TYPE: PRT
<213> ORGANISM: Artificial Sequence
<220> FEATURE:
<223> OTHER INFORMATION: R44P3B3 alpha chain

<400> SEQUENCE: 83

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Ser Gly Leu Tyr Asn Gln Gly Gly Lys Leu
        115                 120                 125

Ile Phe Gly Gln Gly Thr Glu Leu Ser Val Lys Pro Asn Ile Gln Asn
130                 135                 140

Pro Asp Pro Ala Val Tyr Gln Leu Arg Asp Ser Lys Ser Ser Asp Lys
145                 150                 155                 160

Ser Val Cys Leu Phe Thr Asp Phe Asp Ser Gln Thr Asn Val Ser Gln
                165                 170                 175

Ser Lys Asp Ser Asp Val Tyr Ile Thr Asp Lys Thr Val Leu Asp Met
            180                 185                 190

Arg Ser Met Asp Phe Lys Ser Asn Ser Ala Val Ala Trp Ser Asn Lys
        195                 200                 205
```

```
Ser Asp Phe Ala Cys Ala Asn Ala Phe Asn Asn Ser Ile Ile Pro Glu
    210                 215                 220

Asp Thr Phe Phe Pro Ser Pro Glu Ser Ser Cys Asp Val Lys Leu Val
225                 230                 235                 240

Glu Lys Ser Phe Glu Thr Asp Thr Asn Leu Asn Phe Gln Asn Leu Ser
                245                 250                 255

Val Ile Gly Phe Arg Ile Leu Leu Lys Val Ala Gly Phe Asn Leu
                260                 265                 270

Leu Met Thr Leu Arg Leu Trp Ser Ser
            275                 280

<210> SEQ ID NO 84
<211> LENGTH: 311
<212> TYPE: PRT
<213> ORGANISM: Artificial Sequence
<220> FEATURE:
<223> OTHER INFORMATION: R44P3B3 beta chain

<400> SEQUENCE: 84

Met Gly Cys Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
                20                  25                  30

Gln Met Gly Asn Asp Lys Ser Ile Lys Cys Glu Gln Asn Leu Gly His
            35                  40                  45

Asp Thr Met Tyr Trp Tyr Lys Gln Asp Ser Lys Lys Phe Leu Lys Ile
        50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100                 105                 110

Ser Leu Gly Asp Arg Gly Tyr Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285
```

Thr Leu Tyr Ala Val Leu Val Ser Ala Leu Val Leu Met Ala Met Val
            290                 295                 300

Lys Arg Lys Asp Ser Arg Gly
305                 310

<210> SEQ ID NO 85
<211> LENGTH: 272
<212> TYPE: PRT
<213> ORGANISM: Artificial Sequence
<220> FEATURE:
<223> OTHER INFORMATION: R44P3E7 alpha chain

<400> SEQUENCE: 85

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
    50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Ile Asn Asn Asn Ala Arg Leu Met Phe Gly Asp Gly Thr Gln Leu Val
        115                 120                 125

Val Lys Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 86
<211> LENGTH: 320
<212> TYPE: PRT
<213> ORGANISM: Artificial Sequence
<220> FEATURE:
<223> OTHER INFORMATION: R44P3E7 beta chain

<400> SEQUENCE: 86

Met Leu Ser Pro Asp Leu Pro Asp Ser Ala Trp Asn Thr Arg Leu Leu
1               5                   10                  15

-continued

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
                100                 105                 110

Gly Asp Ser Ala Leu Tyr Phe Cys Ala Ser Ser Pro Asp Gln Asn
            115                 120                 125

Thr Gln Tyr Phe Gly Pro Gly Thr Arg Leu Thr Val Leu Glu Asp Leu
    130                 135                 140

Lys Asn Val Phe Pro Pro Glu Val Ala Val Phe Glu Pro Ser Glu Ala
145                 150                 155                 160

Glu Ile Ser His Thr Gln Lys Ala Thr Leu Val Cys Leu Ala Thr Gly
                165                 170                 175

Phe Tyr Pro Asp His Val Glu Leu Ser Trp Trp Val Asn Gly Lys Glu
            180                 185                 190

Val His Ser Gly Val Ser Thr Asp Pro Gln Pro Leu Lys Glu Gln Pro
        195                 200                 205

Ala Leu Asn Asp Ser Arg Tyr Cys Leu Ser Ser Arg Leu Arg Val Ser
    210                 215                 220

Ala Thr Phe Trp Gln Asn Pro Arg Asn His Phe Arg Cys Gln Val Gln
225                 230                 235                 240

Phe Tyr Gly Leu Ser Glu Asn Asp Glu Trp Thr Gln Asp Arg Ala Lys
                245                 250                 255

Pro Val Thr Gln Ile Val Ser Ala Glu Ala Trp Gly Arg Ala Asp Cys
                260                 265                 270

Gly Phe Thr Ser Glu Ser Tyr Gln Gln Gly Val Leu Ser Ala Thr Ile
            275                 280                 285

Leu Tyr Glu Ile Leu Leu Gly Lys Ala Thr Leu Tyr Ala Val Leu Val
    290                 295                 300

Ser Ala Leu Val Leu Met Ala Met Val Lys Arg Lys Asp Ser Arg Gly
305                 310                 315                 320

<210> SEQ ID NO 87
<211> LENGTH: 273
<212> TYPE: PRT
<213> ORGANISM: Artificial Sequence
<220> FEATURE:
<223> OTHER INFORMATION: R49P2B7 alpha chain

<400> SEQUENCE: 87

Met Leu Leu Leu Leu Val Pro Val Leu Glu Val Ile Phe Thr Leu Gly
1               5                   10                  15

Gly Thr Arg Ala Gln Ser Val Thr Gln Leu Gly Ser His Val Ser Val
            20                  25                  30

Ser Glu Gly Ala Leu Val Leu Leu Arg Cys Asn Tyr Ser Ser Ser Val
        35                  40                  45

Pro Pro Tyr Leu Phe Trp Tyr Val Gln Tyr Pro Asn Gln Gly Leu Gln
    50                  55                  60

```
Leu Leu Leu Lys Tyr Thr Thr Gly Ala Thr Leu Val Lys Gly Ile Asn
 65                  70                  75                  80

Gly Phe Glu Ala Glu Phe Lys Lys Ser Glu Thr Ser Phe His Leu Thr
                 85                  90                  95

Lys Pro Ser Ala His Met Ser Asp Ala Ala Glu Tyr Phe Cys Ala Val
            100                 105                 110

Arg Ile Phe Gly Asn Glu Lys Leu Thr Phe Gly Thr Gly Thr Arg Leu
            115                 120                 125

Thr Ile Ile Pro Asn Ile Gln Asn Pro Asp Pro Ala Val Tyr Gln Leu
        130                 135                 140

Arg Asp Ser Lys Ser Asp Lys Ser Val Cys Leu Phe Thr Asp Phe Asp
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Pro Glu
210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 88
<211> LENGTH: 312
<212> TYPE: PRT
<213> ORGANISM: Artificial Sequence
<220> FEATURE:
<223> OTHER INFORMATION: R49P2B7 beta chain

<400> SEQUENCE: 88

Met Gly Ile Arg Leu Leu Cys Arg Val Ala Phe Cys Phe Leu Ala Val
 1               5                  10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
             35                  40                  45

Glu Asn Met Phe Trp Tyr Arg Gln Asp Pro Gly Leu Gly Leu Arg Leu
         50                  55                  60

Ile Tyr Phe Ser Tyr Asp Val Lys Met Lys Glu Lys Gly Asp Ile Pro
 65                  70                  75                  80

Glu Gly Tyr Ser Val Ser Arg Glu Lys Lys Glu Arg Phe Ser Leu Ile
                 85                  90                  95

Leu Glu Ser Ala Ser Thr Asn Gln Thr Ser Met Tyr Leu Cys Ala Ser
            100                 105                 110

Ser Leu Met Gly Glu Leu Thr Gly Glu Leu Phe Phe Gly Glu Gly Ser
            115                 120                 125

Arg Leu Thr Val Leu Glu Asp Leu Lys Asn Val Phe Pro Pro Glu Val
        130                 135                 140
```

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
            165                 170                 175

Ser Trp Trp Val Asn Gly Lys Glu Val His Ser Gly Val Ser Thr Asp
        180                 185                 190

Pro Gln Pro Leu Lys Glu Gln Pro Ala Leu Asn Asp Ser Arg Tyr Cys
    195                 200                 205

Leu Ser Ser Arg Leu Arg Val Ser Ala Thr Phe Trp Gln Asn Pro Arg
210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
            245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 89
<211> LENGTH: 276
<212> TYPE: PRT
<213> ORGANISM: Artificial Sequence
<220> FEATURE:
<223> OTHER INFORMATION: R55P1G7 alpha chain

<400> SEQUENCE: 89

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
            85                  90                  95

Phe Ile Arg Asp Ser Gln Pro Ser Asp Ser Ala Thr Tyr Leu Cys Ala
        100                 105                 110

Met Met Gly Asp Thr Gly Thr Ala Ser Lys Leu Thr Phe Gly Thr Gly
    115                 120                 125

Thr Arg Leu Gln Val Thr Leu Asp Ile Gln Asn Pro Asp Pro Ala Val
130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
            165                 170                 175

Val Tyr Ile Thr Asp Lys Thr Val Leu Asp Met Arg Ser Met Asp Phe
        180                 185                 190

```
Lys Ser Asn Ser Ala Val Ala Trp Ser Asn Lys Ser Asp Phe Ala Cys
            195                 200                 205

Ala Asn Ala Phe Asn Asn Ser Ile Ile Pro Glu Asp Thr Phe Pro
210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
            245                 250                 255

Ile Leu Leu Lys Val Ala Gly Phe Asn Leu Leu Met Thr Leu Arg
            260                 265                 270

Leu Trp Ser Ser
            275

<210> SEQ ID NO 90
<211> LENGTH: 309
<212> TYPE: PRT
<213> ORGANISM: Artificial Sequence
<220> FEATURE:
<223> OTHER INFORMATION: R55P1G7 beta chain

<400> SEQUENCE: 90

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Phe Gly Gly Tyr Glu Gln Tyr Phe Gly Pro Gly Thr Arg Leu Thr
        115                 120                 125

Val Thr Glu Asp Leu Lys Asn Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
            260                 265                 270
```

```
Leu Ser Ala Thr Ile Leu Tyr Glu Ile Leu Gly Lys Ala Thr Leu
        275                 280                 285

Tyr Ala Val Leu Val Ser Ala Leu Val Leu Met Ala Met Val Lys Arg
290                 295                 300

Lys Asp Ser Arg Gly
305
```

<210> SEQ ID NO 91
<211> LENGTH: 270
<212> TYPE: PRT
<213> ORGANISM: Artificial Sequence
<220> FEATURE:
<223> OTHER INFORMATION: R59P2A7 alpha chain

<400> SEQUENCE: 91

```
Met Lys Ser Leu Arg Val Leu Val Ile Leu Trp Leu Gln Leu Ser
 1               5                  10                  15

Trp Val Trp Ser Gln Gln Lys Glu Val Glu Gln Asn Ser Gly Pro Leu
                20                  25                  30

Ser Val Pro Glu Gly Ala Ile Ala Ser Leu Asn Cys Thr Tyr Ser Asp
            35                  40                  45

Arg Gly Ser Gln Ser Phe Phe Trp Tyr Arg Gln Tyr Ser Gly Lys Ser
        50                  55                  60

Pro Glu Leu Ile Met Ser Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Gln Pro His Asp Met Arg Phe Gly Ala Gly Thr Arg Leu Thr Val Lys
        115                 120                 125

Pro Asn Ile Gln Asn Pro Asp Pro Ala Val Tyr Gln Leu Arg Asp Ser
130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270
```

<210> SEQ ID NO 92
<211> LENGTH: 307
<212> TYPE: PRT
<213> ORGANISM: Artificial Sequence
<220> FEATURE:
<223> OTHER INFORMATION: R59P2A7 beta chain

<400> SEQUENCE: 92

Met Leu Cys Ser Leu Leu Ala Leu Leu Leu Gly Thr Phe Phe Gly Val
1               5                   10                  15

Arg Ser Gln Thr Ile His Gln Trp Pro Ala Thr Leu Val Gln Pro Val
                20                  25                  30

Gly Ser Pro Leu Ser Leu Glu Cys Thr Val Glu Gly Thr Ser Asn Pro
            35                  40                  45

Asn Leu Tyr Trp Tyr Arg Gln Ala Ala Gly Arg Gly Leu Gln Leu Leu
    50                  55                  60

Phe Tyr Ser Val Gly Ile Gly Gln Ile Ser Ser Glu Val Pro Gln Asn
65                  70                  75                  80

Leu Ser Ala Ser Arg Pro Gln Asp Arg Gln Phe Ile Leu Ser Ser Lys
                85                  90                  95

Lys Leu Leu Leu Ser Asp Ser Gly Phe Tyr Leu Cys Ala Trp Ser Gly
                100                 105                 110

Leu Val Ala Glu Gln Phe Phe Gly Pro Gly Thr Arg Leu Thr Val Leu
            115                 120                 125

Glu Asp Leu Lys Asn Val Phe Pro Pro Glu Val Ala Val Phe Glu Pro
            130                 135                 140

Ser Glu Ala Glu Ile Ser His Thr Gln Lys Ala Thr Leu Val Cys Leu
145                 150                 155                 160

Ala Thr Gly Phe Tyr Pro Asp His Val Glu Leu Ser Trp Trp Val Asn
                165                 170                 175

Gly Lys Glu Val His Ser Gly Val Ser Thr Asp Pro Gln Pro Leu Lys
            180                 185                 190

Glu Gln Pro Ala Leu Asn Asp Ser Arg Tyr Cys Leu Ser Ser Arg Leu
            195                 200                 205

Arg Val Ser Ala Thr Phe Trp Gln Asn Pro Arg Asn His Phe Arg Cys
210                 215                 220

Gln Val Gln Phe Tyr Gly Leu Ser Glu Asn Asp Glu Trp Thr Gln Asp
225                 230                 235                 240

Arg Ala Lys Pro Val Thr Gln Ile Val Ser Ala Glu Ala Trp Gly Arg
                245                 250                 255

Ala Asp Cys Gly Phe Thr Ser Glu Ser Tyr Gln Gln Gly Val Leu Ser
            260                 265                 270

Ala Thr Ile Leu Tyr Glu Ile Leu Leu Gly Lys Ala Thr Leu Tyr Ala
            275                 280                 285

Val Leu Val Ser Ala Leu Val Leu Met Ala Met Val Lys Arg Lys Asp
            290                 295                 300

Ser Arg Gly
305

<210> SEQ ID NO 93
<211> LENGTH: 19
<212> TYPE: PRT
<213> ORGANISM: Artificial Sequence
<220> FEATURE:
<223> OTHER INFORMATION: P2A

<400> SEQUENCE: 93

Ala Thr Asn Phe Ser Leu Leu Lys Gln Ala Gly Asp Val Glu Glu Asn
1               5                   10                  15

Pro Gly Pro

<210> SEQ ID NO 94
<211> LENGTH: 18

```
<212> TYPE: PRT
<213> ORGANISM: Artificial Sequence
<220> FEATURE:
<223> OTHER INFORMATION: T2A

<400> SEQUENCE: 94

Glu Gly Arg Gly Ser Leu Leu Thr Cys Gly Asp Val Glu Glu Asn Pro
1               5                   10                  15

Gly Pro

<210> SEQ ID NO 95
<211> LENGTH: 20
<212> TYPE: PRT
<213> ORGANISM: Artificial Sequence
<220> FEATURE:
<223> OTHER INFORMATION: E2A

<400> SEQUENCE: 95

Gln Cys Thr Asn Tyr Ala Leu Leu Lys Leu Ala Gly Asp Val Glu Ser
1               5                   10                  15

Asn Pro Gly Pro
            20

<210> SEQ ID NO 96
<211> LENGTH: 22
<212> TYPE: PRT
<213> ORGANISM: Artificial Sequence
<220> FEATURE:
<223> OTHER INFORMATION: F2A

<400> SEQUENCE: 96

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 97
<211> LENGTH: 559
<212> TYPE: PRT
<213> ORGANISM: Artificial Sequence
<220> FEATURE:
<223> OTHER INFORMATION: RD114TR

<400> SEQUENCE: 97

Met Lys Leu Pro Thr Gly Met Val Ile Leu Cys Ser Leu Ile Ile Val
1               5                   10                  15

Arg Ala Gly Phe Asp Asp Pro Arg Lys Ala Ile Ala Leu Val Gln Lys
                20                  25                  30

Gln His Gly Lys Pro Cys Glu Cys Ser Gly Gly Gln Val Ser Glu Ala
        35                  40                  45

Pro Pro Asn Ser Ile Gln Gln Val Thr Cys Pro Gly Lys Thr Ala Tyr
    50                  55                  60

Leu Met Thr Asn Gln Lys Trp Lys Cys Arg Val Thr Pro Lys Ile Ser
65                  70                  75                  80

Pro Ser Gly Gly Glu Leu Gln Asn Cys Pro Cys Asn Thr Phe Gln Asp
                85                  90                  95

Ser Met His Ser Ser Cys Tyr Thr Glu Tyr Arg Gln Cys Arg Arg Ile
                100                 105                 110

Asn Lys Thr Tyr Tyr Thr Ala Thr Leu Leu Lys Ile Arg Ser Gly Ser
        115                 120                 125

Leu Asn Glu Val Gln Ile Leu Gln Asn Pro Asn Gln Leu Leu Gln Ser
```

```
                130             135             140
Pro Cys Arg Gly Ser Ile Asn Gln Pro Val Cys Trp Ser Ala Thr Ala
145                 150                 155                 160

Pro Ile His Ile Ser Asp Gly Gly Pro Leu Asp Thr Lys Arg Val
                165                 170                 175

Trp Thr Val Gln Lys Arg Leu Glu Gln Ile His Lys Ala Met Thr Pro
            180                 185                 190

Glu Leu Gln Tyr His Pro Leu Ala Leu Pro Lys Val Arg Asp Asp Leu
        195                 200                 205

Ser Leu Asp Ala Arg Thr Phe Asp Ile Leu Asn Thr Thr Phe Arg Leu
    210                 215                 220

Leu Gln Met Ser Asn Phe Ser Leu Ala Gln Asp Cys Trp Leu Cys Leu
225                 230                 235                 240

Lys Leu Gly Thr Pro Thr Pro Leu Ala Ile Pro Thr Pro Ser Leu Thr
                245                 250                 255

Tyr Ser Leu Ala Asp Ser Leu Ala Asn Ala Ser Cys Gln Ile Ile Pro
                260                 265                 270

Pro Leu Leu Val Gln Pro Met Gln Phe Ser Asn Ser Ser Cys Leu Ser
            275                 280                 285

Ser Pro Phe Ile Asn Asp Thr Glu Gln Ile Asp Leu Gly Ala Val Thr
        290                 295                 300

Phe Thr Asn Cys Thr Ser Val Ala Asn Val Ser Ser Pro Leu Cys Ala
305                 310                 315                 320

Leu Asn Gly Ser Val Phe Leu Cys Gly Asn Asn Met Ala Tyr Thr Tyr
                325                 330                 335

Leu Pro Gln Asn Trp Thr Arg Leu Cys Val Gln Ala Ser Leu Leu Pro
                340                 345                 350

Asp Ile Asp Ile Asn Pro Gly Asp Glu Pro Val Pro Ile Pro Ala Ile
            355                 360                 365

Asp His Tyr Ile His Arg Pro Lys Arg Ala Val Gln Phe Ile Pro Leu
        370                 375                 380

Leu Ala Gly Leu Gly Ile Thr Ala Ala Phe Thr Thr Gly Ala Thr Gly
385                 390                 395                 400

Leu Gly Val Ser Val Thr Gln Tyr Thr Lys Leu Ser His Gln Leu Ile
                405                 410                 415

Ser Asp Val Gln Val Leu Ser Gly Thr Ile Gln Asp Leu Gln Asp Gln
                420                 425                 430

Val Asp Ser Leu Ala Glu Val Val Leu Gln Asn Arg Arg Gly Leu Asp
            435                 440                 445

Leu Leu Thr Ala Glu Gln Gly Gly Ile Cys Leu Ala Leu Gln Glu Lys
        450                 455                 460

Cys Cys Phe Tyr Ala Asn Lys Ser Gly Ile Val Arg Asn Lys Ile Arg
465                 470                 475                 480

Thr Leu Gln Glu Glu Leu Gln Lys Arg Arg Glu Ser Leu Ala Ser Asn
                485                 490                 495

Pro Leu Trp Thr Gly Leu Gln Gly Phe Leu Pro Tyr Leu Leu Pro Leu
                500                 505                 510

Leu Gly Pro Leu Leu Thr Leu Leu Leu Ile Leu Thr Ile Gly Pro Cys
            515                 520                 525

Val Phe Asn Arg Leu Val Gln Phe Val Lys Asp Arg Ile Ser Val Val
        530                 535                 540

Gln Ala Leu Val Leu Thr Gln Gln Tyr His Gln Leu Lys Pro Leu
545                 550                 555
```

<210> SEQ ID NO 98
<211> LENGTH: 10
<212> TYPE: PRT
<213> ORGANISM: Homo sapiens

<400> SEQUENCE: 98

Tyr Leu Tyr Asp Ser Glu Thr Lys Asn Ala
1               5                   10

<210> SEQ ID NO 99
<211> LENGTH: 9
<212> TYPE: PRT
<213> ORGANISM: Homo sapiens

<400> SEQUENCE: 99

His Leu Met Asp Gln Pro Leu Ser Val
1               5

<210> SEQ ID NO 100
<211> LENGTH: 9
<212> TYPE: PRT
<213> ORGANISM: Homo sapiens

<400> SEQUENCE: 100

Gly Leu Leu Lys Lys Ile Asn Ser Val
1               5

<210> SEQ ID NO 101
<211> LENGTH: 9
<212> TYPE: PRT
<213> ORGANISM: Homo sapiens

<400> SEQUENCE: 101

Phe Leu Val Asp Gly Ser Ser Ala Leu
1               5

<210> SEQ ID NO 102
<211> LENGTH: 10
<212> TYPE: PRT
<213> ORGANISM: Homo sapiens

<400> SEQUENCE: 102

Phe Leu Phe Asp Gly Ser Ala Asn Leu Val
1               5                   10

<210> SEQ ID NO 103
<211> LENGTH: 9
<212> TYPE: PRT
<213> ORGANISM: Homo sapiens

<400> SEQUENCE: 103

Phe Leu Tyr Lys Ile Ile Asp Glu Leu
1               5

<210> SEQ ID NO 104
<211> LENGTH: 11
<212> TYPE: PRT
<213> ORGANISM: Homo sapiens

<400> SEQUENCE: 104

Phe Ile Leu Asp Ser Ala Glu Thr Thr Thr Leu
1               5                   10

```
<210> SEQ ID NO 105
<211> LENGTH: 9
<212> TYPE: PRT
<213> ORGANISM: Homo sapiens

<400> SEQUENCE: 105

Ser Val Asp Val Ser Pro Pro Lys Val
1               5

<210> SEQ ID NO 106
<211> LENGTH: 8
<212> TYPE: PRT
<213> ORGANISM: Homo sapiens

<400> SEQUENCE: 106

Val Ala Asp Lys Ile His Ser Val
1               5

<210> SEQ ID NO 107
<211> LENGTH: 9
<212> TYPE: PRT
<213> ORGANISM: Homo sapiens

<400> SEQUENCE: 107

Ile Val Asp Asp Leu Thr Ile Asn Leu
1               5

<210> SEQ ID NO 108
<211> LENGTH: 9
<212> TYPE: PRT
<213> ORGANISM: Homo sapiens

<400> SEQUENCE: 108

Gly Leu Leu Glu Glu Leu Val Thr Val
1               5

<210> SEQ ID NO 109
<211> LENGTH: 10
<212> TYPE: PRT
<213> ORGANISM: Homo sapiens

<400> SEQUENCE: 109

Thr Leu Asp Gly Ala Ala Val Asn Gln Val
1               5                   10

<210> SEQ ID NO 110
<211> LENGTH: 10
<212> TYPE: PRT
<213> ORGANISM: Homo sapiens

<400> SEQUENCE: 110

Ser Val Leu Glu Lys Glu Ile Tyr Ser Ile
1               5                   10

<210> SEQ ID NO 111
<211> LENGTH: 9
<212> TYPE: PRT
<213> ORGANISM: Homo sapiens

<400> SEQUENCE: 111

Leu Leu Asp Pro Lys Thr Ile Phe Leu
1               5

<210> SEQ ID NO 112
<211> LENGTH: 9
```

```
<212> TYPE: PRT
<213> ORGANISM: Homo sapiens

<400> SEQUENCE: 112

Tyr Thr Phe Ser Gly Asp Val Gln Leu
1               5

<210> SEQ ID NO 113
<211> LENGTH: 9
<212> TYPE: PRT
<213> ORGANISM: Homo sapiens

<400> SEQUENCE: 113

Tyr Leu Met Asp Asp Phe Ser Ser Leu
1               5

<210> SEQ ID NO 114
<211> LENGTH: 9
<212> TYPE: PRT
<213> ORGANISM: Homo sapiens

<400> SEQUENCE: 114

Lys Val Trp Ser Asp Val Thr Pro Leu
1               5

<210> SEQ ID NO 115
<211> LENGTH: 11
<212> TYPE: PRT
<213> ORGANISM: Homo sapiens

<400> SEQUENCE: 115

Leu Leu Trp Gly His Pro Arg Val Ala Leu Ala
1               5                   10

<210> SEQ ID NO 116
<211> LENGTH: 11
<212> TYPE: PRT
<213> ORGANISM: Homo sapiens

<400> SEQUENCE: 116

Lys Ile Trp Glu Glu Leu Ser Val Leu Glu Val
1               5                   10

<210> SEQ ID NO 117
<211> LENGTH: 9
<212> TYPE: PRT
<213> ORGANISM: Homo sapiens

<400> SEQUENCE: 117

Leu Leu Ile Pro Phe Thr Ile Phe Met
1               5

<210> SEQ ID NO 118
<211> LENGTH: 9
<212> TYPE: PRT
<213> ORGANISM: Homo sapiens

<400> SEQUENCE: 118

Phe Leu Ile Glu Asn Leu Leu Ala Ala
1               5

<210> SEQ ID NO 119
<211> LENGTH: 11
<212> TYPE: PRT
<213> ORGANISM: Homo sapiens
```

<400> SEQUENCE: 119

Leu Leu Trp Gly His Pro Arg Val Ala Leu Ala
1               5                   10

<210> SEQ ID NO 120
<211> LENGTH: 9
<212> TYPE: PRT
<213> ORGANISM: Homo sapiens

<400> SEQUENCE: 120

Phe Leu Leu Glu Arg Glu Gln Leu Leu
1               5

<210> SEQ ID NO 121
<211> LENGTH: 9
<212> TYPE: PRT
<213> ORGANISM: Homo sapiens

<400> SEQUENCE: 121

Ser Leu Ala Glu Thr Ile Phe Ile Val
1               5

<210> SEQ ID NO 122
<211> LENGTH: 9
<212> TYPE: PRT
<213> ORGANISM: Homo sapiens

<400> SEQUENCE: 122

Thr Leu Leu Glu Gly Ile Ser Arg Ala
1               5

<210> SEQ ID NO 123
<211> LENGTH: 9
<212> TYPE: PRT
<213> ORGANISM: Homo sapiens

<400> SEQUENCE: 123

Lys Ile Gln Glu Ile Leu Thr Gln Val
1               5

<210> SEQ ID NO 124
<211> LENGTH: 10
<212> TYPE: PRT
<213> ORGANISM: Homo sapiens

<400> SEQUENCE: 124

Val Ile Phe Glu Gly Glu Pro Met Tyr Leu
1               5                   10

<210> SEQ ID NO 125
<211> LENGTH: 9
<212> TYPE: PRT
<213> ORGANISM: Homo sapiens

<400> SEQUENCE: 125

Ser Leu Phe Glu Ser Leu Glu Tyr Leu
1               5

<210> SEQ ID NO 126
<211> LENGTH: 9
<212> TYPE: PRT
<213> ORGANISM: Homo sapiens

<400> SEQUENCE: 126

Ser Leu Leu Asn Gln Pro Lys Ala Val
1               5

<210> SEQ ID NO 127
<211> LENGTH: 9
<212> TYPE: PRT
<213> ORGANISM: Homo sapiens

<400> SEQUENCE: 127

Gly Leu Ala Glu Phe Gln Glu Asn Val
1               5

<210> SEQ ID NO 128
<211> LENGTH: 9
<212> TYPE: PRT
<213> ORGANISM: Homo sapiens

<400> SEQUENCE: 128

Lys Leu Leu Ala Val Ile His Glu Leu
1               5

<210> SEQ ID NO 129
<211> LENGTH: 9
<212> TYPE: PRT
<213> ORGANISM: Homo sapiens

<400> SEQUENCE: 129

Thr Leu His Asp Gln Val His Leu Leu
1               5

<210> SEQ ID NO 130
<211> LENGTH: 11
<212> TYPE: PRT
<213> ORGANISM: Homo sapiens

<400> SEQUENCE: 130

Thr Leu Tyr Asn Pro Glu Arg Thr Ile Thr Val
1               5                   10

<210> SEQ ID NO 131
<211> LENGTH: 9
<212> TYPE: PRT
<213> ORGANISM: Homo sapiens

<400> SEQUENCE: 131

Lys Leu Gln Glu Lys Ile Gln Glu Leu
1               5

<210> SEQ ID NO 132
<211> LENGTH: 10
<212> TYPE: PRT
<213> ORGANISM: Homo sapiens

<400> SEQUENCE: 132

Ser Val Leu Glu Lys Glu Ile Tyr Ser Ile
1               5                   10

<210> SEQ ID NO 133
<211> LENGTH: 11
<212> TYPE: PRT
<213> ORGANISM: Homo sapiens

<400> SEQUENCE: 133

Arg Val Ile Asp Asp Ser Leu Val Val Gly Val

<210> SEQ ID NO 134
<211> LENGTH: 9
<212> TYPE: PRT
<213> ORGANISM: Homo sapiens

<400> SEQUENCE: 134

Val Leu Phe Gly Glu Leu Pro Ala Leu
1               5

<210> SEQ ID NO 135
<211> LENGTH: 9
<212> TYPE: PRT
<213> ORGANISM: Homo sapiens

<400> SEQUENCE: 135

Gly Leu Val Asp Ile Met Val His Leu
1               5

<210> SEQ ID NO 136
<211> LENGTH: 9
<212> TYPE: PRT
<213> ORGANISM: Homo sapiens

<400> SEQUENCE: 136

Phe Leu Asn Ala Ile Glu Thr Ala Leu
1               5

<210> SEQ ID NO 137
<211> LENGTH: 9
<212> TYPE: PRT
<213> ORGANISM: Homo sapiens

<400> SEQUENCE: 137

Ala Leu Leu Gln Ala Leu Met Glu Leu
1               5

<210> SEQ ID NO 138
<211> LENGTH: 9
<212> TYPE: PRT
<213> ORGANISM: Homo sapiens

<400> SEQUENCE: 138

Ala Leu Ser Ser Ser Gln Ala Glu Val
1               5

<210> SEQ ID NO 139
<211> LENGTH: 11
<212> TYPE: PRT
<213> ORGANISM: Homo sapiens

<400> SEQUENCE: 139

Ser Leu Ile Thr Gly Gln Asp Leu Leu Ser Val
1               5                   10

<210> SEQ ID NO 140
<211> LENGTH: 9
<212> TYPE: PRT
<213> ORGANISM: Homo sapiens

<400> SEQUENCE: 140

Gln Leu Ile Glu Lys Asn Trp Leu Leu
1               5

<210> SEQ ID NO 141
<211> LENGTH: 9
<212> TYPE: PRT
<213> ORGANISM: Homo sapiens

<400> SEQUENCE: 141

Leu Leu Asp Pro Lys Thr Ile Phe Leu
1               5

<210> SEQ ID NO 142
<211> LENGTH: 9
<212> TYPE: PRT
<213> ORGANISM: Homo sapiens

<400> SEQUENCE: 142

Arg Leu His Asp Glu Asn Ile Leu Leu
1               5

<210> SEQ ID NO 143
<211> LENGTH: 9
<212> TYPE: PRT
<213> ORGANISM: Homo sapiens

<400> SEQUENCE: 143

Tyr Thr Phe Ser Gly Asp Val Gln Leu
1               5

<210> SEQ ID NO 144
<211> LENGTH: 9
<212> TYPE: PRT
<213> ORGANISM: Homo sapiens

<400> SEQUENCE: 144

Gly Leu Pro Ser Ala Thr Thr Thr Val
1               5

<210> SEQ ID NO 145
<211> LENGTH: 11
<212> TYPE: PRT
<213> ORGANISM: Homo sapiens

<400> SEQUENCE: 145

Gly Leu Leu Pro Ser Ala Glu Ser Ile Lys Leu
1               5                   10

<210> SEQ ID NO 146
<211> LENGTH: 9
<212> TYPE: PRT
<213> ORGANISM: Homo sapiens

<400> SEQUENCE: 146

Lys Thr Ala Ser Ile Asn Gln Asn Val
1               5

<210> SEQ ID NO 147
<211> LENGTH: 9
<212> TYPE: PRT
<213> ORGANISM: Homo sapiens

<400> SEQUENCE: 147

Ser Leu Leu Gln His Leu Ile Gly Leu
1               5

<210> SEQ ID NO 148

```
<211> LENGTH: 9
<212> TYPE: PRT
<213> ORGANISM: Homo sapiens

<400> SEQUENCE: 148

Tyr Leu Met Asp Asp Phe Ser Ser Leu
1               5

<210> SEQ ID NO 149
<211> LENGTH: 9
<212> TYPE: PRT
<213> ORGANISM: Homo sapiens

<400> SEQUENCE: 149

Leu Met Tyr Pro Tyr Ile Tyr His Val
1               5

<210> SEQ ID NO 150
<211> LENGTH: 9
<212> TYPE: PRT
<213> ORGANISM: Homo sapiens

<400> SEQUENCE: 150

Lys Val Trp Ser Asp Val Thr Pro Leu
1               5

<210> SEQ ID NO 151
<211> LENGTH: 11
<212> TYPE: PRT
<213> ORGANISM: Homo sapiens

<400> SEQUENCE: 151

Leu Leu Trp Gly His Pro Arg Val Ala Leu Ala
1               5                   10

<210> SEQ ID NO 152
<211> LENGTH: 9
<212> TYPE: PRT
<213> ORGANISM: Homo sapiens

<400> SEQUENCE: 152

Val Leu Asp Gly Lys Val Ala Val Val
1               5

<210> SEQ ID NO 153
<211> LENGTH: 9
<212> TYPE: PRT
<213> ORGANISM: Homo sapiens

<400> SEQUENCE: 153

Gly Leu Leu Gly Lys Val Thr Ser Val
1               5

<210> SEQ ID NO 154
<211> LENGTH: 9
<212> TYPE: PRT
<213> ORGANISM: Homo sapiens

<400> SEQUENCE: 154

Lys Met Ile Ser Ala Ile Pro Thr Leu
1               5

<210> SEQ ID NO 155
<211> LENGTH: 11
<212> TYPE: PRT
```

```
<213> ORGANISM: Homo sapiens

<400> SEQUENCE: 155

Gly Leu Leu Glu Thr Thr Gly Leu Leu Ala Thr
1               5                   10

<210> SEQ ID NO 156
<211> LENGTH: 9
<212> TYPE: PRT
<213> ORGANISM: Homo sapiens

<400> SEQUENCE: 156

Thr Leu Asn Thr Leu Asp Ile Asn Leu
1               5

<210> SEQ ID NO 157
<211> LENGTH: 9
<212> TYPE: PRT
<213> ORGANISM: Homo sapiens

<400> SEQUENCE: 157

Val Ile Ile Lys Gly Leu Glu Glu Ile
1               5

<210> SEQ ID NO 158
<211> LENGTH: 9
<212> TYPE: PRT
<213> ORGANISM: Homo sapiens

<400> SEQUENCE: 158

Tyr Leu Glu Asp Gly Phe Ala Tyr Val
1               5

<210> SEQ ID NO 159
<211> LENGTH: 11
<212> TYPE: PRT
<213> ORGANISM: Homo sapiens

<400> SEQUENCE: 159

Lys Ile Trp Glu Glu Leu Ser Val Leu Glu Val
1               5                   10

<210> SEQ ID NO 160
<211> LENGTH: 9
<212> TYPE: PRT
<213> ORGANISM: Homo sapiens

<400> SEQUENCE: 160

Leu Leu Ile Pro Phe Thr Ile Phe Met
1               5

<210> SEQ ID NO 161
<211> LENGTH: 10
<212> TYPE: PRT
<213> ORGANISM: Homo sapiens

<400> SEQUENCE: 161

Ile Ser Leu Asp Glu Val Ala Val Ser Leu
1               5                   10

<210> SEQ ID NO 162
<211> LENGTH: 10
<212> TYPE: PRT
<213> ORGANISM: Homo sapiens
```

```
<400> SEQUENCE: 162

Lys Ile Ser Asp Phe Gly Leu Ala Thr Val
1               5                   10

<210> SEQ ID NO 163
<211> LENGTH: 11
<212> TYPE: PRT
<213> ORGANISM: Homo sapiens

<400> SEQUENCE: 163

Lys Leu Ile Gly Asn Ile His Gly Asn Glu Val
1               5                   10

<210> SEQ ID NO 164
<211> LENGTH: 9
<212> TYPE: PRT
<213> ORGANISM: Homo sapiens

<400> SEQUENCE: 164

Ile Leu Leu Ser Val Leu His Gln Leu
1               5

<210> SEQ ID NO 165
<211> LENGTH: 9
<212> TYPE: PRT
<213> ORGANISM: Homo sapiens

<400> SEQUENCE: 165

Leu Asp Ser Glu Ala Leu Leu Thr Leu
1               5

<210> SEQ ID NO 166
<211> LENGTH: 13
<212> TYPE: PRT
<213> ORGANISM: Homo sapiens

<400> SEQUENCE: 166

Val Leu Gln Glu Asn Ser Ser Asp Tyr Gln Ser Asn Leu
1               5                   10

<210> SEQ ID NO 167
<211> LENGTH: 11
<212> TYPE: PRT
<213> ORGANISM: Homo sapiens

<400> SEQUENCE: 167

His Leu Leu Gly Glu Gly Ala Phe Ala Gln Val
1               5                   10

<210> SEQ ID NO 168
<211> LENGTH: 9
<212> TYPE: PRT
<213> ORGANISM: Homo sapiens

<400> SEQUENCE: 168

Ser Leu Val Glu Asn Ile His Val Leu
1               5

<210> SEQ ID NO 169
<211> LENGTH: 9
<212> TYPE: PRT
<213> ORGANISM: Homo sapiens

<400> SEQUENCE: 169
```

Tyr Thr Phe Ser Gly Asp Val Gln Leu
1               5

<210> SEQ ID NO 170
<211> LENGTH: 9
<212> TYPE: PRT
<213> ORGANISM: Homo sapiens

<400> SEQUENCE: 170

Ser Leu Ser Glu Lys Ser Pro Glu Val
1               5

<210> SEQ ID NO 171
<211> LENGTH: 10
<212> TYPE: PRT
<213> ORGANISM: Homo sapiens

<400> SEQUENCE: 171

Ala Met Phe Pro Asp Thr Ile Pro Arg Val
1               5                   10

<210> SEQ ID NO 172
<211> LENGTH: 9
<212> TYPE: PRT
<213> ORGANISM: Homo sapiens

<400> SEQUENCE: 172

Phe Leu Ile Glu Asn Leu Leu Ala Ala
1               5

<210> SEQ ID NO 173
<211> LENGTH: 9
<212> TYPE: PRT
<213> ORGANISM: Homo sapiens

<400> SEQUENCE: 173

Phe Thr Ala Glu Phe Leu Glu Lys Val
1               5

<210> SEQ ID NO 174
<211> LENGTH: 9
<212> TYPE: PRT
<213> ORGANISM: Homo sapiens

<400> SEQUENCE: 174

Ala Leu Tyr Gly Asn Val Gln Gln Val
1               5

<210> SEQ ID NO 175
<211> LENGTH: 9
<212> TYPE: PRT
<213> ORGANISM: Homo sapiens

<400> SEQUENCE: 175

Leu Phe Gln Ser Arg Ile Ala Gly Val
1               5

<210> SEQ ID NO 176
<211> LENGTH: 11
<212> TYPE: PRT
<213> ORGANISM: Homo sapiens

<400> SEQUENCE: 176

Ile Leu Ala Glu Glu Pro Ile Tyr Ile Arg Val
1               5                   10

<210> SEQ ID NO 177
<211> LENGTH: 9
<212> TYPE: PRT
<213> ORGANISM: Homo sapiens

<400> SEQUENCE: 177

Phe Leu Leu Glu Arg Glu Gln Leu Leu
1               5

<210> SEQ ID NO 178
<211> LENGTH: 10
<212> TYPE: PRT
<213> ORGANISM: Homo sapiens

<400> SEQUENCE: 178

Leu Leu Leu Pro Leu Glu Leu Ser Leu Ala
1               5                   10

<210> SEQ ID NO 179
<211> LENGTH: 9
<212> TYPE: PRT
<213> ORGANISM: Homo sapiens

<400> SEQUENCE: 179

Ser Leu Ala Glu Thr Ile Phe Ile Val
1               5

<210> SEQ ID NO 180
<211> LENGTH: 11
<212> TYPE: PRT
<213> ORGANISM: Homo sapiens

<400> SEQUENCE: 180

Ala Ile Leu Asn Val Asp Glu Lys Asn Gln Val
1               5                   10

<210> SEQ ID NO 181
<211> LENGTH: 9
<212> TYPE: PRT
<213> ORGANISM: Homo sapiens

<400> SEQUENCE: 181

Arg Leu Phe Glu Glu Val Leu Gly Val
1               5

<210> SEQ ID NO 182
<211> LENGTH: 9
<212> TYPE: PRT
<213> ORGANISM: Homo sapiens

<400> SEQUENCE: 182

Tyr Leu Asp Glu Val Ala Phe Met Leu
1               5

<210> SEQ ID NO 183
<211> LENGTH: 11
<212> TYPE: PRT
<213> ORGANISM: Homo sapiens

<400> SEQUENCE: 183

Lys Leu Ile Asp Glu Asp Glu Pro Leu Phe Leu
1               5                   10

```
<210> SEQ ID NO 184
<211> LENGTH: 9
<212> TYPE: PRT
<213> ORGANISM: Homo sapiens

<400> SEQUENCE: 184

Lys Leu Phe Glu Lys Ser Thr Gly Leu
1               5

<210> SEQ ID NO 185
<211> LENGTH: 11
<212> TYPE: PRT
<213> ORGANISM: Homo sapiens

<400> SEQUENCE: 185

Ser Leu Leu Glu Val Asn Glu Ala Ser Ser Val
1               5                   10

<210> SEQ ID NO 186
<211> LENGTH: 10
<212> TYPE: PRT
<213> ORGANISM: Homo sapiens

<400> SEQUENCE: 186

Gly Val Tyr Asp Gly Arg Glu His Thr Val
1               5                   10

<210> SEQ ID NO 187
<211> LENGTH: 10
<212> TYPE: PRT
<213> ORGANISM: Homo sapiens

<400> SEQUENCE: 187

Gly Leu Tyr Pro Val Thr Leu Val Gly Val
1               5                   10

<210> SEQ ID NO 188
<211> LENGTH: 9
<212> TYPE: PRT
<213> ORGANISM: Homo sapiens

<400> SEQUENCE: 188

Ala Leu Leu Ser Ser Val Ala Glu Ala
1               5

<210> SEQ ID NO 189
<211> LENGTH: 9
<212> TYPE: PRT
<213> ORGANISM: Homo sapiens

<400> SEQUENCE: 189

Thr Leu Leu Glu Gly Ile Ser Arg Ala
1               5

<210> SEQ ID NO 190
<211> LENGTH: 9
<212> TYPE: PRT
<213> ORGANISM: Homo sapiens

<400> SEQUENCE: 190

Ser Leu Ile Glu Glu Ser Glu Glu Leu
1               5

<210> SEQ ID NO 191
<211> LENGTH: 9
```

<212> TYPE: PRT
<213> ORGANISM: Homo sapiens

<400> SEQUENCE: 191

Ala Leu Tyr Val Gln Ala Pro Thr Val
1               5

<210> SEQ ID NO 192
<211> LENGTH: 10
<212> TYPE: PRT
<213> ORGANISM: Homo sapiens

<400> SEQUENCE: 192

Lys Leu Ile Tyr Lys Asp Leu Val Ser Val
1               5                   10

<210> SEQ ID NO 193
<211> LENGTH: 9
<212> TYPE: PRT
<213> ORGANISM: Homo sapiens

<400> SEQUENCE: 193

Ile Leu Gln Asp Gly Gln Phe Leu Val
1               5

<210> SEQ ID NO 194
<211> LENGTH: 9
<212> TYPE: PRT
<213> ORGANISM: Homo sapiens

<400> SEQUENCE: 194

Ser Leu Leu Asp Tyr Glu Val Ser Ile
1               5

<210> SEQ ID NO 195
<211> LENGTH: 9
<212> TYPE: PRT
<213> ORGANISM: Homo sapiens

<400> SEQUENCE: 195

Leu Leu Gly Asp Ser Ser Phe Phe Leu
1               5

<210> SEQ ID NO 196
<211> LENGTH: 10
<212> TYPE: PRT
<213> ORGANISM: Homo sapiens

<400> SEQUENCE: 196

Val Ile Phe Glu Gly Glu Pro Met Tyr Leu
1               5                   10

<210> SEQ ID NO 197
<211> LENGTH: 9
<212> TYPE: PRT
<213> ORGANISM: Homo sapiens

<400> SEQUENCE: 197

Ala Leu Ser Tyr Ile Leu Pro Tyr Leu
1               5

<210> SEQ ID NO 198
<211> LENGTH: 9
<212> TYPE: PRT
<213> ORGANISM: Homo sapiens

<400> SEQUENCE: 198

Phe Leu Phe Val Asp Pro Glu Leu Val
1               5

<210> SEQ ID NO 199
<211> LENGTH: 11
<212> TYPE: PRT
<213> ORGANISM: Homo sapiens

<400> SEQUENCE: 199

Ser Glu Trp Gly Ser Pro His Ala Ala Val Pro
1               5                   10

<210> SEQ ID NO 200
<211> LENGTH: 9
<212> TYPE: PRT
<213> ORGANISM: Homo sapiens

<400> SEQUENCE: 200

Ala Leu Ser Glu Leu Glu Arg Val Leu
1               5

<210> SEQ ID NO 201
<211> LENGTH: 9
<212> TYPE: PRT
<213> ORGANISM: Homo sapiens

<400> SEQUENCE: 201

Ser Leu Phe Glu Ser Leu Glu Tyr Leu
1               5

<210> SEQ ID NO 202
<211> LENGTH: 9
<212> TYPE: PRT
<213> ORGANISM: Homo sapiens

<400> SEQUENCE: 202

Lys Val Leu Glu Tyr Val Ile Lys Val
1               5

<210> SEQ ID NO 203
<211> LENGTH: 10
<212> TYPE: PRT
<213> ORGANISM: Homo sapiens

<400> SEQUENCE: 203

Val Leu Leu Asn Glu Ile Leu Glu Gln Val
1               5                   10

<210> SEQ ID NO 204
<211> LENGTH: 9
<212> TYPE: PRT
<213> ORGANISM: Homo sapiens

<400> SEQUENCE: 204

Ser Leu Leu Asn Gln Pro Lys Ala Val
1               5

<210> SEQ ID NO 205
<211> LENGTH: 9
<212> TYPE: PRT
<213> ORGANISM: Homo sapiens

<400> SEQUENCE: 205

```
Lys Met Ser Glu Leu Gln Thr Tyr Val
1               5
```

<210> SEQ ID NO 206
<211> LENGTH: 11
<212> TYPE: PRT
<213> ORGANISM: Homo sapiens

<400> SEQUENCE: 206

```
Ala Leu Leu Glu Gln Thr Gly Asp Met Ser Leu
1               5                   10
```

<210> SEQ ID NO 207
<211> LENGTH: 11
<212> TYPE: PRT
<213> ORGANISM: Homo sapiens

<400> SEQUENCE: 207

```
Val Ile Ile Lys Gly Leu Glu Glu Ile Thr Val
1               5                   10
```

<210> SEQ ID NO 208
<211> LENGTH: 9
<212> TYPE: PRT
<213> ORGANISM: Homo sapiens

<400> SEQUENCE: 208

```
Lys Gln Phe Glu Gly Thr Val Glu Ile
1               5
```

<210> SEQ ID NO 209
<211> LENGTH: 9
<212> TYPE: PRT
<213> ORGANISM: Homo sapiens

<400> SEQUENCE: 209

```
Lys Leu Gln Glu Glu Ile Pro Val Leu
1               5
```

<210> SEQ ID NO 210
<211> LENGTH: 9
<212> TYPE: PRT
<213> ORGANISM: Homo sapiens

<400> SEQUENCE: 210

```
Gly Leu Ala Glu Phe Gln Glu Asn Val
1               5
```

<210> SEQ ID NO 211
<211> LENGTH: 9
<212> TYPE: PRT
<213> ORGANISM: Homo sapiens

<400> SEQUENCE: 211

```
Asn Val Ala Glu Ile Val Ile His Ile
1               5
```

<210> SEQ ID NO 212
<211> LENGTH: 9
<212> TYPE: PRT
<213> ORGANISM: Homo sapiens

<400> SEQUENCE: 212

```
Ala Leu Ala Gly Ile Val Thr Asn Val
```

```
1               5

<210> SEQ ID NO 213
<211> LENGTH: 12
<212> TYPE: PRT
<213> ORGANISM: Homo sapiens

<400> SEQUENCE: 213

Asn Leu Leu Ile Asp Asp Lys Gly Thr Ile Lys Leu
1               5                   10

<210> SEQ ID NO 214
<211> LENGTH: 10
<212> TYPE: PRT
<213> ORGANISM: Homo sapiens

<400> SEQUENCE: 214

Val Leu Met Gln Asp Ser Arg Leu Tyr Leu
1               5                   10

<210> SEQ ID NO 215
<211> LENGTH: 9
<212> TYPE: PRT
<213> ORGANISM: Homo sapiens

<400> SEQUENCE: 215

Lys Val Leu Glu His Val Val Arg Val
1               5

<210> SEQ ID NO 216
<211> LENGTH: 9
<212> TYPE: PRT
<213> ORGANISM: Homo sapiens

<400> SEQUENCE: 216

Leu Leu Trp Gly Asn Leu Pro Glu Ile
1               5

<210> SEQ ID NO 217
<211> LENGTH: 9
<212> TYPE: PRT
<213> ORGANISM: Homo sapiens

<400> SEQUENCE: 217

Ser Leu Met Glu Lys Asn Gln Ser Leu
1               5

<210> SEQ ID NO 218
<211> LENGTH: 9
<212> TYPE: PRT
<213> ORGANISM: Homo sapiens

<400> SEQUENCE: 218

Lys Leu Leu Ala Val Ile His Glu Leu
1               5

<210> SEQ ID NO 219
<211> LENGTH: 10
<212> TYPE: PRT
<213> ORGANISM: Homo sapiens

<400> SEQUENCE: 219

Ala Leu Gly Asp Lys Phe Leu Leu Arg Val
1               5                   10
```

```
<210> SEQ ID NO 220
<211> LENGTH: 11
<212> TYPE: PRT
<213> ORGANISM: Homo sapiens

<400> SEQUENCE: 220

Phe Leu Met Lys Asn Ser Asp Leu Tyr Gly Ala
1               5                   10

<210> SEQ ID NO 221
<211> LENGTH: 10
<212> TYPE: PRT
<213> ORGANISM: Homo sapiens

<400> SEQUENCE: 221

Lys Leu Ile Asp His Gln Gly Leu Tyr Leu
1               5                   10

<210> SEQ ID NO 222
<211> LENGTH: 12
<212> TYPE: PRT
<213> ORGANISM: Homo sapiens

<400> SEQUENCE: 222

Gly Pro Gly Ile Phe Pro Pro Pro Pro Gln Pro
1               5                   10

<210> SEQ ID NO 223
<211> LENGTH: 9
<212> TYPE: PRT
<213> ORGANISM: Homo sapiens

<400> SEQUENCE: 223

Ala Leu Asn Glu Ser Leu Val Glu Cys
1               5

<210> SEQ ID NO 224
<211> LENGTH: 9
<212> TYPE: PRT
<213> ORGANISM: Homo sapiens

<400> SEQUENCE: 224

Gly Leu Ala Ala Leu Ala Val His Leu
1               5

<210> SEQ ID NO 225
<211> LENGTH: 9
<212> TYPE: PRT
<213> ORGANISM: Homo sapiens

<400> SEQUENCE: 225

Leu Leu Leu Glu Ala Val Trp His Leu
1               5

<210> SEQ ID NO 226
<211> LENGTH: 9
<212> TYPE: PRT
<213> ORGANISM: Homo sapiens

<400> SEQUENCE: 226

Ser Ile Ile Glu Tyr Leu Pro Thr Leu
1               5

<210> SEQ ID NO 227
```

```
<211> LENGTH: 9
<212> TYPE: PRT
<213> ORGANISM: Homo sapiens

<400> SEQUENCE: 227

Thr Leu His Asp Gln Val His Leu Leu
1               5

<210> SEQ ID NO 228
<211> LENGTH: 9
<212> TYPE: PRT
<213> ORGANISM: Homo sapiens

<400> SEQUENCE: 228

Ser Leu Leu Met Trp Ile Thr Gln Cys
1               5

<210> SEQ ID NO 229
<211> LENGTH: 11
<212> TYPE: PRT
<213> ORGANISM: Homo sapiens

<400> SEQUENCE: 229

Phe Leu Leu Asp Lys Pro Gln Asp Leu Ser Ile
1               5                   10

<210> SEQ ID NO 230
<211> LENGTH: 10
<212> TYPE: PRT
<213> ORGANISM: Homo sapiens

<400> SEQUENCE: 230

Tyr Leu Leu Asp Met Pro Leu Trp Tyr Leu
1               5                   10

<210> SEQ ID NO 231
<211> LENGTH: 9
<212> TYPE: PRT
<213> ORGANISM: Homo sapiens

<400> SEQUENCE: 231

Gly Leu Leu Asp Cys Pro Ile Phe Leu
1               5

<210> SEQ ID NO 232
<211> LENGTH: 9
<212> TYPE: PRT
<213> ORGANISM: Homo sapiens

<400> SEQUENCE: 232

Val Leu Ile Glu Tyr Asn Phe Ser Ile
1               5

<210> SEQ ID NO 233
<211> LENGTH: 11
<212> TYPE: PRT
<213> ORGANISM: Homo sapiens

<400> SEQUENCE: 233

Thr Leu Tyr Asn Pro Glu Arg Thr Ile Thr Val
1               5                   10

<210> SEQ ID NO 234
<211> LENGTH: 9
<212> TYPE: PRT
```

<213> ORGANISM: Homo sapiens

<400> SEQUENCE: 234

Ala Val Pro Pro Pro Ser Ser Val
1               5

<210> SEQ ID NO 235
<211> LENGTH: 9
<212> TYPE: PRT
<213> ORGANISM: Homo sapiens

<400> SEQUENCE: 235

Lys Leu Gln Glu Glu Leu Asn Lys Val
1               5

<210> SEQ ID NO 236
<211> LENGTH: 11
<212> TYPE: PRT
<213> ORGANISM: Homo sapiens

<400> SEQUENCE: 236

Lys Leu Met Asp Pro Gly Ser Leu Pro Pro Leu
1               5                   10

<210> SEQ ID NO 237
<211> LENGTH: 9
<212> TYPE: PRT
<213> ORGANISM: Homo sapiens

<400> SEQUENCE: 237

Ala Leu Ile Val Ser Leu Pro Tyr Leu
1               5

<210> SEQ ID NO 238
<211> LENGTH: 9
<212> TYPE: PRT
<213> ORGANISM: Homo sapiens

<400> SEQUENCE: 238

Phe Leu Leu Asp Gly Ser Ala Asn Val
1               5

<210> SEQ ID NO 239
<211> LENGTH: 10
<212> TYPE: PRT
<213> ORGANISM: Homo sapiens

<400> SEQUENCE: 239

Ala Leu Asp Pro Ser Gly Asn Gln Leu Ile
1               5                   10

<210> SEQ ID NO 240
<211> LENGTH: 9
<212> TYPE: PRT
<213> ORGANISM: Homo sapiens

<400> SEQUENCE: 240

Ile Leu Ile Lys His Leu Val Lys Val
1               5

<210> SEQ ID NO 241
<211> LENGTH: 9
<212> TYPE: PRT
<213> ORGANISM: Homo sapiens

```
<400> SEQUENCE: 241

Val Leu Leu Asp Thr Ile Leu Gln Leu
1               5

<210> SEQ ID NO 242
<211> LENGTH: 9
<212> TYPE: PRT
<213> ORGANISM: Homo sapiens

<400> SEQUENCE: 242

His Leu Ile Ala Glu Ile His Thr Ala
1               5

<210> SEQ ID NO 243
<211> LENGTH: 9
<212> TYPE: PRT
<213> ORGANISM: Homo sapiens

<400> SEQUENCE: 243

Ser Met Asn Gly Gly Val Phe Ala Val
1               5

<210> SEQ ID NO 244
<211> LENGTH: 9
<212> TYPE: PRT
<213> ORGANISM: Homo sapiens

<400> SEQUENCE: 244

Met Leu Ala Glu Lys Leu Leu Gln Ala
1               5

<210> SEQ ID NO 245
<211> LENGTH: 9
<212> TYPE: PRT
<213> ORGANISM: Homo sapiens

<400> SEQUENCE: 245

Tyr Met Leu Asp Ile Phe His Glu Val
1               5

<210> SEQ ID NO 246
<211> LENGTH: 11
<212> TYPE: PRT
<213> ORGANISM: Homo sapiens

<400> SEQUENCE: 246

Ala Leu Trp Leu Pro Thr Asp Ser Ala Thr Val
1               5                   10

<210> SEQ ID NO 247
<211> LENGTH: 9
<212> TYPE: PRT
<213> ORGANISM: Homo sapiens

<400> SEQUENCE: 247

Gly Leu Ala Ser Arg Ile Leu Asp Ala
1               5

<210> SEQ ID NO 248
<211> LENGTH: 9
<212> TYPE: PRT
<213> ORGANISM: Homo sapiens

<400> SEQUENCE: 248
```

-continued

```
Ala Leu Ser Val Leu Arg Leu Ala Leu
1               5

<210> SEQ ID NO 249
<211> LENGTH: 9
<212> TYPE: PRT
<213> ORGANISM: Homo sapiens

<400> SEQUENCE: 249

Ser Tyr Val Lys Val Leu His His Leu
1               5

<210> SEQ ID NO 250
<211> LENGTH: 9
<212> TYPE: PRT
<213> ORGANISM: Homo sapiens

<400> SEQUENCE: 250

Val Tyr Leu Pro Lys Ile Pro Ser Trp
1               5

<210> SEQ ID NO 251
<211> LENGTH: 9
<212> TYPE: PRT
<213> ORGANISM: Homo sapiens

<400> SEQUENCE: 251

Asn Tyr Glu Asp His Phe Pro Leu Leu
1               5

<210> SEQ ID NO 252
<211> LENGTH: 9
<212> TYPE: PRT
<213> ORGANISM: Homo sapiens

<400> SEQUENCE: 252

Val Tyr Ile Ala Glu Leu Glu Lys Ile
1               5

<210> SEQ ID NO 253
<211> LENGTH: 12
<212> TYPE: PRT
<213> ORGANISM: Homo sapiens

<400> SEQUENCE: 253

Val His Phe Glu Asp Thr Gly Lys Thr Leu Leu Phe
1               5                   10

<210> SEQ ID NO 254
<211> LENGTH: 9
<212> TYPE: PRT
<213> ORGANISM: Homo sapiens

<400> SEQUENCE: 254

Val Leu Ser Pro Phe Ile Leu Thr Leu
1               5

<210> SEQ ID NO 255
<211> LENGTH: 9
<212> TYPE: PRT
<213> ORGANISM: Homo sapiens

<400> SEQUENCE: 255

His Leu Leu Glu Gly Ser Val Gly Val
1               5
```

<210> SEQ ID NO 256
<211> LENGTH: 607
<212> TYPE: DNA
<213> ORGANISM: Artificial Sequence
<220> FEATURE:
<223> OTHER INFORMATION: WPREmut1

<400> SEQUENCE: 256

```
cagtctgacg tacgcgtaat caacctctgg attacaaaat tgtgaaaga ttgactggta      60
ttcttaacta tgttgctcct tttacgctat gtggatacgc tgctttaatg cctttgtatc    120
atgctattgc ttcccgtatg gctttcattt tctcctcctt gtataaatcc tggttgctgt    180
ctctttatga ggagttgtgg cccgttgtca ggcaacgtgg cgtggtgtgc actgtgtttg    240
ctgacgcaac ccccactggt tggggcattg ccaccacctg tcagctcctt ccgggactt     300
tcgctttccc cctccctatt gccacggcgg aactcatcgc cgcctgcctt gcccgctgct    360
ggacaggggc tcggctgttg gcactgacaa ttccgtggt gttgtcgggg aaatcatcgt     420
cctttccttg gctgctcgcc tgtgttgcca cctggattct gcgcgggacg tccttctgct    480
acgtcccttc ggccctcaat ccagcggacc ttccttcccg cggcctgctg ccggctctgc    540
ggcctcttcc gcgtcttcgc cttcgccctc agacgagtcg atctcccctt gggccgcct    600
ccccgcc                                                             607
```

<210> SEQ ID NO 257
<211> LENGTH: 581
<212> TYPE: DNA
<213> ORGANISM: Artificial Sequence
<220> FEATURE:
<223> OTHER INFORMATION: WPREmut2

<400> SEQUENCE: 257

```
gagcatctta ccgccattta tacccatatt tgttctgttt ttcttgattt gggtatacat     60
ttaaatgtta ataaaacaaa atggtggggc aatcatttac attttttggg atatgtaatt   120
actagttcag gtgtattgcc acaagacaaa cttgttaaga actttcccg ttatttacgc    180
tctgttcctg ttaatcaacc tctggattac aaaatttgtg aaagattgac tgatattctt   240
aactttgttg ctccttttac gctgtgtgga tttgctgctt tattgcctct gtatcttgct   300
attgcttccc gtacggcttt cgttttctcc tccttgtata atcctggtt gctgtctctt    360
tttgaggagt tgtggcccgt tgtccgtcaa cgtggcgtgg tgtgctctgt gtttgctgac   420
gcaaccccca ctggctgggg cattgccacc acctgtcaac tcctttctgg acttttcgct   480
ttccccctcc cgatcgccac ggcagaactc atcgccgcct gccttgcccg ctgctggaca   540
ggggctaggt tgctgggcac tgataattcc gtggtgttgt c                       581
```

<210> SEQ ID NO 258
<211> LENGTH: 235
<212> TYPE: PRT
<213> ORGANISM: Homo sapiens

<400> SEQUENCE: 258

```
Met Ala Leu Pro Val Thr Ala Leu Leu Leu Pro Leu Ala Leu Leu Leu
1               5                  10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45
```

```
Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235

<210> SEQ ID NO 259
<211> LENGTH: 235
<212> TYPE: PRT
<213> ORGANISM: Homo sapiens

<400> SEQUENCE: 259

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Cys
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
```

-continued

```
                180                 185                 190
Cys Gly Val Leu Leu Ser Leu Val Ile Thr Leu Tyr Cys Asn His
            195                 200                 205
Arg Asn Arg Arg Arg Val Cys Lys Cys Pro Arg Pro Val Val Lys Ser
            210                 215                 220
Gly Asp Lys Pro Ser Leu Ser Ala Arg Tyr Val
225                 230                 235

<210> SEQ ID NO 260
<211> LENGTH: 47
<212> TYPE: PRT
<213> ORGANISM: Artificial Sequence
<220> FEATURE:
<223> OTHER INFORMATION: CD8alpha stalk

<400> SEQUENCE: 260

Lys Pro Thr Thr Thr Pro Ala Pro Arg Pro Pro Thr Pro Ala Pro Thr
1               5                   10                  15
Ile Ala Ser Gln Pro Leu Ser Leu Arg Pro Glu Ala Cys Arg Pro Ala
                20                  25                  30
Ala Gly Gly Ala Val His Thr Arg Gly Leu Asp Phe Ala Cys Asp
            35                  40                  45

<210> SEQ ID NO 261
<211> LENGTH: 114
<212> TYPE: PRT
<213> ORGANISM: Artificial Sequence
<220> FEATURE:
<223> OTHER INFORMATION: CD8alpha Ig-like domain-2

<400> SEQUENCE: 261

Ser Gln Phe Arg Val Ser Pro Leu Asp Arg Thr Trp Asn Leu Gly Glu
1               5                   10                  15
Thr Val Glu Leu Lys Cys Gln Val Leu Leu Ser Asn Pro Thr Ser Gly
                20                  25                  30
Cys Ser Trp Leu Phe Gln Pro Arg Gly Ala Ala Ala Ser Pro Thr Phe
            35                  40                  45
Leu Leu Tyr Leu Ser Gln Asn Lys Pro Lys Ala Ala Glu Gly Leu Asp
        50                  55                  60
Thr Gln Arg Phe Ser Gly Lys Arg Leu Gly Asp Thr Phe Val Leu Thr
65                  70                  75                  80
Leu Ser Asp Phe Arg Arg Glu Asn Glu Gly Cys Tyr Phe Cys Ser Ala
                85                  90                  95
Leu Ser Asn Ser Ile Met Tyr Phe Ser His Phe Val Pro Val Phe Leu
            100                 105                 110
Pro Ala

<210> SEQ ID NO 262
<211> LENGTH: 226
<212> TYPE: PRT
<213> ORGANISM: Artificial Sequence
<220> FEATURE:
<223> OTHER INFORMATION: m2CD8alpha

<400> SEQUENCE: 262

Met Ala Leu Pro Val Thr Ala Leu Leu Leu Pro Leu Ala Leu Leu Leu
1               5                   10                  15
His Ala Ala Arg Pro Ser Gln Phe Arg Val Ser Pro Leu Asp Arg Thr
                20                  25                  30
```

Trp Asn Leu Gly Glu Thr Val Glu Leu Lys Cys Gln Val Leu Leu Ser
             35                  40                  45

Asn Pro Thr Ser Gly Cys Ser Trp Leu Phe Gln Pro Arg Gly Ala Ala
 50                  55                  60

Ala Ser Pro Thr Phe Leu Leu Tyr Leu Ser Gln Asn Lys Pro Lys Ala
 65                  70                  75                  80

Ala Glu Gly Leu Asp Thr Gln Arg Phe Ser Gly Lys Arg Leu Gly Asp
                 85                  90                  95

Thr Phe Val Leu Thr Leu Ser Asp Phe Arg Arg Glu Asn Glu Gly Cys
             100                 105                 110

Tyr Phe Cys Ser Ala Leu Ser Asn Ser Ile Met Tyr Phe Ser His Phe
         115                 120                 125

Val Pro Val Phe Leu Pro Ala Ser Val Val Asp Phe Leu Pro Thr Thr
     130                 135                 140

Ala Gln Pro Thr Lys Lys Ser Thr Leu Lys Lys Arg Val Cys Arg Leu
145                 150                 155                 160

Pro Arg Pro Glu Thr Gln Lys Gly Pro Leu Cys Ser Pro Ile Tyr Ile
                165                 170                 175

Trp Ala Pro Leu Ala Gly Thr Cys Gly Val Leu Leu Leu Ser Leu Val
            180                 185                 190

Ile Thr Leu Tyr Cys Asn His Arg Asn Arg Arg Val Cys Lys Cys
        195                 200                 205

Pro Arg Pro Val Val Lys Ser Gly Asp Lys Pro Ser Leu Ser Ala Arg
    210                 215                 220

Tyr Val
225

<210> SEQ ID NO 263
<211> LENGTH: 367
<212> TYPE: DNA
<213> ORGANISM: Artificial Sequence
<220> FEATURE:
<223> OTHER INFORMATION: MSCV promoter

<400> SEQUENCE: 263
tgaaagaccc cacctgtagg tttggcaagc tagcttaagt aacgccattt tgcaaggcat     60
ggaaaataca taactgagaa tagagaagtt cagatcaagg ttaggaacag agagacagca    120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaaatgacc ctgtgcctta tttgaactaa ccaatcagtt    300
cgcttctcgc ttctgttcgc gcgcttctgc tccccgagct caataaaaga gcccacaacc    360
cctcact                                                              367

<210> SEQ ID NO 264
<211> LENGTH: 607
<212> TYPE: DNA
<213> ORGANISM: Artificial Sequence
<220> FEATURE:
<223> OTHER INFORMATION: WPRE

<400> SEQUENCE: 264
cagtctgacg tacgcgtaat caacctctgg attacaaaat ttgtgaaaga ttgactggta     60
ttcttaacta tgttgctcct tttacgctat gtggatacgc tgctttaatg cctttgtatc    120
atgctattgc ttcccgtatg gctttcattt tctcctcctt gtataaatcc tggttgctgt    180

```
ctctttatga ggagttgtgg cccgttgtca ggcaacgtgg cgtggtgtgc actgtgtttg    240
ctgacgcaac ccccactggt tggggcattg ccaccacctg tcagctcctt tccgggactt    300
tcgctttccc cctccctatt gccacggcgg aactcatcgc cgcctgcctt gcccgctgct    360
ggacaggggc tcggctgttg ggcactgaca attccgtggt gttgtcgggg aagctgacgt    420
cctttccatg gctgctcgcc tgtgttgcca cctggattct gcgcgggacg tccttctgct    480
acgtcccttc ggccctcaat ccagcggacc ttccttcccg cggcctgctg ccggctctgc    540
ggcctcttcc gcgtcttcgc cttcgccctc agacgagtcg gatctccctt gggccgcct    600 ccccgcc                                                              607
```

<210> SEQ ID NO 265
<211> LENGTH: 4
<212> TYPE: PRT
<213> ORGANISM: Artificial Sequence
<220> FEATURE:
<223> OTHER INFORMATION: Furin consensus
<220> FEATURE:
<221> NAME/KEY: misc_feature
<222> LOCATION: (2)..(3)
<223> OTHER INFORMATION: Xaa can be any naturally occurring amino acid

<400> SEQUENCE: 265

Arg Xaa Xaa Arg
1

<210> SEQ ID NO 266
<211> LENGTH: 4
<212> TYPE: PRT
<213> ORGANISM: Artificial Sequence
<220> FEATURE:
<223> OTHER INFORMATION: Linker

<400> SEQUENCE: 266

Ser Gly Ser Gly
1

<210> SEQ ID NO 267
<211> LENGTH: 4320
<212> TYPE: DNA
<213> ORGANISM: Artificial Sequence
<220> FEATURE:
<223> OTHER INFORMATION: CD8b3.CD8a.TCR.WPREmut2 construct nucleotide
      sequence

<400> SEQUENCE: 267

```
tgaaagaccc cacctgtagg tttggcaagc tagcttaagt aacgccattt tgcaaggcat     60
ggaaaataca taactgagaa tagagaagtt cagatcaagg ttaggaacag agagacagca    120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaaatgacc ctgtgcctta tttgaactaa ccaatcagtt    300
cgcttctcgc ttctgttcgc gcgcttctgc tccccgagct caataaaaga gcccacaacc    360
cctcactcag cggccgcccc gggtcgacgc taccaccatg cgcccgagac tgtggctcct    420
gctcgccgcg caactgactg tcctgcacgg aaacagcgtg ctgcagcaga caccggccta    480
catcaaagtg cagaccaaca agatggtcat gctgtcctgc gaggccaaga tttccctctc    540
caacatgcgg atctattggt tgcggcagag acaggcgcct cctcggact cccaccatga    600 gttcttggcc ctgtgggact ccgccaaggg aactattcac ggcgaagaag tggaacagga    660
```

```
gaagatcgcc gtgtttcgcg atgcctcccg ctttatactg aatctgacct ccgtgaagcc      720
cgaagatagc gggatctact tttgcatgat tgtgggctca cccgaactga ccttcgggaa      780
gggcactcag ctgagcgtgg tggacttcct ccccactacc gcccaaccca ctaagaagtc      840
aaccctgaag aagcgggttt gcagactccc acggccggaa acgcagaagg gtccgctgtg      900
ttccccgatc accctggggc tccttgtggc tggagtgctg gtccttctgg tgtcccttgg      960
cgtcgccatt cacctctgct gccggagaag gagggccaga ctgaggttca tgaagcagtt     1020
ctacaagcgg gccaagagat ctggcagcgg cgccaccaat tcagcctgc tgaaacaggc      1080
cggcgacgtg gaagagaacc ctggcccat ggcgcttccc gtgaccgcac tcctgttgcc       1140
ccttgccctg ctgttgcacg ccgcacgacc ttcccaattc cgggtgtccc ctctggatcg     1200
cacctggaac ctcggggaaa cggtggagct caagtgtcaa gtcctcctgt cgaacccgac     1260
cagcggatgc agctggctgt ccagccgag aggagctgcc gcctcaccca ccttcctcct      1320
gtacttgagc cagaacaagc cgaaggccgc tgagggtctg acacccagc gcttctcggg      1380
caaacggctg ggagacactt ttgtgctgac tctctccgac ttccggcggg agaacgaggg     1440
ctactacttc tgctctgcgc tctccaattc aatcatgtac ttctcacact tcgtgccggt     1500
gttcctgcct gccaagccca ccactactcc ggcacccaga cctccaactc ccgctcccac     1560
catcgcgtcc caacccctt cgctgcgccc tgaagcgtgt cggcctgctg ctggaggagc      1620
cgtgcatacc cgcggtctgg acttcgcgtg cgacatctac atttgggccc ctttggctgg     1680
cacctgtgga gtgctgctcc tgtcccttgt gatcaccctg tactgcaacc accggaatag     1740
gcggagagtc tgcaagtgtc cgcggcctgt cgtgaagtca ggagataagc cgagcctgtc     1800
cgcacgctac gtgcgggcca agagatctgg cagcggcgag ggcagaggca gcctgctgac     1860
ctgcggcgac gtggaggaga accccggccc catggactct ggaccttct gctgcgtgag      1920
cctgtgcatc ctggtggcca agcacacaga cgccggcgtg atccagtccc ctaggcacga     1980
ggtgaccgag atgggccagg aggtgacact gcgctgtaag ccaatctctg ccacaacag      2040
cctgttttgg tatagggaga ccatgatgcg cggcctggag ctgctgatct acttcaataa     2100
caatgtgccc atcgacgatt ccggcatgcc tgaggatcgg ttttctgcca agatgcccaa     2160
tgccagcttc tccacactga gatccagcc tagcgagcca agagactccg ccgtgtattt     2220
ttgcgcctct agcccaggca gcaccgatac acagtacttc ggaccaggaa ccaggctgac     2280
agtgctggag gacctgaaga acgtgttccc ccctgaggtg gccgtgtttg agccctctga     2340
ggccgagatc agccacaccc agaaggccac cctggtgtgc ctggcaaccg gcttctatcc     2400
tgatcacgtg gagctgtcct ggtgggtgaa cggcaaggag gtgcacagcg gcgtgtccac     2460
agacccacag cccctgaagg agcagccagc cctgaatgat agccggtatt gcctgtcctc     2520
tcggctgaga gtgtccgcca ccttttggca gaaccccgg aatcacttca gatgtcaggt      2580
gcagttttac ggcctgtccg agaacgatga gtggacccag gaccgggcca agcctgtgac     2640
acagatcgtg tctgccgagg catggggaag agcagactgt ggcttcacct ctgagagcta     2700
ccagcagggc gtgctgagcg ccaccatcct gtatgagatc ctgctgggca aggccacact     2760
gtacgccgtc ctggtctccg ctctggtgct gatggcaatg gtcaaaagaa agatagtcg     2820
gggacgggcc aagagatctg gcagcggcca gtgcaccaac tacgccctgc tgaagctggc     2880
cggcgacgtg gagagcaacc ccggccccat ggagaagaat cccctggctg ccccctgct     2940
gatcctgtgg tttcacctgg actgcgtgtc ctctatcctg aatgtggaac agagcccaca     3000
gagcctgcac gtgcaggagg gcgactccac caacttcaca tgctcttttc ctagctccaa     3060
```

```
cttctacgcc ctgcactggt acagaaagga gaccgcaaag tccccagagg ccctgttcgt    3120
gatgacactg aacggcgatg agaagaagaa gggccgcatc agcgccaccc tgaatacaaa    3180
ggagggctac tcctatctgt acatcaaggg ctcccagcct gaggactctg ccacctatct    3240
gtgcgccctg tacaacaata acgatatgcg gtttggcgcc ggcaccagac tgacagtgaa    3300
gccaaacatc cagaatccag accccgccgt gtatcagctg cgggacagca agtctagcga    3360
taagagcgtg tgcctgttca ccgactttga ttctcagaca aacgtgagcc agtccaagga    3420
cagcgacgtg tacatcaccg acaagacagt gctggatatg agaagcatgg acttcaagtc    3480
taacagcgcc gtggcctggt ccaataagtc tgatttcgcc tgcgccaatg cctttaataa    3540
ctccatcatc cccgaggata ccttctttcc ttctccagag tcctcttgtg acgtgaagct    3600
ggtggagaag tctttcgaga ccgatacaaa cctgaatttt cagaacctga gcgtgatcgg    3660
cttcaggatc ctgctgctga aggtggccgg ctttaatctg ctgatgaccc tgaggctgtg    3720
gagctcctga accggtccgg agcatcttac cgccatttat acccatattt gttctgtttt    3780
tcttgatttg ggtatacatt taaatgttaa taaaacaaaa tggtggggca atcatttaca    3840
ttttttggga tatgtaatta ctagttcagg tgtattgcca caagacaaac ttgttaagaa    3900
actttcccgt tatttacgct ctgttcctgt taatcaacct ctggattaca aaatttgtga    3960
aagattgact gatattctta actttgttgc tccttttacg ctgtgtggat tgctgctttt    4020
attgcctctg tatcttgcta ttgcttcccg tacggctttc gttttctcct ccttgtataa    4080
atcctggttg ctgtctcttt ttgaggagtt gtggcccgtt gtccgtcaac gtggcgtggt    4140
gtgctctgtg tttgctgacg caaccccac tggctggggc attgccacca cctgtcaact    4200
cctttctggg actttcgctt tccccctccc gatcgccacg gcagaactca tcgccgcctg    4260
ccttgcccgc tgctggacag gggctaggtt gctgggcact gataattccg tggtgttgtc    4320
```

<210> SEQ ID NO 268
<211> LENGTH: 1110
<212> TYPE: PRT
<213> ORGANISM: Artificial Sequence
<220> FEATURE:
<223> OTHER INFORMATION: CD8b3.CD8a.TCR.WPREmut2 amino acid sequence

<400> SEQUENCE: 268

```
Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140
```

```
Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
            165                 170                 175

Val Ala Gly Val Leu Val Leu Leu Val Ser Leu Gly Val Ala Ile His
            180                 185                 190

Leu Cys Cys Arg Arg Arg Ala Arg Leu Arg Phe Met Lys Gln Phe
        195                 200                 205

Tyr Lys Arg Ala Lys Arg Ser Gly Ser Gly Ala Thr Asn Phe Ser Leu
        210                 215                 220

Leu Lys Gln Ala Gly Asp Val Glu Glu Asn Pro Gly Pro Met Ala Leu
225                 230                 235                 240

Pro Val Thr Ala Leu Leu Leu Pro Leu Ala Leu Leu Leu His Ala Ala
            245                 250                 255

Arg Pro Ser Gln Phe Arg Val Ser Pro Leu Asp Arg Thr Trp Asn Leu
        260                 265                 270

Gly Glu Thr Val Glu Leu Lys Cys Gln Val Leu Leu Ser Asn Pro Thr
        275                 280                 285

Ser Gly Cys Ser Trp Leu Phe Gln Pro Arg Gly Ala Ala Ala Ser Pro
290                 295                 300

Thr Phe Leu Leu Tyr Leu Ser Gln Asn Lys Pro Lys Ala Ala Glu Gly
305                 310                 315                 320

Leu Asp Thr Gln Arg Phe Ser Gly Lys Arg Leu Gly Asp Thr Phe Val
            325                 330                 335

Leu Thr Leu Ser Asp Phe Arg Arg Glu Asn Glu Gly Tyr Tyr Phe Cys
            340                 345                 350

Ser Ala Leu Ser Asn Ser Ile Met Tyr Phe Ser His Phe Val Pro Val
            355                 360                 365

Phe Leu Pro Ala Lys Pro Thr Thr Thr Pro Ala Pro Arg Pro Pro Thr
370                 375                 380

Pro Ala Pro Thr Ile Ala Ser Gln Pro Leu Ser Leu Arg Pro Glu Ala
385                 390                 395                 400

Cys Arg Pro Ala Ala Gly Gly Ala Val His Thr Arg Gly Leu Asp Phe
            405                 410                 415

Ala Cys Asp Ile Tyr Ile Trp Ala Pro Leu Ala Gly Thr Cys Gly Val
            420                 425                 430

Leu Leu Leu Ser Leu Val Ile Thr Leu Tyr Cys Asn His Arg Asn Arg
        435                 440                 445

Arg Arg Val Cys Lys Cys Pro Arg Pro Val Val Lys Ser Gly Asp Lys
        450                 455                 460

Pro Ser Leu Ser Ala Arg Tyr Val Arg Ala Lys Arg Ser Gly Ser Gly
465                 470                 475                 480

Glu Gly Arg Gly Ser Leu Leu Thr Cys Gly Asp Val Glu Glu Asn Pro
            485                 490                 495

Gly Pro Met Asp Ser Trp Thr Phe Cys Cys Val Ser Leu Cys Ile Leu
            500                 505                 510

Val Ala Lys His Thr Asp Ala Gly Val Ile Gln Ser Pro Arg His Glu
            515                 520                 525

Val Thr Glu Met Gly Gln Glu Val Thr Leu Arg Cys Lys Pro Ile Ser
        530                 535                 540

Gly His Asn Ser Leu Phe Trp Tyr Arg Glu Thr Met Met Arg Gly Leu
545                 550                 555                 560
```

```
Glu Leu Leu Ile Tyr Phe Asn Asn Asn Val Pro Ile Asp Asp Ser Gly
                565                 570                 575

Met Pro Glu Asp Arg Phe Ser Ala Lys Met Pro Asn Ala Ser Phe Ser
            580                 585                 590

Thr Leu Lys Ile Gln Pro Ser Glu Pro Arg Asp Ser Ala Val Tyr Phe
            595                 600                 605

Cys Ala Ser Ser Pro Gly Ser Thr Asp Thr Gln Tyr Phe Gly Pro Gly
            610                 615                 620

Thr Arg Leu Thr Val Leu Glu Asp Leu Lys Asn Val Phe Pro Pro Glu
625                 630                 635                 640

Val Ala Val Phe Glu Pro Ser Glu Ala Glu Ile Ser His Thr Gln Lys
                645                 650                 655

Ala Thr Leu Val Cys Leu Ala Thr Gly Phe Tyr Pro Asp His Val Glu
                660                 665                 670

Leu Ser Trp Trp Val Asn Gly Lys Glu Val His Ser Gly Val Ser Thr
                675                 680                 685

Asp Pro Gln Pro Leu Lys Glu Gln Pro Ala Leu Asn Asp Ser Arg Tyr
                690                 695                 700

Cys Leu Ser Ser Arg Leu Arg Val Ser Ala Thr Phe Trp Gln Asn Pro
705                 710                 715                 720

Arg Asn His Phe Arg Cys Gln Val Gln Phe Tyr Gly Leu Ser Glu Asn
                725                 730                 735

Asp Glu Trp Thr Gln Asp Arg Ala Lys Pro Val Thr Gln Ile Val Ser
                740                 745                 750

Ala Glu Ala Trp Gly Arg Ala Asp Cys Gly Phe Thr Ser Glu Ser Tyr
                755                 760                 765

Gln Gln Gly Val Leu Ser Ala Thr Ile Leu Tyr Glu Ile Leu Leu Gly
                770                 775                 780

Lys Ala Thr Leu Tyr Ala Val Leu Val Ser Ala Leu Val Leu Met Ala
785                 790                 795                 800

Met Val Lys Arg Lys Asp Ser Arg Gly Arg Ala Lys Arg Ser Gly Ser
                805                 810                 815

Gly Gln Cys Thr Asn Tyr Ala Leu Leu Lys Leu Ala Gly Asp Val Glu
                820                 825                 830

Ser Asn Pro Gly Pro Met Glu Lys Asn Pro Leu Ala Ala Pro Leu Leu
                835                 840                 845

Ile Leu Trp Phe His Leu Asp Cys Val Ser Ser Ile Leu Asn Val Glu
                850                 855                 860

Gln Ser Pro Gln Ser Leu His Val Gln Glu Gly Asp Ser Thr Asn Phe
865                 870                 875                 880

Thr Cys Ser Phe Pro Ser Ser Asn Phe Tyr Ala Leu His Trp Tyr Arg
                885                 890                 895

Lys Glu Thr Ala Lys Ser Pro Glu Ala Leu Phe Val Met Thr Leu Asn
                900                 905                 910

Gly Asp Glu Lys Lys Lys Gly Arg Ile Ser Ala Thr Leu Asn Thr Lys
                915                 920                 925

Glu Gly Tyr Ser Tyr Leu Tyr Ile Lys Gly Ser Gln Pro Glu Asp Ser
                930                 935                 940

Ala Thr Tyr Leu Cys Ala Leu Tyr Asn Asn Asn Asp Met Arg Phe Gly
945                 950                 955                 960

Ala Gly Thr Arg Leu Thr Val Lys Pro Asn Ile Gln Asn Pro Asp Pro
                965                 970                 975

Ala Val Tyr Gln Leu Arg Asp Ser Lys Ser Ser Asp Lys Ser Val Cys
```

```
          980             985             990
Leu Phe Thr Asp Phe Asp Ser Gln  Thr Asn Val Ser Gln  Ser Lys Asp
            995             1000            1005

Ser Asp  Val Tyr Ile Thr Asp  Lys Thr Val Leu Asp  Met Arg Ser
    1010            1015            1020

Met Asp  Phe Lys Ser Asn Ser  Ala Val Ala Trp  Ser  Asn Lys Ser
    1025            1030            1035

Asp Phe  Ala Cys Ala Asn Ala  Phe Asn Asn Ser  Ile  Ile Pro Glu
    1040            1045            1050

Asp Thr  Phe Phe Pro Ser Pro  Glu Ser Ser Cys  Asp  Val Lys Leu
    1055            1060            1065

Val Glu  Lys Ser Phe Glu Thr  Asp Thr Asn Leu  Asn  Phe Gln Asn
    1070            1075            1080

Leu Ser  Val Ile Gly Phe Arg  Ile Leu Leu Leu  Lys  Val Ala Gly
    1085            1090            1095

Phe Asn  Leu Leu Met Thr Leu  Arg Leu Trp Ser  Ser
    1100            1105            1110
```

<210> SEQ ID NO 269
<211> LENGTH: 4314
<212> TYPE: DNA
<213> ORGANISM: Artificial Sequence
<220> FEATURE:
<223> OTHER INFORMATION: CD8b1(S19).CD8a.TCR.WPREmut2 construct
      nucleotide sequence

<400> SEQUENCE: 269

```
tgaaagaccc cacctgtagg tttggcaagc tagcttaagt aacgccattt tgcaaggcat    60
ggaaaataca taactgagaa tagagaagtt cagatcaagg ttaggaacag agagacagca   120
gaatatgggc caaacaggat atctgtggta agcagttcct gccccggctc agggccaaga   180
acagatggtc cccagatgcg gtcccgccct cagcagtttc tagagaacca tcagatgttt   240
ccagggtgcc ccaaggacct gaaaatgacc ctgtgcctta tttgaactaa ccaatcagtt   300
cgcttctcgc ttctgttcgc gcgcttctgc tccccgagct caataaaaga gcccacaacc   360
cctcactcag cggccgcccc gggtcgacgc taccaccatg gaattcggcc tgagctggct   420
gttcctggtg gccatcctga agggcgtgca gtgcctgcag cagacaccgg cctacatcaa   480
agtgcagacc aacaagatgg tcatgctgtc ctgcgaggcc aagatttccc tctccaacat   540
gcggatctat tggttgcggc agagacaggc gccttcctcg gactcccacc atgagttctt   600
ggccctgtgg gactccgcca aggaactat tcacggcgaa gagtggaac aggagaagat   660 cgccgtgttt cgcgatgcct cccgctttat actgaatctg acctccgtga gcccgaaga   720 tagcgggatc tactttttgca tgattgtggg ctcacccgaa ctgaccttcg ggaagggcac   780
tcagctgagc gtggtggact tcctccccac taccgcccaa cccactaaga agtcaaccct   840
gaagaagcgg gtttgcagac tcccacggcc ggaaacgcag aagggtccgc tgtgttcccc   900
gatcaccctg ggctccttg tggctggagt gctggtcctt ctggtgtccc ttggcgtcgc   960
cattcacctc tgctgccgga aaggagggc cagactgagg ttcatgaagc agttctacaa   1020
gcgggccaag agatctggca gcggcgccac caatttcagc ctgctgaaac aggccggcga   1080
cgtggaagag aaccctggcc ccatggcgct tccgtgacc gcactcctgt tgccccttgc   1140
cctgctgttg cacgccgcac gaccttccca attccgggtg tcccctctgg atcgcacctg   1200
gaacctcggg gaaacggtgg agctcaagtg tcaagtcctc ctgtcgaacc cgaccagcgg   1260
```

```
atgcagctgg ctgttccagc cgagaggagc tgccgcctca cccaccttcc tcctgtactt    1320
gagccagaac aagccgaagg ccgctgaggg tctggacacc cagcgcttct cgggcaaacg    1380
gctgggagac acttttgtgc tgactctctc cgacttccgg cgggagaacg agggctacta    1440
cttctgctct gcgctctcca attcaatcat gtacttctca cacttcgtgc cggtgttcct    1500
gcctgccaag cccaccacta ctccggcacc cagacctcca actcccgctc ccaccatcgc    1560
gtcccaaccc ctttcgctgc gccctgaagc gtgtcggcct gctgctggag gagccgtgca    1620
tacccgcggt ctggacttcg cgtgcgacat ctacatttgg gccccttggg ctggcacctg    1680
tggagtgctg ctcctgtccc ttgtgatcac cctgtactgc aaccaccgga taggcggag     1740 agtctgcaag tgtccgcggc ctgtcgtgaa gtcaggagat aagccgagcc tgtccgcacg    1800
ctacgtgcgg gccaagagat ctggcagcgg cgagggcaga ggcagcctgc tgacctgcgg    1860
cgacgtggag gagaaccccg gccccatgga ctcttggacc ttctgctgcg tgagcctgtg    1920
catcctggtg gccaagcaca cagacgccgg cgtgatccag tccctaggc acgaggtgac     1980 cgagatgggc caggaggtga cactgcgctg taagccaatc tctggccaca cagcctgtt     2040 ttggtatagg gagaccatga tgcgcggcct ggagctgctg atctacttca ataacaatgt    2100
gcccatcgac gattccggca tgcctgagga tcggtttttct gccaagatgc caatgccag    2160 cttctccaca ctgaagatcc agcctagcga gccaagagac tccgccgtgt attttgcgc    2220 ctctagccca ggcagcaccg atacacagta cttcggacca ggaaccaggc tgacagtgct    2280
ggaggacctg aagaacgtgt ccccctga ggtggccgtg tttgagccct ctgaggccga    2340
gatcagccac acccagaagg ccaccctggt gtgcctggca accggcttct atcctgatca    2400
cgtggagctg tcctggtggg tgaacggcaa ggaggtgcac agcggcgtgt ccacagaccc    2460
acagcccctg aaggagcagc cagccctgaa tgatagccgg tattgcctgt cctctcggct    2520
gagagtgtcc gccaccttt ggcagaaccc ccggaatcac ttcagatgtc aggtgcagtt     2580
ttacggcctg tccgagaacg atgagtggac ccaggaccgg gccaagcctg tgacacagat    2640
cgtgtctgcc gaggcatggg gaagagcaga ctgtggcttc acctctgaga gctaccagca    2700
gggcgtgctg agcgccacca tcctgtatga gatcctgctg gcaaggcca cactgtacgc     2760 cgtcctggtc tccgctctgg tgctgatggc aatggtcaaa gaaaagata gtcgggacg     2820 ggccaagaga tctggcagcg gccagtgcac caactacgcc ctgctgaagc tggccggcga    2880
cgtggagagc aaccccggcc ccatggagaa gaatcccctg gctgcccccc tgctgatcct    2940
gtggtttcac ctggactgcg tgtcctctat cctgaatgtg aacagagcc cacagagcct    3000 gcacgtgcag gagggcgact ccaccaactt cacatgctct tttcctagct ccaacttcta    3060
cgccctgcac tggtacagaa aggaccgcaa aagtcccca gaggccctgt cgtgatgac     3120 actgaacggc gatgagaaga gaagggccg catcagcgcc accctgaata caaaggaggg    3180
ctactcctat ctgtacatca agggctccca gcctgaggac tctgccacct atctgtgcgc    3240
cctgtacaac aataacgata tgcggtttgg cgccggcacc agactgacag tgaagccaaa    3300
catccagaat ccagaccccg ccgtgtatca gctgcgggac agcaagtcta gcgataagag    3360
cgtgtgcctt ttcaccgact tgattctca gacaaacgtg agccagtcca aggacagcga    3420
cgtgtacatc accgacaaga cagtgctgga tatgagaagc atggacttca gtctaacag    3480 cgccgtggcc tggtccaata agtctgattt cgcctgcgcc aatgccttta ataactccat    3540
catccccgag gataccttct ttccttctcc agagtcctct tgtgacgtga agctggtgga    3600
gaagtctttc gagaccgata caaacctgaa ttttcagaac ctgagcgtga tcggcttcag    3660
```

-continued

```
gatcctgctg ctgaaggtgg ccggctttaa tctgctgatg accctgaggc tgtggagctc    3720
ctgaaccggt ccggagcatc ttaccgccat ttatacccat atttgttctg tttttcttga    3780
tttgggtata catttaaatg ttaataaaac aaaatggtgg ggcaatcatt tacatttttt    3840
gggatatgta attactagtt caggtgtatt gccacaagac aaacttgtta agaaactttc    3900
ccgttattta cgctctgttc ctgttaatca acctctggat tacaaaattt gtgaaagatt    3960
gactgatatt cttaactttg ttgctccttt tacgctgtgt ggatttgctg ctttattgcc    4020
tctgtatctt gctattgctt cccgtacggc tttcgttttc tcctccttgt ataaatcctg    4080
gttgctgtct cttttgagg agttgtggcc cgttgtccgt caacgtggcg tggtgtgctc     4140
tgtgtttgct gacgcaaccc ccactggctg ggcattgcc accacctgtc aactcctttc     4200
tgggactttc gctttccccc tcccgatcgc cacggcagaa ctcatcgccg cctgccttgc    4260
ccgctgctgg acagggcta ggttgctggg cactgataat tccgtggtgt tgtc           4314
```

<210> SEQ ID NO 270
<211> LENGTH: 1108
<212> TYPE: PRT
<213> ORGANISM: Artificial Sequence
<220> FEATURE:
<223> OTHER INFORMATION: CD8b1(S19).CD8a.TCR.WPREmut2 amino acid
     sequence

<400> SEQUENCE: 270

```
Met Glu Phe Gly Leu Ser Trp Leu Phe Leu Val Ala Ile Leu Lys Gly
1               5                   10                  15

Val Gln Cys Leu Gln Gln Thr Pro Ala Tyr Ile Lys Val Gln Thr Asn
            20                  25                  30

Lys Met Val Met Leu Ser Cys Glu Ala Lys Ile Ser Leu Ser Asn Met
        35                  40                  45

Arg Ile Tyr Trp Leu Arg Gln Arg Gln Ala Pro Ser Ser Asp Ser His
    50                  55                  60

His Glu Phe Leu Ala Leu Trp Asp Ser Ala Lys Gly Thr Ile His Gly
65                  70                  75                  80

Glu Glu Val Glu Gln Lys Ile Ala Val Phe Arg Asp Ala Ser Arg
                85                  90                  95

Phe Ile Leu Asn Leu Thr Ser Val Lys Pro Glu Asp Ser Gly Ile Tyr
            100                 105                 110

Phe Cys Met Ile Val Gly Ser Pro Glu Leu Thr Phe Gly Lys Gly Thr
        115                 120                 125

Gln Leu Ser Val Val Asp Phe Leu Pro Thr Thr Ala Gln Pro Thr Lys
    130                 135                 140

Lys Ser Thr Leu Lys Lys Arg Val Cys Arg Leu Pro Arg Pro Glu Thr
145                 150                 155                 160

Gln Lys Gly Pro Leu Cys Ser Pro Ile Thr Leu Gly Leu Leu Val Ala
                165                 170                 175

Gly Val Leu Val Leu Leu Val Ser Leu Gly Val Ala Ile His Leu Cys
            180                 185                 190

Cys Arg Arg Arg Arg Ala Arg Leu Arg Phe Met Lys Gln Phe Tyr Lys
        195                 200                 205

Arg Ala Lys Arg Ser Gly Ser Gly Ala Thr Asn Phe Ser Leu Leu Lys
    210                 215                 220

Gln Ala Gly Asp Val Glu Glu Asn Pro Gly Pro Met Ala Leu Pro Val
225                 230                 235                 240
```

```
Thr Ala Leu Leu Leu Pro Leu Ala Leu Leu Leu His Ala Ala Arg Pro
                    245                 250                 255

Ser Gln Phe Arg Val Ser Pro Leu Asp Arg Thr Trp Asn Leu Gly Glu
            260                 265                 270

Thr Val Glu Leu Lys Cys Gln Val Leu Leu Ser Asn Pro Thr Ser Gly
        275                 280                 285

Cys Ser Trp Leu Phe Gln Pro Arg Gly Ala Ala Ala Ser Pro Thr Phe
    290                 295                 300

Leu Leu Tyr Leu Ser Gln Asn Lys Pro Lys Ala Ala Glu Gly Leu Asp
305                 310                 315                 320

Thr Gln Arg Phe Ser Gly Lys Arg Leu Gly Asp Thr Phe Val Leu Thr
                325                 330                 335

Leu Ser Asp Phe Arg Arg Glu Asn Glu Gly Tyr Tyr Phe Cys Ser Ala
            340                 345                 350

Leu Ser Asn Ser Ile Met Tyr Phe Ser His Phe Val Pro Val Phe Leu
        355                 360                 365

Pro Ala Lys Pro Thr Thr Thr Pro Ala Pro Arg Pro Pro Thr Pro Ala
    370                 375                 380

Pro Thr Ile Ala Ser Gln Pro Leu Ser Leu Arg Pro Glu Ala Cys Arg
385                 390                 395                 400

Pro Ala Ala Gly Gly Ala Val His Thr Arg Gly Leu Asp Phe Ala Cys
                405                 410                 415

Asp Ile Tyr Ile Trp Ala Pro Leu Ala Gly Thr Cys Gly Val Leu Leu
            420                 425                 430

Leu Ser Leu Val Ile Thr Leu Tyr Cys Asn His Arg Asn Arg Arg Arg
        435                 440                 445

Val Cys Lys Cys Pro Arg Pro Val Val Lys Ser Gly Asp Lys Pro Ser
    450                 455                 460

Leu Ser Ala Arg Tyr Val Arg Ala Lys Arg Ser Gly Ser Gly Glu Gly
465                 470                 475                 480

Arg Gly Ser Leu Leu Thr Cys Gly Asp Val Glu Glu Asn Pro Gly Pro
                485                 490                 495

Met Asp Ser Trp Thr Phe Cys Cys Val Ser Leu Cys Ile Leu Val Ala
            500                 505                 510

Lys His Thr Asp Ala Gly Val Ile Gln Ser Pro Arg His Glu Val Thr
        515                 520                 525

Glu Met Gly Gln Glu Val Thr Leu Arg Cys Lys Pro Ile Ser Gly His
    530                 535                 540

Asn Ser Leu Phe Trp Tyr Arg Glu Thr Met Met Arg Gly Leu Glu Leu
545                 550                 555                 560

Leu Ile Tyr Phe Asn Asn Asn Val Pro Ile Asp Asp Ser Gly Met Pro
                565                 570                 575

Glu Asp Arg Phe Ser Ala Lys Met Pro Asn Ala Ser Phe Ser Thr Leu
            580                 585                 590

Lys Ile Gln Pro Ser Glu Pro Arg Asp Ser Ala Val Tyr Phe Cys Ala
        595                 600                 605

Ser Ser Pro Gly Ser Thr Asp Thr Gln Tyr Phe Gly Pro Gly Thr Arg
    610                 615                 620

Leu Thr Val Leu Glu Asp Leu Lys Asn Val Phe Pro Pro Glu Val Ala
625                 630                 635                 640

Val Phe Glu Pro Ser Glu Ala Glu Ile Ser His Thr Gln Lys Ala Thr
                645                 650                 655

Leu Val Cys Leu Ala Thr Gly Phe Tyr Pro Asp His Val Glu Leu Ser
```

```
              660                 665                 670
Trp Trp Val Asn Gly Lys Glu Val His Ser Gly Val Ser Thr Asp Pro
            675                 680                 685

Gln Pro Leu Lys Glu Gln Pro Ala Leu Asn Asp Ser Arg Tyr Cys Leu
690                 695                 700

Ser Ser Arg Leu Arg Val Ser Ala Thr Phe Trp Gln Asn Pro Arg Asn
705                 710                 715                 720

His Phe Arg Cys Gln Val Gln Phe Tyr Gly Leu Ser Glu Asn Asp Glu
                725                 730                 735

Trp Thr Gln Asp Arg Ala Lys Pro Val Thr Gln Ile Val Ser Ala Glu
            740                 745                 750

Ala Trp Gly Arg Ala Asp Cys Gly Phe Thr Ser Glu Ser Tyr Gln Gln
            755                 760                 765

Gly Val Leu Ser Ala Thr Ile Leu Tyr Glu Ile Leu Leu Gly Lys Ala
            770                 775                 780

Thr Leu Tyr Ala Val Leu Val Ser Ala Leu Val Leu Met Ala Met Val
785                 790                 795                 800

Lys Arg Lys Asp Ser Arg Gly Arg Ala Lys Arg Ser Gly Ser Gly Gln
                805                 810                 815

Cys Thr Asn Tyr Ala Leu Leu Lys Leu Ala Gly Asp Val Glu Ser Asn
                820                 825                 830

Pro Gly Pro Met Glu Lys Asn Pro Leu Ala Ala Pro Leu Leu Ile Leu
            835                 840                 845

Trp Phe His Leu Asp Cys Val Ser Ser Ile Leu Asn Val Glu Gln Ser
            850                 855                 860

Pro Gln Ser Leu His Val Gln Glu Gly Asp Ser Thr Asn Phe Thr Cys
865                 870                 875                 880

Ser Phe Pro Ser Ser Asn Phe Tyr Ala Leu His Trp Tyr Arg Lys Glu
                885                 890                 895

Thr Ala Lys Ser Pro Glu Ala Leu Phe Val Met Thr Leu Asn Gly Asp
            900                 905                 910

Glu Lys Lys Lys Gly Arg Ile Ser Ala Thr Leu Asn Thr Lys Glu Gly
            915                 920                 925

Tyr Ser Tyr Leu Tyr Ile Lys Gly Ser Gln Pro Glu Asp Ser Ala Thr
            930                 935                 940

Tyr Leu Cys Ala Leu Tyr Asn Asn Asn Asp Met Arg Phe Gly Ala Gly
945                 950                 955                 960

Thr Arg Leu Thr Val Lys Pro Asn Ile Gln Asn Pro Asp Pro Ala Val
                965                 970                 975

Tyr Gln Leu Arg Asp Ser Lys Ser Ser Asp Lys Ser Val Cys Leu Phe
            980                 985                 990

Thr Asp Phe Asp Ser Gln Thr Asn Val Ser Gln Ser Lys Asp Ser Asp
            995                 1000                1005

Val Tyr Ile Thr Asp Lys Thr Val Leu Asp Met Arg Ser Met Asp
      1010                1015                1020

Phe Lys Ser Asn Ser Ala Val Ala Trp Ser Asn Lys Ser Asp Phe
      1025                1030                1035

Ala Cys Ala Asn Ala Phe Asn Asn Ser Ile Ile Pro Glu Asp Thr
      1040                1045                1050

Phe Phe Pro Ser Pro Glu Ser Cys Asp Val Lys Leu Val Glu
      1055                1060                1065

Lys Ser Phe Glu Thr Asp Thr Asn Leu Asn Phe Gln Asn Leu Ser
      1070                1075                1080
```

Val Ile Gly Phe Arg Ile Leu Leu Leu Lys Val Ala Gly Phe Asn
  1085              1090              1095

Leu Leu Met Thr Leu Arg Leu Trp Ser Ser
  1100              1105

<210> SEQ ID NO 271
<211> LENGTH: 4428
<212> TYPE: DNA
<213> ORGANISM: Artificial Sequence
<220> FEATURE:
<223> OTHER INFORMATION: CD8b4.CD8a.TCR.WPREmut2 construct nucleotide
      sequence

<400> SEQUENCE: 271

| | | | | | | |
|---|---|---|---|---|---|---|
| tgaaagaccc | cacctgtagg | tttggcaagc | tagcttaagt | aacgccattt | tgcaaggcat | 60 |
| ggaaaataca | taactgagaa | tagagaagtt | cagatcaagg | ttaggaacag | agagacagca | 120 |
| gaatatgggc | caaacaggat | atctgtggta | agcagttcct | gccccggctc | agggccaaga | 180 |
| acagatggtc | cccagatgcg | gtcccgccct | cagcagtttc | tagagaacca | tcagatgttt | 240 |
| ccagggtgcc | ccaaggacct | gaaaatgacc | ctgtgcctta | tttgaactaa | ccaatcagtt | 300 |
| cgcttctcgc | ttctgttcgc | gcgcttctgc | tccccgagct | caataaaaga | gcccacaacc | 360 |
| cctcactcag | cggccgcccc | gggtcgacgc | taccaccatg | cgcccgagac | tgtggcttct | 420 |
| gctcgccgcg | caactgactg | tcctgcacgg | aaacagcgtg | ctgcagcaga | caccggccta | 480 |
| catcaaagtg | cagaccaaca | agatggtcat | gctgtcctgc | gaggccaaga | tttccctctc | 540 |
| caacatgcgc | atctattggt | tgcggcagag | acaggcgcct | cctcggact | cccaccatga | 600 |
| gttcttggcc | ctgtgggact | ccgccaaggg | aactattcac | ggcgaagaag | tggaacagga | 660 |
| gaagatcgcg | gtgtttcgcg | atgcctcccg | ctttatactg | aatctgacct | ccgtgaagcc | 720 |
| cgaagatagc | gggatctact | tttgcatgat | tgtgggctca | cccgaactga | ccttcgggaa | 780 |
| gggcactcag | ctgagcgtgg | tggacttcct | ccccactacc | gcccaaccca | ctaagaagtc | 840 |
| aaccctgaag | aagcgggttt | gcagactccc | acggccggaa | acgcagaagg | gtccgctgtg | 900 |
| ttccccgatc | accctggggc | tccttgtggc | tggagtgctg | gtccttctgg | tgtcccttgg | 960 |
| cgtcgccatt | cacctctgct | gccggagaag | gagggccaga | ctgaggttca | tgaagcagaa | 1020 |
| gttcaacata | gtctgcctga | agatttccgg | gttcactact | tgctgctgct | tccaaatact | 1080 |
| ccagatttca | cgagaatatg | ggttcggtgt | gttgctccaa | aaagacatcg | gtcaacgggc | 1140 |
| caagagatct | ggcagcggcg | ccaccaattt | cagcctgctg | aaacaggccg | gcgacgtgga | 1200 |
| agagaaccct | ggccccatgg | cgcttcccgt | gaccgcactc | ctgttgcccc | ttgccctgct | 1260 |
| gttgcacgcc | gcacgacctt | ccaattccg | ggtgtcccct | ctggatcgca | cctggaacct | 1320 |
| cggggaaacg | gtggagctca | agtgtcaagt | cctcctgtcg | aacccgacca | gcggatgcag | 1380 |
| ctggctgttc | cagccgagag | gagctgccgc | ctcacccacc | ttcctcctgt | acttgagcca | 1440 |
| gaacaagccg | aaggccgctg | agggtctgga | cacccagcgc | ttctcgggca | acggctgggg | 1500 |
| agacactttt | gtgctgactc | tctccgactt | ccggcgggag | aacgagggct | actacttctg | 1560 |
| ctctgcgctc | tccaattcaa | tcatgtactt | ctcacacttc | gtgccggtgt | tcctgcctgc | 1620 |
| caagcccacc | actactccgg | cacccagacc | tccaactccc | gctcccacca | tcgcgtccca | 1680 |
| accccttcg | ctgcgccctg | aagcgtgtcg | gcctgctgct | ggaggagccg | tgcatacccg | 1740 |
| cggtctggac | ttcgcgtgcg | acatctacat | ttggggcccct | ttggctggca | cctgtggagt | 1800 |
| gctgctcctg | tcccttgtga | tcaccctgta | ctgcaaccac | cggaataggc | ggagagtctg | 1860 |

```
caagtgtccg cggcctgtcg tgaagtcagg agataagccg agcctgtccg cacgctacgt    1920
gcgggccaag agatctggca gcggcgaggg cagaggcagc ctgctgacct gcggcgacgt    1980
ggaggagaac cccggcccca tggactcttg gaccttctgc tgcgtgagcc tgtgcatcct    2040
ggtggccaag cacacagacg ccggcgtgat ccagtcccct aggcacgagg tgaccgagat    2100
gggccaggag gtgacactgc gctgtaagcc aatctctggc cacaacagcc tgttttggta    2160
tagggagacc atgatgcgcg gcctggagct gctgatctac ttcaataaca atgtgcccat    2220
cgacgattcc ggcatgcctg aggatcggtt ttctgccaag atgcccaatg ccagcttctc    2280
cacactgaag atccagccta gcgagccaag agactccgcc gtgtattttt gcgcctctag    2340
cccaggcagc accgatacac agtacttcgg accaggaacc aggctgacag tgctggagga    2400
cctgaagaac gtgttccccc ctgaggtggc cgtgtttgag ccctctgagg ccagatcag    2460
ccacacccag aaggccaccc tggtgtgcct ggcaaccggc ttctatcctg atcacgtgga    2520
gctgtcctgg tgggtgaacg gcaaggaggg gcacagcggc gtgtccacag acccacagcc    2580
cctgaaggag cagccagccc tgaatgatag ccggtattgc ctgtcctctc ggctgagagt    2640
gtccgccacc ttttggcaga accccggaa tcacttcaga tgtcaggtgc agttttacgg    2700
cctgtccgag aacgatgagt ggacccagga ccgggccaag cctgtgacac agatcgtgtc    2760
tgccgaggca tggggaagag cagactgtgg cttcacctct gagagctacc agcagggcgt    2820
gctgagcgcc accatcctgt atgagatcct gctgggcaag gccacactgt acgccgtcct    2880
ggtctccgct ctggtgctga tggcaatggt caaaagaaaa gatagtcggg gacgggccaa    2940
gagatctggc agcggccagt gcaccaacta cgccctgctg aagctggccg cgacgtgga    3000
gagcaacccc ggccccatgg agaagaatcc cctggctgcc ccctgctga tcctgtggtt    3060
tcacctggac tgcgtgtcct ctatcctgaa tgtggaacag agcccacaga gcctgcacgt    3120
gcaggagggc gactccacca acttcacatg ctcttttcct agctccaact ctacgccct    3180
gcactggtac agaaaggaga ccgcaaagtc cccagaggcc ctgttcgtga tgacactgaa    3240
cggcgatgag aagaagaagg gccgcatcag cgccaccctg aatacaaagg agggctactc    3300
ctatctgtac atcaagggct cccagcctga ggactctgcc acctatctgt gcgccctgta    3360
caacaataac gatatgcggt ttggcgccgg caccagactg acagtgaagc aaacatcca    3420
gaatccagac cccgccgtgt atcagctgcg ggacagcaag tctagcgata gagcgtgtg    3480
cctgttcacc gactttgatt ctcagacaaa cgtgagccag tccaaggaca gcgacgtgta    3540
catcaccgac aagacagtgc tggatatgag aagcatggac ttcaagtcta acagcgccgt    3600
ggcctggtcc aataagtctg atttcgcctg cgccaatgcc tttaataact ccatcatccc    3660
cgaggatacc ttctttcctt ctccagagtc tctcttgtgac gtgaagctgg tggagaagtc    3720
tttcgagacc gatacaaacc tgaattttca gaacctgagc gtgatcggct tcaggatcct    3780
gctgctgaag gtgccggct ttaatctgct gatgacccc aggctgtgga gctcctgaac    3840
cggtccggag catcttaccg ccatttatac ccatatttgt tctgttttc ttgattgg    3900
tatacattta aatgttaata aaacaaaatg gtggggcaat catttacatt ttttgggata    3960
tgtaattact agttcaggtg tattgccaca agacaaactt gttaagaaac tttcccgtta    4020
tttacgctct gttcctgtta atcaacctct ggattacaaa atttgtgaaa gattgactga    4080
tattcttaac tttgttgctc cttttacgct gtgtggattt gctgctttat tgcctctgta    4140
tcttgctatt gcttcccgta cggctttcgt tttctcctcc ttgtataaat cctggttgct    4200
```

```
gtctcttttt gaggagttgt ggcccgttgt ccgtcaacgt ggcgtggtgt gctctgtgtt    4260
tgctgacgca accccccactg gctggggcat tgccaccacc tgtcaactcc tttctgggac    4320
tttcgctttc ccctcccga tcgccacggc agaactcatc gccgcctgcc ttgcccgctg     4380
ctggacaggg gctaggttgc tgggcactga taattccgtg gtgttgtc                 4428
```

<210> SEQ ID NO 272
<211> LENGTH: 1146
<212> TYPE: PRT
<213> ORGANISM: Artificial Sequence
<220> FEATURE:
<223> OTHER INFORMATION: CD8b4.CD8a.TCR.WPREmut2 amino acid sequence

<400> SEQUENCE: 272

```
Met Arg Pro Arg Leu Trp Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
            180                 185                 190

Leu Cys Cys Arg Arg Arg Arg Ala Arg Leu Arg Phe Met Lys Gln Lys
        195                 200                 205

Phe Asn Ile Val Cys Leu Lys Ile Ser Gly Phe Thr Thr Cys Cys
210                 215                 220

Phe Gln Ile Leu Gln Ile Ser Arg Glu Tyr Gly Phe Gly Val Leu Leu
225                 230                 235                 240

Gln Lys Asp Ile Gly Gln Arg Ala Lys Arg Ser Gly Ser Gly Ala Thr
                245                 250                 255

Asn Phe Ser Leu Leu Lys Gln Ala Gly Asp Val Glu Glu Asn Pro Gly
            260                 265                 270

Pro Met Ala Leu Pro Val Thr Ala Leu Leu Leu Pro Leu Ala Leu Leu
        275                 280                 285

Leu His Ala Ala Arg Pro Ser Gln Phe Arg Val Ser Pro Leu Asp Arg
        290                 295                 300

Thr Trp Asn Leu Gly Glu Thr Val Glu Leu Lys Cys Gln Val Leu Leu
305                 310                 315                 320

Ser Asn Pro Thr Ser Gly Cys Ser Trp Leu Phe Gln Pro Arg Gly Ala
```

```
                    325                 330                 335
Ala Ala Ser Pro Thr Phe Leu Leu Tyr Leu Ser Gln Asn Lys Pro Lys
                340                 345                 350

Ala Ala Glu Gly Leu Asp Thr Gln Arg Phe Ser Gly Lys Arg Leu Gly
                355                 360                 365

Asp Thr Phe Val Leu Thr Leu Ser Asp Phe Arg Arg Glu Asn Glu Gly
370                 375                 380

Tyr Tyr Phe Cys Ser Ala Leu Ser Asn Ser Ile Met Tyr Phe Ser His
385                 390                 395                 400

Phe Val Pro Val Phe Leu Pro Ala Lys Pro Thr Thr Thr Pro Ala Pro
                405                 410                 415

Arg Pro Pro Thr Pro Ala Pro Thr Ile Ala Ser Gln Pro Leu Ser Leu
                420                 425                 430

Arg Pro Glu Ala Cys Arg Pro Ala Ala Gly Gly Ala Val His Thr Arg
                435                 440                 445

Gly Leu Asp Phe Ala Cys Asp Ile Tyr Ile Trp Ala Pro Leu Ala Gly
                450                 455                 460

Thr Cys Gly Val Leu Leu Leu Ser Leu Val Ile Thr Leu Tyr Cys Asn
465                 470                 475                 480

His Arg Asn Arg Arg Arg Val Cys Lys Cys Pro Arg Pro Val Val Lys
                485                 490                 495

Ser Gly Asp Lys Pro Ser Leu Ser Ala Arg Tyr Val Arg Ala Lys Arg
                500                 505                 510

Ser Gly Ser Gly Glu Gly Arg Gly Ser Leu Leu Thr Cys Gly Asp Val
                515                 520                 525

Glu Glu Asn Pro Gly Pro Met Asp Ser Trp Thr Phe Cys Cys Val Ser
530                 535                 540

Leu Cys Ile Leu Val Ala Lys His Thr Asp Ala Gly Val Ile Gln Ser
545                 550                 555                 560

Pro Arg His Glu Val Thr Glu Met Gly Gln Glu Val Thr Leu Arg Cys
                565                 570                 575

Lys Pro Ile Ser Gly His Asn Ser Leu Phe Trp Tyr Arg Glu Thr Met
                580                 585                 590

Met Arg Gly Leu Glu Leu Leu Ile Tyr Phe Asn Asn Asn Val Pro Ile
                595                 600                 605

Asp Asp Ser Gly Met Pro Glu Asp Arg Phe Ser Ala Lys Met Pro Asn
610                 615                 620

Ala Ser Phe Ser Thr Leu Lys Ile Gln Pro Ser Glu Pro Arg Asp Ser
625                 630                 635                 640

Ala Val Tyr Phe Cys Ala Ser Ser Pro Gly Ser Thr Asp Thr Gln Tyr
                645                 650                 655

Phe Gly Pro Gly Thr Arg Leu Thr Val Leu Glu Asp Leu Lys Asn Val
                660                 665                 670

Phe Pro Pro Glu Val Ala Val Phe Glu Pro Ser Glu Ala Glu Ile Ser
                675                 680                 685

His Thr Gln Lys Ala Thr Leu Val Cys Leu Ala Thr Gly Phe Tyr Pro
                690                 695                 700

Asp His Val Glu Leu Ser Trp Trp Val Asn Gly Lys Glu Val His Ser
705                 710                 715                 720

Gly Val Ser Thr Asp Pro Gln Pro Leu Lys Glu Gln Pro Ala Leu Asn
                725                 730                 735

Asp Ser Arg Tyr Cys Leu Ser Ser Arg Leu Arg Val Ser Ala Thr Phe
                740                 745                 750
```

-continued

Trp Gln Asn Pro Arg Asn His Phe Arg Cys Gln Val Gln Phe Tyr Gly
            755                 760                 765

Leu Ser Glu Asn Asp Glu Trp Thr Gln Asp Arg Ala Lys Pro Val Thr
        770                 775                 780

Gln Ile Val Ser Ala Glu Ala Trp Gly Arg Ala Asp Cys Gly Phe Thr
785                 790                 795                 800

Ser Glu Ser Tyr Gln Gln Gly Val Leu Ser Ala Thr Ile Leu Tyr Glu
                805                 810                 815

Ile Leu Leu Gly Lys Ala Thr Leu Tyr Ala Val Leu Val Ser Ala Leu
            820                 825                 830

Val Leu Met Ala Met Val Lys Arg Lys Asp Ser Arg Gly Arg Ala Lys
            835                 840                 845

Arg Ser Gly Ser Gly Gln Cys Thr Asn Tyr Ala Leu Leu Lys Leu Ala
850                 855                 860

Gly Asp Val Glu Ser Asn Pro Gly Pro Met Glu Lys Asn Pro Leu Ala
865                 870                 875                 880

Ala Pro Leu Leu Ile Leu Trp Phe His Leu Asp Cys Val Ser Ser Ile
                885                 890                 895

Leu Asn Val Glu Gln Ser Pro Gln Ser Leu His Val Gln Glu Gly Asp
                900                 905                 910

Ser Thr Asn Phe Thr Cys Ser Phe Pro Ser Ser Asn Phe Tyr Ala Leu
            915                 920                 925

His Trp Tyr Arg Lys Glu Thr Ala Lys Ser Pro Glu Ala Leu Phe Val
        930                 935                 940

Met Thr Leu Asn Gly Asp Glu Lys Lys Lys Gly Arg Ile Ser Ala Thr
945                 950                 955                 960

Leu Asn Thr Lys Glu Gly Tyr Ser Tyr Leu Tyr Ile Lys Gly Ser Gln
                965                 970                 975

Pro Glu Asp Ser Ala Thr Tyr Leu Cys Ala Leu Tyr Asn Asn Asn Asp
            980                 985                 990

Met Arg Phe Gly Ala Gly Thr Arg Leu Thr Val Lys Pro Asn Ile Gln
        995                 1000                1005

Asn Pro Asp Pro Ala Val Tyr Gln Leu Arg Asp Ser Lys Ser Ser
    1010                1015                1020

Asp Lys Ser Val Cys Leu Phe Thr Asp Phe Asp Ser Gln Thr Asn
    1025                1030                1035

Val Ser Gln Ser Lys Asp Ser Asp Val Tyr Ile Thr Asp Lys Thr
    1040                1045                1050

Val Leu Asp Met Arg Ser Met Asp Phe Lys Ser Asn Ser Ala Val
    1055                1060                1065

Ala Trp Ser Asn Lys Ser Asp Phe Ala Cys Ala Asn Ala Phe Asn
    1070                1075                1080

Asn Ser Ile Ile Pro Glu Asp Thr Phe Phe Pro Ser Pro Glu Ser
    1085                1090                1095

Ser Cys Asp Val Lys Leu Val Glu Lys Ser Phe Glu Thr Asp Thr
    1100                1105                1110

Asn Leu Asn Phe Gln Asn Leu Ser Val Ile Gly Phe Arg Ile Leu
    1115                1120                1125

Leu Leu Lys Val Ala Gly Phe Asn Leu Leu Met Thr Leu Arg Leu
    1130                1135                1140

Trp Ser Ser
    1145

<210> SEQ ID NO 273
<211> LENGTH: 4308
<212> TYPE: DNA
<213> ORGANISM: Artificial Sequence
<220> FEATURE:
<223> OTHER INFORMATION: CD8b1(S19).CD8a(S19).TCR.WPREmut2 construct nucleotide sequence

<400> SEQUENCE: 273

```
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga     180
acagatggtc cccagatgcg gtcccgccct cagcagtttc tagagaacca tcagatgttt     240
ccagggtgcc caaggacct gaaaatgacc ctgtgcctta tttgaactaa ccaatcagtt      300
cgcttctcgc ttctgttcgc gcgcttctgc tccccgagct caataaaaga gcccacaacc     360
cctcactcag cggccgcccc gggtcgacgc taccaccatg gaattcggcc tgagctggct     420
gttcctggtg gccatcctga agggcgtgca gtgcctgcag cagacaccgg cctacatcaa     480
agtgcagacc aacaagatgg tcatgctgtc ctgcgaggcc aagatttccc tctccaacat     540
gcggatctat tggttgcggc agagacaggc gccttcctcg gactcccacc atgagttctt     600
ggccctgtgg gactccgcca aggaactat tcacggcgaa gaagtggaac aggagaagat      660
cgccgtgttt cgcgatgcct cccgctttat actgaatctg acctccgtga gcccgaaga     720
tagcgggatc tacttttgca tgattgtggg ctcacccgaa ctgaccttcg ggaagggcac     780
tcagctgagc gtggtggact cctcccccac taccgcccaa cccactaaga agtcaaccct     840
gaagaagcgg gtttgcagac tcccacggcc ggaaacgcag aagggtccgc tgtgttcccc     900
gatcaccctg ggctccttg tggctggagt gctggtcctt ctggtgtccc ttggcgtcgc     960
cattcacctc tgctgccgga aggagggc cagactgagg ttcatgaagc agttctacaa    1020
gcgggccaag agatctggca gcggcgccac caatttcagc ctgctgaaac aggccggcga   1080
cgtggaagag aaccctggcc ccatggagtt cggcctgagc tggctgttcc tggtggccat   1140
cctgaagggc gtgcagtgct cccaattccg ggtgtcccct ctggatcgca cctggaacct   1200
cggggaaacg gtggagctca gtgtcaagt cctcctgtcg aacccgacca gcggatgcag   1260
ctggctgttc cagccgagag gagctgccgc ctcacccacc ttcctcctgt acttgagcca   1320
gaacaagccg aaggccgctg agggtctgga cacccagcgc ttctcgggca acggctggg   1380
agacactttt gtgctgactc tctccgactt ccggcgggag aacgagggct actacttctg   1440
ctctgcgctc tccaattcaa tcatgtactt ctcacacttc gtgccggtgt tcctgcctgc   1500
caagcccacc actactccgg cacccagacc tccaactccc gctcccacca tcgcgtccca   1560
acccctttcg ctgcgccctg aagcgtgtcg gcctgctgct ggaggagccg tgcatacccg   1620
cggtctggac ttcgcgtgcg acatctacat ttgggccct ttggctggca cctgtggagt   1680
gctgctcctg tcccttgtga tcaccctgta ctgcaaccac cggaataggc ggagagtctg   1740
caagtgtccg cggcctgtcg tgaagtcagg agataagccg agcctgtccg cacgctacgt   1800
gcgggccaag agatctggca gcggcgaggg cagaggcagc ctgctgacct gcggcgacgt   1860
ggaggagaac cccggcccca tggactcttg gaccttctgc tgcgtgagcc tgtgcatcct   1920
ggtggccaag cacacagacg ccggcgtgat ccagtcccct aggcacgagg tgaccgagat   1980
gggccaggag gtgacactgc gctgtaagcc aatctctggc cacaacagcc tgttttggta   2040
```

```
tagggagacc atgatgcgcg gcctggagct gctgatctac ttcaataaca atgtgcccat   2100
cgacgattcc ggcatgcctg aggatcggtt ttctgccaag atgcccaatg ccagcttctc   2160
cacactgaag atccagccta gcgagccaag agactccgcc gtgtatttt gcgcctctag    2220
cccaggcagc accgatacac agtacttcgg accaggaacc aggctgacag tgctggagga   2280
cctgaagaac gtgttccccc ctgaggtggc cgtgtttgag ccctctgagg ccgagatcag   2340
ccacacccag aaggccaccc tggtgtgcct ggcaaccggc ttctatcctg atcacgtgga   2400
gctgtcctgg tgggtgaacg gcaaggaggt gcacagcggc gtgtccacag acccacagcc   2460
cctgaaggag cagccagccc tgaatgatag ccggtattgc ctgtcctctc ggctgagagt   2520
gtccgccacc tttggcaga acccccggaa tcacttcaga tgtcaggtgc agttttacgg    2580
cctgtccgag aacgatgagt ggacccagga ccgggccaag cctgtgacac agatcgtgtc   2640
tgccgaggca tggggaagag cagactgtgg cttcacctct gagagctacc agcagggcgt   2700
gctgagcgcc accatcctgt atgagatcct gctgggcaag gccacactgt acgccgtcct   2760
ggtctccgct ctggtgctga tggcaatggt caaaagaaaa gatagtcggg gacgggccaa   2820
gagatctggc agcggccagt gcaccaacta cgccctgctg aagctggccg gcgacgtgga   2880
gagcaacccc ggccccatgg agaagaatcc cctggctgcc cccctgctga tcctgtggtt   2940
tcacctggac tgcgtgtcct ctatcctgaa tgtggaacag agcccacaga gcctgcacgt   3000
gcaggaggc gactccacca acttcacatg ctcttttcct agctccaact tctacgccct    3060
gcactggtac agaaaggaga ccgcaaagtc cccagaggcc ctgttcgtga tgacactgaa   3120
cggcgatgag aagaagaagg gccgcatcag cgccaccctg aatacaaagg agggctactc   3180
ctatctgtac atcaagggct cccagcctga ggactctgcc acctatctgt gcgccctgta   3240
caacaataac gatatgcggt ttggcgccgg caccagactg acagtgaagc aaacatccca   3300
gaatccagac cccgccgtgt atcagctgcg ggacagcaag tctagcgata gagcgtgtg    3360
cctgttcacc gactttgatt ctcagacaaa cgtgagccag tccaaggaca gcgacgtgta   3420
catcaccgac aagacagtgc tggatatgag aagcatggac ttcaagtcta acagcgccgt   3480
ggcctggtcc aataagtctg atttcgcctg cgccaatgcc tttaataact ccatcatccc   3540
cgaggatacc ttctttcctt ctccagagtc ctcttgtgac gtgaagctgg tggagaagtc   3600
tttcgagacc gatacaaacc tgaattttca gaacctgagc gtgatcggct tcaggatcct   3660
gctgctgaag gtggccggct ttaatctgct gatgaccctg aggctgtgga gctcctgaac   3720
cggtccggag catcttaccg ccatttatac ccatatttgt tctgttttc ttgatttggg    3780
tatacattta aatgttaata aaacaaaatg gtggggcaat catttacatt ttttgggata   3840
tgtaattact agttcaggtg tattgccaca agacaaactt gttaagaaac tttcccgtta   3900
tttacgctct gttcctgtta atcaacctct ggattacaaa atttgtgaaa gattgactga   3960
tattcttaac tttgttgctc cttttacgct gtgtggattt gctgctttat tgcctctgta   4020
tcttgctatt gcttcccgta cggctttcgt tttctcctcc ttgtataaat cctggttgct   4080
gtctcttttt gaggagttgt ggcccgttgt ccgtcaacgt ggcgtggtgt gctctgtgtt   4140
tgctgacgca accccactg gctggggcat tgccaccacc tgtcaactcc tttctgggac    4200
tttcgctttc cccctcccga tcgccacggc agaactcatc gccgcctgcc ttgcccgctg   4260
ctggacaggg gctaggttgc tgggcactga taattccgtg gtgttgtc              4308
```

<210> SEQ ID NO 274
<211> LENGTH: 1106

<212> TYPE: PRT
<213> ORGANISM: Artificial Sequence
<220> FEATURE:
<223> OTHER INFORMATION: CD8b1(S19).CD8a(S19).TCR.WPREmut2 amino acid sequence

<400> SEQUENCE: 274

```
Met Glu Phe Gly Leu Ser Trp Leu Phe Leu Val Ala Ile Leu Lys Gly
1               5                   10                  15

Val Gln Cys Leu Gln Gln Thr Pro Ala Tyr Ile Lys Val Gln Thr Asn
            20                  25                  30

Lys Met Val Met Leu Ser Cys Glu Ala Lys Ile Ser Leu Ser Asn Met
        35                  40                  45

Arg Ile Tyr Trp Leu Arg Gln Arg Gln Ala Pro Ser Ser Asp Ser His
    50                  55                  60

His Glu Phe Leu Ala Leu Trp Asp Ser Ala Lys Gly Thr Ile His Gly
65                  70                  75                  80

Glu Glu Val Glu Gln Glu Lys Ile Ala Val Phe Arg Asp Ala Ser Arg
                85                  90                  95

Phe Ile Leu Asn Leu Thr Ser Val Lys Pro Glu Asp Ser Gly Ile Tyr
            100                 105                 110

Phe Cys Met Ile Val Gly Ser Pro Glu Leu Thr Phe Gly Lys Gly Thr
        115                 120                 125

Gln Leu Ser Val Val Asp Phe Leu Pro Thr Thr Ala Gln Pro Thr Lys
    130                 135                 140

Lys Ser Thr Leu Lys Lys Arg Val Cys Arg Leu Pro Arg Pro Glu Thr
145                 150                 155                 160

Gln Lys Gly Pro Leu Cys Ser Pro Ile Thr Leu Gly Leu Leu Val Ala
                165                 170                 175

Gly Val Leu Val Leu Leu Val Ser Leu Gly Val Ala Ile His Leu Cys
            180                 185                 190

Cys Arg Arg Arg Arg Ala Arg Leu Arg Phe Met Lys Gln Phe Tyr Lys
        195                 200                 205

Arg Ala Lys Arg Ser Gly Ser Gly Ala Thr Asn Phe Ser Leu Leu Lys
    210                 215                 220

Gln Ala Gly Asp Val Glu Glu Asn Pro Gly Pro Met Glu Phe Gly Leu
225                 230                 235                 240

Ser Trp Leu Phe Leu Val Ala Ile Leu Lys Gly Val Gln Cys Ser Gln
                245                 250                 255

Phe Arg Val Ser Pro Leu Asp Arg Thr Trp Asn Leu Gly Glu Thr Val
            260                 265                 270

Glu Leu Lys Cys Gln Val Leu Leu Ser Asn Pro Thr Ser Gly Cys Ser
        275                 280                 285

Trp Leu Phe Gln Pro Arg Gly Ala Ala Ala Ser Pro Thr Phe Leu Leu
    290                 295                 300

Tyr Leu Ser Gln Asn Lys Pro Lys Ala Ala Glu Gly Leu Asp Thr Gln
305                 310                 315                 320

Arg Phe Ser Gly Lys Arg Leu Gly Asp Thr Phe Val Leu Thr Leu Ser
                325                 330                 335

Asp Phe Arg Glu Asn Glu Gly Tyr Tyr Phe Cys Ser Ala Leu Ser
            340                 345                 350

Asn Ser Ile Met Tyr Phe Ser His Phe Val Pro Val Phe Leu Pro Ala
        355                 360                 365

Lys Pro Thr Thr Thr Pro Ala Pro Arg Pro Pro Thr Pro Ala Pro Thr
    370                 375                 380
```

-continued

```
Ile Ala Ser Gln Pro Leu Ser Leu Arg Pro Glu Ala Cys Arg Pro Ala
385                 390                 395                 400

Ala Gly Gly Ala Val His Thr Arg Gly Leu Asp Phe Ala Cys Asp Ile
                405                 410                 415

Tyr Ile Trp Ala Pro Leu Ala Gly Thr Cys Gly Val Leu Leu Leu Ser
            420                 425                 430

Leu Val Ile Thr Leu Tyr Cys Asn His Arg Asn Arg Arg Val Cys
        435                 440                 445

Lys Cys Pro Arg Pro Val Val Lys Ser Gly Asp Lys Pro Ser Leu Ser
    450                 455                 460

Ala Arg Tyr Val Arg Ala Lys Arg Ser Gly Ser Gly Glu Gly Arg Gly
465                 470                 475                 480

Ser Leu Leu Thr Cys Gly Asp Val Glu Glu Asn Pro Gly Pro Met Asp
                485                 490                 495

Ser Trp Thr Phe Cys Cys Val Ser Leu Cys Ile Leu Val Ala Lys His
            500                 505                 510

Thr Asp Ala Gly Val Ile Gln Ser Pro Arg His Glu Val Thr Glu Met
        515                 520                 525

Gly Gln Glu Val Thr Leu Arg Cys Lys Pro Ile Ser Gly His Asn Ser
530                 535                 540

Leu Phe Trp Tyr Arg Glu Thr Met Met Arg Gly Leu Glu Leu Leu Ile
545                 550                 555                 560

Tyr Phe Asn Asn Asn Val Pro Ile Asp Asp Ser Gly Met Pro Glu Asp
                565                 570                 575

Arg Phe Ser Ala Lys Met Pro Asn Ala Ser Phe Ser Thr Leu Lys Ile
            580                 585                 590

Gln Pro Ser Glu Pro Arg Asp Ser Ala Val Tyr Phe Cys Ala Ser Ser
        595                 600                 605

Pro Gly Ser Thr Asp Thr Gln Tyr Phe Gly Pro Gly Thr Arg Leu Thr
    610                 615                 620

Val Leu Glu Asp Leu Lys Asn Val Phe Pro Pro Glu Val Ala Val Phe
625                 630                 635                 640

Glu Pro Ser Glu Ala Glu Ile Ser His Thr Gln Lys Ala Thr Leu Val
                645                 650                 655

Cys Leu Ala Thr Gly Phe Tyr Pro Asp His Val Glu Leu Ser Trp Trp
            660                 665                 670

Val Asn Gly Lys Glu Val His Ser Gly Val Ser Thr Asp Pro Gln Pro
        675                 680                 685

Leu Lys Glu Gln Pro Ala Leu Asn Asp Ser Arg Tyr Cys Leu Ser Ser
    690                 695                 700

Arg Leu Arg Val Ser Ala Thr Phe Trp Gln Asn Pro Arg Asn His Phe
705                 710                 715                 720

Arg Cys Gln Val Gln Phe Tyr Gly Leu Ser Glu Asn Asp Glu Trp Thr
                725                 730                 735

Gln Asp Arg Ala Lys Pro Val Thr Gln Ile Val Ser Ala Glu Ala Trp
            740                 745                 750

Gly Arg Ala Asp Cys Gly Phe Thr Ser Glu Ser Tyr Gln Gln Gly Val
        755                 760                 765

Leu Ser Ala Thr Ile Leu Tyr Glu Ile Leu Leu Gly Lys Ala Thr Leu
    770                 775                 780

Tyr Ala Val Leu Val Ser Ala Leu Val Leu Met Ala Met Val Lys Arg
785                 790                 795                 800
```

| | | | | | | | | | | | |
|---|---|---|---|---|---|---|---|---|---|---|---|
|Lys|Asp|Ser|Arg|Gly|Arg|Ala|Lys|Arg|Ser|Gly|Gly|Gln|Cys|Thr|
| | | | |805| | | |810| | | |815| | |

Lys Asp Ser Arg Gly Arg Ala Lys Arg Ser Gly Gly Gln Cys Thr
                805                 810                 815

Asn Tyr Ala Leu Leu Lys Leu Ala Gly Asp Val Glu Ser Asn Pro Gly
            820                 825                 830

Pro Met Glu Lys Asn Pro Leu Ala Ala Pro Leu Leu Ile Leu Trp Phe
            835                 840                 845

His Leu Asp Cys Val Ser Ser Ile Leu Asn Val Glu Gln Ser Pro Gln
            850                 855                 860

Ser Leu His Val Gln Glu Gly Asp Ser Thr Asn Phe Thr Cys Ser Phe
865                 870                 875                 880

Pro Ser Ser Asn Phe Tyr Ala Leu His Trp Tyr Arg Lys Glu Thr Ala
            885                 890                 895

Lys Ser Pro Glu Ala Leu Phe Val Met Thr Leu Asn Gly Asp Glu Lys
            900                 905                 910

Lys Lys Gly Arg Ile Ser Ala Thr Leu Asn Thr Lys Glu Gly Tyr Ser
            915                 920                 925

Tyr Leu Tyr Ile Lys Gly Ser Gln Pro Glu Asp Ser Ala Thr Tyr Leu
            930                 935                 940

Cys Ala Leu Tyr Asn Asn Asn Asp Met Arg Phe Gly Ala Gly Thr Arg
945                 950                 955                 960

Leu Thr Val Lys Pro Asn Ile Gln Asn Pro Asp Pro Ala Val Tyr Gln
            965                 970                 975

Leu Arg Asp Ser Lys Ser Ser Asp Lys Ser Val Cys Leu Phe Thr Asp
            980                 985                 990

Phe Asp Ser Gln Thr Asn Val Ser Gln Ser Lys Asp Ser Asp Val Tyr
            995                 1000                1005

Ile Thr Asp Lys Thr Val Leu Asp Met Arg Ser Met Asp Phe Lys
            1010                1015                1020

Ser Asn Ser Ala Val Ala Trp Ser Asn Lys Ser Asp Phe Ala Cys
            1025                1030                1035

Ala Asn Ala Phe Asn Asn Ser Ile Ile Pro Glu Asp Thr Phe Phe
            1040                1045                1050

Pro Ser Pro Glu Ser Ser Cys Asp Val Lys Leu Val Glu Lys Ser
            1055                1060                1065

Phe Glu Thr Asp Thr Asn Leu Asn Phe Gln Asn Leu Ser Val Ile
            1070                1075                1080

Gly Phe Arg Ile Leu Leu Leu Lys Val Ala Gly Phe Asn Leu Leu
            1085                1090                1095

Met Thr Leu Arg Leu Trp Ser Ser
            1100                1105

<210> SEQ ID NO 275
<211> LENGTH: 4416
<212> TYPE: DNA
<213> ORGANISM: Artificial Sequence
<220> FEATURE:
<223> OTHER INFORMATION: CD8b4(S19).CD8a(S19).TCR.WPREmut2 construct
      nucleotide sequence

<400> SEQUENCE: 275
tgaaagaccc cacctgtagg tttggcaagc tagcttaagt aacgccattt tgcaaggcat     60
ggaaaataca taactgagaa tagagaagtt cagatcaagg ttaggaacag agagacagca    120
gaatatgggc caaacaggat atctgtggta agcagttcct gccccggctc agggccaaga    180
acagatggtc cccagatgcg gtcccgccct cagcagtttc tagagaacca tcagatgttt    240

```
ccagggtgcc ccaaggacct gaaaatgacc ctgtgcctta tttgaactaa ccaatcagtt      300
cgcttctcgc ttctgttcgc gcgcttctgc tccccgagct caataaaaga gcccacaacc      360
cctcactcag cggccgcccc gggtcgacgc taccaccatg gaattcggcc tgagctggct      420
gttcctggtg gccatcctga agggcgtgca gtgcctgcag cagacaccgg cctacatcaa      480
agtgcagacc aacaagatgg tcatgctgtc ctgcgaggcc aagatttccc tctccaacat      540
gcggatctat tggttgcggc agagacaggc gccttcctcg gactcccacc atgagttctt      600
ggccctgtgg gactccgcca agggaactat tcacggcgaa gaagtggaac aggagaagat      660
cgccgtgttt cgcgatgcct cccgctttat actgaatctg acctccgtga agcccgaaga      720
tagcgggatc tacttttgca tgattgtggg ctcacccgaa ctgaccttcg ggaagggcac      780
tcagctgagc gtggtggact cctccccac taccgcccaa cccactaaga agtcaaccct      840
gaagaagcgg gtttgcagac tcccacggcc ggaaacgcag aagggtccgc tgtgttcccc      900
gatcaccctg gggctccttg tggctggagt gctggtcctt ctggtgtccc ttggcgtcgc      960
cattcacctc tgctgccgga aaggagggc cagactgagg ttcatgaagc agaagttcaa     1020
catagtctgc ctgaagattt ccgggttcac tacttgctgc tgcttccaaa tactccagat     1080
ttcacgagaa tatgggttcg gtgtgttgct ccaaaaagac atcggtcaac gggccaagag     1140
atctggcagc ggcgccacca atttcagcct gctgaaacag gccggcgacg tggaagagaa     1200
ccctggcccc atggagttcg gcctgagctg gctgttcctg gtggccatcc tgaagggcgt     1260
gcagtgctcc caattccggg tgtcccctct ggatcgcacc tggaacctcg gggaaacggt     1320
ggagctcaag tgtcaagtcc tcctgtcgaa cccgaccagc ggatgcagct ggctgttcca     1380
gccgagagga gctgccgcct cacccacctt cctcctgtac ttgagccaga acaagccgaa     1440
ggccgctgag ggtctggaca cccagcgctt ctcgggcaaa cggctgggag acactttgt     1500 gctgactctc tccgacttcc ggcgggagaa cgagggctac tacttctgct ctgcgctctc     1560
caattcaatc atgtacttct cacacttcgt gccggtgttc ctgcctgcca agcccaccac     1620
tactccggca cccagacctc caactcccgc tcccaccatc gcgtcccaac cctttcgct     1680 gcgcccgaa gcgtgtcggc ctgctgctgg aggagccgtg catacccgcg gtctggactt     1740
cgcgtgcgac atctacattt gggcccctt ggctggcacc tgtggagtgc tgctcctgtc     1800
ccttgtgatc accctgtact gcaaccaccg gaataggcgg agagtctgca agtgtccgcg     1860
gcctgtcgtg aagtcaggag ataagccgag cctgtccgca cgctacgtgc gggccaagag     1920
atctggcagc ggcgagggca gaggcagcct gctgacctgc ggcgacgtgg aggagaaccc     1980
cggccccatg gactcttgga ccttctgctg cgtgagcctg tgcatcctgg tggccaagca     2040
cacagacgcc ggcgtgatcc agtccccctag gcacgaggtg accgagatgg gccaggaggt     2100
gacactgcgc tgtaagccaa tctctggcca caacagcctg ttttggtata gggagaccat     2160
gatgcgcggc ctggagctgc tgatctactt caataacaat gtgcccatcg acgattccgg     2220
catgcctgag gatcggtttt ctgccaagat gcccaatgcc agcttctcca cactgaagat     2280
ccagcctagc gagccaagag actccgccgt gtattttgc gcctctagcc caggcagcac     2340
cgatacacag tacttcggac caggaaccag gctgacagtg ctggaggacc tgaagaacgt     2400 gttccccct gaggtggccg tgtttgagcc ctctgaggcc gagatcagcc acacccagaa     2460
ggccaccctg gtgtgcctgg caaccggctt ctatcctgat cacgtggagc tgtcctggtg     2520
ggtgaacggc aaggaggtgc acagcggcgt gtccacagac ccacagcccc tgaaggagca     2580
gccagccctg aatgatagcc ggtattgcct gtcctctcgg ctgagagtgt ccgccacctt     2640
```

```
ttggcagaac ccccggaatc acttcagatg tcaggtgcag ttttacggcc tgtccgagaa    2700
cgatgagtgg acccaggacc gggccaagcc tgtgacacag atcgtgtctg ccgaggcatg    2760
gggaagagca gactgtggct tcacctctga gagctaccag cagggcgtgc tgagcgccac    2820
catcctgtat gagatcctgc tgggcaaggc cacactgtac gccgtcctgg tctccgctct    2880
ggtgctgatg gcaatggtca aaagaaaaga tagtcgggga cgggccaaga gatctggcag    2940
cggccagtgc accaactacg ccctgctgaa gctggccggc gacgtggaga gcaaccccgg    3000
ccccatggag aagaatcccc tggctgcccc cctgctgatc ctgtggtttc acctggactg    3060
cgtgtcctct atcctgaatg tggaacagag cccacagagc ctgcacgtgc aggagggcga    3120
ctccaccaac ttcacatgct cttttcctag ctccaacttc tacgccctgc actggtacag    3180
aaaggagacc gcaaagtccc cagaggccct gttcgtgatg acactgaacg gcgatgagaa    3240
gaagaagggc cgcatcagcg ccaccctgaa tacaaaggag ggctactcct atctgtacat    3300
caagggctcc cagcctgagg actctgccac ctatctgtgc gccctgtaca acaataacga    3360
tatgcggttt ggcgccggca ccagactgac agtgaagcca acatccagaa tccagacccc    3420
cgccgtgtat cagctgcggg acagcaagtc tagcgataag agcgtgtgcc tgttcaccga    3480
ctttgattct cagacaaacg tgagccagtc caaggacagc gacgtgtaca tcaccgacaa    3540
gacagtgctg gatatgagaa gcatggactt caagtctaac agcgccgtgg cctggtccaa    3600
taagtctgat ttcgcctgcg ccaatgcctt taataactcc atcatccccg aggataccct    3660
ctttccttct ccagagtcct cttgtgacgt gaagctggtg gagaagtctt tcgagaccga    3720
tacaaacctg aattttcaga acctgagcgt gatcggcttc aggatcctgc tgctgaaggt    3780
ggccggcttt aatctgctga tgaccctgag gctgtggagc tcctgaaccg gtccggagca    3840
tcttaccgcc atttataccc atatttgttc tgttttctt gatttgggta tacatttaaa    3900
tgttaataaa acaaaatggt ggggcaatca tttacatttt ttgggatatg taattactag    3960
ttcaggtgta ttgccacaag acaaacttgt taagaaactt tcccgttatt tacgctctgt    4020
tcctgttaat caacctctgg attacaaaat ttgtgaaaga ttgactgata ttcttaactt    4080
tgttgctcct tttacgctgt gtggatttgc tgctttattg cctctgtatc ttgctattgc    4140
ttcccgtacg gctttcgttt tctcctcctt gtataaatcc tggttgctgt ctctttttga    4200
ggagttgtgg cccgttgtcc gtcaacgtgg cgtggtgtgc tctgtgtttg ctgacgcaac    4260
ccccactggc tggggcattg ccaccacctg tcaactcctt tctgggactt tcgctttccc    4320
cctcccgatc gccacggcag aactcatcgc cgcctgcctt gcccgctgct ggacaggggc    4380
taggttgctg ggcactgata attccgtggt gttgtc                              4416
```

<210> SEQ ID NO 276
<211> LENGTH: 1142
<212> TYPE: PRT
<213> ORGANISM: Artificial Sequence
<220> FEATURE:
<223> OTHER INFORMATION: CD8b4(S19).CD8a(S19).TCR.WPREmut2 amino acid
      sequence

<400> SEQUENCE: 276

Met Glu Phe Gly Leu Ser Trp Leu Phe Leu Val Ala Ile Leu Lys Gly
1               5                   10                  15

Val Gln Cys Leu Gln Gln Thr Pro Ala Tyr Ile Lys Val Gln Thr Asn
            20                  25                  30

Lys Met Val Met Leu Ser Cys Glu Ala Lys Ile Ser Leu Ser Asn Met

```
            35                  40                  45
Arg Ile Tyr Trp Leu Arg Gln Arg Gln Ala Pro Ser Ser Asp Ser His
 50                  55                  60

His Glu Phe Leu Ala Leu Trp Asp Ser Ala Lys Gly Thr Ile His Gly
 65                  70                  75                  80

Glu Glu Val Glu Gln Glu Lys Ile Ala Val Phe Arg Asp Ala Ser Arg
                 85                  90                  95

Phe Ile Leu Asn Leu Thr Ser Val Lys Pro Glu Asp Ser Gly Ile Tyr
                100                 105                 110

Phe Cys Met Ile Val Gly Ser Pro Glu Leu Thr Phe Gly Lys Gly Thr
            115                 120                 125

Gln Leu Ser Val Val Asp Phe Leu Pro Thr Thr Ala Gln Pro Thr Lys
130                 135                 140

Lys Ser Thr Leu Lys Lys Arg Val Cys Arg Leu Pro Arg Pro Glu Thr
145                 150                 155                 160

Gln Lys Gly Pro Leu Cys Ser Pro Ile Thr Leu Gly Leu Leu Val Ala
                165                 170                 175

Gly Val Leu Val Leu Leu Val Ser Leu Gly Val Ala Ile His Leu Cys
            180                 185                 190

Cys Arg Arg Arg Ala Arg Leu Arg Phe Met Lys Gln Leu Lys Phe Asn
            195                 200                 205

Ile Val Cys Leu Lys Ile Ser Gly Phe Thr Thr Cys Cys Cys Phe Gln
210                 215                 220

Ile Leu Gln Ile Ser Arg Glu Tyr Gly Phe Gly Val Leu Leu Gln Lys
225                 230                 235                 240

Asp Ile Gly Gln Arg Ala Lys Arg Ser Gly Ser Gly Ala Thr Asn Phe
                245                 250                 255

Ser Leu Leu Lys Gln Ala Gly Asp Val Glu Glu Asn Pro Gly Pro Met
                260                 265                 270

Glu Phe Gly Leu Ser Trp Leu Phe Leu Val Ala Ile Leu Lys Gly Val
            275                 280                 285

Gln Cys Ser Gln Phe Arg Val Ser Pro Leu Asp Arg Thr Trp Asn Leu
290                 295                 300

Gly Glu Thr Val Glu Leu Lys Cys Gln Val Leu Leu Ser Asn Pro Thr
305                 310                 315                 320

Ser Gly Cys Ser Trp Leu Phe Gln Pro Arg Gly Ala Ala Ala Ser Pro
                325                 330                 335

Thr Phe Leu Leu Tyr Leu Ser Gln Asn Lys Pro Lys Ala Ala Glu Gly
            340                 345                 350

Leu Asp Thr Gln Arg Phe Ser Gly Lys Arg Leu Gly Asp Thr Phe Val
            355                 360                 365

Leu Thr Leu Ser Asp Phe Arg Arg Glu Asn Glu Gly Tyr Tyr Phe Cys
            370                 375                 380

Ser Ala Leu Ser Asn Ser Ile Met Tyr Phe Ser His Phe Val Pro Val
385                 390                 395                 400

Phe Leu Pro Ala Lys Pro Thr Thr Thr Pro Ala Pro Arg Pro Pro Thr
                405                 410                 415

Pro Ala Pro Thr Ile Ala Ser Gln Pro Leu Ser Leu Arg Pro Glu Ala
                420                 425                 430

Cys Arg Pro Ala Ala Gly Gly Ala Val His Thr Arg Gly Leu Asp Phe
            435                 440                 445

Ala Cys Asp Ile Tyr Ile Trp Ala Pro Leu Ala Gly Thr Cys Gly Val
            450                 455                 460
```

-continued

```
Leu Leu Leu Ser Leu Val Ile Thr Leu Tyr Cys Asn His Arg Asn Arg
465                 470                 475                 480

Arg Arg Val Cys Lys Cys Pro Arg Pro Val Lys Ser Gly Asp Lys
            485                 490                 495

Pro Ser Leu Ser Ala Arg Tyr Val Arg Ala Lys Arg Ser Gly Ser Gly
        500                 505                 510

Glu Gly Arg Gly Ser Leu Leu Thr Cys Gly Asp Val Glu Glu Asn Pro
            515                 520                 525

Gly Pro Met Asp Ser Trp Thr Phe Cys Cys Val Ser Leu Cys Ile Leu
        530                 535                 540

Val Ala Lys His Thr Asp Ala Gly Val Ile Gln Ser Pro Arg His Glu
545                 550                 555                 560

Val Thr Glu Met Gly Gln Glu Val Thr Leu Arg Cys Lys Pro Ile Ser
            565                 570                 575

Gly His Asn Ser Leu Phe Trp Tyr Arg Glu Thr Met Met Arg Gly Leu
        580                 585                 590

Glu Leu Leu Ile Tyr Phe Asn Asn Val Pro Ile Asp Asp Ser Gly
        595                 600                 605

Met Pro Glu Asp Arg Phe Ser Ala Lys Met Pro Asn Ala Ser Phe Ser
610                 615                 620

Thr Leu Lys Ile Gln Pro Ser Glu Pro Arg Asp Ser Ala Val Tyr Phe
625                 630                 635                 640

Cys Ala Ser Ser Pro Gly Ser Thr Asp Thr Gln Tyr Phe Gly Pro Gly
                645                 650                 655

Thr Arg Leu Thr Val Leu Glu Asp Leu Lys Asn Val Phe Pro Pro Glu
            660                 665                 670

Val Ala Val Phe Glu Pro Ser Glu Ala Glu Ile Ser His Thr Gln Lys
            675                 680                 685

Ala Thr Leu Val Cys Leu Ala Thr Gly Phe Tyr Pro Asp His Val Glu
            690                 695                 700

Leu Ser Trp Trp Val Asn Gly Lys Glu Val His Ser Gly Val Ser Thr
705                 710                 715                 720

Asp Pro Gln Pro Leu Lys Glu Gln Pro Ala Leu Asn Asp Ser Arg Tyr
                725                 730                 735

Cys Leu Ser Ser Arg Leu Arg Val Ser Ala Thr Phe Trp Gln Asn Pro
                740                 745                 750

Arg Asn His Phe Arg Cys Gln Val Gln Phe Tyr Gly Leu Ser Glu Asn
                755                 760                 765

Asp Glu Trp Thr Gln Asp Arg Ala Lys Pro Val Thr Gln Ile Val Ser
        770                 775                 780

Ala Glu Ala Trp Gly Arg Ala Asp Cys Gly Phe Thr Ser Glu Ser Tyr
785                 790                 795                 800

Gln Gln Gly Val Leu Ser Ala Thr Ile Leu Tyr Glu Ile Leu Leu Gly
                805                 810                 815

Lys Ala Thr Leu Tyr Ala Val Leu Val Ser Ala Leu Val Leu Met Ala
            820                 825                 830

Met Val Lys Arg Lys Asp Ser Arg Gly Arg Ala Lys Arg Ser Gly Ser
            835                 840                 845

Gly Gln Cys Thr Asn Tyr Ala Leu Leu Lys Leu Ala Gly Asp Val Glu
    850                 855                 860

Ser Asn Pro Gly Pro Met Glu Lys Asn Pro Leu Ala Ala Pro Leu Leu
865                 870                 875                 880
```

```
Ile Leu Trp Phe His Leu Asp Cys Val Ser Ser Ile Leu Asn Val Glu
                885                 890                 895

Gln Ser Pro Gln Ser Leu His Val Gln Glu Gly Asp Ser Thr Asn Phe
            900                 905                 910

Thr Cys Ser Phe Pro Ser Ser Asn Phe Tyr Ala Leu His Trp Tyr Arg
        915                 920                 925

Lys Glu Thr Ala Lys Ser Pro Glu Ala Leu Phe Val Met Thr Leu Asn
    930                 935                 940

Gly Asp Glu Lys Lys Gly Arg Ile Ser Ala Thr Leu Asn Thr Lys
945                 950                 955                 960

Glu Gly Tyr Ser Tyr Leu Tyr Ile Lys Gly Ser Gln Pro Glu Asp Ser
            965                 970                 975

Ala Thr Tyr Leu Cys Ala Leu Tyr Asn Asn Asn Asp Met Arg Phe Gly
        980                 985                 990

Ala Gly Thr Arg Leu Thr Val Lys Pro Asn Ile Gln Asn Pro Asp Pro
    995                 1000                1005

Ala Val Tyr Gln Leu Arg Asp Ser Lys Ser Ser Asp Lys Ser Val
    1010                1015                1020

Cys Leu Phe Thr Asp Phe Asp Ser Gln Thr Asn Val Ser Gln Ser
    1025                1030                1035

Lys Asp Ser Asp Val Tyr Ile Thr Asp Lys Thr Val Leu Asp Met
    1040                1045                1050

Arg Ser Met Asp Phe Lys Ser Asn Ser Ala Val Ala Trp Ser Asn
    1055                1060                1065

Lys Ser Asp Phe Ala Cys Ala Asn Ala Phe Asn Asn Ser Ile Ile
    1070                1075                1080

Pro Glu Asp Thr Phe Phe Pro Ser Pro Glu Ser Ser Cys Asp Val
    1085                1090                1095

Lys Leu Val Glu Lys Ser Phe Glu Thr Asp Thr Asn Leu Asn Phe
    1100                1105                1110

Gln Asn Leu Ser Val Ile Gly Phe Arg Ile Leu Leu Leu Lys Val
    1115                1120                1125

Ala Gly Phe Asn Leu Leu Met Thr Leu Arg Leu Trp Ser Ser
    1130                1135                1140

<210> SEQ ID NO 277
<211> LENGTH: 4407
<212> TYPE: DNA
<213> ORGANISM: Artificial Sequence
<220> FEATURE:
<223> OTHER INFORMATION: CD8b5(S19).CD8a(S19).TCR.WPREmut2 construct
      nucleotide sequence

<400> SEQUENCE: 277
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaaatgacc ctgtgcctta tttgaactaa ccaatcagtt    300
cgcttctcgc ttctgttcgc gcgcttctgc tccccgagct caataaaaga gcccacaacc    360
cctcactcag cggccgcccc gggtcgacgc taccaccatg gaattcggcc tgagctggct    420
gttcctggtg gccatcctga agggcgtgca gtgcctgcag cagacaccgg cctacatcaa    480
agtgcagacc aacaagatgg tcatgctgtc ctgcgaggcc aagatttccc tctccaacat    540
```

```
gcggatctat tggttgcggc agagacaggc gccttcctcg gactcccacc atgagttctt     600
ggccctgtgg gactccgcca agggaactat tcacggcgaa gaagtggaac aggagaagat     660
cgccgtgttt cgcgatgcct cccgctttat actgaatctg acctccgtga agcccgaaga     720
tagcgggatc tacttttgca tgattgtggg ctcacccgaa ctgaccttcg ggaagggcac     780
tcagctgagc gtggtggact tcctccccac taccgcccaa cccactaaga agtcaaccct     840
gaagaagcgg gtttgcagac tcccacggcc ggaaacgcag aagggtccgc tgtgttcccc     900
gatcaccctg gggctccttg tggctggagt gctggtcctt ctggtgtccc ttggcgtcgc     960
cattcacctc tgctgccgga aaggagggc cagactgagg ttcatgaagc agcctcaggg    1020
agagggatc agtggcactt tcgtgccaca atgcctccat ggctactatt ccaacaccac    1080
cacctcgcaa aagctgctga acccctggat cctgaaaacc cgggccaaga gatctggcag    1140
cggcgccacc aatttcagcc tgctgaaaca ggccggcgac gtggaagaga accctggccc    1200
catggagttc ggcctgagct ggctgttcct ggtggccatc ctgaagggcg tgcagtgctc    1260
ccaattccgg gtgtcccctc tggatcgcac ctggaacctc ggggaaacgg tggagctcaa    1320
gtgtcaagtc ctcctgtcga acccgaccag cggatgcagc tggctgttcc agccgagagg    1380
agctgccgcc tcacccacct tcctcctgta cttgagccag aacaagccga aggccgctga    1440
gggtctggac acccagcgct ctcgggcaa acggctggga gacacttttg tgctgactct    1500
ctccgacttc cggcgggaga acgagggcta ctacttctgc tctgcgctct ccaattcaat    1560
catgtacttc tcacacttcg tgccggtgtt cctgcctgcc aagcccacca ctactccggc    1620
acccagacct ccaactcccg ctcccaccat cgcgtcccaa ccccttttcgc tgcgccctga    1680
agcgtgtcgg cctgctgctg gaggagccgt gcatacccgc ggtctggact tcgcgtgcga    1740
catctacatt tgggcccctt tggctggcac ctgtggagtg ctgctcctgt cccttgtgat    1800
caccctgtac tgcaaccacc ggaataggcg gagagtctgc aagtgtccgc ggcctgtcgt    1860
gaagtcagga gataagccga gcctgtccgc acgctacgtg cgggccaaga gatctggcag    1920
cggcgagggc agaggcagcc tgctgacctg cggcgacgtg gaggagaacc ccggccccat    1980
ggactcttgg accttctgct gcgtgagcct gtgcatcctg gtggccaagc acacagacgc    2040
cggcgtgatc cagtccccta ggcacgaggt gaccgagatg ggccaggagt gacactgcg    2100
ctgtaagcca atctctggcc acaacagcct gttttggtat agggagacca tgatgcgcgg    2160
cctggagctg ctgatctact tcaataacaa tgtgcccatc gacgattccg gcatgcctga    2220
ggatcggttt tctgccaaga tgcccaatgc cagcttctcc acactgaaga tccagcctag    2280
cgagccaaga gactccgccg tgtatttttg cgcctctagc ccaggcagca ccgatacaca    2340
gtacttcgga ccaggaacca ggctgacagt gctggaggac ctgaagaacg tgttcccccc    2400
tgaggtggcc gtgtttgagc cctctgaggc cgagatcagc cacacccaga aggccaccct    2460
ggtgtgcctg gcaaccggct tctatcctga tcacgtggag ctgtcctggt gggtgaacgg    2520
caaggaggtg cacagcggcg tgtccacaga cccacagccc ctgaaggagc agccagccct    2580
gaatgatagc cggtattgcc tgtcctctcg gctgagagtg tccgccacct ttggcagaa    2640
cccccggaat cacttcagat gtcaggtgca gttttacggc ctgtccgaga cgatgagtg    2700
gacccaggac cgggccaagc ctgtgacaca gatcgtgtct gccgaggcat ggggaagagc    2760
agactgtggc ttcacctctg agagctacca gcagggcgtg ctgagcgcca ccatcctgta    2820
tgagatcctg ctgggcaagg ccacactgta cgccgtcctg gtctccgctc tggtgctgat    2880
```

```
ggcaatggtc aaaagaaaag atagtcgggg acgggccaag agatctggca gcggccagtg    2940
caccaactac gccctgctga agctggccgg cgacgtggag agcaacccg gccccatgga     3000 gaagaatccc ctggctgccc ccctgctgat cctgtggttt cacctggact gcgtgtcctc    3060
tatcctgaat gtggaacaga gcccacagag cctgcacgtg caggagggcg actccaccaa    3120
cttcacatgc tcttttccta gctccaactt ctacgccctg cactggtaca gaaaggagac    3180
cgcaaagtcc ccagaggccc tgttcgtgat gacactgaac ggcgatgaga agaagaaggg    3240
ccgcatcagc gccaccctga atacaaagga gggctactcc tatctgtaca tcaagggctc    3300
ccagcctgag gactctgcca cctatctgtg cgccctgtac aacaataacg atatgcggtt    3360
tggcgccggc accagactga cagtgaagcc aaacatccag aatccagacc cgccgtgta    3420 tcagctgcgg gacagcaagt ctagcgataa gagcgtgtgc ctgttcaccg actttgattc    3480
tcagacaaac gtgagccagt ccaaggacag cgacgtgtac atcaccgaca agacagtgct    3540
ggatatgaga agcatggact tcaagtctaa cagcgccgtg gcctggtcca ataagtctga    3600
tttcgcctgc gccaatgcct taataactc catcatcccc gaggatacct tcttccttc     3660 tccagagtcc tcttgtgacg tgaagctggt ggagaagtct ttcgagaccg atacaaacct    3720
gaattttcag aacctgagcg tgatcggctt caggatcctg ctgctgaagg tggccggctt    3780
taatctgctg atgaccctga ggctgtggag ctcctgaacc ggtccggagc atcttaccgc    3840
catttatacc catatttgtt ctgtttttct tgatttgggt atacatttaa atgttaataa    3900
aacaaaatgg tggggcaatc atttacattt tttgggatat gtaattacta gttcaggtgt    3960
attgccacaa gacaaacttg ttaagaaact tcccgttat ttacgctctg ttcctgttaa    4020
tcaacctctg gattacaaaa tttgtgaaag attgactgat attcttaact ttgttgctcc    4080
ttttacgctg tgtggatttg ctgctttatt gcctctgtat cttgctattg cttccgtac    4140 ggctttcgtt ttctcctcct tgtataaatc ctggttgctg tctcttttg aggagttgtg    4200 gcccgttgtc cgtcaacgtg gcgtggtgtg ctctgtgttt gctgacgcaa ccccactgg    4260 ctggggcatt gccaccacct gtcaactcct ttctgggact ttcgctttcc cctcccgat    4320 cgccacggca gaactcatcg ccgcctgcct tgcccgctgc tggacagggg ctaggttgct    4380
gggcactgat aattccgtgg tgttgtc                                        4407
```

<210> SEQ ID NO 278  
<211> LENGTH: 1139  
<212> TYPE: PRT  
<213> ORGANISM: Artificial Sequence  
<220> FEATURE:  
<223> OTHER INFORMATION: CD8b5(S19).CD8a(S19).TCR.WPREmut2 amino acid  
    sequence

<400> SEQUENCE: 278

```
Met Glu Phe Gly Leu Ser Trp Leu Phe Leu Val Ala Ile Leu Lys Gly
1               5                   10                  15

Val Gln Cys Leu Gln Gln Thr Pro Ala Tyr Ile Lys Val Gln Thr Asn
            20                  25                  30

Lys Met Val Met Leu Ser Cys Glu Ala Lys Ile Ser Leu Ser Asn Met
        35                  40                  45

Arg Ile Tyr Trp Leu Arg Gln Arg Gln Ala Pro Ser Ser Asp Ser His
    50                  55                  60

His Glu Phe Leu Ala Leu Trp Asp Ser Ala Lys Gly Thr Ile His Gly
65                  70                  75                  80

Glu Glu Val Glu Gln Glu Lys Ile Ala Val Phe Arg Asp Ala Ser Arg
```

```
                    85                  90                  95
Phe Ile Leu Asn Leu Thr Ser Val Lys Pro Glu Asp Ser Gly Ile Tyr
                100                 105                 110
Phe Cys Met Ile Val Gly Ser Pro Glu Leu Thr Phe Gly Lys Gly Thr
                115                 120                 125
Gln Leu Ser Val Val Asp Phe Leu Pro Thr Thr Ala Gln Pro Thr Lys
                130                 135                 140
Lys Ser Thr Leu Lys Lys Arg Val Cys Arg Leu Pro Arg Pro Glu Thr
145                 150                 155                 160
Gln Lys Gly Pro Leu Cys Ser Pro Ile Thr Leu Gly Leu Leu Val Ala
                165                 170                 175
Gly Val Leu Val Leu Leu Val Ser Leu Gly Val Ala Ile His Leu Cys
                180                 185                 190
Cys Arg Arg Arg Ala Arg Leu Arg Phe Met Lys Gln Pro Gln Gly
                195                 200                 205
Glu Gly Ile Ser Gly Thr Phe Val Pro Gln Cys Leu His Gly Tyr Tyr
                210                 215                 220
Ser Asn Thr Thr Thr Ser Gln Lys Leu Leu Asn Pro Trp Ile Leu Lys
225                 230                 235                 240
Thr Arg Ala Lys Arg Ser Gly Ser Gly Ala Thr Asn Phe Ser Leu Leu
                245                 250                 255
Lys Gln Ala Gly Asp Val Glu Glu Asn Pro Gly Pro Met Glu Phe Gly
                260                 265                 270
Leu Ser Trp Leu Phe Leu Val Ala Ile Leu Lys Gly Val Gln Cys Ser
                275                 280                 285
Gln Phe Arg Val Ser Pro Leu Asp Arg Thr Trp Asn Leu Gly Glu Thr
                290                 295                 300
Val Glu Leu Lys Cys Gln Val Leu Leu Ser Asn Pro Thr Ser Gly Cys
305                 310                 315                 320
Ser Trp Leu Phe Gln Pro Arg Gly Ala Ala Ala Ser Pro Thr Phe Leu
                325                 330                 335
Leu Tyr Leu Ser Gln Asn Lys Pro Lys Ala Ala Glu Gly Leu Asp Thr
                340                 345                 350
Gln Arg Phe Ser Gly Lys Arg Leu Gly Asp Thr Phe Val Leu Thr Leu
                355                 360                 365
Ser Asp Phe Arg Arg Glu Asn Glu Gly Tyr Tyr Phe Cys Ser Ala Leu
                370                 375                 380
Ser Asn Ser Ile Met Tyr Phe Ser His Phe Val Pro Val Phe Leu Pro
385                 390                 395                 400
Ala Lys Pro Thr Thr Thr Pro Ala Pro Arg Pro Pro Thr Pro Ala Pro
                405                 410                 415
Thr Ile Ala Ser Gln Pro Leu Ser Leu Arg Pro Glu Ala Cys Arg Pro
                420                 425                 430
Ala Ala Gly Gly Ala Val His Thr Arg Gly Leu Asp Phe Ala Cys Asp
                435                 440                 445
Ile Tyr Ile Trp Ala Pro Leu Ala Gly Thr Cys Gly Val Leu Leu Leu
                450                 455                 460
Ser Leu Val Ile Thr Leu Tyr Cys Asn His Arg Asn Arg Arg Val
465                 470                 475                 480
Cys Lys Cys Pro Arg Pro Val Val Lys Ser Gly Asp Lys Pro Ser Leu
                485                 490                 495
Ser Ala Arg Tyr Val Arg Ala Lys Arg Ser Gly Ser Gly Glu Gly Arg
                500                 505                 510
```

```
Gly Ser Leu Leu Thr Cys Gly Asp Val Glu Asn Pro Gly Pro Met
            515                 520                 525

Asp Ser Trp Thr Phe Cys Cys Val Ser Leu Cys Ile Leu Val Ala Lys
530                 535                 540

His Thr Asp Ala Gly Val Ile Gln Ser Pro Arg His Glu Val Thr Glu
545                 550                 555                 560

Met Gly Gln Glu Val Thr Leu Arg Cys Lys Pro Ile Ser Gly His Asn
                565                 570                 575

Ser Leu Phe Trp Tyr Arg Glu Thr Met Met Arg Gly Leu Glu Leu Leu
            580                 585                 590

Ile Tyr Phe Asn Asn Val Pro Ile Asp Asp Ser Gly Met Pro Glu
            595                 600                 605

Asp Arg Phe Ser Ala Lys Met Pro Asn Ala Ser Phe Ser Thr Leu Lys
            610                 615                 620

Ile Gln Pro Ser Glu Pro Arg Asp Ser Ala Val Tyr Phe Cys Ala Ser
625                 630                 635                 640

Ser Pro Gly Ser Thr Asp Thr Gln Tyr Phe Gly Pro Gly Thr Arg Leu
                645                 650                 655

Thr Val Leu Glu Asp Leu Lys Asn Val Phe Pro Pro Glu Val Ala Val
            660                 665                 670

Phe Glu Pro Ser Glu Ala Glu Ile Ser His Thr Gln Lys Ala Thr Leu
            675                 680                 685

Val Cys Leu Ala Thr Gly Phe Tyr Pro Asp His Val Glu Leu Ser Trp
            690                 695                 700

Trp Val Asn Gly Lys Glu Val His Ser Gly Val Ser Thr Asp Pro Gln
705                 710                 715                 720

Pro Leu Lys Glu Gln Pro Ala Leu Asn Asp Ser Arg Tyr Cys Leu Ser
                725                 730                 735

Ser Arg Leu Arg Val Ser Ala Thr Phe Trp Gln Asn Pro Arg Asn His
            740                 745                 750

Phe Arg Cys Gln Val Gln Phe Tyr Gly Leu Ser Glu Asn Asp Glu Trp
            755                 760                 765

Thr Gln Asp Arg Ala Lys Pro Val Thr Gln Ile Val Ser Ala Glu Ala
            770                 775                 780

Trp Gly Arg Ala Asp Cys Gly Phe Thr Ser Glu Ser Tyr Gln Gln Gly
785                 790                 795                 800

Val Leu Ser Ala Thr Ile Leu Tyr Glu Ile Leu Leu Gly Lys Ala Thr
                805                 810                 815

Leu Tyr Ala Val Leu Val Ser Ala Leu Val Leu Met Ala Met Val Lys
            820                 825                 830

Arg Lys Asp Ser Arg Gly Arg Ala Lys Arg Ser Gly Ser Gly Gln Cys
            835                 840                 845

Thr Asn Tyr Ala Leu Leu Lys Leu Ala Gly Asp Val Glu Ser Asn Pro
850                 855                 860

Gly Pro Met Glu Lys Asn Pro Leu Ala Ala Pro Leu Leu Ile Leu Trp
865                 870                 875                 880

Phe His Leu Asp Cys Val Ser Ser Ile Leu Asn Val Glu Gln Ser Pro
                885                 890                 895

Gln Ser Leu His Val Gln Glu Gly Asp Ser Thr Asn Phe Thr Cys Ser
            900                 905                 910

Phe Pro Ser Ser Asn Phe Tyr Ala Leu His Trp Tyr Arg Lys Glu Thr
            915                 920                 925
```

Ala Lys Ser Pro Glu Ala Leu Phe Val Met Thr Leu Asn Gly Asp Glu
        930                 935                 940
Lys Lys Lys Gly Arg Ile Ser Ala Thr Leu Asn Thr Lys Glu Gly Tyr
945                 950                 955                 960
Ser Tyr Leu Tyr Ile Lys Gly Ser Gln Pro Glu Asp Ser Ala Thr Tyr
                965                 970                 975
Leu Cys Ala Leu Tyr Asn Asn Asn Asp Met Arg Phe Gly Ala Gly Thr
            980                 985                 990
Arg Leu Thr Val Lys Pro Asn Ile Gln Asn Pro Asp Pro Ala Val Tyr
        995                 1000                1005
Gln Leu Arg Asp Ser Lys Ser Ser Asp Lys Ser Val Cys Leu Phe
    1010                1015                1020
Thr Asp Phe Asp Ser Gln Thr Asn Val Ser Gln Ser Lys Asp Ser
    1025                1030                1035
Asp Val Tyr Ile Thr Asp Lys Thr Val Leu Asp Met Arg Ser Met
    1040                1045                1050
Asp Phe Lys Ser Asn Ser Ala Val Ala Trp Ser Asn Lys Ser Asp
    1055                1060                1065
Phe Ala Cys Ala Asn Ala Phe Asn Asn Ser Ile Ile Pro Glu Asp
    1070                1075                1080
Thr Phe Phe Pro Ser Pro Glu Ser Ser Cys Asp Val Lys Leu Val
    1085                1090                1095
Glu Lys Ser Phe Glu Thr Asp Thr Asn Leu Asn Phe Gln Asn Leu
    1100                1105                1110
Ser Val Ile Gly Phe Arg Ile Leu Leu Leu Lys Val Ala Gly Phe
    1115                1120                1125
Asn Leu Leu Met Thr Leu Arg Leu Trp Ser Ser
    1130                1135

<210> SEQ ID NO 279
<211> LENGTH: 3573
<212> TYPE: DNA
<213> ORGANISM: Artificial Sequence
<220> FEATURE:
<223> OTHER INFORMATION: CD8a(S19).CD8bstalk.TCR.WPREmut2 construct
      nucleotide sequence

<400> SEQUENCE: 279

| | | | | | |
|---|---|---|---|---|---|
| tgaaagaccc | cacctgtagg | tttggcaagc | tagcttaagt | aacgccattt | tgcaaggcat | 60 |
| ggaaaataca | taactgagaa | tagagaagtt | cagatcaagg | ttaggaacag | agagacagca | 120 |
| gaatatgggc | caaacaggat | atctgtggta | agcagttcct | gccccggctc | agggccaaga | 180 |
| acagatggtc | cccagatgcg | gtcccgccct | cagcagtttc | tagagaacca | tcagatgttt | 240 |
| ccagggtgcc | ccaaggacct | gaaaatgacc | ctgtgcctta | tttgaactaa | ccaatcagtt | 300 |
| cgcttctcgc | ttctgttcgc | gcgcttctgc | tccccgagct | caataaaaga | gcccacaacc | 360 |
| cctcactcag | cggccgcccc | gggtcgacgt | accaccatg | gagttcggcc | tgagctggct | 420 |
| gttcctggtg | gccatcctga | agggcgtgca | gtgctcccaa | ttccgggtgt | ccctctgga | 480 |
| tcgcacctgg | aacctcgggg | aaacggtgga | gctcaagtgt | caagtcctcc | tgtcgaaccc | 540 |
| gaccagcgga | tgcagctggc | tgttccagcc | gagaggagc | gccgcctcac | ccaccttcct | 600 |
| cctgtacttg | agccagaaca | agccgaaggc | cgctgagggt | ctggacaccc | agcgcttctc | 660 |
| gggcaaacgg | ctgggagaca | cttttgtgct | gactctctcc | gacttccggc | gggagaacga | 720 |
| gggctactac | ttctgctctg | cgctctccaa | ttcaatcatg | tacttctcac | acttcgtgcc | 780 |

```
ggtgttcctg cctgccagcg tgtggactt cctcccact accgcccaac ccactaagaa    840
gtcaaccctg aagaagcggg tttgcagact cccacggccg gaaacgcaga agggtccgct    900
gtgttccccg atctacattt gggccccttt ggctggcacc tgtggagtgc tgctcctgtc    960
ccttgtgatc accctgtact gcaaccaccg gaataggcgg agagtctgca agtgtccgcg   1020
gcctgtcgtg aagtcaggag ataagccgag cctgtccgca cgctacgtgc gggccaagag   1080
atctggcagc ggcgccacca atttcagcct gctgaaacag gccggcgacg tggaagagaa   1140
ccctggcccc atggactctt ggaccttctg ctgcgtgagc ctgtgcatcc tggtggccaa   1200
gcacacagac gccggcgtga tccagtcccc taggcacgag gtgaccgaga tgggccagga   1260
ggtgacactg cgctgtaagc caatctctgg ccacaacagc ctgttttggt atagggagac   1320
catgatgcgc ggcctggagc tgctgatcta cttcaataac aatgtgccca tcgacgattc   1380
cggcatgcct gaggatcggt tttctgccaa gatgcccaat gccagcttct ccacactgaa   1440
gatccagcct agcgagccaa gagactccgc cgtgtatttt tgcgcctcta gcccaggcag   1500
caccgataca cagtacttcg gaccaggaac caggctgaca gtgctggagg acctgaagaa   1560
cgtgttcccc cctgaggtgg ccgtgtttga gccctctgag gccgagatca gccacaccca   1620
gaaggccacc ctggtgtgcc tggcaaccgg cttctatcct gatcacgtgg agctgtcctg   1680
gtgggtgaac ggcaaggagt tgcacagcgg cgtgtccaca gacccacagc ccctgaagga   1740
gcagccagcc ctgaatgata ccggtattg cctgtcctct cggctgagag tgtccgccac   1800
ctttttggcag aaccccggga atcacttcag atgtcaggtg cagtttttacg gcctgtccga   1860
gaacgatgag tggacccagg accgggccaa gcctgtgaca cagatcgtgt ctgccgaggc   1920
atggggaaga gcagactgtg gcttcacctc tgagagctac cagcagggcg tgctgagcgc   1980
caccatcctg tatgagatcc tgctgggcaa ggccacactg tacgccgtcc tggtctccgc   2040
tctggtgctg atggcaatgg tcaaaagaaa agatagtcgg gacgggcca agagatctgg   2100
cagcggcgag ggcagaggca gcctgctgac ctgcggcgac gtggaggaga accccggccc   2160
catggagaag aatccccctgg ctgccccct gctgatcctg tggtttcacc tggactgcgt   2220
gtcctctatc ctgaatgtgg aacagagccc acagagcctg cacgtgcagg agggcgactc   2280
caccaacttc acatgctctt tcctagctc caacttctac gccctgcact ggtacagaaa   2340
ggagaccgca aagtccccag aggccctgtt cgtgatgaca ctgaacggcg atgagaagaa   2400
gaagggccgc atcagcgcca ccctgaatac aaaggagggc tactcctatc tgtacatcaa   2460
gggctcccag cctgaggact ctgccaccta tctgtgcgcc ctgtacaaca ataacgatat   2520
gcggtttggc gccggcacca gactgacagt gaagccaaac atccagaatc agacccccgc   2580
cgtgtatcag ctgcgggaca gcaagtctag cgataagagc gtgtgcctgt tcaccgactt   2640
tgattctcag acaaacgtga gccagtccaa ggacagcgac gtgtacatca ccgacaagac   2700
agtgctggat atgagaagca tggacttcaa gtctaacagc gccgtggcct ggtccaataa   2760
gtctgatttc gcctgcgcca atgcctttaa taactccatc atccccgagg ataccttctt   2820
tccttctcca gagtcctctt gtgacgtgaa gctggtggag aagtctttcg agaccgatac   2880
aaacctgaat tttcagaacc tgagcgtgat cggcttcagg atcctgctgc tgaaggtggc   2940
cggctttaat ctgctgatga ccctgaggct gtggagctcc tgaaccggtc cggagcatct   3000
taccgccatt tatacccata tttgttctgt ttttcttgat ttgggtatac atttaaatgt   3060
taataaaaca aatggtggg gcaatcattt acatttttttg ggatatgtaa ttactagttc   3120
aggtgtattg ccacaagaca aacttgttaa gaaactttcc cgttatttac gctctgttcc   3180
```

-continued

```
tgttaatcaa cctctggatt acaaaatttg tgaaagattg actgatattc ttaactttgt    3240 tgctccttt  acgctgtgtg gatttgctgc tttattgcct ctgtatcttg ctattgcttc    3300
ccgtacggct ttcgttttct cctccttgta taaatcctgg ttgctgtctc tttttgagga   3360
gttgtggccc gttgtccgtc aacgtggcgt ggtgtgctct gtgtttgctg acgcaacccc    3420
cactggctgg ggcattgcca ccacctgtca actccttct  gggactttcg ctttcccct     3480 cccgatcgcc acggcagaac tcatcgccgc ctgccttgcc cgctgctgga caggggctag    3540
gttgctgggc actgataatt ccgtggtgtt gtc                                 3573
```

```
<210> SEQ ID NO 280
<211> LENGTH: 861
<212> TYPE: PRT
<213> ORGANISM: Artificial Sequence
<220> FEATURE:
<223> OTHER INFORMATION: CD8a(S19).CD8bstalk.TCR.WPREmut2 amino acid
      sequence

<400> SEQUENCE: 280

Met Glu Phe Gly Leu Ser Trp Leu Phe Leu Val Ala Ile Leu Lys Gly
1               5                   10                  15

Val Gln Cys Ser Gln Phe Arg Val Ser Pro Leu Asp Arg Thr Trp Asn
            20                  25                  30

Leu Gly Glu Thr Val Glu Leu Lys Cys Gln Val Leu Leu Ser Asn Pro
        35                  40                  45

Thr Ser Gly Cys Ser Trp Leu Phe Gln Pro Arg Gly Ala Ala Ala Ser
    50                  55                  60

Pro Thr Phe Leu Leu Tyr Leu Ser Gln Asn Lys Pro Lys Ala Ala Glu
65                  70                  75                  80

Gly Leu Asp Thr Gln Arg Phe Ser Gly Lys Arg Leu Gly Asp Thr Phe
                85                  90                  95

Val Leu Thr Leu Ser Asp Phe Arg Arg Glu Asn Glu Gly Tyr Tyr Phe
            100                 105                 110

Cys Ser Ala Leu Ser Asn Ser Ile Met Tyr Phe Ser His Phe Val Pro
        115                 120                 125

Val Phe Leu Pro Ala Ser Val Val Asp Phe Leu Pro Thr Thr Ala Gln
    130                 135                 140

Pro Thr Lys Lys Ser Thr Leu Lys Lys Arg Val Cys Arg Leu Pro Arg
145                 150                 155                 160

Pro Glu Thr Gln Lys Gly Pro Leu Cys Ser Pro Ile Tyr Ile Trp Ala
                165                 170                 175

Pro Leu Ala Gly Thr Cys Gly Val Leu Leu Leu Ser Leu Val Ile Thr
            180                 185                 190

Leu Tyr Cys Asn His Arg Asn Arg Arg Val Cys Lys Cys Pro Arg
        195                 200                 205

Pro Val Val Lys Ser Gly Asp Lys Pro Ser Leu Ser Ala Arg Tyr Val
    210                 215                 220

Arg Ala Lys Arg Ser Gly Ser Gly Ala Thr Asn Phe Ser Leu Leu Lys
225                 230                 235                 240

Gln Ala Gly Asp Val Glu Glu Asn Pro Gly Pro Met Asp Ser Trp Thr
                245                 250                 255

Phe Cys Cys Val Ser Leu Cys Ile Leu Val Ala Lys His Thr Asp Ala
            260                 265                 270

Gly Val Ile Gln Ser Pro Arg His Glu Val Thr Glu Met Gly Gln Glu
        275                 280                 285
```

```
Val Thr Leu Arg Cys Lys Pro Ile Ser Gly His Asn Ser Leu Phe Trp
    290                 295                 300

Tyr Arg Glu Thr Met Met Arg Gly Leu Glu Leu Leu Ile Tyr Phe Asn
305                 310                 315                 320

Asn Asn Val Pro Ile Asp Asp Ser Gly Met Pro Glu Asp Arg Phe Ser
                325                 330                 335

Ala Lys Met Pro Asn Ala Ser Phe Ser Thr Leu Lys Ile Gln Pro Ser
                340                 345                 350

Glu Pro Arg Asp Ser Ala Val Tyr Phe Cys Ala Ser Ser Pro Gly Ser
            355                 360                 365

Thr Asp Thr Gln Tyr Phe Gly Pro Gly Thr Arg Leu Thr Val Leu Glu
    370                 375                 380

Asp Leu Lys Asn Val Phe Pro Pro Glu Val Ala Val Phe Glu Pro Ser
385                 390                 395                 400

Glu Ala Glu Ile Ser His Thr Gln Lys Ala Thr Leu Val Cys Leu Ala
                405                 410                 415

Thr Gly Phe Tyr Pro Asp His Val Glu Leu Ser Trp Trp Val Asn Gly
                420                 425                 430

Lys Glu Val His Ser Gly Val Ser Thr Asp Pro Gln Pro Leu Lys Glu
            435                 440                 445

Gln Pro Ala Leu Asn Asp Ser Arg Tyr Cys Leu Ser Ser Arg Leu Arg
    450                 455                 460

Val Ser Ala Thr Phe Trp Gln Asn Pro Arg Asn His Phe Arg Cys Gln
465                 470                 475                 480

Val Gln Phe Tyr Gly Leu Ser Glu Asn Asp Glu Trp Thr Gln Asp Arg
                485                 490                 495

Ala Lys Pro Val Thr Gln Ile Val Ser Ala Glu Ala Trp Gly Arg Ala
            500                 505                 510

Asp Cys Gly Phe Thr Ser Glu Ser Tyr Gln Gln Gly Val Leu Ser Ala
    515                 520                 525

Thr Ile Leu Tyr Glu Ile Leu Leu Gly Lys Ala Thr Leu Tyr Ala Val
    530                 535                 540

Leu Val Ser Ala Leu Val Leu Met Ala Met Val Lys Arg Lys Asp Ser
545                 550                 555                 560

Arg Gly Arg Ala Lys Arg Ser Gly Ser Gly Glu Gly Arg Gly Ser Leu
                565                 570                 575

Leu Thr Cys Gly Asp Val Glu Glu Asn Pro Gly Pro Met Glu Lys Asn
            580                 585                 590

Pro Leu Ala Ala Pro Leu Leu Ile Leu Trp Phe His Leu Asp Cys Val
            595                 600                 605

Ser Ser Ile Leu Asn Val Glu Gln Ser Pro Gln Ser Leu His Val Gln
    610                 615                 620

Glu Gly Asp Ser Thr Asn Phe Thr Cys Ser Phe Pro Ser Ser Asn Phe
625                 630                 635                 640

Tyr Ala Leu His Trp Tyr Arg Lys Glu Thr Ala Lys Ser Pro Glu Ala
                645                 650                 655

Leu Phe Val Met Thr Leu Asn Gly Asp Glu Lys Lys Gly Arg Ile
                660                 665                 670

Ser Ala Thr Leu Asn Thr Lys Glu Gly Tyr Ser Tyr Leu Tyr Ile Lys
            675                 680                 685

Gly Ser Gln Pro Glu Asp Ser Ala Thr Tyr Leu Cys Ala Leu Tyr Asn
            690                 695                 700
```

| | | | | | | | | | | | | |
|---|---|---|---|---|---|---|---|---|---|---|---|---|
|Asn|Asn|Asp|Met|Arg|Phe|Gly|Ala|Gly|Thr|Arg|Leu|Thr|Val|Lys|Pro|
|705| | | | |710| | | | |715| | | | |720|

Asn Ile Gln Asn Pro Asp Pro Ala Val Tyr Gln Leu Arg Asp Ser Lys
                725                 730                 735

Ser Ser Asp Lys Ser Val Cys Leu Phe Thr Asp Phe Asp Ser Gln Thr
            740                 745                 750

Asn Val Ser Gln Ser Lys Asp Ser Asp Val Tyr Ile Thr Asp Lys Thr
            755                 760                 765

Val Leu Asp Met Arg Ser Met Asp Phe Lys Ser Asn Ser Ala Val Ala
    770                 775                 780

Trp Ser Asn Lys Ser Asp Phe Ala Cys Ala Asn Ala Phe Asn Asn Ser
785                 790                 795                 800

Ile Ile Pro Glu Asp Thr Phe Phe Pro Ser Pro Glu Ser Ser Cys Asp
                805                 810                 815

Val Lys Leu Val Glu Lys Ser Phe Glu Thr Asp Thr Asn Leu Asn Phe
            820                 825                 830

Gln Asn Leu Ser Val Ile Gly Phe Arg Ile Leu Leu Leu Lys Val Ala
            835                 840                 845

Gly Phe Asn Leu Leu Met Thr Leu Arg Leu Trp Ser Ser
850                 855                 860

<210> SEQ ID NO 281
<211> LENGTH: 4284
<212> TYPE: DNA
<213> ORGANISM: Artificial Sequence
<220> FEATURE:
<223> OTHER INFORMATION: TCRba.CD8a.CD8b1.2.WPREmut2 construct
      nucleotide sequence

<400> SEQUENCE: 281

| | | | | | |
|---|---|---|---|---|---|
|tgaaagaccc|cacctgtagg|tttggcaagc|tagcttaagt|aacgccattt|tgcaaggcat|60|
|ggaaaataca|taactgagaa|tagagaagtt|cagatcaagg|ttaggaacag|agagacagca|120|
|gaatatgggc|caaacaggat|atctgtggta|agcagttcct|gccccggctc|agggccaaga|180|
|acagatggtc|cccagatgcg|gtcccgccct|cagcagtttc|tagagaacca|tcagatgttt|240|
|ccagggtgcc|ccaaggacct|gaaaatgacc|ctgtgcctta|tttgaactaa|ccaatcagtt|300|
|cgcttctcgc|ttctgttcgc|gcgcttctgc|tccccgagct|caataaaaga|gcccacaacc|360|
|cctcactcag|cggccgcccc|gggtcgacgc|taccaccatg|gactcttgga|ccttctgctg|420|
|cgtgagcctg|tgcatcctgg|tggccaagca|cacagacgcc|ggcgtgatcc|agtcccctag|480|
|gcacgaggtg|accgagatgg|gccaggaggt|gacactgcgc|tgtaagccaa|tctctggcca|540|
|caacagcctg|ttttggtata|gggagaccat|gatgcgcggc|ctggagctgc|tgatctactt|600|
|caataacaat|gtgccatcg|acgattccgg|catgcctgag|gatcggtttt|ctgccaagat|660|
|gcccaatgcc|agcttctcca|cactgaagat|ccagcctagc|gagccaagag|actccgccgt|720|
|gtattttgc|gcctctagcc|caggcagcac|cgatacacag|tacttcggac|aggaaccag|780|
|gctgacagtg|ctggaggacc|tgaagaacgt|gttccccct|gaggtggccg|tgtttgagcc|840|
|ctctgaggcc|gagatcagcc|acacccagaa|ggccaccctg|gtgtgcctgg|caaccggctt|900|
|ctatcctgat|cacgtggagc|tgtcctggtg|ggtgaacggc|aaggaggtgc|acagcggcgt|960|
|gtccacagac|ccacagcccc|tgaaggagca|gccagccctg|aatgatagcc|ggtattgcct|1020|
|gtcctctcgg|ctgagagtgt|ccgccacctt|ttggcagaac|ccccggaatc|acttcagatg|1080|
|tcaggtgcag|ttttacggcc|tgtccgagaa|cgatgagtgg|acccaggacc|gggccaagcc|1140|

```
tgtgacacag atcgtgtctg ccgaggcatg gggaagagca gactgtggct tcacctctga      1200
gagctaccag cagggcgtgc tgagcgccac catcctgtat gagatcctgc tgggcaaggc      1260
cacactgtac gccgtcctgg tctccgctct ggtgctgatg gcaatggtca aaagaaaaga      1320
tagtcgggga cgggccaaga gatctggcag cggcgagggc agaggcagcc tgctgacctg      1380
cggcgacgtg gaggagaacc ccggccccat ggagaagaat cccctggctg cccccctgct      1440
gatcctgtgg tttcacctgg actgcgtgtc ctctatcctg aatgtggaac agagcccaca      1500
gagcctgcac gtgcaggagg cgactccac caacttcaca tgctcttttc ctagctccaa      1560
cttctacgcc ctgcactggt acagaaagga gaccgcaaag tccccagagg ccctgttcgt      1620
gatgacactg aacggcgatg agaagaagaa gggccgcatc agcgccaccc tgaatacaaa      1680
ggagggctac tcctatctgt acatcaaggg ctcccagcct gaggactctg ccacctatct      1740
gtgcgccctg tacaacaata cgatatgcg gtttggcgcc ggcaccagac tgacagtgaa      1800
gccaaacatc cagaatccag accccgccgt gtatcagctg cgggacagca agtctagcga      1860
taagagcgtg tgcctgttca ccgactttga ttctcagaca aacgtgagcc agtccaagga      1920
cagcgacgtg tacatcaccg acaagacagt gctggatatg agaagcatgg acttcaagtc      1980
taacagcgcc gtggcctggt ccaataagtc tgatttcgcc tgcgccaatg cctttaataa      2040
ctccatcatc cccgaggata ccttcttccc ttctccagag tcctcttgtg acgtgaagct      2100
ggtggagaag tctttcgaga ccgatacaaa cctgaatttt cagaacctga gcgtgatcgg      2160
cttcaggatc ctgctgctga aggtggccgg ctttaatctg ctgatgaccc tgaggctgtg      2220
gagctcccgg gccaagagat ctggcagcgg ccagtgcacc aactacgccc tgctgaagct      2280
ggccggcgac gtggagagca accccggccc catggcgctt cccgtgaccg cactcctgtt      2340
gccccttgcc ctgctgttgc acgccgcacg acctagccag ttcagagtgt cccccctgga      2400
ccggacctgg aacctgggag agacagtgga actgaagtgc caggtgctgc tgagcaaccc      2460
caccagcggc tgctcttggc tgtttcagcc tagaggcgcc gctgccagcc ctacctttct      2520
gctgtacctg agccagaaca gcccaaggc cgccgagggc ctggacaccc agagattcag      2580
cggcaagaga ctgggcgaca ccttcgtgct gaccctgagc gacttcagaa gagagaacga      2640
gggctactac ttctgcagcg ccctgagcaa cagcatcatg tacttcagcc acttcgtgcc      2700
cgtgtttctg cccgccaagc ctaccacaac ccctgccct agacctccta ccccagcccc      2760
tacaatcgcc agccagcctc tgtctctgag gcccgaggct tgtagacctg ctgctggcgg      2820
agccgtgcac accagaggac tggatttcgc ctgcgacatc tacatctggg cccctctggc      2880
cggcacatgt ggcgtgctgc tgctgtccct cgtgatcacc ctgtactgca accaccggaa      2940
ccggcggaga gtgtgcaagt gccctagacc cgtcgtgaag tccggcgaca gcctagcct      3000 gagcgccaga tacgtgcggg ccaagagatc tggcagcggc gccaccaatt tcagcctgct      3060
gaaacaggcc ggcgacgtgg aagagaaccc tggccccatg cgcccgagac tgtggcttct      3120
gctcgccgcg caactgactg tcctgcacgg aaacagcgtg ctgcagcaga caccggccta      3180
catcaaagtg cagaccaaca agatggtcat gctgtcctgc gaggccaaga tttccctctc      3240
caacatgcga atctattggt tgcggcagag acaggcgcct tcctcggact cccaccatga      3300
gttcttggcc ctgtgggact ccgccaaggg aactattcac ggcgaagaag tggaacagga      3360
gaagatcgcc gtgtttcgcg atgcctcccg ctttatactg aatctgacct ccgtgaagcc      3420
cgaagatagc gggatctact tttgcatgat tgtgggctca cccgaactga ccttcggaaa      3480
gggcactcag ctgagcgtgg tggacttcct ccccactacc gcccaaccca ctaagaagtc      3540
```

```
aaccctgaag aagcgggttt gcagactccc acggccggaa acgcagaagg gtctgaaagg    3600
taaggtttac caagagcctt tgtcaccgaa cgcttgtatg gacacgaccg ctatcctcca    3660
accgcatagg tcttgtctca ctcacgggtc atgaaccggt ccggagcatc ttaccgccat    3720
ttatacccat atttgttctg tttttcttga tttgggtata catttaaatg ttaataaaac    3780
aaaatggtgg ggcaatcatt tacatttttt gggatatgta attactagtt caggtgtatt    3840
gccacaagac aaacttgtta agaaactttc ccgttattta cgctctgttc ctgttaatca    3900
acctctggat tacaaaattt gtgaaagatt gactgatatt cttaactttg ttgctccttt    3960
tacgctgtgt ggatttgctg ctttattgcc tctgtatctt gctattgctt cccgtacggc    4020
tttcgttttc tcctccttgt ataaatcctg gttgctgtct cttttgagg agttgtggcc    4080 cgttgtccgt caacgtggcg tggtgtgctc tgtgtttgct gacgcaaccc ccactggctg    4140
gggcattgcc accacctgtc aactcctttc tgggactttc gctttccccc tcccgatcgc    4200
cacggcagaa ctcatcgccg cctgccttgc ccgctgctgg acaggggcta ggttgctggg    4260
cactgataat tccgtggtgt tgtc                                            4284
```

<210> SEQ ID NO 282
<211> LENGTH: 1098
<212> TYPE: PRT
<213> ORGANISM: Artificial Sequence
<220> FEATURE:
<223> OTHER INFORMATION: TCRba.CD8a.CD8b1.2.WPREmut2 amino acid sequence

<400> SEQUENCE: 282

```
Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Glu Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Pro Gly Ser Thr Asp Thr Gln Tyr Phe Gly Pro Gly Thr Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220
```

-continued

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
    290                 295                 300

Lys Arg Lys Asp Ser Arg Gly Arg Ala Lys Arg Ser Gly Ser Gly Glu
305                 310                 315                 320

Gly Arg Gly Ser Leu Leu Thr Cys Gly Asp Val Glu Glu Asn Pro Gly
                325                 330                 335

Pro Met Glu Lys Asn Pro Leu Ala Ala Pro Leu Leu Ile Leu Trp Phe
            340                 345                 350

His Leu Asp Cys Val Ser Ser Ile Leu Asn Val Glu Gln Ser Pro Gln
            355                 360                 365

Ser Leu His Val Gln Glu Gly Asp Ser Thr Asn Phe Thr Cys Ser Phe
    370                 375                 380

Pro Ser Ser Asn Phe Tyr Ala Leu His Trp Tyr Arg Lys Glu Thr Ala
385                 390                 395                 400

Lys Ser Pro Glu Ala Leu Phe Val Met Thr Leu Asn Gly Asp Glu Lys
                405                 410                 415

Lys Lys Gly Arg Ile Ser Ala Thr Leu Asn Thr Lys Glu Gly Tyr Ser
            420                 425                 430

Tyr Leu Tyr Ile Lys Gly Ser Gln Pro Glu Asp Ser Ala Thr Tyr Leu
    435                 440                 445

Cys Ala Leu Tyr Asn Asn Asn Asp Met Arg Phe Gly Ala Gly Thr Arg
450                 455                 460

Leu Thr Val Lys Pro Asn Ile Gln Asn Pro Asp Pro Ala Val Tyr Gln
465                 470                 475                 480

Leu Arg Asp Ser Lys Ser Ser Asp Lys Ser Val Cys Leu Phe Thr Asp
                485                 490                 495

Phe Asp Ser Gln Thr Asn Val Ser Gln Ser Lys Asp Ser Asp Val Tyr
            500                 505                 510

Ile Thr Asp Lys Thr Val Leu Asp Met Arg Ser Met Asp Phe Lys Ser
            515                 520                 525

Asn Ser Ala Val Ala Trp Ser Asn Lys Ser Asp Phe Ala Cys Ala Asn
530                 535                 540

Ala Phe Asn Asn Ser Ile Ile Pro Glu Asp Thr Phe Phe Pro Ser Pro
545                 550                 555                 560

Glu Ser Ser Cys Asp Val Lys Leu Val Glu Lys Ser Phe Glu Thr Asp
            565                 570                 575

Thr Asn Leu Asn Phe Gln Asn Leu Ser Val Ile Gly Phe Arg Ile Leu
            580                 585                 590

Leu Leu Lys Val Ala Gly Phe Asn Leu Leu Met Thr Leu Arg Leu Trp
            595                 600                 605

Ser Ser Arg Ala Lys Arg Ser Gly Ser Gly Gln Cys Thr Asn Tyr Ala
            610                 615                 620

Leu Leu Lys Leu Ala Gly Asp Val Glu Ser Asn Pro Gly Pro Met Ala
625                 630                 635                 640

Leu Pro Val Thr Ala Leu Leu Leu Pro Leu Ala Leu Leu Leu His Ala

```
                   645                 650                 655
Ala Arg Pro Ser Gln Phe Arg Val Ser Pro Leu Asp Arg Thr Trp Asn
                660                 665                 670

Leu Gly Glu Thr Val Glu Leu Lys Cys Gln Val Leu Leu Ser Asn Pro
            675                 680                 685

Thr Ser Gly Cys Ser Trp Leu Phe Gln Pro Arg Gly Ala Ala Ala Ser
        690                 695                 700

Pro Thr Phe Leu Leu Tyr Leu Ser Gln Asn Lys Pro Lys Ala Ala Glu
705                 710                 715                 720

Gly Leu Asp Thr Gln Arg Phe Ser Gly Lys Arg Leu Gly Asp Thr Phe
                725                 730                 735

Val Leu Thr Leu Ser Asp Phe Arg Arg Glu Asn Glu Gly Tyr Tyr Phe
                740                 745                 750

Cys Ser Ala Leu Ser Asn Ser Ile Met Tyr Phe Ser His Phe Val Pro
            755                 760                 765

Val Phe Leu Pro Ala Lys Pro Thr Thr Thr Pro Ala Pro Arg Pro Pro
    770                 775                 780

Thr Pro Ala Pro Thr Ile Ala Ser Gln Pro Leu Ser Leu Arg Pro Glu
785                 790                 795                 800

Ala Cys Arg Pro Ala Ala Gly Gly Ala Val His Thr Arg Gly Leu Asp
                805                 810                 815

Phe Ala Cys Asp Ile Tyr Ile Trp Ala Pro Leu Ala Gly Thr Cys Gly
                820                 825                 830

Val Leu Leu Leu Ser Leu Val Ile Thr Leu Tyr Cys Asn His Arg Asn
            835                 840                 845

Arg Arg Arg Val Cys Lys Cys Pro Arg Pro Val Val Lys Ser Gly Asp
        850                 855                 860

Lys Pro Ser Leu Ser Ala Arg Tyr Val Arg Ala Lys Arg Ser Gly Ser
865                 870                 875                 880

Gly Ala Thr Asn Phe Ser Leu Leu Lys Gln Ala Gly Asp Val Glu Glu
                885                 890                 895

Asn Pro Gly Pro Met Arg Pro Arg Leu Trp Leu Leu Leu Ala Ala Gln
                900                 905                 910

Leu Thr Val Leu His Gly Asn Ser Val Leu Gln Gln Thr Pro Ala Tyr
            915                 920                 925

Ile Lys Val Gln Thr Asn Lys Met Val Met Leu Ser Cys Glu Ala Lys
    930                 935                 940

Ile Ser Leu Ser Asn Met Arg Ile Tyr Trp Leu Arg Gln Arg Gln Ala
945                 950                 955                 960

Pro Ser Ser Asp Ser His His Glu Phe Leu Ala Leu Trp Asp Ser Ala
                965                 970                 975

Lys Gly Thr Ile His Gly Glu Glu Val Glu Gln Glu Lys Ile Ala Val
                980                 985                 990

Phe Arg Asp Ala Ser Arg Phe Ile Leu Asn Leu Thr Ser Val Lys Pro
            995                 1000                1005

Glu Asp Ser Gly Ile Tyr Phe Cys Met Ile Val Gly Ser Pro Glu
    1010                1015                1020

Leu Thr Phe Gly Lys Gly Thr Gln Leu Ser Val Val Asp Phe Leu
    1025                1030                1035

Pro Thr Thr Ala Gln Pro Thr Lys Lys Ser Thr Leu Lys Lys Arg
    1040                1045                1050

Val Cys Arg Leu Pro Arg Pro Glu Thr Gln Lys Gly Leu Lys Gly
    1055                1060                1065
```

Lys Val Tyr Gln Glu Pro Leu Ser Pro Asn Ala Cys Met Asp Thr
    1070                1075                1080

Thr Ala Ile Leu Gln Pro His Arg Ser Cys Leu Thr His Gly Ser
    1085                1090                1095

<210> SEQ ID NO 283
<211> LENGTH: 3606
<212> TYPE: DNA
<213> ORGANISM: Artificial Sequence
<220> FEATURE:
<223> OTHER INFORMATION: WT-SPa/CD8a-Ig like domain 1/CD8bstalk/CD4
      TM+IC/TCRba/WPREmut2 construct nucleotide sequence

<400> SEQUENCE: 283
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga     180
acagatggtc cccagatgcg gtcccgccct cagcagtttc tagagaacca tcagatgttt     240
ccagggtgcc ccaaggacct gaaaatgacc ctgtgcctta tttgaactaa ccaatcagtt     300
cgcttctcgc ttctgttcgc gcgcttctgc tccccgagct caataaaaga gcccacaacc     360
cctcactcag cggccgcccc gggtcgacgc taccaccatg gcgcttcccg tgaccgcact     420
cctgttgccc cttgccctgc tgttgcacgc gcacgacct tcccaattcc gggtgtcccc     480
tctggatcgc acctggaacc tcggggaaac ggtggagctc aagtgtcaag tcctcctgtc     540
gaacccgacc agcggatgca gctggctgtt ccagccgaga ggagctgccg cctcacccac     600
cttcctcctg tacttgagcc agaacaagcc gaaggccgct gagggtctgg acaccagcg     660 cttctcgggc aaacggctgg agacactttt tgtgctgact ctctccgact ccggcggga     720 gaacgagggc tactacttct gctctgcgct ctccaattca atcatgtact ctcacactt     780 cgtgccggtg ttcctgcctg ccagcgtggt ggacttcctc cccactaccg cccaacccac     840
taagaagtca accctgaaga agcgggtttg cagactccca cggccggaaa cgcagaaggg     900
tccgctgtgt tccccgatgg ccctgattgt gctgggggc gtcgccggcc tcctgctttt     960
cattgggcta ggcatcttct tctgtgtcag gtgccggcac cgaaggcgcc aagcagagcg    1020
gatgtctcag atcaagagac tcctcagtga agaagacc tgccagtgtc ctcaccggtt    1080
tcagaagaca tgtagcccca ttcgggccaa gagatctggc agcggcgcca ccaatttcag    1140
cctgctgaaa caggccggcg acgtggaaga gaacccggc cccatggact cttggacctt    1200
ctgctgcgtg agcctgtgca tcctggtggc caagcacaca gacgccggcg tgatccagtc    1260
ccctaggcac gaggtgaccg agatgggcca ggaggtgaca ctgcgctgta gccaatctc    1320 tggccacaac agcctgtttt ggtataggga gaccatgatg cgcggctgg agctgctgat    1380 ctacttcaat aacaatgtgc ccatcgacga ttccggcatg cctgaggatc ggttttctgc    1440
caagatgccc aatgccagct ctccacact gaagatccag cctagcgagc aagagactc    1500 cgccgtgtat ttttgcgcct ctagcccagg cagcaccgat acacagtact cggaccagg    1560 aaccaggctg acagtgctgg aggacctgaa gaacgtgttc ccccctgagg tggccgtgtt    1620
tgagccctct gaggccgaga tcagccacac ccagaaggcc accctggtgt gcctggcaac    1680
cggcttctat cctgatcacg tggagctgtc ctggtgggtg aacggcaagg aggtgcacag    1740
cggcgtgtcc acagacccac agcccctgaa ggagcagcca gccctgaatg atagccggta    1800
ttgcctgtcc tctcggctga gagtgtccgc cacctttgg cagaaccccc ggaatcactt    1860

```
cagatgtcag gtgcagtttt acggcctgtc cgagaacgat gagtggaccc aggaccgggc    1920
caagcctgtg acacagatcg tgtctgccga ggcatgggga agagcagact gtggcttcac    1980
ctctgagagc taccagcagg gcgtgctgag cgccaccatc ctgtatgaga tcctgctggg    2040
caaggccaca ctgtacgccg tcctggtctc cgctctggtg ctgatggcaa tggtcaaaag    2100
aaaagatagt cggggacggg ccaagagatc tggcagcggc gagggcagag gcagcctgct    2160
gacctgcggc gacgtggagg agaacccgg ccccatggga aagaatcccc tggctgcccc    2220
cctgctgatc ctgtggtttc acctggactg cgtgtcctct atcctgaatg tggaacagag    2280
cccacagagc ctgcacgtgc aggagggcga ctccaccaac ttcacatgct cttttcctag    2340
ctccaacttc tacgccctgc actggtacag aaaggagacc gcaaagtccc cagaggccct    2400
gttcgtgatg acactgaacg gcgatgagaa gaagaagggc cgcatcagcg ccaccctgaa    2460
tacaaaggag ggctactcct atctgtacat caagggctcc cagcctgagg actctgccac    2520
ctatctgtgc gccctgtaca acaataacga tatgcggttt ggcgccggca ccagactgac    2580
agtgaagcca aacatccaga tccagacccc gccgtgtat cagctgcggg acagcaagtc    2640
tagcgataag agcgtgtgcc tgttcaccga ctttgattct cagacaaacg tgagccagtc    2700
caaggacagc gacgtgtaca tcaccgacaa gacagtgctg gatatgagaa gcatggactt    2760
caagtctaac agcgccgtgg cctggtccaa taagtctgat ttcgcctgcg ccaatgcctt    2820
taataactcc atcatccccg aggataccti ctttccttct ccagagtcct cttgtgacgt    2880
gaagctggtg gagaagtctt tcgagaccga tacaaacctg aattttcaga acctgagcgt    2940
gatcggcttc aggatcctgc tgctgaaggt ggccggcttt aatctgctga tgaccctgag    3000
gctgtggagc tcctgaaccg gtccggagca tcttaccgcc atttataccc atatttgttc    3060 tgttttctt gatttgggta tacatttaaa tgttaataaa acaaaatggt ggggcaatca    3120
tttacatttt ttgggatatg taattactag ttcaggtgta ttgccacaag acaaacttgt    3180
taagaaactt tcccgttatt tacgctctgt tcctgttaat caacctctgg attacaaaat    3240
ttgtgaaaga ttgactgata ttcttaactt tgttgctcct tttacgctgt gtggatttgc    3300
tgctttattg cctctgtatc ttgctattgc ttcccgtacg ctttcgtttt ctcctccttg    3360
gtataaatcc tggttgctgt ctcttttga ggagttgtgg cccgttgtcc gtcaacgtgg    3420
cgtggtgtgc tctgtgtttg ctgacgcaac ccccactggc tggggcattg ccaccacctg    3480
tcaactcctt tctgggactt tcgctttccc cctcccgatc gccacggcag aactcatcgc    3540
cgcctgcctt gcccgctgct ggacaggggc taggttgctg ggcactgata attccgtggt    3600
gttgtc                                                                3606
```

<210> SEQ ID NO 284
<211> LENGTH: 872
<212> TYPE: PRT
<213> ORGANISM: Artificial Sequence
<220> FEATURE:
<223> OTHER INFORMATION: WT-SPa/CD8a-Ig like domain 1/CD8bstalk/CD4
      TM+IC/TCRba/WPREmut2 amino acid sequence

<400> SEQUENCE: 284

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser

```
              35                  40                  45
Asn Pro Thr Ser Gly Cys Ser Trp Leu Phe Gln Pro Arg Gly Ala Ala
 50                  55                  60
Ala Ser Pro Thr Phe Leu Leu Tyr Leu Ser Gln Asn Lys Pro Lys Ala
 65                  70                  75                  80
Ala Glu Gly Leu Asp Thr Gln Arg Phe Ser Gly Lys Arg Leu Gly Asp
                     85                  90                  95
Thr Phe Val Leu Thr Leu Ser Asp Phe Arg Arg Glu Asn Glu Gly Tyr
                    100                 105                 110
Tyr Phe Cys Ser Ala Leu Ser Asn Ser Ile Met Tyr Phe Ser His Phe
                115                 120                 125
Val Pro Val Phe Leu Pro Ala Ser Val Val Asp Phe Leu Pro Thr Thr
                130                 135                 140
Ala Gln Pro Thr Lys Lys Ser Thr Leu Lys Lys Arg Val Cys Arg Leu
145                 150                 155                 160
Pro Arg Pro Glu Thr Gln Lys Gly Pro Leu Cys Ser Pro Met Ala Leu
                    165                 170                 175
Ile Val Leu Gly Gly Val Ala Gly Leu Leu Leu Phe Ile Gly Leu Gly
                180                 185                 190
Ile Phe Phe Cys Val Arg Cys Arg His Arg Arg Arg Gln Ala Glu Arg
                195                 200                 205
Met Ser Gln Ile Lys Arg Leu Leu Ser Glu Lys Lys Thr Cys Gln Cys
210                 215                 220
Pro His Arg Phe Gln Lys Thr Cys Ser Pro Ile Arg Ala Lys Arg Ser
225                 230                 235                 240
Gly Ser Gly Ala Thr Asn Phe Ser Leu Leu Lys Gln Ala Gly Asp Val
                    245                 250                 255
Glu Glu Asn Pro Gly Pro Met Asp Ser Trp Thr Phe Cys Cys Val Ser
                260                 265                 270
Leu Cys Ile Leu Val Ala Lys His Thr Asp Ala Gly Val Ile Gln Ser
                275                 280                 285
Pro Arg His Glu Val Thr Glu Met Gly Gln Glu Val Thr Leu Arg Cys
                290                 295                 300
Lys Pro Ile Ser Gly His Asn Ser Leu Phe Trp Tyr Arg Glu Thr Met
305                 310                 315                 320
Met Arg Gly Leu Glu Leu Leu Ile Tyr Phe Asn Asn Asn Val Pro Ile
                    325                 330                 335
Asp Asp Ser Gly Met Pro Glu Asp Arg Phe Ser Ala Lys Met Pro Asn
                340                 345                 350
Ala Ser Phe Ser Thr Leu Lys Ile Gln Pro Ser Glu Pro Arg Asp Ser
                355                 360                 365
Ala Val Tyr Phe Cys Ala Ser Ser Pro Gly Ser Thr Asp Thr Gln Tyr
                370                 375                 380
Phe Gly Pro Gly Thr Arg Leu Thr Val Leu Glu Asp Leu Lys Asn Val
385                 390                 395                 400
Phe Pro Pro Glu Val Ala Val Phe Glu Pro Ser Glu Ala Glu Ile Ser
                    405                 410                 415
His Thr Gln Lys Ala Thr Leu Val Cys Leu Ala Thr Gly Phe Tyr Pro
                420                 425                 430
Asp His Val Glu Leu Ser Trp Trp Val Asn Gly Lys Glu Val His Ser
                435                 440                 445
Gly Val Ser Thr Asp Pro Gln Pro Leu Lys Glu Gln Pro Ala Leu Asn
                450                 455                 460
```

```
Asp Ser Arg Tyr Cys Leu Ser Ser Arg Leu Arg Val Ser Ala Thr Phe
465                 470                 475                 480

Trp Gln Asn Pro Arg Asn His Phe Arg Cys Gln Val Gln Phe Tyr Gly
                485                 490                 495

Leu Ser Glu Asn Asp Glu Trp Thr Gln Asp Arg Ala Lys Pro Val Thr
            500                 505                 510

Gln Ile Val Ser Ala Glu Ala Trp Gly Arg Ala Asp Cys Gly Phe Thr
        515                 520                 525

Ser Glu Ser Tyr Gln Gln Gly Val Leu Ser Ala Thr Ile Leu Tyr Glu
    530                 535                 540

Ile Leu Leu Gly Lys Ala Thr Leu Tyr Ala Val Leu Val Ser Ala Leu
545                 550                 555                 560

Val Leu Met Ala Met Val Lys Arg Lys Asp Ser Arg Gly Arg Ala Lys
                565                 570                 575

Arg Ser Gly Ser Gly Glu Gly Arg Gly Ser Leu Leu Thr Cys Gly Asp
            580                 585                 590

Val Glu Glu Asn Pro Gly Pro Met Glu Lys Asn Pro Leu Ala Ala Pro
        595                 600                 605

Leu Leu Ile Leu Trp Phe His Leu Asp Cys Val Ser Ser Ile Leu Asn
    610                 615                 620

Val Glu Gln Ser Pro Gln Ser Leu His Val Gln Glu Gly Asp Ser Thr
625                 630                 635                 640

Asn Phe Thr Cys Ser Phe Pro Ser Ser Asn Phe Tyr Ala Leu His Trp
                645                 650                 655

Tyr Arg Lys Glu Thr Ala Lys Ser Pro Glu Ala Leu Phe Val Met Thr
            660                 665                 670

Leu Asn Gly Asp Glu Lys Lys Lys Gly Arg Ile Ser Ala Thr Leu Asn
        675                 680                 685

Thr Lys Glu Gly Tyr Ser Tyr Leu Tyr Ile Lys Gly Ser Gln Pro Glu
    690                 695                 700

Asp Ser Ala Thr Tyr Leu Cys Ala Leu Tyr Asn Asn Asn Asp Met Arg
705                 710                 715                 720

Phe Gly Ala Gly Thr Arg Leu Thr Val Lys Pro Asn Ile Gln Asn Pro
                725                 730                 735

Asp Pro Ala Val Tyr Gln Leu Arg Asp Ser Lys Ser Ser Asp Lys Ser
            740                 745                 750

Val Cys Leu Phe Thr Asp Phe Asp Ser Gln Thr Asn Val Ser Gln Ser
        755                 760                 765

Lys Asp Ser Asp Val Tyr Ile Thr Asp Lys Thr Val Leu Asp Met Arg
    770                 775                 780

Ser Met Asp Phe Lys Ser Asn Ser Ala Val Ala Trp Ser Asn Lys Ser
785                 790                 795                 800

Asp Phe Ala Cys Ala Asn Ala Phe Asn Asn Ser Ile Ile Pro Glu Asp
                805                 810                 815

Thr Phe Phe Pro Ser Pro Glu Ser Ser Cys Asp Val Lys Leu Val Glu
            820                 825                 830

Lys Ser Phe Glu Thr Asp Thr Asn Leu Asn Phe Gln Asn Leu Ser Val
        835                 840                 845

Ile Gly Phe Arg Ile Leu Leu Leu Lys Val Ala Gly Phe Asn Leu Leu
    850                 855                 860

Met Thr Leu Arg Leu Trp Ser Ser
865                 870
```

<210> SEQ ID NO 285
<211> LENGTH: 3579
<212> TYPE: DNA
<213> ORGANISM: Artificial Sequence
<220> FEATURE:
<223> OTHER INFORMATION: CD8a.CD8bstalk.TCR.WRPEmut2 construct
      nucleotide sequence

<400> SEQUENCE: 285

| | | | | | |
|---|---|---|---|---|---|
| tgaaagaccc | cacctgtagg | tttggcaagc | tagcttaagt | aacgccattt | tgcaaggcat | 60 |
| ggaaaataca | taactgagaa | tagagaagtt | cagatcaagg | ttaggaacag | agagacagca | 120 |
| gaatatgggc | caaacaggat | atctgtggta | agcagttcct | gccccggctc | agggccaaga | 180 |
| acagatggtc | cccagatgcg | gtcccgccct | cagcagtttc | tagagaacca | tcagatgttt | 240 |
| ccagggtgcc | ccaaggacct | gaaaatgacc | ctgtgcctta | tttgaactaa | ccaatcagtt | 300 |
| cgcttctcgc | ttctgttcgc | gcgcttctgc | tccccgagct | caataaaaga | gcccacaacc | 360 |
| cctcactcag | cggccgcccc | gggtcgacgc | taccaccatg | gcgcttcccg | tgaccgcact | 420 |
| cctgttgccc | cttgccctgc | tgttgcacgc | cgcacgacct | tcccaattcc | gggtgtcccc | 480 |
| tctggatcgc | acctggaacc | tcggggaaac | ggtggagctc | aagtgtcaag | tcctcctgtc | 540 |
| gaacccgacc | agcggatgca | gctggctgtt | ccagccgaga | ggagctgccg | cctcacccac | 600 |
| cttcctcctg | tacttgagcc | agaacaagcc | gaaggccgct | gagggtctgg | acacccagcg | 660 |
| cttctcgggc | aaacggctgg | agagacactt | tgtgctgact | ctctccgact | ccggcggga | 720 |
| gaacgagggc | tactacttct | gctctgcgct | ctccaattca | atcatgtact | tctcacactt | 780 |
| cgtgccggtg | ttcctgcctg | ccagcgtggt | ggacttcctc | cccactaccg | cccaacccac | 840 |
| taagaagtca | accctgaaga | gcgggttttg | cagactccca | cggccggaaa | cgcagaaggg | 900 |
| tccgctgtgt | tccccgatct | acatttgggc | ccctttggct | ggcacctgtg | gagtgctgct | 960 |
| cctgtccctt | gtgatcaccc | tgtactgcaa | ccaccggaat | aggcggagag | tctgcaagtg | 1020 |
| tccgcggcct | gtcgtgaagt | caggagataa | gccgagcctg | tccgcacgct | acgtgcgggc | 1080 |
| caagagatct | ggcagcggcg | ccaccaattt | cagcctgctg | aaacaggccg | gcgacgtgga | 1140 |
| agagaaccct | ggccccatgg | actcttggac | cttctgctgc | gtgagcctgt | gcatcctggt | 1200 |
| ggccaagcac | acagacgccg | gcgtgatcca | gtcccctagg | cacgaggtga | ccgagatggg | 1260 |
| ccaggaggtg | acactgcgct | gtaagccaat | ctctggccac | aacagcctgt | tttggtatag | 1320 |
| ggagaccatg | atgcgcggcc | tggagctgct | gatctacttc | aataacaatg | tgcccatcga | 1380 |
| cgattccggc | atgcctgagg | atcggttttc | tgccaagatg | cccaatgcca | gcttctccac | 1440 |
| actgaagatc | cagcctagcg | agccaagaga | ctccgccgtg | tatttttgcg | cctctagccc | 1500 |
| aggcagcacc | gatacacagt | acttcggacc | aggaaccagg | ctgacagtgc | tggaggacct | 1560 |
| gaagaacgtg | ttcccccctg | aggtggccgt | gtttgagccc | tctgaggccg | agatcagcca | 1620 |
| cacccagaag | gccaccctgg | tgtgcctggc | aaccggcttc | tatcctgatc | acgtggagct | 1680 |
| gtcctggtgg | gtgaacggca | aggaggtgca | cagcggcgtg | tccacagacc | cacagccct | 1740 |
| gaaggagcag | ccagccctga | atgatagccg | gtattgcctg | tcctctcggc | tgagagtgtc | 1800 |
| cgccaccttt | tggcagaacc | cccggaatca | cttcagatgt | caggtgcagt | tttacggcct | 1860 |
| gtccgagaac | gatgagtgga | cccaggaccg | ggccaagcct | gtgacacaga | tcgtgtctgc | 1920 |
| cgaggcatgg | ggaagagcag | actgtggctt | cacctctgag | agctaccagc | agggcgtgct | 1980 |
| gagcgccacc | atcctgtatg | agatcctgct | gggcaaggcc | acactgtacg | ccgtcctggt | 2040 |

```
ctccgctctg tgctgatgg caatggtcaa agaaaagat agtcgggac gggccaagag    2100 atctggcagc ggcgagggca gaggcagcct gctgacctgc ggcgacgtgg aggagaaccc    2160
cggccccatg gagaagaatc ccctggctgc ccccctgctg atcctgtggt tcacctgga    2220 ctgcgtgtcc tctatcctga atgtggaaca gagcccacag agcctgcacg tgcaggaggg    2280
cgactccacc aacttcacat gctcttttcc tagctccaac ttctacgccc tgcactggta    2340
cagaaaggag accgcaaagt ccccagaggc cctgttcgtg atgacactga acggcgatga    2400
gaagaagaag ggccgcatca cgccaccct gaatacaaag gagggctact cctatctgta    2460
catcaagggc tcccagcctg aggactctgc cacctatctg tgcgccctgt acaacaataa    2520
cgatatgcgg tttggcgccg gcaccagact gacagtgaag ccaaacatcc agaatccaga    2580
ccccgccgtg tatcagctgc gggacagcaa gtctagcgat aagagcgtgt gcctgttcac    2640
cgactttgat tctcagacaa acgtgagcca gtccaaggac agcgacgtgt acatcaccga    2700
caagacagtg ctggatatga agcatgga cttcaagtct aacagcgccg tggcctggtc    2760
caataagtct gatttcgcct gcgccaatgc ctttaataac tccatcatcc ccgaggatac    2820
cttctttcct tctccagagt cctcttgtga cgtgaagctg gtggagaagt ctttcgagac    2880
cgatacaaac ctgaattttc agaacctgag cgtgatcggc ttcaggatcc tgctgctgaa    2940
ggtggccggc tttaatctgc tgatgaccct gaggctgtgg agctcctgaa ccggtccgga    3000
gcatcttacc gccatttata cccatatttg ttctgttttt cttgatttgg gtatacattt    3060
aaatgttaat aaaacaaaat ggtggggcaa tcatttacat ttttgggat atgtaattac    3120 tagttcaggt gtattgccac aagacaaact tgttaagaaa cttcccgtt atttacgctc    3180 tgttcctgtt aatcaacctc tggattacaa aatttgtgaa agattgactg atattcttaa    3240
ctttgttgct ccttttacgc tgtgtggatt tgctgctttta ttgcctctgt atcttgctat    3300
tgcttcccgt acggctttcg ttttctcctc cttgtataaa tcctggttgc tgtctctttt    3360
tgaggagttg tggcccgttg tccgtcaacg tggcgtggtg tgctctgtgt ttgctgacgc    3420 aaccccccact ggctggggca ttgccaccac ctgtcaactc ctttctggga ctttcgcttt    3480 cccccctcccg atcgccacgg cagaactcat cgccgcctgc cttgcccgct gctggacagg    3540
ggctaggttg ctgggcactg ataattccgt ggtgttgtc                          3579
```

<210> SEQ ID NO 286
<211> LENGTH: 863
<212> TYPE: PRT
<213> ORGANISM: Artificial Sequence
<220> FEATURE:
<223> OTHER INFORMATION: CD8a.CD8bstalk.TCR.WRPEmut2 amino acid sequence

<400> SEQUENCE: 286

```
Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95
```

```
Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
            115                 120                 125

Val Pro Val Phe Leu Pro Ala Ser Val Val Asp Phe Leu Pro Thr Thr
130                 135                 140

Ala Gln Pro Thr Lys Lys Ser Thr Leu Lys Lys Arg Val Cys Arg Leu
145                 150                 155                 160

Pro Arg Pro Glu Thr Gln Lys Gly Pro Leu Cys Ser Pro Ile Tyr Ile
                165                 170                 175

Trp Ala Pro Leu Ala Gly Thr Cys Gly Val Leu Leu Leu Ser Leu Val
            180                 185                 190

Ile Thr Leu Tyr Cys Asn His Arg Asn Arg Arg Val Cys Lys Cys
            195                 200                 205

Pro Arg Pro Val Val Lys Ser Gly Asp Lys Pro Ser Leu Ser Ala Arg
210                 215                 220

Tyr Val Arg Ala Lys Arg Ser Gly Ser Gly Ala Thr Asn Phe Ser Leu
225                 230                 235                 240

Leu Lys Gln Ala Gly Asp Val Glu Glu Asn Pro Gly Pro Met Asp Ser
                245                 250                 255

Trp Thr Phe Cys Cys Val Ser Leu Cys Ile Leu Val Ala Lys His Thr
            260                 265                 270

Asp Ala Gly Val Ile Gln Ser Pro Arg His Glu Val Thr Glu Met Gly
            275                 280                 285

Gln Glu Val Thr Leu Arg Cys Lys Pro Ile Ser Gly His Asn Ser Leu
            290                 295                 300

Phe Trp Tyr Arg Glu Thr Met Met Arg Gly Leu Glu Leu Leu Ile Tyr
305                 310                 315                 320

Phe Asn Asn Asn Val Pro Ile Asp Asp Ser Gly Met Pro Glu Asp Arg
                325                 330                 335

Phe Ser Ala Lys Met Pro Asn Ala Ser Phe Ser Thr Leu Lys Ile Gln
            340                 345                 350

Pro Ser Glu Pro Arg Asp Ser Ala Val Tyr Phe Cys Ala Ser Ser Pro
            355                 360                 365

Gly Ser Thr Asp Thr Gln Tyr Phe Gly Pro Gly Thr Arg Leu Thr Val
370                 375                 380

Leu Glu Asp Leu Lys Asn Val Phe Pro Pro Glu Val Ala Val Phe Glu
385                 390                 395                 400

Pro Ser Glu Ala Glu Ile Ser His Thr Gln Lys Ala Thr Leu Val Cys
                405                 410                 415

Leu Ala Thr Gly Phe Tyr Pro Asp His Val Glu Leu Ser Trp Trp Val
            420                 425                 430

Asn Gly Lys Glu Val His Ser Gly Val Ser Thr Asp Pro Gln Pro Leu
            435                 440                 445

Lys Glu Gln Pro Ala Leu Asn Asp Ser Arg Tyr Cys Leu Ser Ser Arg
            450                 455                 460

Leu Arg Val Ser Ala Thr Phe Trp Gln Asn Pro Arg Asn His Phe Arg
465                 470                 475                 480

Cys Gln Val Gln Phe Tyr Gly Leu Ser Glu Asn Asp Glu Trp Thr Gln
                485                 490                 495

Asp Arg Ala Lys Pro Val Thr Gln Ile Val Ser Ala Glu Ala Trp Gly
            500                 505                 510
```

```
Arg Ala Asp Cys Gly Phe Thr Ser Glu Ser Tyr Gln Gln Gly Val Leu
            515                 520                 525
Ser Ala Thr Ile Leu Tyr Glu Ile Leu Leu Gly Lys Ala Thr Leu Tyr
    530                 535                 540
Ala Val Leu Val Ser Ala Leu Val Leu Met Ala Met Val Lys Arg Lys
545                 550                 555                 560
Asp Ser Arg Gly Arg Ala Lys Arg Ser Gly Ser Gly Glu Gly Arg Gly
                565                 570                 575
Ser Leu Leu Thr Cys Gly Asp Val Glu Glu Asn Pro Gly Pro Met Glu
            580                 585                 590
Lys Asn Pro Leu Ala Ala Pro Leu Leu Ile Leu Trp Phe His Leu Asp
    595                 600                 605
Cys Val Ser Ser Ile Leu Asn Val Glu Gln Ser Pro Gln Ser Leu His
            610                 615                 620
Val Gln Glu Gly Asp Ser Thr Asn Phe Thr Cys Ser Phe Pro Ser Ser
625                 630                 635                 640
Asn Phe Tyr Ala Leu His Trp Tyr Arg Lys Glu Thr Ala Lys Ser Pro
                645                 650                 655
Glu Ala Leu Phe Val Met Thr Leu Asn Gly Asp Glu Lys Lys Lys Gly
            660                 665                 670
Arg Ile Ser Ala Thr Leu Asn Thr Lys Glu Gly Tyr Ser Tyr Leu Tyr
    675                 680                 685
Ile Lys Gly Ser Gln Pro Glu Asp Ser Ala Thr Tyr Leu Cys Ala Leu
            690                 695                 700
Tyr Asn Asn Asn Asp Met Arg Phe Gly Ala Gly Thr Arg Leu Thr Val
705                 710                 715                 720
Lys Pro Asn Ile Gln Asn Pro Asp Pro Ala Val Tyr Gln Leu Arg Asp
                725                 730                 735
Ser Lys Ser Ser Asp Lys Ser Val Cys Leu Phe Thr Asp Phe Asp Ser
            740                 745                 750
Gln Thr Asn Val Ser Gln Ser Lys Asp Ser Asp Val Tyr Ile Thr Asp
    755                 760                 765
Lys Thr Val Leu Asp Met Arg Ser Met Asp Phe Lys Ser Asn Ser Ala
770                 775                 780
Val Ala Trp Ser Asn Lys Ser Asp Phe Ala Cys Ala Asn Ala Phe Asn
785                 790                 795                 800
Asn Ser Ile Ile Pro Glu Asp Thr Phe Phe Pro Ser Pro Glu Ser Ser
                805                 810                 815
Cys Asp Val Lys Leu Val Glu Lys Ser Phe Glu Thr Asp Thr Asn Leu
            820                 825                 830
Asn Phe Gln Asn Leu Ser Val Ile Gly Phe Arg Ile Leu Leu Leu Lys
    835                 840                 845
Val Ala Gly Phe Asn Leu Leu Met Thr Leu Arg Leu Trp Ser Ser
850                 855                 860

<210> SEQ ID NO 287
<211> LENGTH: 3606
<212> TYPE: DNA
<213> ORGANISM: Artificial Sequence
<220> FEATURE:
<223> OTHER INFORMATION: CD8a.TCR.WPREmut2 construct nucleotide sequence

<400> SEQUENCE: 287
tgaaagaccc cacctgtagg tttggcaagc tagcttaagt aacgccattt tgcaaggcat      60
ggaaaataca taactgagaa tagagaagtt cagatcaagg ttaggaacag agagacagca     120
```

-continued

```
gaatatgggc caaacaggat atctgtggta agcagttcct gccccggctc agggccaaga      180
acagatggtc cccagatgcg gtcccgccct cagcagtttc tagagaacca tcagatgttt      240
ccagggtgcc ccaaggacct gaaaatgacc ctgtgcctta tttgaactaa ccaatcagtt      300
cgcttctcgc ttctgttcgc gcgcttctgc tccccgagct caataaaaga gcccacaacc      360
cctcactcag cggccgcccc gggtcgacgc taccaccatg gcgcttcccg tgaccgcact      420
cctgttgccc cttgccctgc tgttgcacgc cgcacgacct tcccaattcc gggtgtcccc      480
tctggatcgc acctggaacc tcggggaaac ggtggagctc aagtgtcaag tcctcctgtc      540
gaacccgacc agcggatgca gctggctgtt ccagccgaga ggagctgccg cctcacccac      600
cttcctcctg tacttgagcc agaacaagcc gaaggccgct gagggtctgg acacccagcg      660
cttctcgggc aaacggctgg agacactttt tgtgctgact ctctccgact tccggcggga      720
gaacgagggc tactacttct gctctgcgct ctccaattca atcatgtact tctcacactt      780
cgtgccggtg ttcctgcctg ccaagcccac cactactccg gcacccagac ctccaactcc      840
cgctcccacc atcgcgtccc aacccctttc gctgcgccct gaagcgtgtc ggcctgctgc      900
tggaggagcg gtgcataccc gcggtctgga cttcgcgtgc gacatctaca tttgggcccc      960
tttggctggc acctgtggag tgctgctcct gtcccttgtg atcaccctgt actgcaacca     1020
ccggaatagg cggagagtct gcaagtgtcc gcggcctgtc gtgaagtcag agataagcc      1080 gagcctgtcc gcacgctacg tgcgggccaa gagatctggc agcggcgcca ccaatttcag     1140
cctgctgaaa caggccggcg acgtggaaga gaacccctggc cccatggact cttggacctt    1200
ctgctgcgtg agcctgtgca tcctggtggc caagcacaca gacgccggcg tgatccagtc     1260
ccctaggcac gaggtgaccg agatgggcca ggaggtgaca ctgcgctgta agccaatctc     1320
tggccacaac agcctgtttt ggtatgggga gaccatgatg cgcggcctgg agctgctgat     1380
ctacttcaat aacaatgtgc ccatcgacga ttccggcatg cctgaggatc ggttttctgc     1440
caagatgccc aatgccagct tctccacact gaagatccag cctagcgagc caagagactc     1500
cgccgtgtat ttttgcgcct ctagcccagg cagcaccgat acacagtact tcggaccagg     1560
aaccaggctg acagtgctgg aggacctgaa gaacgtgttc ccccctgagg tggccgtgtt     1620
tgagccctct gaggccgaga tcagccacac ccagaaggcc accctggtgt gcctggcaac     1680
cggcttctat cctgatcacg tggagctgtc ctggtgggtg aacggcaagg aggtgcacag     1740
cggcgtgtcc acagacccac agccctgaa ggagcagcca gccctgaatg atagccggta     1800
ttgcctgtcc tctcggctga gagtgtccgc caccttttgg cagaaccccc ggaatcactt     1860
cagatgtcag gtgcagtttt acggcctgtc cgagaacgat gagtggaccc aggaccgggc     1920
caagcctgtg acacagatcg tgtctgccga ggcatgggga agagcagact gtggcttcac     1980
ctctgagagc taccagcagg gcgtgctgag cgccaccatc ctgtatgaga tcctgctggg     2040
caaggccaca ctgtacgccg tcctggtctc cgctctggtg ctgatggcaa tggtcaaaag     2100
aaaagatagt cggggacggg ccaagagatc tggcagcggc gagggcagag gcagcctgct     2160
gacctgcggc gacgtggagg agaacccccgg ccccatggag aagaatcccc tggctgcccc    2220
cctgctgatc ctgtggttc acctggactg cgtgtcctct atcctgaatg tggaacagag     2280
cccacagagc ctgcacgtgc aggagggcga ctccaccaac ttcacatgct cttttcctag     2340
ctccaacttc tacgccctgc actggtacag aaaggagacc gcaaagtccc cagaggccct    2400
gttcgtgatg acactgaacg gcgatgagaa gaagaagggc cgcatcagcg ccaccctgaa     2460
```

```
tacaaaggag ggctactcct atctgtacat caagggctcc cagcctgagg actctgccac   2520
ctatctgtgc gccctgtaca acaataacga tatgcggttt ggcgccggca ccagactgac   2580
agtgaagcca acatccaga atccagaccc cgccgtgtat cagctgcggg acagcaagtc   2640
tagcgataag agcgtgtgcc tgttcaccga ctttgattct cagacaaacg tgagccagtc   2700
caaggacagc gacgtgtaca tcaccgacaa gacagtgctg gatatgagaa gcatggactt   2760
caagtctaac agcgccgtgg cctggtccaa taagtctgat ttcgcctgcg ccaatgcctt   2820
taataactcc atcatccccg aggatacctt ctttccttct ccagagtcct cttgtgacgt   2880
gaagctggtg gagaagtctt tcgagaccga tacaaacctg aattttcaga acctgagcgt   2940
gatcggcttc aggatcctgc tgctgaaggt ggccggcttt aatctgctga tgaccctgag   3000
gctgtggagc tcctgaaccg gtccggagca tcttaccgcc atttataccc atatttgttc   3060 tgttttctt gatttgggta tacatttaaa tgttaataaa acaaaatggt ggggcaatca   3120
tttacatttt ttgggatatg taattactag ttcaggtgta ttgccacaag acaaacttgt   3180
taagaaactt tcccgttatt tacgctctgt tcctgttaat caacctctgg attacaaaat   3240
ttgtgaaaga ttgactgata ttcttaactt tgttgctcct tttacgctgt gtggatttgc   3300
tgctttattg cctctgtatc ttgctattgc ttcccgtacg gctttcgttt tctcctcctt   3360
gtataaatcc tggttgctgt ctcttttga ggagttgtgg cccgttgtcc gtcaacgtgg   3420
cgtggtgtgc tctgtgtttg ctgacgcaac ccccactggc tggggcattg ccaccacctg   3480
tcaactcctt tctgggactt tcgctttccc cctcccgatc gccacggcag aactcatcgc   3540
cgcctgcctt gcccgctgct ggacaggggc taggttgctg gcactgata attccgtggt   3600 gttgtc                                                              3606
```

<210> SEQ ID NO 288
<211> LENGTH: 872
<212> TYPE: PRT
<213> ORGANISM: Artificial Sequence
<220> FEATURE:
<223> OTHER INFORMATION: CD8a.TCR.WPREmut2 amino acid sequence

<400> SEQUENCE: 288

```
Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160
```

```
Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
                180                 185                 190

Cys Gly Val Leu Leu Leu Ser Leu Val Ile Thr Leu Tyr Cys Asn His
                195                 200                 205

Arg Asn Arg Arg Arg Val Cys Lys Cys Pro Arg Pro Val Val Lys Ser
            210                 215                 220

Gly Asp Lys Pro Ser Leu Ser Ala Arg Tyr Val Arg Ala Lys Arg Ser
225                 230                 235                 240

Gly Ser Gly Ala Thr Asn Phe Ser Leu Leu Lys Gln Ala Gly Asp Val
                245                 250                 255

Glu Glu Asn Pro Gly Pro Met Asp Ser Trp Thr Phe Cys Cys Val Ser
                260                 265                 270

Leu Cys Ile Leu Val Ala Lys His Thr Asp Ala Gly Val Ile Gln Ser
            275                 280                 285

Pro Arg His Glu Val Thr Glu Met Gly Gln Glu Val Thr Leu Arg Cys
            290                 295                 300

Lys Pro Ile Ser Gly His Asn Ser Leu Phe Trp Tyr Arg Glu Thr Met
305                 310                 315                 320

Met Arg Gly Leu Glu Leu Leu Ile Tyr Phe Asn Asn Asn Val Pro Ile
                325                 330                 335

Asp Asp Ser Gly Met Pro Glu Asp Arg Phe Ser Ala Lys Met Pro Asn
                340                 345                 350

Ala Ser Phe Ser Thr Leu Lys Ile Gln Pro Ser Glu Pro Arg Asp Ser
            355                 360                 365

Ala Val Tyr Phe Cys Ala Ser Ser Pro Gly Ser Thr Asp Thr Gln Tyr
370                 375                 380

Phe Gly Pro Gly Thr Arg Leu Thr Val Leu Glu Asp Leu Lys Asn Val
385                 390                 395                 400

Phe Pro Pro Glu Val Ala Val Phe Glu Pro Ser Glu Ala Glu Ile Ser
                405                 410                 415

His Thr Gln Lys Ala Thr Leu Val Cys Leu Ala Thr Gly Phe Tyr Pro
            420                 425                 430

Asp His Val Glu Leu Ser Trp Trp Val Asn Gly Lys Glu Val His Ser
            435                 440                 445

Gly Val Ser Thr Asp Pro Gln Pro Leu Lys Glu Gln Pro Ala Leu Asn
450                 455                 460

Asp Ser Arg Tyr Cys Leu Ser Ser Arg Leu Arg Val Ser Ala Thr Phe
465                 470                 475                 480

Trp Gln Asn Pro Arg Asn His Phe Arg Cys Gln Val Gln Phe Tyr Gly
                485                 490                 495

Leu Ser Glu Asn Asp Glu Trp Thr Gln Asp Arg Ala Lys Pro Val Thr
            500                 505                 510

Gln Ile Val Ser Ala Glu Ala Trp Gly Arg Ala Asp Cys Gly Phe Thr
            515                 520                 525

Ser Glu Ser Tyr Gln Gln Gly Val Leu Ser Ala Thr Ile Leu Tyr Glu
            530                 535                 540

Ile Leu Leu Gly Lys Ala Thr Leu Tyr Ala Val Leu Val Ser Ala Leu
545                 550                 555                 560

Val Leu Met Ala Met Val Lys Arg Lys Asp Ser Arg Gly Arg Ala Lys
                565                 570                 575
```

Arg Ser Gly Ser Gly Glu Gly Arg Gly Ser Leu Leu Thr Cys Gly Asp
                580                 585                 590

Val Glu Glu Asn Pro Gly Pro Met Glu Lys Asn Pro Leu Ala Ala Pro
            595                 600             605

Leu Leu Ile Leu Trp Phe His Leu Asp Cys Val Ser Ser Ile Leu Asn
            610             615             620

Val Glu Gln Ser Pro Gln Ser Leu His Val Gln Glu Gly Asp Ser Thr
625             630                 635                 640

Asn Phe Thr Cys Ser Phe Pro Ser Ser Asn Phe Tyr Ala Leu His Trp
                645             650                 655

Tyr Arg Lys Glu Thr Ala Lys Ser Pro Glu Ala Leu Phe Val Met Thr
            660             665             670

Leu Asn Gly Asp Glu Lys Lys Lys Gly Arg Ile Ser Ala Thr Leu Asn
            675             680             685

Thr Lys Glu Gly Tyr Ser Tyr Leu Tyr Ile Lys Gly Ser Gln Pro Glu
690             695             700

Asp Ser Ala Thr Tyr Leu Cys Ala Leu Tyr Asn Asn Asn Asp Met Arg
705             710                 715                 720

Phe Gly Ala Gly Thr Arg Leu Thr Val Lys Pro Asn Ile Gln Asn Pro
                725             730             735

Asp Pro Ala Val Tyr Gln Leu Arg Asp Ser Lys Ser Ser Asp Lys Ser
            740             745             750

Val Cys Leu Phe Thr Asp Phe Asp Ser Gln Thr Asn Val Ser Gln Ser
            755             760             765

Lys Asp Ser Asp Val Tyr Ile Thr Asp Lys Thr Val Leu Asp Met Arg
770             775             780

Ser Met Asp Phe Lys Ser Asn Ser Ala Val Ala Trp Ser Asn Lys Ser
785             790             795             800

Asp Phe Ala Cys Ala Asn Ala Phe Asn Asn Ser Ile Ile Pro Glu Asp
                805             810             815

Thr Phe Phe Pro Ser Pro Glu Ser Ser Cys Asp Val Lys Leu Val Glu
            820             825             830

Lys Ser Phe Glu Thr Asp Thr Asn Leu Asn Phe Gln Asn Leu Ser Val
            835             840             845

Ile Gly Phe Arg Ile Leu Leu Leu Lys Val Ala Gly Phe Asn Leu Leu
850             855             860

Met Thr Leu Arg Leu Trp Ser Ser
865             870

<210> SEQ ID NO 289
<211> LENGTH: 3633
<212> TYPE: DNA
<213> ORGANISM: Artificial Sequence
<220> FEATURE:
<223> OTHER INFORMATION: WT-SPa/CD8a-Ig like domain
    1(co)/CD8astalk(co)/CD4 TM+IC/TCRba/WPREmut2 construct nucleotide
    sequence

<400> SEQUENCE: 289
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga     180
acagatggtc cccagatgcg gtcccgccct cagcagtttc tagagaacca tcagatgttt     240
ccagggtgcc caaggacct gaaaatgacc ctgtgcctta tttgaactaa ccaatcagtt      300

```
cgcttctcgc ttctgttcgc gcgcttctgc tccccgagct caataaaaga gcccacaacc    360
cctcactcag cggccgcccc gggtcgacgc taccaccatg gcgcttcccg tgaccgcact    420
cctgttgccc cttgccctgc tgttgcacgc cgcacgacct tcccaattcc gggtgtcccc    480
tctggatcgc acctggaacc tcggggaaac ggtggagctc aagtgtcaag tcctcctgtc    540
gaacccgacc agcggatgca gctggctgtt ccagccgaga ggagctgccg cctcacccac    600
cttcctcctg tacttgagcc agaacaagcc gaaggccgct gagggtctgg acacccagcg    660
cttctcgggc aaacggctgg agacactttt tgtgctgact ctctccgact ccggcgggga    720
gaacgagggc tactacttct gctctgcgct ctccaattca atcatgtact tctcacactt    780
cgtgccggtg ttcctgcctg ccaagcccac cactactccg gcacccagac ctccaactcc    840
cgctcccacc atcgcgtccc aaccccttc gctgcgccct gaagcgtgtc ggcctgctgc    900
tggaggagcc gtgcataccc gcggtctgga cttcgcgtgc gacatggccc tgattgtgct    960
ggggggcgtc gccggcctcc tgcttttcat tgggctaggc atcttcttct gtgtcaggtg   1020
ccggcaccga aggcgccaag cagagcggat gtctcagatc aagagactcc tcagtgagaa   1080
gaagaccctgc cagtgtcctc accggtttca gaagacatgt agccccattc gggccaagag   1140
atctggcagc ggcgccacca atttcagcct gctgaaacag gccggcgacg tggaagagaa   1200
ccctggcccc atggactctt ggaccttctg ctgcgtgagc ctgtgcatcc tggtggccaa   1260
gcacacagac gccggcgtga tccagtcccc taggcacgag gtgaccgaga tgggccagga   1320
ggtgacactg cgctgtaagc caatctctgg ccacaacagc ctgttttggt atagggagac   1380
catgatgcgc ggcctggagc tgctgatcta cttcaataac aatgtgccca tcgacgattc   1440
cggcatgcct gaggatcggt tttctgccaa gatgcccaat gccagcttct ccacactgaa   1500
gatccagcct agcgagccaa gagactccgc cgtgtatttt tgcgcctcta gcccaggcag   1560
caccgataca cagtacttcg gaccaggaac caggctgaca gtgctggagg acctgaagaa   1620
cgtgttcccc cctgaggtgg ccgtgtttga gccctctgag ccgagatcag ccacacccca   1680
gaaggccacc ctggtgtgcc tggcaaccgg cttctatcct gatcacgtgg agctgtcctg   1740
gtgggtgaac ggcaaggagg tgcacagcgg cgtgtccaca gacccacagc ccctgaagga   1800
gcagccagcc ctgaatgata gccggtattg cctgtcctct cggctgagag tgtccgccac   1860
cttttggcag aaccccggga atcacttcag atgtcaggtg cagttttacg gcctgtccga   1920
gaacgatgag tggacccagg accgggccaa gcctgtgaca cagatcgtgt ctgccgaggc   1980
atggggaaga gcagactgtg gcttcacctc tgagagctac cagcagggcg tgctgagcgc   2040
caccatcctg tatgagatcc tgctgggcaa ggccacactg tacgccgtcc tggtctccgc   2100
tctggtgctg atggcaatgg tcaaaagaaa agatagtcgg ggacgggcca agagatctgg   2160
cagcggcgag ggcagaggca gcctgctgac ctgcggcgac gtggaggaga acccccggcc   2220
catggagaag aatcccctgg ctgccccccct gctgatcctg tggtttcacc tggactgcgt   2280
gtcctctatc ctgaatgtgg aacagagccc acagagcctg cacgtgcagg agggcgactc   2340
caccaacttc acatgctctt ttcctagctc caacttctac gccctgcact ggtacagaaa   2400
ggagaccgca aagtccccag aggccctgtt cgtgatgaca ctgaacggcg atgagaagaa   2460
gaagggccgc atcagcgcca ccctgaatac aaaggagggc tactcctatc tgtacatcaa   2520
gggctcccag cctgaggact ctgccaccta tctgtgcgcc ctgtacaaca ataacgatat   2580
gcggtttggc gccggcacca gactgacagt gaagccaaac atccagaatc cagacccccgc   2640
cgtgtatcag ctgcgggaca gcaagtctag cgataagagc gtgtgcctgt tcaccgactt   2700
```

```
tgattctcag acaaacgtga gccagtccaa ggacagcgac gtgtacatca ccgacaagac    2760
agtgctggat atgagaagca tggacttcaa gtctaacagc gccgtggcct ggtccaataa    2820
gtctgatttc gcctgcgcca atgcctttaa taactccatc atccccgagg ataccttctt    2880
tccttctcca gagtcctctt gtgacgtgaa gctggtggag aagtctttcg agaccgatac    2940
aaacctgaat tttcagaacc tgagcgtgat cggcttcagg atcctgctgc tgaaggtggc    3000
cggctttaat ctgctgatga ccctgaggct gtggagctcc tgaaccggtc cggagcatct    3060
taccgccatt tatacccata tttgttctgt ttttcttgat ttgggtatac atttaaatgt    3120
taataaaaca aaatggtggg gcaatcattt acatttttg ggatatgtaa ttactagttc    3180
aggtgtattg ccacaagaca aacttgttaa gaaactttcc cgttatttac gctctgttcc    3240
tgttaatcaa cctctggatt acaaaatttg tgaaagattg actgatattc ttaactttgt    3300
tgctcctttt acgctgtgtg gatttgctgc tttattgcct ctgtatcttg ctattgcttc    3360
ccgtacggct ttcgttttct cctccttgta taaatcctgg ttgctgtctc tttttgagga    3420
gttgtggccc gttgtccgtc aacgtggcgt ggtgtgctct gtgtttgctg acgcaacccc    3480
cactggctgg ggcattgcca ccacctgtca actccttct gggactttcg ctttcccct    3540 cccgatcgcc acggcagaac tcatcgccgc ctgccttgcc cgctgctgga cagggctag    3600 gttgctgggc actgataatt ccgtggtgtt gtc                                 3633
```

<210> SEQ ID NO 290
<211> LENGTH: 881
<212> TYPE: PRT
<213> ORGANISM: Artificial Sequence
<220> FEATURE:
<223> OTHER INFORMATION: WT-SPa/CD8a-Ig like domain
      1(co)/CD8astalk(co)/CD4 TM+IC/TCRba/WPREmut2 amino acid sequence

<400> SEQUENCE: 290

```
Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Met Ala Leu Ile Val Leu Gly Gly Val Ala
            180                 185                 190
```

```
Gly Leu Leu Leu Phe Ile Gly Leu Gly Ile Phe Phe Cys Val Arg Cys
            195                 200                 205

Arg His Arg Arg Arg Gln Ala Glu Arg Met Ser Gln Ile Lys Arg Leu
            210                 215                 220

Leu Ser Glu Lys Lys Thr Cys Gln Cys Pro His Arg Phe Gln Lys Thr
225                 230                 235                 240

Cys Ser Pro Ile Arg Ala Lys Arg Ser Gly Ser Gly Ala Thr Asn Phe
            245                 250                 255

Ser Leu Leu Lys Gln Ala Gly Asp Val Glu Asn Pro Gly Pro Met
            260                 265                 270

Asp Ser Trp Thr Phe Cys Cys Val Ser Leu Cys Ile Leu Val Ala Lys
            275                 280                 285

His Thr Asp Ala Gly Val Ile Gln Ser Pro Arg His Glu Val Thr Glu
            290                 295                 300

Met Gly Gln Glu Val Thr Leu Arg Cys Lys Pro Ile Ser Gly His Asn
305                 310                 315                 320

Ser Leu Phe Trp Tyr Arg Glu Thr Met Met Arg Gly Leu Glu Leu Leu
            325                 330                 335

Ile Tyr Phe Asn Asn Asn Val Pro Ile Asp Asp Ser Gly Met Pro Glu
            340                 345                 350

Asp Arg Phe Ser Ala Lys Met Pro Asn Ala Ser Phe Ser Thr Leu Lys
            355                 360                 365

Ile Gln Pro Ser Glu Pro Arg Asp Ser Ala Val Tyr Phe Cys Ala Ser
            370                 375                 380

Ser Pro Gly Ser Thr Asp Thr Gln Tyr Phe Gly Pro Gly Thr Arg Leu
385                 390                 395                 400

Thr Val Leu Glu Asp Leu Lys Asn Val Phe Pro Pro Glu Val Ala Val
            405                 410                 415

Phe Glu Pro Ser Glu Ala Glu Ile Ser His Thr Gln Lys Ala Thr Leu
            420                 425                 430

Val Cys Leu Ala Thr Gly Phe Tyr Pro Asp His Val Glu Leu Ser Trp
            435                 440                 445

Trp Val Asn Gly Lys Glu Val His Ser Gly Val Ser Thr Asp Pro Gln
            450                 455                 460

Pro Leu Lys Glu Gln Pro Ala Leu Asn Asp Ser Arg Tyr Cys Leu Ser
465                 470                 475                 480

Ser Arg Leu Arg Val Ser Ala Thr Phe Trp Gln Asn Pro Arg Asn His
            485                 490                 495

Phe Arg Cys Gln Val Gln Phe Tyr Gly Leu Ser Glu Asn Asp Glu Trp
            500                 505                 510

Thr Gln Asp Arg Ala Lys Pro Val Thr Gln Ile Val Ser Ala Glu Ala
            515                 520                 525

Trp Gly Arg Ala Asp Cys Gly Phe Thr Ser Glu Ser Tyr Gln Gln Gly
            530                 535                 540

Val Leu Ser Ala Thr Ile Leu Tyr Glu Ile Leu Leu Gly Lys Ala Thr
545                 550                 555                 560

Leu Tyr Ala Val Leu Val Ser Ala Leu Val Leu Met Ala Met Val Lys
            565                 570                 575

Arg Lys Asp Ser Arg Gly Arg Ala Lys Arg Ser Gly Ser Gly Glu Gly
            580                 585                 590

Arg Gly Ser Leu Leu Thr Cys Gly Asp Val Glu Glu Asn Pro Gly Pro
            595                 600                 605
```

```
Met Glu Lys Asn Pro Leu Ala Ala Pro Leu Leu Ile Leu Trp Phe His
    610                 615                 620
Leu Asp Cys Val Ser Ser Ile Leu Asn Val Glu Gln Ser Pro Gln Ser
625                 630                 635                 640
Leu His Val Gln Glu Gly Asp Ser Thr Asn Phe Thr Cys Ser Phe Pro
                    645                 650                 655
Ser Ser Asn Phe Tyr Ala Leu His Trp Tyr Arg Lys Glu Thr Ala Lys
                660                 665                 670
Ser Pro Glu Ala Leu Phe Val Met Thr Leu Asn Gly Asp Glu Lys Lys
            675                 680                 685
Lys Gly Arg Ile Ser Ala Thr Leu Asn Thr Lys Glu Gly Tyr Ser Tyr
690                 695                 700
Leu Tyr Ile Lys Gly Ser Gln Pro Glu Asp Ser Ala Thr Tyr Leu Cys
705                 710                 715                 720
Ala Leu Tyr Asn Asn Asn Asp Met Arg Phe Gly Ala Gly Thr Arg Leu
                    725                 730                 735
Thr Val Lys Pro Asn Ile Gln Asn Pro Asp Pro Ala Val Tyr Gln Leu
                740                 745                 750
Arg Asp Ser Lys Ser Ser Asp Lys Ser Val Cys Leu Phe Thr Asp Phe
            755                 760                 765
Asp Ser Gln Thr Asn Val Ser Gln Ser Lys Asp Ser Asp Val Tyr Ile
770                 775                 780
Thr Asp Lys Thr Val Leu Asp Met Arg Ser Met Asp Phe Lys Ser Asn
785                 790                 795                 800
Ser Ala Val Ala Trp Ser Asn Lys Ser Asp Phe Ala Cys Ala Asn Ala
                    805                 810                 815
Phe Asn Asn Ser Ile Ile Pro Glu Asp Thr Phe Phe Pro Ser Pro Glu
                820                 825                 830
Ser Ser Cys Asp Val Lys Leu Val Glu Lys Ser Phe Glu Thr Asp Thr
            835                 840                 845
Asn Leu Asn Phe Gln Asn Leu Ser Val Ile Gly Phe Arg Ile Leu Leu
850                 855                 860
Leu Lys Val Ala Gly Phe Asn Leu Leu Met Thr Leu Arg Leu Trp Ser
865                 870                 875                 880
Ser

<210> SEQ ID NO 291
<211> LENGTH: 4419
<212> TYPE: DNA
<213> ORGANISM: Artificial Sequence
<220> FEATURE:
<223> OTHER INFORMATION: PTE.CD8ab.TCR.WPREmut2 construct nucleotide
      sequence

<400> SEQUENCE: 291
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaaatgacc ctgtgcctta tttgaactaa ccaatcagtt    300
cgcttctcgc ttctgttcgc gcgcttctgc tccccgagct caataaaaga gcccacaacc    360
cctcactcag cggccgcccc gggtcgacgc taccaccatg cgcccagac tgtggcttct    420 gctcgccgcg caactgactg tcctgcacgg aaacagcgtg ctgcagcaga caccggccta    480
```

-continued

```
catcaaagtg cagaccaaca agatggtcat gctgtcctgc gaggccaaga tttccctctc    540
caacatgcgg atctattggt tgcggcagag acaggcgcct tcctcggact cccaccatga    600
gttcttggcc ctgtgggact ccgccaaggg aactattcac ggcgaagaag tggaacagga    660
gaagatcgcc gtgtttcgcg atgcctcccg ctttatactg aatctgacct ccgtgaagcc    720
cgaagatagc gggatctact tttgcatgat tgtgggctca cccgaactga ccttcgggaa    780
gggcactcag ctgagcgtgg tggacttcct ccccactacc gcccaaccca ctaagaagtc    840
aaccctgaag aagcgggttt gcagactccc acggccggaa acgcagaagg gtccgctgtg    900
ttccccgatc accctggggc tccttgtggc tggagtgctg gtccttctgg tgtcccttgg    960
cgtcgccatt cacctctgct gccggagaag gagggccaga ctgaggttca tgaagcagcc   1020
tcagggagag gggatcagtg gcactttcgt gccacaatgc ctccatggct actattccaa   1080
caccaccacc tcgcaaaagc tgctgaaccc ctggatcctg aaaacccggg ccaagagatc   1140
tggcagcggc gccaccaatt tcagcctgct gaaacaggcc ggcgacgtgg aagagaaccc   1200 tggcccccatg gcgcttcccg tgaccgcact cctgttgccc cttgccctgc tgttgcacgc   1260
cgcacgacct tcccaattcc gggtgtcccc tctggatcgc acctggaacc tcggggaaac   1320
ggtggagctc aagtgtcaag tcctcctgtc gaacccgacc agcggatgca gctggctgtt   1380
ccagccgaga ggagctgccg cctcacccac cttcctcctg tacttgagcc agaacaagcc   1440
gaaggccgct gagggtctgg acaccagcg cttctcgggc aaacggctgg agacactttt   1500
tgtgctgact ctctccgact ccggcggga gaacgagggc tactacttct gctctgcgct   1560
ctccaattca atcatgtact tctcacactt cgtgccggtg ttcctgcctg ccaagcccac   1620
cactactccg gcacccagac ctccaactcc cgctcccacc atcgcgtccc aacccctttc   1680
gctgcgccct gaagcgtgtc ggcctgctgc tggaggagcc gtgcataccc gcggtctgga   1740
cttcgcgtgc gacatctaca tttgggcccc tttggctggc acctgtggag tgctgctcct   1800
gtcccttgtg atcaccctgt actgcaacca ccggaatagg cggagagtct gcaagtgtcc   1860
gcggcctgtc gtgaagtcag gagataagcc gagcctgtcc gcacgctacg tgcgggccaa   1920
gagatctggc agcggcgagg gcagaggcag cctgctgacc tgcggcgacg tggaggagaa   1980
cccccggccc catggactctt ggaccttctg ctgcgtgagc ctgtgcatcc tggtggccaa   2040
gcacacagac gccggcgtga tccagtcccc taggcacgag gtgaccgaga tgggccagga   2100
ggtgacactg cgctgtaagc caatctctgg ccacaacagc ctgttttggt ataggagac    2160 catgatcgcg ggcctggagc tgctgatcta cttcaataac aatgtgccca tcgacgattc   2220
cggcatgcct gaggatcggt tttctgccaa gatgcccaat gccagcttct ccacactgaa   2280
gatccagcct agcgagccaa gagactccgc cgtgtatttt tgcgcctcta gcccaggcag   2340
caccgataca cagtacttcg gaccaggaac caggctgaca gtgctggagg acctgaagaa   2400
cgtgttcccc cctgaggtgg ccgtgtttga gccctctgag gccagatcca gccacaccca   2460
gaaggccacc ctggtgtgcc tggcaaccgg cttctatcct gatcacgtgg agctgtcctg   2520
gtgggtgaac ggcaaggagg tgcacagcgg cgtgtccaca gacccacagc ccctgaagga   2580
gcagccagcc ctgaatgata gccggtattg cctgtcctct cggctgagag tgtccgccac   2640
cttttggcag aaccccgga atcacttcag atgtcaggtg cagttttacg gcctgtccga   2700
gaacgatgag tggacccagg accgggccaa gcctgtgaca cagatcgtgt ctgccgaggc   2760
atggggaaga gcagactgtg gcttcacctc tgagagctac cagcagggcg tgctgagcgc   2820
```

```
caccatcctg tatgagatcc tgctgggcaa ggccacactg tacgccgtcc tggtctccgc    2880
tctggtgctg atggcaatgg tcaaaagaaa agatagtcgg ggacgggcca agagatctgg    2940
cagcggccag tgcaccaact acgccctgct gaagctggcc ggcgacgtgg agagcaaccc    3000
cggccccatg gagaagaatc ccctggctgc ccccctgctg atcctgtggt tcacctgga    3060 ctgcgtgtcc tctatcctga atgtggaaca gagcccacag agcctgcacg tgcaggaggg    3120
cgactccacc aacttcacat gctcttttcc tagctccaac ttctacgccc tgcactggta    3180
cagaaaggag accgcaaagt ccccagaggc cctgttcgtg atgacactga acggcgatga    3240
gaagaagaag ggccgcatca cgccaccct gaatacaaag gagggctact cctatctgta    3300 catcaaggc tcccagcctg aggactctgc cacctatctg tgcgccctgt acaacaataa    3360
cgatatgcgg tttggcgccg gcaccagact gacagtgaag ccaaacatcc agaatccaga    3420
ccccgccgtg tatcagctgc gggacagcaa gtctagcgat aagagcgtgt gcctgttcac    3480
cgactttgat tctcagacaa acgtgagcca gtccaaggac agcgacgtgt acatcaccga    3540
caagacagtg ctggatatga aagcatgga cttcaagtct aacagcgccg tggcctggtc    3600
caataagtct gatttcgcct gcgccaatgc ctttaataac tccatcatcc ccgaggatac    3660
cttctttcct tctccagagt cctcttgtga cgtgaagctg gtggagaagt ctttcgagac    3720
cgatacaaac ctgaatttc agaacctgag cgtgatcggc ttcaggatcc tgctgctgaa    3780
ggtggccggc tttaatctgc tgatgaccct gaggctgtgg agctcctgaa ccggtccgga    3840
gcatcttacc gccatttata cccatatttg ttctgttttt cttgatttgg gtatacattt    3900
aaatgttaat aaaacaaaat ggtggggcaa tcatttacat ttttgggat atgtaattac    3960 tagttcaggt gtattgccac aagacaaact tgttaagaaa cttcccgtt atttacgctc    4020 tgttcctgtt aatcaacctc tggattacaa aatttgtgaa agattgactg atattcttaa    4080
ctttgttgct ccttttacgc tgtgtggatt tgctgcttta ttgcctctgt atcttgctat    4140
tgcttcccgt acggctttcg tttctcctc cttgtataaa tcctggttgc tgtctcttt    4200 tgaggagttg tggcccgttg tccgtcaacg tggcgtggtg tgctctgtgt ttgctgacgc    4260 aaccccact ggctggggca ttgccaccac ctgtcaactc ctttctggga ctttcgcttt    4320 cccctcccg atcgccacgg cagaactcat cgccgcctgc cttgcccgct gctggacagg    4380
ggctaggttg ctgggcactg ataattccgt ggtgttgtc                         4419
```

<210> SEQ ID NO 292
<211> LENGTH: 1143
<212> TYPE: PRT
<213> ORGANISM: Artificial Sequence
<220> FEATURE:
<223> OTHER INFORMATION: PTE.CD8ab.TCR.WPREmut2 amino acid sequence

<400> SEQUENCE: 292

```
Met Arg Pro Arg Leu Trp Leu Leu Ala Ala Gln Leu Thr Val Leu
1               5                   10                  15

His Gly Asn Ser Val Leu Gln Gln Thr Pro Ala Tyr Ile Lys Val Gln
                20                  25                  30

Thr Asn Lys Met Val Met Leu Ser Cys Glu Ala Lys Ile Ser Leu Ser
            35                  40                  45

Asn Met Arg Ile Tyr Trp Leu Arg Gln Arg Gln Ala Pro Ser Ser Asp
        50                  55                  60

Ser His His Glu Phe Leu Ala Leu Trp Asp Ser Ala Lys Gly Thr Ile
65                  70                  75                  80
```

```
His Gly Glu Glu Val Glu Gln Glu Lys Ile Ala Val Phe Arg Asp Ala
                 85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
            115                 120                 125

Gly Thr Gln Leu Ser Val Val Asp Phe Leu Pro Thr Thr Ala Gln Pro
130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
                180                 185                 190

Leu Cys Cys Arg Arg Arg Arg Ala Arg Leu Arg Phe Met Lys Gln Pro
        195                 200                 205

Gln Gly Glu Gly Ile Ser Gly Thr Phe Val Pro Gln Cys Leu His Gly
210                 215                 220

Tyr Tyr Ser Asn Thr Thr Thr Ser Gln Lys Leu Leu Asn Pro Trp Ile
225                 230                 235                 240

Leu Lys Thr Arg Ala Lys Arg Ser Gly Ser Gly Ala Thr Asn Phe Ser
            245                 250                 255

Leu Leu Lys Gln Ala Gly Asp Val Glu Glu Asn Pro Gly Pro Met Ala
            260                 265                 270

Leu Pro Val Thr Ala Leu Leu Leu Pro Leu Ala Leu Leu Leu His Ala
        275                 280                 285

Ala Arg Pro Ser Gln Phe Arg Val Ser Pro Leu Asp Arg Thr Trp Asn
290                 295                 300

Leu Gly Glu Thr Val Glu Leu Lys Cys Gln Val Leu Leu Ser Asn Pro
305                 310                 315                 320

Thr Ser Gly Cys Ser Trp Leu Phe Gln Pro Arg Gly Ala Ala Ala Ser
            325                 330                 335

Pro Thr Phe Leu Leu Tyr Leu Ser Gln Asn Lys Pro Lys Ala Ala Glu
            340                 345                 350

Gly Leu Asp Thr Gln Arg Phe Ser Gly Lys Arg Leu Gly Asp Thr Phe
        355                 360                 365

Val Leu Thr Leu Ser Asp Phe Arg Arg Glu Asn Glu Gly Tyr Tyr Phe
        370                 375                 380

Cys Ser Ala Leu Ser Asn Ser Ile Met Tyr Phe Ser His Phe Val Pro
385                 390                 395                 400

Val Phe Leu Pro Ala Lys Pro Thr Thr Thr Pro Ala Pro Arg Pro Pro
                405                 410                 415

Thr Pro Ala Pro Thr Ile Ala Ser Gln Pro Leu Ser Leu Arg Pro Glu
                420                 425                 430

Ala Cys Arg Pro Ala Ala Gly Gly Ala Val His Thr Arg Gly Leu Asp
        435                 440                 445

Phe Ala Cys Asp Ile Tyr Ile Trp Ala Pro Leu Ala Gly Thr Cys Gly
        450                 455                 460

Val Leu Leu Leu Ser Leu Val Ile Thr Leu Tyr Cys Asn His Arg Asn
465                 470                 475                 480

Arg Arg Arg Val Cys Lys Cys Pro Arg Pro Val Val Lys Ser Gly Asp
                485                 490                 495

Lys Pro Ser Leu Ser Ala Arg Tyr Val Arg Ala Lys Arg Ser Gly Ser
```

```
            500                 505                 510
Gly Glu Gly Arg Gly Ser Leu Leu Thr Cys Gly Asp Val Glu Glu Asn
            515                 520                 525

Pro Gly Pro Met Asp Ser Trp Thr Phe Cys Cys Val Ser Leu Cys Ile
530                 535                 540

Leu Val Ala Lys His Thr Asp Ala Gly Val Ile Gln Ser Pro Arg His
545                 550                 555                 560

Glu Val Thr Glu Met Gly Gln Glu Val Thr Leu Arg Cys Lys Pro Ile
                565                 570                 575

Ser Gly His Asn Ser Leu Phe Trp Tyr Arg Glu Thr Met Met Arg Gly
            580                 585                 590

Leu Glu Leu Leu Ile Tyr Phe Asn Asn Val Pro Ile Asp Asp Ser
            595                 600                 605

Gly Met Pro Glu Asp Arg Phe Ser Ala Lys Met Pro Asn Ala Ser Phe
            610                 615                 620

Ser Thr Leu Lys Ile Gln Pro Ser Glu Pro Arg Asp Ser Ala Val Tyr
625                 630                 635                 640

Phe Cys Ala Ser Ser Pro Gly Ser Thr Asp Thr Gln Tyr Phe Gly Pro
                645                 650                 655

Gly Thr Arg Leu Thr Val Leu Glu Asp Leu Lys Asn Val Phe Pro Pro
            660                 665                 670

Glu Val Ala Val Phe Glu Pro Ser Glu Ala Glu Ile Ser His Thr Gln
            675                 680                 685

Lys Ala Thr Leu Val Cys Leu Ala Thr Gly Phe Tyr Pro Asp His Val
            690                 695                 700

Glu Leu Ser Trp Trp Val Asn Gly Lys Glu Val His Ser Gly Val Ser
705                 710                 715                 720

Thr Asp Pro Gln Pro Leu Lys Glu Gln Pro Ala Leu Asn Asp Ser Arg
                725                 730                 735

Tyr Cys Leu Ser Ser Arg Leu Arg Val Ser Ala Thr Phe Trp Gln Asn
                740                 745                 750

Pro Arg Asn His Phe Arg Cys Gln Val Gln Phe Tyr Gly Leu Ser Glu
            755                 760                 765

Asn Asp Glu Trp Thr Gln Asp Arg Ala Lys Pro Val Thr Gln Ile Val
770                 775                 780

Ser Ala Glu Ala Trp Gly Arg Ala Asp Cys Gly Phe Thr Ser Glu Ser
785                 790                 795                 800

Tyr Gln Gln Gly Val Leu Ser Ala Thr Ile Leu Tyr Glu Ile Leu Leu
                805                 810                 815

Gly Lys Ala Thr Leu Tyr Ala Val Leu Val Ser Ala Leu Val Leu Met
            820                 825                 830

Ala Met Val Lys Arg Lys Asp Ser Arg Gly Arg Ala Lys Arg Ser Gly
            835                 840                 845

Ser Gly Gln Cys Thr Asn Tyr Ala Leu Leu Lys Leu Ala Gly Asp Val
            850                 855                 860

Glu Ser Asn Pro Gly Pro Met Glu Lys Asn Pro Leu Ala Ala Pro Leu
865                 870                 875                 880

Leu Ile Leu Trp Phe His Leu Asp Cys Val Ser Ser Ile Leu Asn Val
                885                 890                 895

Glu Gln Ser Pro Gln Ser Leu His Val Gln Glu Gly Asp Ser Thr Asn
            900                 905                 910

Phe Thr Cys Ser Phe Pro Ser Ser Asn Phe Tyr Ala Leu His Trp Tyr
            915                 920                 925
```

Arg Lys Glu Thr Ala Lys Ser Pro Glu Ala Leu Phe Val Met Thr Leu
    930             935             940

Asn Gly Asp Glu Lys Lys Gly Arg Ile Ser Ala Thr Leu Asn Thr
945             950             955             960

Lys Glu Gly Tyr Ser Tyr Leu Tyr Ile Lys Gly Ser Gln Pro Glu Asp
            965             970             975

Ser Ala Thr Tyr Leu Cys Ala Leu Tyr Asn Asn Asn Asp Met Arg Phe
            980             985             990

Gly Ala Gly Thr Arg Leu Thr Val  Lys Pro Asn Ile Gln  Asn Pro Asp
        995             1000                1005

Pro Ala Val Tyr Gln Leu Arg  Asp Ser Lys Ser  Ser Asp Lys Ser
    1010            1015                1020

Val Cys Leu Phe Thr Asp Phe  Asp Ser Gln Thr Asn  Val Ser Gln
    1025            1030                1035

Ser Lys Asp Ser Asp Val Tyr  Ile Thr Asp Lys Thr  Val Leu Asp
    1040            1045                1050

Met Arg Ser Met Asp Phe Lys  Ser Asn Ser Ala Val  Ala Trp Ser
    1055            1060                1065

Asn Lys Ser Asp Phe Ala Cys  Ala Asn Ala Phe Asn  Asn Ser Ile
    1070            1075                1080

Ile Pro Glu Asp Thr Phe Phe  Pro Ser Pro Glu Ser  Ser Cys Asp
    1085            1090                1095

Val Lys Leu Val Glu Lys Ser  Phe Glu Thr Asp Thr  Asn Leu Asn
    1100            1105                1110

Phe Gln Asn Leu Ser Val Ile  Gly Phe Arg Ile Leu  Leu Leu Lys
    1115            1120                1125

Val Ala Gly Phe Asn Leu Leu  Met Thr Leu Arg Leu  Trp Ser Ser
    1130            1135                1140

<210> SEQ ID NO 293
<211> LENGTH: 21
<212> TYPE: PRT
<213> ORGANISM: Artificial Sequence
<220> FEATURE:
<223> OTHER INFORMATION: Signal peptide

<400> SEQUENCE: 293

Met Arg Pro Arg Leu Trp Leu Leu Leu Ala Ala Gln Leu Thr Val Leu
1               5                   10                  15

His Gly Asn Ser Val
            20

<210> SEQ ID NO 294
<211> LENGTH: 19
<212> TYPE: PRT
<213> ORGANISM: Artificial Sequence
<220> FEATURE:
<223> OTHER INFORMATION: Signal peptide

<400> SEQUENCE: 294

Met Glu Phe Gly Leu Ser Trp Leu Phe Leu Val Ala Ile Leu Lys Gly
1               5                   10                  15

Val Gln Cys

<210> SEQ ID NO 295
<211> LENGTH: 3631
<212> TYPE: DNA
<213> ORGANISM: Artificial Sequence
<220> FEATURE:
<223> OTHER INFORMATION: CD8a.TCR.WPRE construct nucleotide sequence

<400> SEQUENCE: 295

```
tgaaagaccc cacctgtagg tttggcaagc tagcttaagt aacgccattt tgcaaggcat     60
ggaaaataca taactgagaa tagagaagtt cagatcaagg ttaggaacag agagacagca    120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaaatgacc ctgtgcctta tttgaactaa ccaatcagtt    300
cgcttctcgc ttctgttcgc gcgcttctgc tccccgagct caataaaaga gcccacaacc    360
cctcactagc ggccgccccg ggtcgacgct accaccatgg cgcttcccgt gaccgcactc    420
ctgttgcccc ttgccctgct gttgcacgcc gcacgacctt cccaattccg ggtgtcccct    480
ctggatcgca cctggaacct cggggaaacg gtggagctca agtgtcaagt cctcctgtcg    540
aacccgacca gcggatgcag ctggctgttc cagccgagag gagctgccgc ctcacccacc    600
ttcctcctgt acttgagcca gaacaagccg aaggccgctg agggtctgga cacccagcgc    660
ttctcgggca acggctggga agacactttt gtgctgactc tctccgactt ccggcgggag    720
aacgagggct actacttctg ctctgcgctc tccaattcaa tcatgtactt ctcacacttc    780
gtgccggtgt tcctgcctgc caagcccacc actactccgg cacccagacc tccaactccc    840
gctcccacca tcgcgtccca ccccttttcg ctgcgccctg aagcgtgtcg gcctgctgct    900
ggaggagccg tgcataccog cggtctggac ttcgcgtgcg acatctacat ttgggcccct    960
ttggctggca cctgtggagt gctgctcctg tcccttgtga tcaccctgta ctgcaaccac   1020
cggaataggc ggagagtctg caagtgtccg cggcctgtcg tgaagtcagg agataagccg   1080
agcctgtccg cacgctacgt gcgggccaag agatctggca gcggcgccac caatttcagc   1140
ctgctgaaac aggccggcga cgtggaagag aaccctggcc ccatggactc ttggaccttc   1200
tgctgcgtga gcctgtgcat cctggtggcc aagcacacag acgccggcgt gatccagtcc   1260
cctaggcacg aggtgaccga gatgggccag gaggtgacac tgcgctgtaa gccaatctct   1320
ggccacaaca gcctgttttg gtatagggag accatgatgc gcggcctgga gctgctgatc   1380
tacttcaata caatgtgcc catcgacgat tccggcatgc ctgaggatcg gtttctgcc   1440
aagatgccca atgccagctt ctccacactg aagatccagc ctagcgagcc aagagactcc   1500
gccgtgtatt tttgcgcctc tagcccaggc agcaccgata cacagtactt cggaccagga   1560
accaggctga cagtgctgga ggacctgaag aacgtgttcc cccctgaggt ggccgtgttt   1620
gagccctctg aggccgagat cagccacacc cagaaggcca cctggtgtg cctggcaacc   1680
ggcttctatc ctgatcacgt ggagctgtcc tggtgggtga acggcaagga ggtgcacagc   1740
ggcgtgtcca cagacccaca gcccctgaag gagcagccag ccctgaatga tagccggtat   1800
tgcctgtcct ctcggctgag agtgtccgcc acctttggc agaaccccg gaatcacttc   1860
agatgtcagg tgcagtttta cggcctgtcc gagaacgatg agtggaccca ggaccgggcc   1920
aagcctgtga cacagatcgt gtctgccgag catggggaa gagcagactg tggcttcacc   1980
tctgagagct accagcaggg cgtgctgagc gccaccatcc tgtatgagat cctgctgggc   2040
aaggccacac tgtacgccgt cctggtctcc gctctggtgc tgatggcaat ggtcaaaaga   2100
aaagatagtc ggggacgggc caagagatct ggcagcggcg agggcagagg cagcctgctg   2160
acctgcggcg acgtggagga gaaccccggc cccatggaga agaatccct ggctgccccc   2220
```

```
ctgctgatcc tgtggtttca cctggactgc gtgtcctcta tcctgaatgt ggaacagagc    2280
ccacagagcc tgcacgtgca ggagggcgac tccaccaact tcacatgctc ttttcctagc    2340
tccaacttct acgccctgca ctggtacaga aaggagaccg caaagtcccc agaggccctg    2400
ttcgtgatga cactgaacgg cgatgagaag aagaagggcc gcatcagcgc caccctgaat    2460
acaaaggagg gctactccta tctgtacatc aagggctccc agcctgagga ctctgccacc    2520
tatctgtgcg ccctgtacaa caataacgat atgcggtttg cgccggcac cagactgaca     2580 gtgaagccaa acatccagaa tccagacccc gccgtgtatc agctgcggga cagcaagtct    2640
agcgataaga gcgtgtgcct gttcaccgac tttgattctc agacaaacgt gagccagtcc    2700
aaggacagcg acgtgtacat caccgacaag acagtgctgg atatgagaag catggacttc    2760
aagtctaaca gcgccgtggc ctggtccaat aagtctgatt tcgcctgcgc caatgccttt    2820
aataactcca tcatccccga ggatacettc tttccttctc cagagtcctc ttgtgacgtg    2880
aagctggtgg agaagtcttt cgagaccgat acaaacctga attttcagaa cctgagcgtg    2940
atcggcttca ggatcctgct gctgaaggtg gccggcttta tctgctgat gaccctgagg     3000 ctgtggagct cctgaaccgg tccgcagtct gacgtacgcg taatcaacct ctggattaca    3060
aaatttgtga agattgact ggtattctta actatgttgc tccttttacg ctatgtggat      3120
acgctgcttt aatgcctttg tatcatgcta ttgcttcccg tatggctttc attttctcct     3180
ccttgtataa atcctggttg ctgtctcttt atgaggagtt gtggcccgtt gtcaggcaac    3240
gtggcgtggt gtgcactgtg tttgctgacg caacccccac tggttggggc attgccacca    3300
cctgtcagct cctttccggg actttcgctt tccccctccc tattgccacg cggaactca     3360 tcgccgcctg ccttgcccgc tgctggacag gggctcggct gttgggcact gacaattccg    3420
tggtgttgtc ggggaagctg acgtcctttc catggctgct cgcctgtgtt gccacctgga    3480
ttctgcgcgg gacgtccttc tgctacgtcc cttcggccct caatccagcg gaccttcctt    3540
cccgcggcct gctgccggct ctgcggcctc ttccgcgtct tcgccttcgc cctcagacga    3600
gtcggatctc cctttgggcc gcctccccgc c                                   3631
```

<210> SEQ ID NO 296
<211> LENGTH: 872
<212> TYPE: PRT
<213> ORGANISM: Artificial Sequence
<220> FEATURE:
<223> OTHER INFORMATION: CD8a.TCR.WPRE amino acid sequence

<400> SEQUENCE: 296

```
Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110
```

-continued

```
Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
            195                 200                 205

Arg Asn Arg Arg Arg Val Cys Lys Cys Pro Arg Pro Val Val Lys Ser
210                 215                 220

Gly Asp Lys Pro Ser Leu Ser Ala Arg Tyr Val Arg Ala Lys Arg Ser
225                 230                 235                 240

Gly Ser Gly Ala Thr Asn Phe Ser Leu Leu Lys Gln Ala Gly Asp Val
                245                 250                 255

Glu Glu Asn Pro Gly Pro Met Asp Ser Trp Thr Phe Cys Cys Val Ser
            260                 265                 270

Leu Cys Ile Leu Val Ala Lys His Thr Asp Ala Gly Val Ile Gln Ser
            275                 280                 285

Pro Arg His Glu Val Thr Glu Met Gly Gln Glu Val Thr Leu Arg Cys
            290                 295                 300

Lys Pro Ile Ser Gly His Asn Ser Leu Phe Trp Tyr Arg Glu Thr Met
305                 310                 315                 320

Met Arg Gly Leu Glu Leu Leu Ile Tyr Phe Asn Asn Asn Val Pro Ile
                325                 330                 335

Asp Asp Ser Gly Met Pro Glu Asp Arg Phe Ser Ala Lys Met Pro Asn
            340                 345                 350

Ala Ser Phe Ser Thr Leu Lys Ile Gln Pro Ser Glu Pro Arg Asp Ser
            355                 360                 365

Ala Val Tyr Phe Cys Ala Ser Ser Pro Gly Ser Thr Asp Thr Gln Tyr
370                 375                 380

Phe Gly Pro Gly Thr Arg Leu Thr Val Leu Glu Asp Leu Lys Asn Val
385                 390                 395                 400

Phe Pro Pro Glu Val Ala Val Phe Glu Pro Ser Glu Ala Glu Ile Ser
                405                 410                 415

His Thr Gln Lys Ala Thr Leu Val Cys Leu Ala Thr Gly Phe Tyr Pro
            420                 425                 430

Asp His Val Glu Leu Ser Trp Trp Val Asn Gly Lys Glu Val His Ser
            435                 440                 445

Gly Val Ser Thr Asp Pro Gln Pro Leu Lys Glu Gln Pro Ala Leu Asn
450                 455                 460

Asp Ser Arg Tyr Cys Leu Ser Ser Arg Leu Arg Val Ser Ala Thr Phe
465                 470                 475                 480

Trp Gln Asn Pro Arg Asn His Phe Arg Cys Gln Val Gln Phe Tyr Gly
                485                 490                 495

Leu Ser Glu Asn Asp Glu Trp Thr Gln Asp Arg Ala Lys Pro Val Thr
            500                 505                 510

Gln Ile Val Ser Ala Glu Ala Trp Gly Arg Ala Asp Cys Gly Phe Thr
            515                 520                 525

Ser Glu Ser Tyr Gln Gln Gly Val Leu Ser Ala Thr Ile Leu Tyr Glu
```

| | | | | | | | | | | | |
|---|---|---|---|---|---|---|---|---|---|---|---|
| | | 530 | | | 535 | | | 540 | | | |
| Ile | Leu | Leu | Gly | Lys | Ala | Thr | Leu | Tyr | Ala | Val | Leu |
| 545 | | | | 550 | | | | 555 | | | 560 |

Ile Leu Leu Gly Lys Ala Thr Leu Tyr Ala Val Leu Val Ser Ala Leu
545                 550                 555                 560

Val Leu Met Ala Met Val Lys Arg Lys Asp Ser Arg Gly Arg Ala Lys
                565                 570                 575

Arg Ser Gly Ser Gly Glu Gly Arg Gly Ser Leu Leu Thr Cys Gly Asp
            580                 585                 590

Val Glu Glu Asn Pro Gly Pro Met Glu Lys Asn Pro Leu Ala Ala Pro
                595                 600                 605

Leu Leu Ile Leu Trp Phe His Leu Asp Cys Val Ser Ser Ile Leu Asn
            610                 615                 620

Val Glu Gln Ser Pro Gln Ser Leu His Val Gln Glu Gly Asp Ser Thr
625                 630                 635                 640

Asn Phe Thr Cys Ser Phe Pro Ser Ser Asn Phe Tyr Ala Leu His Trp
            645                 650                 655

Tyr Arg Lys Glu Thr Ala Lys Ser Pro Glu Ala Leu Phe Val Met Thr
                660                 665                 670

Leu Asn Gly Asp Glu Lys Lys Lys Gly Arg Ile Ser Ala Thr Leu Asn
            675                 680                 685

Thr Lys Glu Gly Tyr Ser Tyr Leu Tyr Ile Lys Gly Ser Gln Pro Glu
690                 695                 700

Asp Ser Ala Thr Tyr Leu Cys Ala Leu Tyr Asn Asn Asn Asp Met Arg
705                 710                 715                 720

Phe Gly Ala Gly Thr Arg Leu Thr Val Lys Pro Asn Ile Gln Asn Pro
                725                 730                 735

Asp Pro Ala Val Tyr Gln Leu Arg Asp Ser Lys Ser Ser Asp Lys Ser
            740                 745                 750

Val Cys Leu Phe Thr Asp Phe Asp Ser Gln Thr Asn Val Ser Gln Ser
            755                 760                 765

Lys Asp Ser Asp Val Tyr Ile Thr Asp Lys Thr Val Leu Asp Met Arg
770                 775                 780

Ser Met Asp Phe Lys Ser Asn Ser Ala Val Ala Trp Ser Asn Lys Ser
785                 790                 795                 800

Asp Phe Ala Cys Ala Asn Ala Phe Asn Asn Ser Ile Ile Pro Glu Asp
            805                 810                 815

Thr Phe Phe Pro Ser Pro Glu Ser Ser Cys Asp Val Lys Leu Val Glu
            820                 825                 830

Lys Ser Phe Glu Thr Asp Thr Asn Leu Asn Phe Gln Asn Leu Ser Val
            835                 840                 845

Ile Gly Phe Arg Ile Leu Leu Leu Lys Val Ala Gly Phe Asn Leu Leu
850                 855                 860

Met Thr Leu Arg Leu Trp Ser Ser
865                 870

<210> SEQ ID NO 297
<211> LENGTH: 4419
<212> TYPE: DNA
<213> ORGANISM: Artificial Sequence
<220> FEATURE:
<223> OTHER INFORMATION: CD8ba.TCR.WPRE nucleotide sequence

<400> SEQUENCE: 297
tgaaagaccc cacctgtagg tttggcaagc tagcttaagt aacgccattt tgcaaggcat      60
ggaaaataca taactgagaa tagagaagtt cagatcaagg ttaggaacag agagacagca     120

```
gaatatgggc caaacaggat atctgtggta agcagttcct gccccggctc agggccaaga      180
acagatggtc cccagatgcg gtcccgccct cagcagtttc tagagaacca tcagatgttt      240
ccagggtgcc ccaaggacct gaaaatgacc ctgtgcctta tttgaactaa ccaatcagtt      300
cgcttctcgc ttctgttcgc gcgcttctgc tccccgagct caataaaaga gcccacaacc      360
cctcactcag cggccgcccc gggtcgacgc taccaccatg cgcccgagac tgtggcttct      420
gctcgccgcg caactgactg tcctgcacgg aaacagcgtg ctgcagcaga caccggccta      480
catcaaagtg cagaccaaca agatggtcat gctgtcctgc gaggccaaga tttccctctc      540
caacatgcgg atctattggt tgcggcagag acaggcgcct tcctcggact cccaccatga      600
gttcttggcc ctgtgggact ccgccaaggg aactattcac ggcgaagaag tggaacagga      660
gaagatcgcc gtgtttcgcg atgcctcccg ctttatactg aatctgacct ccgtgaagcc      720
cgaagatagc gggatctact tttgcatgat tgtgggctca cccgaactga ccttcgggaa      780
gggcactcag ctgagcgtgg tggacttcct ccccactacc gcccaaccca ctaagaagtc      840
aaccctgaag aagcgggttt gcagactccc acggccggaa acgcagaagg gtccgctgtg      900
ttccccgatc accctggggc ccttgtggc tggagtgctg gtccttctgg tgtcccttgg      960
cgtcgccatt cacctctgct gccggagaag gagggccaga ctgaggttca tgaagcagcc     1020
tcagggagag gggatcagtg gcactttcgt gccacaatgc ctccatggct actattccaa     1080
caccaccacc tcgcaaaagc tgctgaaccc ctggatcctg aaaacccggg ccaagagatc     1140
tggcagcggc gccaccaatt tcagcctgct gaaacaggcc ggcgacgtgg aagagaaccc     1200
tggccccatg gcgcttcccg tgaccgcact cctgttgccc cttgccctgc tgttgcacgc     1260
cgcacgacct tcccaattcc gggtgtcccc tctggatcgc acctggaacc tcggggaaac     1320
ggtggagctc aagtgtcaag tcctcctgtc gaacccgacc agcggatgca gctggctgtt     1380
ccagccgaga ggagctgccg cctcacccac cttcctcctg tacttgagcc agaacaagcc     1440
gaaggccgct gagggtctgg acacccagcg cttctcgggc aaacggctgg agacactttt     1500
tgtgctgact ctctccgact ccggcgggaa gaacgagggc tactacttct gctctgcgct     1560
ctccaattca atcatgtact ctcacactt cgtgccggtg ttcctgcctg ccaagcccac     1620
cactactccg gcacccagac tccaactcc cgctcccacc atcgcgtccc aacccctttc     1680
gctgcgccct gaagcgtgtc ggcctgctgc tggaggagcc gtgcataccc gcggtctgga     1740
cttcgcgtgc gacatctaca tttgggcccc tttggctggc acctgtggag tgctgctcct     1800
gtcccttgtg atcaccctgt actgcaacca ccggaatagg cggagagtct gcaagtgtcc     1860
gcggcctgtc gtgaagtcag gagataagcc gagcctgtcc gcacgctacg tgcgggccaa     1920
gagatctggc agcggcgagg gcagaggcag cctgctgacc tgcggcgacg tggaggagaa     1980
ccccggcccc atggactctt ggaccttctg ctgcgtgagc ctgtgcatcc tggtggccaa     2040
gcacacagac gccggcgtga tccagtccc taggcacgag gtgaccgaga tgggccagga     2100
ggtgacactg cgctgtaagc caatctctgg ccacaacagc ctgtttggt ataggagac      2160 catgatgcgc ggcctggagc tgctgatcta cttcaataac aatgtgccca tcgacgattc     2220
cggcatgcct gaggatcggt tttctgccaa gatgcccaat gccagcttct ccacactgaa     2280
gatccagcct agcgagccaa gagactccgc cgtgtatttt tgcgcctcta gcccaggcag     2340
caccgataca cagtacttcg gaccaggaac caggctgaca gtgctggagg acctgaagaa     2400
cgtgttcccc cctgaggtgg ccgtgtttga gccctctgag gccgagatca gccacaccca     2460
gaaggccacc ctggtgtgcc tggcaaccgg cttctatcct gatcacgtgg agctgtcctg     2520
```

```
gtgggtgaac ggcaaggagg tgcacagcgg cgtgtccaca gacccacagc ccctgaagga    2580
gcagccagcc ctgaatgata gccggtattg cctgtcctct cggctgagag tgtccgccac    2640
cttttggcag aaccccggga atcacttcag atgtcaggtg cagttttacg gcctgtccga    2700
gaacgatgag tggacccagg accgggccaa gcctgtgaca cagatcgtgt ctgccgaggc    2760
atggggaaga gcagactgtg gcttcacctc tgagagctac cagcagggcg tgctgagcgc    2820
caccatcctg tatgagatcc tgctgggcaa ggccacactg tacgccgtcc tggtctccgc    2880
tctggtgctg atggcaatgg tcaaaagaaa agatagtcgg ggacgggcca agagatctgg    2940
cagcggccag tgcaccaact acgccctgct gaagctggcc ggcgacgtgg agagcaaccc    3000
cggccccatg gagaagaatc ccctggctgc ccccctgctg atcctgtggt tcacctgga    3060 ctgcgtgtcc tctatcctga atgtggaaca gagcccacag agcctgcacg tgcaggaggg    3120
cgactccacc aacttcacat gctcttttcc tagctccaac ttctacgccc tgcactggta    3180
cagaaaggag accgcaaagt ccccagaggc cctgttcgtg atgacactga acggcgatga    3240
gaagaagaag ggccgcatca gcgccaccct gaatacaaag gagggctact cctatctgta    3300
catcaagggc tcccagcctg aggactctgc cacctatctg tgcgccctgt acaacaataa    3360
cgatatgcgg tttggcgccg gcaccagact gacagtgaag ccaaacatcc agaatccaga    3420
ccccgccgtg tatcagctgc gggacagcaa gtctagcgat aagagcgtgt gcctgttcac    3480
cgactttgat tctcagacaa acgtgagcca gtccaaggac agcgacgtgt acatcaccga    3540
caagacagtg ctggatatga agcatgga cttcaagtct aacagcgccg tggcctggtc    3600
caataagtct gatttcgcct gcgccaatgc ctttaataac tccatcatcc ccgaggatac    3660
cttctttcct tctccagagt cctcttgtga cgtgaagctg gtggagaagt ctttcgagac    3720
cgatacaaac ctgaattttc agaacctgag cgtgatcggc ttcaggatcc tgctgctgaa    3780
ggtggccggc tttaatctgc tgatgaccct gaggctgtgg agctcctgaa ccggtccgga    3840
gcatcttacc gccatttata cccatatttg ttctgttttt cttgatttgg gtatacattt    3900
aaatgttaat aaaacaaaat ggtggggcaa tcatttacat ttttgggat atgtaattac    3960 tagttcaggt gtattgccac aagacaaact tgttaagaaa ctttcccgtt atttacgctc    4020
tgttcctgtt aatcaacctc tggattacaa aatttgtgaa agattgactg atattcttaa    4080
ctttgttgct cctttacgc tgtgtggatt tgctgcttta ttgcctctgt atcttgctat    4140
tgcttcccgt acggctttcg ttttctcctc cttgtataaa tcctggttgc tgtctctttt    4200
tgaggagttg tggcccgttg tccgtcaacg tggcgtggtg tgctctgtgt ttgctgacgc    4260
aacccccact ggctggggca ttgccaccac ctgtcaactc ctttctggga ctttcgcttt    4320 cccccctcccg atcgccacgg cagaactcat cgccgcctgc cttgcccgct gctggacagg    4380
ggctaggttg ctgggcactg ataattccgt ggtgttgtc                          4419
```

<210> SEQ ID NO 298
<211> LENGTH: 1143
<212> TYPE: PRT
<213> ORGANISM: Artificial Sequence
<220> FEATURE:
<223> OTHER INFORMATION: CD8ba.TCR.WPRE amino acid sequence

<400> SEQUENCE: 298

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln

```
            20                  25                  30
Thr Asn Lys Met Val Met Leu Ser Cys Glu Ala Lys Ile Ser Leu Ser
        35                  40                  45
Asn Met Arg Ile Tyr Trp Leu Arg Gln Arg Gln Ala Pro Ser Ser Asp
    50                  55                  60
Ser His His Glu Phe Leu Ala Leu Trp Asp Ser Ala Lys Gly Thr Ile
65                  70                  75                  80
His Gly Glu Glu Val Glu Gln Glu Lys Ile Ala Val Phe Arg Asp Ala
                85                  90                  95
Ser Arg Phe Ile Leu Asn Leu Thr Ser Val Lys Pro Glu Asp Ser Gly
            100                 105                 110
Ile Tyr Phe Cys Met Ile Val Gly Ser Pro Glu Leu Thr Phe Gly Lys
            115                 120                 125
Gly Thr Gln Leu Ser Val Val Asp Phe Leu Pro Thr Thr Ala Gln Pro
        130                 135                 140
Thr Lys Lys Ser Thr Leu Lys Lys Arg Val Cys Arg Leu Pro Arg Pro
145                 150                 155                 160
Glu Thr Gln Lys Gly Pro Leu Cys Ser Pro Ile Thr Leu Gly Leu Leu
                165                 170                 175
Val Ala Gly Val Leu Val Leu Leu Val Ser Leu Gly Val Ala Ile His
            180                 185                 190
Leu Cys Cys Arg Arg Arg Ala Arg Leu Arg Phe Met Lys Gln Pro
        195                 200                 205
Gln Gly Glu Gly Ile Ser Gly Thr Phe Val Pro Gln Cys Leu His Gly
    210                 215                 220
Tyr Tyr Ser Asn Thr Thr Thr Ser Gln Lys Leu Leu Asn Pro Trp Ile
225                 230                 235                 240
Leu Lys Thr Arg Ala Lys Arg Ser Gly Ser Gly Ala Thr Asn Phe Ser
                245                 250                 255
Leu Leu Lys Gln Ala Gly Asp Val Glu Glu Asn Pro Gly Pro Met Ala
            260                 265                 270
Leu Pro Val Thr Ala Leu Leu Leu Pro Leu Ala Leu Leu Leu His Ala
        275                 280                 285
Ala Arg Pro Ser Gln Phe Arg Val Ser Pro Leu Asp Arg Thr Trp Asn
    290                 295                 300
Leu Gly Glu Thr Val Glu Leu Lys Cys Gln Val Leu Leu Ser Asn Pro
305                 310                 315                 320
Thr Ser Gly Cys Ser Trp Leu Phe Gln Pro Arg Gly Ala Ala Ala Ser
                325                 330                 335
Pro Thr Phe Leu Leu Tyr Leu Ser Gln Asn Lys Pro Lys Ala Ala Glu
            340                 345                 350
Gly Leu Asp Thr Gln Arg Phe Ser Gly Lys Arg Leu Gly Asp Thr Phe
        355                 360                 365
Val Leu Thr Leu Ser Asp Phe Arg Arg Glu Asn Glu Gly Tyr Tyr Phe
    370                 375                 380
Cys Ser Ala Leu Ser Asn Ser Ile Met Tyr Phe Ser His Phe Val Pro
385                 390                 395                 400
Val Phe Leu Pro Ala Lys Pro Thr Thr Thr Pro Ala Pro Arg Pro Pro
                405                 410                 415
Thr Pro Ala Pro Thr Ile Ala Ser Gln Pro Leu Ser Leu Arg Pro Glu
            420                 425                 430
Ala Cys Arg Pro Ala Ala Gly Gly Ala Val His Thr Arg Gly Leu Asp
        435                 440                 445
```

```
Phe Ala Cys Asp Ile Tyr Ile Trp Ala Pro Leu Ala Gly Thr Cys Gly
    450                 455                 460

Val Leu Leu Leu Ser Leu Val Ile Thr Leu Tyr Cys Asn His Arg Asn
465                 470                 475                 480

Arg Arg Arg Val Cys Lys Cys Pro Arg Pro Val Val Lys Ser Gly Asp
                485                 490                 495

Lys Pro Ser Leu Ser Ala Arg Tyr Val Arg Ala Lys Arg Ser Gly Ser
            500                 505                 510

Gly Glu Gly Arg Gly Ser Leu Leu Thr Cys Gly Asp Val Glu Glu Asn
        515                 520                 525

Pro Gly Pro Met Asp Ser Trp Thr Phe Cys Cys Val Ser Leu Cys Ile
    530                 535                 540

Leu Val Ala Lys His Thr Asp Ala Gly Val Ile Gln Ser Pro Arg His
545                 550                 555                 560

Glu Val Thr Glu Met Gly Gln Glu Val Thr Leu Arg Cys Lys Pro Ile
                565                 570                 575

Ser Gly His Asn Ser Leu Phe Trp Tyr Arg Glu Thr Met Met Arg Gly
            580                 585                 590

Leu Glu Leu Leu Ile Tyr Phe Asn Asn Asn Val Pro Ile Asp Asp Ser
    595                 600                 605

Gly Met Pro Glu Asp Arg Phe Ser Ala Lys Met Pro Asn Ala Ser Phe
    610                 615                 620

Ser Thr Leu Lys Ile Gln Pro Ser Glu Pro Arg Asp Ser Ala Val Tyr
625                 630                 635                 640

Phe Cys Ala Ser Ser Pro Gly Ser Thr Asp Thr Gln Tyr Phe Gly Pro
                645                 650                 655

Gly Thr Arg Leu Thr Val Leu Glu Asp Leu Lys Asn Val Phe Pro Pro
            660                 665                 670

Glu Val Ala Val Phe Glu Pro Ser Glu Ala Glu Ile Ser His Thr Gln
    675                 680                 685

Lys Ala Thr Leu Val Cys Leu Ala Thr Gly Phe Tyr Pro Asp His Val
    690                 695                 700

Glu Leu Ser Trp Trp Val Asn Gly Lys Glu Val His Ser Gly Val Ser
705                 710                 715                 720

Thr Asp Pro Gln Pro Leu Lys Glu Gln Pro Ala Leu Asn Asp Ser Arg
                725                 730                 735

Tyr Cys Leu Ser Ser Arg Leu Arg Val Ser Ala Thr Phe Trp Gln Asn
            740                 745                 750

Pro Arg Asn His Phe Arg Cys Gln Val Gln Phe Tyr Gly Leu Ser Glu
    755                 760                 765

Asn Asp Glu Trp Thr Gln Asp Arg Ala Lys Pro Val Thr Gln Ile Val
    770                 775                 780

Ser Ala Glu Ala Trp Gly Arg Ala Asp Cys Gly Phe Thr Ser Glu Ser
785                 790                 795                 800

Tyr Gln Gln Gly Val Leu Ser Ala Thr Ile Leu Tyr Glu Ile Leu Leu
                805                 810                 815

Gly Lys Ala Thr Leu Tyr Ala Val Leu Val Ser Ala Leu Val Leu Met
            820                 825                 830

Ala Met Val Lys Arg Lys Asp Ser Arg Gly Arg Ala Lys Arg Ser Gly
    835                 840                 845

Ser Gly Gln Cys Thr Asn Tyr Ala Leu Leu Lys Leu Ala Gly Asp Val
    850                 855                 860
```

```
Glu Ser Asn Pro Gly Pro Met Glu Lys Asn Pro Leu Ala Ala Pro Leu
865                 870                 875                 880

Leu Ile Leu Trp Phe His Leu Asp Cys Val Ser Ser Ile Leu Asn Val
            885                 890                 895

Glu Gln Ser Pro Gln Ser Leu His Val Gln Glu Gly Asp Ser Thr Asn
        900                 905                 910

Phe Thr Cys Ser Phe Pro Ser Ser Asn Phe Tyr Ala Leu His Trp Tyr
            915                 920                 925

Arg Lys Glu Thr Ala Lys Ser Pro Glu Ala Leu Phe Val Met Thr Leu
        930                 935                 940

Asn Gly Asp Glu Lys Lys Lys Gly Arg Ile Ser Ala Thr Leu Asn Thr
945                 950                 955                 960

Lys Glu Gly Tyr Ser Tyr Leu Tyr Ile Lys Gly Ser Gln Pro Glu Asp
            965                 970                 975

Ser Ala Thr Tyr Leu Cys Ala Leu Tyr Asn Asn Asn Asp Met Arg Phe
        980                 985                 990

Gly Ala Gly Thr Arg Leu Thr Val  Lys Pro Asn Ile Gln  Asn Pro Asp
            995                 1000                1005

Pro Ala Val Tyr Gln Leu Arg  Asp Ser Lys Ser  Asp Lys Ser
    1010                1015                1020

Val Cys Leu Phe Thr Asp Phe  Asp Ser Gln Thr  Asn Val Ser Gln
    1025                1030                1035

Ser Lys Asp Ser Asp Val Tyr  Ile Thr Asp Lys  Thr Val Leu Asp
    1040                1045                1050

Met Arg Ser Met Asp Phe Lys  Ser Asn Ser Ala  Val Ala Trp Ser
    1055                1060                1065

Asn Lys Ser Asp Phe Ala Cys  Ala Asn Ala Phe  Asn Asn Ser Ile
    1070                1075                1080

Ile Pro Glu Asp Thr Phe Phe  Pro Ser Pro Glu  Ser Ser Cys Asp
    1085                1090                1095

Val Lys Leu Val Glu Lys Ser  Phe Glu Thr Asp  Thr Asn Leu Asn
    1100                1105                1110

Phe Gln Asn Leu Ser Val Ile  Gly Phe Arg Ile  Leu Leu Leu Lys
    1115                1120                1125

Val Ala Gly Phe Asn Leu Leu  Met Thr Leu Arg  Leu Trp Ser Ser
    1130                1135                1140

<210> SEQ ID NO 299
<211> LENGTH: 7751
<212> TYPE: DNA
<213> ORGANISM: Artificial Sequence
<220> FEATURE:
<223> OTHER INFORMATION: TCR.WPRE nucleotide sequence

<400> SEQUENCE: 299
aaacgccagc aacgcggcct ttttacggtt cctggccttt tgctggcctt ttgctcacat      60
gttcttgctg cttcgcgatg tacgggccag atatacgcgt tgacattgat tattgactag     120
ttattaatag taatcaatta cggggtcatt agttcatagc ccatatatgg agttccgcgt     180
tacataactt acggtaaatg gcccgcctgg ctgaccgccc aacgaccccc gcccattgac     240
gtcaataatg acgtatgttc ccatagtaac gccaataggg actttccatt gacgtcaatg     300
ggtggagtat ttacggtaaa ctgcccactt ggcagtacat caagtgtatc atatgccaag     360
tacgccccct attgacgtca atgacggtaa atggcccgcc tggcattatg cccagtacat     420
gaccttatgg gactttccta cttggcagta catctacgta ttagtcatcg ctattaccat     480
```

-continued

```
ggtgatgcgg ttttggcagt acatcaatgg gcgtggatag cggtttgact cacgggatt    540
tccaagtctc caccccattg acgtcaatgg gagtttgttt tggcaccaaa atcaacggga    600
ctttccaaaa tgtcgtaaca actccgcccc attgacgcaa atgggcggta ggcgtgtacg    660
gtgggaggtc tatataagca gagctcgttt agtgaaccgg ggtctctctg gttagaccag    720
atctgagcct gggagctctc tggctaacta gggaacccac tgcttaagcc tcaataaagc    780
ttgccttgag tgcttcaagt agtgtgtgcc cgtctgttgt gtgactctgg taactagaga    840
tccctcagac ccttttagtc agtgtggaaa atctctagca gtggcgcccg aacagggact    900
tgaaagcgaa agggaaacca gaggagctct ctcgacgcag gactcggctt gctgaagcgc    960
gcacggcaag aggcgagggg cggcgactgg tgagtacgcc aaaaattttg actagcggag   1020
gctagaagga gagagatggg tgcgagagcg tcagtattaa gcgggggaga attagatcgc   1080
gatgggaaaa aattcggtta aggccagggg gaaagaaaaa atataaatta aaacatatag   1140
tatgggcaag cagggagcta gaacgattcg cagttaatcc tggcctgtta gaaacatcag   1200
aaggctgtag acaaatactg ggacagctac aaccatccct tcagacagga tcagaagaac   1260
ttagatcatt atataataca gtagcaaccc tctattgtgt gcatcaaagg atagagataa   1320
aagacaccaa ggaagcttta gacaagatag aggaagagca aaacaaaagt aagaccaccg   1380
cacagcaaga ggcctctgat cttcagacct ggaggaggag atatgaggga caattggaga   1440
agtgaattat ataaatataa agtagtaaaa attgaaccat taggagtagc acccaccaag   1500
gcaaagagaa gagtggtgca gagagaaaaa agagcagtgg gaataggagc tttgttcctt   1560
gggttcttgg gagcagcagg aagcactatg ggcgcagcgt caatgacgct gacggtacag   1620
gccagacaat tattgtctgg tatagtgcag cagcagaaca atttgctgag gctattgag    1680
gcgcaacagc atctgttgca actcacagtc tggggcatca agcagctcca ggcaagaatc   1740
ctggctgtgg aaagatacct aaaggatcaa cagctcctgg ggatttgggg ttgctctgga   1800
aaactcattt gcaccactgc tgtgccttgg aatgctagtt ggagtaataa atctctggaa   1860
cagatttgga atcacacgac ctggatggag tgggacagag aaattaacaa ttacacaagc   1920
ttaatacact ccttaattga agaatcgcaa aaccagcaag aaaagaatga acaagaatta   1980
ttggaattag ataaatgggc aagtttgtgg aattggttta acataacaaa ttggctgtgg   2040
tatataaaat tattcataat gatagtagga ggcttggtag gtttaagaat agttttgct    2100
gtactttcta tagtgaatag agttaggcag ggatattcac cattatcggt taacttttaa   2160
aagaaaggg gggattgggg ggtacagtgc aggggaaaga atagtagaca taatagcaac   2220
agacatacaa actaaagaat tacaaaaaca aattacaaaa attcaaaatt ttatcgatca   2280
cgagactagc ctcgaatctg cagaattcgc ccttatcgat tgaaagaccc cacctgtagg   2340
tttggcaagc tagcttaagt aacgccattt tgcaaggcat ggaaaataca taactgagaa   2400
tagagaagtt cagatcaagg ttaggaacag agagacagca gaatatgggc caaacaggat   2460
atctgtggta agcagttcct gccccggctc agggccaaga acagatggtc cccagatgcg   2520
gtcccgccct cagcagtttc tagagaacca tcagatgttt ccagggtgcc ccaaggacct   2580
gaaaatgacc ctgtgcctta tttgaactaa ccaatcagtt cgcttctcgc ttctgttcgc   2640
gcgcttctgc tccccgagct caataaaaga gcccacaacc cctcactcag cggccgcccc   2700
gggtcgacgc taccaccatg gactcttgga ccttctgctg cgtgagcctg tgcatcctgg   2760
tggccaagca cacagacgcc ggcgtgatcc agtcccctag gcacgaggtg accgagatgg   2820
```

```
gccaggaggt gacactgcgc tgtaagccaa tctctggcca caacagcctg ttttggtata    2880
gggagaccat gatgcgcggc ctggagctgc tgatctactt caataacaat gtgcccatcg    2940
acgattccgg catgcctgag gatcggtttt ctgccaagat gcccaatgcc agcttctcca    3000
cactgaagat ccagcctagc gagccaagag actccgccgt gtattttgc gcctctagcc     3060
caggcagcac cgatacacag tacttcggac caggaaccag gctgacagtg ctggaggacc    3120
tgaagaacgt gttccccct gaggtggccg tgtttgagcc ctctgaggcc gagatcagcc     3180
acacccagaa ggccaccctg gtgtgcctgg caaccggctt ctatcctgat cacgtggagc    3240
tgtcctggtg ggtgaacggc aaggaggtgc acagcggcgt gtccacagac ccacagcccc    3300
tgaaggagca gccagccctg aatgatagcc ggtattgcct gtcctctcgg ctgagagtgt    3360
ccgccacctt ttggcagaac ccccggaatc acttcagatg tcaggtgcag ttttacggcc    3420
tgtccgagaa cgatgagtgg acccaggacc gggccaagcc tgtgacacag atcgtgtctg    3480
ccgaggcatg gggaagagca gactgtggct tcacctctga gagctaccag cagggcgtgc    3540
tgagcgccac catcctgtat gagatcctgc tgggcaaggc cacactgtac gccgtcctgg    3600
tctccgctct ggtgctgatg gcaatggtca aagaaaaga tagtcgggga tctggcagcg    3660
gcgccaccaa tttcagcctg ctgaaacagg ccggcgacgt ggaagagaac cctggcccca    3720
tggagaagaa tccccctggct gcccccctgc tgatcctgtg gtttcacctg gactgcgtgt    3780
cctctatcct gaatgtggaa cagagcccac agagcctgca cgtgcaggag ggcgactcca    3840
ccaacttcac atgctctttt cctagctcca acttctacgc cctgcactgg tacagaaagg    3900
agaccgcaaa gtccccagag gccctgttcg tgatgacact gaacggcgat gagaagaaga    3960
agggccgcat cagcgccacc ctgaatacaa aggagggcta ctcctatctg tacatcaagg    4020
gctcccagcc tgaggactct gccacctatc tgtgcgccct gtacaacaat aacgatatgc    4080
ggtttggcgc cggcaccaga ctgacagtga agccaaacat ccagaatcca gaccccgccg    4140
tgtatcagct gcgggacagc aagtctagcg ataagagcgt gtgcctgttc accgactttg    4200
attctcagac aaacgtgagc cagtccaagg acagcgacgt gtacatcacc gacaagacag    4260
tgctggatat gagaagcatg gacttcaagt ctaacagcgc cgtggcctgg tccaataagt    4320
ctgatttcgc ctgcgccaat gcctttaata actccatcat ccccgaggat accttctttc    4380
cttctccaga gtcctcttgt gacgtgaagc tggtggagaa gtctttcgag accgatacaa    4440
acctgaattt tcagaacctg agcgtgatcg gcttcaggat cctgctgctg aaggtggccg    4500
gctttaatct gctgatgacc ctgaggctgt ggagctcctg aaccggtccg cagtctgacg    4560
tacgcgtaat caacctctgg attacaaaat ttgtgaaaga ttgactggta ttcttaacta    4620
tgttgctcct tttacgctat gtggatacgc tgctttaatg cctttgtatc atgctattgc    4680
ttcccgtatg gctttcattt tctcctcctt gtataaatcc tggttgctgt ctctttatga    4740
ggagttgtgg cccgttgtca ggcaacgtgg cgtggtgtgc actgtgtttg ctgacgcaac    4800
ccccactggt tggggcattg ccaccacctg tcagctcctt ccgggactt tcgctttccc    4860
cctccctatt gccacggcgg aactcatcgc cgcctgcctt gcccgctgct ggacaggggc    4920
tcggctgttg ggcactgaca attccgtggt gttgtcgggg aagctgacgt cctttccatg    4980
gctgctcgcc tgtgttgcca cctggattct gcgcgggacg tccttctgct acgtcccttc    5040
ggccctcaat ccagcggacc ttccttcccg cggcctgctg ccggctctgc ggcctcttcc    5100
gcgtcttcgc cttcgccctc agacgagtcg gatctccctt tgggccgcct ccccgcccgt    5160
acgtgtacat tacgcgccta ggatttaaat ccactcctga caactactct ttaatgcacg    5220
```

```
aggtgtcagt aggtgaagga gtcgtagttg tcgataagca gcaacatctt actacactgg    5280
tctcaactcc ggatccgagc tcggtacctt aagaccaat gacttacaag gcagctgtag     5340
atcttagcca cttttaaaa gaaaaggggg gactggaagg gctaattcac tcccaacgaa     5400
gacaagatct gcttttgct tgtactgggt ctctctggtt agaccagatc tgagcctggg     5460
agctctctgg ctaactaggg aacccactgc ttaagcctca ataaagcttg ccttgagtgc    5520
ttcaagtagt gtgtgcccgt ctgttgtgtg actctggtaa ctagagatcc ctcagaccct    5580
tttagtcagt gtggaaaatc tctagcagca tctagagggc ccgtttaaac ccgctgatca    5640
gcctcgactg tgccttctag ttgccagcca tctgttgttt gcccctcccc cgtgccttcc    5700
ttgaccctgg aaggtgccac tcccactgtc ctttcctaat aaaatgagga aattgcatcg    5760
cattgtctga gtaggtgtca ttctattctg ggggtgggg tggggcagga cagcaagggg     5820
gaggattggg aagacaatag caggcatgct ggggatgcgg tgggctctat ggcttctact    5880
gggcggtttt atggacagca agcgaaccgg aattgccagc tggggcgccc tctggtaagg    5940
ttgggaagcc ctgcaaagta aactggatgg cttctcttgcc gccaaggatc tgatggcgca   6000
ggggatcaag ctctgatcaa gagacaggat gaggatcgtt tcgcatgatt gaacaagatg    6060
gattgcacgc aggttctccg gccgcttggg tggagaggct attcggctat gactgggcac    6120
aacagacaat cggctgctct gatgccgccg tgttccggct gtcagcgcag gggcgcccgg    6180
ttcttttgt caagaccgac ctgtccggtg ccctgaatga actgcaagac gaggcagcgc     6240
ggctatcgtg gctggccacg acgggcgttc cttgcgcagc tgtgctcgac gttgtcactg    6300
aagcgggaag ggactggctg ctattgggcg aagtgccggg gcaggatctc ctgtcatctc    6360
accttgctcc tgccgagaaa gtatccatca tggctgatgc aatgcggcgg ctgcatacgc    6420
ttgatccggc tacctgccca ttcgaccacc aagcgaaaca tcgcatcgag cgagcacgta    6480
ctcggatgga agccggtctt gtcgatcagg atgatctgga cgaagagcat caggggctcg    6540
cgccagccga actgttcgcc aggctcaagg cgagcatgcc cgacggcgag gatctcgtcg    6600
tgacccatgg cgatgcctgc ttgccgaata tcatggtgga aaatggccgc ttttctggat    6660
tcatcgactg tggccggctg ggtgtggcgg accgctatca ggacatagcg ttggctaccc    6720
gtgatattgc tgaagagctt ggcggcgaat gggctgaccg cttcctcgtg ctttacggta    6780
tcgccgctcc cgattcgcag cgcatcgcct tctatcgcct tcttgacgag ttcttctgaa    6840
ttattaacgc ttacaatttc ctgatgcggt attttctcct tacgcatctg tgcggtattt    6900
cacaccgcat caggtggcac ttttcgggga aatgtgcgcg gaacccctat ttgtttattt    6960
ttctaaatac attcaaatat gtatccgctc atgagacaat aaccctgata aatgcttcaa    7020
taatagcacg tgctaaaact tcatttttaa tttaaaagga tctaggtgaa gatcctttt    7080
gataatctca tgaccaaaat cccttaacgt gagttttcgt tccactgagc gtcagacccc    7140
gtagaaaaga tcaaaggatc ttcttgagat cctttttttc tgcgcgtaat ctgctgcttg    7200
caaacaaaaa aaccaccgct accagcggtg gtttgtttgc cggatcaaga gctaccaact    7260
ctttttccga aggtaactgg cttcagcaga gcgcagatac caaatactgt tcttctagtg    7320
tagccgtagt taggccacca cttcaagaac tctgtagcac cgcctacata cctcgctctg    7380
ctaatcctgt taccagtggc tgctgccagt ggcgataagt cgtgtcttac cgggttggac    7440
tcaagacgat agttaccgga taaggcgcag cggtcgggct gaacggggg ttcgtgcaca    7500
cagcccagct tggagcgaac gacctacacc gaactgagat acctacagcg tgagctatga    7560
```

-continued

```
gaaagcgcca cgcttcccga agggagaaag gcggacaggt atccggtaag cggcagggtc    7620
ggaacaggag agcgcacgag ggagcttcca gggggaaacg cctggtatct ttatagtcct    7680
gtcgggtttc gccacctctg acttgagcgt cgattttttgt gatgctcgtc agggggggcgg    7740 agcctatgga a                                                          7751
```

<210> SEQ ID NO 300
<211> LENGTH: 607
<212> TYPE: PRT
<213> ORGANISM: Artificial Sequence
<220> FEATURE:
<223> OTHER INFORMATION: TCR.WPRE amino acid sequence

<400> SEQUENCE: 300

```
Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
                20                  25                  30

Glu Met Gly Gln Glu Val Thr Leu Arg Cys Lys Pro Ile Ser Gly His
            35                  40                  45

Asn Ser Leu Phe Trp Tyr Arg Glu Thr Met Met Arg Gly Leu Glu Leu
        50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Pro Gly Ser Thr Asp Thr Gln Tyr Phe Gly Pro Gly Thr Arg
        115                 120                 125

Leu Thr Val Leu Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
290                 295                 300

Lys Arg Lys Asp Ser Arg Gly Ser Gly Ser Gly Ala Thr Asn Phe Ser
305                 310                 315                 320

Leu Leu Lys Gln Ala Gly Asp Val Glu Glu Asn Pro Gly Pro Met Glu
```

|  |  |  |  | 325 |  |  |  |  | 330 |  |  |  |  | 335 |  |
|---|---|---|---|---|---|---|---|---|---|---|---|---|---|---|---|
| Lys | Asn | Pro | Leu | Ala | Ala | Pro | Leu | Leu | Ile | Leu | Trp | Phe | His | Leu | Asp |
|  |  |  | 340 |  |  |  |  | 345 |  |  |  |  | 350 |  |  |
| Cys | Val | Ser | Ser | Ile | Leu | Asn | Val | Glu | Gln | Ser | Pro | Gln | Ser | Leu | His |
|  |  |  | 355 |  |  |  |  | 360 |  |  |  |  | 365 |  |  |
| Val | Gln | Glu | Gly | Asp | Ser | Thr | Asn | Phe | Thr | Cys | Ser | Phe | Pro | Ser | Ser |
|  |  |  | 370 |  |  |  |  | 375 |  |  |  |  | 380 |  |  |
| Asn | Phe | Tyr | Ala | Leu | His | Trp | Tyr | Arg | Lys | Glu | Thr | Ala | Lys | Ser | Pro |
| 385 |  |  |  |  | 390 |  |  |  |  | 395 |  |  |  |  | 400 |
| Glu | Ala | Leu | Phe | Val | Met | Thr | Leu | Asn | Gly | Asp | Glu | Lys | Lys | Lys | Gly |
|  |  |  |  | 405 |  |  |  |  | 410 |  |  |  |  | 415 |  |
| Arg | Ile | Ser | Ala | Thr | Leu | Asn | Thr | Lys | Glu | Gly | Tyr | Ser | Tyr | Leu | Tyr |
|  |  |  | 420 |  |  |  |  | 425 |  |  |  |  | 430 |  |  |
| Ile | Lys | Gly | Ser | Gln | Pro | Glu | Asp | Ser | Ala | Thr | Tyr | Leu | Cys | Ala | Leu |
|  |  |  | 435 |  |  |  |  | 440 |  |  |  |  | 445 |  |  |
| Tyr | Asn | Asn | Asn | Asp | Met | Arg | Phe | Gly | Ala | Gly | Thr | Arg | Leu | Thr | Val |
|  |  |  | 450 |  |  |  |  | 455 |  |  |  |  | 460 |  |  |
| Lys | Pro | Asn | Ile | Gln | Asn | Pro | Asp | Pro | Ala | Val | Tyr | Gln | Leu | Arg | Asp |
| 465 |  |  |  |  | 470 |  |  |  |  | 475 |  |  |  |  | 480 |
| Ser | Lys | Ser | Ser | Asp | Lys | Ser | Val | Cys | Leu | Phe | Thr | Asp | Phe | Asp | Ser |
|  |  |  |  | 485 |  |  |  |  | 490 |  |  |  |  | 495 |  |
| Gln | Thr | Asn | Val | Ser | Gln | Ser | Lys | Asp | Ser | Asp | Val | Tyr | Ile | Thr | Asp |
|  |  |  | 500 |  |  |  |  | 505 |  |  |  |  | 510 |  |  |
| Lys | Thr | Val | Leu | Asp | Met | Arg | Ser | Met | Asp | Phe | Lys | Ser | Asn | Ser | Ala |
|  |  |  | 515 |  |  |  |  | 520 |  |  |  |  | 525 |  |  |
| Val | Ala | Trp | Ser | Asn | Lys | Ser | Asp | Phe | Ala | Cys | Ala | Asn | Ala | Phe | Asn |
|  |  |  | 530 |  |  |  |  | 535 |  |  |  |  | 540 |  |  |
| Asn | Ser | Ile | Ile | Pro | Glu | Asp | Thr | Phe | Phe | Pro | Ser | Pro | Glu | Ser | Ser |
| 545 |  |  |  |  | 550 |  |  |  |  | 555 |  |  |  |  | 560 |
| Cys | Asp | Val | Lys | Leu | Val | Glu | Lys | Ser | Phe | Glu | Thr | Asp | Thr | Asn | Leu |
|  |  |  |  | 565 |  |  |  |  | 570 |  |  |  |  | 575 |  |
| Asn | Phe | Gln | Asn | Leu | Ser | Val | Ile | Gly | Phe | Arg | Ile | Leu | Leu | Leu | Lys |
|  |  |  | 580 |  |  |  |  | 585 |  |  |  |  | 590 |  |  |
| Val | Ala | Gly | Phe | Asn | Leu | Leu | Met | Thr | Leu | Arg | Leu | Trp | Ser | Ser |  |
|  |  |  | 595 |  |  |  |  | 600 |  |  |  |  | 605 |  |  |

<210> SEQ ID NO 301
<211> LENGTH: 3828
<212> TYPE: DNA
<213> ORGANISM: Artificial Sequence
<220> FEATURE:
<223> OTHER INFORMATION: CD8aNCAM1Fusion.TCR.WPREmut2 nucleotide
    sequence

<400> SEQUENCE: 301

| tgaaagaccc cacctgtagg tttggcaagc tagcttaagt aacgccattt tgcaaggcat | 60 |
| ggaaaataca taactgagaa tagagaagtt cagatcaagg ttaggaacag agagacagca | 120 |
| gaatatgggc caaacaggat atctgtggta agcagttcct gccccggctc agggccaaga | 180 |
| acagatggtc cccagatgcg gtcccgccct cagcagtttc tagagaacca tcagatgttt | 240 |
| ccagggtgcc ccaaggacct gaaaatgacc ctgtgcctta tttgaactaa ccaatcagtt | 300 |
| cgcttctcgc ttctgttcgc gcgcttctgc tccccgagct caataaaaga gcccacaacc | 360 |
| cctcactcag cggccgcccc gggtcgacgc taccaccatg gcgcttcccg tgaccgcact | 420 |
| cctgttgccc cttgccctgc tgttgcacgc cgcacgacct tcccaattcc gggtgtcccc | 480 |

-continued

```
tctggatcgc acctggaacc tcggggaaac ggtggagctc aagtgtcaag tcctcctgtc    540
gaacccgacc agcggatgca gctggctgtt ccagccgaga ggagctgccg cctcacccac    600
cttcctcctg tacttgagcc agaacaagcc gaaggccgct gagggtctgg acacccagcg    660
cttctcgggc aaacggctgg agacactttt tgtgctgact ctctccgact ccggcgggga   720
gaacgagggc tactacttct gctctgcgct ctccaattca atcatgtact tctcacactt    780
cgtgccggtg ttcctgcctg ccagcgtggt ggacttcctc cccactaccg cccaacccac    840
taagaagtca accctgaaga agcgggtttg cagactccca cggccggaaa cgcagaaggg    900
tccgctgtgt tccccggcca tcgtgggcat cctgatcgtg atcttcgtgc tgctgctggt    960
ggtggtggac atcacctgct acttcctgaa caagtgcggc ctgttcatgt gcatcgccgt   1020
gaacctgtgc ggcaaggccg cccccggcgc caagggcaag acatggagg agggcaaggc     1080 cgccttcagc aaggacgaga gcaaggagcc catcgtggag gtgaggaccg aggaggagag    1140
gacccccaac cacgacggcg gcaagcacac cgagcccaac gagaccaccc ccctgaccga    1200
gcccgagaag ggccccgtgg aggccaagcc cgagtgccag gagaccgaga ccaagcccgc    1260
ccccgccgag gtgaagaccg tgcccaacga cgccacccag accaaggaga acgagagcaa    1320
ggcccgggcc aagagatctg gcagcggcgc caccaatttc agcctgctga acaggccgg     1380 cgacgtggaa gagaaccctg gccccatgga ctcttggacc ttctgctgcg tgagcctgtg    1440
catcctggtg gccaagcaca cagacgccgg cgtgatccag tccctaggc acgaggtgac     1500 cgagatgggc caggaggtga cactgcgctg taagccaatc tctggccaca cagcctgtt     1560 ttggtatagg gagaccatga tgcgcggcct ggagctgctg atctacttca ataacaatgt    1620
gcccatcgac gattccggca tgcctgagga tcggttttct gccaagatgc caatgccag     1680 cttctccaca ctgaagatcc agcctagcga gccaagagac tccgccgtgt attttgcgc     1740 ctctagccca ggcagcaccg atacacagta cttcggacca ggaaccaggc tgacagtgct    1800
ggaggacctg aagaacgtgt cccccctga ggtggccgtg tttgagcct ctgaggccga     1860 gatcagccac acccagaagg ccaccctggt gtgcctggca accggcttct atcctgatca    1920
cgtggagctg tcctggtggg tgaacggcaa ggaggtgcac agcggcgtgt ccacagaccc    1980
acagcccctg aaggagcagc cagccctgaa tgatagccgg tattgcctgt cctctcggct    2040
gagagtgtcc gccacctttt ggcagaaccc ccggaatcac ttcagatgtc aggtgcagtt    2100
ttacggcctg tccgagaacg atgagtggac ccaggaccgg gccaagcctg tgacacagat    2160
cgtgtctgcc gaggcatggg gaagagcaga ctgtggcttc acctctgaga gctaccagca    2220
gggcgtgctg agcgccacca tcctgtatga tcctgctg ggcaaggcca cactgtacgc      2280
cgtcctggtc tccgctctgg tgctgatggc aatggtcaaa agaaagata gtcgggacg       2340 ggccaagaga tctggcagcg gcgagggcag aggcagcctg ctgacctgcg gcgacgtgga    2400
ggagaacccc ggccccatgg agaagaatcc cctggctgcc ccctgctga tcctgtggtt     2460 tcacctggac tgcgtgtcct ctatcctgaa tgtggaacag agcccacaga gcctgcacgt    2520 gcaggaggc gactccacca acttcacatg ctctttttcct agctccaact tctacgccct     2580
gcactggtac agaaaggaga ccgcaaagtc cccagaggc ctgttcgtga tgacactgaa     2640
cggcgatgag aagaagaagg gccgcatcag cgccaccctg aatacaaagg agggctactc    2700
ctatctgtac atcaagggct cccagccga ggactctgcc acctatctgt gcgccctgta     2760
caacaataac gatatgcggt ttggcgccgg caccagactg acagtgaagc caaacatcca    2820
```

```
gaatccagac cccgccgtgt atcagctgcg ggacagcaag tctagcgata agagcgtgtg    2880
cctgttcacc gactttgatt ctcagacaaa cgtgagccag tccaaggaca gcgacgtgta    2940
catcaccgac aagacagtgc tggatatgag aagcatggac ttcaagtcta acagcgccgt    3000
ggcctggtcc aataagtctg atttcgcctg cgccaatgcc tttaataact ccatcatccc    3060
cgaggatacc ttctttcctt ctccagagtc ctcttgtgac gtgaagctgg tggagaagtc    3120
tttcgagacc gatacaaacc tgaattttca gaacctgagc gtgatcggct tcaggatcct    3180
gctgctgaag gtggccggct ttaatctgct gatgaccctg aggctgtgga gctcctgaac    3240
cggtccggag catcttaccg ccatttatac ccatatttgt tctgttttc ttgatttggg    3300 tatacattta atgttaata aaacaaaatg gtggggcaat catttacatt ttttgggata    3360
tgtaattact agttcaggtg tattgccaca agacaaactt gttaagaaac tttcccgtta    3420
tttacgctct gttcctgtta atcaacctct ggattacaaa atttgtgaaa gattgactga    3480
tattcttaac tttgttgctc cttttacgct gtgtggattt gctgctttat tgcctctgta    3540
tcttgctatt gcttcccgta cggctttcgt tttctcctcc ttgtataaat cctgttgct    3600 gtctcttttt gaggagttgt ggcccgttgt ccgtcaacgt ggcgtggtgt gctctgtgtt    3660
tgctgacgca acccccactg gctggggcat tgccaccacc tgtcaactcc tttctgggac    3720
tttcgctttc ccctcccga tcgccacggc agaactcatc gccgcctgcc ttgcccgctg    3780
ctggacaggg gctaggttgc tgggcactga taattccgtg gtgttgtc                3828
```

<210> SEQ ID NO 302
<211> LENGTH: 946
<212> TYPE: PRT
<213> ORGANISM: Artificial Sequence
<220> FEATURE:
<223> OTHER INFORMATION: CD8aNCAM1Fusion.TCR.WPREmut2 amino acid
      sequence

<400> SEQUENCE: 302

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Ser Val Val Asp Phe Leu Pro Thr Thr
    130                 135                 140

Ala Gln Pro Thr Lys Lys Ser Thr Leu Lys Lys Arg Val Cys Arg Leu
145                 150                 155                 160

Pro Arg Pro Glu Thr Gln Lys Gly Pro Leu Cys Ser Pro Ala Ile Val
                165                 170                 175

Gly Ile Leu Ile Val Ile Phe Val Leu Leu Leu Val Val Val Asp Ile

```
                180             185             190
Thr Cys Tyr Phe Leu Asn Lys Cys Gly Leu Phe Met Cys Ile Ala Val
            195             200             205
Asn Leu Cys Gly Lys Ala Gly Pro Gly Ala Lys Gly Lys Asp Met Glu
            210             215             220
Glu Gly Lys Ala Ala Phe Ser Lys Asp Glu Ser Lys Glu Pro Ile Val
225             230             235             240
Glu Val Arg Thr Glu Glu Arg Thr Pro Asn His Asp Gly Gly Lys
            245             250             255
His Thr Glu Pro Asn Glu Thr Thr Pro Leu Thr Glu Pro Lys Gly
            260             265             270
Pro Val Glu Ala Lys Pro Glu Cys Gln Glu Thr Glu Thr Lys Pro Ala
            275             280             285
Pro Ala Glu Val Lys Thr Val Pro Asn Asp Ala Thr Gln Thr Lys Glu
            290             295             300
Asn Glu Ser Lys Ala Arg Ala Lys Arg Ser Gly Ser Gly Ala Thr Asn
305             310             315             320
Phe Ser Leu Leu Lys Gln Ala Gly Asp Val Glu Glu Asn Pro Gly Pro
            325             330             335
Met Asp Ser Trp Thr Phe Cys Cys Val Ser Leu Cys Ile Leu Val Ala
            340             345             350
Lys His Thr Asp Ala Gly Val Ile Gln Ser Pro Arg His Glu Val Thr
            355             360             365
Glu Met Gly Gln Glu Val Thr Leu Arg Cys Lys Pro Ile Ser Gly His
            370             375             380
Asn Ser Leu Phe Trp Tyr Arg Glu Thr Met Met Arg Gly Leu Glu Leu
385             390             395             400
Leu Ile Tyr Phe Asn Asn Asn Val Pro Ile Asp Asp Ser Gly Met Pro
            405             410             415
Glu Asp Arg Phe Ser Ala Lys Met Pro Asn Ala Ser Phe Ser Thr Leu
            420             425             430
Lys Ile Gln Pro Ser Glu Pro Arg Asp Ser Ala Val Tyr Phe Cys Ala
            435             440             445
Ser Ser Pro Gly Ser Thr Asp Thr Gln Tyr Phe Gly Pro Gly Thr Arg
            450             455             460
Leu Thr Val Leu Glu Asp Leu Lys Asn Val Phe Pro Pro Glu Val Ala
465             470             475             480
Val Phe Glu Pro Ser Glu Ala Glu Ile Ser His Thr Gln Lys Ala Thr
            485             490             495
Leu Val Cys Leu Ala Thr Gly Phe Tyr Pro Asp His Val Glu Leu Ser
            500             505             510
Trp Trp Val Asn Gly Lys Glu Val His Ser Gly Val Ser Thr Asp Pro
            515             520             525
Gln Pro Leu Lys Glu Gln Pro Ala Leu Asn Asp Ser Arg Tyr Cys Leu
            530             535             540
Ser Ser Arg Leu Arg Val Ser Ala Thr Phe Trp Gln Asn Pro Arg Asn
545             550             555             560
His Phe Arg Cys Gln Val Gln Phe Tyr Gly Leu Ser Glu Asn Asp Glu
            565             570             575
Trp Thr Gln Asp Arg Ala Lys Pro Val Thr Gln Ile Val Ser Ala Glu
            580             585             590
Ala Trp Gly Arg Ala Asp Cys Gly Phe Thr Ser Glu Ser Tyr Gln Gln
            595             600             605
```

```
Gly Val Leu Ser Ala Thr Ile Leu Tyr Glu Ile Leu Leu Gly Lys Ala
            610                 615                 620

Thr Leu Tyr Ala Val Leu Val Ser Ala Leu Val Leu Met Ala Met Val
625                 630                 635                 640

Lys Arg Lys Asp Ser Arg Gly Arg Ala Lys Arg Ser Gly Ser Gly Glu
                645                 650                 655

Gly Arg Gly Ser Leu Leu Thr Cys Gly Asp Val Glu Glu Asn Pro Gly
                660                 665                 670

Pro Met Glu Lys Asn Pro Leu Ala Ala Pro Leu Leu Ile Leu Trp Phe
        675                 680                 685

His Leu Asp Cys Val Ser Ile Leu Asn Val Glu Gln Ser Pro Gln
        690                 695                 700

Ser Leu His Val Gln Glu Gly Asp Ser Thr Asn Phe Thr Cys Ser Phe
705                 710                 715                 720

Pro Ser Ser Asn Phe Tyr Ala Leu His Trp Tyr Arg Lys Glu Thr Ala
                725                 730                 735

Lys Ser Pro Glu Ala Leu Phe Val Met Thr Leu Asn Gly Asp Glu Lys
                740                 745                 750

Lys Lys Gly Arg Ile Ser Ala Thr Leu Asn Thr Lys Glu Gly Tyr Ser
                755                 760                 765

Tyr Leu Tyr Ile Lys Gly Ser Gln Pro Glu Asp Ser Ala Thr Tyr Leu
770                 775                 780

Cys Ala Leu Tyr Asn Asn Asn Asp Met Arg Phe Gly Ala Gly Thr Arg
785                 790                 795                 800

Leu Thr Val Lys Pro Asn Ile Gln Asn Pro Asp Pro Ala Val Tyr Gln
                805                 810                 815

Leu Arg Asp Ser Lys Ser Ser Asp Lys Ser Val Cys Leu Phe Thr Asp
                820                 825                 830

Phe Asp Ser Gln Thr Asn Val Ser Gln Ser Lys Asp Ser Asp Val Tyr
                835                 840                 845

Ile Thr Asp Lys Thr Val Leu Asp Met Arg Ser Met Asp Phe Lys Ser
850                 855                 860

Asn Ser Ala Val Ala Trp Ser Asn Lys Ser Asp Phe Ala Cys Ala Asn
865                 870                 875                 880

Ala Phe Asn Asn Ser Ile Ile Pro Glu Asp Thr Phe Phe Pro Ser Pro
                885                 890                 895

Glu Ser Ser Cys Asp Val Lys Leu Val Glu Lys Ser Phe Glu Thr Asp
                900                 905                 910

Thr Asn Leu Asn Phe Gln Asn Leu Ser Val Ile Gly Phe Arg Ile Leu
                915                 920                 925

Leu Leu Lys Val Ala Gly Phe Asn Leu Leu Met Thr Leu Arg Leu Trp
930                 935                 940

Ser Ser
945

<210> SEQ ID NO 303
<211> LENGTH: 311
<212> TYPE: PRT
<213> ORGANISM: Artificial Sequence
<220> FEATURE:
<223> OTHER INFORMATION: R11P3D3KE beta chain

<400> SEQUENCE: 303

Met Asp Ser Trp Thr Phe Cys Cys Val Ser Leu Cys Ile Leu Val Ala
1               5                   10                  15
```

```
Lys His Thr Asp Ala Gly Val Ile Gln Ser Pro Arg His Glu Val Thr
                20                  25                  30

Glu Met Gly Gln Glu Val Thr Leu Arg Cys Lys Pro Ile Ser Gly His
            35                  40                  45

Asn Ser Leu Phe Trp Tyr Arg Glu Thr Met Met Arg Gly Leu Glu Leu
 50                  55                  60

Leu Ile Tyr Phe Asn Asn Val Pro Ile Asp Asp Ser Gly Met Pro
 65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
                100                 105                 110

Ser Ser Pro Gly Ser Thr Asp Thr Gln Tyr Phe Gly Pro Gly Thr Arg
            115                 120                 125

Leu Thr Val Leu Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
                180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
            290                 295                 300

Lys Arg Lys Asp Ser Arg Gly
305                 310

<210> SEQ ID NO 304
<211> LENGTH: 273
<212> TYPE: PRT
<213> ORGANISM: Artificial Sequence
<220> FEATURE:
<223> OTHER INFORMATION: R39P1C12 alpha chain

<400> SEQUENCE: 304

Met Lys Thr Phe Ala Gly Phe Ser Phe Leu Phe Leu Trp Leu Gln Leu
 1               5                   10                  15

Asp Cys Met Ser Arg Gly Glu Asp Val Glu Gln Ser Leu Phe Leu Ser
                20                  25                  30

Val Arg Glu Gly Asp Ser Ser Val Ile Asn Cys Thr Tyr Thr Asp Ser
            35                  40                  45

Ser Ser Thr Tyr Leu Tyr Trp Tyr Lys Gln Glu Pro Gly Ala Gly Leu
 50                  55                  60
```

```
Gln Leu Leu Thr Tyr Ile Phe Ser Asn Met Asp Met Lys Gln Asp Gln
 65              70              75              80

Arg Leu Thr Val Leu Leu Asn Lys Lys Asp Lys His Leu Ser Leu Arg
             85              90              95

Ile Ala Asp Thr Gln Thr Gly Asp Ser Ala Ile Tyr Phe Cys Ala Glu
            100             105             110

Ile Asp Asn Gln Gly Gly Lys Leu Ile Phe Gly Gln Gly Thr Glu Leu
            115             120             125

Ser Val Lys Pro Asn Ile Gln Asn Pro Asp Pro Ala Val Tyr Gln Leu
            130             135             140

Arg Asp Ser Lys Ser Ser Asp Lys Ser Val Cys Leu Phe Thr Asp Phe
145             150             155             160

Asp Ser Gln Thr Asn Val Ser Gln Ser Lys Asp Ser Asp Val Tyr Ile
            165             170             175

Thr Asp Lys Thr Val Leu Asp Met Arg Ser Met Asp Phe Lys Ser Asn
            180             185             190

Ser Ala Val Ala Trp Ser Asn Lys Ser Asp Phe Ala Cys Ala Asn Ala
            195             200             205

Phe Asn Asn Ser Ile Ile Pro Glu Asp Thr Phe Phe Pro Ser Pro Glu
            210             215             220

Ser Ser Cys Asp Val Lys Leu Val Glu Lys Ser Phe Glu Thr Asp Thr
225             230             235             240

Asn Leu Asn Phe Gln Asn Leu Ser Val Ile Gly Phe Arg Ile Leu Leu
            245             250             255

Leu Lys Val Ala Gly Phe Asn Leu Leu Met Thr Leu Arg Leu Trp Ser
            260             265             270

Ser
```